United States Patent
Chen et al.

(10) Patent No.: US 9,260,439 B2
(45) Date of Patent: Feb. 16, 2016

(54) DIHYDROPYRROLOPYRIMIDINE DERIVATIVES

(71) Applicant: PFIZER INC., New York, NY (US)

(72) Inventors: Ping Chen, San Diego, CA (US); Hengmiao Cheng, San Diego, CA (US); Judith Gail Deal, Wildomar, CA (US); Gary Michael Gallego, San Diego, CA (US); Mehran Jalaie, San Diego, CA (US); John Charles Kath, La Mesa, CA (US); Suvi Tuula Marjukka Orr, San Diego, CA (US); Hong Shen, San Diego, CA (US); Luke Raymond Zehnder, San Diego, CA (US)

(73) Assignee: PFIZER INC., New York, NY (US)

( * ) Notice: Subject to any disclaimer, the term of this patent is extended or adjusted under 35 U.S.C. 154(b) by 0 days.

(21) Appl. No.: 14/677,112

(22) Filed: Apr. 2, 2015

(65) Prior Publication Data

US 2015/0291604 A1    Oct. 15, 2015

Related U.S. Application Data

(60) Provisional application No. 61/978,168, filed on Apr. 10, 2014.

(51) Int. Cl.
| | |
|---|---|
| *A61K 31/5377* | (2006.01) |
| *C07D 487/04* | (2006.01) |
| *C07F 9/6561* | (2006.01) |
| *A61K 45/06* | (2006.01) |
| *A61N 5/10* | (2006.01) |

(52) U.S. Cl.
CPC .......... *C07D 487/04* (2013.01); *A61K 31/5377* (2013.01); *A61K 45/06* (2013.01); *A61N 5/10* (2013.01); *C07F 9/65616* (2013.01)

(58) Field of Classification Search
CPC .................... C07D 487/04; A61K 31/5377
See application file for complete search history.

(56) References Cited

U.S. PATENT DOCUMENTS

| 8,022,205 B2 | 9/2011 | Shimma et al. |
| 2010/0069629 A1 | 3/2010 | Shimma et al. |

FOREIGN PATENT DOCUMENTS

| EP | 2050749 A1 | 4/2009 |
| WO | 2010056320 A2 | 5/2010 |

OTHER PUBLICATIONS

International Search Report for International Appln No. PCT/IB2015/052271 completed May 12, 2015.
National Center for Biotechnology Information. PubChem Compound Database; CID=87380394, https://pubchenn.ncbi.nlm.nih.gov/compound/87380394, Feb. 12, 2015.
Ohwada, J., et al., "Discovery and biological activity of a novel class I PI3K inhibitor, CH5132799," Bioorganic & Medicinal Chemistry Letters, 2011, 1767-1772, vol. 21, No. 6.
Written Opinion of the International Searching Authority for International Appln. No. PCT/IB2015/052271 with a mail date of May 22, 2015.

*Primary Examiner* — Rebecca Anderson
(74) *Attorney, Agent, or Firm* — Suzanne M. Bates; Stephen D. Prodnuk

(57) ABSTRACT

The present invention relates to compounds of formula (X)

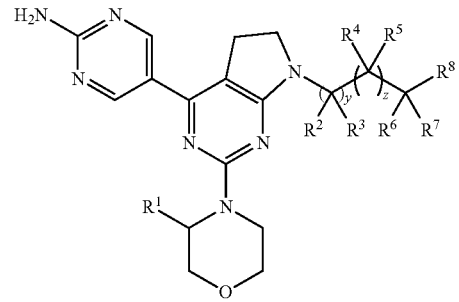

or pharmaceutically acceptable salts thereof, wherein $R^1$-$R^{50}$, a, b, d, e, f, g, h, i, j, k, l, o, p, q, r, s, t, u, y, and z are defined herein. The novel dihydropyrrolopyrimidine derivatives are useful in the treatment of abnormal cell growth, such as cancer, in mammals. Additional embodiments relate to pharmaceutical compositions containing the compounds and to methods of using the compounds and compositions in the treatment of abnormal cell growth in mammals.

18 Claims, No Drawings

DIHYDROPYRROLOPYRIMIDINE DERIVATIVES

This application claims the benefit of U.S. Provisional Application No. 61/978,168 filed on Apr. 10, 2014, the contents of which is hereby incorporated by reference in its entirety.

FIELD OF THE INVENTION

The present invention relates to novel dihydropyrrolopyrimidine derivatives that are useful in the treatment of abnormal cell growth, such as cancer, in mammals. The present invention also relates to pharmaceutical compositions containing the compounds and to methods of using the compounds and compositions in the treatment of abnormal cell growth in mammals.

BACKGROUND

Phosphoinositide 3-kinases ("PI3Ks") comprise a family of lipid kinases that catalyze the synthesis of the phosphatidylinositol ("PI") second messengers PI(3)P ("PIP"), PI(3,4)P$_2$ ("PIP$_2$"), and PI(3,4,5)P$_3$ ("PIP$_3$"). (Fruman et al., "Phosphoinositide kinases", *Annu. Rev. Biochem.* 67 (1998), pp. 481-507; Knight et al., "A Pharmacological Map of the PI3-K Family Defines a Role for p110α in Insulin Signaling", *Cell* 125 (2006), pp. 733-747.) In the appropriate cellular context, these lipids mediate diverse physiological processes including cell growth, survival, differentiation, and chemotaxis. (Katso et al., "Cellular function of phosphoinositide 3-kinases: implications for development, homeostasis, and cancer", *Annu. Rev. Cell Dev. Biol.* 17 (2001), pp. 615-675.) The PI3K family comprises at least 15 different lipid and serine/threonine kinases, sub-classified by structural homology, with distinct substrate specificities, expression patterns, and mode of regulation. Class I PI3Kα is the main PI3-kinase isoform in cancer, and consists of catalytic (p110α) and adapter (p85) subunits. (Stirdivant et al., "Cloning and mutagenesis of the p110α subunit of human phosphoinositide 3'-hydroxykinase", *Bioorg. Med. Chem.* 5 (1997), pp. 65-74.)

The 3-phosphorylated phospholipid, PIP$_3$, acts as a second messenger recruiting kinases with lipid binding domains (including plekstrin homology ("PH") regions), such as Akt, the product of the human homologue of the viral oncogene v-Akt, and phosphoinositide-dependent kinase-1 ("PDK1"). (Vivanco & Sawyers, "The Phosphatidylinositol 3-Kinase-Akt Pathway In Human Cancer", *Nature Reviews Cancer* 2 (2002), pp. 489-501.) Binding of Akt to PIP$_3$ induces Akt to translocate to the plasma membrane, bringing Akt into contact with PDK1, which activates Akt. The tumor-suppressor phosphatase, PTEN, dephosphorylates PIP$_3$, and therefore acts as a negative regulator of Akt activation. The PI3Ks, Akt and PDK1 are important in the regulation of many cellular processes including cell cycle regulation, proliferation, survival, apoptosis and motility and are significant components of the molecular mechanisms of diseases such as cancer, diabetes and immune inflammation. Functional loss of PTEN (the most commonly mutated tumor-suppressor gene in cancer after p53), oncogenic mutations in the PIK3CA gene encoding PI3Kα, amplification of the PIK3CA gene and overexpression of Akt have been established in many malignancies. (see, for example, Samuels, et al., "High frequency of mutations of the PIK3CA gene in human cancers", *Science* 304 (2004), p. 554; Broderick et al., "Mutations in PIK3CA in anaplastic oligodendrogliomas, high-grade astrocytomas, and medulloblastomas", *Cancer Research* 64 (2004), pp. 5048-5050.) Therefore, the deregulation of PI3k and the upstream and downstream components of this signaling pathway is one of the most common deregulations associated with human cancers and proliferative diseases. (Parsons et al., *Nature*, 436 (2005), p. 792; Hennessey et al., *Nature Rev. Drug Disc.* 4 (2005) 988-1004.)

PI3Kα is thus an attractive target for cancer drug development because PI3Kα inhibitors would be expected to inhibit proliferation and summon resistance to cytotoxic agents in cancer cells.

SUMMARY OF THE INVENTION

Each of the embodiments described below can be combined with any other embodiment described herein not inconsistent with the embodiment with which it is combined. Furthermore, each of the embodiments described herein envisions within its scope pharmaceutically acceptable salts of the compounds described herein. Accordingly, the phrase "or a pharmaceutically acceptable salt thereof" is implicit in the description of all compounds described herein.

Some embodiments described herein relate to a compound of formula (I)

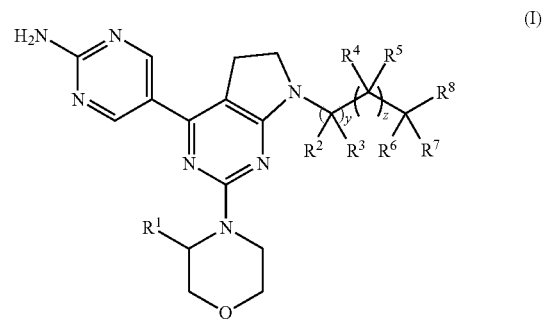

or a pharmaceutically acceptable salt thereof,
wherein
$R^1$ is hydrogen, methyl, —CH$_2$OH, or —CH$_2$F;
y is 0 or 1;
$R^2$ is hydrogen, cyano, C$_1$-C$_3$ alkyl, or —CF$_3$;
$R^3$ is hydrogen or C$_1$-C$_3$ alkyl;
z is 0 or 1;
$R^4$ is hydrogen, cyano, C$_1$-C$_3$ alkyl, —CH$_2$F, —CHF$_2$, —CF$_3$, —CH$_2$CN, —CH$_2$OH, hydroxy, or C$_1$-C$_3$ alkoxy,
provided that $R^4$ is not hydroxy or C$_1$-C$_3$ alkoxy, when y is 0;
$R^5$ is hydrogen or C$_1$-C$_3$ alkyl; or
$R^4$ and $R^5$ combine to form a C$_3$-C$_4$ cycloalkyl ring, wherein a carbon atom in the C$_4$ cycloalkyl ring formed is optionally replaced with —NH— or —O—;
$R^6$ is hydrogen or C$_1$-C$_3$ alkyl;
$R^7$ is hydrogen or C$_1$-C$_3$ alkyl;
$R^8$ is hydrogen,
cyano,
—CF$_3$,
hydroxy,
C$_1$-C$_3$ alkoxy,
—S(O)R$^{18}$,
—[N(R$^{12}$)]$_a$—C(O)R$^{19}$,
—[N(R$^{13}$)]$_b$—C(O)[N(R$^{20}$)(R$^{21}$)],
—[N(R$^{14}$)]$_d$—C(O)OR$^{22}$,
—[N(R$^{15}$)]$_e$—S(O)$_2$R$^{23}$, —[N($R^{16}$)]$_f$—S(O)$_2$[N($R^{24}$)($R^{25}$)],
—[N($R^{17}$)]$_g$—P(O)(CH$_3$)$_2$, or
$R^8$ is C$_1$-C$_3$ alkyl and combines with $R^5$ to form a C$_3$-C$_8$ cycloalkyl ring, wherein a carbon atom of the C$_3$-C$_8$ cycloalkyl ring formed is —C($R^9$)($R^{10}$)— or a carbon atom in the C$_3$-C$_8$ cycloalkyl ring formed is replaced with —N($R^{11}$)— or —O— to form a 4-8 membered heterocycloalkyl ring, further wherein the C$_3$-C$_8$ cycloalkyl and the 4-8 membered heterocycloalkyl rings formed may be optionally substituted by one, two, three, or four substituents selected from the group consisting of fluorine, cyano, oxo, methyl, —CH$_2$F, —CHF$_2$, —CF$_3$, —CH$_2$OH, hydroxy, and methoxy;

$R^9$ is hydrogen,
fluorine,
cyano,
hydroxy,
C$_1$-C$_3$ alkoxy,
—S(O)$R^{32}$,
—O—S(O)$_2R^{33}$,
—[N($R^{26}$)]$_h$—C(O)$R^{34}$,
—[N($R^{27}$)]$_i$—C(O)[N($R^{35}$)($R^{36}$)],
—[N($R^{25}$)]$_j$—C(O)O$R^{37}$,
—[N($R^{29}$)]$_k$—S(O)$_2R^{38}$,
—[N($R^{30}$)]$_l$—S(O)$_2$[N($R^{39}$)($R^{40}$)], or
—[N($R^{31}$)]$_o$—P(O)(CH$_3$)$_2$;

$R^{10}$ is hydrogen, fluorine, or C$_1$-C$_3$ alkyl;

$R^{11}$ is hydrogen,
—(CH$_2$)$_p$—C(O)$R^{41}$,
—(CH$_2$)$_q$—C(O)[N($R^{42}$)($R^{43}$)],
—(CH$_2$)$_r$—C(O)O$R^{44}$,
—(CH$_2$)$_s$—S(O)$_2R^{45}$,
—(CH$_2$)$_t$—S(O)$_2$[N($R^{46}$)($R^{47}$)],
—(CH$_2$)$_u$—$R^{48}$, or
—P(O)(CH$_3$)$_2$;

$R^{12}$, $R^{13}$, $R^{14}$, $R^{15}$, $R^{16}$, $R^{17}$, $R^{26}$, $R^{27}$, $R^{28}$, $R^{29}$, $R^{30}$, and $R^{31}$ are each independently hydrogen or methyl;

a, b, d, e, f, g, h, i, j, k, l, o, p, q, r, s, t, and u are each independently 0 or 1;

$R^{18}$ and $R^{32}$ are each independently C$_1$-C$_4$ alkyl, wherein the C$_1$-C$_4$ alkyl is optionally substituted by one substituent selected from the group consisting of fluorine, cyano, hydroxy, C$_1$-C$_4$ alkoxy, —NH$_2$, —NHCH$_3$, and —N(CH$_3$)$_2$;

$R^{33}$ is C$_1$-C$_4$ alkyl, —NH$_2$, —NHCH$_3$, —N(CH$_3$)$_2$, or C$_3$-C$_5$ cycloalkyl, wherein the C$_1$-C$_4$ alkyl is optionally substituted by one substituent selected from the group consisting of fluorine, cyano, hydroxy, C$_1$-C$_4$ alkoxy, —NH$_2$, —NHCH$_3$, and —N(CH$_3$)$_2$;

$R^{19}$, $R^{34}$, and $R^{41}$ are each independently hydrogen, C$_1$-C$_4$ alkyl, C$_3$-C$_6$ cycloalkyl, 4-6 membered heterocycloalkyl, or 5 membered heteroaryl, wherein the C$_1$-C$_4$ alkyl, the C$_3$-C$_6$ cycloalkyl, and the 4-6 membered heterocycloalkyl are each independently optionally substituted by one, two, or three substituents selected from the group consisting of fluorine, cyano, oxo, C$_1$-C$_4$ alkyl, —CH$_2$F, —CHF$_2$, —CF$_3$, hydroxy, C$_1$-C$_4$ alkoxy, —C(O)NH$_2$, —C(O)OH, —C(O)OCH$_3$, —NH$_2$, —NHCH$_3$, —N(CH$_3$)$_2$, —[N($R^{49}$)]-C(O)$R^{50}$, C$_3$-C$_4$ cycloalkyl, and 4-5 membered heterocycloalkyl, further wherein the 5 membered heteroaryl is optionally substituted by one substituent selected from the group consisting of fluorine, cyano, hydroxy, methoxy, —NH$_2$, and —NHCH$_3$;

$R^{20}$, $R^{35}$, and $R^{42}$ are each independently hydrogen, C$_1$-C$_4$ alkyl, C$_3$-C$_4$ cycloalkyl, or 4-5 membered heterocycloalkyl;

$R^{21}$ is C$_1$-C$_4$ alkyl;

$R^{36}$ and $R^{43}$ are each independently hydrogen or C$_1$-C$_4$ alkyl; or $R^{20}$ and $R^{21}$ together with the nitrogen to which they are attached, $R^{35}$ and $R^{36}$ together with the nitrogen to which they are attached, and $R^{42}$ and $R^{43}$ together with the nitrogen to which they are attached, each independently form a 4-5 membered heterocycloalkyl ring, wherein the 4-5 membered heterocycloalkyl ring formed is optionally substituted by one, two, or three substituents selected from the group consisting of fluorine, cyano, oxo, C$_1$-C$_4$ alkyl, hydroxy, and methoxy;

$R^{22}$, $R^{37}$, and $R^{44}$ are each independently C$_1$-C$_4$ alkyl, C$_3$-C$_4$ cycloalkyl, or 4-5 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH—S(O)$_2$NH$_2$, —NH—S(O)$_2$NHCH$_3$, and —NH—S(O)$_2$N(CH$_3$)$_2$, further wherein the C$_3$-C$_4$ cycloalkyl and the 4-5 membered heterocycloalkyl are each optionally substituted by one or two substituents selected from the group consisting of fluorine, cyano, methyl, hydroxy, methoxy, and —C(O)CH$_3$;

$R^{23}$, $R^{38}$, and $R^{45}$ are each independently C$_1$-C$_4$ alkyl, —CF$_3$, C$_1$-C$_4$ alkoxy, —(CH$_2$)$_v$—(C$_3$-C$_4$ cycloalkyl), 4-5 membered heterocycloalkyl, or 5-6 membered heteroaryl, wherein the C$_1$-C$_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, C$_1$-C$_4$ alkyl, hydroxy, methoxy, —C(O)(C$_1$-C$_4$ alkyl), and —C(O)[O—(C$_1$-C$_4$ alkyl)];

v is 0 or 1;

$R^{24}$, $R^{39}$, and $R^{46}$ are each independently hydrogen, C$_1$-C$_4$ alkyl, C$_3$-C$_4$ cycloalkyl, or 4-5 membered heterocycloalkyl;

$R^{25}$, $R^{40}$, and $R^{47}$ are each independently hydrogen or C$_1$-C$_4$ alkyl; or $R^{24}$ and $R^{25}$ together with the nitrogen to which they are attached, $R^{39}$ and $R^{40}$ together with the nitrogen to which they are attached, and $R^{46}$ and $R^{47}$ together with the nitrogen to which they are attached, each independently form a 4-5 membered heterocycloalkyl ring, wherein the 4-5 membered heterocycloalkyl ring formed is optionally substituted by one or two substituents selected from the group consisting of fluorine, cyano, C$_1$-C$_4$ alkyl, hydroxy, and methoxy;

$R^{48}$ is C$_1$-C$_4$ alkyl, C$_3$-C$_4$ cycloalkyl, or 4-6 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH$_2$, —NHCH$_3$, and —N(CH$_3$)$_2$, further wherein the C$_3$-C$_4$ cycloalkyl and the 4-6 membered heterocycloalkyl are each optionally substituted by one, two, three, or four substituents selected from the group consisting of fluorine, cyano, methyl, hydroxy, methoxy, oxo, —CF$_3$, and —C(O)CH$_3$;

$R^{49}$ is hydrogen or methyl; and $R^{50}$ is C$_1$-C$_4$ alkyl, —CF$_3$, C$_1$-C$_4$ alkoxy, —NH$_2$, —NHCH$_3$, —N(CH$_3$)$_2$, C$_3$-C$_5$ cycloalkyl, or 4-6 membered heterocycloalkyl.

Some embodiments described herein relate to a compound of formula (I), or a pharmaceutically acceptable salt thereof, wherein $R^8$ is hydrogen,
cyano,
—CF$_3$,
hydroxy,
C$_1$-C$_3$ alkoxy,
—S(O)$R^{18}$,
—[N($R^{12}$)]$_a$—C(O)$R^{19}$, —[N(R$^{13}$)]$_b$—C(O)[N(R$^{20}$)(R$^{21}$)],
—[N(R$^{14}$)]$_d$—C(O)OR$^{22}$,
—[N(R$^{15}$)]$_e$—S(O)$_2$R$^{23}$,
—[N(R$^{16}$)]$_f$—S(O)$_2$[N(R$^{24}$)(R$^{25}$)], or
—[N(R$^{17}$)]$_g$—P(O)(CH$_3$)$_2$;

R$^{12}$, R$^{13}$, R$^{14}$, R$^{15}$, R$^{16}$, and R$^{17}$ are each independently hydrogen or methyl;

a, b, d, e, f, and g are independently 0 or 1;

R$^{18}$ is C$_1$-C$_4$ alkyl, wherein the C$_1$-C$_4$ alkyl is optionally substituted by one substituent selected from the group consisting of fluorine, cyano, hydroxy, C$_1$-C$_4$ alkoxy, —NH$_2$, —NHCH$_3$, and —N(CH$_3$)$_2$;

R$^{19}$ is hydrogen, C$_1$-C$_4$ alkyl, C$_3$-C$_6$ cycloalkyl, 4-6 membered heterocycloalkyl, or 5 membered heteroaryl, wherein the C$_1$-C$_4$ alkyl, the C$_3$-C$_6$ cycloalkyl, and the 4-6 membered heterocycloalkyl are each independently optionally substituted by one, two, or three substituents selected from the group consisting of fluorine, cyano, oxo, C$_1$-C$_4$ alkyl, —CH$_2$F, —CHF$_2$, —CF$_3$, hydroxy, C$_1$-C$_4$ alkoxy, —C(O)NH$_2$, —C(O)OH, —C(O)OCH$_3$, —NH$_2$, —NHCH$_3$, —N(CH$_3$)$_2$, —N(R$^{49}$)C(O)R$^{50}$, C$_3$-C$_4$ cycloalkyl, and 4-5 membered heterocycloalkyl, further wherein the 5 membered heteroaryl is optionally substituted by one substituent selected from the group consisting of fluorine, cyano, hydroxy, methoxy, —NH$_2$, and —NHCH$_3$;

R$^{20}$ is hydrogen, C$_1$-C$_4$ alkyl, C$_3$-C$_4$ cycloalkyl, or 4-5 membered heterocycloalkyl;

R$^{21}$ is C$_1$-C$_4$ alkyl; or

R$^{20}$ and R$^{21}$ together with the nitrogen to which they are attached form a 4-5 membered heterocycloalkyl ring, wherein the 4-5 membered heterocycloalkyl ring formed is optionally substituted by one, two, or three substituents selected from the group consisting of fluorine, cyano, oxo, C$_1$-C$_4$ alkyl, hydroxy, and methoxy;

R$^{22}$ is C$_1$-C$_4$ alkyl, C$_3$-C$_4$ cycloalkyl, or 4-5 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH—S(O)$_2$NH$_2$, —NH—S(O)$_2$NHCH$_3$, and —NH—S(O)$_2$N(CH$_3$)$_2$, further wherein the C$_3$-C$_4$ cycloalkyl and the 4-5 membered heterocycloalkyl are each optionally substituted by one or two substituents selected from the group consisting of fluorine, cyano, methyl, hydroxy, methoxy, and —C(O)CH$_3$;

R$^{23}$ is C$_1$-C$_4$ alkyl, —CF$_3$, C$_1$-C$_4$ alkoxy, —(CH$_2$)$_v$—C$_3$-C$_4$ cycloalkyl, 4-5 membered heterocycloalkyl, or 5-6 membered heteroaryl, wherein the C$_1$-C$_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, C$_1$-C$_4$ alkyl, hydroxy methoxy, —C(O)(C$_1$-C$_4$ alkyl), and —C(O)[O—(C$_1$-C$_4$ alkyl)];

v is 0 or 1;

R$^{24}$ is hydrogen, C$_1$-C$_4$ alkyl, C$_3$-C$_4$ cycloalkyl, or 4-5 membered heterocycloalkyl;

R$^{25}$ is hydrogen or C$_1$-C$_4$ alkyl; or

R$^{24}$ and R$^{25}$ together with the nitrogen to which they are attached form a 4-5 membered heterocycloalkyl ring, wherein the 4-5 membered heterocycloalkyl ring formed is optionally substituted by one or two substituents selected from the group consisting of fluorine, cyano, C$_1$-C$_4$ alkyl, hydroxy, and methoxy;

R$^{49}$ is hydrogen or methyl; and

R$^{50}$ is C$_1$-C$_4$ alkyl, —CF$_3$, C$_1$-C$_4$ alkoxy, —NH$_2$, —NHCH$_3$, —N(CH$_3$)$_2$, C$_3$-C$_5$ cycloalkyl, or 4-6 membered heterocycloalkyl.

Some embodiments relate to a compound of formula (I), or a pharmaceutically acceptable salt thereof, wherein R$^1$ is hydrogen or methyl.

Further embodiments relate to a compound of formula (I), or a pharmaceutically acceptable salt thereof, wherein y is 1.

Some embodiments relate to a compound of formula (I), or a pharmaceutically acceptable salt thereof, wherein z is 1.

Additional embodiments relate to a compound of formula (I), or a pharmaceutically acceptable salt thereof, wherein z is 0.

More embodiments relate to a compound of formula (I), or a pharmaceutically acceptable salt thereof, wherein R$^2$ is hydrogen or C$_1$-C$_3$ alkyl.

Some embodiments relate to a compound of formula (I), or a pharmaceutically acceptable salt thereof, wherein R$^2$ is C$_1$-C$_3$ alkyl.

More embodiments relate to a compound of formula (I), or a pharmaceutically acceptable salt thereof, wherein R$^2$ is methyl.

Further embodiments relate to a compound of formula (I), or a pharmaceutically acceptable salt thereof, wherein R$^3$ is methyl.

Additional embodiments relate to a compound of formula (I), or a pharmaceutically acceptable salt thereof, wherein R$^2$ and R$^3$ are methyl.

Additional embodiments relate to a compound of formula (I), or a pharmaceutically acceptable salt thereof, wherein R$^4$ is hydrogen or C$_1$-C$_3$ alkyl.

Further embodiments relate to a compound of formula (I), or a pharmaceutically acceptable salt thereof, wherein R$^6$, R$^7$, and R$^8$ are hydrogen.

Some embodiments relate to a compound of formula (I), or a pharmaceutically acceptable salt thereof, wherein R$^8$ is hydrogen.

Some embodiments relate to a compound of formula (I), or a pharmaceutically acceptable salt thereof, wherein R$^8$ is hydroxy or methoxy.

More embodiments relate to a compound of formula (I), or a pharmaceutically acceptable salt thereof, wherein R$^8$ is —[N(R$^{14}$)]$_d$—C(O)OR$^{22}$.

More embodiments relate to a compound of formula (I), or a pharmaceutically acceptable salt thereof, wherein d is 0.

Some embodiments relate to a compound of formula (I), or a pharmaceutically acceptable salt thereof, wherein R$^8$ is —[N(R$^{15}$)]$_e$—S(O)$_2$R$^{23}$.

Additional embodiments relate to a compound of formula (I), or a pharmaceutically acceptable salt thereof, wherein e is 1.

Further embodiments relate to a compound of formula (I), or a pharmaceutically acceptable salt thereof, wherein R$^{22}$ is C$_1$-C$_4$ alkyl.

Some embodiments relate to a compound of formula (I), or a pharmaceutically acceptable salt thereof, wherein R$^{23}$ is C$_1$-C$_4$ alkyl.

Some embodiments described herein relate to a compound of formula (II)

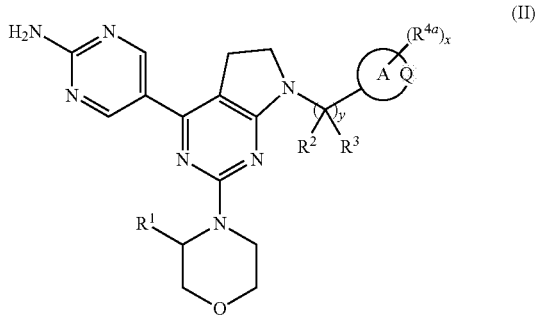

(II)

or a pharmaceutically acceptable salt thereof,
wherein
  $R^1$ is hydrogen, methyl, —CH$_2$OH, or —CH$_2$F;
  y is 0 or 1;
  $R^2$ is hydrogen, cyano, C$_1$-C$_3$ alkyl, or —CF$_3$;
  $R^3$ is hydrogen or C$_1$-C$_3$ alkyl;
  ring A is C$_3$-C$_8$ cycloalkyl or 4-8 membered heterocycloalkyl;
  Q is —C(R$^9$)(R$^{10}$)—, —N(R$^{11}$)— or —O—;
  x is 0, 1, 2, 3, or 4;
  each $R^{4a}$ is independently selected from the group consisting of fluorine, cyano, oxo, methyl, —CH$_2$F, —CHF$_2$, —CF$_3$, —CH$_2$OH, hydroxy, and methoxy;
  $R^9$ is hydrogen,
  fluorine,
  cyano,
  hydroxy,
  C$_1$-C$_3$ alkoxy,
  —S(O)R$^{32}$,
  —O—S(O)$_2$R$^{33}$,
  —[N(R$^{26}$)]$_h$—C(O)R$^{34}$,
  —[N(R$^{27}$)]$_i$—C(O)[N(R$^{35}$)(R$^{36}$)],
  —[N(R$^{28}$)]$_j$—C(O)OR$^{37}$,
  —[N(R$^{29}$)]$_k$—S(O)$_2$R$^{38}$,
  —[N(R$^{30}$)]$_l$—S(O)$_2$[N(R$^{39}$)(R$^{40}$)], or
  —[N(R$^{31}$)]$_o$—P(O)(CH$_3$)$_2$;
  $R^{10}$ is hydrogen, fluorine, or C$_1$-C$_3$ alkyl;
  $R^{11}$ is hydrogen,
  —(CH$_2$)$_p$—C(O)R$^{41}$,
  —(CH$_2$)$_q$—C(O)[N(R$^{42}$)(R$^{43}$)],
  —(CH$_2$)$_r$—C(O)OR$^{44}$,
  —(CH$_2$)$_s$—S(O)$_2$R$^{45}$,
  —(CH$_2$)$_t$—S(O)$_2$[N(R$^{46}$)(R$^{47}$)],
  —(CH$_2$)$_u$—R$^{48}$, or
  —P(O)(CH$_3$)$_2$;
  $R^{26}$, $R^{27}$, $R^{28}$, $R^{29}$, $R^{30}$, and $R^{31}$ are each independently hydrogen or methyl;
  h, i, j, k, l, o, p, q, r, s, t, and u are each independently 0 or 1;
  $R^{32}$ is C$_1$-C$_4$ alkyl, wherein the C$_1$-C$_4$ alkyl is optionally substituted by one substituent selected from the group consisting of fluorine, cyano, hydroxy, C$_1$-C$_4$ alkoxy, —NH$_2$, —NHCH$_3$, and —N(CH$_3$)$_2$;
  $R^{33}$ is C$_1$-C$_4$ alkyl, —NH$_2$, —NHCH$_3$, —N(CH$_3$)$_2$, or C$_3$-C$_5$ cycloalkyl, wherein the C$_1$-C$_4$ alkyl is optionally substituted by one substituent selected from the group consisting of fluorine, cyano, hydroxy, C$_1$-C$_4$ alkoxy, —NH$_2$, —NHCH$_3$, and —N(CH$_3$)$_2$;
  $R^{34}$ and $R^{41}$ are each independently hydrogen, C$_1$-C$_4$ alkyl, C$_3$-C$_6$ cycloalkyl, 4-6 membered heterocycloalkyl, or 5 membered heteroaryl, wherein the C$_1$-C$_4$ alkyl, the C$_3$-C$_6$ cycloalkyl, and the 4-6 membered heterocycloalkyl are each independently optionally substituted by one, two, or three substituents selected from the group consisting of fluorine, cyano, oxo, C$_1$-C$_4$ alkyl, —CH$_2$F, —CHF$_2$, —CF$_3$, hydroxy, C$_1$-C$_4$ alkoxy, —C(O)NH$_2$, —C(O)OH, —C(O)OCH$_3$, —NH$_2$, —NHCH$_3$, —N(CH$_3$)$_2$, —[N(R$^{49}$)]-C(O)R$^{50}$, C$_3$-C$_4$ cycloalkyl, and 4-5 membered heterocycloalkyl, further wherein the 5 membered heteroaryl is optionally substituted by one substituent selected from the group consisting of fluorine, cyano, hydroxy, methoxy, —NH$_2$, and —NHCH$_3$;
  $R^{35}$ and $R^{42}$ are each independently hydrogen, C$_1$-C$_4$ alkyl, C$_3$-C$_4$ cycloalkyl, or 4-5 membered heterocycloalkyl;
  $R^{36}$ and $R^{43}$ are each independently hydrogen or C$_1$-C$_4$ alkyl; or
  $R^{35}$ and $R^{36}$ together with the nitrogen to which they are attached and $R^{42}$ and $R^{43}$ together with the nitrogen to which they are attached, each independently form a 4-5 membered heterocycloalkyl ring, wherein the 4-5 membered heterocycloalkyl ring formed is optionally substituted by one, two, or three substituents selected from the group consisting of fluorine, cyano, oxo, C$_1$-C$_4$ alkyl, hydroxy, and methoxy;
  $R^{37}$ and $R^{44}$ are each independently C$_1$-C$_4$ alkyl, C$_3$-C$_4$ cycloalkyl, or 4-5 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH—S(O)$_2$NH$_2$, —NH—S(O)$_2$NHCH$_3$, and —NH—S(O)$_2$N(CH$_3$)$_2$, further wherein the C$_3$-C$_4$ cycloalkyl and the 4-5 membered heterocycloalkyl are each optionally substituted by one or two substituents selected from the group consisting of fluorine, cyano, methyl, hydroxy, methoxy, and —C(O)CH$_3$;
  $R^{38}$ and $R^{45}$ are each independently C$_1$-C$_4$ alkyl, —CF$_3$, C$_1$-C$_4$ alkoxy, —(CH$_2$)$_v$—(C$_3$-C$_4$ cycloalkyl), 4-5 membered heterocycloalkyl, or 5-6 membered heteroaryl, wherein the C$_1$-C$_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, C$_1$-C$_4$ alkyl, hydroxy, methoxy, —C(O)(C$_1$-C$_4$ alkyl), and —C(O)[O—(C$_1$-C$_4$ alkyl)];
  v is 0 or 1;
  $R^{39}$ and $R^{46}$ are each independently hydrogen, C$_1$-C$_4$ alkyl, C$_3$-C$_4$ cycloalkyl, or 4-5 membered heterocycloalkyl;
  $R^{40}$ and $R^{47}$ are each independently hydrogen or C$_1$-C$_4$ alkyl; or
  $R^{39}$ and $R^{40}$ together with the nitrogen to which they are attached and $R^{46}$ and $R^{47}$ together with the nitrogen to which they are attached, each independently form a 4-5 membered heterocycloalkyl ring, wherein the 4-5 membered heterocycloalkyl ring formed is optionally substituted by one or two substituents selected from the group consisting of fluorine, cyano, C$_1$-C$_4$ alkyl, hydroxy, and methoxy;
  $R^{48}$ is C$_1$-C$_4$ alkyl, C$_3$-C$_4$ cycloalkyl, or 4-6 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH$_2$, —NHCH$_3$, and —N(CH$_3$)$_2$, further wherein the C$_3$-C$_4$ cycloalkyl and the 4-6 membered heterocycloalkyl are each optionally substituted by one, two, three, or four substituents selected from the group consisting of fluorine, cyano, methyl, hydroxy, methoxy, oxo, —CF$_3$, and —C(O)CH$_3$;

$R^{49}$ is hydrogen or methyl; and $R^{50}$ is $C_1$-$C_4$ alkyl, —$CF_3$, $C_1$-$C_4$ alkoxy, —$NH_2$, —$NHCH_3$, —$N(CH_3)_2$, $C_3$-$C_5$ cycloalkyl, or 4-6 membered heterocycloalkyl.

More embodiments relate to a compound of formula (II), or a pharmaceutically acceptable salt thereof, wherein $R^1$ is hydrogen, methyl, or —$CH_2OH$.

More embodiments relate to a compound of formula (II), or a pharmaceutically acceptable salt thereof, wherein $R^1$ is hydrogen or methyl.

Some embodiments relate to a compound of formula (II), or a pharmaceutically acceptable salt thereof, wherein $R^1$ is hydrogen.

Additional embodiments relate to a compound of formula (II), or a pharmaceutically acceptable salt thereof, wherein $R^1$ is methyl.

Further embodiments relate to a compound of formula (II), or a pharmaceutically acceptable salt thereof, wherein y is 0.

More embodiments relate to a compound of formula (II), or a pharmaceutically acceptable salt thereof, wherein x is 0.

Some embodiments relate to a compound of formula (II), or a pharmaceutically acceptable salt thereof, wherein x is 1.

Additional embodiments relate to a compound of formula (II), or a pharmaceutically acceptable salt thereof, wherein x is 0, 1, or 2.

Additional embodiments relate to a compound of formula (II), or a pharmaceutically acceptable salt thereof, wherein x is 4.

Additional embodiments relate to a compound of formula (II), or a pharmaceutically acceptable salt thereof, wherein each $R^{4a}$ is independently fluorine, methyl, —$CH_2F$, —$CHF_2$, —$CF_3$, hydroxy, or methoxy.

Some embodiments relate to a compound of formula (II), or a pharmaceutically acceptable salt thereof, wherein each $R^{4a}$ is independently fluorine, methyl, —$CHF_2$, hydroxy, or methoxy.

Some embodiments relate to a compound of formula (II), or a pharmaceutically acceptable salt thereof, wherein each $R^{4a}$ is independently methyl.

Additional embodiments relate to a compound of formula (II), or a pharmaceutically acceptable salt thereof, wherein each $R^{4a}$ is methyl and x is 1 or 2.

Further embodiments relate to a compound of formula (II), or a pharmaceutically acceptable salt thereof, wherein each $R^{4a}$ is oxo and x is 1.

Further embodiments relate to a compound of formula (II), or a pharmaceutically acceptable salt thereof, wherein ring A is $C_3$-$C_8$ cycloalkyl.

More embodiments relate to a compound of formula (II), or a pharmaceutically acceptable salt thereof, wherein Q is —$C(R^9)(R^{10})$—.

Further embodiments relate to a compound of formula (II), or a pharmaceutically acceptable salt thereof, wherein $R^9$ is hydrogen, fluorine, cyano, hydroxy, or $C_1$-$C_3$ alkoxy.

More embodiments relate to a compound of formula (II), or a pharmaceutically acceptable salt thereof, wherein $R^9$ is fluorine.

Some embodiments relate to a compound of formula (II), or a pharmaceutically acceptable salt thereof, wherein $R^9$ is —O—$S(O)_2R^{33}$.

Additional embodiments relate to a compound of formula (II), or a pharmaceutically acceptable salt thereof, wherein $R^{33}$ is —$NH_2$, —$NHCH_3$, or —$N(CH_3)_2$.

Additional embodiments relate to a compound of formula (II), or a pharmaceutically acceptable salt thereof, wherein $R^9$ is —$[N(R^{26})]_h$—$C(O)R^{34}$.

Some embodiments relate to a compound of formula (II), or a pharmaceutically acceptable salt thereof, wherein h is 1.

More embodiments relate to a compound of formula (II), or a pharmaceutically acceptable salt thereof, wherein $R^{34}$ is $C_1$-$C_4$ alkyl, optionally substituted by hydroxy.

Additional embodiments relate to a compound of formula (II), or a pharmaceutically acceptable salt thereof, wherein $R^{34}$ is methyl.

Some embodiments relate to a compound of formula (II), or a pharmaceutically acceptable salt thereof, wherein $R^9$ is —$[N(R^{27})]_i$—$C(O)[N(R^{35})(R^{36})]$.

Some embodiments relate to a compound of formula (II), or a pharmaceutically acceptable salt thereof, wherein i is 0.

More embodiments relate to a compound of formula (II), or a pharmaceutically acceptable salt thereof, wherein $R^{35}$ is hydrogen or $C_1$-$C_4$ alkyl.

More embodiments relate to a compound of formula (II), or a pharmaceutically acceptable salt thereof, wherein $R^{35}$ is hydrogen or methyl.

Further embodiments relate to a compound of formula (II), or a pharmaceutically acceptable salt thereof, wherein $R^{36}$ is hydrogen or methyl.

More embodiments relate to a compound of formula (II), or a pharmaceutically acceptable salt thereof, wherein $R^9$ is —$[N(R^{29})]_k$—$S(O)_2R^{38}$.

Some embodiments relate to a compound of formula (II), or a pharmaceutically acceptable salt thereof, wherein k is 0.

More embodiments relate to a compound of formula (II), or a pharmaceutically acceptable salt thereof, wherein k is 1.

Some embodiments relate to a compound of formula (II), or a pharmaceutically acceptable salt thereof, wherein $R^{38}$ is $C_1$-$C_4$ alkyl.

Some embodiments relate to a compound of formula (II), or a pharmaceutically acceptable salt thereof, wherein $R^{38}$ is methyl.

Additional embodiments relate to a compound of formula (II), or a pharmaceutically acceptable salt thereof, wherein $R^9$ is —$[N(R^{30})]_l$—$S(O)_2[N(R^{39})(R^{40})]$.

Additional embodiments relate to a compound of formula (II), or a pharmaceutically acceptable salt thereof, wherein l is 0.

More embodiments relate to a compound of formula (II), or a pharmaceutically acceptable salt thereof, wherein l is 1.

Some embodiments relate to a compound of formula (II), or a pharmaceutically acceptable salt thereof, wherein $R^{39}$ is hydrogen or $C_1$-$C_4$ alkyl.

More embodiments relate to a compound of formula (II), or a pharmaceutically acceptable salt thereof, wherein $R^{39}$ is hydrogen or methyl.

Further embodiments relate to a compound of formula (II), or a pharmaceutically acceptable salt thereof, wherein $R^{40}$ is hydrogen or methyl.

Some embodiments relate to a compound of formula (II), or a pharmaceutically acceptable salt thereof, wherein $R^{10}$ is hydrogen.

Additional embodiments relate to a compound of formula (II), or a pharmaceutically acceptable salt thereof, wherein $R^{10}$ is fluorine.

Some embodiments relate to a compound of formula (II), or a pharmaceutically acceptable salt thereof, wherein $R^{10}$ is methyl.

More embodiments relate to a compound of formula (II), or a pharmaceutically acceptable salt thereof, wherein $R^9$ is fluorine and $R^{10}$ is fluorine.

Some embodiments relate to a compound of formula (II), or a pharmaceutically acceptable salt thereof, wherein ring A is 4-8 membered heterocycloalkyl.

Further embodiments relate to a compound of formula (II), or a pharmaceutically acceptable salt thereof, wherein Q is $-N(R^{11})-$.

Some embodiments relate to a compound of formula (II), or a pharmaceutically acceptable salt thereof, wherein $R^{11}$ is hydrogen.

Additional embodiments relate to a compound of formula (II), or a pharmaceutically acceptable salt thereof, wherein $R^{11}$ is $-(CH_2)_p-C(O)R^{41}$.

More embodiments relate to a compound of formula (II), or a pharmaceutically acceptable salt thereof, wherein p is 0.

Some embodiments relate to a compound of formula (II), or a pharmaceutically acceptable salt thereof, wherein $R^{41}$ is hydrogen or $C_1$-$C_4$ alkyl, wherein the $C_1$-$C_4$ alkyl is optionally substituted by one substituent selected from the group consisting of hydroxy, $C_1$-$C_4$ alkoxy, and $-[N(R^{49})]$-$C(O)R^{50}$.

Further embodiments relate to a compound of formula (II), or a pharmaceutically acceptable salt thereof, wherein $R^{41}$ is $C_1$-$C_4$ alkyl, optionally substituted by hydroxy.

Additional embodiments relate to a compound of formula (II), or a pharmaceutically acceptable salt thereof, wherein $R^{41}$ is $C_1$-$C_4$ alkyl, optionally substituted by $-NH_2$.

Further embodiments relate to a compound of formula (II), or a pharmaceutically acceptable salt thereof, wherein $R^{41}$ is methyl.

Some embodiments relate to a compound of formula (II), or a pharmaceutically acceptable salt thereof, wherein $R^{41}$ is methoxy.

Additional embodiments relate to a compound of formula (II), or a pharmaceutically acceptable salt thereof, wherein $R^{41}$ is $C_1$-$C_4$ alkyl, optionally substituted by $-[N(R^{49})]-C(O)R^{50}$.

Additional embodiments relate to a compound of formula (II), or a pharmaceutically acceptable salt thereof, wherein $R^{49}$ is hydrogen.

Some embodiments relate to a compound of formula (II), or a pharmaceutically acceptable salt thereof, wherein $R^{50}$ is $C_1$-$C_4$ alkyl.

More embodiments relate to a compound of formula (II), or a pharmaceutically acceptable salt thereof, wherein $R^{11}$ is $-(CH_2)_q-C(O)[N(R^{42})(R^{43})]$.

Some embodiments relate to a compound of formula (II), or a pharmaceutically acceptable salt thereof, wherein q is 0.

More embodiments relate to a compound of formula (II), or a pharmaceutically acceptable salt thereof, wherein $R^{42}$ is hydrogen or $C_1$-$C_4$ alkyl.

Some embodiments relate to a compound of formula (II), or a pharmaceutically acceptable salt thereof, wherein $R^{43}$ is hydrogen.

Further embodiments relate to a compound of formula (II), or a pharmaceutically acceptable salt thereof, wherein $R^{11}$ is $-(CH_2)_r-C(O)OR^{44}$.

Some embodiments relate to a compound of formula (II), or a pharmaceutically acceptable salt thereof, wherein r is 0.

More embodiments relate to a compound of formula (II), or a pharmaceutically acceptable salt thereof, wherein $R^{44}$ is $C_1$-$C_4$ alkyl or 4-5 membered heterocycloalkyl, wherein the $C_1$-$C_4$ alkyl is optionally substituted by one substituent selected from the group consisting of hydroxy, methoxy, $-C(O)NH_2$, $-C(O)NHCH_3$, $-C(O)N(CH_3)_2$, $-NH-S(O)_2NH_2$, $-NH-S(O)_2NHCH_3$, and $-NH-S(O)_2N(CH_3)_2$, further wherein the 4-5 membered heterocycloalkyl is optionally substituted by $-C(O)CH_3$.

More embodiments relate to a compound of formula (II), or a pharmaceutically acceptable salt thereof, wherein $R^{44}$ is $C_1$-$C_4$ alkyl optionally substituted by hydroxy.

Additional embodiments relate to a compound of formula (II), or a pharmaceutically acceptable salt thereof, wherein $R^{11}$ is $-(CH_2)_s-S(O)_2R^{45}$.

Additional embodiments relate to a compound of formula (II), or a pharmaceutically acceptable salt thereof, wherein s is 0.

Further embodiments relate to a compound of formula (II), or a pharmaceutically acceptable salt thereof, wherein $R^{45}$ is $C_1$-$C_4$ alkyl, $-CF_3$, $-(CH_2)_v-(C_3$-$C_4$ cycloalkyl), or 4-5 membered heterocycloalkyl, wherein the $C_1$-$C_4$ alkyl is optionally substituted by methoxy, further wherein the 4-5 membered heterocycloalkyl is optionally substituted by one substituent selected from the group consisting of $C_1$-$C_4$ alkyl, $-C(O)(C_1$-$C_4$ alkyl), and $-C(O)[O-(C_1$-$C_4$ alkyl)]$.

Some embodiments relate to a compound of formula (II), or a pharmaceutically acceptable salt thereof, wherein $R^{45}$ is $C_1$-$C_4$ alkyl.

Some embodiments relate to a compound of formula (II), or a pharmaceutically acceptable salt thereof, wherein $R^{45}$ is $-(CH_2)_v-(C_3$-$C_4$ cycloalkyl).

Some embodiments relate to a compound of formula (II), or a pharmaceutically acceptable salt thereof, wherein v is 0.

More embodiments relate to a compound of formula (II), or a pharmaceutically acceptable salt thereof, wherein $R^{11}$ is $-(CH_2)_t-S(O)_2[N(R^{46})(R^{47})]$.

More embodiments relate to a compound of formula (II), or a pharmaceutically acceptable salt thereof, wherein t is 0.

Further embodiments relate to a compound of formula (II), or a pharmaceutically acceptable salt thereof, wherein $R^{46}$ is hydrogen or $C_1$-$C_4$ alkyl.

Further embodiments relate to a compound of formula (II), or a pharmaceutically acceptable salt thereof, wherein $R^{46}$ is hydrogen or methyl.

Some embodiments relate to a compound of formula (II), or a pharmaceutically acceptable salt thereof, wherein $R^{47}$ is hydrogen or methyl.

More embodiments relate to a compound of formula (II), or a pharmaceutically acceptable salt thereof, wherein $R^{11}$ is $-P(O)(CH_3)_2$.

More embodiments relate to a compound of formula (II), or a pharmaceutically acceptable salt thereof, wherein Q is $-O-$.

Some embodiments described herein relate to a compound of formula (III)

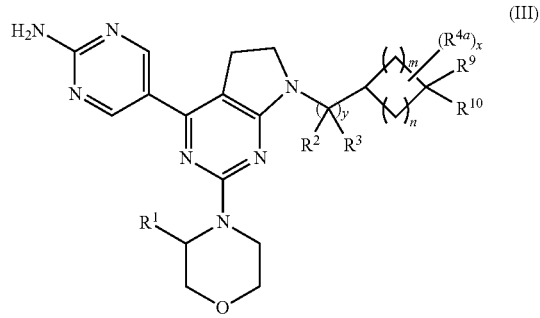

(III)

or a pharmaceutically acceptable salt thereof,
wherein
m is 1 or 2;
n is 1 or 2;
$R^1$ is hydrogen, methyl, $-CH_2OH$, or $-CH_2F$;
y is 0 or 1;
$R^2$ is hydrogen, cyano, $C_1$-$C_3$ alkyl, or $-CF_3$;

$R^3$ is hydrogen or $C_1$-$C_3$ alkyl;

x is 0, 1, 2, 3, or 4;

each $R^{4a}$ is independently selected from the group consisting of fluorine, cyano, oxo, methyl, —$CH_2F$, $CHF_2$, —$CF_3$, —$CH_2OH$, hydroxy, and methoxy;

$R^9$ is hydrogen,
fluorine,
cyano,
hydroxy,
$C_1$-$C_3$ alkoxy,
—S(O)$R^{32}$,
—O—S(O)$_2R^{33}$,
—[N($R^{26}$)]$_h$—C(O)$R^{34}$,
—[N($R^{27}$)]$_i$—C(O)[N($R^{35}$)($R^{36}$)],
—[N($R^{28}$)]$_j$—C(O)O$R^{37}$,
—[N($R^{29}$)]$_k$—S(O)$_2R^{38}$,
—[N($R^2$)]$_l$—S(O)$_2$[N($R^{39}$)($R^{40}$)], or
—[N($R^{31}$)]$_o$—P(O)($CH_3$)$_2$;

$R^{10}$ is hydrogen, fluorine, or $C_1$-$C_3$ alkyl;

$R^{26}$, $R^{27}$, $R^{28}$, $R^{29}$, $R^{30}$ and $R^{31}$ are each independently hydrogen or methyl;

h, i, j, k, l, and o are each independently 0 or 1;

$R^{32}$ is $C_1$-$C_4$ alkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —N($CH_3$)$_2$;

$R^{33}$ is $C_1$-$C_4$ alkyl, —$NH_2$, —$NHCH_3$, —N($CH_3$)$_2$, or $C_3$-$C_5$ cycloalkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —N($CH_3$)$_2$;

$R^{34}$ is hydrogen, $C_1$-$C_4$ alkyl, $C_3$-$C_6$ cycloalkyl, 4-6 membered heterocycloalkyl, or 5 membered heteroaryl, wherein the $C_1$-$C_4$ alkyl, the $C_3$-$C_6$ cycloalkyl, and the 4-6 membered heterocycloalkyl are each independently optionally substituted by one, two, or three substituents selected from the group consisting of fluorine, cyano, oxo, $C_1$-$C_4$ alkyl, —$CH_2F$, —$CHF_2$, —$CF_3$, hydroxy, $C_1$-$C_4$ alkoxy, —C(O)$NH_2$, —C(O)OH, —C(O)O$CH_3$, —$NH_2$, —$NHCH_3$, —N($CH_3$)$_2$, —[N($R^{49}$)]-C(O)$R^{50}$, $C_3$-$C_4$ cycloalkyl, and 4-5 membered heterocycloalkyl, further wherein the 5 membered heteroaryl is optionally substituted by one substituent selected from the group consisting of fluorine, cyano, hydroxy, methoxy, —$NH_2$, and —$NHCH_3$;

$R^{35}$ is hydrogen, $C_1$-$C_4$ alkyl, $C_3$-$C_4$ cycloalkyl, or 4-5 membered heterocycloalkyl;

$R^{36}$ is hydrogen or $C_1$-$C_4$ alkyl; or $R^{35}$ and $R^{36}$ together with the nitrogen to which they are attached form a 4-5 membered heterocycloalkyl ring, wherein the 4-5 membered heterocycloalkyl ring formed is optionally substituted by one, two, or three substituents selected from the group consisting of fluorine, cyano, oxo, $C_1$-$C_4$ alkyl, hydroxy, and methoxy;

$R^{37}$ is $C_1$-$C_4$ alkyl, $C_3$-$C_4$ cycloalkyl, or 4-5 membered heterocycloalkyl, wherein the $C_1$-$C_4$ alkyl is optionally substituted by one, two, or three substituents selected from the group consisting of fluorine, cyano, hydroxy, methoxy, —C(O)$NH_2$, —C(O)$NHCH_3$, —C(O)N($CH_3$)$_2$, —NH—S(O)$_2NH_2$, —NH—S(O)$_2NHCH_3$, and —NH—S(O)$_2$N($CH_3$)$_2$, further wherein the $C_3$-$C_4$ cycloalkyl and the 4-5 membered heterocycloalkyl are each optionally substituted by one or two substituents selected from the group consisting of fluorine, cyano, methyl, hydroxy, methoxy, and —C(O)$CH_3$;

$R^{38}$ is $C_1$-$C_4$ alkyl, —$CF_3$, $C_1$-$C_4$ alkoxy, —(CH$_2$)$_v$—($C_3$-$C_4$ cycloalkyl), 4-5 membered heterocycloalkyl, or 5-6 membered heteroaryl, wherein the $C_1$-$C_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, $C_1$-$C_4$ alkyl, hydroxy, methoxy, —C(O)($C_1$-$C_4$ alkyl), and —C(O)[O—($C_1$-$C_4$ alkyl)];

v is 0 or 1;

$R^{39}$ is hydrogen, $C_1$-$C_4$ alkyl, $C_3$-$C_4$ cycloalkyl, or 4-5 membered heterocycloalkyl;

$R^{40}$ is hydrogen or $C_1$-$C_4$ alkyl; or $R^{39}$ and $R^{40}$ together with the nitrogen to which they are attached form a 4-5 membered heterocycloalkyl ring, wherein the 4-5 membered heterocycloalkyl ring formed is optionally substituted by one or two substituents selected from the group consisting of fluorine, cyano, $C_1$-$C_4$ alkyl, hydroxy, and methoxy;

$R^{49}$ is hydrogen or methyl; and $R^{50}$ is $C_1$-$C_4$ alkyl, —$CF_3$, $C_1$-$C_4$ alkoxy, —$NH_2$, —$NHCH_3$, —N($CH_3$)$_2$, $C_3$-$C_5$ cycloalkyl, or 4-6 membered heterocycloalkyl.

More embodiments relate to a compound of formula (III), or a pharmaceutically acceptable salt thereof, wherein $R^1$ is hydrogen, methyl, or —$CH_2OH$.

Further embodiments relate to a compound of formula (III), or a pharmaceutically acceptable salt thereof, wherein $R^1$ is hydrogen or methyl.

Some embodiments relate to a compound of formula (III), or a pharmaceutically acceptable salt thereof, wherein $R^1$ is hydrogen.

More embodiments relate to a compound of formula (III), or a pharmaceutically acceptable salt thereof, wherein $R^1$ is methyl.

Additional embodiments relate to a compound of formula (III), or a pharmaceutically acceptable salt thereof, wherein y is 0.

More embodiments relate to a compound of formula (III), or a pharmaceutically acceptable salt thereof, wherein x is 0.

Further embodiments relate to a compound of formula (III), or a pharmaceutically acceptable salt thereof, wherein x is 1.

More embodiments relate to a compound of formula (III), or a pharmaceutically acceptable salt thereof, wherein x is 4.

Some embodiments relate to a compound of formula (III), or a pharmaceutically acceptable salt thereof, wherein each $R^{4a}$ is independently methyl.

More embodiments relate to a compound of formula (III), or a pharmaceutically acceptable salt thereof, wherein $R^9$ is hydrogen, fluorine, cyano, hydroxy, or $C_1$-$C_3$ alkoxy.

Some embodiments relate to a compound of formula (III), or a pharmaceutically acceptable salt thereof, wherein $R^9$ is fluorine.

More embodiments relate to a compound of formula (III), or a pharmaceutically acceptable salt thereof, wherein $R^9$ is —O—S(O)$_2R^{33}$.

Some embodiments relate to a compound of formula (III), or a pharmaceutically acceptable salt thereof, wherein $R^{33}$ is —$NH_2$, —$NHCH_3$, or —N($CH_3$)$_2$.

Further embodiments relate to a compound of formula (III), or a pharmaceutically acceptable salt thereof, wherein $R^9$ is —[N($R^{26}$)]$_h$—C(O)$R^{34}$.

Additional embodiments relate to a compound of formula (III), or a pharmaceutically acceptable salt thereof, wherein h is 1.

More embodiments relate to a compound of formula (III), or a pharmaceutically acceptable salt thereof, wherein $R^{34}$ is $C_1$-$C_4$ alkyl, optionally substituted by hydroxy.

More embodiments relate to a compound of formula (III), or a pharmaceutically acceptable salt thereof, wherein $R^{34}$ is methyl.

Some embodiments relate to a compound of formula (III), or a pharmaceutically acceptable salt thereof, wherein $R^9$ is —[N($R^{27}$)]$_i$—C(O)[N($R^{35}$)($R^{36}$)].

Further embodiments relate to a compound of formula (III), or a pharmaceutically acceptable salt thereof, wherein i is 0.

Further embodiments relate to a compound of formula (III), or a pharmaceutically acceptable salt thereof, wherein $R^{35}$ is hydrogen or $C_1$-$C_4$ alkyl.

Some embodiments relate to a compound of formula (III), or a pharmaceutically acceptable salt thereof, wherein $R^{35}$ is hydrogen or methyl.

More embodiments relate to a compound of formula (III), or a pharmaceutically acceptable salt thereof, wherein $R^{36}$ is hydrogen or methyl.

More embodiments relate to a compound of formula (III), or a pharmaceutically acceptable salt thereof, wherein $R^9$ is —[N($R^{29}$)]$_k$—S(O)$_2$$R^{38}$.

Some embodiments relate to a compound of formula (III), or a pharmaceutically acceptable salt thereof, wherein k is 0.

Additional embodiments relate to a compound of formula (III), or a pharmaceutically acceptable salt thereof, wherein k is 1.

Additional embodiments relate to a compound of formula (III), or a pharmaceutically acceptable salt thereof, wherein $R^{38}$ is $C_1$-$C_4$ alkyl.

More embodiments relate to a compound of formula (III), or a pharmaceutically acceptable salt thereof, wherein $R^{38}$ is methyl.

More embodiments relate to a compound of formula (III), or a pharmaceutically acceptable salt thereof, wherein $R^9$ is —[N($R^{30}$)]$_l$—S(O)$_2$[N($R^{39}$)($R^4$)].

Some embodiments relate to a compound of formula (III), or a pharmaceutically acceptable salt thereof, wherein l is 0.

Some embodiments relate to a compound of formula (III), or a pharmaceutically acceptable salt thereof, wherein l is 1.

Further embodiments relate to a compound of formula (III), or a pharmaceutically acceptable salt thereof, wherein $R^{39}$ is hydrogen or $C_1$-$C_4$ alkyl.

Further embodiments relate to a compound of formula (III), or a pharmaceutically acceptable salt thereof, wherein $R^{39}$ is hydrogen or methyl.

More embodiments relate to a compound of formula (III), or a pharmaceutically acceptable salt thereof, wherein $R^{40}$ is hydrogen or methyl.

More embodiments relate to a compound of formula (III), or a pharmaceutically acceptable salt thereof, wherein $R^{10}$ is hydrogen.

More embodiments relate to a compound of formula (III), or a pharmaceutically acceptable salt thereof, wherein $R^{10}$ is fluorine.

Some embodiments relate to a compound of formula (III), or a pharmaceutically acceptable salt thereof, wherein $R^{10}$ is methyl.

Some embodiments relate to a compound of formula (III), or a pharmaceutically acceptable salt thereof, wherein $R^9$ is fluorine and $R^{10}$ is fluorine.

Additional embodiments relate to a compound of formula (III), or a pharmaceutically acceptable salt thereof, wherein m is 2 and n is 2.

More embodiments relate to a compound of formula (III), or a pharmaceutically acceptable salt thereof, having formula (IIIa)

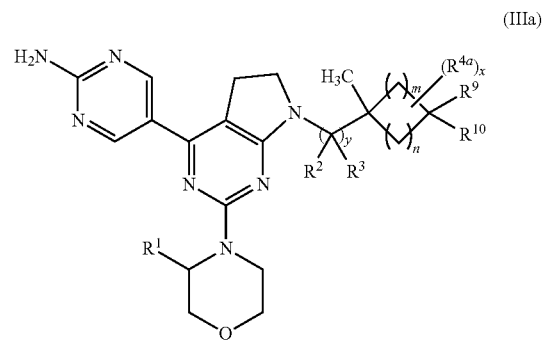

wherein
x is 0, 1, or 2.

More embodiments relate to a compound of formula (III), or a pharmaceutically acceptable salt thereof, having formula (IV):

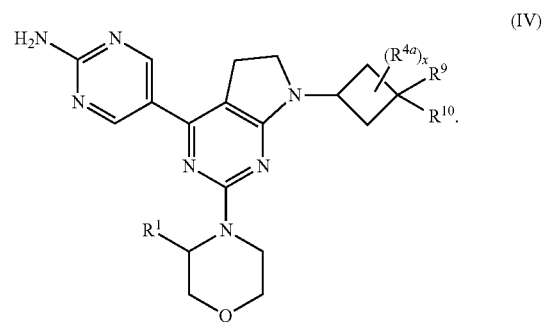

Further embodiments relate to a compound of formula (IV), or a pharmaceutically acceptable salt thereof, having formula (IVa):

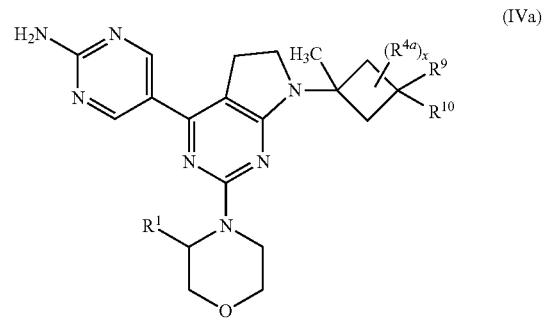

wherein
x is 0, 1, or 2.

More embodiments relate to a compound of formula (III), or a pharmaceutically acceptable salt thereof, having formula (V):

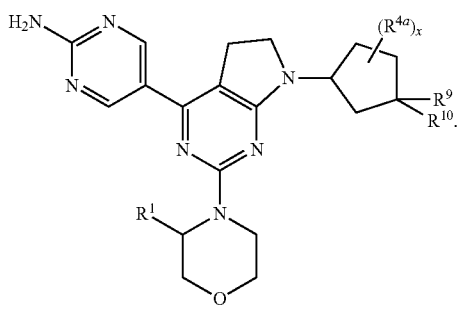

Further embodiments relate to a compound of formula (V), or a pharmaceutically acceptable salt thereof, having formula (Va):

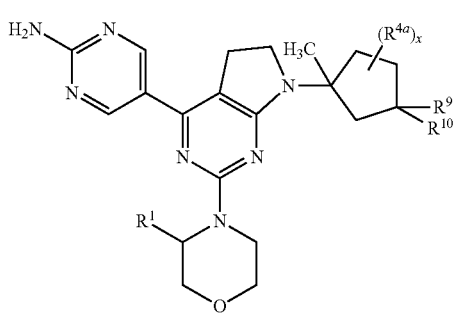

wherein
x is 0, 1, or 2.

Some embodiments described herein relate to a compound of formula (VI)

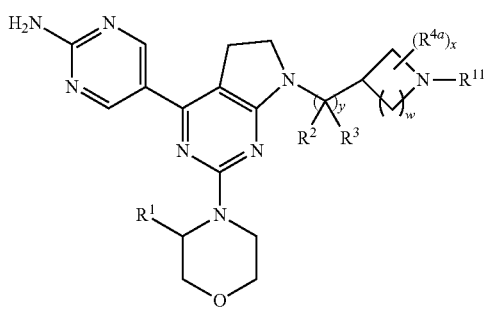

or a pharmaceutically acceptable salt thereof,
wherein
w is 1, 2, or 3;
$R^1$ is hydrogen, methyl, —$CH_2OH$, or —$CH_2F$;
y is 0 or 1;
$R^2$ is hydrogen, cyano, $C_1$-$C_3$ alkyl, or —$CF_3$;
$R^3$ is hydrogen or $C_1$-$C_3$ alkyl;
x is 0, 1, 2, 3, or 4;
each $R^{4a}$ is independently selected from the group consisting of fluorine, cyano, oxo, methyl, —$CH_2F$, $CHF_2$, —$CF_3$, —$CH_2OH$, hydroxy, and methoxy;
$R^{11}$ is hydrogen,
—$(CH_2)_p$—$C(O)R^{41}$,
—$(CH_2)_q$—$C(O)[N(R^{42})(R^{43})]$,
—$(CH_2)_r$—$C(O)OR^{44}$,
—$(CH_2)_s$—$S(O)_2R^{45}$,
—$(CH_2)_t$—$S(O)_2[N(R^{46})(R^{47})]$,
—$(CH_2)_u$—$R^{48}$, or
—$P(O)(CH_3)_2$;
p, q, r, s, t, and u are each independently 0 or 1;
$R^{41}$ is hydrogen, $C_1$-$C_4$ alkyl, $C_3$-$C_6$ cycloalkyl, 4-6 membered heterocycloalkyl, or 5 membered heteroaryl, wherein the $C_1$-$C_4$ alkyl, the $C_3$-$C_6$ cycloalkyl, and the 4-6 membered heterocycloalkyl are each independently optionally substituted by one, two, or three substituents selected from the group consisting of fluorine, cyano, oxo, $C_1$-$C_4$ alkyl, —$CH_2F$, —$CHF_2$, —$CF_3$, hydroxy, $C_1$-$C_4$ alkoxy, —$C(O)NH_2$, —$C(O)OH$, —$C(O)OCH_3$, —$NH_2$, —$NHCH_3$, —$N(CH_3)_2$, —$[N(R^{49})]$-$C(O)R^{50}$, $C_3$-$C_4$ cycloalkyl, and 4-5 membered heterocycloalkyl, further wherein the 5 membered heteroaryl is optionally substituted by one substituent selected from the group consisting of fluorine, cyano, hydroxy, methoxy, —$NH_2$, and —$NHCH_3$;

$R^{42}$ is hydrogen, $C_1$-$C_4$ alkyl, $C_3$-$C_4$ cycloalkyl, or 4-5 membered heterocycloalkyl;
$R^{43}$ is hydrogen or $C_1$-$C_4$ alkyl; or
$R^{42}$ and $R^{43}$ together with the nitrogen to which they are attached form a 4-5 membered heterocycloalkyl ring, wherein the 4-5 membered heterocycloalkyl ring formed is optionally substituted by one, two, or three substituents selected from the group consisting of fluorine, cyano, oxo, $C_1$-$C_4$ alkyl, hydroxy, and methoxy;
$R^{44}$ is $C_1$-$C_4$ alkyl, $C_3$-$C_4$ cycloalkyl, or 4-5 membered heterocycloalkyl, wherein the $C_1$-$C_4$ alkyl is optionally substituted by one, two, or three substituents selected from the group consisting of fluorine, cyano, hydroxy, methoxy, —$C(O)NH_2$, —$C(O)NHCH_3$, —$C(O)N(CH_3)_2$, —$NH$—$S(O)_2NH_2$, —$NH$—$S(O)_2NHCH_3$, and —$NH$—$S(O)_2N(CH_3)_2$, further wherein the $C_3$-$C_4$ cycloalkyl and the 4-5 membered heterocycloalkyl are each optionally substituted by one or two substituents selected from the group consisting of fluorine, cyano, methyl, hydroxy, methoxy, and —$C(O)CH_3$;
$R^{45}$ is $C_1$-$C_4$ alkyl, —$CF_3$, $C_1$-$C_4$ alkoxy, —$(CH_2)_v$—($C_3$-$C_4$ cycloalkyl), 4-5 membered heterocycloalkyl, or 5-6 membered heteroaryl, wherein the $C_1$-$C_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, $C_1$-$C_4$ alkyl, hydroxy, methoxy, —$C(O)(C_1$-$C_4$ alkyl), and —$C(O)[O$—($C_1$-$C_4$ alkyl)]$;
v is 0 or 1;
$R^{46}$ is hydrogen, $C_1$-$C_4$ alkyl, $C_3$-$C_4$ cycloalkyl, or 4-5 membered heterocycloalkyl;
$R^{47}$ is hydrogen or $C_1$-$C_4$ alkyl; or
$R^{46}$ and $R^{47}$ together with the nitrogen to which they are attached form a 4-5 membered heterocycloalkyl ring, wherein the 4-5 membered heterocycloalkyl ring formed is optionally substituted by one or two substituents selected from the group consisting of fluorine, cyano, $C_1$-$C_4$ alkyl, hydroxy, and methoxy;
$R^{48}$ is $C_1$-$C_4$ alkyl, $C_3$-$C_4$ cycloalkyl, or 4-6 membered heterocycloalkyl, wherein the $C_1$-$C_4$ alkyl is optionally substituted by one, two, or three substituents selected from the group consisting of fluorine, cyano, hydroxy, methoxy, —$C(O)NH_2$, —$C(O)NHCH_3$, —$C(O)N(CH_3)_2$, —$NH_2$, —$NHCH_3$, and —$N(CH_3)_2$, further wherein the $C_3$-$C_4$ cycloalkyl and the 4-6 membered heterocycloalkyl are each optionally substituted by one, two, three, or substituents selected from the group consisting of fluorine, cyano, methyl, hydroxy, methoxy, oxo, —$CF_3$, and —$C(O)CH_3$;

$R^{49}$ is hydrogen or methyl; and $R^{50}$ is $C_1$-$C_4$ alkyl, —$CF_3$, $C_1$-$C_4$ alkoxy, —$NH_2$, —$NHCH_3$, —$N(CH_3)_2$, $C_3$-$C_5$ cycloalkyl, or 4-6 membered heterocycloalkyl.

Further embodiments relate to a compound of formula (VI), or a pharmaceutically acceptable salt thereof, wherein $R^1$ is hydrogen or methyl.

Some embodiments relate to a compound of formula (VI), or a pharmaceutically acceptable salt thereof, wherein $R^1$ is hydrogen.

Additional embodiments relate to a compound of formula (VI), or a pharmaceutically acceptable salt thereof, wherein $R^1$ is methyl.

Additional embodiments relate to a compound of formula (VI), or a pharmaceutically acceptable salt thereof, wherein y is 0.

Some embodiments relate to a compound of formula (VI), or a pharmaceutically acceptable salt thereof, wherein x is 0.

More embodiments relate to a compound of formula (VI), or a pharmaceutically acceptable salt thereof, wherein x is 1.

More embodiments relate to a compound of formula (VI), or a pharmaceutically acceptable salt thereof, wherein each $R^{4a}$ is independently fluorine, methyl, —$CH_2F$, —$CHF_2$, —$CF_3$, hydroxy, or methoxy.

Some embodiments relate to a compound of formula (VI), or a pharmaceutically acceptable salt thereof, wherein each $R^{4a}$ is independently fluorine, methyl, —$CHF_{23}$ hydroxy, or methoxy.

Further embodiments relate to a compound of formula (VI), or a pharmaceutically acceptable salt thereof, wherein each $R^{4a}$ is independently methyl.

Further embodiments relate to a compound of formula (VI), or a pharmaceutically acceptable salt thereof, wherein $R^{11}$ is hydrogen.

More embodiments relate to a compound of formula (VI), or a pharmaceutically acceptable salt thereof, wherein $R^{11}$ is —$(CH_2)_p$—$C(O)R^{41}$.

Some embodiments relate to a compound of formula (VI), or a pharmaceutically acceptable salt thereof, wherein p is 0.

More embodiments relate to a compound of formula (VI), or a pharmaceutically acceptable salt thereof, wherein $R^{41}$ is hydrogen or $C_1$-$C_4$ alkyl, wherein the $C_1$-$C_4$ alkyl is optionally substituted by one substituent selected from the group consisting of hydroxy, $C_1$-$C_4$ alkoxy, and —$[N(R^{49})]$-$C(O)R^{50}$.

Some embodiments relate to a compound of formula (VI), or a pharmaceutically acceptable salt thereof, wherein $R^{41}$ is $C_1$-$C_4$ alkyl, optionally substituted by hydroxy.

Further embodiments relate to a compound of formula (VI), or a pharmaceutically acceptable salt thereof, wherein $R^{41}$ is methyl.

More embodiments relate to a compound of formula (VI), or a pharmaceutically acceptable salt thereof, wherein $R^{41}$ is methoxy.

Additional embodiments relate to a compound of formula (VI), or a pharmaceutically acceptable salt thereof, wherein $R^{41}$ is $C_1$-$C_4$ alkyl, optionally substituted by —$[N(R^{49})]$-$C(O)R^{50}$.

Additional embodiments relate to a compound of formula (VI), or a pharmaceutically acceptable salt thereof, wherein $R^{49}$ is hydrogen.

More embodiments relate to a compound of formula (VI), or a pharmaceutically acceptable salt thereof, wherein $R^{50}$ is $C_1$-$C_4$ alkyl.

Some embodiments relate to a compound of formula (VI), or a pharmaceutically acceptable salt thereof, wherein $R^{11}$ is —$(CH_2)_q$—$C(O)[N(R^{42})(R^{43})]$.

Some embodiments relate to a compound of formula (VI), or a pharmaceutically acceptable salt thereof, wherein q is 0.

More embodiments relate to a compound of formula (VI), or a pharmaceutically acceptable salt thereof, wherein $R^{42}$ is hydrogen or $C_1$-$C_4$ alkyl.

Further embodiments relate to a compound of formula (VI), or a pharmaceutically acceptable salt thereof, wherein $R^{43}$ is hydrogen.

More embodiments relate to a compound of formula (VI), or a pharmaceutically acceptable salt thereof, wherein $R^{11}$ is —$(CH_2)_r$—$C(O)OR^{44}$.

Further embodiments relate to a compound of formula (VI), or a pharmaceutically acceptable salt thereof, wherein r is 0.

Some embodiments relate to a compound of formula (VI), or a pharmaceutically acceptable salt thereof, wherein $R^{44}$ is $C_1$-$C_4$ alkyl or 4-5 membered heterocycloalkyl, wherein the $C_1$-$C_4$ alkyl is optionally substituted by one substituent selected from the group consisting of hydroxy, methoxy, —$C(O)NH_2$, —$C(O)NHCH_3$, —$C(O)N(CH_3)_2$, —NH—$S(O)_2NH_2$, —NH—$S(O)_2NHCH_3$, and —NH—$S(O)_2N(CH_3)_2$, further wherein the 4-5 membered heterocycloalkyl is optionally substituted by —$C(O)CH_3$.

Some embodiments relate to a compound of formula (VI), or a pharmaceutically acceptable salt thereof, wherein $R^{44}$ is $C_1$-$C_4$ alkyl optionally substituted by hydroxy.

Further embodiments relate to a compound of formula (VI), or a pharmaceutically acceptable salt thereof, wherein $R^{11}$ is —$(CH_2)_s$—$S(O)_2R^{45}$.

Additional embodiments relate to a compound of formula (VI), or a pharmaceutically acceptable salt thereof, wherein s is 0.

Additional embodiments relate to a compound of formula (VI), or a pharmaceutically acceptable salt thereof, wherein $R^{45}$ is $C_1$-$C_4$ alkyl, —$CF_3$, —$(CH_2)_v$—$(C_3$-$C_4$ cycloalkyl), or 4-5 membered heterocycloalkyl, wherein the $C_1$-$C_4$ alkyl is optionally substituted by methoxy, further wherein the 4-5 membered heterocycloalkyl is optionally substituted by one substituent selected from the group consisting of $C_1$-$C_4$ alkyl, —$C(O)(C_1$-$C_4$ alkyl), and —$C(O)[O$—$(C_1$-$C_4$ alkyl)]$.

More embodiments relate to a compound of formula (VI), or a pharmaceutically acceptable salt thereof, wherein $R^{45}$ is $C_1$-$C_4$ alkyl.

Some embodiments relate to a compound of formula (VI), or a pharmaceutically acceptable salt thereof, wherein $R^{45}$ is —$(CH_2)_v$—$(C_3$-$C_4$ cycloalkyl).

Some embodiments relate to a compound of formula (VI), or a pharmaceutically acceptable salt thereof, wherein v is 0.

More embodiments relate to a compound of formula (VI), or a pharmaceutically acceptable salt thereof, wherein $R^{11}$ is —$(CH_2)_t$—$S(O)_2[N(R^{46})(R^{47})]$. Additional embodiments relate to a compound of formula (VI), or a pharmaceutically acceptable salt thereof, wherein t is 0.

Additional embodiments relate to a compound of formula (VI), or a pharmaceutically acceptable salt thereof, wherein $R^{46}$ is hydrogen or $C_1$-$C_4$ alkyl.

Some embodiments relate to a compound of formula (VI), or a pharmaceutically acceptable salt thereof, wherein $R^{46}$ is hydrogen or methyl.

Some embodiments relate to a compound of formula (VI), or a pharmaceutically acceptable salt thereof, wherein $R^{47}$ is hydrogen or methyl.

Further embodiments relate to a compound of formula (VI), or a pharmaceutically acceptable salt thereof, wherein $R^{11}$ is —P(O)(CH$_3$)$_2$.

More embodiments relate to a compound of formula (VI), or a pharmaceutically acceptable salt thereof, wherein $R^{11}$ is —(CH$_2$)$_u$—R$^{48}$.

Further embodiments relate to a compound of formula (VI), or a pharmaceutically acceptable salt thereof, wherein $R^{48}$ is

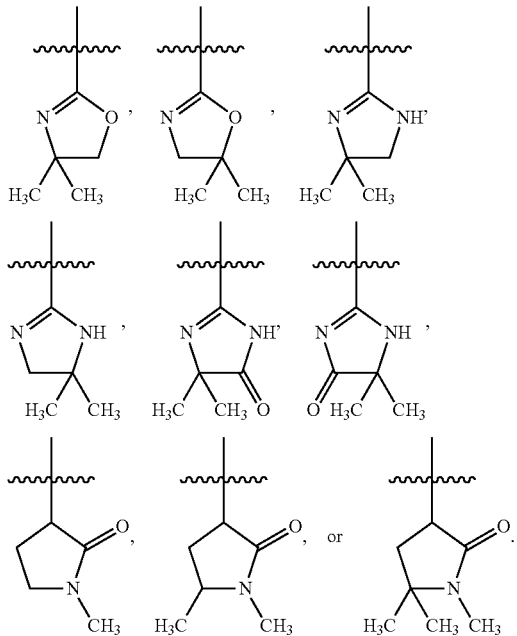

Some embodiments relate to a compound of formula (VI), or a pharmaceutically acceptable salt thereof, wherein w is 3.

Further embodiments relate to a compound of formula (VI), or a pharmaceutically acceptable salt thereof, having formula (VIa):

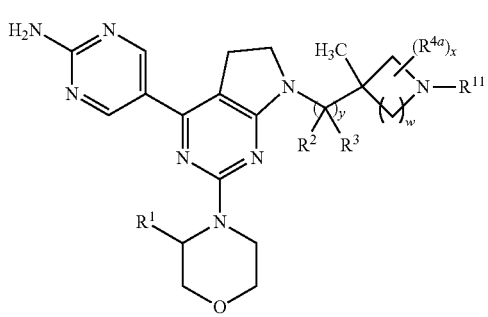

wherein x is 0, 1, or 2.

More embodiments relate to a compound of formula (VI), or a pharmaceutically acceptable salt thereof, having formula (VII):

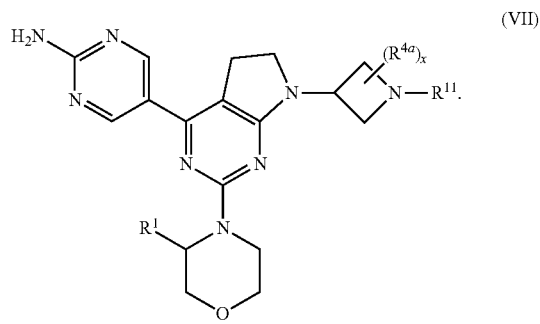

Further embodiments relate to a compound of formula (VII), or a pharmaceutically acceptable salt thereof, having formula (VIIa):

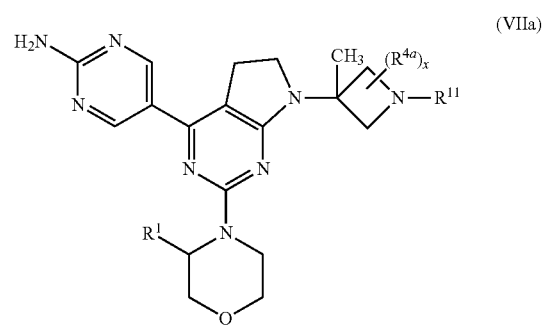

wherein x is 0, 1, or 2.

Further embodiments relate to a compound of formula (VI), having formula (VIII):

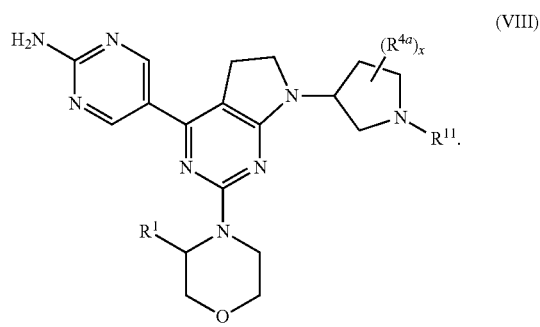

Further embodiments relate to a compound of formula (VIII), having formula (VIIIa):

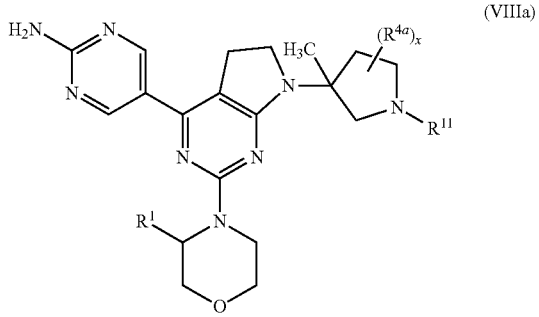

(VIIIa)

wherein
x is 0, 1, or 2.

An embodiment of the present invention relates to a compound of formula (X)

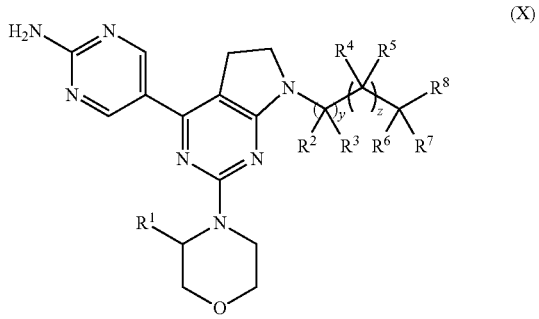

(X)

or a pharmaceutically acceptable salt thereof,
wherein
$R^1$ is hydrogen, methyl, —$CH_2OH$, or —$CH_2F$;
y is 0 or 1;
$R^2$ is hydrogen, cyano, $C_1$-$C_3$ alkyl, or —$CF_3$;
$R^3$ is hydrogen or $C_1$-$C_3$ alkyl;
z is 0 or 1;
$R^4$ is hydrogen, cyano, $C_1$-$C_3$ alkyl, —$CH_2F$, —$CHF_2$, —$CF_3$, —$CH_2CN$, —$CH_2OH$, hydroxy, or $C_1$-$C_3$ alkoxy, provided that $R^4$ is not hydroxy or $C_1$-$C_3$ alkoxy, when y is 0;
$R^5$ is hydrogen or $C_1$-$C_3$ alkyl; or
$R^4$ and $R^5$ combine to form a $C_3$-$C_4$ cycloalkyl ring, wherein a carbon atom in the $C_4$ cycloalkyl ring formed is optionally replaced with —NH— or —O—;
$R^6$ is hydrogen or $C_1$-$C_3$ alkyl;
$R^7$ is hydrogen or $C_1$-$C_3$ alkyl;
$R^8$ is hydrogen,
cyano,
—$CF_3$,
hydroxy,
$C_1$-$C_3$ alkoxy,
—$S(O)R^{18}$,
—$[N(R^{12})]_a$—$C(O)R^{19}$,
—$[N(R^{13})]_b$—$C(O)[N(R^2)(R^{21})]$,
—$[N(R^{14})]_d$—$C(O)OR^{22}$,
—$[N(R^{15})]_e$—$S(O)_2R^{23}$,
—$[N(R^{16})]_f$—$S(O)_2[N(R^{24})(R^{25})]$,
—$[N(R^{17})]_g$—$P(O)(CH_3)_2$, or
$R^8$ is $C_1$-$C_3$ alkyl and combines with $R^5$ to form a $C_3$-$C_8$ cycloalkyl ring, wherein a carbon atom of the $C_3$-$C_8$ cycloalkyl ring formed is —$C(R^9)(R^{10})$— or a carbon atom in the $C_3$-$C_8$ cycloalkyl ring formed is replaced with —$N(R^{11})$— or —O— to form a 4-8 membered heterocycloalkyl ring, further wherein the $C_3$-$C_8$ cycloalkyl and the 4-8 membered heterocycloalkyl rings formed may be optionally substituted by one, two, three, or four substituents selected from the group consisting of fluorine, cyano, oxo, $C_1$-$C_3$ alkyl, —$CH_2F$, —$CHF_2$, —$CF_3$, —$CH_2OH$, hydroxy, and methoxy;
$R^9$ is hydrogen,
fluorine,
cyano,
hydroxy,
$C_1$-$C_3$ alkoxy,
—$S(O)R^{32}$,
—O—$S(O)_2R^{33}$,
—$NH_2$,
—$NHCH_3$,
—$NH(CH_3)_2$,
—$[N(R^{26})]_h$—$C(O)R^{34}$,
—$[N(R^{27})]_i$—$C(O)[N(R^{35})(R^{36})]$,
—$[N(R^{28})]_j$—$C(O)OR^{37}$,
—$[N(R^{29})]_k$—$S(O)_2R^{38}$,
—$[N(R^{30})]_l$—$S(O)_2[N(R^{39})(R^{40})]$, or
—$[N(R^{31})]_o$—$P(O)(CH_3)_2$;
$R^{10}$ is hydrogen, fluorine, or $C_1$-$C_3$ alkyl;
$R^{11}$ is hydrogen,
—$(CH_2)_p$—$C(O)R^{41}$,
—$(CH_2)_q$—$C(Z)[N(R^{42})(R^{43})]$,
—$(CH_2)_r$—$C(O)OR^{44}$,
—$(CH_2)_s$—$S(O)_2R^{45}$,
—$(CH_2)_t$—$S(O)_2[N(R^{46})(R^{47})]$,
—$(CH_2)_u$—$R^{48}$, or
—$P(O)(CH_3)_2$;
$R^{12}$, $R^{13}$, $R^{14}$, $R^{15}$, $R^{16}$, $R^{17}$, $R^{26}$, $R^{27}$, $R^{28}$, $R^{29}$, $R^{30}$, and $R^{31}$ are each independently hydrogen or methyl;
a, b, d, e, f, g, h, i, j, k, l, o, p, q, r, s, t, and u are each independently 0 or 1;
Z is O or NH;
$R^{18}$ and $R^{32}$ are each independently $C_1$-$C_4$ alkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;
$R^{33}$ is $C_1$-$C_4$ alkyl, —$NH_2$, —$NHCH_3$, —$N(CH_3)_2$, or $C_3$-$C_5$ cycloalkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;
$R^{19}$, $R^{34}$, and $R^{41}$ are each independently hydrogen, $C_1$-$C_4$ alkyl, $C_3$-$C_6$ cycloalkyl, 4-6 membered heterocycloalkyl, or 5 membered heteroaryl, wherein the $C_1$-$C_4$ alkyl, the $C_3$-$C_6$ cycloalkyl, and the 4-6 membered heterocycloalkyl are each independently optionally substituted by one, two, or three substituents selected from the group consisting of fluorine, cyano, oxo, $C_1$-$C_4$ alkyl, —$CH_2OH$, —$CH_2NH_2$, —$CH_2F$, —$CHF_2$, —$CF_3$, hydroxy, $C_1$-$C_4$ alkoxy, —$C(O)NH_2$, —$C(O)OH$, —$C(O)O$—($C_1$-$C_4$ alkyl), —$NH_2$, —$NHCH_3$, —$N(CH_3)_2$, —$[N(R^{49})]$-$C(O)R^{50}$, $C_3$-$C_4$ cycloalkyl, and 4-5 membered heterocycloalkyl, further wherein the 5 membered heteroaryl is optionally substituted by one substituent selected from the group consisting of fluorine, cyano, hydroxy, methoxy, —$NH_2$, and —$NHCH_3$;
$R^{20}$, $R^{35}$, and $R^{42}$ are each independently hydrogen, $C_1$-$C_4$ alkyl, $C_3$-$C_4$ cycloalkyl, or 4-5 membered heterocycloalkyl;
$R^{21}$ is $C_1$-$C_4$ alkyl;
$R^{36}$ and $R^{43}$ are each independently hydrogen or $C_1$-$C_4$ alkyl; or
$R^{20}$ and $R^{21}$ together with the nitrogen to which they are attached, $R^{35}$ and $R^{36}$ together with the nitrogen to which they are attached, and $R^{42}$ and $R^{43}$ together with the nitrogen to which they are attached, each independently form a 4-5 membered heterocycloalkyl ring, wherein the 4-5 membered heterocycloalkyl ring formed is optionally substituted by one, two, or three substituents selected from the group consisting of fluorine, cyano, oxo, $C_1$-$C_4$ alkyl, hydroxy, and methoxy;

$R^{22}$, $R^{37}$, and $R^{44}$ are each independently $C_1$-$C_4$ alkyl, $C_3$-$C_4$ cycloalkyl, or —$(CH_2)_v$-(4-5 membered heterocycloalkyl), wherein the $C_1$-$C_4$ alkyl is optionally substituted by one, two, or three substituents selected from the group consisting of fluorine, cyano, hydroxy, methoxy, —$C(O)NH_2$, —$C(O)NHCH_3$, —$C(O)N(CH_3)_2$, —$NH_2$, —NH—$S(O)_2$$NH_2$, —NH—$S(O)_2NHCH_3$, and —NH—$S(O)_2N(CH_3)_2$, further wherein the $C_3$-$C_4$ cycloalkyl and the —$(CH_2)_v$-(4-5 membered heterocycloalkyl) are each optionally substituted by one or two substituents selected from the group consisting of fluorine, cyano, methyl, hydroxy, methoxy, and —C(O)$CH_3$;

$R^{23}$, $R^{38}$, and $R^{45}$ are each independently $C_1$-$C_4$ alkyl, —$CF_3$, $C_1$-$C_4$ alkoxy, —$(CH_2)_v$—($C_3$-$C_4$ cycloalkyl), 4-5 membered heterocycloalkyl, or 5-6 membered heteroaryl, wherein the $C_1$-$C_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, $C_1$-$C_4$ alkyl, hydroxy, methoxy, —C(O)($C_1$-$C_4$ alkyl), and —C(O)[O—($C_1$-$C_4$ alkyl)];

v is 0 or 1;

$R^{24}$, $R^{39}$, and $R^{46}$ are each independently hydrogen, $C_1$-$C_4$ alkyl, $C_3$-$C_4$ cycloalkyl, or 4-5 membered heterocycloalkyl;

$R^{25}$, $R^{40}$, and $R^{47}$ are each independently hydrogen or $C_1$-$C_4$ alkyl; or $R^{24}$ and $R^{25}$ together with the nitrogen to which they are attached, $R^{39}$ and $R^{40}$ together with the nitrogen to which they are attached, and $R^{46}$ and $R^{47}$ together with the nitrogen to which they are attached, each independently form a 4-5 membered heterocycloalkyl ring, wherein the 4-5 membered heterocycloalkyl ring formed is optionally substituted by one or two substituents selected from the group consisting of fluorine, cyano, $C_1$-$C_4$ alkyl, hydroxy, and methoxy;

$R^{48}$ is $C_1$-$C_4$ alkyl, $C_3$-$C_5$ cycloalkyl, or 4-6 membered heterocycloalkyl, wherein the $C_1$-$C_4$ alkyl is optionally substituted by one, two, or three substituents selected from the group consisting of fluorine, cyano, hydroxy, methoxy, —$C(O)OCH_3$, —$C(O)NH_2$, —$C(O)NHCH_3$, —$C(O)N(CH_3)_2$, —$NH_2$, —$NHCH_3$, and —$N(CH_3)_2$, further wherein the $C_3$-$C_5$ cycloalkyl and the 4-6 membered heterocycloalkyl are each optionally substituted by one, two, three, or four substituents selected from the group consisting of fluorine, cyano, methyl, hydroxy, methoxy, oxo, —$CF_3$, and —C(O)$CH_3$;

$R^{49}$ is hydrogen or methyl; and $R^{50}$ is $C_1$-$C_4$ alkyl, —$CF_3$, $C_1$-$C_4$ alkoxy, —$NH_2$, —$NHCH_3$, —$N(CH_3)_2$, $C_3$-$C_5$ cycloalkyl, or 4-6 membered heterocycloalkyl.

Some embodiments described herein relate to a compound of formula (XI)

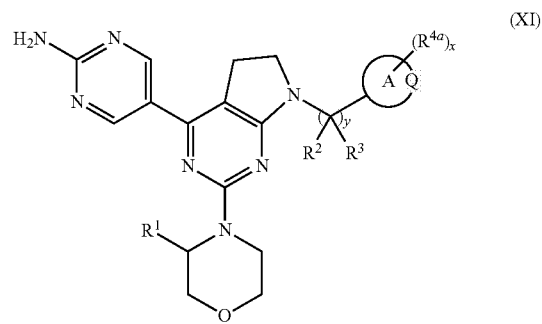

(XI)

or a pharmaceutically acceptable salt thereof,
wherein
$R^1$ is hydrogen, methyl, —$CH_2OH$, or —$CH_2F$;
y is 0 or 1;
$R^2$ is hydrogen, cyano, $C_1$-$C_3$ alkyl, or —$CF_3$;
$R^3$ is hydrogen or $C_1$-$C_3$ alkyl;
ring A is $C_3$-$C_8$ cycloalkyl or 4-8 membered heterocycloalkyl;
Q is —$C(R^9)(R^{10})$—, —$N(R^{11})$— or —O—;
x is 0, 1, 2, 3, or 4;
each $R^{4a}$ is independently selected from the group consisting of fluorine, cyano, oxo, $C_1$-$C_3$ alkyl, —$CH_2F$, —$CHF_2$, —$CF_3$, —$CH_2OH$, hydroxy, and methoxy;
$R^9$ is hydrogen,
fluorine,
cyano,
hydroxy,
$C_1$-$C_3$ alkoxy,
—$S(O)R^{32}$,
—O—$S(O)_2R^{33}$,
—$NH_2$,
—$NHCH_3$,
—$NH(CH_3)_2$,
—$[N(R^{26})]_h$—$C(O)R^{34}$,
—$[N(R^{27})]_i$—$C(O)[N(R^{35})(R^{36})]$,
—$[N(R^{28})]_j$—$C(O)OR^{37}$,
—$[N(R^{29})]_k$—$S(O)_2R^{38}$,
—$[N(R^{30})]_l$—$S(O)_2[N(R^{39})(R^{40})]$, or
—$[N(R^{31})]_o$—$P(O)(CH_3)_2$;
$R^{10}$ is hydrogen, fluorine, or $C_1$-$C_3$ alkyl;
$R^{11}$ is hydrogen,
—$(CH_2)_p$—$C(O)R^{41}$,
—$(CH_2)_q$—$C(Z)[N(R^{42})(R^{43})]$,
—$(CH_2)_r$—$C(O)OR^{44}$,
—$(CH_2)_s$—$S(O)_2R^{45}$,
—$(CH_2)_t$—$S(O)_2[N(R^{46})(R^{47})]$,
—$(CH_2)_u$—$R^{48}$, or
—$P(O)(CH_3)_2$,
$R^{26}$, $R^{27}$, $R^{28}$, $R^{29}$, $R^{30}$, and $R^{31}$ are each independently hydrogen or methyl;
h, i, j, k, l, o, p, q, r, s, t, and u are each independently 0 or 1;
Z is O or NH;
$R^{32}$ is $C_1$-$C_4$ alkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;
$R^{33}$ is $C_1$-$C_4$ alkyl, —$NH_2$, —$NHCH_3$, —$N(CH_3)_2$, or $C_3$-$C_5$ cycloalkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;

$R^{34}$ and $R^{41}$ are each independently hydrogen, $C_1$-$C_4$ alkyl, $C_3$-$C_6$ cycloalkyl, 4-6 membered heterocycloalkyl, or 5 membered heteroaryl, wherein the $C_1$-$C_4$ alkyl, the $C_3$-$C_6$ cycloalkyl, and the 4-6 membered heterocycloalkyl are each independently optionally substituted by one, two, or three substituents selected from the group consisting of fluorine, cyano, oxo, $C_1$-$C_4$ alkyl, —$CH_2OH$, —$CH_2NH_2$, —$CH_2F$, —$CHF_2$, —$CF_3$, hydroxy, $C_1$-$C_4$ alkoxy, —$C(O)NH_2$, —$C(O)OH$, —$C(O)O$—$(C_1$-$C_4$ alkyl), —$NH_2$, —$NHCH_3$, —$N(CH_3)_2$, —$[N(R^{49})]$-$C(O)R^{50}$, $C_3$-$C_4$ cycloalkyl, and 4-5 membered heterocycloalkyl, further wherein the 5 membered heteroaryl is optionally substituted by one substituent selected from the group consisting of fluorine, cyano, hydroxy, methoxy, —$NH_2$, and —$NHCH_3$;

$R^{35}$ and $R^{42}$ are each independently hydrogen, $C_1$-$C_4$ alkyl, $C_3$-$C_4$ cycloalkyl, or 4-5 membered heterocycloalkyl;

$R^{36}$ and $R^{43}$ are each independently hydrogen or $C_1$-$C_4$ alkyl; or $R^{35}$ and $R^{36}$ together with the nitrogen to which they are attached and $R^{42}$ and $R^{43}$ together with the nitrogen to which they are attached, each independently form a 4-5 membered heterocycloalkyl ring, wherein the 4-5 membered heterocycloalkyl ring formed is optionally substituted by one, two, or three substituents selected from the group consisting of fluorine, cyano, oxo, $C_1$-$C_4$ alkyl, hydroxy, and methoxy;

$R^{37}$ and $R^{44}$ are each independently $C_1$-$C_4$ alkyl, $C_3$-$C_4$ cycloalkyl, or —$(CH_2)_v$-(4-5 membered heterocycloalkyl), wherein the $C_1$-$C_4$ alkyl is optionally substituted by one, two, or three substituents selected from the group consisting of fluorine, cyano, hydroxy, methoxy, —$C(O)NH_2$, —$C(O)NHCH_3$, —$C(O)N(CH_3)_2$, —$NH_2$, —$NH$—$S(O)_2NH_2$, —$NH$—$S(O)_2NHCH_3$, and —$NH$—$S(O)_2N(CH_3)_2$, further wherein the $C_3$-$C_4$ cycloalkyl and the —$(CH_2)_v$-(4-5 membered heterocycloalkyl) are each optionally substituted by one or two substituents selected from the group consisting of fluorine, cyano, methyl, hydroxy, methoxy, and —$C(O)CH_3$;

$R^{38}$ and $R^{45}$ are each independently $C_1$-$C_4$ alkyl, —$CF_3$, $C_1$-$C_4$ alkoxy, —$(CH_2)_v$—$(C_3$-$C_4$ cycloalkyl), 4-5 membered heterocycloalkyl, or 5-6 membered heteroaryl, wherein the $C_1$-$C_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, $C_1$-$C_4$ alkyl, hydroxy, methoxy, —$C(O)(C_1$-$C_4$ alkyl), and —$C(O)[O$—$(C_1$-$C_4$ alkyl)]$;

v is 0 or 1;

$R^{39}$ and $R^{46}$ are each independently hydrogen, $C_1$-$C_4$ alkyl, $C_3$-$C_4$ cycloalkyl, or 4-5 membered heterocycloalkyl;

$R^{40}$ and $R^{47}$ are each independently hydrogen or $C_1$-$C_4$ alkyl; or $R^{39}$ and $R^{40}$ together with the nitrogen to which they are attached and $R^{46}$ and $R^{47}$ together with the nitrogen to which they are attached, each independently form a 4-5 membered heterocycloalkyl ring, wherein the 4-5 membered heterocycloalkyl ring formed is optionally substituted by one or two substituents selected from the group consisting of fluorine, cyano, $C_1$-$C_4$ alkyl, hydroxy, and methoxy;

$R^{48}$ is $C_1$-$C_4$ alkyl, $C_3$-$C_5$ cycloalkyl, or 4-6 membered heterocycloalkyl, wherein the $C_1$-$C_4$ alkyl is optionally substituted by one, two, or three substituents selected from the group consisting of fluorine, cyano, hydroxy, methoxy, —$C(O)OCH_3$, —$C(O)NH_2$, —$C(O)NHCH_3$, —$C(O)N(CH_3)_2$, —$NH_2$, —$NHCH_3$, and —$N(CH_3)_2$, further wherein the $C_3$-$C_5$ cycloalkyl and the 4-6 membered heterocycloalkyl are each optionally substituted by one, two, three, or four substituents selected from the group consisting of fluorine, cyano, methyl, hydroxy, methoxy, oxo, —$CF_3$, and —$C(O)CH_3$;

$R^{49}$ is hydrogen or methyl; and $R^{50}$ is $C_1$-$C_4$ alkyl, —$CF_3$, $C_1$-$C_4$ alkoxy, —$NH_2$, —$NHCH_3$, —$N(CH_3)_2$, $C_3$-$C_5$ cycloalkyl, or 4-6 membered heterocycloalkyl.

In some embodiments, a compound of the present invention is a compound provided in Table 1, 2, or 3, or a pharmaceutically acceptable salt thereof.

Some embodiments relate to a pharmaceutical composition comprising a compound of any of the embodiments of the compounds of formulas (I), (II), (III), (IIIa), (IV), (IVa) (V), (Va), (VI), (VIa), (VII), (VIIa), (VIII), or (VIIIa), or a pharmaceutically acceptable salt thereof, and a pharmaceutically acceptable carrier or diluent.

Additional embodiments relate to a pharmaceutical composition comprising a compound of any of the embodiments of the compounds of formulas (I), (II), (III), (IIIa), (IV), (IVa) (V), (Va), (VI), (VIa), (VII), (VIIa), (VIII), or (VIIIa), or a pharmaceutically acceptable salt thereof, with an anti-tumor agent or with radiation therapy, for the treatment of cancer.

Further embodiments relate to a pharmaceutical composition comprising a compound of any of the embodiments of the compounds of formulas (I), (II), (III), (IIIa), (IV), (IVa) (V), (Va), (VI), (VIa), (VII), (VIIa), (VIII), or (VIIIa), or a pharmaceutically acceptable salt thereof, with an anti-tumor agent, for the treatment of cancer.

More embodiments relate to a method of treating abnormal cell growth in a mammal comprising administering to the mammal an amount of a composition of any of the embodiments of the compounds of formulas (I), (II), (III), (IIIa), (IV), (IVa) (V), (Va), (VI), (VIa), (VII), (VIIa), (VIII), or (VIIIa), or a pharmaceutically acceptable salt thereof, that is effective in treating abnormal cell growth.

Further embodiments relate to a method of treating abnormal cell growth in a mammal comprising administering to the mammal an amount of a compound of any of the embodiments of the compounds of formulas (I), (II), (III), (IIIa), (IV), (IVa) (V), (Va), (VI), (VIa), (VII), (VIIa), (VIII), or (VIIIa), or a pharmaceutically acceptable salt thereof, that is effective in treating abnormal cell growth.

Additional embodiments relate to the method of treating abnormal cell growth, wherein the abnormal cell growth is cancer.

Further embodiments relate to the method of treating cancer, wherein the cancer is selected from the group consisting of basal cell cancer, medulloblastoma cancer, liver cancer, rhabdomyosarcoma, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system, primary central nervous system lymphoma, spinal axis tumors, brain stem glioma and pituitary adenoma, or a combination of one or more of the foregoing cancers.

Further embodiments relate to the method of treating lung cancer, wherein the cancer is selected from the group consisting of lung cancer, cancer of the head or neck, colon cancer, breast cancer, and ovarian cancer, or a combination of one or more of the foregoing cancers.

DETAILED DESCRIPTION OF THE INVENTION

The following abbreviations may be used herein: Boc (tert-butoxycarbonyl); CDI (1,1'-carbonyldiimidazole); DBU (1,8-diazabicyclo[5.4.0]undec-7-ene); DCM (dichloromethane); DIPEA (N,N-diisopropylethylamine); DMAP (4-dimethylaminopyridine); DMF (N,N-dimethylformamide); DMSO (dimethylsulfoxide); dppf (1,1'-bis(diphenylphosphanyl)ferrocene); DTT ((2S,3S)-1,4-bis(sulfanyl)butane-2,3-diol); EDCI (1-ethyl-3-(3-dimethylaminopropyl) carbodiimide); EDTA (2-({2-[bis(carboxymethyl)amino]ethyl}(carboxymethyl)amino)acetic acid); EtOH (ethanol); EtOAc (ethyl acetate); h (hour or hours); HATU (O-(7-azabenzotriazole-1-yl)-1,1,3,3-tetramethyluroniumhexafluorophosphate); HEPES (2-[4-(2-hydroxyethyl)piperazin-1-yl]ethanesulfonic acid); HPLC (high-performance liquid chromatography); LCMS (liquid chromatography-mass spectrometry); Me (methyl); min (minute or minutes); N (normal); N/A (not available); N/D (not determined); NMP (N-methyl-2-pyrrolidone); NMR (nuclear magnetic resonance); OMe (methoxy); phosgene (carbonyl dichloride); SEC (size exclusion chromatography); SFC (supercritical fluid chromatography); TCEP (tris(2-carboxyethyl)phosphine); THF (tetrahydrofuran); TMS-Cl (trimethylsilyl chloride); triphosgene (bis(trichloromethyl) carbonate); and Tris (tris(hydroxymethyl)aminomethane).

The term "halogen", as used herein, refers to a fluorine, chlorine, bromine, or iodine atom or fluoro, chloro, bromo, or iodo. Additionally, the term "halogen" refers to F, Cl, Br, or I. The terms fluorine, fluoro and F, for example, are understood to be equivalent herein.

The term "alkyl", as used herein, refers to a saturated monovalent hydrocarbon radical containing, in certain embodiments, from one to six, or from one to three carbon atoms, having straight or branched moieties. The term "$C_1$-$C_6$ alkyl" refers to an alkyl radical containing from one to six carbon atoms, having straight or branched moieties. The term "$C_1$-$C_6$ alkyl" includes within its definition the terms "$C_1$-$C_3$ alkyl" and "$C_1$-$C_4$ alkyl". Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. Alkyl groups may be substituted by one or more substituent at any substitutable position on the straight or branched alkyl moiety.

The term "alkenyl", as used herein, refers to a saturated monovalent hydrocarbon radical containing, in certain embodiments, from two to six carbon atoms having at least one carbon-carbon double bond. Alkenyl radicals include both straight and branched moieties. The term "$C_2$-$C_6$ alkenyl", refers to an alkenyl radical containing from two to six carbon atoms, having straight or branched moieties. The double bond may or may not be the point of attachment to another group. Alkenyl groups include, but are not limited to, ethenyl, 1-propenyl, 2-propenyl, 2-methyl-2-propenyl, butenyl, pentenyl, 3-hexenyl, and the like.

The term "alkoxy", as used herein, refers to an alkyl radical that is single bonded to an oxygen atom. The attachment point of an alkoxy radical to a molecule is through the oxygen atom. An alkoxy radical may be depicted as alkyl-O—. The term "$C_1$-$C_6$ alkoxy", refers to an alkoxy radical containing from one to six carbon atoms, having straight or branched moieties. The term "$C_1$-$C_6$ alkoxy" includes within its definition the term "$C_1$-$C_3$ alkoxy". Alkoxy groups, include, but are not limited to, methoxy, ethoxy, propoxy, isopropoxy, butoxy, hexyloxy, and the like.

The term "cycloalkyl", as used herein, refers to a non-aromatic, monocyclic, fused or bridged bicyclic or tricyclic carbocyclic ring group containing, in certain embodiments, from three to ten carbon atoms. As used herein, a cycloalkyl group may optionally contain one or two double bonds. The term "cycloalkyl" also includes spiro cycloalkyl groups, including multi-ring systems joined by a single atom. The terms "$C_3$-$C_{10}$ cycloalkyl", "$C_3$-$C_8$ cycloalkyl", "$C_3$-$C_6$ cycloalkyl", "$C_3$-$C_5$ cycloalkyl", "$C_3$-$C_4$ cycloalkyl", and "$C_5$-$C_7$ cycloalkyl" contain from three to ten, from three to seven, from three to six, from three to five, from three to four, and from five to seven carbon atoms, respectively. Cycloalkyl groups include, but are not limited to, cyclopropyl, cyclobutyl, cyclopentyl, cyclohexyl, cycloheptyl, cyclopentenyl, cyclohexenyl, octahydropentalenyl, octahydro-1H-indenyl, bicyclo[1.1.1]pent-1-yl, bicyclo[2.2.1]heptanyl, bicyclo[3.2.1]octanyl, bicyclo[5.2.0]nonanyl, adamantanyl, and the like.

The term "heterocycloalkyl", as used herein, refers to a non-aromatic, monocyclic, fused or bridged bicyclic or tricyclic, or spirocyclic ring group containing, in certain embodiments, a total of three to ten ring atoms, in which one to four ring atoms are heteroatoms independently selected from nitrogen, oxygen, and sulfur, and wherein the sulfur atom may be optionally oxidized with one or two oxygen atoms, the remaining ring atoms being carbon, with the proviso that such ring systems may not contain two adjacent oxygen atoms or two adjacent sulfur atoms. The heterocycloalkyl ring may also be substituted by an oxo (=O) group at any available carbon atom. The rings may also have one or more double bonds. Furthermore, such groups may be bonded to the remainder of the compounds of embodiments disclosed herein through either a carbon atom or a heteroatom, if possible. The terms "3-10 membered heterocycloalkyl", "3-7 membered heterocycloalkyl", "4-8 membered heterocycloalkyl", "4-6 membered heterocycloalkyl" and "4-5 membered heterocycloalkyl" contain from three to ten, from three to seven, from four to eight, from four to six carbon atoms, and from four to five carbons, respectively. Examples of saturated heterocycloalkyl groups include, but are not limited to:

Examples of suitable partially unsaturated heterocycloalkyl groups include, but are not limited to:

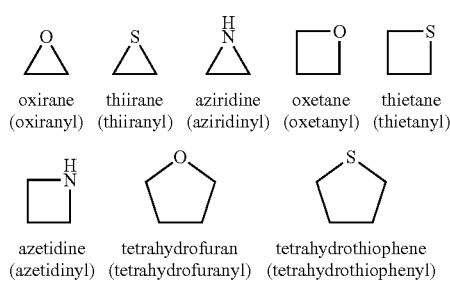

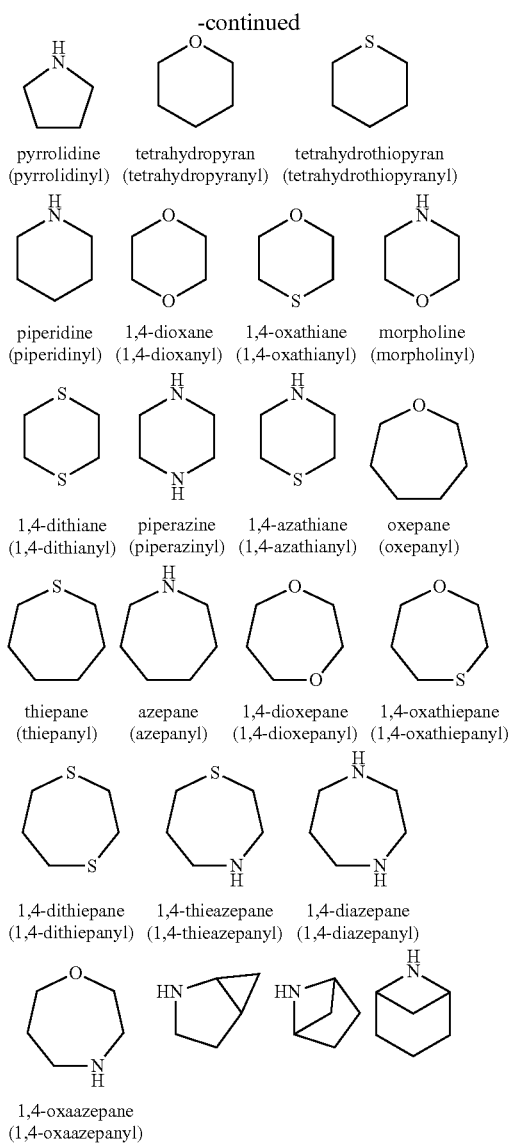

The term "aryl", as used herein, refers to a group derived from an aromatic hydrocarbon containing in certain embodiments, from six to ten carbon atoms. The term "$C_6$-$C_{10}$ aryl" contains from six to ten carbon atoms. Examples of such groups include, but are not limited to, phenyl and naphthyl. The term "aryl" also includes fused polycyclic aromatic ring systems in which an aromatic ring is fused to one or more rings. Examples include, but are not limited to, 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl, or tetrahydronaphthyl, where the radical or point of attachment is on the aromatic ring.

The term "heteroaryl, as used herein, refers to an aromatic monocyclic or bicyclic heterocyclic group having a total of from 5 to 12 atoms in its ring, and containing from 2 to 9 carbon atoms and from one to four heteroatoms each independently selected from nitrogen, oxygen, and sulfur, with the proviso that the ring of said group does not contain two adjacent oxygen atoms or two adjacent sulfur atoms. The terms "5-12 membered heteroaryl", "5-6 membered heteroaryl", "4-6 membered heteroaryl", and "3-5 membered heteroaryl" contain from five to twelve, contain from five to six, from four to six ring atoms, and from three to five ring atoms, respectively. The heteroaryl groups include benzo-fused ring systems. Examples of heteroaryl groups include, but are not limited to, pyrrolyl, furyl, thienyl, imidazolyl, pyrazolyl, oxazolyl, isoxazolyl, isothiazolyl, triazolyl, oxadiazolyl, furazanyl, thiadiazolyl, thiazolyl, tetrazolyl, pyridinyl, pyrazinyl, pyrimidinyl, pyridazinyl, triazinyl, indolyl, isoindolyl, indolizinyl, benzofuranyl, benzothiophenyl, indazolyl, benzimidazolyl, benzoxazolyl, furo[3,2-b]pyridinyl, benzothiazolyl, benzofurazanyl, purinyl, quinolinyl, isoquinolinyl, quinazolinyl, quinoxalinyl, naphthyridinyl, cinnolinyl, phthalazinyl, pyrido[3,4-d]pyrimidinyl, pteridinyl, and the like.

Also included within the scope of the term "5-12 membered heteroaryl", as used herein, are benzo-fused unsaturated nitrogen heterocycles, which refer to a heterocyclic group in which a heteroatomic ring is fused to one or more aromatic rings. Examples include, but are not limited to, indolinyl, isoindolinyl, tetrahydroquinolinyl, tetrahydroisoquinolinyl, and the like.

The term "reversing", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

As used herein, an "effective" amount refers to an amount of a substance, agent, compound, or composition that is of sufficient quantity to result in a decrease in severity of disease symptoms, an increase in frequency and duration of disease symptom-free periods, or a prevention of impairment or disability due to the disease affliction—either as a single dose or according to a multiple dose regimen, alone or in combination with other agents or substances. One of ordinary skill in the art would be able to determine such amounts based on such factors as the subject's size, the severity of the subject's symptoms, and the particular composition or route of administration selected. The subject may be a human or non-human mammal (e.g., rabbit, rat, mouse, monkey or other lower-order primate).

Embodiments disclosed herein include isotopically-labeled compounds, which are identical to those recited in formulas (I), (II), (III), (IIIa), (IV), (IVa) (V), (Va), (VI), (VIa), (VII), (VIIa), (VIII), (VIIIa), (X) or (XI) but for the fact that one or more atoms are replaced by an atom having an atomic mass or mass number different from the atomic mass or mass number usually found in nature. Examples of isotopes that can be incorporated into compounds of the embodiments disclosed herein include isotopes of hydrogen, carbon, nitrogen, oxygen, phosphorous, sulfur, fluorine and chlorine, such as, but not limited to, $^2$H, $^3$H, $^{13}$O, $^{14}$O, $^{15}$N, $^{18}$O, $^{17}$O, $^{31}$P, $^{32}$P, $^{35}$S, $^{18}$F, and $^{36}$Cl, respectively. Compounds described herein and pharmaceutically acceptable salts of said compounds which contain the aforementioned isotopes and/or other isotopes of other atoms are within the scope of the present embodiments. Certain isotopically-labeled compounds of the embodiments disclosed herein, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example, increased in vivo half-life or reduced dosage requirements and, hence, may be preferred in some circumstances. Isotopically-labeled compounds of embodiments disclosed herein can generally be prepared by carrying out the procedures disclosed in the Schemes and/or in the Examples and Preparations below, by substituting a readily available isotopically-labeled reagent for a non-isotopically-labeled reagent.

Some embodiments relate to the pharmaceutically acceptable salts of the compounds described herein. Pharmaceutically acceptable salts of the compounds described herein include the acid addition and base addition salts thereof.

Some embodiments also relate to the pharmaceutically acceptable acid addition salts of the compounds described herein. Suitable acid addition salts are formed from acids which form non-toxic salts. Non-limiting examples of suitable acid addition salts, i.e., salts containing pharmacologically acceptable anions, include, but are not limited to, the acetate, acid citrate, adipate, aspartate, benzoate, besylate, bicarbonate/carbonate, bisulphate/sulphate, bitartrate, borate, camsylate, citrate, cyclamate, edisylate, esylate, ethanesulfonate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methanesulfonate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, p-toluenesulfonate, tosylate, trifluoroacetate and xinofoate salts.

Additional embodiments relate to base addition salts of the compounds described herein. Suitable base addition salts are formed from bases which form non-toxic salts. Non-limiting examples of suitable base salts include the aluminium, arginine, benzathine, calcium, choline, diethylamine, diolamine, glycine, lysine, magnesium, meglumine, olamine, potassium, sodium, tromethamine and zinc salts.

The compounds described herein that are basic in nature are capable of forming a wide variety of salts with various inorganic and organic acids. The acids that may be used to prepare pharmaceutically acceptable acid addition salts of such basic compounds described herein are those that form non-toxic acid addition salts, e.g., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds described herein that include a basic moiety, such as an amino group, may form pharmaceutically acceptable salts with various amino acids, in addition to the acids mentioned above.

The chemical bases that may be used as reagents to prepare pharmaceutically acceptable base salts of those compounds of the compounds described herein that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of the embodiments described herein include all stereoisomers (e.g., cis and trans isomers) and all optical isomers of compounds described herein (e.g., R and S enantiomers), as well as racemic, diastereomeric and other mixtures of such isomers. While all stereoisomers are encompassed within the scope of our claims, one skilled in the art will recognize that particular stereoisomers may be preferred.

In some embodiments, the compounds described herein can exist in several tautomeric forms, including the enol and imine form, and the keto and enamine form and geometric isomers and mixtures thereof. All such tautomeric forms are included within the scope of the present embodiments. Tautomers exist as mixtures of a tautomeric set in solution. In solid form, usually one tautomer predominates. Even though one tautomer may be described, the present embodiments includes all tautomers of the present compounds.

The present embodiments also include atropisomers of the compounds described herein. Atropisomers refer to compounds that can be separated into rotationally restricted isomers.

Hemisalts of acids and bases may also be formed, for example, hemisulphate and hemicalcium salts.

For a review on suitable salts, see Handbook of Pharmaceutical Salts: Properties, Selection, and Use by Stahl and Wermuth (Wiley-VCH, 2002). Methods for making pharmaceutically acceptable salts of compounds described herein are known to one of skill in the art.

The term "solvate" is used herein to describe a molecular complex comprising a compound described herein and one or more pharmaceutically acceptable solvent molecules, for example, ethanol.

The compounds described herein may also exist in unsolvated and solvated forms. Accordingly, some embodiments relate to the hydrates and solvates of the compounds described herein.

Compounds described herein containing one or more asymmetric carbon atoms can exist as two or more stereoisomers. Where a compound described herein contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds described herein containing, for example, an imino, keto, or oxime group, or so-called valence tautomerism in compounds which contain an aromatic moiety. A single compound may exhibit more than one type of isomerism.

Included within the scope of the present embodiments are all stereoisomers, geometric isomers and tautomeric forms of the compounds described herein, including compounds exhibiting more than one type of isomerism, and mixtures of one or more thereof. Also included within the scope of the present embodiments are rotational isomers (rotamers). For example, certain compounds, including certain amides and carbamates are rotational isomers by 1H NMR at room temperature. The rotamer peaks coalesce if an NMR is taken at 80° C. Further included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or SFC.

Alternatively, the racemate (or a racemic precursor) may be reacted with a suitable optically active compound, for example, an alcohol, or, in the case where a compound described herein contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

Further embodiments relate to methods of treating abnormal cell growth in a mammal. Additional embodiments relate to a method of treating abnormal cell growth in a mammal comprising administering to the mammal an amount of a compound described herein that is effective in treating abnormal cell growth.

In other embodiments, the abnormal cell growth is cancer.

In some embodiments, the cancer is selected from the group consisting of lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of two or more of the foregoing cancers.

Additional embodiments relate to methods of treating cancer solid tumors in a mammal. Some embodiments relate to the treatment of cancer solid tumor in a mammal comprising administering to the mammal an amount of a compound described herein that is effective in treating said cancer solid tumor.

In other embodiments, the cancer solid tumor is breast, lung, colon, brain, prostate, stomach, pancreatic, ovarian, skin (melanoma), endocrine, uterine, testicular, or bladder.

Further embodiments relate to methods of treating abnormal cell growth in a mammal which comprises administering to said mammal an amount of a compound described herein that is effective in treating abnormal cell growth in combination with an anti-tumor agent selected from the group consisting of mitotic inhibitors, alkylating agents, anti-metabolites, intercalating antibiotics, growth factor inhibitors, radiation, cell cycle inhibitors, enzymes, topoisomerase inhibitors, biological response modifiers, antibodies, cytotoxics, anti-hormones, and anti-androgens.

More embodiments relate to pharmaceutical compositions for treating abnormal cell growth in a mammal comprising an amount of a compound described herein that is effective in treating abnormal cell growth, and a pharmaceutically acceptable carrier.

Additional embodiments relate to a method of treating abnormal cell growth in a mammal, including a human, comprising administering to the mammal an amount of a compound described herein, or a pharmaceutically acceptable salt, solvate, hydrate or prodrug thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In one embodiment the method comprises comprising administering to a mammal an amount of a compound described herein that is effective in treating said cancer solid tumor. In one preferred embodiment the solid tumor is breast, lung, colon, brain, prostate, stomach, pancreatic, ovarian, skin (melanoma), endocrine, uterine, testicular, and bladder cancer.

In another embodiment of said method, said abnormal cell growth is a benign proliferative disease, including, but not limited to, psoriasis, benign prostatic hypertrophy or restinosis.

Some embodiments relate to a method of treating abnormal cell growth in a mammal which comprises administering to said mammal an amount of a compound described herein, or a pharmaceutically acceptable salt, solvate, hydrate or prodrug thereof, that is effective in treating abnormal cell growth in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, and anti-androgens.

Additional embodiments relate to a pharmaceutical composition for treating abnormal cell growth in a mammal, including a human, comprising an amount of a compound described herein, or a pharmaceutically acceptable salt, solvate, hydrate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

Further embodiments relate to a method of treating abnormal cell growth in a mammal which comprises administering to said mammal an amount of a compound described herein, or a pharmaceutically acceptable salt, solvate, or hydrate thereof, that is effective in treating abnormal cell growth in combination with another anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, anti-hormones, and anti-androgens. Some embodiments contemplate a pharmaceutical composition for treating abnormal cell growth wherein the composition includes a compound described herein, or a pharmaceutically acceptable salt, solvate, or hydrate thereof, that is effective in treating abnormal cell growth, and another anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, anti-hormones, and anti-androgens.

Yet more embodiments relate to a method of treating a disorder associated with angiogenesis in a mammal, including a human, comprising administering to said mammal an amount of a compound described herein, as defined above, or a pharmaceutically acceptable salt, solvate, hydrate or prodrug thereof, that is effective in treating said disorder in combination with one or more anti-tumor agents listed above. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

Some embodiments relate to a method of (and to a pharmaceutical composition for) treating abnormal cell growth in a mammal which comprise an amount of a compound described herein, or a pharmaceutically acceptable salt, solvate, or hydrate thereof, in combination with an amount of one or more substances selected from anti-angiogenesis agents, signal transduction inhibitors inhibitor (e.g., inhibiting the means by which regulatory molecules that govern the fundamental processes of cell growth, differentiation, and survival communicated within the cell), and antiproliferative agents, which amounts are together effective in treating said abnormal cell growth.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound described herein in the methods and pharmaceutical compositions described herein. Examples of useful COX-inhibitors include CELEBREX™ (celecoxib), Bextra (valdecoxib), paracoxib, Vioxx (rofecoxib), and Arcoxia (etoricoxib). Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in combination with the compounds described herein are AG-3340, RO 32-3555, RS 13-0830, and the following compounds:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxamide; and 3-[4-(4-fluoro-phenoxy)-benzenesulfonylamino]-tetrahydro-furan-3-carboxylic acid hydroxyamide;

and pharmaceutically acceptable salts and solvates of said compounds.

VEGF inhibitors, for example, sutent and axitinib, can also be combined with a compound described herein. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are 1M862 (Cytran Inc. of Kirkland, Wash., USA); Avastin, an anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound described herein. Such erbB2 inhibitors include Herceptin, 2C4, and pertuzumab. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the embodiments described herein are also described in U.S. Provisional Application No. 60/117,341, filed Jan. 27, 1999, and in U.S. Provisional Application No. 60/117,346, filed Jan. 27, 1999, both of which are herein incorporated by reference in their entirety. Other erbb2 receptor inhibitors include TAK-165 (Takeda) and GW-572016 (Glaxo-Wellcome).

Various other compounds, such as styrene derivatives, have also been shown to possess tyrosine kinase inhibitory properties, and some of tyrosine kinase inhibitors have been identified as erbB2 receptor inhibitors. More recently, five European patent publications, namely EP 0 566 226 A1 (published Oct. 20, 1993), EP 0 602 851 A1 (published Jun. 22, 1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997), WO 98/02434 (published Jan. 22, 1998), WO 98/02437 (published Jan. 22, 1998), and WO 98/02438 (published Jan. 22, 1998), also refer to substituted bicyclic heteroaromatic derivatives as tyrosine kinase inhibitors that are useful for the same purpose. Other patent applications that refer to anti-cancer compounds are World Patent Application WO00/44728 (published Aug. 3, 2000), EP 1029853A1 (published Aug. 23, 2000), and WO01/98277 (published Dec. 12, 2001) all of which are incorporated herein by reference in their entirety.

Epidermal growth factor receptor (EGFR) inhibitors may be administered in combination with a compound of the presentation invention. Such EGFR inhibitors include gefinitib, erlotinib, icotinib, afatinib and dacomitinib. Monoclonal antibody inhibitors of EGFR, such as cetuximab, may also be combined with a compound of the present invention.

PI3K inhibitors, such as PI3K beta inhibitors, may be administered in combination with a compound of the presentation invention.

Mammalian target of rapamycin (mTOR) inhibitors may be administered in combination with a compound of the presentation invention. Such mTOR inhibitors include rapamycin analogs and ATP competitive inhibitors.

c-Met inhibitors may be administered in combination with a compound of the presentation invention. Such c-Met inhibitors include crizotinib and ARQ-197. Monoclonal antibody inhibitors of c-Met, such as METMab, may also be combined with a compound of the present invention.

CDK inhibitors may be administered in combination with a compound of the presentation invention. Such CDK inhibitors include palbociclib.

MEK inhibitors may be administered in combination with a compound of the presentation invention. Such MEK inhibitors include PD-325901.

PARP inhibitors may be administered in combination with a compound of the presentation invention.

JAK inhibitors may be administered in combination with a compound of the presentation invention.

An antagonist of a Programmed Death 1 protein (PD-1) may be administered in combination with a compound of the presentation invention.

Other antiproliferative agents that may be used with the compounds described herein include inhibitors of the enzyme farnesyl protein transferase and inhibitors of the receptor tyrosine kinase PDGFr, including the compounds disclosed and claimed in the following U.S. patent application Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following U.S. provisional patent applications 60/168,207 (filed Nov. 30, 1999); 60/170,119 (filed Dec. 10, 1999); 60/177,718 (filed Jan. 21, 2000); 60/168,217 (filed Nov. 30, 1999), and 60/200834 (filed May 1, 2000). Each of the foregoing patent applications and provisional patent applications is herein incorporated by reference in their entirety.

A compound described herein may also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present embodiments include those described in U.S. Provisional Application 60/113,647 (filed Dec. 23, 1998) which is herein incorporated by reference in its entirety.

A compound described herein may be applied as a sole therapy or may involve one or more other anti-tumor substances, for example those selected from, for example, mitotic inhibitors, for example vinblastine; alkylating agents, for example cis-platin, oxaliplatin, carboplatin and cyclophosphamide; anti-metabolites, for example 5-fluorouracil, capecitabine, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex (tamoxifen) or, for example anti-androgens such as Casodex (4'-cyano-3-(4-fluorophenylsulphonyl)-2-hydroxy-2-methyl-3'-(trifluoromethyl)propionanilide).

The compounds described herein may be used alone or in combination with one or more of a variety of anti-cancer agents or supportive care agents. For example, the compounds described herein may be used with cytotoxic agents, e.g., one or more selected from the group consisting of a camptothecin, irinotecan HCl (Camptosar), edotecarin, SU-11248, epirubicin (Ellence), docetaxel (Taxotere), paclitaxel, rituximab (Rituxan) bevacizumab (Avastin), imatinib mesylate (Gleevac), Erbitux, gefitinib (Iressa), and combinations thereof. Some embodiments also contemplate the use of the compounds described herein together with hormonal therapy, e.g., exemestane (Aromasin), Lupron, anastrozole (Arimidex), tamoxifen citrate (Nolvadex), Trelstar, and combinations thereof. Further, some embodiments provide a compound described herein alone or in combination with one or more supportive care products, e.g., a product selected from the group consisting of Filgrastim (Neupogen), ondansetron (Zofran), Fragmin, Procrit, Aloxi, Emend, or combinations thereof. Such conjoint treatment may be achieved by way of the simultaneous, sequential or separate dosing of the individual components of the treatment.

The compounds described herein may be used with anti-tumor agents, alkylating agents, antimetabolites, antibiotics, plant-derived antitumor agents, camptothecin derivatives, tyrosine kinase inhibitors, antibodies, interferons, and/or biological response modifiers. In this regard, the following is a non-limiting list of examples of secondary agents that may be used with the compounds described herein.

Alkylating agents include, but are not limited to, nitrogen mustard N-oxide, cyclophosphamide, ifosfamide, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, ifosfamide, KW-2170, mafosfamide, and mitolactol; platinum-coordinated alkylating compounds include but are not limited to, cisplatin, carboplatin, eptaplatin, lobaplatin, nedaplatin, oxaliplatin or satrplatin.

Antimetabolites include but are not limited to, methotrexate, 6-mercaptopurine riboside, mercaptopurine, 5-fluorouracil (5-FU) alone or in combination with leucovorin, tegafur, UFT, doxifluridine, carmofur, cytarabine, cytarabine ocfosfate, enocitabine, S-1, gemcitabine, fludarabin, 5-azacitidine, capecitabine, cladribine, clofarabine, decitabine, eflornithine, ethynylcytidine, cytosine arabinoside, hydroxyurea, TS-1, melphalan, nelarabine, nolatrexed, ocfosfate, disodium premetrexed, pentostatin, pelitrexol, raltitrexed, triapine, trimetrexate, vidarabine, vincristine, vinorelbine; or for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid.

Antibiotics include but are not limited to: aclarubicin, actinomycin D, amrubicin, annamycin, bleomycin, daunorubicin, doxorubicin, elsamitrucin, epirubicin, galarubicin, idarubicin, mitomycin C, nemorubicin, neocarzinostatin, peplomycin, pirarubicin, rebeccamycin, stimalamer, streptozocin, valrubicin or zinostatin.

Hormonal therapy agents, e.g., exemestane (Aromasin), Lupron, anastrozole (Arimidex), doxercalciferol, fadrozole, formestane, anti-estrogens such as tamoxifen citrate (Nolvadex) and fulvestrant, Trelstar, toremifene, raloxifene, lasofoxifene, letrozole (Femara), or anti-androgens such as bicalutamide, flutamide, mifepristone, nilutamide, Casodex® (4'-cyano-3-(4-fluorophenylsulphonyl)-2-hydroxy-2-methyl-3'-(trifluoromethyl)propionanilide) and combinations thereof.

Plant derived anti-tumor substances include for example those selected from mitotic inhibitors, for example vinblastine, docetaxel (Taxotere) and paclitaxel.

Cytotoxic topoisomerase inhibiting agents include one or more agents selected from the group consisting of aclarubicn, amonafide, belotecan, camptothecin, 10-hydroxycamptothecin, 9-aminocamptothecin, diflomotecan, irinotecan HCl (Camptosar), edotecarin, epirubicin (Ellence), etoposide, exatecan, gimatecan, lurtotecan, mitoxantrone, pirarubicin, pixantrone, rubitecan, sobuzoxane, SN-38, tafluposide, and topotecan, and combinations thereof.

Immunologicals include interferons and numerous other immune enhancing agents. Interferons include interferon alpha, interferon alpha-2a, interferon, alpha-2b, interferon beta, interferon gamma-1a or interferon gamma-n1. Other agents include PF3512676, filgrastim, lentinan, sizofilan, TheraCys, ubenimex, WF-10, aldesleukin, alemtuzumab, BAM-002, dacarbazine, daclizumab, denileukin, gemtuzumab ozogamicin, ibritumomab, imiquimod, lenograstim, lentinan, melanoma vaccine (Corixa), molgramostim, OncoVAX-CL, sargramostim, tasonermin, tecleukin, thymalasin, tositumomab, Virulizin, Z-100, epratuzumab, mitumomab, oregovomab, pemtumomab, Provenge.

Biological response modifiers are agents that modify defense mechanisms of living organisms or biological responses, such as survival, growth, or differentiation of tissue cells to direct them to have anti-tumor activity. Such agents include krestin, lentinan, sizofiran, picibanil, or ubenimex.

Other anticancer agents include alitretinoin, ampligen, atrasentan bexarotene, bortezomib. Bosentan, calcitriol, exisulind, finasteride,fotemustine, ibandronic acid, miltefosine, mitoxantrone, l-asparaginase, procarbazine, dacarbazine, hydroxycarbamide, pegaspargase, pentostatin, tazarotne, TLK-286, Velcade, Tarceva, or tretinoin.

Other anti-angiogenic compounds include acitretin, fenretinide, thalidomide, zoledronic acid, angiostatin, aplidine, cilengtide, combretastatin A-4, endostatin, halofuginone, rebimastat, removab, Revlimid, squalamine, ukrain and Vitaxin.

Platinum-coordinated compounds include but are not limited to, cisplatin, carboplatin, nedaplatin, or oxaliplatin.

Camptothecin derivatives include but are not limited to camptothecin, 10-hydroxycamptothecin, 9-aminocamptothecin, irinotecan, SN-38, edotecarin, and topotecan.

Tyrosine kinase inhibitors include, for example, Iressa and SU5416.

Antibodies include, for example, Herceptin, Erbitux, Avastin, and Rituximab.

Interferons include, for example, interferon alpha, interferon alpha-2a, interferon, alpha-2b, interferon beta, interferon gamma-1a and interferon gamma-n1.

Biological response modifiers include agents that modify defense mechanisms of living organisms or biological responses, such as survival, growth, or differentiation of tissue cells to direct them to have anti-tumor activity. Such agents include, for example, krestin, lentinan, sizofiran, picibanil, and ubenimex.

Other antitumor agents include, for example, mitoxantrone, l-asparaginase, procarbazine, dacarbazine, hydroxycarbamide, pentostatin, and tretinoin. Additionally, PI3K inhibitors and RAS-targeted cancer treatments may be combined with the compounds described herein.

Some embodiments also relate to a pharmaceutical composition comprising a compound of formulas (I), (II), (III), (IIIa), (IV), (IVa) (V), (Va), (VI), (VIa), (VII), (VIIa), (VIII), (VIIIa), (X), or (XI), or a pharmaceutically acceptable salt or solvate thereof, as hereinbefore defined in association with a pharmaceutically acceptable adjuvant, diluent or carrier.

Further embodiments relate to a pharmaceutical composition which comprises mixing a compound of formulas (I), (II), (III), (IIIa), (IV), (IVa) (V), (Va), (VI), (VIa), (VII), (VIIa), (VIII), (VIIIa), (X), or (XI), or a pharmaceutically acceptable salt or solvate thereof, as hereinbefore defined with a pharmaceutically acceptable adjuvant, diluent or carrier.

For the above-mentioned therapeutic uses the dosage administered will, of course, vary with the compound employed, the mode of administration, the treatment desired and the disorder indicated. The daily dosage of the compound of formulas (I), (II), (III), (IIIa), (IV), (IVa) (V), (Va), (VI), (VIa), (VII), (VIIa), (VIII), (VIIIa), (X), or (XI), or pharmaceutically acceptable salt thereof, may be in the range from 1 mg to 1 gram, preferably 1 mg to 250 mg, more preferably 1 mg to 100 mg.

The present embodiments also encompass sustained release compositions.

Administration of the compounds described herein (hereinafter the "active compound(s)") can be effected by any method that enables delivery of the compounds to the site of action. These methods include oral routes, intraduodenal routes, parenteral injection (including intravenous, subcutaneous, intramuscular, intravascular, intraperitoneal, or infusion), topical, and rectal administration.

The active compound may be applied as a sole therapy or may involve one or more other anti-tumor substances, for example those selected from, for example, mitotic inhibitors, for example vinblastine; alkylating agents, for example cisplatin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound described herein as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

The examples and preparations provided below further illustrate and exemplify the compounds described herein and methods of preparing such compounds. The scope of the embodiments described herein is not limited in any way by the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

In the examples shown, salt forms were occasionally isolated as a consequence of the mobile phase additives during HPLC based chromatographic purification. In these cases, salts such as formate, trifluorooacetate and acetate were isolated and tested without further processing. It will be recognized that one of ordinary skill in the art will be able to realize the free base form by standard methodology (such as using ion exchange columns, or performing simple basic extractions using a mild aqueous base).

In general, the compounds described herein may be prepared by processes known in the chemical arts, particularly in light of the description contained herein. Certain processes for the manufacture of the compounds described herein are provided as further features of the embodiments and are illustrated in the reaction schemes provided below and in the experimental section.

Unless stated otherwise, the variables in Schemes A and B have the same meanings as defined herein.

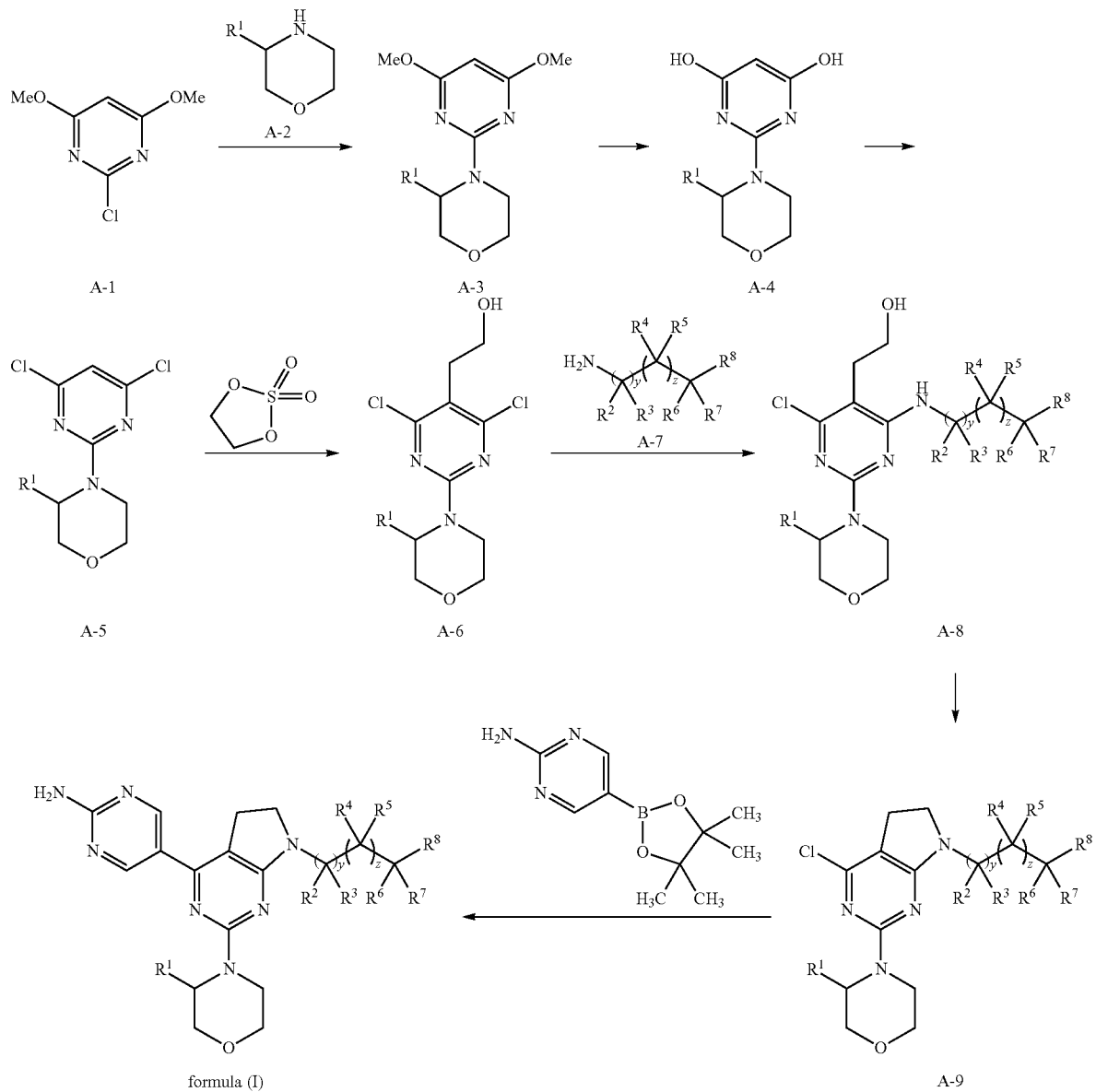

As exemplified in Scheme A, a pyrimidine A-1 is subjected to chlorine displacement with an amine A-2 in the presence of a suitable base (such as DIPEA, NaH, $K_2CO_3$, or CsF) in a suitable solvent (such as DMSO, acetonitrile, NMP, THF, or DMF) to afford A-3. A-3 is then treated under demethylation conditions known in the art with sodium iodide and TMS-Cl in acetonitrile to provide A-4. A-4 is treated with $POCl_3$ (neat or in suitable solvent, such as acetonitrile) to provide A-5. A-5 is subjected to alkylation using 1,3,2-dioxathiolane 2,2-dioxide in the presence of n-butyl lithium to give A-6. A-6 is subjected to chlorine displacement with an amine A-7 in the presence of a suitable base (such as DIPEA, CsF, or NaH) in a suitable solvent (such as DMSO, acetonitrile, NMP, THF, or DMF) to afford A-8. A-8 is then treated with methanesulfonyl chloride in suitable base (such as TEA or DIPEA) in the presence of DMAP in a suitable solvent (such as DCM) followed by treatment with a base (such as DBU) in suitable solvent (such as DMF, THF) to provide A-9. A-9 is then treated under Suzuki cross-coupling conditions with a boronic acid or a boronate to afford formula (I). The compounds of formula (X) are prepared in a similar manner.

Furthermore, if the $R^4$-$R^8$ groups of formula (I) or formula (X) contain an N-Boc group, the NBoc group may be deprotected under acidic conditions (such as HCl or TFA) and the resultant amine may be subjected to amide, carbamate, urea, sulfonamide, sulfamide or phosphinic amide formation. Amide formation can be achieved using a suitable amide coupling agent (such as CDI, EDCI, HATU) in the presence of a suitable base (such as DIPEA, TEA) and an appropriate carboxylic acid. Carbamate formation can be achieved using an appropriate chloroformate in the presence of a suitable base (such as DIPEA or TEA). Urea formation can be achieved by using an appropriate isocyanate in the presence of a suitable base (such as TEA), or in the presence of triphosgene or phosgene and an amine in the presence of a suitable base (such as sodium carbonate, sodium bicarbonate, or TEA). Sulfonamide formation can be achieved with a sulfonyl chloride in the presence of a suitable base (such as DIPEA or TEA). Sulfamide formation can be achieved with sulfamoyl chloride or sulfamoylcarbamate in the presence of a suitable base (such as DIPEA or TEA). Phosphinic amide formation can be achieved with phosphinic chloride in the presence of a suitable base (such as DIPEA or TEA). These amine functionalizations may be performed either before or after the Suzuki cross-coupling step.

Scheme B:

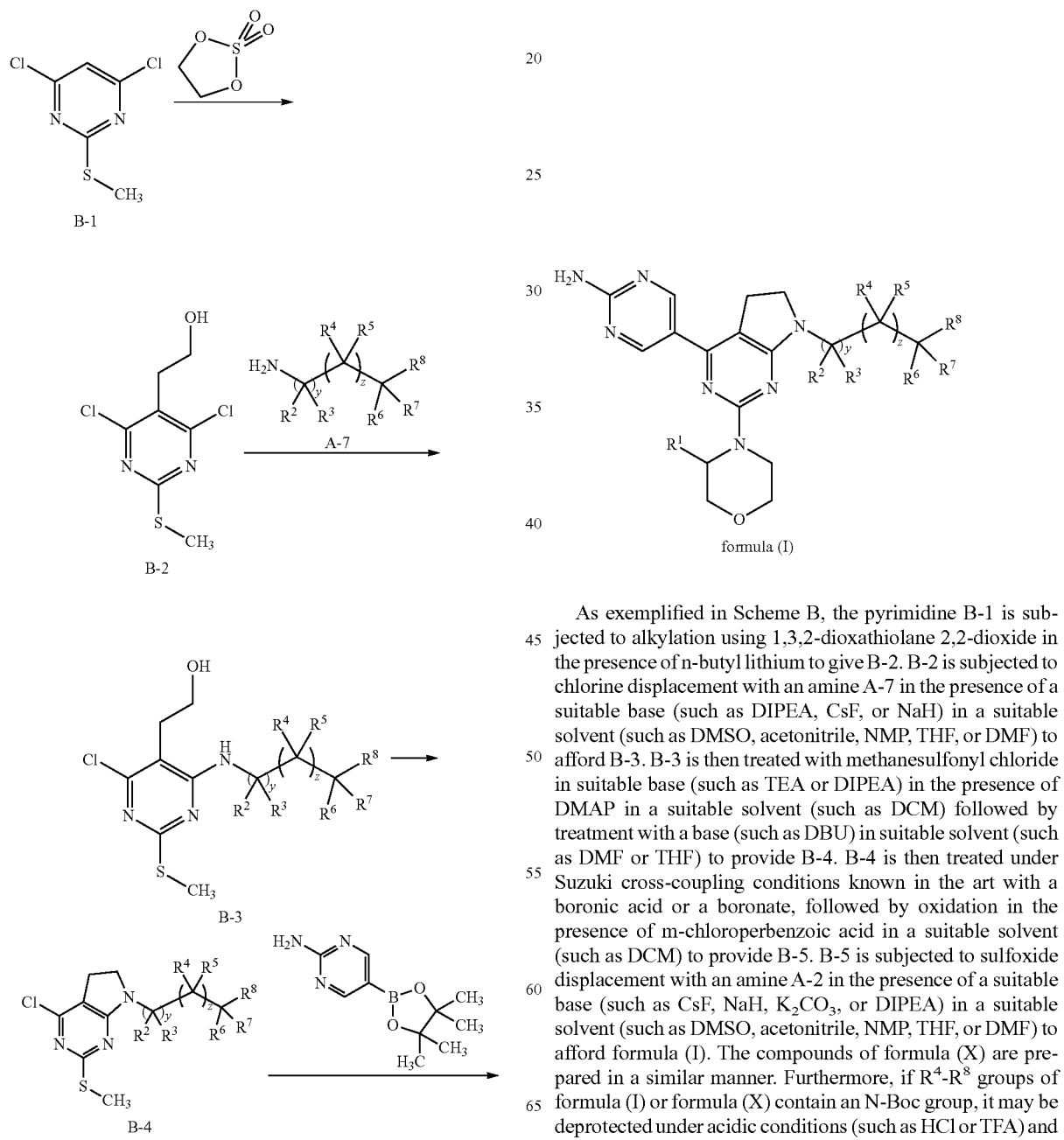

formula (I)

As exemplified in Scheme B, the pyrimidine B-1 is subjected to alkylation using 1,3,2-dioxathiolane 2,2-dioxide in the presence of n-butyl lithium to give B-2. B-2 is subjected to chlorine displacement with an amine A-7 in the presence of a suitable base (such as DIPEA, CsF, or NaH) in a suitable solvent (such as DMSO, acetonitrile, NMP, THF, or DMF) to afford B-3. B-3 is then treated with methanesulfonyl chloride in suitable base (such as TEA or DIPEA) in the presence of DMAP in a suitable solvent (such as DCM) followed by treatment with a base (such as DBU) in suitable solvent (such as DMF or THF) to provide B-4. B-4 is then treated under Suzuki cross-coupling conditions known in the art with a boronic acid or a boronate, followed by oxidation in the presence of m-chloroperbenzoic acid in a suitable solvent (such as DCM) to provide B-5. B-5 is subjected to sulfoxide displacement with an amine A-2 in the presence of a suitable base (such as CsF, NaH, $K_2CO_3$, or DIPEA) in a suitable solvent (such as DMSO, acetonitrile, NMP, THF, or DMF) to afford formula (I). The compounds of formula (X) are prepared in a similar manner. Furthermore, if $R^4$-$R^8$ groups of formula (I) or formula (X) contain an N-Boc group, it may be deprotected under acidic conditions (such as HCl or TFA) and subjected to amide, carbamate, urea, sulfonamide, sulfamide, or phosphinic amide formation either before or after the Suzuki cross-coupling step as described above in Scheme A.

EXAMPLE

Example 1 (Scheme A)

Preparation of 5-{2-[(3S)-3-methylmorpholin-4-yl]-7-[1-(propan-2-ylsulfonyl)azetidin-3-yl]-6j-dihydro-5H-pyrrolo[2,3-d]pyrimidin-4-yl}Pyrimidin-2-amine

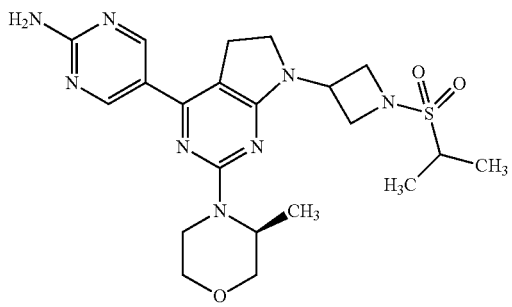 [SMILES: CC(C)S(=O)(=O)N1CC(N2CCc3c(-c4cnc(N)nc4)nc(N4CCOC[C@@H]4C)nc32)C1]

Step 1: Preparation of tert-butyl 3-({6-chloro-5-(2-hydroxyethyl)-2-[(3S)-3-methylmorpholin-4-yl]pyrimidin-4-yl}amino)azetidine-1-carboxylate

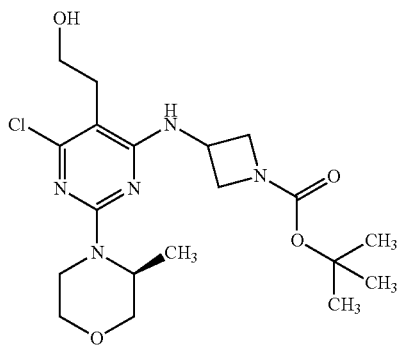 [SMILES: C[C@H]1COCCN1c1nc(Cl)c(CCO)c(NC2CN(C(=O)OC(C)(C)C)C2)n1]

A solution of 2-{4,6-dichloro-2-[(3S)-3-methylmorpholin-4-yl]pyrimidin-5-yl}ethanol (as prepared in Preparation 2)(0.652 g, 2.23 mmol) and 3-amino-azetidine-1-carboxylic acid tert-butyl ester (0.5 g, 2.9 mmol) in DMSO (10.0 mL) was treated with DIPEA (0.7 mL, 4 mmol) and heated at 75° C. for 5 days in a sealed tube. The mixture was poured into a flask containing water and the resulting solids were collected by filtration and rinsed with water. The solids were taken up in DCM, dried over MgSO$_4$ and filtered. The filtrate was purified directly by silica gel chromatography using a gradient of 25-100% EtOAc/heptane as eluent to give 0.823 g (86%) of the title compound as a crisp foam. $^1$H NMR (400 MHz, DMSO-d$_6$) δ 7.30 (d, J=5.6 Hz, 1 H), 4.71 (t, J=5.2 Hz, 1 H), 4.62-4.53 (m, 1 H), 4.47-4.40 (m, 1 H), 4.13-4.04 (m, 3 H), 3.89-3.78 (m, 3 H), 3.66 (d, J=11.4 Hz, 1 H), 3.55-3.44 (m, 3 H), 3.36 (dt, J=11.7, 2.9 Hz, 1 H), 3.04 (dt, J=12.9, 3.7 Hz, 1 H), 2.69 (t, J=6.9 Hz, 2 H), 1.39 (s, 9 H), 1.14 (d, J=6.7 Hz, 3 H).

Step 2: Preparation of tert-butyl 3-{4-chloro-2[(3S)-3-methylmorpholin-4-yl]-5,6-dihydro-7H-pyrrolo[2,3-d]pyrimidin-7-yl}azetidine-1-carboxylate

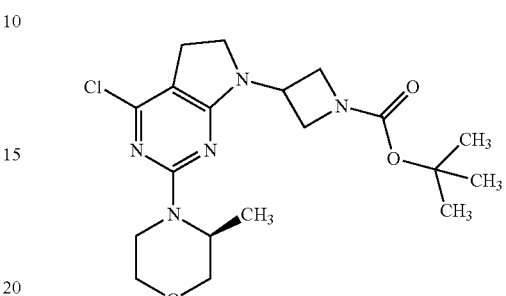

A solution of tert-butyl 3-({6-chloro-5-(2-hydroxyethyl)-2-[(3S)-3-methylmorpholin-4-yl]pyrimidin-4-yl}amino) azetidine-1-carboxylate (0.1 g, 0.234 mmol) in DCM (4 mL) was treated with TEA (0.08 mL, 0.57 mmol) and methanesulfonyl chloride (0.026 mL, 0.34 mmol) at 0° C., followed by addition of a catalytic amount of DMAP. The reaction mixture was stirred for 2 h, letting the ice bath slowly warm to about 15° C. The reaction mixture was partitioned between DCM (2×10 mL) and water (10 mL). The organic layer was dried over MgSO$_4$ and reduced to a minimum volume. The residue was taken up in DMF (5 mL), and DBU (0.13 mL, 0.85 mmol) was added. The resulting mixture was crimp sealed and heated at 75° C. for 4 h. The crude mixture was poured into a brine solution (50 mL) and the resulting white solids were collected by filtration and rinsed with water. The solids were dried in a vacuum oven at 50° C. overnight to provide (80 mg, 83%) of the title compound. $^1$H NMR (400 MHz, DMSO-d$_6$) δ 4.74-4.65 (m, 1 H), 4.49-4.41 (m, 1 H), 4.18-3.98 (m, 5 H), 3.84 (dd, J=11.3, 3.4 Hz, 1 H), 3.71 (t, J=8.7 Hz, 2 H), 3.66-3.61 (m, 1 H), 3.51 (dd, J=11.4, 3.1 Hz, 1 H), 3.36 (dt, J=11.8, 3.0 Hz, 1 H), 3.05 (dt, J=12.9, 3.7 Hz, 1 H), 2.85 (t, J=8.3 Hz, 2 H), 1.38 (s, 9 H), 1.13 (d, J=6.7 Hz, 3 H).

Step 3: Preparation of tert-butyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate

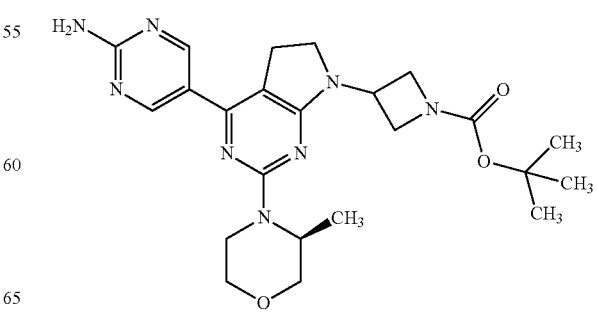

To a stirred mixture of tert-butyl 3-{4-chloro-2-[(3S)-3-methylmorpholin-4-yl]-5,6-dihydro-7H-pyrrolo[2,3-d]pyrimidin-7-yl}azetidine-1-carboxylate (8.33 g, 20.32 mmol), 5-(4,4,5,5-tetramethyl-1,3,2-dioxaborolan-2-yl)pyrimidin-2-amine (9.88 g, 44.7 mmol) and CsF (9.26 g, 61 mmol) in 1,4-dioxane (250 mL) and water (50 mL) was added Pd(dppf)$_2$Cl$_2$ (2.23 g, 3.05 mmol) under nitrogen. The mixture was heated under reflux for 18 h. The mixture was diluted with EtOAc (300 mL) and washed with water (300 mL), brine (300 mL×2), dried over Na$_2$SO$_4$ and concentrated under reduced pressure. The residue was purified by silica gel column chromatography eluting with a gradient of petroleum ether/EtOAc (from 1:1 to 0:1) to give 9.52 g (100%) of the title compound as a yellow solid. $^1$H NMR (400 MHz, DMSO-d$_6$) δ 8.74 (s, 2 H), 6.97 (s, 2 H), 4.75-4.67 (m, 1 H), 4.63-4.56 (m, 1 H), 4.26-4.13 (m, 3 H), 4.08-4.00 (m, 2 H), 3.90-3.84 (m, 1 H), 3.71-3.64 (m, 3 H), 3.56 (dd, J=11.3, 3.0 Hz, 1 H), 3.40 (dt, J=11.7, 2.7 Hz, 1H), 3.17-3.02 (m, 3 H), 1.39 (s, 9 H), 1.15 (d, J=6.7 Hz, 3 H).

Step 4: Preparation of 5-{7-(azetidin-3-yl)-2[(3S)-3-methylmorpholin-4-yl]-6,7-dihydro-5H-pyrrolo[2,3-d]pyrimidin-4-yl}pyrimidin-2-amine dihydrochloride

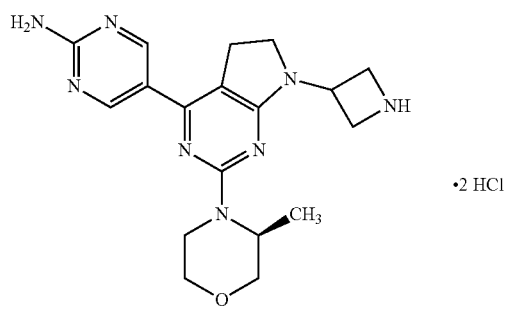 [SMILES: C[C@H]1COCCN1c1nc(-c2cnc(N)nc2)c2c(n1)N(C1CNC1)CC2]

To a solution of tert-butyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate (760 mg, 1.62 mmol) in methanol (8 mL), was added 4 N HCl in 1,4-dioxane (8 mL, 32 mmol). The reaction was stirred at room temperature for 1 h. The mixture was diluted with toluene and the solvent was removed under reduced pressure to give a foamy residue. The residue was triturated in acetone to get a free flowing tan solid which was collected by filtration to give the title compound in quantitative yield. The material was taken directly in the next step without purification. $^1$H NMR (400 MHz, CD$_3$OD) δ 8.78 (br s, 2 H), 5.32 (br s, 1 H), 4.62 (br s, 3 H), 4.34 (br s, 2 H), 4.19-3.99 (m, 4 H), 3.85-3.72 (m, 2 H), 3.64-3.46 (m, 2 H), 3.23 (br s, 2 H), 1.41 (d, J=5.5 Hz, 3 H).

Step 5: Preparation of 5-{2-[(3S)-3-methylmorpholin-4-yl]-7-[1-(propan-2-ylsulfonyl)azetidin-3-yl]-6,7-dihydro-5H-pyrrolo[2,3-d]pyrimidin-4-yl}pyrimidin-2-amine

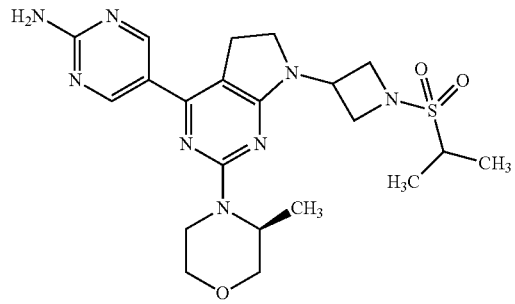 [SMILES: CC(C)S(=O)(=O)N1CC(N2CCc3c(-c4cnc(N)nc4)nc(N4CCOC[C@@H]4C)nc32)C1]

To a suspension of 5-{7-(azetidin-3-yl)-2-[(3S)-3-methylmorpholin-4-yl]-6,7-dihydro-5H-pyrrolo[2,3-d]pyrimidin-4-yl}pyrimidin-2-amine dihydrochloride (100 mg, 0.20 mmol) in DCM (5.0 mL) was added DIPEA (0.2 mL, 1.15 mmol). After a few minutes, the mixture became almost homogeneous, and a fine precipitation began to form. The reaction mixture was cooled to 0° C. and isopropylsulfonyl chloride (0.023 mL, 0.21 mmol) was added. The mixture was stirred at 0° C. for 45 min resulting in an amber solution. The mixture was concentrated to a minimum volume and the residue was purified by SFC column to give 50.4 mg (51%) of the title compound. $^1$H NMR (400 MHz, DMSO-d$_6$) δ 8.74 (s, 2 H), 6.98 (s, 2 H), 4.80 (p, J=7.2 Hz, 1 H), 4.68-4.59 (m, 1H), 4.29-4.21 (m, 3 H), 3.98 (dt, J=7.9, 4.4 Hz, 2 H), 3.88 (dd, J=11.1, 3.0 Hz, 1 H), 3.72-3.65 (m, 3 H), 3.56 (dd, J=11.3, 2.9 Hz, 1 H), 3.40 (dt, J=11.7, 2.8 Hz, 1 H), 3.28-3.21 (m, 1H, partially overlapped with water), 3.15 (t, J=8.2 Hz, 2 H), 3.07 (dt, J=12.9, 3.7 Hz, 1 H), 1.24 (d, J=6.8 Hz, 6 H), 1.16 (d, J=6.7 Hz, 3 H). m/z (APCI+) for C$_{21}$H$_{30}$N$_8$O$_3$S 475.2 (M+H)$^+$.

Example 2 (Scheme A)

Preparation of (3R)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-carboxamide

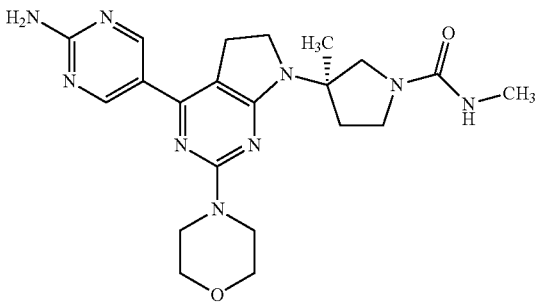 [SMILES: CNC(=O)N1CC[C@@](C)(N2CCc3c(-c4cnc(N)nc4)nc(N4CCOCC4)nc32)C1]

Step 1: Preparation of tert-butyl 3-{[6-chloro-5-(2-hydroxyethyl)-2-(morpholin-4-yl)pyrimidin-4-yl]amino}-3-methylpyrrolidine-1-carboxylate

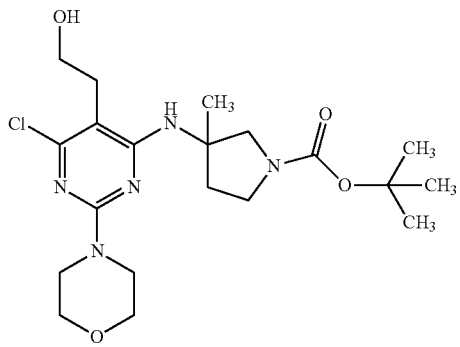 [SMILES: CC1(Nc2nc(N3CCOCC3)nc(Cl)c2CCO)CCN(C(=O)OC(C)(C)C)C1]

To a solution of 2-[4,6-dichloro-2-(morpholin-4-yl)pyrimidin-5-yl]ethanol (Preparation 1)(3.47 g, 12.5 mmol) and tert-butyl 3-amino-3-methylpyrrolidine-1-carboxylate (racemic from a commercial source or Preparation 3 for a chirally pure enantiomer) (5.00 g, 24.97 mmol) in NMP (40 mL) was added DIPEA (8.07 g, 62.44 mmol) at 10° C. The resulting mixture was stirred at 130° C. for 30 h. The mixture was diluted with EtOAc (30 mL) and washed with brine (20 mL×3). The organic layer was dried over anhydrous $Na_2SO_4$, filtered and concentrated under reduced pressure to give a residue, which was purified by silica gel chromatography, eluting with petroleum ether/EtOAc (1:1) to give the title compound (4.40 g, 80%) as a light yellow gum. $^1$H NMR (400 MHz, 80° C., DMSO-$d_6$) δ 6.48 (s, 1 H), 4.76 (t, J=5.0 Hz, 1 H), 3.76 (d, J=11.1 Hz, 1 H), 3.68-3.53 (m, 10 H), 3.45-3.28 (m, 3 H), 2.69 (t, J=6.24 Hz, 2 H), 2.35-2.26 (m, 1 H), 2.01-1.92 (m, 1 H), 1.49 (s, 3 H), 1.40 (s, 9 H). m/z (APCI+) for $C_{20}H_{32}ClN_5O_4$ 442.2 (M+H)$^+$.

Step 2: Preparation of tert-butyl(3R)-3-[4-chloro-2-(morpholin-4-yl)-5,6-dihydro-7H-pyrrolo[2,3-d]pyrimidin-7-yl]-3-methylpyrrolidine-1-carboxylate and (3S)-3-[4-chloro-2-(morpholin-4-yl)-5,6-dihydro-7H-pyrrolo[2,3-d]pyrimidin-7-yl]-3-methylpyrrolidine-1-carboxylate

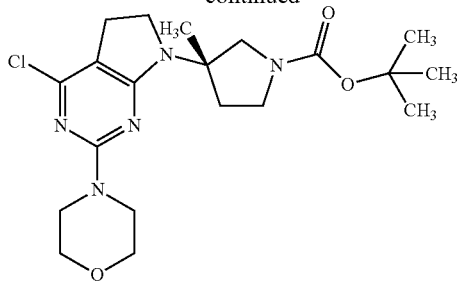

To a solution of tert-butyl 3-{[6-chloro-5-(2-hydroxyethyl)-2-(morpholin-4-yl)pyrimidin-4-yl]amino}-3-methylpyrrolidine-1-carboxylate (1760 mg, 3.982 mmol), TEA (1210 mg, 11.9 mmol) and DMAP (29.2 mg, 0.239 mmol) in anhydrous DCM (20 mL) was added methanesulfonyl chloride (778 mg, 6.79 mmol) dropwise at 0° C. and the mixture was stirred at 10° C. for 4 h. The mixture was diluted with 20 mL of DCM, washed with saturated aqueous $NaHCO_3$ (10 mL×2) and brine (10 mL×2), dried over $Na_2SO_4$ and concentrated under reduced pressure to give 2070 mg of a light yellow oil. This oil and DBU (1820 mg, 11.9 mmol) in DMF (20 mL) was stirred at 60° C. for 18 h. The mixture was diluted with EtOAc (20 mL) and washed with brine (30 mL×3). The organic layer was dried over $Na_2SO_4$ and concentrated under reduced pressure to give a residue, which was purified by silica gel chromatography, eluting with petroleum ether/EtOAc (1:1) to give the racemate of the title compound (1560 mg, 92%) as a light yellow solid. The racemate was separated by chiral SFC column (Column: OJ 300 mm*50 mm, 10 μm, mobile phase: 20% EtOH $NH_3/H_2O$, 200 mL/min, wavelength: 220 nm) to give both the R-enantiomer (retention Time: 5.29 min) and the S-enantiomer (retention Time: 5.86 min). R-enantiomer: $^1$H NMR (400 MHz, CDCl$_3$) δ 3.84-3.81 (m, 1H), 3.71-3.70 (m, 8 H), 3.60-3.53 (m, 1 H), 3.51-3.49 (m, 2 H), 3.49-3.34 (m, 1 H), 2.89 (t, J=8.8 Hz, 2 H), 2.47-1.99 (m, 3 H), 1.46 (s, 9 H), 1.32 (d, J=11.6 Hz, 3 H). m/z (APCI+) for $C_{20}H_{30}ClN_6O_3$ 424.2 (M+H)$^+$; [α]20D=25.0° (c=mg/mL, EtOH); 5-enantiomer: $^1$H NMR (400 MHz, CDCl$_3$) δ 3.84-3.81 (m, 1 H), 3.71-3.70 (m, 8 H), 3.60-3.51 (m, 3 H), 3.49-3.35 (m, 1 H), 2.90 (t, J=8.0 Hz, 2 H), 2.44-2.28 (m, 2 H), 2.06-1.99 (m, 1 H), 1.46 (s, 9 H), 1.32 (d, J=11.6 Hz, 3 H); m/z (APCI+) for $C_{20}H_{30}ClN_6O_3$ 424.2 (M+H)$^+$; [α]20D=−22.62° (c=mg/mL, EtOH)

Step 3: Preparation of tert-butyl(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate

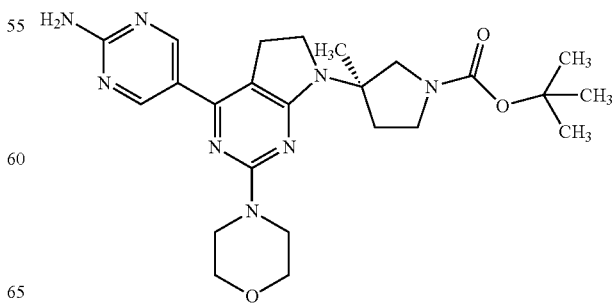

To a solution of tert-butyl(3R)-3-[4-chloro-2-(morpholin-4-yl)-5,6-dihydro-7H-pyrrolo[2,3-d]pyrimidin-7-yl]-3-methylpyrrolidine-1-carboxylate (150 mg, 0.354 mmol) in dioxane (3 mL) was added 5-(4,4,5,5-tetramethyl-1,3,2-dioxaborolan-2-yl)pyrimidin-2-amine (104 mg, 0.471 mmol), and 1 M aqueous $Na_2CO_3$ (1.3 mL, 51.3 mmol). Nitrogen was bubbled through the suspension for a few minutes before $PdCl_2(dppf)_2$-DCM (24 mg, 0.029 mmol) was added. The vial was crimp sealed and the reaction was heated at 120° C. for 30 min in a microwave reactor. The mixture was partitioned between EtOAc and aqueous $NaHCO_3$. The aqueous layer was extracted with EtOAc (2x). The combined organic layers were dried over $MgSO_4$ and concentrated under reduced pressure. The residue was purified by silica gel column chromatography using a gradient of 0-10% (MeOH with 10% $NH_4OH$)/(EtOAc/DCM, 1:1) to give 150 mg (88%) of the title compound as a crisp foam (~85% pure). This material was taken into the next step without further purification. $^1$H NMR (400 MHz, 80° C., DMSO-$d_6$) δ 8.72 (s, 2 H), 6.60 (br s, 2 H), 3.80-3.62 (m, 11 H), 3.54 (q, J=8.9 Hz, 1 H), 3.42-3.34 (m, 1 H), 3.33-3.23 (m, 1 H), 3.09 (t, J=8.1 Hz, 2 H), 2.44-2.34 (m, 1 H), 2.08-1.99 (m, 1 H), 1.42 (s, 9 H), 1.31 (s, 3 H).

Step 4: Preparation of (3R)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-carboxamide

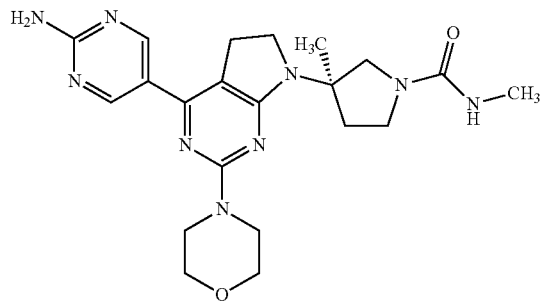 [SMILES: CNC(=O)N1CC[C@@](C)(N2CCc3c(-c4cnc(N)nc4)nc(N4CCOCC4)nc32)C1]

To a solution of tert-butyl(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate (150 mg, 0.311 mmol) in MeOH (1.5 mL) was added 4 N HCl in dioxane (1.5 mL, 6 mmol), and the mixture was stirred at room temperature for 45 min. The mixture was diluted with toluene and concentrated under reduced pressure. The residue was triturated again with toluene to give a yellow foam. To a solution of this residue in DMSO (3 mL) was added DIPEA (0.25 mL, 1.43 mmol) and methyl isocyanate (0.021 mL, 0.342 mmol), and the mixture was stirred for 45 min. Another portion of methylisocyanate (0.005 mL) was added and the mixture was stirred at room temperature for 18 h. The mixture was dropped into 50% saturated $NaHCO_3$ (30 mL) and extracted with EtOAc (3×). The combined organic layers were dried over $MgSO_4$ and concentrated under reduced pressure. The residue was purified by silica gel chromatography using a gradient of 0-10% (MeOH with 10% $NH_4OH$)/(EtOAC/DCM, 1:1) as eluent. The desired fractions were concentrated to a minimum volume and the residue was taken up in MeOH/water and lyophilized to give 93 mg (68%) of the title compound as a white solid. $^1$H NMR (600 MHz, 80° C., DMSO-$d_6$) δ 8.72 (s, 2 H), 6.59 (br s, 2 H), 5.72 (br d, J=3.7 Hz, 1 H), 3.75 (d, J=10.6 Hz, 1 H), 3.71-3.50 (m, 11 H), 3.41-3.24 (m, 2 H), 3.08 (t, J=8.2 Hz, 2H), 2.60 (d, J=4.5 Hz, 3 H), 2.48-2.43 (m, 1H, partially overlapped with DMSO), 2.14-2.05 (m, 1 H), 1.34 (s, 3 H). m/z (APCI+) for $C_{21}H_{29}N_9O_2$ 440.2 $(M+H)^+$.

Example 3 (Scheme B)

Preparation of {(3R)-4-[4-(2-aminopyrimidin-5-yl)-7-(3,3-difluorocyclobutyl)-6,7-dihydro-5H-pyrrolo[2,3-d]pyrimidin-2-yl]morpholin-3-yl}methanol

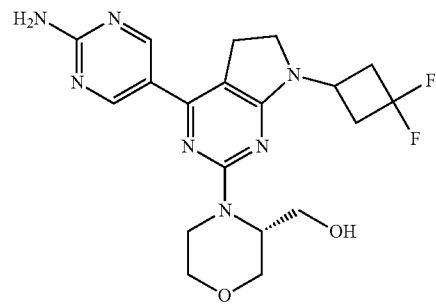 [SMILES: Nc1ncc(-c2nc(N3CCOC[C@H]3CO)nc3c2CCN3C2CC(F)(F)C2)cn1]

Step 1: Preparation of 2-[4,6-dichloro-2-(methylsulfanyl)pyrimidin-5-yl]ethanol

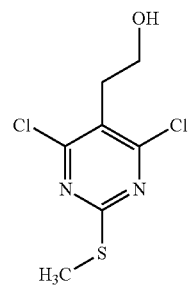

To a vial containing 4,6-dichloro-2-(methylsulfanyl)pyrimidine (200 mg, 0.102 mmol) in THF (10 mL) was added n-butyllithium (0.554 mL, 1.38 mmol, 2.5 M in hexane) at −78° C. and the resulting mixture was stirred for 30 min. 1,3,2-dioxathiolane 2,2-dioxide (172 mg, 1.39 mmol) was added at −78° C. and stirring was continued for 2 h. The reaction vial was removed from the dry ice bath, 6 N HCl (3.5 mL, 21 mmol) was added, and the mixture was stirred at room temperature for 18 h. 2-Methyltetrahydrofuran (20 mL) was added and the solution was washed with a 1:1 mixture of brine/water and then with saturated aqueous $NaHCO_3$. The organic layer was dried over $Na_2SO_4$, filtered, concentrated and purified via silica gel chromatography using a gradient of EtOAC/heptane (30-50%) to give the title compound (185 mg, 76% yield) as a white solid. $^1$H NMR (400 MHz, DMSO-d$_6$) δ 4.84 (t, J=5.4 Hz, 1 H), 3.61 (q, J=6.3 Hz, 2 H), 2.93 (t, J=6.8 Hz, 2 H), 2.52 (s, 3 H). m/z (APCI+) for C$_7$H$_8$Cl$_2$N$_2$OS 239.0 (M+H)$^+$.

Step 2: Preparation of 2-{4-chloro-6-[(3,3-difluoro-cyclobutyl)amino]-2-(methylsulfanyl)pyrimidin-5-yl}ethanol

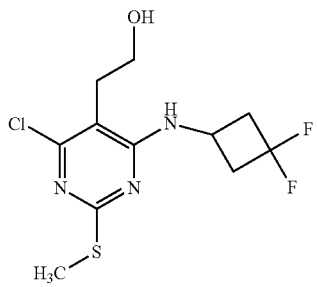 [SMILES: CSc1nc(Cl)c(CCO)c(NC2CC(F)(F)C2)n1]

To a vial containing 2-[4,6-dichloro-2-(methylsulfanyl)pyrimidin-5-yl]ethanol (600 mg, 2.51 mmol) and 3,3-difluorocyclobutylamine (540 mg, 3.76 mmol) in acetonitrile (12.5 mL) was added DIPEA (2.21 mL, 12.5 mmol) at room temperature, and the mixture was stirred at 100° C. in an oil bath for 6.5 h. The reaction mixture was concentrated under reduced pressure, and the residue was purified via silica gel chromatography using a gradient of EtOAc/heptane (20-40%) to afford the title compound (722.5 mg, 93%) as light yellow solid. $^1$H NMR (400 MHz, DMSO-d$_6$) δ 7.60 (d, J=5.5 Hz, 1 H), 4.82 (br s, 1 H), 4.38-4.26 (m, 1 H), 3.56-3.47 (m, 2 H), 3.03-2.87 (m, 2 H), 2.83-2.65 (m, 4 H), 2.42 (s, 3 H). m/z (APCI+) for C$_{11}$H$_{14}$ClF$_2$N$_3$OS 310.1 (M+H)$^+$.

Step 3: Preparation of 2-{4-chloro-6-[(3,3-difluoro-cyclobutyl)amino]-2-(methylsulfanyl)pyrimidin-5-yl}ethyl methanesulfonate

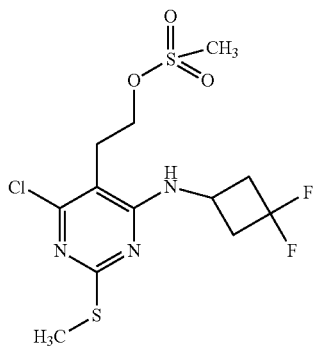 [SMILES: CSc1nc(Cl)c(CCOS(C)(=O)=O)c(NC2CC(F)(F)C2)n1]

To a solution of 2-{4-chloro-6-[(3,3-difluorocyclobutyl)amino]-2-(methylsulfanyl)pyrimidin-5-yl}ethanol (714 mg, 2.31 mmol) in DCM (38.5 mL) was added TEA (1.12 mL, 8.06 mmol), methanesulfonyl chloride (0.455 mL, 5.76 mmol) and DMAP (17 mg, 0.138 mmol) at 0° C. The mixture was stirred at 0° C. for 1 h and at room temperature for 1 h. The reaction mixture was washed with water (3×), and the organic layer was dried (Na$_2$SO$_4$) and concentrated under reduced pressure to give 925 mg (>99%) of the title compound as a yellow solid. This material was used in the next step without further purification. $^1$H NMR (400 MHz, DMSO-d$_6$) δ 7.67 (d, J=5.7 Hz, 1 H), 4.40-4.29 (m, 1 H), 4.26 (t, J=6.8 Hz, 2 H), 3.14 (s, 3 H), 3.05 (t, J=6.8 Hz, 2 H), 3.02-2.89 (m, 2 H), 2.85-2.68 (m, 2 H), 2.44 (s, 3 H). m/z (APCI+) for C$_{12}$H$_{16}$ClF$_2$N$_3$O$_3$S$_2$ 388.0 (M+H)$^+$.

Step 4: Preparation of 4-chloro-7-(3,3-difluorocyclobutyl)-2-(methylsulfanyl)-6,7-dihydro-5H-pyrrolo[2,3-d]pyrimidine

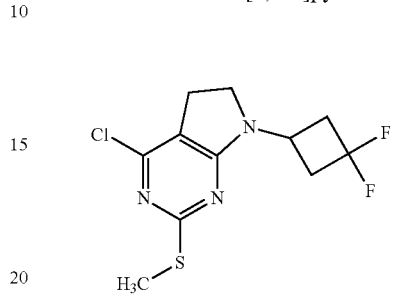

To a solution of 2-{4-chloro-6-[(3,3-difluorocyclobutyl)amino]-2-(methylsulfanyl)pyrimidin-5-yl}ethyl methanesulfonate (922 mg, 2.38 mmol) in DMF (23 mL) was added DBU (0.725 mL, 4.75 mmol). The mixture was stirred at 80° C. for 1 h, whereupon the reaction mixture was diluted with EtOAc (40 mL), washed with water (20 mL) and brine (20 mL), dried over Na$_2$SO$_4$ and concentrated under reduced pressure to give 649 mg (94%) of the title compound as a yellow solid. $^1$H NMR (400 MHz, DMSO-d$_6$) δ 4.44-4.33 (m, 1 H), 3.75 (t, J=8.5 Hz, 2 H), 3.13-2.99 (m, 2 H), 2.98-2.92 (m, 2 H), 2.91-2.81 (m, 2 H), 2.42 (s, 3 H). m/z (APCI+) for C$_{11}$H$_{12}$ClF$_2$N$_3$S 292.0 (M+H)$^+$.

Step 5: Preparation of 5-[7-(3,3-difluorocyclobutyl)-2-(methylsulfanyl)-6,7-dihydro-5H-pyrrolo[2,3-d]pyrimidin-4-yl]pyrimidin-2-amine

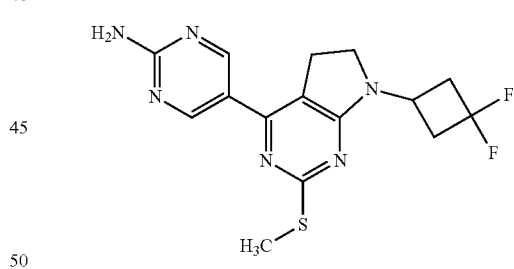

To a suspension of 4-chloro-7-(3,3-difluorocyclobutyl)-2-(methylsulfanyl)-6,7-dihydro-5H-pyrrolo[2,3-d]pyrimidine (844 mg, 2.89 mmol) and 5-(4,4,5,5-tetramethyl-1,3,2-dioxaborolan-2-yl)pyrimidin-2-amine (920 mg, 4.20 mmol) in 1,4-dioxane (24 mL), was added 1 M aqueous solution of Na$_2$CO$_3$ (9 mL, 8.68 mmol) at room temperature. The reaction was purged with nitrogen for a few minutes before adding PdCl$_2$(dppf)-DCM (354 mg, 0.434 mmol). The reaction was heated at 120° C. for 1 h in a microwave reactor. The mixture was cooled to room temperature and filtered through Celite® rinsing with EtOAc. The filtrate was concentrated and DCM was added, resulting in precipitation that was filtered to give a crude title compound (768 mg, ~80% purity). The mother liquor was purified via silica gel chromatography using a gradient of EtOAc/heptane to afford an additional 250 mg of the title compound as a white solid (95% purity). $^1$H NMR (400 MHz, DMSO-d$_6$) δ 8.76 (s, 2 H), 7.08 (s, 2 H), 4.51-4.36 (m, 1 H), 3.71 (t, J=8.2 Hz, 2 H), 3.22 (t, J=8.2 Hz, 2 H), 3.13-2.94 (m, 2 H), 2.94-2.80 (m, 2 H), 2.47 (s, 3 H). m/z (APCI+) for C$_{15}$H$_{16}$F$_2$N$_6$S 351.1 (M+H)$^+$.

Step 6: Preparation of 5-[7-(3,3-difluorocyclobutyl)-2-(methylsulfinyl)-6,7-dihydro-5H-pyrrolo[2,3-d]pyrimidin-4-yl]pyrimidin-2-amine

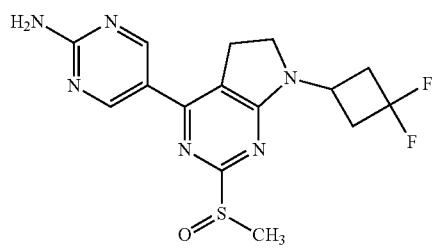 [SMILES: CS(=O)c1nc(-c2cnc(N)nc2)c2c(n1)N(C1CC(F)(F)C1)CC2]

To a suspension of crude 5-[7-(3,3-difluorocyclobutyl)-2-(methylsulfanyl)-6,7-dihydro-5H-pyrrolo[2,3-d]pyrimidin-4-yl]pyrimidin-2-amine (~80% purity) (768 mg, 2.63 mmol) in DCM (87 mL) at 0° C. was added m-chloroperbenzoic acid (844 mg, 3.42 mmol, 70% purity) in three portions over 1 min. The reaction mixture was stirred at 0° C. for 15 min, whereupon it was diluted with DCM and washed with saturated aqueous NaHCO$_3$ and water. The organic layer was concentrated and purified via HPLC reversed phase column (0-50% of gradient A to B over 25 min; A: water with 0.1% acetic acid, B: acetonitrile with 0.1% acetic acid) to afford the title compound (251 mg, 26%). $^1$H NMR (400 MHz, DMSO-d$_6$) δ 8.80 (s, 2 H), 7.19 (s, 2 H), 4.61-4.48 (m, 1 H), 3.83 (t, J=8.4 Hz, 2 H), 3.38-3.31 (m, 2 H), 3.14-2.98 (m, 2 H), 2.97-2.85 (m, 2 H), 2.83 (s, 3 H). m/z (APCI+) for C$_{15}$H$_{16}$F$_2$N$_6$OS 367.1 (M+H)$^+$.

Step 7: Preparation of {(3R)-4-[4-(2-aminopyrimidin-5-yl)-7-(3,3-difluorocyclobutyl)-6,7-dihydro-5H-pyrrolo[2,3-d]pyrimidin-2-yl]morpholin-3-yl}methanol

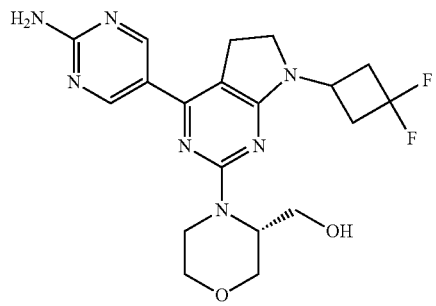 [SMILES: Nc1ncc(-c2nc(N3CCOC[C@H]3CO)nc3c2CCN3C2CC(F)(F)C2)cn1]

To a solution of 5-[7-(3,3-difluorocyclobutyl)-2-(methylsulfinyl)-6,7-dihydro-5H-pyrrolo[2,3-d]pyrimidin-4-yl]pyrimidin-2-amine (35 mg, 0.096 mmol) in acetonitrile (0.3 mL) was added (3R)-morpholin-3-ylmethanol (68 mg, 0.576 mmol) and CsF (56 mg, 0.288 mmol), and the reaction mixture was sealed and heated at 120° C. for 96 h.

The reaction mixture was cooled to room temperature and the resulting mixture was purified by HPLC reversed phase column (Waters CSH C18. 3.5 μm, 10 mM NH$_4$OAc, 2.25 mL/min, 140 bar) to afford the title compound as a white solid (3.44 mg 8.5%). $^1$H NMR (600 MHz, DMSO-d$_6$) δ 8.73 (s, 2 H), 6.96 (s, 2 H), 4.46-4.40 (m, 1 H), 4.36-4.25 (m, 2 H), 4.05 (d, J=11.2 Hz, 1 H), 3.85 (dd, J=11.1, 3.4 Hz, 1 H), 3.72-3.65 (m, 1 H), 3.64-3.57 (m, 2 H), 3.42-3.39 (m, 1 H), 3.38-3.33 (m, 4 H), 3.14-3.08 (m, 2H), 3.05-2.95 (m, 2 H), 2.90-2.79 (m, 2 H). m/z (APCI+) for C$_{19}$H$_{23}$F$_2$N$_7$O$_2$ 420.2 (M+H)$^+$.

Example 4 (Scheme A)

Preparation of 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one

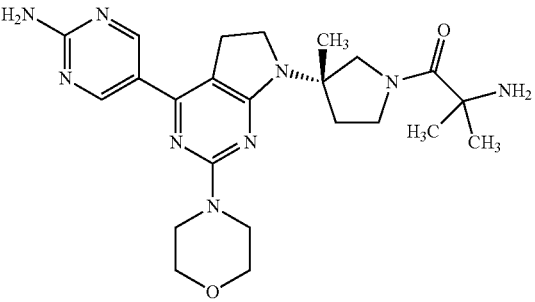 [SMILES: CC(C)(N)C(=O)N1CC[C@](C)(N2CCc3c(-c4cnc(N)nc4)nc(N4CCOCC4)nc32)C1]

Step 1: Preparation of tert-butyl 3-{[6-chloro-5-(2-hydroxyethyl)-2-(morpholin-4-yl)pyrimidin-4-yl]amino}-(S)-3-methylpyrrolidine-1-carboxylate

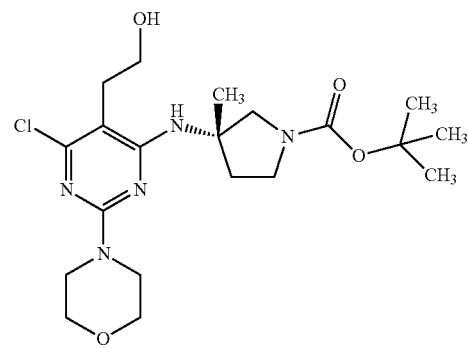 [SMILES: CC(C)(C)OC(=O)N1CC[C@](C)(Nc2nc(N3CCOCC3)nc(Cl)c2CCO)C1]

To a solution of 2-[4,6-dichloro-2-(morpholin-4-yl)pyrimidin-5-yl]ethanol (Preparation 1) (7.8 g, 28.0 mmol) and tert-butyl(3S)-3-amino-3-methylpyrrolidine-1-carboxylate (Preparation 4) (8.4 g, 42.1 mmol) in NMP (58 mL) was added DIPEA (18.1 g, 140 mmol) at 15° C. and the resulting mixture was stirred at 130° C. for 60 h. The mixture was diluted with EtOAc (100 mL) and washed with water (100 mL). The aqueous layer was extracted with EtOAc (100 mL×2). The combined organic layers were washed with brine (100 mL×5), dried over Na$_2$SO$_4$, filtered and concentrated to give 16 g of a brown gum. The crude product was purified by silica gel column chromatography eluting with a gradient of petroleum ether/EtOAc (20:1 to 8:1) to give the title compound (9.1 g, 73%) as a light yellow solid. m/z (APCI+) for $C_{20}H_{32}N_5O_4Cl$ 442.0 [M+H]+.

Step 2: Preparation of (3S)-3-[4-chloro-2-(morpholin-4-yl)-5,6-dihydro-7H-pyrrolo[2,3-d]pyrimidin-7-yl]-3-methylpyrrolidine-1-carboxylate

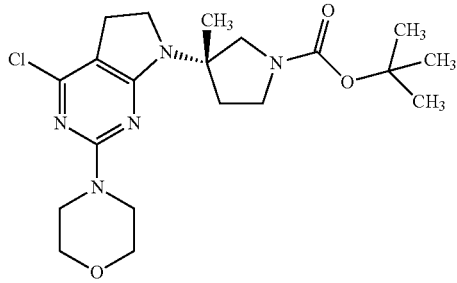 [SMILES: CC(C)(C)OC(=O)N1CC[C@](C)(N2CCc3c(Cl)nc(N4CCOCC4)nc32)C1]

To a stirred brown solution of tert-butyl 3-{[6-chloro-5-(2-hydroxyethyl)-2-(morpholin-4-yl)pyrimidin-4-yl]amino}-(S)-3-methylpyrrolidine-1-carboxylate (9.1 g, 20.59 mmol), TEA (6.2 g, 61.8 mmol) and DMAP (252 mg, 2.06 mmol) in anhydrous DCM (125 mL) was added methanesulfonyl chloride (3.54 g, 30.9 mmol) dropwise at 5-10° C. The mixture was stirred at 15° C. for 3 h, whereupon it was transferred to a separatory funnel and washed with saturated aqueous NaHCO$_3$ (100 mL×2). The combined aqueous layers were extracted with DCM (100 mL). The combined organic layers were washed with brine (200 mL), dried over Na$_2$SO$_4$, filtered and concentrated under reduced pressure to give 10.6 g of a light yellow solid, which was dissolved in DMF (90 mL). DBU (9.2 g, 60.4 mmol) was added and the mixture was heated at 80° C. for 5 h. Water was added and the mixture was extracted with EtOAc (150 mL×3). The combined organic layers were washed with brine (100 mL×5), dried over Na$_2$SO$_4$, filtered and concentrated to give 9 g of a yellow gum. The crude product was purified by silica gel column chromatography eluting with a gradient of petroleum ether/EtOAc (30:1 to 5:1) to give the title compound (7.5 g, 88%) as a white solid. m/z (APCI+) for $C_{20}H_{30}N_5O_3$ 424.0 [M+H]+.

Step 3: Preparation of tert-butyl 3-[4-(2-aminopyrimidin-5-yl)-2-(morpholin-4-yl)-5,6-dihydro-7H-pyrrolo[2,3-d]pyrimidin-7-yl]-(3S)-3-methylpyrrolidine-1-carboxylate

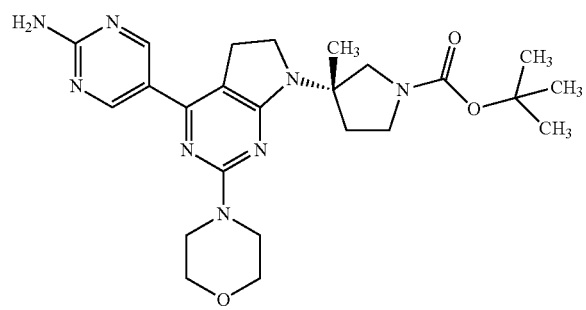 [SMILES: CC(C)(C)OC(=O)N1CC[C@](C)(N2CCc3c(-c4cnc(N)nc4)nc(N4CCOCC4)nc32)C1]

Two separate reaction vessels containing a yellow mixture of (3S)-3-[4-chloro-2-(morpholin-4-yl)-5,6-dihydro-7H-pyrrolo[2,3-d]pyrimidin-7-yl]-3-methylpyrrolidine-1-carboxylate (prepared from 2-[4,6-dichloro-2-(morpholin-4-yl)pyrimidin-5-yl]ethanol (Preparation 1) and tert-butyl(3S)-3-amino-3-methylpyrrolidine-1-carboxylate (Preparation 4)) (3500 mg, 8.256 mmol), 5-(4,4,5,5-tetramethyl-1,3,2-dioxaborolan-2-yl)pyrimidin-2-amine (2.37 g, 10.7 mmol) and Na$_2$CO$_3$ (2630 mg, 24.8 mmol) in 1,4-dioxane (90 mL) and water (30 mL), were prepared. To each reaction mixture was added Pd(dppf)Cl$_2$-DCM (362 mg, 0.495 mmol) in one portion at 15° C. under nitrogen atmosphere, and the reaction mixtures were heated at 120° C. for 16 h. The reaction mixtures were combined and concentrated to give 16 g of a black gum. The material was purified by silica gel column chromatography eluting with a gradient of 30-75% EtOAc in petroleum ether, followed by a gradient of 0-1% MeOH in EtOAc to give the title compound (7.0 g, 87%) as a yellow solid. $^1$H NMR (400 MHz, 80° C., DMSO-d$_6$) δ 8.73 (s, 2 H), 6.61 (br s, 2 H), 3.80-3.63 (m, 11 H), 3.54 (q, J=8.7 Hz, 1 H), 3.42-3.35 (m, 1 H), 3.33-3.25 (m, 1 H), 3.09 (t, J=8.2 Hz, 2 H), 2.44-2.35 (m, 1 H), 2.07-2.00 (m, 1 H), 1.42 (s, 9 H), 1.32 (s, 3 H). m/z (APCI+) for $C_{24}H_{34}N_8O_3$ 483.2 [M+H]+.

Step 4: Preparation of 5-{7-[(3S)-3-methylpyrrolidin-3-yl]-2-(morpholin-4-yl)-6,7-dihydro-5H-pyrrolo[2,3-d]pyrimidin-4-yl}pyrimidin-2-amine hydrochloride

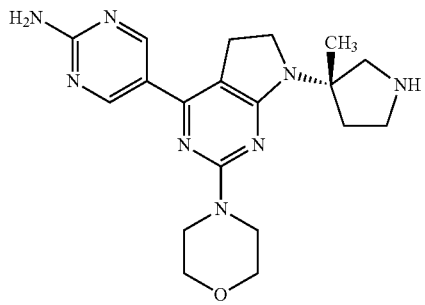 [SMILES: C[C@]1(N2CCc3c(-c4cnc(N)nc4)nc(N4CCOCC4)nc32)CCNC1]

To a stirred yellow solution of tert-butyl 3-[4-(2-aminopyrimidin-5-yl)-2-(morpholin-4-yl)-5,6-dihydro-7H-pyrrolo[2,3-d]pyrimidin-7-yl]-(3S)-3-methylpyrrolidine-1-carboxylate (5600 mg, 11.6 mmol) in DCM (30 mL) was added HCl (g) in EtOAc (80 mL, 4 M) dropwise at 0° C. and the solution was stirred at 10° C. for 2.5 h. The resultant yellow solids were collected by filtration, and the filter cake was dried under vacuum to give a yellow solid (6.5 g). The yellow solid was dissolved in water (50 mL) and lyophilized for 48 h to give the title compound (5.085 g, 88%) as a yellow gum. $^1$H NMR (400 MHz, D$_2$O) δ 8.60-8.57 (m, 2 H), 4.10 (d, J=12.4 Hz, 1 H), 3.88-3.70 (m, 10 H), 3.54 (d, J=12.5 Hz, 1 H), 3.41

(t, J=7.4 Hz, 2 H), 3.03-2.98 (m, 2 H), 2.63-2.55 (m, 1 H), 2.24-2.17 (m, 1 H), 1.47 (s, 3 H). m/z (APCI+) for $C_{19}H_{26}N_8O$ 383.0 $[M+H]^+$.

Step 5: Preparation of tert-butyl(1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-1-oxopropan-2-yl)carbamate

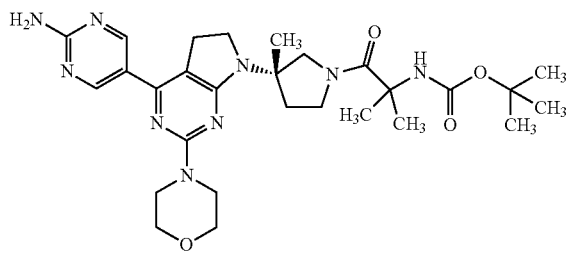 [SMILES: CC(C)(C)OC(=O)NC(C)(C)C(=O)N1CC[C@](C)(N2CCc3c(-c4cnc(N)nc4)nc(N4CCOCC4)nc32)C1]

To a mixture of the product of Example 4, Step 2, 5-{7-[(3S)-3-methylpyrrolidin-3-yl]-2-(morpholin-4-yl)-6,7-dihydro-5H-pyrrolo[2,3-d]pyrimidin-4-yl}pyrimidin-2-amine hydrochloride (~1.0 g, ~1.77 mmol), 2-tert-butoxycarbonylamino-2-methyl-propionic acid (504 mg, 2.48 mmol) and DIEA (2.16 mL, 12.4 mmol) in 10 mL NMP, was added HATU (1.0 g, 2.67 mmol). The reaction was covered with foil and stirred at room temperature for 18 h. The reaction mixture was dropped into aqueous NaHCO$_3$ and the resulting precipitate was collected by filtration. The filtrate was extracted with DCM (3 times). The filtrate and solids were combined, washed with brine, dried over MgSO$_4$ and concentrated. The residue was purified by Biotage (40-FM cartridge) using a gradient of 0-10% MeOH/EtOAc as eluent to give the title compound (771 mg, 76%) as a foamy solid. $^1$H NMR (400 MHz, 80° C., DMSO-d$_6$) δ 8.73 (s, 2 H), 6.71-6.54 (m, 3 H), 4.06-3.83 (m, 2 H), 3.70-3.41 (m, 12 H), 3.08 (t, J=8.1 Hz, 2 H), 2.47-2.35 (m, 1H, partially overlapped with DMSO), 2.10-2.01 (m, 1 H), 1.39-1.28 (m, 18 H). m/z (APCI+) for $C_{28}H_{41}CN_9O_4$ 568.3 $(M+H)^+$.

Step 6: Preparation of 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one

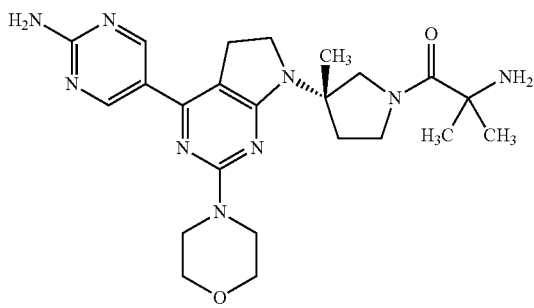 [SMILES: CC(C)(N)C(=O)N1CC[C@](C)(N2CCc3c(-c4cnc(N)nc4)nc(N4CCOCC4)nc32)C1]

In a foil covered flask, a solution of tert-butyl(1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-1-oxopropan-2-yl)carbamate (369 mg, 0.65 mmol) in MeON (3 mL) was treated with HCl (3 mL, 4N in dioxane) and the mixture was stirred at room temperature for 18 h. The mixture was diluted with toluene and concentrated. The residue was dissolved in a minimum amount of MeOH, dropped into aqueous NaHCO$_3$ and extracted with 15% i-PrOH in DCM (4×). The extracts were washed with brine, dried over MgSO$_4$ and concentrated. The oily residue was suspended in a few mL of acetonitrile and sonicated briefly, inducing crystallization. The resulting solids were collected by filtration to give the title compound (206 mg, 68%) as an off-white solid. $^1$H NMR (400 MHz, 80° C., DMSO-d$_6$) δ 8.73 (s, 2 H), 6.68 (br s, 2 H), 4.40-4.00 (m, 2 H), 3.73-3.50 (m, 12 H), 3.12-3.07 (m, 2H, partially overlapped with water), 2.41-2.30 (m, 1 H), 2.06-1.97 (m, 1 H), 1.74 (br s, 2 H), 1.31 (s, 3 H), 1.27 (s, 6 H). m/z (APCI+) for $C_{23}H_{33}CN_9O_2$ 468.3 $(M+H)^+$.

Salt formation: Preparation of 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one hemifumarate

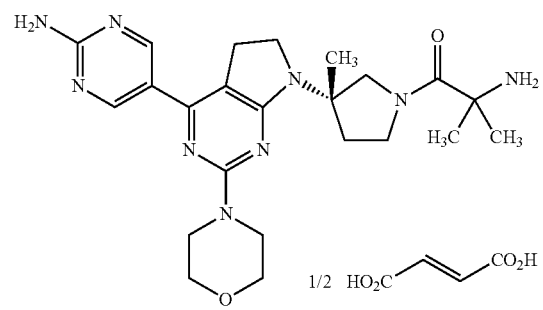

To a suspension of fumaric acid (136 mg, 1.07 mmol) in acetone (20 mL) at 60° C. was added water (0.4 mL) and the mixture was stirred until homogeneous. The fumaric acid solution was added to a freshly prepared mixture of 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one (500 mg, 1.07 mmol) in acetone (20 mL) resulting in a thick slurry. The suspension was stirred at 60° C. for 1 h, and allowed slowly to cool to room temperature overnight. The solids were collected by filtration rinsing with acetone. The solids were allowed to suction dry for ~5 min, whereupon they were suspended in 10% water/acetone (20 mL). The suspension was stirred at 60° C. for 1 h, and allowed to stand with gradual cooling for 18 h. The solids were collected by filtration rinsing with acetone and dried in a vacuum oven at ~50° C. for 1 h to give the title compound (390 mg, 69%) as a cream colored solid. $^1$H NMR (400 MHz, 80° C., DMSO-d$_6$) δ 8.73 (s, 2 H), 6.68 (s, 2 H), 6.54 (s, 1 H), 4.38-4.02 (m, 2 H), 3.72-3.47 (m, 12 H), 3.10 (t, J=8.2 Hz, 2H, partially overlapped with water), 2.41-2.34 (m, 1H, partially overlapped with DMSO), 2.08-1.99 (m, 1 H), 1.32 (s, 9 H).

Example 5 (Scheme A)

Preparation of 2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-methylpropan-1-one

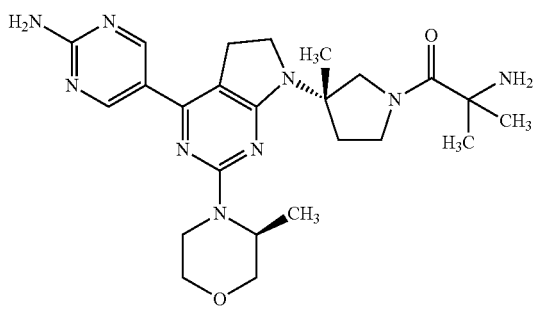 [SMILES: C[C@H]1COCCN1c1nc(-c2cnc(N)nc2)c2c(n1)N([C@@]1(C)CCN(C(=O)C(C)(C)N)C1)CC2]

Step 1: Preparation of tert-butyl 3-{[6-chloro-5-(2-hydroxyethyl)-2[(3S)-3-methylmorpholin-4-yl]pyrimidin-4-yl]amino}-(3S)-3-methylpyrrolidine-1-carboxylate

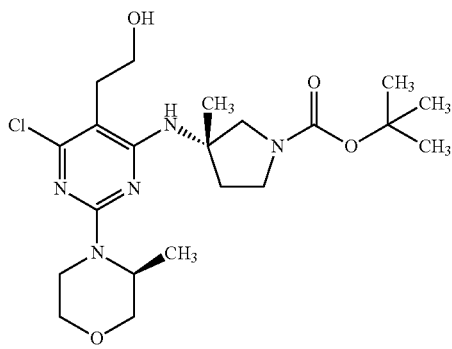 [SMILES: C[C@H]1COCCN1c1nc(Cl)c(CCO)c(N[C@@]2(C)CCN(C(=O)OC(C)(C)C)C2)n1]

To a solution of 2-{4,6-dichloro-2-[(3S)-3-methylmorpholin-4-yl]pyrimidin-5-yl}ethanol (Preparation 2) (4.8 g, 16.43 mmol) and tert-butyl(3S)-3-amino-3-methylpyrrolidine-1-carboxylate (Preparation 4) (4.94 g, 24.6 mmol) in DMSO (27 mL) was added DIPEA (10.6 g, 82.1 mmol) at 15° C. The resulting mixture was stirred at 110° C. for 60 h. The mixture was diluted with EtOAc (50 mL) and washed with water (50 mL). The aqueous layer was extracted with EtOAc (50 mL×2). The combined organic layers were washed with brine (50 mL×5), dried over Na₂SO₄, filtered and concentrated to give 9.5 g of a brown gum. The above was repeated and 2×9.5 g brown gum were combined and purified by silica gel column chromatography eluting with a gradient of petroleum ether/EtOAc (10:1 to 8:1) to give the title compound (9.0 g, 60%) as a light yellow solid. m/z (APCI+) for C₂₁H₃₄N₅O₄Cl 456.2 [M+H]⁺.

Step 2: Preparation of (3S)-3-[4-chloro-2[(3S)-3-methylmorpholin-4-yl)]-5,6-dihydro-7H-pyrrolo[2,3-d]pyrimidin-7-yl]-3-methylpyrrolidine-1-carboxylate

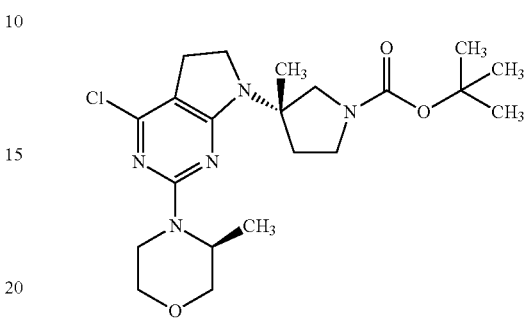

To a stirred brown solution of tert-butyl 3-{[6-chloro-5-(2-hydroxyethyl)-2[(3S)-3-methylmorpholin-4-yl)]pyrimidin-4-yl]amino}-(S)-3-methylpyrrolidine-1-carboxylate (9.0 g, 19.74 mmol), TEA (5.99 g, 59.2 mmol) and DMAP (193 mg, 1.58 mmol) in anhydrous DCM (200 mL) was added methanesulfonyl chloride (3.39 g, 29.6 mmol) dropwise at 5-10° C. The mixture was stirred at 25° C. for 2 h, whereupon it was diluted with DCM (80 mL) and washed with saturated aqueous NaHCO₃ (100 mL×2). The combined aqueous layers were extracted with DCM (100 mL). The combined organic layers were washed with brine (200 mL), dried over Na₂SO₄, filtered and concentrated under reduced pressure to give 10.5 g of a light yellow solid, which was dissolved in DMF (100 mL). DBU (9.02 g, 59.2 mmol) was added and the mixture was heated at 80° C. for 5 h. Water (300 mL) was added and the mixture was extracted with EtOAc (150 mL×3). The combined organic layers were washed with brine (100 mL×5), dried over Na₂SO₄, filtered and concentrated to give 8.5 g of a yellow gum. The crude product was purified by silica gel column chromatography eluting with a gradient of petroleum ether/EtOAc (8:1 to 7:1) to give the title compound (7.1 g, 82%) as a white solid. m/z (APCI+) for C₂₁H₃₂N₅O₃ 438.0 [M+H]⁺.

Step 3: Preparation of tert-butyl(3S)-3-{4-(2-aminopyrimidin-5-yl)-2[(3S)-3-methylmorpholin-4-yl]-5,6-dihydro-7H-pyrrolo[2,3-d]pyrimidin-7-yl}-3-methylpyrrolidine-1-carboxylate

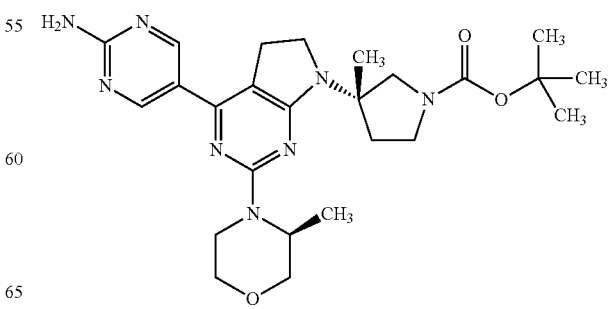

To a vial containing tert-butyl(3S)-3-{4-chloro-2-[(3S)-3-methylmorpholin-4-yl]-5,6-dihydro-7H-pyrrolo[2,3-d]pyrimidin-7-yl}-3-methylpyrrolidine-1-carboxylate hydrochloride (3796 mg, 8.68 mmol) in 1,4-dioxane (41.2 mL) was added 5-(4,4,5,5-tetramethyl-1,3,2-dioxaborolan-2-yl)pyrimidin-2-amine (2492 mg, 11.28 mmol), and 1 M aqueous Na$_2$CO$_3$ (26 mL). Nitrogen was bubbled through the suspension for a few minutes before PdCl$_2$(dppf)-DCM (516 mg, 0.632 mmol) was added and the mixture was heated in a microwave reactor at 120° C. for 30 min. The mixture was filtered through a pad of Celite® rinsing with EtOAc, and the filtrate was concentrated. The residue was purified by ISCO (80 g cartridge) using a gradient of 25-100% EtOAc/heptanes to give the title compound (3.94 g, 91%) as a yellow foamy solid. $^1$H NMR (400 MHz, DMSO-d$_6$) δ 8.73 (s, 2 H), 6.60 (s, 2 H), 4.64-4.54 (m, 1 H), 4.23 (dd, J=13.5, 2.3 Hz, 1 H), 3.89 (dd, J=11.2, 3.4 Hz, 1 H), 3.79-3.35 (m, 8 H), 3.33-3.24 (m, 1 H), 3.19-3.05 (m, 3 H), 2.44-2.30 (m, 1 H), 2.10-1.95 (m, 1 H), 1.42 (s, 9 H), 1.32 (s, 3 H), 1.21 (d, J=6.7 Hz, 3 H). m/z (APCI+) for C$_{25}$H$_{36}$N$_8$O$_3$ 497.6 (M+H)$^+$.

Step 4: Preparation of 5-{2-[(3S)-3-methylmorpholin-4-yl]-7-[(3S)-3-methylpyrrolidin-3-yl]-6,7-dihydro-5H-pyrrolo[2,3-d]pyrimidin-4-yl}pyrimidin-2-amine hydrochloride

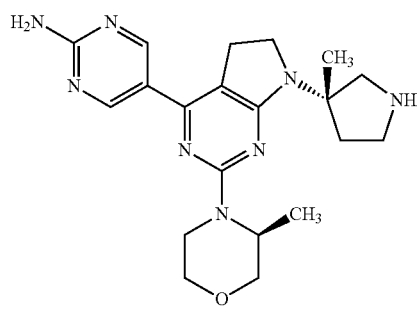 [SMILES: C[C@H]1COCCN1c1nc(-c2cnc(N)nc2)c2c(n1)N([C@@]1(C)CCNC1)CC2]

To a flask containing tert-butyl(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidine-1-carboxylate (3290 mg, 6.625 mmol) in 31 mL MeOH was added 4 N HCl in dioxane (33 mL, 132 mmol) dropwise at 0° C. and the mixture was stirred at room temperature for 2 h. The mixture was diluted with toluene and concentrated. Additional toluene was added and the solution was concentrated to give the title compound (3.73 g, >99%) as a yellow foam. $^1$H NMR (400 MHz, DMSO-d$_6$) δ 9.62 (br s, 2 H), 8.69 (s, 2 H), 7.33-7.11 (m, 2H), 4.63-4.52 (m, 1 H), 4.20 (d, J=11.5 Hz, 1 H), 4.03-3.89 (m, 2 H), 3.83-3.18 (m, 10 H), 3.14-3.03 (m, 2 H), 2.71-2.55 (m, 1 H), 2.20-2.04 (m, 1 H), 1.48 (s, 3 H), 1.28 (d, J=6.7 Hz, 3 H). m/z (APCI+) for C$_{20}$H$_{28}$N$_8$O 397.5 (M+H)$^+$.

Step 5: Preparation of tert-butyl {1-[(3S)-3-{4-(2-aminopyrimidin-5-yl)-2[(3S)-3-methylmorpholin-4-yl]-5,6-dihydro-7H-pyrrolo[2,3-d]pyrimidin-7-yl}-3-methylpyrrolidin-1-yl]-2-methyl-1-oxopropan-2-yl}carbamate

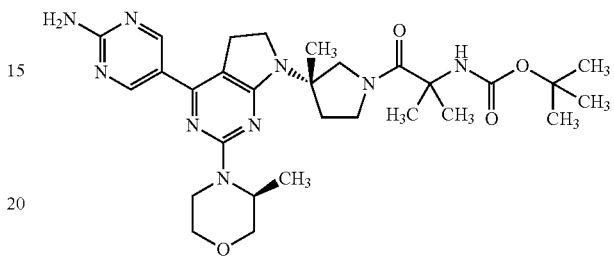

To a solution of 2-tert-butoxycarbonylamino-2-methylpropionic acid (728 mg, 3.58 mmol) in anhydrous DMF (13.8 mL) at 0° C. was added HATU (1570 mg, 4.13 mmol) portionwise, and the mixture was stirred at 0° C. for 40 min. 5-{2-[(3S)-3-methylmorpholin-4-yl]-7-[(3S)-3-methylpyrrolidin-3-yl]-6,7-dihydro-5H-pyrrolo[2,3-d]pyrimidin-4-yl}pyrimidin-2-amine hydrochloride (1294 mg, 2.757 mmol) and TEA (1.92 ml, 13.8 mmol) were added and the reaction mixture was stirred at room temperature for 2 h. Water was added, the mixture was extracted with EtOAc (3 times), the combined organic layers were washed with brine, and dried over Na$_2$SO$_4$. The residue was purified via ISCO silica gel chromatography (40 g column) using a gradient of 0-100% EtOAc containing 10% MeOH/EtOAc to give the title compound (1247 mg, 78%) as a yellow solid. $^1$H NMR (400 MHz, DMSO-d$_6$) δ 8.73 (s, 2 H), 6.59 (br s, 3 H), 4.67-4.54 (m, 1 H), 4.23 (d, J=11.5 Hz, 1 H), 3.92 (d, J=14.2 Hz, 1 H), 3.83 (d, J=11.4 Hz, 1 H), 3.70-3.40 (m, 7 H), 3.22-3.05 (m, 6 H), 2.12-2.02 (m, 1 H), 1.37 (s, 9 H), 1.35 (s, 6 H), 1.31 (s, 3 H). m/z (APCI+) for C$_{29}$H$_{43}$N$_9$O$_4$ 582.7 (M+H)$^+$.

Step 6: Preparation of 2-amino-1-[(3S)-3-{4-(2-aminopyrimidin-5-yl)-2[(3S)-3-methylmorpholin-4-yl]-5,6-dihydro-7H-pyrrolo[2,3-d]pyrimidin-7-yl}-3-methylpyrrolidin-1-yl]-2-methylpropan-1-one

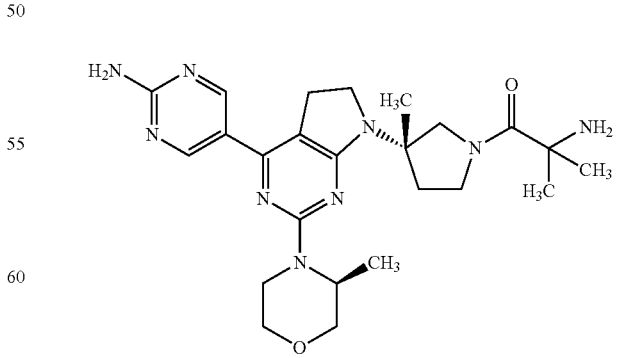

To a solution of tert-butyl {1-[(3S)-3-{4-(2-aminopyrimidin-5-yl)-2[(3S)-3-methylmorpholin-4-yl]-5,6-dihydro-7H-pyrrolo[2,3-d]pyrimidin-7-yl}-3-methylpyrrolidin-1-yl]-2- methyl-1-oxopropan-2-yl}carbamate (778 mg, 0.1 mmol) in MeOH (6.5 mL) was added 4 N HCl in dioxane (6.7 mL, 26.8 mmol) dropwise at 0° C. and the reaction was stirred at room temperature for 2 h. Toluene was added and the mixture was concentrated to give a residue that was purified by SFC/ZymorSpher HAP column (150×21.2 mm) eluting with 15-35% $CO_2$ in MeOH over 6 min at 120 bar and with a flow of 100 mL/min to give 468 mg of the title compound as a white solid. The solid was treated with hydroxide resin in MeOH for 15 min or until pH~8 was reached. The resin was removed by filtration washing with MeOH and 7 N ammonia in MeOH several times. The filtrate was concentrated under reduced pressure, dried under high vacuum and lyophilized to give the title compound (387.8 mg, 60%) as a white solid. $^1$H NMR (400 MHz, DMSO-$d_6$, 80° C.) δ 8.73 (s, 2 H), 6.60 (br s, 2 H), 4.63 (d, J=6.6 Hz, 1 H), 4.36-4.16 (m, 2 H), 4.00 (d, J=11.6 Hz, 1 H), 3.94-3.85 (m, 1 H), 3.75-3.37 (m, 7 H), 3.22-3.05 (m, 3 H), 2.44-2.29 (m, 1 H), 2.08-1.95 (m, 1 H), 1.69 (br s, 2 H), 1.32 (s, 3 H), 1.28 (s, 6 H), 1.22 (d, J=6.72 Hz, 3 H). m/z (APCI+) for $C_{24}H_{35}N_9O_2$ 482.6 (M+H)$^+$.

Examples 6 and 7 (Scheme A)

Preparation of (3S)-3-[4-(2-aminopyrimidin-5-yl)-2-(morpholin-4-yl)-5,6-dihydro-7H-pyrrolo[2,3-d]pyrimidin-7-yl]-3-methyl-1,3'-bipyrrolidin-2'-one

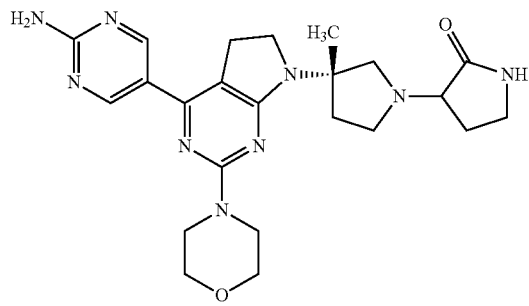 [SMILES: C[C@]1(N2CCc3c(-c4cnc(N)nc4)nc(N4CCOCC4)nc32)CCN(C2CCNC2=O)C1]

To a stirred solution of the product of Example 4, Step 2, 5-{7-[(3S)-3-methylpyrrolidin-3-yl]-2-(morpholin-4-yl)-6,7-dihydro-5H-pyrrolo[2,3-d]pyrimidin-4-yl}pyrimidin-2-amine hydrochloride (320 mg, 0.764 mmol) and TEA (232 mg, 2.29 mmol) in DCM (16 mL) was added 3-bromo-pyrrolidin-2-one (188 mg, 1.15 mmol) at 25° C. The mixture was stirred at 40° C. for 3 days, whereupon water (10 mL) was added. The mixture was extracted with DCM (20 mL×3). The combined organic layers were washed with brine (20 mL×3), dried over $Na_2SO_4$, filtered and concentrated to give a crude product (400 mg) as a yellow solid. The residue was purified by preparative TLC (silica gel, 10:1 DCM/MeOH) to give the racemic title compound (170 mg, 48%) as a yellow solid. This material was separated by preparative SFC column (AS, 250 mm×30 mm, 10 μm), mobile phase: 45% MeOH and $NH_3$ in $H_2O$, with a flowrate of 80 mL/min) to give the title compounds: Enantiomer 1 (Example 6), retention time 6.23 min (50 mg, 29%) as a yellow solid and enantiomer 2, retention time 6.21 min (19 mg) as a yellow solid. Enantiomer 1: SFC Retention time: 6.23 min; $^1$H NMR (400 MHz, CD$_3$OD) δ 8.79 (s, 2 H), 3.76-3.68 (m, 10 H), 3.43-3.33 (m, 5 H), 3.14-3.12 (m, 2 H), 3.05-3.00 (m, 1 H), 2.89-2.85 (m, 1 H), 2.56-2.53 (m, 1 H), 2.35-2.30 (m, 1 H), 2.14-2.10 (m, 1H), 2.00-1.95 (m, 1 H), 1.44 (s, 3 H). m/z (APCI+) for $C_{23}H_{31}N_9O_2$ 466.2 (M+H)$^+$. Enantiomer 2 (Example 7): SFC Retention time 6.21 min; $^1$H NMR (400 MHz, CD$_3$OD) δ 8.79 (s, 2 H), 3.82-3.68 (m, 12 H), 3.46-3.40 (m, 1 H), 3.36-3.33 (m, 1 H), 3.14-3.10 (m, 3 H), 3.03-3.00 (m, 1 H), 2.95-2.90 (m, 1 H), 2.54-2.51 (m, 1 H), 2.40-2.35 (m, 1 H), 2.14-2.11 (m, 1 H), 2.04-2.02 (m, 1 H), 1.44 (s, 3 H). m/z (APCI+) for $C_{23}H_{31}N_9O_2$ 466.2 (M+H)$^+$.

Example 8 (Scheme A)

Preparation of 5-{7-[(3S)-1-(5,5-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine

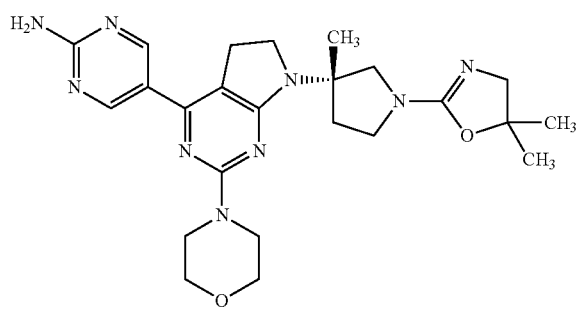 [SMILES: CC1(C)CN=C(N2CC[C@](C)(N3CCc4c(-c5cnc(N)nc5)nc(N5CCOCC5)nc43)C2)O1]

Step 1: Preparation of (3S)-3-[4-chloro-2-(morpholin-4-yl)-5,6-dihydro-7H-pyrrolo[2,3-d]pyrimidin-7-yl]-N-(2-hydroxy-2-methylpropyl)-3-methylpyrrolidine-1-carbothioamide

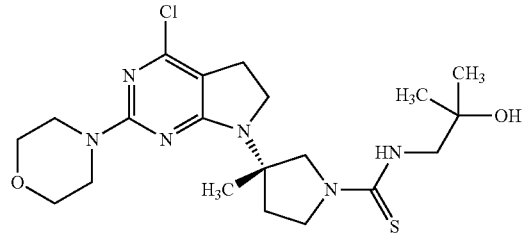 [SMILES: CC(C)(O)CNC(=S)N1CC[C@](C)(N2CCc3c(Cl)nc(N4CCOCC4)nc32)C1]

A solution of 4 M hydrochloric acid in dioxane (5 mL) was added to a solution of the product of Example 4, step 2, tert-butyl(3S)-3-[4-chloro-2-(morpholin-4-yl)-5,6-dihydro-7H-pyrrolo[2,3-d]pyrimidin-7-yl]-3-methylpyrrolidine-1-carboxylate (424 mg, 1.00 mmol) in DCM (5 mL) at room temperature, and the mixture was stirred for 20 h. The reaction mixture was concentrated to give 4-chloro-7-[(3S)-3-methylpyrrolidin-3-yl]-2-(morpholin-4-yl)-6,7-dihydro-5H-pyrrolo[2,3-d]pyrimidine hydrochloride (550 mg). This material was dissolved in a biphasic mixture of DCM (10 mL) and saturated aqueous $Na_2CO_3$ (20 mL) and cooled to 0° C. Thiophosgene (383 μL, 5.00 mmol) was added and after 10 min of stirring, the organic layer was separated, dried with $Na_2SO_4$, filtered and concentrated to give (3S)-3-[4-chloro-2-(morpholin-4-yl)-5,6-dihydro-7H-pyrrolo[2,3-d]pyrimidin-7-yl]-3-methylpyrrolidine-1-carbothioyl chloride (429 mg). To a half of this material (201 mg, 0.50 mmol) in DCM (5 mL) was added a solution of 1-amino-2-methylpropan-2-ol (66.9 mg, 0.75 mmol) and triethylamine (36.1 μL, 0.50 mmol) in DCM (1.0 mL) at room temperature and the mixture was stirred for 20.5 h. The reaction mixture was concentrated, the residue was suspended in THF (5 mL) followed by addition of triethylamine (36.1 μL, 0.50 mmol). After 22 h of stirring at room temperature, the reaction mixture was partitioned between DCM and 50% brine solution. The organic layer was separated, dried with $Na_2SO_4$, filtered and concentrated. The residue was purified by silica gel chromatography using a 0-100% gradient elution with 20% ethanol in ethyl acetate and heptane to give the title compound (62 mg, 27%). $^1$H NMR (400 MHz, DMSO-$d_6$) δ 6.66 (br s, 1 H), 4.56 (s, 1 H), 4.09 (br s, 1 H), 3.93 (d, J=1.3 Hz, 1 H), 3.75-3.64 (m, 2 H), 3.59 (d, J=4.7 Hz, 9 H), 3.57-3.49 (m, 3 H), 3.46 (br s, 1 H), 2.82 (t, J=8.3 Hz, 2 H), 2.10 (br s, 1 H), 1.30 (s, 3 H), 1.08 (s, 6 H). m/z (APCI+) for $C_{20}H_{31}N_6O_2SCl$ 455.2 (M+H)$^+$.

Step 2: Preparation of 5-{7-[(3S)-1-(5,5-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine

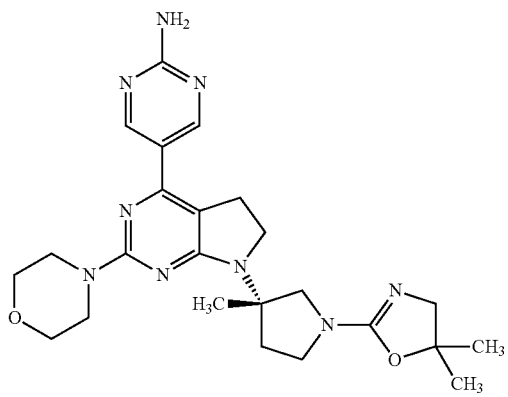 [SMILES: CC1(C)CN=C(N2CC[C@](C)(N3CCc4c(-c5cnc(N)nc5)nc(N5CCOCC5)nc43)C2)O1]

To a solution of (3S)-3-[4-chloro-2-(morpholin-4-yl)-5,6-dihydro-7H-pyrrolo[2,3-d]pyrimidin-7-yl]-N-(2-hydroxy-2-methylpropyl)-3-methylpyrrolidine-1-carbothioamide (62 mg, 0.14 mmol) in ethanol (1.36 mL) was added diisopropylethylamine (52.2 μL, 0.30 mmol) and methyl iodide (28.1 μL, 0.45 mmol) followed by DCM (1.36 mL) at room temperature and the mixture was stirred for 24 h. Additional diisopropylethylamine (52.2 μL, 0.30 mmol) was added and stirring was continued for 1.5 h, whereupon additional methyl iodide (20.0 μL, 0.32 mmol) was added. After stirring for 25 h, the reaction mixture was partitioned between dichloromethane and 50% brine solution. The organic layer was separated, dried with $Na_2SO_4$, filtered and concentrated to give 4-chloro-7-[(3S)-1-(5,5-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidine (86 mg) which was used in the next step directly without purification. This material (86 mg, 0.14 mmol) and 5-(4,4,5,5-tetramethyl-1,3,2-dioxaborolan-2-yl)pyrimidin-2-amine (45.4 mg, 0.21 mmol) were suspended in acetonitrile (2.74 mL) and argon was bubbled into the mixture. A 1 M solution of aqueous cesium fluoride (0.21 mL) and 1,1'-bis(di-tert-butylphosphino)ferrocene palladium dichloride (8.9 mg, 0.014 mmol) were added at room temperature. The argon line was removed and the reaction vessel was sealed. The reaction mixture was heated at 80° C. for 4 h, and allowed to cool to room temperature. The reaction mixture was then heated at 100° C. for 30 min in a microwave reactor and then heated to 120° C. for 15 min in a microwave reactor. After cooling to room temperature, argon was bubbled into the reaction mixture and 5-(4,4,5,5-tetramethyl-1,3,2-dioxaborolan-2-yl)pyrimidin-2-amine (20.0 mg, 0.092 mmol) and 1,1'-bis(di-tert-butylphosphino)ferrocene palladium dichloride (5 mg, 0.0079 mmol) were added. The argon line was removed and the reaction vessel was sealed. The reaction mixture was heated at 120° C. for 30 min in a microwave reactor. Additional 1,1'-bis(di-tert-butylphosphino)ferrocene palladium dichloride (5 mg, 0.0079 mmol) was added and the reaction mixture was heated at 120° C. for 30 min in a microwave reactor. The reaction mixture was partitioned between DCM (containing ~5% ethanol) and 50% brine solution. The organic layer was separated, dried with $Na_2SO_4$, filtered and concentrated. The residue was purified by preparative HPLC (Phenomenex Gemini-NX C18 150×21.2 mm, 5 μm, 100A column) eluting with 18-50% acetonitrile containing 10 mM ammonium acetate with a flow rate of 40 mL/min to give the title compound (14 mg, 21%) as a white solid. $^1$H NMR (400 MHz, DMSO-$d_6$) δ 8.73 (s, 2 H), 6.60 (s, 2 H), 3.80 (d, J=10.7 Hz, 1 H), 3.67 (s, 8 H), 3.52-3.65 (m, 3 H), 3.30-3.44 (m, 4 H), 3.06-3.11 (m, 2 H), 2.41-2.48 (m, 1 H), 2.08 (ddd, J=12.4, 7.2, 5.1 Hz, 1 H), 1.34 (br s, 3 H), 1.34 (s, 3 H), 1.33 (s, 3 H). m/z (APCI+) for $C_{24}H_{33}N_9O_4$ 480.2 (M+H)$^+$.

Example 9 (Scheme A)

Preparation of 5-{7-[(3S)-1-(4,4-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine

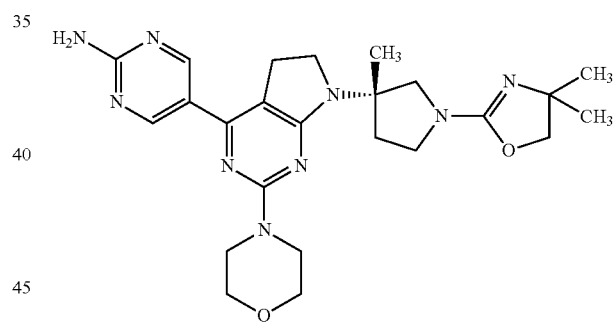

Step 1: Preparation of 2-[(tert-butoxycarbonyl)amino]-2-methylpropyl 4-methoxybenzoate

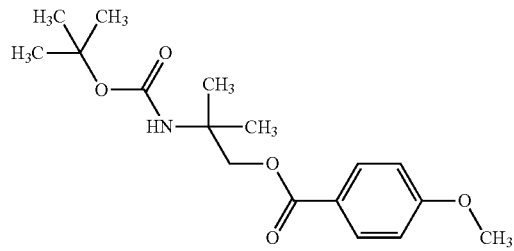 [SMILES: COc1ccc(C(=O)OCC(C)(C)NC(=O)OC(C)(C)C)cc1]

To a solution of tert-butyl(1-hydroxy-2-methylpropan-2-yl)carbamate (0.95 g, 5.0 mmol) and diisopropylethylamine (0.87 mL, 5.0 mmol) in DCM (25 mL) was added 4-methoxybenzoyl chloride (0.69 mL, 5.0 mmol) at room temperature and the mixture was stirred for 4 h. The reaction mixture was partitioned between DCM and 50% brine solution. The organic layer was separated, dried with $Na_2SO_4$, filtered and concentrated. The residue was dissolved in ethyl acetate and washed with 0.5 M hydrochloric acid. The organic layer was separated, dried with $Na_2SO_4$, filtered, and concentrated. The residue was purified by silica gel chromatography using gradient elution of ethyl acetate in heptane (0-25%) to give the title compound (0.55 g, 34%) as a white solid. $^1$H NMR (400 MHz, $CDCl_3$) δ 8.09-7.90 (m, 2 H), 7.04-6.81 (m, 2 H), 4.65 (br s, 1 H), 4.35 (s, 2H), 3.88 (s, 3 H), 1.44 (s, 9 H), 1.40 (s, 6 H). m/z (APCI+) for $C_{17}H_{25}NO_5$ 224.1 (M-tBuCO$_2$—+H)$^+$.

Step 2: Preparation of 2-amino-2-methylpropyl 4-methoxybenzoate hydrochloride

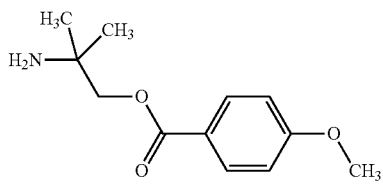

A solution of hydrochloric acid in dioxane (5.0 mL, 20.0 mmol) was added to a solution of 2-[(tert-butoxycarbonyl)amino]-2-methylpropyl 4-methoxybenzoate (0.32 g, 1.0 mmol) in DCM (10 mL) and the mixture was stirred for 1.5 h at room temperature. The reaction mixture was concentrated to give the title compound (0.26 g, 100%) as a white solid. $^1$H NMR (400 MHz, DMSO-$d_6$) δ 8.32 (br s, 3 H), 8.11 (m, J=8.9 Hz, 2 H), 7.06 (m, J=8.9 Hz, 2 H), 4.24 (s, 2 H), 3.85 (s, 3 H), 1.35 (s, 6 H). m/z (APCI+) for $C_{12}H_{17}NO_3$ 224.0 (M+H)$^+$.

Step 3: Preparation of 2-isothiocyanato-2-methylpropyl 4-methoxybenzoate

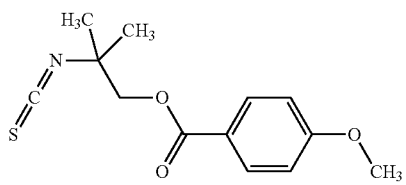

A biphasic mixture of 2-amino-2-methylpropyl 4-methoxybenzoate hydrochloride (0.24 g, 0.92 mmol), DCM (9.2 mL) and saturated aqueous $Na_2CO_3$ (18.5 mL) was cooled to 0° C. Thiophosgene (0.35 mL, 4.62 mmol) was added and the mixture was stirred for 15 min. The organic layer was separated, dried with $Na_2SO_4$, filtered and concentrated to give the title compound (0.24 g, 99%) as a colorless oil. $^1$H NMR (400 MHz, $CDCl_3$) δ 8.17-7.92 (m, 2 H), 7.06-6.81 (m, 2 H), 4.27 (s, 2 H), 3.89 (s, 3 H), 1.50 (s, 6 H).

Step 4: Preparation of 2-[({(3S)-3-[4-(2-aminopyrimidin-5-yl)-2-(morpholin-4-yl)-5,6-dihydro-7H-pyrrolo[2,3-d]pyrimidin-7-yl]-3-methyl pyrrolidin-1-yl}carbothioyl)amino]-2-methylpropyl 4-methoxybenzoate

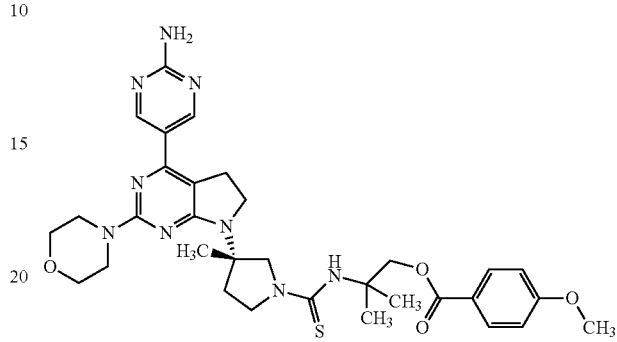

To a solution of the product of Example 4, Step 2, 5-{7-[(3S)-3-methylpyrrolidin-3-yl]-2-(morpholin-4-yl)-6,7-dihydro-5H-pyrrolo[2,3-d]pyrimidin-4-yl}pyrimidin-2-amine hydrochloride (45.2 mg, 0.092 mmol), 2-isothiocyanato-2-methylpropyl 4-g methoxybenzoate (24.5 mg, 0.092 mmol) and diisopropylethylamine (19.4 μL, 0.11 mmol) in DCM (0.92 mL) was added isopropanol (0.10 mL) at room temperature and the mixture was stirred for 24 h. Diisopropylethylamine (19.4 μL, 0.11 mmol) was added and the mixture was stirred for 1.5 h, whereupon the reaction mixture was partitioned between DCM and brine. The organic layer was separated, dried with $Na_2SO_4$, filtered and concentrated to give the title compound (59.9 mg, 97%). $^1$H NMR (400 MHz, DMSO-$d_6$) δ 8.78-8.66 (m, 2 H), 7.96-7.85 (m, 2 H), 7.05-6.94 (m, 2 H), 6.62 (s, 2H), 6.03 (s, 1 H), 4.81-4.62 (m, 2 H), 4.33 (s, 1 H), 4.20 (d, J=11.9 Hz, 1 H), 3.95 (d, J=11.4 Hz, 1 H), 3.84-3.79 (m, 3 H), 3.74-3.60 (m, 8 H), 3.60-3.44 (m, 2 H), 3.16-3.03 (m, 2 H), 2.65-2.54 (m, 1 H), 2.13 (dt, J=12.4, 6.3 Hz, 1 H), 1.59 (d, J=6.2 Hz, 6H), 1.50 (s, 3 H), 1.28 (br s, 9 H). m/z (APCI+) for $C_{32}H_{41}N_9O_4S$ 647.8 (M+H)$^+$.

Step 5: Preparation of (3S)-3-[4-(2-aminopyrimidin-5-yl)-2-(morpholin-4-yl)-5,6-dihydro-7H-pyrrolo[2,3-d]pyrimidin-7-yl]-N-(1-hydroxy-2-methylpropan-2-yl)-3-methylpyrrolidine-1-carbothioamide

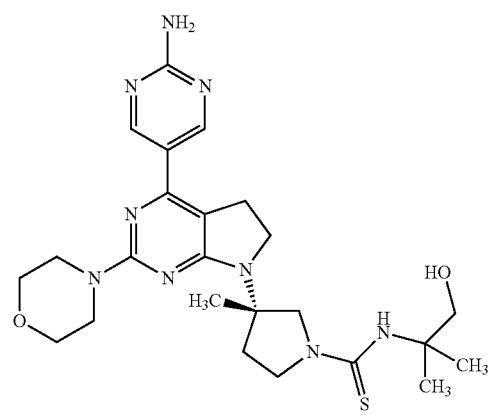 [SMILES: CC(C)(CO)NC(=S)N1CC[C@](C)(N2CCc3c(-c4cnc(N)nc4)nc(N4CCOCC4)nc32)C1]

A 1 M solution of lithium hydroxide in water (86.4 µL) was added to a solution of 2-[({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbothioyl)amino]-2-methylpropyl 4-g methoxybenzoate (56.0 mg, 0.086 mmol) in tetrahydrofuran (0.43 mL) and methanol (0.22 mL) and the mixture was stirred for 20 h at room temperature. The reaction mixture was partitioned between ethyl acetate and 50% brine solution. The organic layer was separated, dried with $Na_2SO_4$, filtered and concentrated to give the title compound (41.0 mg, 92%). $^1H$ NMR (400 MHz, DMSO-$d_6$) δ 8.73 (s, 2 H), 6.62 (br s, 2H), 5.94 (s, 1 H), 4.25 (s, 1 H), 4.13 (d, J=11.7 Hz, 1 H), 3.95 (d, J=10.9 Hz, 1 H), 3.68 (br s, 10 H), 3.60-3.49 (m, 4 H), 3.13-3.08 (m, 3 H), 2.16-2.08 (m, 1 H), 1.47 (s, 6 H), 1.35 (s, 3 H). m/z (APCI+) for $C_{24}H_{35}N_9O_2S$ 513.8 (M+H)$^+$.

Step 6: Preparation of 5-{7-[(3S)-1-(4,4-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine

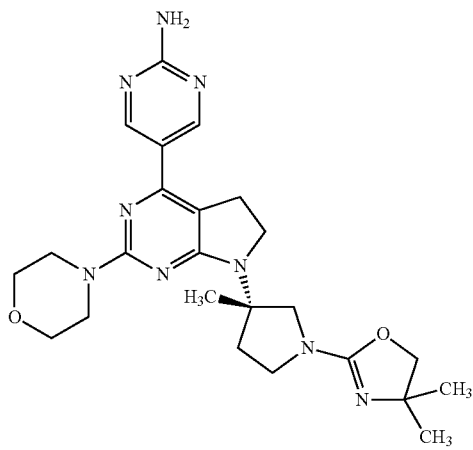 [SMILES: CC1(C)COC(N2CC[C@](C)(N3CCc4c(-c5cnc(N)nc5)nc(N5CCOCC5)nc43)C2)=N1]

Methyl iodide (15.2 µL, 0.24 mmol) was added to a solution of (S)-3-(4-(2-aminopyrimidin-5-yl)-2-morpholino-5,6-dihydro-7H-pyrrolo[2,3-d]pyrimidin-7-yl)-N-(1-hydroxy-2-methylpropan-2-yl)-3-methylpyrrolidine-1-carbothioamide (38.0 mg, 0.074 mmol) and diisopropylethylamine (28.3 µL, 0.16 mmol) in DCM (0.74 mL) and ethanol (0.74 mL) and the mixture was stirred at room temperature for 23 h. The reaction mixture was partitioned between DCM and 50% brine solution. The organic layer was separated, dried with $Na_2SO_4$, filtered and concentrated. The residue was purified by preparative SFC (Cosmosil 3-hydroxyphenyl bonded 150×21.2 mm, 5 µm, 100A column) eluting with 15%-50% $CO_2$ in MeOH with a flow rate of 80 mL/min, at 100 bar to give the title compound (12.9 mg, 36%) as a white solid. $^1H$ NMR (700 MHz, DMSO-$d_6$) δ 8.72 (s, 2 H), 6.99 (s, 2 H), 3.94-3.86 (m, 2 H), 3.74 (d, J=10.4 Hz, 1 H), 3.68-3.59 (m, 8H), 3.55-3.52 (m, 1 H), 3.11-3.06 (m, 2 H), 2.41 (dt, J=12.4, 7.9 Hz, 1 H), 2.10 (ddd, J=12.4, 7.3, 5.0 Hz, 1 H), 1.29 (s, 3 H), 1.17-1.10 (m, 6 H). m/z (APCI+) for $C_{24}H_{33}N_9O_2$ 479.9 (M+H)$^+$.

Example 10 (Scheme B)

Preparation of (S)-2-amino-1-(3-(4-(2-aminopyrimidin-5-yl)-2-morpholino-$d_8$)-5,6-dihydro-7H-pyrrolo[2,3-d]pyrimidin-7-yl)-3-methylpyrrolidin-1-yl)-2-methylpropan-1-one hydrochloride

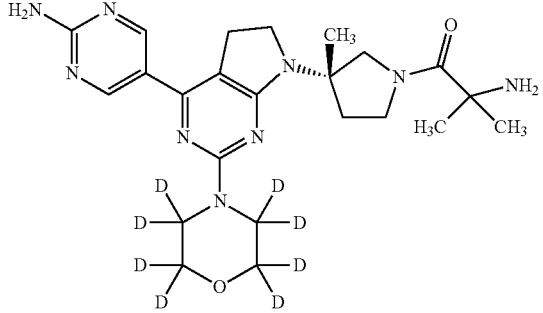 [SMILES: [2H]C1([2H])OC([2H])([2H])C([2H])([2H])N(c2nc(-c3cnc(N)nc3)c3c(n2)N([C@@]2(C)CCN(C(=O)C(C)(C)N)C2)CC3)C1([2H])[2H]]

Step 1: Preparation of tert-butyl(3S)-3-{[6-chloro-5-(2-hydroxyethyl)-2-(methylsulfanyl)pyrimidin-4-yl]amino}-3-methylpyrrolidine-1-carboxylate

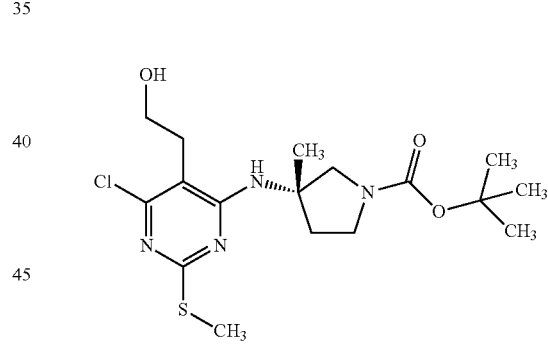

To a solution of 2-[4,6-dichloro-2-(methylsulfanyl)pyrimidin-5-yl]ethanol (1.25 g, 5.23 mmol) and tert-butyl(3S)-3-amino-3-methylpyrrolidine-1-carboxylate (1.57 g, 7.84 mmol) in DMSO (13 mL) was added DIEA (4.6 mL, 26.1 mmol) at room temperature. The reaction mixture was stirred at 110° C. for 42 h, whereupon the mixture was poured into EtOAc and washed with water. The water layer was extracted with EtOAc (3 times). The combined organic layers were washed with brine, dried over $Na_2SO_4$, filtered and concentrated. The residue was purified via ISCO normal phase silica gel chromatography (80 g column) eluting with a 0-100% gradient of EtOAc/Heptane to give the title compound (1.37 g, 65%) as a light yellow-white foamy solid. $^1H$ NMR (400 MHz, DMSO-$d_6$) δ 6.96 (d, J=17.0 Hz, 1 H), 5.06 (br s, 1 H), 3.75 (dd, J=20.6, 11.2 Hz, 1 H), 3.54 (br s, 2 H), 3.50-3.33 (m, 3 H), 2.77 (t, J=6.3 Hz, 2 H), 2.44 (s, 3 H), 2.40-2.23 (m, 1 H), 2.03-1.93 (m, 1 H), 1.47 (d, J=11.1 Hz, 3 H), 1.38 (d, J=13.4 Hz, 9 H). m/z (APCI+) for $C_{17}H_{27}ClN_4O_3S$ 403.9 (M+H)+.

Step 2: Preparation of tert-butyl(3S)-3-{[6-chloro-2-(methylsulfanyl)-5-{2-[(methylsulfonyl)oxy]ethyl}pyrimidin-4-yl]amino}-3-methylpyrrolidine-1-carboxylate

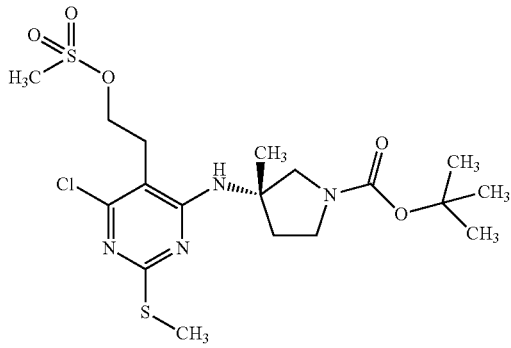 [SMILES: CSc1nc(Cl)c(CCOS(C)(=O)=O)c(N[C@@]2(C)CCN(C(=O)OC(C)(C)C)C2)n1]

To a solution of tert-butyl(3S)-3-{[6-chloro-5-(2-hydroxyethyl)-2-(methylsulfanyl)pyrimidin-4-yl]amino}-3-methylpyrrolidine-1-carboxylate (1.37 g, 3.40 mmol) in DCM (57 mL) was added TEA (1.66 mL, 11.9 mmol), methanesulfonylchloride (0.7 mL, 8.5 mmol) and DMAP (25 mg, 0.204 mmol) at 0° C. The mixture was stirred at 0° C. for 1 h and then at room temperature for 1 h. The reaction mixture was transferred to a separatory funnel with the aid of DCM. The solution was washed with water (3 times), dried over $Na_2SO_4$ and concentrated to give 1.86 g (>99%) of the title compound as a yellow solid. $^1$H NMR (400 MHz, DMSO-$d_6$) δ 6.90 (d, J=18.5 Hz, 1 H), 4.28-4.19 (m, 2 H), 3.82-3.61 (m, 1 H), 3.60-3.42 (m, 1H), 3.41-3.36 (m, 1 H), 3.32-3.23 (m, 1 H), 3.13 (s, 3 H), 3.12-3.06 (m, 2 H), 2.45 (s, 3 H), 2.41-2.26 (m, 1 H), 2.07-1.97 (m, 1 H), 1.46 (d, J=11.4 Hz, 3 H), 1.38 (s, 9 H). m/z (APCI+) for $C_{18}H_{29}ClN_4O_5S_2$ 481.1 (M+H)+.

Step 3: Preparation of tert-butyl(3S)-3-[4-chloro-2-(methylsulfanyl)-5,6-dihydro-7H-pyrrolo[2,3-d]pyrimidin-7-yl]-3-methylpyrrolidine-1-carboxylate

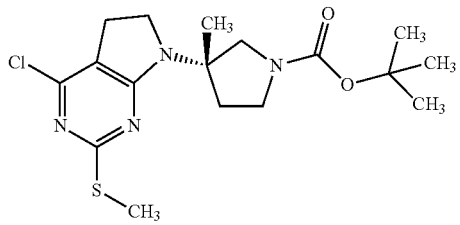 [SMILES: CSc1nc(Cl)c2c(n1)N([C@@]1(C)CCN(C(=O)OC(C)(C)C)C1)CC2]

To a solution of tert-butyl(3S)-3-{[6-chloro-2-(methylsulfanyl)-5-{2-[(methylsulfonyl)oxy]ethyl}pyrimidin-4-yl]amino}-3-methylpyrrolidine-1-carboxylate (1635 mg, 3.4 mmol) in DMF (34 mL) was added DBU (1.1 mL, 6.8 mmol) and the mixture was stirred at 80° C. for 90 min. The reaction mixture was diluted with EtOAc (20 mL), washed with water (20 mL) and brine (20 mL), dried over $Na_2SO_4$ and concentrated to give the title compound (1.24 g, 95%) as a light yellow-white solid. $^1$H NMR (400 MHz, DMSO-$d_6$) δ 3.80-3.57 (m, 4 H), 3.40-3.35 (m, 1 H), 3.28-3.19 (m, 1 H), 2.91 (t, J=8.9 Hz, 2 H), 2.42 (s, 3 H), 2.39-2.24 (m, 1 H), 2.07-1.94 (m, 1 H), 1.39 (d, J=5.4 Hz, 9 H), 1.28 (s, 3 H). m/z (APCI+) for $C_{17}H_{25}ClN_4O_2S$ 385.1 (M+H)+.

Step 4: Preparation of tert-butyl(3S)-3-[4-(2-aminopyrimidin-5-yl)-2-(methylsulfanyl)-5,6-dihydro-7H-pyrrolo[2,3-d]pyrimidin-7-yl]-3-methylpyrrolidine-1-carboxylate

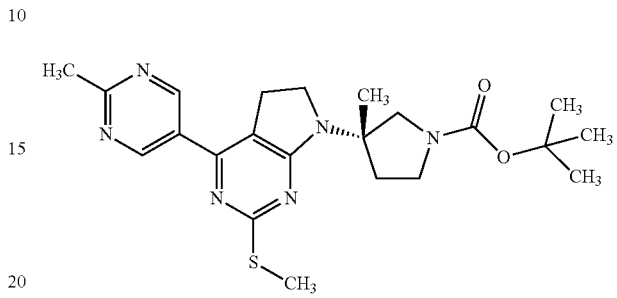

To a suspension of tert-butyl(3S)-3-[4-chloro-2-(methylsulfanyl)-5,6-dihydro-7H-pyrrolo[2,3-d]pyrimidin-7-yl]-3-methylpyrrolidine-1-carboxylate (1.24 g, 3.22 mmol) and 5-(4,4,5,5-tetramethyl-1,3,2-dioxaborolan-2-yl)pyrimidin-2-amine (1.0 g, 4.6 mmol) in dioxane (16 mL) was added 1 M $Na_2CO_3$ solution (13 mL, 12.9 mmol) at room temperature. The reaction mixture was purged with nitrogen for a few minutes before adding $PdCl_2$(dppf)-DCM (395 mg, 0.484 mmol). The reaction mixture was heated at 120° C. for 40 h in a microwave reactor. The mixture was filtered through a pad of Celite® rinsing with EtOAc several times, concentrated and purified via ISCO normal phase silica gel chromatography (40 g column) with a 0-100% gradient of EtOAc/Heptane to give the title compound (828 mg, 58%) as a white solid. $^1$H NMR (400 MHz, DMSO-$d_6$) δ 8.72 (d, J=4.6 Hz, 2 H), 7.06 (s, 2 H), 3.79-3.64 (m, 3 H), 3.63-3.51 (m, 1 H), 3.39-3.34 (m, 2 H), 3.21-3.14 (m, 2 H), 2.45 (s, 3 H), 2.41-2.27 (m, 1 H), 2.10-1.99 (m, 1 H), 1.40 (s, 9 H), 1.28 (s, 3 H). m/z (APCI+) for $C_{21}H_{29}N_7O_2S$ 444.2 (M+H)+.

Step 5: Preparation of tert-butyl(3S)-3-[4-(2-aminopyrimidin-5-yl)-2-(methylsulfinyl)-5,6-dihydro-7H-pyrrolo[2,3-d]pyrimidin-7-yl]-3-methylpyrrolidine-1-carboxylate

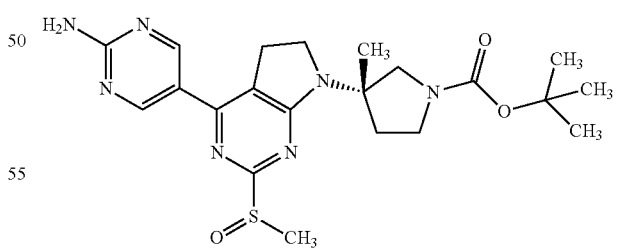

To a suspension of tert-butyl(3S)-3-[4-(2-aminopyrimidin-5-yl)-2-(methylsulfanyl)-5,6-dihydro-7H-pyrrolo[2,3-d]pyrimidin-7-yl]-3-methylpyrrolidine-1-carboxylate (352 mg, 0.794 mmol) in DCM (8 mL) was added m-chloroperoxybenzoic acid (254 mg, 1.03 mmol, 70% purity) in three portions over 1 min at 0° C. The reaction mixture was stirred at 0° C. for 30 min. Four drops of DMSO was added and the reaction mixture was stirred for 5 min. The reaction mixture was purified via HPLC reversed phase column (XBridge C18 30×250 mm, mobile phase: 0%-50% of water with 0.1% EtOAc to acetonitrile with 0.1% EtOAc over 30 min, flow rate 80 mL/min) to give the title compound (200 mg, 55%) as a white solid. $^1$H NMR (400 MHz, DMSO-$d_6$) δ 8.78 (s, 2 H), 7.18 (s, 2 H), 3.89-3.75 (m, 2 H), 3.73-3.62 (m, 3 H), 3.42-3.34 (m, 3 H), 2.82 (s, 3 H), 2.41 (br s, 1 H), 2.15-2.01 (m, 1 H), 1.41 (s, 9 H), 1.33 (s, 3 H). m/z (APCI+) for $C_{21}H_{29}N_7O_3S$ 460.6 (M+H)$^+$.

Step 6: Preparation of tert-butyl(S)-3-(4-(2-aminopyrimidin-5-yl)-2-(morpholino-$d_8$)-5,6-dihydro-7H-pyrrolo[2,3-d]pyrimidin-7-yl)-3-methylprrolidine-1-carboxylate

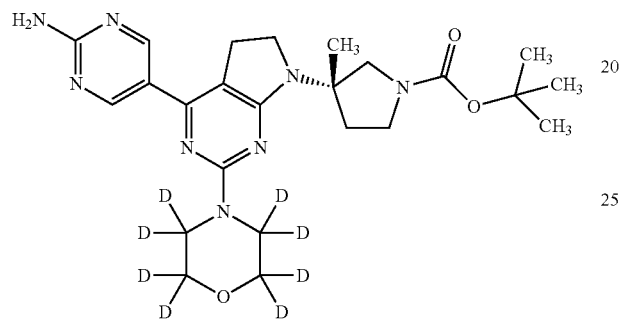

To a solution of tert-butyl(3S)-3-[4-(2-aminopyrimidin-5-yl)-2-(methylsulfinyl)-5,6-dihydro-7H-pyrrolo[2,3-d]pyrimidin-7-yl]-3-methylpyrrolidine-1-carboxylate (98.9 mg, 0.215 mmol) in acetonitrile (0.8 mL) was added morpholine-$d_8$ (61.4 mg, 0.646 mmol) and DIEA (0.2 mL, 0.131 mmol) and the reaction mixture was heated at 110° C. for 144 h. The crude material was directly purified via HPLC reversed phase column (XBridge C18 30×250 mm, mobile phase: 0%-40% of water with 0.1% EtOAc to acetonitrile with 0.1% of EtOAc over 25 min, flowrate 80 mL/min) to give the title compound (70.6 mg, 67%). $^1$H NMR (400 MHz, DMSO-$d_6$) δ 8.72 (s, 2 H), 6.96 (s, 2 H), 3.83 (d, J=10.9 Hz, 1 H), 3.67 (dd, J=24.2, 15.0 Hz, 3 H), 3.55-3.45 (m, 1 H), 3.41-3.34 (m, 1 H), 3.13-3.04 (m, 2 H), 2.36-2.23 (m, 1 H), 2.08-1.96 (m, 1 H), 1.40 (s, 9 H), 1.29-1.21 (m, 3H). m/z (APCI+) for $C_{24}H_{26}D_8N_8O_3$ 491.6 (M+H)$^+$.

Step 7: Preparation of (S)-5-(7-(3-methylpyrrolidin-3-yl)-2-(morpholine-$d_8$)-6,7-dihydro-5H-pyrrolo[2,3-d]pyrimidin-4-yl)pyrimidin-2-amine hydrochloride

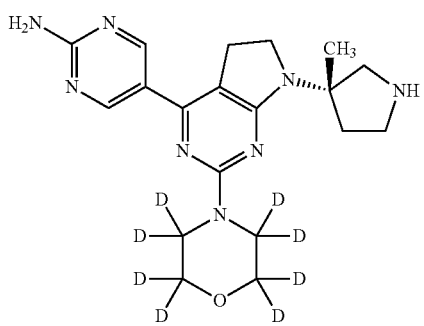 [SMILES: [2H]C1([2H])OC([2H])([2H])C([2H])([2H])N(c2nc(-c3cnc(N)nc3)c3c(n2)N([C@@]2(C)CCNC2)CC3)C1([2H])[2H]]

To a solution of tert-butyl(S)-3-(4-(2-aminopyrimidin-5-yl)(morpholino-$d_8$) 5,6-dihydro-7H-pyrrolo[2,3-d]pyrimidin-7-yl)-3-methylpyrrolidine-1-carboxylate (29.6 mg, 0.060 mmol) in MeOH (0.3 mL) was added 4 N HCl in dioxane (0.3 mL, 1.21 mmol) dropwise at 0° C., and the reaction mixture was stirred at room temperature for 3 h. The mixture was diluted with toluene, concentrated, diluted again with toluene and concentrated to give the title compound (37.2 mg) as a yellow gum which was used directly without further purification. m/z (APCI+) for $C_{19}H_{18}D_8N_8O$ 391.5 (M+H)$^+$.

Step 8: Preparation of tert-butyl(S)-(1-(3-(4-(2-aminopyrimidin-5-yl)-2-(morpholino-$d_8$)-5,6-dihydro-7H-pyrrolo[2,3-d]pyrimidin-7-yl)-3-methylpyrrolidin-1-yl)-2-methyl-1-oxopropan-2-yl)carbamate

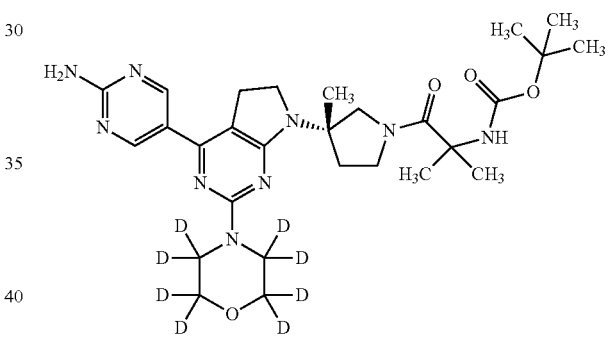

To a solution of 1-methyl-cyclopropanecarboxylic acid (49 mg, 0.243 mmol) in anhydrous DMF (1.9 mL) was added HATU (110 mg, 0.279 mmol) and the mixture was stirred at 0° C. for 30 min, whereupon (S)-5-(7-(3-methylpyrrolidin-3-yl)-2-(morpholino-$d_8$)-6,7-dihydro-5H-pyrrolo[2,3-d]pyrimidin-4-yl)pyrimidin-2-amine hydrochloride (72.4 mg, 0.097 mmol) and DIEA (0.161 mL, 0.927 mmol) were added at 0° C. and the mixture was stirred for 15 min. The reaction mixture was purified via preparative reversed phase HPLC (Column: XBridge C18 30×250 mm, mobile phase: 0%-40% of water with 0.1% EtOAc to acetonitrile with 0.1% of EtOAc over 25 min, flowrate 80 mL/min) to give the title compound (53.8 mg, 50%) as a white solid. $^1$H NMR (400 MHz, DMSO-$d_6$) δ 8.73 (s, 2 H), 6.98 (s, 2 H), 3.80-3.56 (m, 3 H), 3.58-3.38

(m, 3 H), 3.14-3.00 (m, 2 H), 2.26-1.93 (m, 2 H), 1.36 (s, 9 H), 1.32-1.24 (m, 9 H). m/z (APCI+) for $C_{28}H_{33}D_8N_9O_4$ 576.7 (M+H)+.

Step 9: Preparation of 2-amino-1-[(3S)-3-{4-(2-aminopyrimidin-5-yl)-2-[(~2~H8)morpholin-4-yl]-5,6-dihydro-7H-pyrrolo[2,3-d]pyrimidin-7-yl}-3-methylpyrrolidin-1-yl]-2-methylpropan-1-one hydrochloride

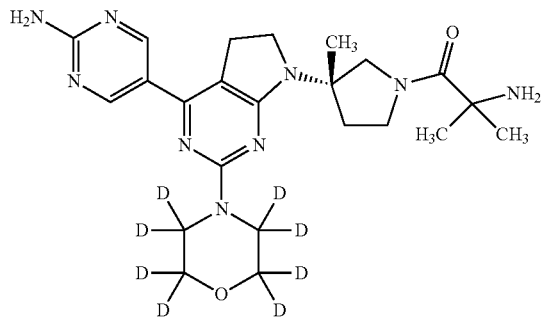 [SMILES: [2H]C1([2H])OC([2H])([2H])C([2H])([2H])N(c2nc(-c3cnc(N)nc3)c3c(n2)N([C@@]2(C)CCN(C(=O)C(C)(C)N)C2)CC3)C1([2H])[2H]]

To a solution of tert-butyl(S)-(1-(3-(4-(2-aminopyrimidin-5-yl(morpholino-d8)-5,6-dihydro-7H-pyrrolo[2,3-d]pyrimidin-7-yl)-3-methylpyrrolidin-1-yl)-2-methyl-1-oxopropan-2-yl)carbamate (48.9 mg, 0.085 mmol) in MeOH (0.4 mL) was added 4 N HCl in dioxane (0.5 mL, 1.5 mmol) dropwise at 0° C., and the reaction mixture was stirred at room temperature for 30 min. The mixture was diluted with toluene, concentrated, diluted again with toluene and concentrated to give the title compound as a yellow solid which was purified via preparative SFC (Column: ZymorSpher HADP 150×21.2 mm) using 10-20% $CO_2$ in MeOH over 6 min at 120 bar, with a flowrate of 100 mL/min to give the title compound (38.1 mg, 94%) as a white solid. $^1$H NMR (400 MHz, DMSO-d6) δ 8.74 (s, 2 H), 6.63 (s, 2 H), 4.26-4.11 (m, 1 H), 4.04-3.91 (m, 1 H), 3.80-3.49 (m, 5 H), 3.16-3.06 (m, 2 H), 2.09 (br s, 1 H), 1.53 (d, J=11.5 Hz, 6 H), 1.36 (s, 3H). m/z (APCI+) for $C_{23}H_{25}D_8N_9O_2$ 476.6 (M+H)+.

Preparation 1: Preparation of 2-[4,6-dichloro-2-(morpholin-4-yl)pyrimidin-5-yl]ethanol

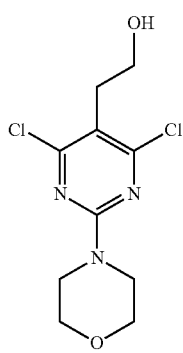 [SMILES: OCCc1c(Cl)nc(N2CCOCC2)nc1Cl]

To a solution of 4-(4,6-dichloropyrimidin-2-yl)morpholine (468 mg, 2.0 mmol) in THF (20 mL) was added n-butyllithium (1.56 mL, 1.6 M) dropwise at −78° C. After stirring for 30 min, 1,3,2-dioxathiolane 2,2-dioxide (336 mg, 2.71 mmol) was added, and after stirring for an additional 40 min, 6 N HCl (6.67 mL) was added. The reaction was stirred at room temperature for 18 h and then at 40° C. for 4 h. The reaction mixture was extracted with ethyl acetate and the organic layer was washed with brine, dried with $MgSO_4$, filtered and concentrated by rotary evaporation. The resulting residue was purified by silica gel chromatography using a gradient of EtOAc/heptane (25-75%) to give the title compound (231 mg, 42%). $^1$H NMR (400 MHz, $CDCl_3$) δ 3.84 (t, J=7.0 Hz, 2 H), 3.80-3.76 (m, 4 H), 3.76-3.72 (m, 4 H), 3.04 (t, J=7.0 Hz, 2 H). m/z (APCI+) for $C_{10}H_{13}Cl_2N_3O_2$ 277.9 (M+H)+.

Preparation 2: Preparation of 2-{4,6-dichloro-2-[(3S)-3-methylmorpholin-4-yl]pyrimidin-5-yl}ethanol Step 1: Preparation of (3S)-4-(4,6-dimethoxypyrimidin-2-yl)-3-methylmorpholine

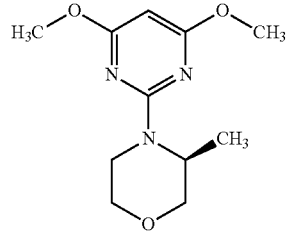

A solution of (S)-3-methylmorpholine (4.86 g, 48.0 mmol), 2-chloro-4,6-dimethoxypyrimidine (6.98 g, 40 mmol) and DIPEA (8.36 mL, 48.0 mmol) in DMSO (40 mL) was heated at 100° C. in a sealed flask for 22 h, and then allowed to cool to room temperature. The reaction mixture was placed in an ice bath, and water (120 mL) was added drop-wise. The mixture was decanted and the gummy precipitate was dissolved in ethyl acetate. The ethyl acetate solution was washed with brine, dried with $MgSO_4$, filtered and concentrated by rotary evaporation to give the title compound (8.58 g, 90%). $^1$H NMR (400 MHz, $CDCl_3$) δ 5.40 (s, 1 H), 4.69 (qd, J=6.8, 3.1 Hz, 1 H), 4.33 (dd, J=13.7, 2.9 Hz, 1 H), 4.01-3.93 (m, 1 H), 3.86 (s, 6 H), 3.78-3.73 (m, 1 H), 3.73-3.66 (m, 1 H), 3.54 (ddd, J=12.2, 11.4, 3.1 Hz, 1 H), 3.25 (ddd, J=13.5, 12.4, 3.8 Hz, 1 H), 1.29 (d, J=6.8 Hz, 3 H). m/z (APCI+) for $C_{11}H_{17}N_3O_3$ 240.0 (M+H)+.

Step 2: Preparation of 2-[(3S)-3-methylmorpholin-4-yl]pyrimidine-4,6-diol

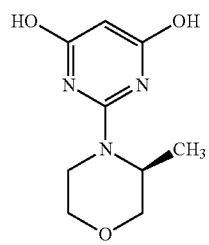

(3S)-4-(4,6-Dimethoxypyrimidin-2-yl)-3-methylmorpholine (6.3 g, 26.3 mmol) was dissolved in acetonitrile (88 mL).

Argon was bubbled into the solution and sodium iodide (11.8 g, 79.0 mmol) and TMS-Cl (10.3 mL, 79.0 mmol) were added. The reaction was heated under reflux for 2 h, and then allowed to cool to room temperature. Water (50 mL) and sodium bisulfate (2.74 g, 26.3 mmol) was added. Acetonitrile was removed by rotary evaporation and the resulting slurry was filtered. The precipitate was suspended in ethanol and concentrated to dryness by rotary evaporation to give the title compound (3.81 g, 68%). $^1$H NMR (400 MHz, DMSO-d$_6$) δ 10.61 (br s, 2 H), 4.80 (br s, 1 H), 4.40 (d, J=5.9 Hz, 1 H), 3.98 (d, J=12.7 Hz, 1 H), 3.85 (dd, J=11.3, 3.5 Hz, 1 H), 3.68-3.62 (m, 1 H), 3.56-3.50 (m, 1 H), 3.38 (td, J=11.8, 3.0 Hz, 1 H), 3.16-3.04 (m, 1 H), 1.16 (d, J=6.7 Hz, 3 H).

Step 3: Preparation of (3S)-4-(4,6-dichloropyrimidin-2-yl)-3-methylmorpholine

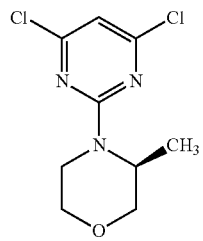

2-[(3S)-3-methylmorpholin-4-yl]pyrimidine-4,6-diol (4.06 g, 19.2 mmol) was suspended in acetonitrile (38.4 mL) and phosphorous oxychloride (14.3 mL, 154 mmol) was added. The reaction mixture was heated in a sealed vial for 2 h and then concentrated by rotary evaporation. A 1:1 mixture of acetonitrile and water (10 mL) was added dropwise with stirring keeping the temperature below 40° C. Additional water (20 mL) was added and the acetonitrile was removed by rotary evaporation. The resulting slurry was cooled to 0° C. and filtered. The precipitate was dissolved in DCM, dried with Na$_2$SO$_4$, filtered and concentrated by rotary evaporation to give the title compound (4.38 g, 92%). $^1$H NMR (400 MHz, CDCl$_3$) δ 6.56 (s, 1 H), 4.68 (qd, J=6.8, 3.1 Hz, 1 H), 4.33 (dd, J=13.7, 2.9 Hz, 1 H), 3.97 (dd, J=11.5, 3.7 Hz, 1 H), 3.79-3.73 (m, 1 H), 3.69-3.64 (m, 1 H), 3.51 (td, J=11.9, 3.0 Hz, 1 H), 3.30 (ddd, J=13.6, 12.4, 3.8 Hz, 1 H), 1.32 (d, J=6.5 Hz, 3 H). m/z (APCI+) for C$_9$H$_{11}$Cl$_2$N$_3$O 247.9 (M+H)$^+$.

Step 4: Preparation of 2-{4,6-dichloro-2-[(3S)-3-methylmorpholin-4-yl]pyrimidin-5-yl}ethanol

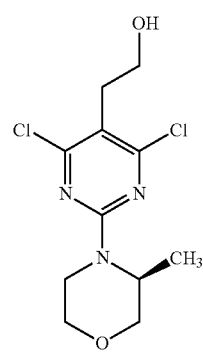 [SMILES: C[C@H]1COCCN1c1nc(Cl)c(CCO)c(Cl)n1]

To a solution of (3S)-4-(4,6-dichloropyrimidin-2-yl)-3-methylmorpholine (992 mg, 4.0 mmol) in THF (20 mL) was added n-butyllithium (1.56 mL, 1.6 M) dropwise at −78° C. and the mixture was stirred for 30 min. 1,3,2-dioxathiolane 2,2-dioxide (672 mg, 5.41 mmol) was added, and stirring was continued for 30 min, whereupon 6 N HCl (13.3 mL) was added. The reaction mixture was stirred for 18 h and then heated at 40° C. for 4 h. The reaction mixture was extracted with ethyl acetate, and the organic layer was washed with brine, dried with MgSO$_4$, filtered and concentrated by rotary evaporation.

The resulting residue was purified by silica gel chromatography using a gradient of EtOAc/heptane (0-50%) to give the title compound (991 mg, 85%). $^1$H NMR (400 MHz, CDCl$_3$) δ 4.62 (qd, J=6.7, 3.4 Hz, 1 H), 4.26 (dd, J=13.7, 2.8 Hz, 1 H), 3.97 (dd, J=11.4, 3.7 Hz, 1 H), 3.87-3.82 (m, 2 H), 3.78-3.74 (m, 1 H), 3.68-3.63 (m, 1 H), 3.50 (td, J=11.9, 3.0 Hz, 1 H), 3.28 (ddd, J=13.5, 12.4, 3.8 Hz, 1 H), 3.03 (t, J=7.0 Hz, 2H), 1.31 (d, J=6.8 Hz, 3 H). m/z (APCI+) for C$_{11}$H$_{15}$Cl$_2$N$_3$O$_2$ 291.9 (M+H)$^+$.

Preparation 3: Preparation of tert-butyl(3R)-3-amino-3-methylpyrrolidine-1-carboxylate Step 1: Preparation of N-[(3R)-1-benzyl-3-methylpyrrolidin-3-yl]acetamide(+)-di-p-anisoyl-D-tartrate

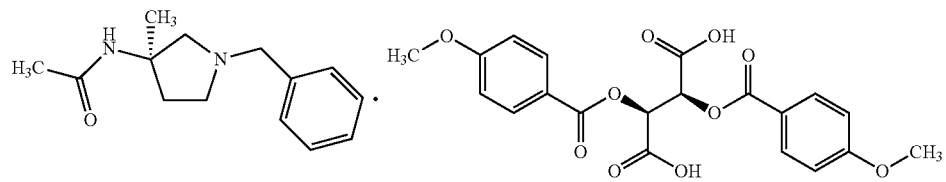

To a stirred solution of (+)-di-p-anisoyl-D-tartaric acid (25.2 g, 60.3 mmol) in EtOH (400 mL) was added N-(1-benzyl-3-methylpyrrolidin-3-yl)acetamide (20.0 g, 86.1 mmol) under nitrogen atmosphere. The mixture was stirred at 10° C. for 15 min, then at 70° C. for 10 min, whereupon the reaction mixture was cooled to room temperature and stirred for 48 h. The resultant solid was collected by filtration, the filter cake was washed with EtOH (100 mL×2) and dried under reduced pressure to give 29 g of an off-white solid. The solid was dissolved in EtOH (200 mL) and the mixture was heated at 100° C. for 30 min. The solution was cooled to room temperature, and the resultant white slurry was filtered to give 25 g of a white solid. This was repeated twice to give the title compound (20.9 g, 37%) as a white solid. This material was used in the next step without further purification.

Step 2: Preparation of (3R)-1-benzyl-3-methylpyrrolidin-3-amine

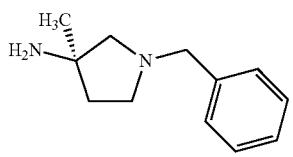

A mixture of N-[(3R)-1-benzyl-3-methylpyrrolidin-3-yl]acetamide(+)-di-p-anisoyl-D-tartrate (39.6 g, 60.9 mmol) and K₂CO₃ (25.3 g, 183 mmol) in water (500 mL) was stirred at 10° C. for 2 h. The solution was extracted with EtOAc (200 mL×3), the combined organic layers were washed with brine (150 mL), dried over Na₂SO₄ and concentrated under reduced pressure to give 14 g of a yellow oil. This material was used without further purification in the next step. A solution of this yellow oil (28.0 g, 120.5 mmol) in 6 N HCl (400 mL) was heated under reflux for 18 h. The mixture was cooled to room temperature and diluted with EtOAc (150 mL). The pH of the aqueous layer was adjusted to pH-12 with 10 N NaOH, and extracted with EtOAc (200 mL×3). The combined organic layers were washed with brine (250 mL), dried over anhydrous Na₂SO₄, filtered and concentrated under reduced pressure to provide the title compound (20.7 g, 90%) as a brown liquid. $^1$H NMR (400 MHz, DMSO-$d_6$) δ 7.34-7.16 (m, 5 H), 3.58-3.48 (m, 2 H), 2.63 (dt, J=6.1, 8.6 Hz, 1 H), 2.45 (dt, J=6.0, 8.6 Hz, 1H), 2.33-2.26 (m, 2 H), 1.86 (br s, 2 H), 1.71-1.54 (m, 2 H), 1.15 (s, 3 H). m/z (APCI+) for $C_{12}H_{18}N_2$ 191.1 (M+H)$^+$.

Step 3: Preparation of tert-butyl(3R)-3-amino-3-methylpyrrolidine-1-carboxylate

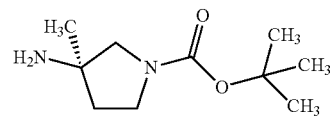

To a stirred solution of (3R)-1-benzyl-3-methylpyrrolidin-3-amine (20.7 g, 108.8 mmol) in EtOH (800 mL) was added 20% Pd(OH)₂ on carbon (9.17 g). The resulting mixture was stirred at 70° C. under 50 psi of hydrogen for 12 h. The mixture was cooled to room temperature and a solution of (Boc)₂O (23.8 g, 109 mmol) in EtOH (50 mL) was added dropwise during a period of 2 h at room temperature. After the addition, the resulting mixture was stirred at room temperature for 12 h. The mixture was filtered through a pad of Celite® washing with EtOH (50 mL×3). The filtrate was concentrated under reduced pressure to provide a residue which was purified by silica gel column chromatography eluting with a gradient of DCM/methanol (methanol containing 10% NH₄OH) (10:1), to give 8.50 g (39%) of the title compound as a white solid. $^1$H NMR (400 MHz, 80° C., DMSO-$d_6$) δ 3.42-3.34 (m, 1 H), 3.32-3.24 (m, 1 H), 3.05 (s, 2H, partially overlapped with H₂O), 1.71-1.64 (m, 2 H), 1.51 (br s, 2 H), 1.41 (s, 9 H), 1.18 (s, 3 H). m/z (APCI+) for $C_{10}H_{20}N_2O_2$ 145.1 (M—t-butylCO₂)$^-$.

Preparation 4: Preparation of tert-butyl(3S)-3-amino-3-methylpyrrolidine-1-carboxylate Step 1: Preparation of (2R)-4-(1,3-dioxo-1,3-dihydro-2H-isoindol-2-yl)-2-(ethoxycarbonyl)-2-methylbutanoic acid

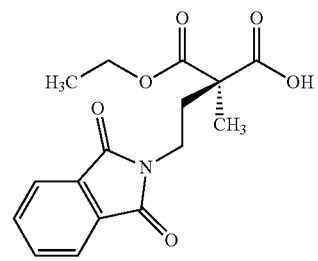 [SMILES: CCOC(=O)[C@](C)(CCN1C(=O)c2ccccc2C1=O)C(=O)O]

In a 1 L round bottom flask, diethyl[2-(1,3-dioxo-1,3-dihydro-2H-isoindol-2-yl)ethyl](methyl)propanedioate (Banerjee, S.; Wiggins, W. J.; Geoghegan, J. L.; Anthony, C. T.; Woltering, E. A.; Masterson, D. S. *Org. Biomol. Chem.*, 2013, 11, 6307-6319) (9.56 g, 27.5 mmol) was suspended into a 0.1 M phosphate buffer at pH 7.4 (784 mL) and ethanol (16 mL). Pig liver esterase (0.90 mL, technical grade, 2.8 kilounits/mL) was then added and the reaction was stirred rapidly at room temperature for 17 h. The mixture was sonicated, additional pig liver esterase was added (0.1 mL) and the pH was adjusted to ~7-8 with 1.0 M aqueous NaOH and stirring was continued for 7 h. Additional pig liver esterase (0.05 mL) was added, the pH was adjusted to ~7-8 with 1.0 M aqueous NaOH and stirring was continued for 16 h. The mixture was transferred to a separatory funnel and extracted with tert-butylmethylether (2×300 mL). The aqueous phase was acidified to pH 1 with concentrated HCl and extracted with tert-butylmethylether (3×300 mL) and EtOAc (3×300 mL). The combined organic phases were dried over MgSO$_4$, filtered, washed with brine, dried again over MgSO$_4$, filtered and concentrated. The crude product was purified via silica gel chromatography eluting with 15-50% EtOAc/heptanes to give the title compound (6.29 g, 72%) as a white solid whose spectroscopic properties were identical to previous reports.

Step 2: Preparation of 4-methoxybenzyl[(3S)-3-methyl-2-oxopyrrolidin-3-yl]carbamate

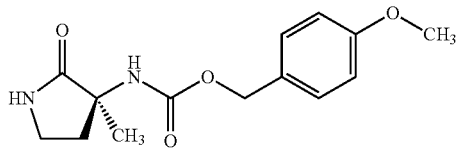 [SMILES: COc1ccc(COC(=O)N[C@@]2(C)CCNC2=O)cc1]

To a solution of ethyl 4-(1,3-dioxo-1,3-dihydro-2H-isoindol-2-yl)-N-[(4-methoxyphenoxy)carbonyl]-L-isovalinate (prepared from the above (2R)-4-(1,3-dioxo-1,3-dihydro-2H-isoindol-2-yl)-2-(ethoxycarbonyl)-2-methylbutanoic acid according to Banerjee, S.; Wiggins, W. J.; Geoghegan, J. L.; Anthony, C. T.; Woltering, E. A.; Masterson, D. S. *Org. Biomol. Chem.*, 2013, 11, 6307-6319) (3.64 g, 8.01 mmol) in methanol (40 mL) was added hydrazine (0.27 mL, 8.81 mmol) at room temperature and the reaction heated under reflux for 23 h. The heterogeneous reaction mixture was cooled to room temperature, and the solids were removed by filtration. The filtrate was concentrated and the residue was suspended into water and DCM, the layers were separated and the aqueous phase was extracted with DCM (3×20 mL). The combined organic phases were dried over MgSO$_4$, filtered and concentrated. The crude product was purified by silica gel chromatography eluting with 60-100% EtOAc/heptanes to give the title compound (1.66 g, 75%) as a white solid. $^1$H NMR (400 MHz, CDCl$_3$) δ 7.30-7.27 (m, 2 H), 6.91-6.83 (m, 2 H), 5.74 (br s, 1 H), 5.31 (br s, 1 H), 5.06-4.97 (m, 2H), 3.81 (s, 3 H), 3.47-3.37 (m, 1 H), 3.35-3.25 (m, 1 H), 2.61-2.50 (m, 1 H), 2.40-2.32 (m, 1 H), 1.41 (s, 3 H). m/z (HRMS) for C$_{14}$H$_{18}$N$_2$O$_4$Na$^+$ calculated 301.1159, found 301.1164.

Step 3: Preparation of tert-butyl(3S)-3-amino-3-methylpyrrolidine-1-carboxylate

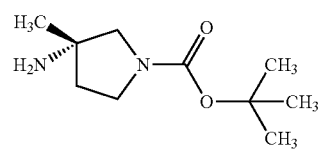

To a solution of 4-methoxybenzyl [(3S)-3-methyl-2-oxopyrrolidin-3-yl]carbamate (504 mg, 1.81 mmol) in methanol (2.04 mL) was added 10% palladium on carbon (50 mg) portion-wise at room temperature and the mixture was stirred under hydrogen (1 atm) for 2 h. The mixture was filtered through a pad of Celite® and concentrated. The residue was diluted with THF (4 mL) and cooled to 0° C. Lithium aluminum hydride (18.0 mL, 18.0 mmol, 1.0 M in THF) was added via a syringe under nitrogen and the reaction vessel was allowed to warm to room temperature. The reaction mixture was heated at 70° C. for 17 h, whereupon the reduction was complete by LCMS. The reaction mixture was cooled to 0° C., 2 mL of 5.0 M KOH was added slowly, and 4 mL diethyl ether was added to break up emulsion. The reaction mixture was warmed to room temperature, stirred for 30 min and filtered. To the filtrate was added diisopropylamine (1.58 mL) and Boc-anhydride (370 mg, 1.67 mmol) portion-wise over 3.5 h at 0° C. The reaction mixture was warmed to room temperature and the mixture was stirred for 15 h. The mixture was filtered through a pad of Celite® washing with methanol and the filtrate was concentrated. The residue was purified by silica gel chromatography eluting with 0-10% MeOH (containing 10% NH$_4$OH)/EtOAc to give the title compound (226 mg, 62%) as a waxy solid. $^1$H NMR (400 MHz, CDCl$_3$) δ 3.54-3.35 (m, 2 H), 3.27-3.09 (m, 2 H), 1.85-1.67 (m, 2 H), 1.46 (s, 9 H), 1.28 (s, 3 H). m/z (APCI) for C$_6$H$_{13}$N$_2$O$_2$ 145.1 (M+H)$^+$. The enantiomeric excess was determined to be 95% by chiral HPLC (Chiralpak AD-3 4.6×100 mm 3μ column, 10% MeOH+10 mM NH$_3$, 120 bar, 4 mL/min) the retention times of the enantiomers were 0.84 min (R, minor) and 1.35 min (S, major).

The following examples were made with non-critical changes or substitutions to the exemplified procedures that would be understood to one skilled in the art.

TABLE 1

| Example No./ Scheme | Structure and Compound Name | LRMS m/z [M + H]+ | 1H NMR or HPLC retention time and method |
|---|---|---|---|
| 1 Scheme A | 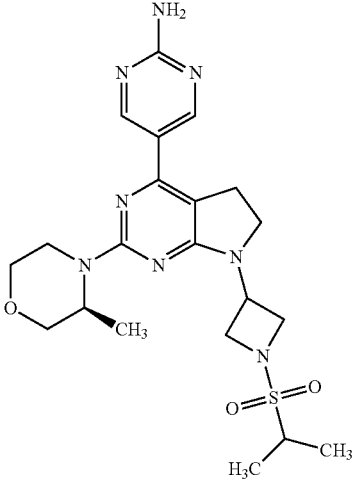 5-{2-[(3S)-3-methylmorpholin-4-yl]-7-[1-(propan-2-ylsulfonyl)azetidin-3-yl]-6,7-dihydro-5H-pyrrolo[2,3-d]pyrimidin-4-yl}pyrimidin-2-amine | 475.2 | 1H NMR (400 MHz, DMSO-d6) δ 8.74 (s, 2H) 6.98 (s, 2H) 4.80 (p, J = 7.2 Hz, 1H) 4.68-4.59 (m, 1H) 4.29-4.21 (m, 3H) 3.98 (dt, J = 7.9, 4.4 Hz, 2H) 3.88 (dd, J = 11.1, 3.0 Hz, 1H) 3.72-3.65 (m, 3H) 3.56 (dd, J = 11.3, 2.9 Hz, 1H) 3.40 (dt, J = 11.7, 2.8 Hz, 1H) 3.28-3.21 (m, 1H, partially overlapped with water) 3.15 (t, J = 8.2 Hz, 2H) 3.07 (dt, J = 12.9, 3.7 Hz, 1H), 1.24 (d, J = 6.8 Hz, 6H) 1.16 (d, J = 6.7 Hz, 3H). |
| 2 Scheme A | 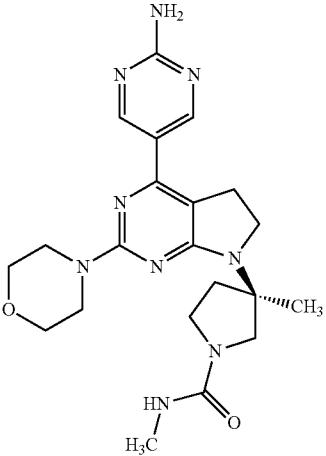 (3R)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-carboxamide | 440.2 | 1H NMR (600 MHz, 80° C., DMSO-d6) δ 8.72 (s, 2H) 6.59 (br s, 2H) 5.72 (br d, J = 3.7 Hz, 1H) 3.75 (d, J = 10.6 Hz, 1H) 3.71-3.50 (m, 11H) 3.41-3.24 (m, 2H) 3.08 (t, J = 8.2 Hz, 2H) 2.60 (d, J = 4.5 Hz, 3H) 2.48-2.43 (m, 1H, partially overlapped with DMSO) 2.14-2.05 (m, 1H) 1.34 (s, 3H). |

TABLE 1-continued

| Example No./ Scheme | Structure and Compound Name | LRMS m/z [M + H]+ | 1H NMR or HPLC retention time and method |
|---|---|---|---|
| 3 Scheme B | 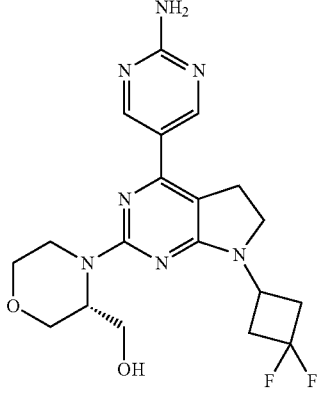<br>{(3R)-4-[4-(2-aminopyrimidin-5-yl)-7-(3,3-difluorocyclobutyl)-6,7-dihydro-5H-pyrrolo[2,3-d]pyrimidin-2-yl]morpholin-3-yl}methanol | 420.2 | 1H NMR (600 MHz, DMSO-d6) δ ppm 8.73 (s, 2H) 6.96 (s, 2H) 4.46-4.40 (m, 1H) 4.36-4.25 (m, 2H) 4.05 (d, J = 11.2 Hz, 1H) 3.85 (dd, J = 11.1, 3.4 Hz, 1H) 3.72-3.65 (m, 1H) 3.64-3.57 (m, 2H) 3.42-3.39 (m, 1H) 3.38-3.33 (m, 4H) 3.14-3.08 (m, 2H) 3.05-2.95 (m, 2H) 2.90-2.79 (m, 2H). |
| 4 Scheme A | 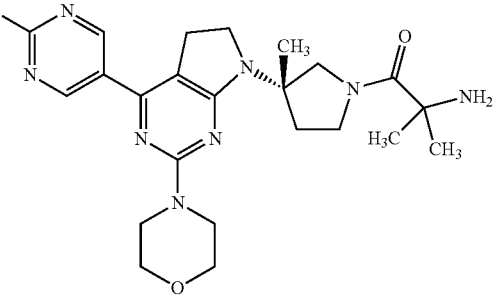<br>2-amino-1-{[(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one | 468.3 | 1H NMR (400 MHz, 80° C., DMSO-d6) δ 8.73 (s, 2H) 6.68 (br s, 2H) 4.40-4.00 (m, 2H) 3.73-3.50 (m, 12H) 3.12-3.07 (m, 2H, partially overlapped with water) 2.41-2.30 (m, 1H) 2.06-1.97 (m, 1H) 1.74 (br s, 2H) 1.31 (s, 3H) 1.27 (s, 6H). |
| 5 Scheme A | 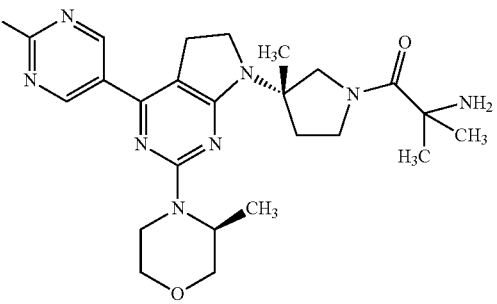<br>2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-methylpropan-1-one | 482.0 | 1H NMR (400 MHz, 80° C., DMSO-d6) δ 8.73 (s, 2 H) 6.59 (br s, 2 H) 4.58-4.67 (m, 1 H) 4.28 (d, J = 13.8 Hz, 2 H) 4.00 (d, J = 11.5 Hz, 1H) 3.84-3.95 (m, 1H) 3.38-3.75 (m, 7H) 3.06-3.21 (m, 3H) 2.27-2.44 (m, 1H) 1.98-2.09 (m, 1H) 1.67 (s, 2H) 1.32 (s, 3H) 1.28 (s, 6H) 1.22 (d, J = 6.7 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 6* Scheme A | (3S)-3-[4-(2-aminopyrimidin-5-yl)-2-(morpholin-4-yl)-5,6-dihydro-7H-pyrrolo[2,3-d]pyrimidin-7-yl]-3-methyl-1,3'-bipyrrolidin-2'-one | 466.1 | $^1$H NMR (400 MHz, Methanol-d$_4$) δ 8.79 (s, 2H), 3.76-3.68 (m, 10H), 3.43-3.33 (m, 5H), 3.14-3.12 (m, 2H), 3.05-3.00 (m, 1H), 2.89-2.85 (m, 1H), 2.56-2.53 (m, 1H), 2.35-2.30 (m, 1H), 2.14-2.10 (m, 1H) 2.00-1.95 (m, 1H) 1.44 (s, 3H). |
| 7* Scheme A | (3S)-3-[4-(2-aminopyrimidin-5-yl)-2-(morpholin-4-yl)-5,6-dihydro-7H-pyrrolo[2,3-d]pyrimidin-7-yl]-3-methyl-1,3'-bipyrrolidin-2'-one | 466.1 | $^1$H NMR (400 MHz, Methanol-d$_4$) δ 8.79 (s, 2H) 3.82-3.68 (m, 12H) 3.46-3.40 (m, 1H) 3.36-3.33 (m, 1H) 3.14-3.10 (m, 3H) 3.03-3.00 (m, 1H) 2.95-2.90 (m, 1H) 2.54-2.51 (m, 1H) 2.40-2.35 (m, 1H) 2.14-2.11 (m, 1H) 2.04-2.02 (m, 1H) 1.44 (s, 3H). |
| 8 Scheme A | 5-{7-[(3S)-1-(5,5-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine | 480.2 | $^1$H NMR (400 MHz, DMSO-d$_6$) δ 8.73 (s, 2H) 6.60 (s, 2 H) 3.80 (d, J = 10.7 Hz, 1H) 3.67 (s, 8H) 3.52-3.65 (m, 3H) 3.30-3.44 (m, 4H) 3.06-3.11 (m, 2H) 2.41-2.48 (m, 1H) 2.08 (ddd, J = 12.4, 7.2, 5.1 Hz, 1H) 1.34 (br s, 3H) 1.34 (s, 3H)1.33 (s, 3H). |

TABLE 1-continued

| Example No./ Scheme | Structure and Compound Name | LRMS m/z [M + H]+ | 1H NMR or HPLC retention time and method |
|---|---|---|---|
| 9 Scheme A | 5-{7-[(3S)-1-(4,4-dimethyl-4,5-dihydro-1,3-oxazol-2-yl)-3-methylpyrrolidin-3-yl]-2-(morpholin-4-yl)-6,7-dihydro-5H-pyrrolo[2,3-d]pyrimidin-4-yl}pyrimidin-2-amine | 479.9 | 1H NMR (700 MHz, DMSO-d$_6$) δ 8.72 (s, 2H) 6.99 (s, 2H) 3.86-3.94 (m, 2H) 3.74 (d, J = 10.4 Hz, 1H) 3.59-3.68 (m, 8H) 3.52-3.55 (m, 1H) 3.06-3.11 (m, 2H) 2.41 (dt, J = 12.4, 7.9 Hz, 1H) 2.10 (ddd, J = 12.43, 7.3, 5.0 Hz, 1H) 1.29 (s, 3H) 1.10-1.17 (m, 6H). |
| 10 Scheme B | (S)-2-amino-1-(3-(4-(2-aminopyrimidin-5-yl)-2-(morpholino-d$_8$)-5,6-dihydro-7H-pyrrolo[2,3-d]pyrimidin-7-yl)-3-methylpyrrolidin-1-yl)-2-methylpropan-1-one hydrochloride | 476.6 | 1H NMR (400 MHz, DMSO-d$_6$) δ 8.74 (s, 2H) 6.63 (s, 2H) 4.11-4.26 (m, 1H) 3.91-4.04 (m, 1H) 3.49-3.80 (m, 5H) 3.06-3.16 (m, 2H) 2.09 (br s, 1H) 1.53 (d, J = 11.4 Hz, 6H) 1.36 (s, 3H). |
| 11 Scheme A | 1-{(3R)-3-[4-(2-aminopyrimidin-5-yl)-2-(morpholin-4-yl)-5,6-dihydro-7H-pyrrolo[2,3-d]pyrimidin-7-yl]pyrrolidin-1-yl}ethanone | 411.0 | 1H NMR (400 MHz, DMSO-d$_6$) δ ppm 8.74 (s, 2H) 6.61 (br s, 2H) 4.72-4.45 (m, 1H) 3.80-3.47 (m, 13H) 3.47-3.28 (m, 1H) 3.13 (t, J = 7.95 Hz, 2H) 2.26-2.06 (m, 2H) 1.96 (s, 3H). |

TABLE 1-continued

| Example No./Scheme | Structure and Compound Name | LRMS m/z [M + H]⁺ | ¹H NMR or HPLC retention time and method |
|---|---|---|---|
| 12 Scheme A | 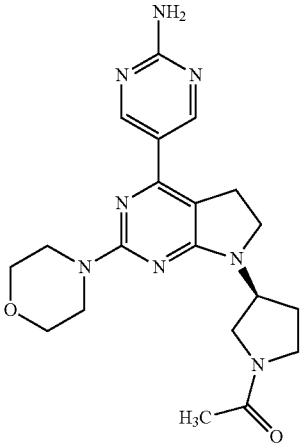<br>1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}ethanone | 411.0 | ¹H NMR (400 MHz, DMSO-d₆) δ ppm 8.74 (d, J = 2.20 Hz, 2H) 6.97 (s, 2H) 4.76-4.47 (m, 1H) 3.74-3.46 (m, 13H) 3.37-3.24 (m, 1H) 3.17-3.09 (m, 2H) 2.20-1.99 (m, 2H) 1.95 (s, 3H). |
| 13 Scheme A | 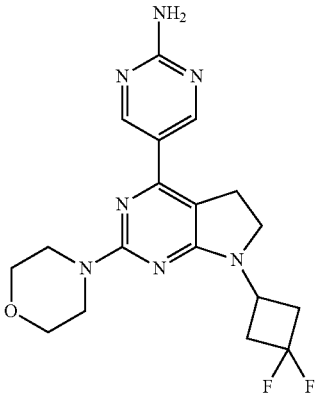<br>5-[7-(3,3-difluorocyclobutyl)-2-(morpholin-4-yl)-6,7-dihydro-5H-pyrrolo[2,3-d]pyrimidin-4-yl]pyrimidin-2-amine | 390.0 | ¹H NMR (400 MHz, DMSO-d₆) δ ppm 8.74 (s, 2H) 6.98 (s, 2H) 4.35 (br s, 1H) 3.69-3.59 (m, 10H) 3.13 (t, J = 8.07 Hz, 2H) 3.10-3.00 (m, 2H) 2.92-2.79 (m, 2H). |
| 14 Scheme A | 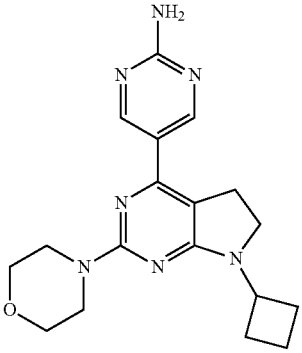<br>5-[7-cyclobutyl-2-(morpholin-4-yl)-6,7-dihydro-5H-pyrrolo[2,3-d]pyrimidin-4-yl]pyrimidin-2-amine | 354.0 | ¹H NMR (400 MHz, DMSO-d₆) δ ppm 8.73 (s, 2H) 6.94 (s, 2H) 4.65-4.49 (m, 1H) 3.64 (br s, 10H) 3.11 (t, J = 8.25 Hz, 2H) 2.37-2.22 (m, 2H) 2.06 (br s, 2H) 1.73-1.62 (m, 2H). |

TABLE 1-continued

| Example No./ Scheme | Structure and Compound Name | LRMS m/z [M + H]+ | ¹H NMR or HPLC retention time and method |
|---|---|---|---|
| 15 Scheme A | 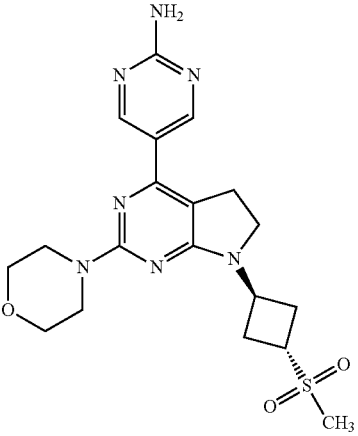<br>5-{7-[trans-3-(methylsulfonyl)cyclobutyl]-2-(morpholin-4-yl)-6,7-dihydro-5H-pyrrolo[2,3-d]pyrimidin-4-yl}pyrimidin-2-amine | 432.0 | ¹H NMR (400 MHz, DMSO-d$_6$) δ ppm 8.74 (s, 2H) 6.97 (s, 2H) 4.78-4.69 (m, 1H) 3.88-3.76 (m, 1H) 3.73-3.60 (m, 10H) 3.13 (t, J = 8.07 Hz, 2H) 2.97 (s, 3H) 2.91-2.79 (m, 2H) 2.58 (ddd, J = 14.76, 8.77, 3.36 Hz, 2H). |
| 16 Scheme A | 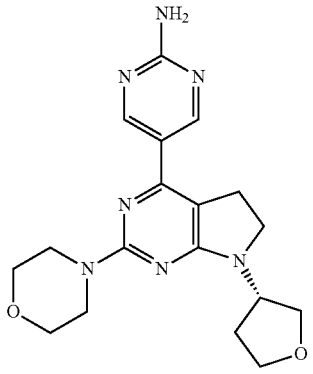<br>5-{2-(morpholin-4-yl)-7-[(3S)-tetrahydrofuran-3-yl]-6,7-dihydro-5H-pyrrolo[2,3-d]pyrimidin-4-yl}pyrimidin-2-amine | 370.0 | ¹H NMR (400 MHz, DMSO-d$_6$) δ ppm 8.75 (s, 2H) 7.01(s, 2H) 4.76-4.70 (m, 1H) 3.91-3.90 (m, 1H) 3.76 (d, J = 5.6 Hz, 2H) 3.70-3.60 (m, 11H) 3.13 (t, J = 8.2 Hz, 2H) 2.18-2.13 (m, 1H) 2.01-1.97 (m, 1H). |
| 17 Scheme A | 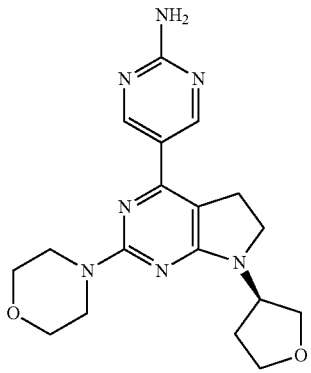<br>5-{2-(morpholin-4-yl)-7-[(3R)-tetrahydrofuran-3-yl]-6,7-dihydro-5H-pyrrolo[2,3-d]pyrimidin-4-yl}pyrimidin-2-amine | 370.0 | ¹H NMR (400 MHz, CDCl$_3$) δ ppm 8.84 (s, 2H) 5.31 (s, 2H) 4.88-4.85 (m, 1H) 4.07-4.01 (m, 2H) 3.89-3.63 (m, 12H) 3.14 (t, J = 8.2 Hz, 2H) 2.29-2.20 (m, 1H) 2.06-2.02 (m, 1H). |

TABLE 1-continued

| Example No./ Scheme | Structure and Compound Name | LRMS m/z [M + H]⁺ | ¹H NMR or HPLC retention time and method |
|---|---|---|---|
| 18 Scheme A | 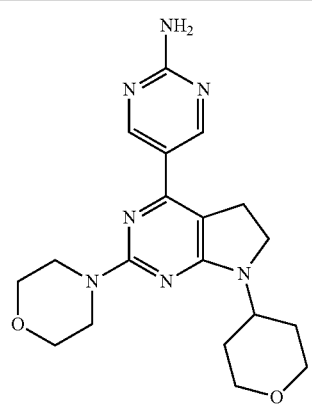 5-[2-(morpholin-4-yl)-7-(tetrahydro-2H-pyran-4-yl)-6,7-dihydro-5H-pyrrolo[2,3-d]pyrimidin-4-yl]pyrimidin-2-amine | 384.2 | ¹H NMR (400 MHz, D₂O) δ ppm 8.65-8.53 (m, 2H) 4.29-4.27 (m, 1H) 4.02-4.00 (m, 2H) 3.84-3.75 (m, 10H) 3.55-3.50 (m, 2H) 3.03-2.99 (m, 2H) 1.90-1.83 (m, 2H) 1.75-1.72 (m, 2H). |
| 19** Scheme A | 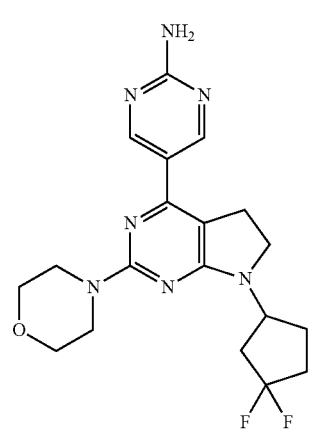 5-[7-(3,3-difluorocyclopentyl)-2-(morpholin-4-yl)-6,7-dihydro-5H-pyrrolo[2,3-d]pyrimidin-4-yl]pyrimidin-2-amine | 403.9 | ¹H NMR (400 MHz, CDCl₃) δ ppm 8.84 (s, 2H) 5.25 (br s, 2H) 4.74-4.31 (m, 1H) 3.81-3.76 (m, 8H) 3.61 (t, J = 9 Hz, 2H) 3.15 (t, J = 8.2 Hz, 2H) 2.50-2.38 (m, 1H) 2.35-2.21 (m, 2H) 2.18-1.95 (m, 3H). |
| 20 Scheme A | 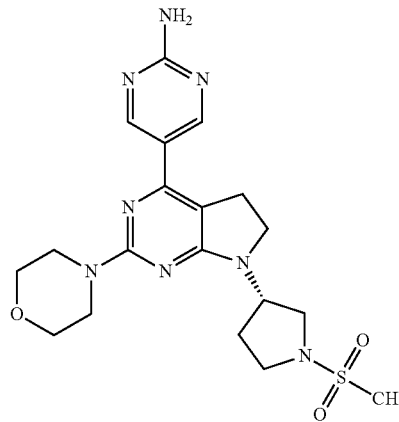 5-{7-[(3S)-1-(methylsulfonyl)pyrrolidin-3-yl]-2-(morpholin-4-yl)-6,7-dihydro-5H-pyrrolo[2,3-d]pyrimidin-4-yl}pyrimidin-2-amine | 447.0 | ¹H NMR (400 MHz, CDCl₃) δ ppm 8.83 (s, 2H) 5.26 (s, 2H) 4.80-4.73 (m, 1H) 3.80-3.75 (m, 8H) 3.71-3.57 (m, 4H) 3.48-3.35 (m, 2H) 3.19-3.13 (m, 2H) 2.88 (s, 3H) 2.30-2.18 (m, 2H). |

| Example No./ Scheme | Structure and Compound Name | LRMS m/z [M + H]+ | 1H NMR or HPLC retention time and method |
|---|---|---|---|
| 21 Scheme A | 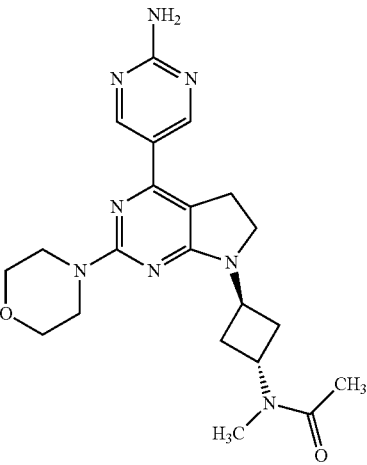<br>N-{trans-3-[4-(2-aminopyrimidin-5-yl)-2-(morpholin-4-yl)-5,6-dihydro-7H-pyrrolo[2,3-d]pyrimidin-7-yl]cyclobutyl}-N-methylacetamide | 425.0 | 1H NMR (400 MHz, CDCl$_3$) δ ppm 8.84 (s, 2H) 5.20 (s, 2H) 4.64-4.51 (m, 2H) 3.79-3.67 (m, 10H) 3.16 (t, J = 8 Hz, 2H) 3.05 (s, 3H) 2.77-2.70 (m, 1H) 2.69-2.56 (m, 2H) 2.55-2.46 (m, 1H) 2.10 (s, 3H). |
| 22 Scheme A | 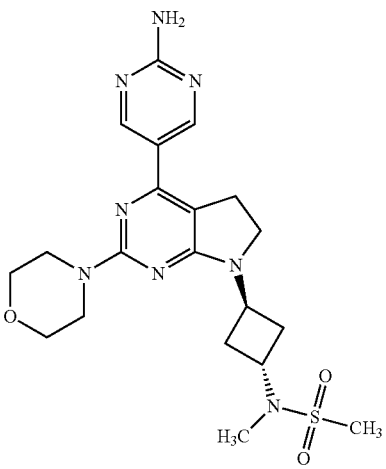<br>N-{trans-3-[4-(2-aminopyrimidin-5-yl)-2-(morpholin-4-yl)-5,6-dihydro-7H-pyrrolo[2,3-d]pyrimidin-7-yl]cyclobutyl}-N-methylmethanesulfonamide | 461.1 | 1H NMR (400 MHz, CDCl$_3$) δ ppm 8.84 (s, 2H) 5.22 (s, 2H) 4.64-4.60 (m, 1H) 4.53-4.44 (m, 1H) 3.84-3.73 (m, 8H) 3.69 (t, J = 8.2 Hz, 2H) 3.16 (t, J = 8.2 Hz, 2H) 2.94 (s, 3H) 2.78 (s, 3H) 2.68-2.62 (m, 4H). |

TABLE 1-continued

| Example No./ Scheme | Structure and Compound Name | LRMS m/z [M + H]+ | 1H NMR or HPLC retention time and method |
|---|---|---|---|
| 23 Scheme A | N-{cis-3-[4-(2-aminopyrimidin-5-yl)-2-(morpholin-4-yl)-5,6-dihydro-7H-pyrrolo[2,3-d]pyrimidin-7-yl]cyclobutyl}acetamide | 411.1 | 1H NMR (400 MHz, DMSO-d6) δ ppm 8.74 (s, 2H) 8.13 (d, J = 8 Hz, 1H) 7.00 (s, 2H) 4.28-4.24 (m, 1H) 3.96-3.94 (m, 1H) 3.70-3.61 (m, 10H) 3.16-3.14 (m, 2H) 2.44-2.34 (m, 2H) 2.18-2.15 (m, 2H) 1.79 (s, 3H). |
| 24 Scheme A | trans-3-[4-(2-aminopyrimidin-5-yl)-2-(morpholin-4-yl)-5,6-dihydro-7H-pyrrolo[2,3-d]pyrimidin-7-yl]cyclobutanol | 370.0 | 1H NMR (400 MHz, DMSO-d6) δ ppm 8.73 (s, 2H) 6.99 (s, 2H) 5.06 (d, J = 3.6 Hz, 1H) 4.79-4.75 (m, 1H) 4.28-4.26 (m, 1H) 3.64-3.61 (m, 10H) 3.12 (t, J = 8 Hz, 2H) 2.53-2.48 (m, 2H) 2.10-2.05 (m, 2H). |
| 25 Scheme A | 1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-hydroxyethanone | 427.0 | 1H NMR (400 MHz, DMSO-d6) δ ppm 9.01-8.74 (m, 2H) 7.01 (br s, 2H) 4.72-4.57 (m, 2H) 4.04-4.01 (m, 2H) 3.66-3.56 (m, 13H) 3.15-3.13 (m, 3H) 2.19-2.15 (m, 1H) 2.07-2.02 (m, 1H). |

TABLE 1-continued

| Example No./ Scheme | Structure and Compound Name | LRMS m/z [M + H]+ | 1H NMR or HPLC retention time and method |
|---|---|---|---|
| 26 Scheme A | 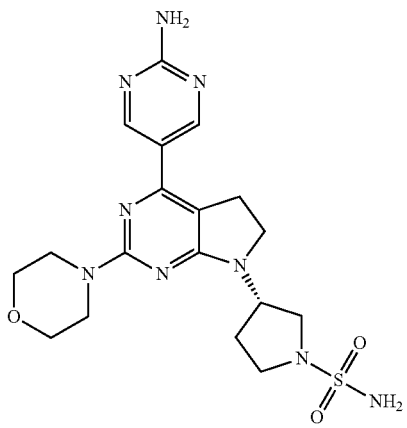<br>(3S)-3-[4-(2-aminopyrimidin-5-yl)-2-(morpholin-4-yl)-5,6-dihydro-7H-pyrrolo[2,3-d]pyrimidin-7-yl]pyrrolidine-1-sulfonamide | 448.0 | 1H NMR (400 MHz, D$_2$O) δ ppm 8.61 (s, 2H) 5.03-4.96 (m, 1H) 3.98-3.96 (m, 2H) 3.84-3.77 (m, 8H) 3.55-3.51 (m, 3H) 3.47-3.46 (m, 1H) 3.11 (t, J = 7.8 Hz, 2H) 2.38-2.35 (m, 1H) 2.29-2.25 (m, 1H). |
| 27 Scheme A | 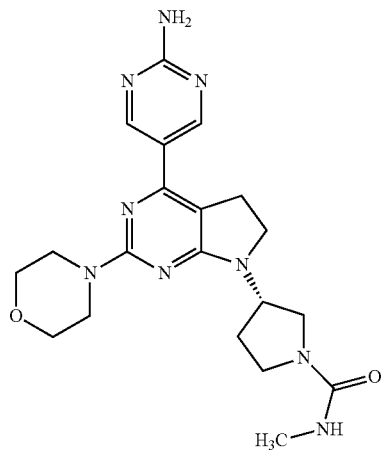<br>(3S)-3-[4-(2-aminopyrimidin-5-yl)-2-(morpholin-4-yl)-5,6-dihydro-7H-pyrrolo[2,3-d]pyrimidin-7-yl]-N-methylpyrrolidine-1-carboxamide | 426.0 | 1H NMR (400 MHz, DMSO-d$_6$) δ ppm 8.74 (s, 2H) 7.00 (s, 2H) 6.10-6.08 (br s, 1H) 4.62-4.59 (m, 1H) 3.66-3.65 (m, 8H) 3.40-3.38 (m, 2H) 3.38-3.37 (m, 2H) 3.33-2.32 (m, 2H) 3.15-3.10 (m, 2H) 2.57-2.53 (m, 2H) 2.09-2.07 (m, 3H) (m, 2H). |

TABLE 1-continued

| Example No./ Scheme | Structure and Compound Name | LRMS m/z [M + H]⁺ | ¹H NMR or HPLC retention time and method |
|---|---|---|---|
| 28 Scheme A | 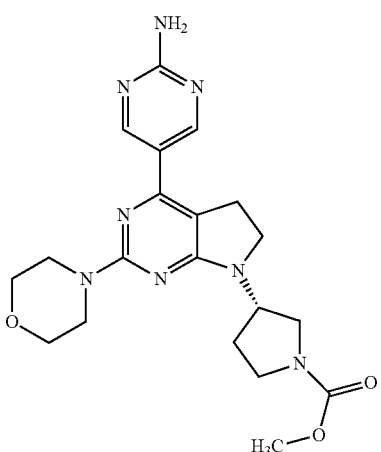<br>methyl (3S)-3-[4-(2-aminopyrimidin-5-yl)-2-(morpholin-4-yl)-5,6-dihydro-7H-pyrrolo[2,3-d]pyrimidin-7-yl]pyrrolidine-1-carboxylate | 427.1 | ¹H NMR (400 MHz. DMSO-d₆) δ ppm 8.73 (s, 2H) 7.00 (s, 2H) 4.64-4.56 (m, 1H) 3.64-3.56 (m, 15H) 3.50-3.45 (m, 2H) 3.13-3.10 (m, 2H) 2.13-2.08 (m, 2H). |
| 29 Scheme A | 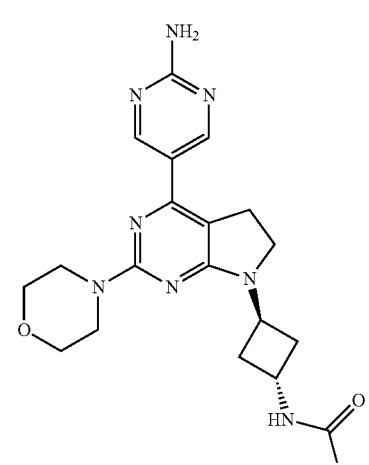<br>N-{trans-3-[4-(2-aminopyrimidin-5-yl)-2-(morpholin-4-yl)-5,6-dihydro-7H-pyrrolo[2,3-d]pyrimidin-7-yl]cyclobutyl}acetamide | 411.1 | ¹H NMR (400 MHz, DMSO-d₆) δ ppm 8.74 (s, 2H) 8.33 (d, J = 6.4 Hz, 1H) 7.00 (s, 2H) 4.77-4.73 (m, 1H) 4.15-4.12 (m, 1H) 3.69-3.65 (m, 10H) 3.13 (t, J = 8 Hz, 2H) 2.63-2.60 (m, 2H) 2.13-2.11 (m, 2H) 1.82 (s, 3H). |

TABLE 1-continued

| Example No./ Scheme | Structure and Compound Name | LRMS m/z [M + H]+ | 1H NMR or HPLC retention time and method |
|---|---|---|---|
| 30 Scheme A | 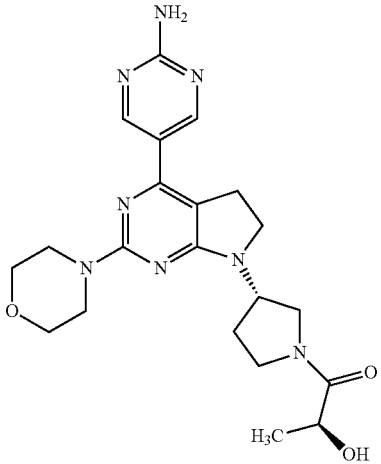 (2S)-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-hydroxypropan-1-one | 441.0 | 1H NMR (400 MHz, DMSO-d6) δ ppm 8.75 (s, 2H) 7.01 (br s, 2H) 4.92-4.89 (m, 1H) 4.65-4.58 (m, 1H) 4.30-4.26 (m, 1H) 3.90-3.86 (m, 1H) 3.66-3.62 (m, 10H) 3.61-3.59 (m, 2H) 3.15-3.13 (m, 2H) 2.18-2.14 (m, 1H) 2.09-2.05 (m, 1H) 1.19(t, J = 6.0 Hz, 3H). |
| 31 Scheme A | 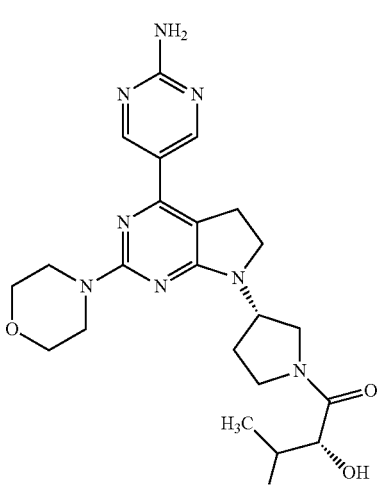 (2R)-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-hydroxy-3-methylbutan-1-one | 469.0 | 1H NMR (400 MHz, DMSO-d6) δ ppm 8.75 (s, 2H) 7.01 (br s, 2H) 4.71-4.69 (m, 1H) 4.65-4.54 (m, 1H) 3.90-3.80 (m, 2H) 3.72-3.55 (m, 13H) 3.13 (t, J = 8.2 Hz, 2H) 2.18-2.02 (m, 2H) 1.93-1.86 (m, 1H) 0.89-0.84 (m, 6H). |

TABLE 1-continued

| Example No./ Scheme | Structure and Compound Name | LRMS m/z [M + H]+ | 1H NMR or HPLC retention time and method |
|---|---|---|---|
| 32 Scheme A | 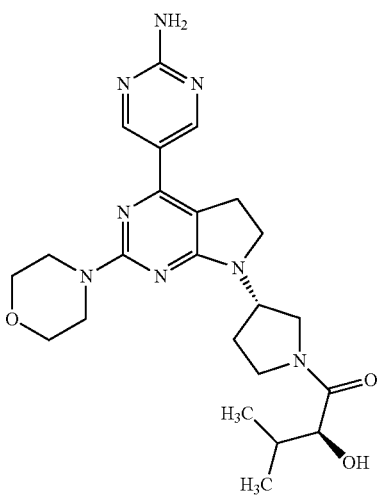<br>(2S)-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-hydroxy-3-methylbutan-1-one | 469.0 | 1H NMR (400 MHz, DMSO-d6) δ ppm 8.75 (s, 2H) 7.01 (brs, 2H) 4.71-4.66 (m, 1H) 4.62-4.56 (m, 1H) 3.92-3.77 (m, 2H) 3.7-3.47 (m, 13H) 3.14 (t, J = 7.6 Hz, 2H) 2.17-2.05 (m, 2H) 1.95-1.85 (m, 1H) 0.89-0.82 (m, 6H). |
| 33 Scheme A | 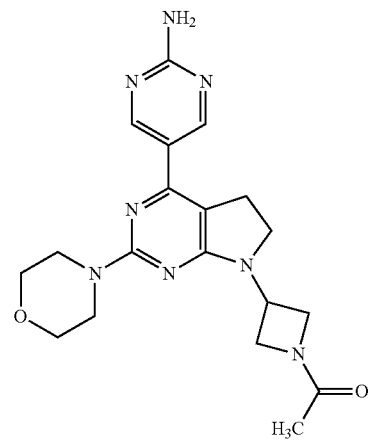<br>1-{3-[4-(2-aminopyrimidin-5-yl)-2-(morpholin-4-yl)-5,6-dihydro-7H-pyrrolo[2,3-d]pyrimidin-7-yl]azetidin-1-yl}ethanone | 397.1 | 1H NMR (400 MHz, CDCl3) δ ppm 8.85 (s, 2H) 5.22 (s, 2H) 4.90-4.80 (m, 1H) 4.38-4.25 (m, 4H) 3.80-3.65 (m, 8H) 3.69 (t, J = 8 Hz, 2H) 3.20 (t, J = 8 Hz, 2H) 1.93 (s, 3H). |

TABLE 1-continued

| Example No./ Scheme | Structure and Compound Name | LRMS m/z [M + H]+ | 1H NMR or HPLC retention time and method |
|---|---|---|---|
| 34* Scheme A | 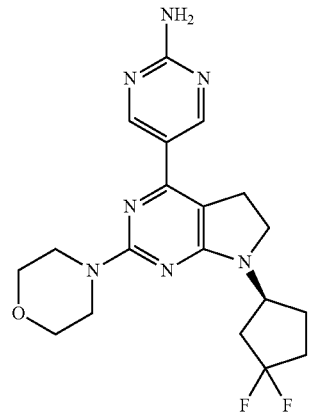<br>5-{7-[(1S)-3,3-difluorocyclopentyl]-2-(morpholin-4-yl)-6,7-dihydro-5H-pyrrolo[2,3-d]pyrimidin-4-yl}pyrimidin-2-amine | 404.1 | 1H NMR (400 MHz, DMSO-$d_6$) δ ppm 8.72 (s, 2H) 6.98 (br s, 2H) 4.65-4.56 (m, 1H) 3.64-3.56 (m, 10H) 3.11 (t, J = 8.2 Hz, 2H) 2.41-2.07 (m, 4H) 2.03-1.96 (m, 2H). |
| 35* Scheme A | 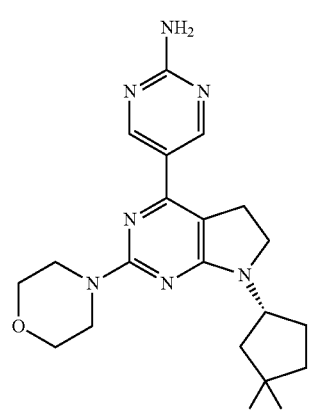<br>5-{7-[(1R)-3,3-difluorocyclopentyl]-2-(morpholin-4-yl)-6,7-dihydro-5H-pyrrolo[2,3-d]pyrimidin-4-yl}pyrimidin-2-amine | 404.0 | 1H NMR (400 MHz, DMSO-$d_6$) δ ppm 8.73 (s, 2H) 6.99 (br s, 2H) 4.65-4.56 (m, 1H) 3.64-3.56 (m, 10H) 3.12 (t, J = 8.2 Hz, 2H) 2.41-2.07 (m, 4H) 2.03-1.96 (m, 2H). |
| 36 Scheme A | 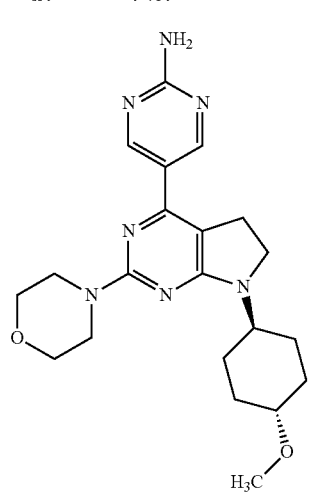<br>5-[7-(trans-4-methoxycyclohexyl)-2-(morpholin-4-yl)-6,7-dihydro-5H-pyrrolo[2,3-d]pyrimidin-4-yl]pyrimidin-2-amine | 412.0 | 1H NMR (400 MHz, DMSO-$d_6$) δ ppm 8.73 (s, 2H) 6.97 (s, 2H) 3.86-3.85 (m, 1H) 3.70-3.60 (m, 8H) 3.57-3.53 (m, 2H) 3.25 (s, 3H) 3.14-3.08 (m, 3H) 2.09-2.06 (m, 2H) 1.73-1.70 (m, 2H) 1.60-1.57 (m, 2H) 1.26-1.20 (m, 2H). |

TABLE 1-continued

| Example No./ Scheme | Structure and Compound Name | LRMS m/z [M + H]+ | 1H NMR or HPLC retention time and method |
|---|---|---|---|
| 37** Scheme A | 5-[2-(morpholin-4-yl)-7-(tetrahydro-2H-pyran-3-yl)-6,7-dihydro-5H-pyrrolo[2,3-d]pyrimidin-4-yl]pyrimidin-2-amine | 384.1 | 1H NMR (400 MHz, DMSO-$d_6$) δ 8.74 (s, 2H) 6.99 (s, 2H) 3.96-3.95 (m, 1H) 3.79-3.76 (m, 2H) 3.70-3.60 (m, 9H) 3.59-3.55 (m, 1H) 3.45-3.42 (m, 1H) 3.29-3.25 (m, 1H) 3.14-3.12 (m, 2H) 1.86-1.84 (m, 2H) 1.73-1.65 (m, 2H). |
| 38 Scheme A | (3S)-3-[4-(2-aminopyrimidin-5-yl)-2-(morpholin-4-yl)-5,6-dihydro-7H-pyrrolo[2,3-d]pyrimidin-7-yl]-N-methylpyrrolidine-1-sulfonamide | 462.0 | 1H NMR (400 MHz, CD$_3$OD) δ ppm 8.74 (s, 2H) 3.82-3.72 (m, 10H) 3.57-3.35 (m, 5H) 3.18 (t, J = 8 Hz, 2H) 2.70 (s, 3H) 2.32-2.24 (m, 2H). |
| 39 Scheme A | trans-3-[4-(2-aminopyrimidin-5-yl)-2-(morpholin-4-yl)-5,6-dihydro-7H-pyrrolo[2,3-d]pyrimidin-7-yl]-1-methylcyclobutanol | 384.0 | 1H NMR (400 MHz, DMSO-$d_6$) δ ppm 8.75 (s, 2H) 6.97 (br s, 2H) 4.83 (br s, 1H) 4.72-4.63 (m, 1H) 3.71-3.53 (m, 10H) 3.10 (m, 2H) 2.27 (m, 2H) 2.11 (m, 2H) 1.27 (s, 3H). |

TABLE 1-continued

| Example No./ Scheme | Structure and Compound Name | LRMS m/z [M + H]+ | 1H NMR or HPLC retention time and method |
|---|---|---|---|
| 40 Scheme A | 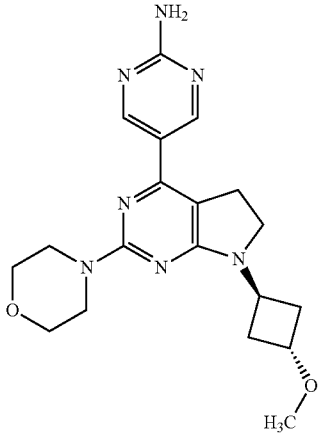<br>5-[7-(trans-3-methoxycyclobutyl)-2-(morpholin-4-yl)-6,7-dihydro-5H-pyrrolo[2,3-d]pyrimidin-4-yl]pyrimidin-2-amine | 384.0 | 1H NMR (400 MHz, CDCl$_3$) δ ppm 8.83 (s, 2H) 5.26 (s, 2H) 4.82-4.78 (m, 1H) 4.01-4.00 (m, 1H) 3.79-3.76 (m, 8H) 3.66 (t, J = 8 Hz, 2H) 3.29 (s, 3H) 3.13 (t, J = 8 Hz, 2H) 2.55-2.52 (m, 2H) 2.36-2.33 (m, 2H). |
| 41 Scheme A | 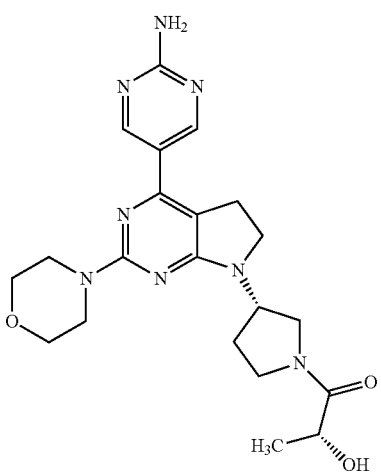<br>(2R)-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-hydroxypropan-1-one | 441.0 | 1H NMR (400 MHz, DMSO-d$_6$) δ ppm 8.75 (s, 2H) 7.00 (br s, 2H) 4.94-4.90 (m, 1H) 4.66-4.56 (m, 1H) 4.29-4.26 (m, 1H) 3.76-3.59 (m, 13H) 3.15-3.13 (m, 2H) 2.18-2.14 (m, 1H) 2.09-2.05 (m, 1H) 1.19 (t, J = 6.0 Hz, 3H). |

TABLE 1-continued

| Example No./ Scheme | Structure and Compound Name | LRMS m/z [M + H]+ | 1H NMR or HPLC retention time and method |
|---|---|---|---|
| 42 Scheme A | N-{cis-3-[4-(2-aminopyrimidin-5-yl)-2-(morpholin-4-yl)-5,6-dihydro-7H-pyrrolo[2,3-d]pyrimidin-7-yl]-2,2,4,4-tetramethylcyclobutyl}acetamide | 467.2 | 1H NMR (400 MHz, DMSO-$d_6$) δ ppm 8.74 (s, 2H) 7.47 (d, J = 9.2 Hz, 1H) 7.00 (s, 2H) 3.80-3.64 (m, 12H) 3.14-3.12 (m, 2H) 1.92 (s, 3H) 1.24-1.16 (m, 12H). |
| 43 Scheme A | (3S)-3-[4-(2-aminopyrimidin-5-yl)-2-(morpholin-4-yl)-5,6-dihydro-7H-pyrrolo[2,3-d]pyrimidin-7-yl]pyrrolidine-1-carbaldehyde | 397.0 | 1H NMR (400 MHz, CDCl$_3$) δ ppm 8.36 (s, 2H) 8.28-8.25 (m, 1H) 5.22 (s, 2H) 4.78-4.65 (m, 1H) 3.78-3.61 (m, 10H) 3.58-3.52 (m, 3H) 3.50-3.45 (m, 1H) 3.18-3.14 (m, 2H) 2.25-2.13 (m, 2H). |

TABLE 1-continued

| Example No./ Scheme | Structure and Compound Name | LRMS m/z [M + H]+ | 1H NMR or HPLC retention time and method |
|---|---|---|---|
| 44 Scheme A | 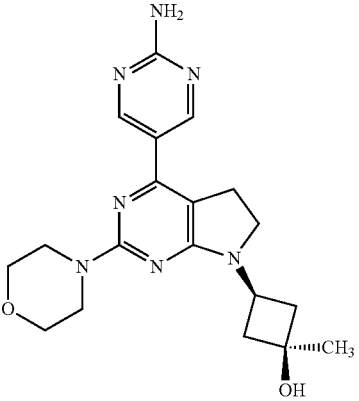 cis-3-[4-(2-aminopyrimidin-5-yl)-2-(morpholin-4-yl)-5,6-dihydro-7H-pyrrolo[2,3-d]pyrimidin-7-yl]-1-methylcyclobutanol | 384.0 | 1H NMR (400 MHz, DMSO-$d_6$) δ ppm 8.82 (s, 2H) 5.24 (br s, 2H) 4.18-4.17 (m, 1H) 3.82-3.77 (m, 8H) 3.67-3.66 (m, 2H) 3.15-3.11 (m, 2H) 2.44-2.38 (m, 4H) 1.48 (s, 3H). |
| 45 Scheme A | 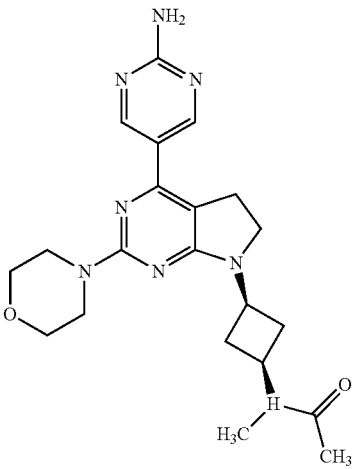 N-{cis-3-[4-(2-aminopyrimidin-5-yl)-2-(morpholin-4-yl)-5,6-dihydro-7H-pyrrolo[2,3-d]pyrimidin-7-yl]cyclobutyl}-N-methylacetamide | 425.1 | 1H NMR (400 MHz, CDCl$_3$) δ ppm 8.83 (s, 2H) 5.21 (s, 2H) 4.82-4.00 (m, 2H) 3.80-3.76 (m, 8H) 3.67-3.61 (m, 2H) 3.17-3.11 (m, 2H) 2.97-2.95 (m, 3H) 2.54-2.37 (m, 4H) 2.13-2.10 (m, 3H). |

TABLE 1-continued

| Example No./ Scheme | Structure and Compound Name | LRMS m/z [M + H]+ | 1H NMR or HPLC retention time and method |
|---|---|---|---|
| 46 Scheme A | 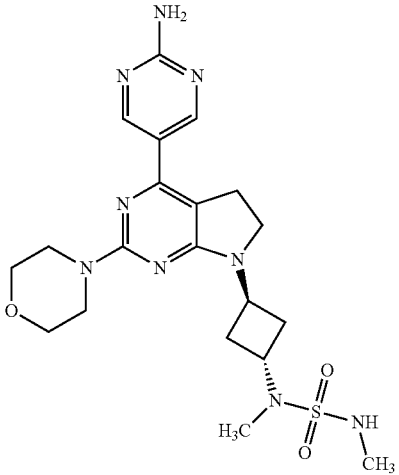 N-{trans-3-[4-(2-aminopyrimidin-5-yl)-2-(morpholin-4-yl)-5,6-dihydro-7H-pyrrolo[2,3-d]pyrimidin-7-yl]cyclobutyl}-N,N'-dimethylsulfuric diamide | 476.1 | 1H NMR (400 MHz, CDCl3) δ 8.83 (s, 2H) 5.20 (s, 2H) 4.57-4.48 (m, 2H) 4.07-4.05 (m, 1H) 3.79-3.76 (m, 8H) 3.70 (t, J = 8 Hz, 2H) 3.15 (t, J = 8 Hz, 2H) 2.80 (s, 3H), 2.69-2.68 (m, 3H) 2.65-2.61 (m, 4H). |
| 47 Scheme A | 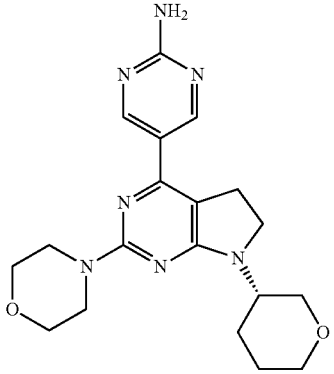 5-{2-(morpholin-4-yl)-7-[(3S)-tetrahydro-2H-pyran-3-yl]-6,7-dihydro-5H-pyrrolo[2,3-d]pyrimidin-4-yl}pyrimidin-2-amine | 384.1 | 1H NMR (400 MHz, DMSO-d6) δ 8.74 (s, 2H) 6.99 (s, 2H) 3.96-3.95 (m, 1H) 3.79-3.76 (m, 2H) 3.70-3.60 (m, 9H) 3.59-3.55 (m, 1H) 3.45-3.42 (m, 1H) 3.29-3.25 (m, 1H) 3.14-3.12 (m, 2H) 1.86-1.84 (m, 2H) 1.73-1.65 (m, 2H). |
| 48 Scheme A | 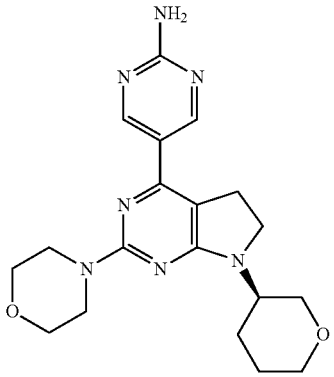 5-{2-(morpholin-4-yl)-7-[(3R)-tetrahydro-2H-pyran-3-yl]-6,7-dihydro-5H-pyrrolo[2,3-d]pyrimidin-4-yl}pyrimidin-2-amine | 384.1 | 1H NMR (400 MHz, DMSO-d6) δ ppm 8.74 (s, 2H) 6.99 (s, 2H) 3.96-3.95 (m, 1H) 3.79-3.76 (m, 2H) 3.70-3.60 (m, 9H) 3.59-3.55 (m, 1H) 3.45-3.42 (m, 1H) 3.29-3.25 (m, 1H) 3.14-3.12 (m, 2H) 1.86-1.84 (m, 2H) 1.73-1.65 (m, 2H). |

TABLE 1-continued

| Example No./ Scheme | Structure and Compound Name | LRMS m/z [M + H]+ | 1H NMR or HPLC retention time and method |
|---|---|---|---|
| 49 Scheme A | 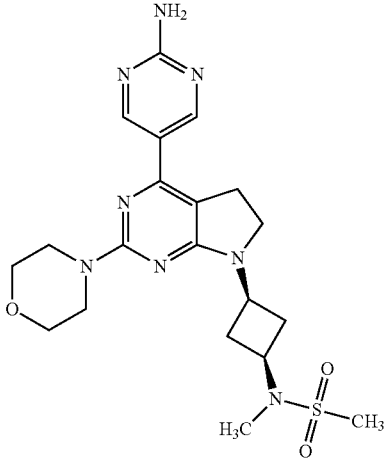 N-{cis-3-[4-(2-aminopyrimidin-5-yl)-2-(morpholin-4-yl)-5,6-dihydro-7H-pyrrolo[2,3-d]pyrimidin-7-yl]cyclobutyl}-N-methylmethanesulfonamide | 461.1 | 1H NMR (400 MHz, CDCl3) δ ppm 8.84 (s, 2H) 5.23 (s, 2H) 4.27-4.25 (m, 1H) 3.90-3.88 (m, 1H) 3.80-3.75 (m, 8H) 3.63 (t, J = 8 Hz, 2H) 3.14 (t, J = 8 Hz, 2H) 2.85 (s, 3H) 2.79 (s, 3H) 2.53-2.48 (m, 4H). |
| 50 Scheme A | 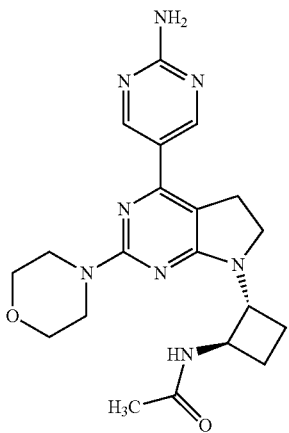 N-{(1R,2R)-2-[4-(2-aminopyrimidin-5-yl)-2-(morpholin-4-yl)-5,6-dihydro-7H-pyrrolo[2,3-d]pyrimidin-7-yl]cyclobutyl}acetamide | 411.1 | 1H NMR (400 MHz, DMSO-d6) δ ppm 8.73 (s, 2H) 8.24 (d, J = 8.4 Hz, 1H) 6.98 (s, 2H) 4.51-4.46 (m, 1H) 4.41-4.35 (m, 1H) 3.66-3.65 (m, 10H) 3.33-3.10 (m, 2H) 1.97-1.96 (m, 1H) 1.85-1.81 (m, 2H) 1.76 (s, 3H) 1.58-1.53 (m, 1H). |

TABLE 1-continued

| Example No./ Scheme | Structure and Compound Name | LRMS m/z [M + H]⁺ | ¹H NMR or HPLC retention time and method |
|---|---|---|---|
| 51** Scheme A | 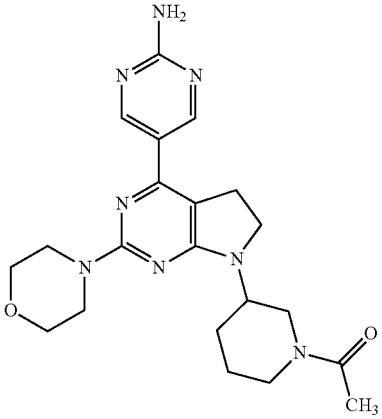<br>1-{3-[4-(2-aminopyrimidin-5-yl)-2-(morpholin-4-yl)-5,6-dihydro-7H-pyrrolo[2,3-d]pyrimidin-7-yl]piperidin-1-yl}ethanone | 425.1 | ¹H NMR (400 MHz, DMSO-d₆) δ ppm 8.74 (s, 2H) 7.01 (s, 2H) 4.40-4.30 (m, 1H) 3.80-3.55 (m, 13H) 3.20-3.05 (m, 3H) 3.00-2.65 (m, 1H) 2.02 (s, 3H) 1.95-1.70 (m, 3H). |
| 52 Scheme A | 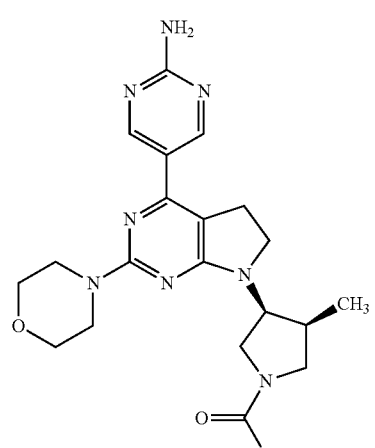<br>1-{(3S,4S)-3-[4-(2-aminopyrimidin-5-yl)-2-(morpholin-4-yl)-5,6-dihydro-7H-pyrrolo[2,3-d]pyrimidin-7-yl]-4-methylpyrrolidin-1-yl}ethanone | 425.1 | ¹H NMR (400 MHz, CDCl₃) δ ppm 8.84 (s, 2H) 5.26 (br s, 2H) 4.83-4.72 (m, 1H) 3.85-3.63 (m, 13H) 3.24-3.17 (m, 3H) 2.76-2.62 (m, 1H) 2.09 (s, 3H) 1.07 (d, J = 6.0 Hz, 3H). |

TABLE 1-continued

| Example No./ Scheme | Structure and Compound Name | LRMS m/z [M + H]+ | 1H NMR or HPLC retention time and method |
|---|---|---|---|
| 53 Scheme A | trans-3-[4-(2-aminopyrimidin-5-yl)-2-(morpholin-4-yl)-5,6-dihydro-7H-pyrrolo[2,3-d]pyrimidin-7-yl]cyclobutanecarboxamide | 397.1 | 1H NMR (400 MHz, DMSO-$d_6$) δ ppm 8.74-8.49 (m, 2H) 7.28 (br s, 1H) 7.01 (s, 2H) 6.81 (br s, 1H) 4.75-4.43 (m, 1H) 3.65-3.61 (m, 10H) 3.13 (t, J = 8 Hz, 2H) 2.68-2.66 (m, 1H) 2.44-2.37 (m, 2H) 2.25-2.21 (m, 2H). |
| 54 Scheme A | 1-{(3S)-3-[4-(2-aminopyrimidin-5-yl)-2-(morpholin-4-yl)-5,6-dihydro-7H-pyrrolo[2,3-d]pyrimidin-7-yl]piperidin-1-yl}ethanone | 425.0 | 1H NMR (400 MHz, DMSO-$d_6$) δ ppm 8.74 (s, 2H) 7.01 (s, 2H) 4.40-4.30 (m, 1H) 3.80-3.55 (m, 13H) 3.20-3.05 (m, 3H) 3.00-2.65 (m, 1H) 2.02 (s, 3H) 1.95-1.70 (m, 3H). |
| 55 Scheme A | 1-{(3R)-3-[4-(2-aminopyrimidin-5-yl)-2-(morpholin-4-yl)-5,6-dihydro-7H-pyrrolo[2,3-d]pyrimidin-7-yl]piperidin-1-yl}ethanone | 425.0 | 1H NMR (400 MHz, DMSO-$d_6$) δ ppm 8.74 (s, 2H) 7.01 (s, 2H) 4.40-4.30 (m, 1H) 3.80-3.55 (m, 13H) 3.20-3.05 (m, 3H) 3.00-2.65 (m, 1H) 2.02 (s, 3H) 1.95-1.70 (m, 3H). |

TABLE 1-continued

| Example No./ Scheme | Structure and Compound Name | LRMS m/z [M + H]+ | 1H NMR or HPLC retention time and method |
|---|---|---|---|
| 56 Scheme A | 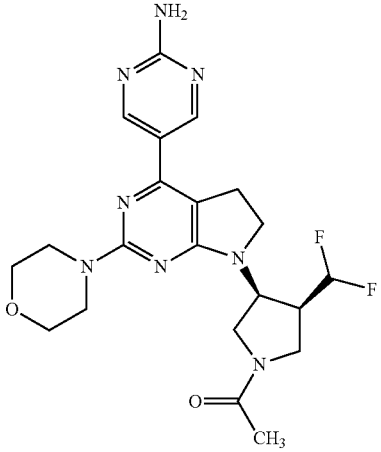 1-[(3S,4S)-3-[4-(2-aminopyrimidin-5-yl)-2-(morpholin-4-yl)-5,6-dihydro-7H-pyrrolo[2,3-d]pyrimidin-7-yl]-4-(difluoromethyl)pyrrolidin-1-yl]ethanone | 461.1 | 1H NMR (400 MHz, CDCl$_3$) δ ppm 8.88 (s, 2H) 6.18-5.81 (m, 1H) 5.26 (br s, 2H) 4.86-4.69 (m, 1H) 3.85-3.57 (m, 14H) 3.20-3.17 (m, 3H) 2.17-2.11 (m, 3H). |
| 57 Scheme A | 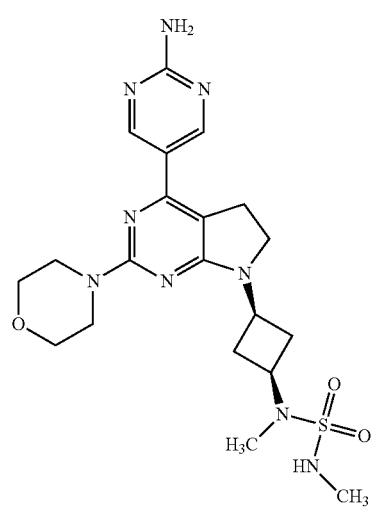 N-{cis-3-[4-(2-aminopyrimidin-5-yl)-2-(morpholin-4-yl)-5,6-dihydro-7H-pyrrolo[2,3-d]pyrimidin-7-yl]cyclobutyl]-N,N'-dimethylsulfuric diamide | 476.1 | 1H NMR (400 MHz, CDCl$_3$) δ ppm 8.83 (s, 2H) 5.21 (s, 2H) 4.27-4.25 (m, 1H) 4.07-4.05 (m, 1H) 3.91-3.88 (m, 1H) 3.79-3.77 (m, 8H) 3.63 (t, J = 8 Hz, 2H) 3.13 (t, J = 8 Hz, 2H) 2.80 (s, 3H), 2.72-2.71 (m, 3H) 2.52-2.43 (m, 4H). |

TABLE 1-continued

| Example No./ Scheme | Structure and Compound Name | LRMS m/z [M + H]+ | 1H NMR or HPLC retention time and method |
|---|---|---|---|
| 58 Scheme A | 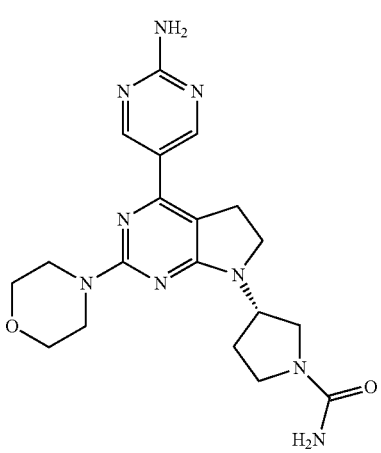 (3S)-3-[4-(2-aminopyrimidin-5-yl)-2-(morpholin-4-yl)-5,6-dihydro-7H-pyrrolo[2,3-d]pyrimidin-7-yl]pyrrolidine-1-carboxamide | 412.1 | 1H NMR (400 MHz, DMSO-$d_6$) δ ppm 8.74 (s, 2H) 7.00 (s, 2H) 5.79 (s, 2H) 4.63-4.60 (m, 1H) 3.66-3.51 (m, 11H) 3.50-3.49 (m, 2H) 3.29-3.25 (m, 1H) 3.14 (m, 2H) 2.11-2.08 (m, 2H). |
| 59 Scheme A | 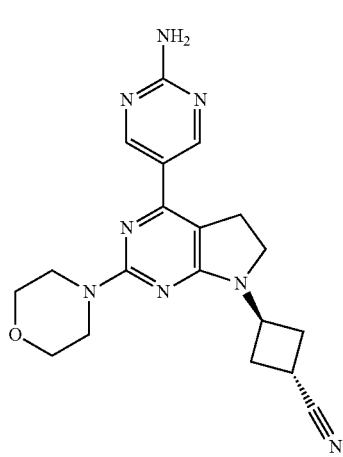 trans-3-[4-(2-aminopyrimidin-5-yl)-2-(morpholin-4-yl)-5,6-dihydro-7H-pyrrolo[2,3-d]pyrimidin-7-yl]cyclobutanecarbonitrile | 379.1 | 1H NMR (400 MHz, DMSO-$d_6$) δ ppm 8.74 (s, 2H) 7.02 (s, 2H) 4.85-4.48 (m, 1H) 3.66-3.65 (m, 10H) 3.17-3.09 (m, 3H) 2.74-2.69 (m, 2H) 2.42-2.40 (m, 2H). |

TABLE 1-continued

| Example No./ Scheme | Structure and Compound Name | LRMS m/z [M + H]+ | 1H NMR or HPLC retention time and method |
|---|---|---|---|
| 60 Scheme A | 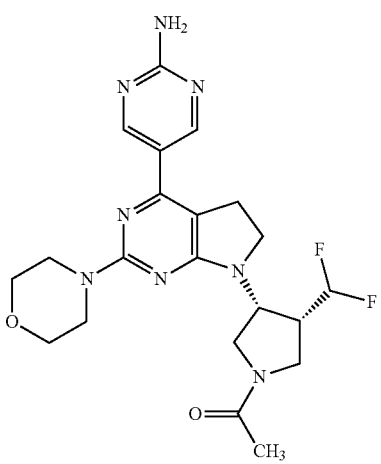<br>1-[(3R,4R)-3-[4-(2-aminopyrimidin-5-yl)-2-(morpholin-4-yl)-5,6-dihydro-7H-pyrrolo[2,3-d]pyrimidin-7-yl]-4-(difluoromethyl)pyrrolidin-1-yl]ethanone | 461.1 | 1H NMR(400 MHz, CD3OD) δ ppm 8.83 (s, 2H) 6.21-5.94 (m, 1H) 3.93-3.63 (m, 15H) 3.23-3.21 (m, 3H) 2.13 (d, J = 6.8 Hz, 3H). |
| 61 Scheme A | 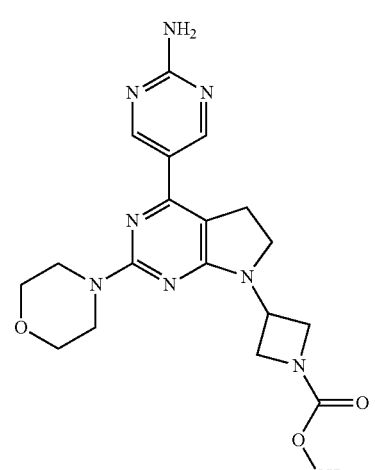<br>methyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 413.1 | 1H NMR (400 MHz, DMSO-d6) δ ppm 8.75 (s, 2H) 7.03 (s, 2H) 4.79-4.77 (m, 1H) 4.25-4.20 (m, 2H) 4.14-4.12 (m, 2H) 3.70 (t, J = 8 Hz, 2H) 3.66-3.65 (m, 8H) 3.58 (s, 3H) 3.15 (t, J = 8 Hz, 2H). |

TABLE 1-continued

| Example No./ Scheme | Structure and Compound Name | LRMS m/z [M + H]+ | 1H NMR or HPLC retention time and method |
|---|---|---|---|
| 62 Scheme A | 3-[4-(2-aminopyrimidin-5-yl)-2-(morpholin-4-yl)-5,6-dihydro-7H-pyrrolo[2,3-d]pyrimidin-7-yl]azetidine-1-carbaldehyde | 383.2 | 1H NMR (400 MHz, DMSO-d6) δ ppm 8.76 (s, 2H) 8.01 (s, 1H) 7.04 (s, 2H) 4.92-4.90 (m, 1H) 4.41-4.36 (m, 2H) 4.17-4.11 (m, 2H) 3.71-3.69 (m, 2H) 3.66-3.65 (m, 8H) 3.17 (t, J = 8 Hz, 2H). |
| 63 Scheme A | 1-[(3S,4R)-3-[4-(2-aminopyrimidin-5-yl)-2-(morpholin-4-yl)-5,6-dihydro-7H-pyrrolo[2,3-d]pyrimidin-7-yl]-4-(difluoromethyl)pyrrolidin-1-yl]ethanone | 461.1 | 1H NMR (400 MHz, DMSO-d6) δ ppm 8.75 (s, 2H) 7 (br s, 2H) 6.35-6.07 (m, 1H) 4.93-4.76 (m, 1H) 3.82-3.42 (m, 14H) 3.17-3.12 (m, 3H) 1.98-1.96 (m, 3H). |
| 64 Scheme A | 5-[7-(cis-3-fluorocyclobutyl)-2-(morpholin-4-yl)-6,7-dihydro-5H-pyrrolo[2,3-d]pyrimidin-4-yl]pyrimidin-2-amine | 372.0 | 1H NMR (400 MHz, DMSO-d6) δ ppm 8.66 (s, 2H) 6.89 (s, 2H) 5.31-4.56 (m, 1H) 4.03 (t, J = 8.1 Hz, 1H) 3.57 (br s, 10H) 3.06 (t, J = 8.1 Hz, 2H) 2.52 (ddd, J = 7.0, 7.2, 9.5 Hz, 3H) 2.39 (d, J = 2.6 Hz, 1H). |

TABLE 1-continued

| Example No./ Scheme | Structure and Compound Name | LRMS m/z [M + H]+ | 1H NMR or HPLC retention time and method |
|---|---|---|---|
| 65 Scheme A | 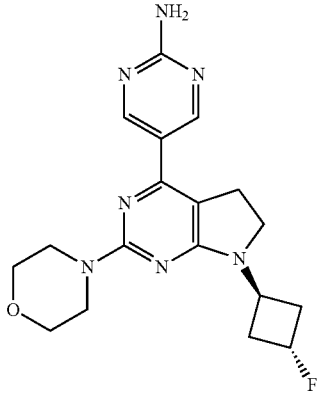<br>5-[7-(trans-3-fluorocyclobutyl)-2-(morpholin-4-yl)-6,7-dihydro-5H-pyrrolo[2,3-d]pyrimidin-4-yl]pyrimidin-2-amine | 372.0 | 1H NMR (400 MHz, DMSO-d$_6$) δ ppm 8.74 (s, 2H) 6.97 (s, 2H) 5.38-5.12 (m, 1H) 4.82 (t, J = 7.8 Hz, 1H) 3.69-3.55 (m, 10H) 3.13 (t, J = 7.8 Hz, 2H) 2.82-2.63 (m, 2H) 2.47-2.25 (m, 2H). |
| 66* Scheme A | 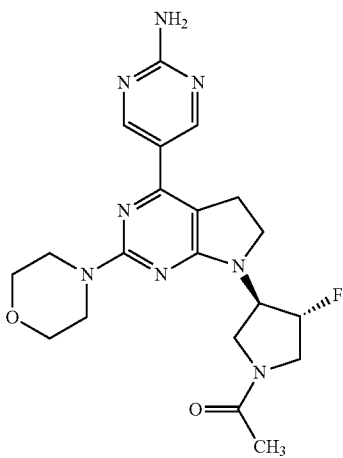<br>1-{(3R,4R)-3-[4-(2-aminopyrimidin-5-yl)-2-(morpholin-4-yl)-5,6-dihydro-7H-pyrrolo[2,3-d]pyrimidin-7-yl]-4-fluoropyrrolidin-1-yl}ethanone | 429.2 | 1H NMR (400 MHz, CDCl$_3$) δ ppm 8.83 (s, 2H) 5.46-5.24 (m, 3H) 4.76-4.60 (m, 1H) 4.32-3.55 (m, 14H) 3.16 (t, J = 8 Hz, 2H) 2.12 (s, 3H). |

TABLE 1-continued

| Example No./ Scheme | Structure and Compound Name | LRMS m/z [M + H]+ | 1H NMR or HPLC retention time and method |
|---|---|---|---|
| 67* Scheme A | 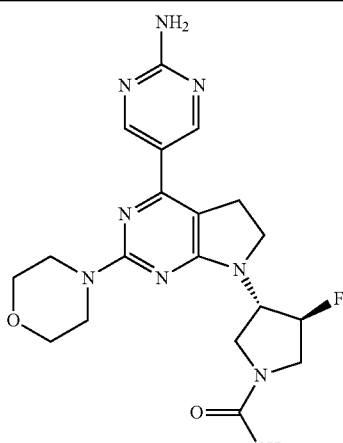<br>1-{(3S,4S)-3-[4-(2-aminopyrimidin-5-yl)-2-(morpholin-4-yl)-5,6-dihydro-7H-pyrrolo[2,3-d]pyrimidin-7-yl]-4-fluoropyrrolidin-1-yl}ethanone | 429.2 | 1H NMR (400 MHz, CDCl$_3$) δ ppm 8.83 (s, 2H) 5.46-5.24 (m, 3H) 4.76-4.60 (m, 1H) 4.32-3.55 (m, 14H) 3.16 (t, J = 8 Hz, 2H) 2.12 (s, 3H). |
| 68 Scheme A | 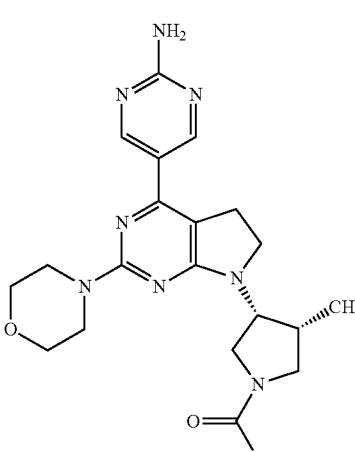<br>1-{(3R,4R)-3-[4-(2-aminopyrimidin-5-yl)-2-(morpholin-4-yl)-5,6-dihydro-7H-pyrrolo[2,3-d]pyrimidin-7-yl]-4-methylpyrrolidin-1-yl}ethanone | 425.1 | 1H NMR (400 MHz, CDCl$_3$) δ ppm 8.84 (s, 2H) 5.23 (s, 2H) 4.83-4.71 (m, 1H) 3.89-3.62 (m, 13H) 3.20-3.14 (m, 3H) 2.77-2.61 (m, 1H) 2.08 (s, 3H) 1.05 (d, J = 6.8 Hz, 3H). |

TABLE 1-continued

| Example No./ Scheme | Structure and Compound Name | LRMS m/z [M + H]+ | ¹H NMR or HPLC retention time and method |
|---|---|---|---|
| 69 Scheme A | 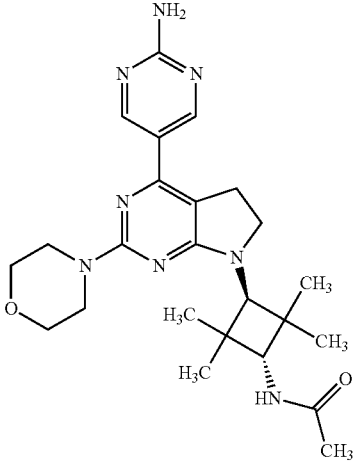<br>N-{trans-3-[4-(2-aminopyrimidin-5-yl)-2-(morpholin-4-yl)-5,6-dihydro-7H-pyrrolo[2,3-d]pyrimidin-7-yl]-2,2,4,4-tetramethylcyclobutyl}acetamide | 411.1 | ¹H NMR (400 MHz, DMSO-$d_6$) δ ppm 8.74 (s, 2H) 7.72 (d, J = 10 Hz, 1H) 6.98 (s, 2H) 4.03 (s, 1H) 3.84 (q, J = 8.9 Hz, 3H) 3.67-3.65 (m, 8H) 3.14 (t, J = 8 Hz, 2H) 1.91 (s, 3H) 1.29 (s, 6H) 1.08 (s, 6H). |
| 70 Scheme A | 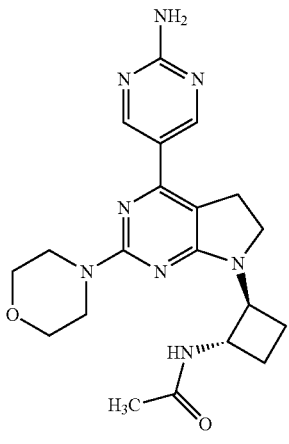<br>N-{(1S,2S)-2-[4-(2-aminopyrimidin-5-yl)-2-(morpholin-4-yl)-5,6-dihydro-7H-pyrrolo[2,3-d]pyrimidin-7-yl]cyclobutyl}acetamide | 411.1 | ¹H NMR (400 MHz, DMSO-$d_6$) δ ppm 8.72 (s, 2H) 8.26 (d, J = 8.4 Hz, 1H) 7.00 (s, 2H) 4.50-4.46 (m, 1H) 4.42-4.35 (m, 1H) 3.67-3.66 (m, 10H) 3.13 (m, 2H) 1.98 (s, 1H) 1.85 (m, 2H) 1.76 (s, 3H) 1.59-1.54 (m, 1H). |

TABLE 1-continued

| Example No./ Scheme | Structure and Compound Name | LRMS m/z [M + H]+ | 1H NMR or HPLC retention time and method |
|---|---|---|---|
| 71 Scheme A | 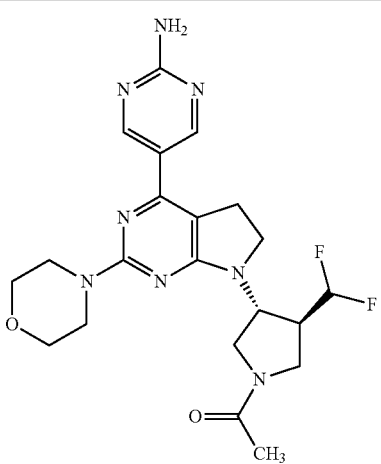<br>1-[(3R,4S)-3-[4-(2-aminopyrimidin-5-yl)-2-(morpholin-4-yl)-5,6-dihydro-7H-pyrrolo[2,3-d]pyrimidin-7-yl]-4-(difluoromethyl)pyrrolidin-1-yl]ethanone | 461.1 | 1H NMR (400 MHz, DMSO-$d_6$) δ ppm 8.74 (s, 2H) 7.01 (s, 2H) 6.33-6.05 (m, 1H) 4.92-4.76 (m, 1H) 3.78-3.42 (m, 13H) 3.35-3.14 (m, 4H) 2.02-1.96 (m, 3H). |
| 72 Scheme A | 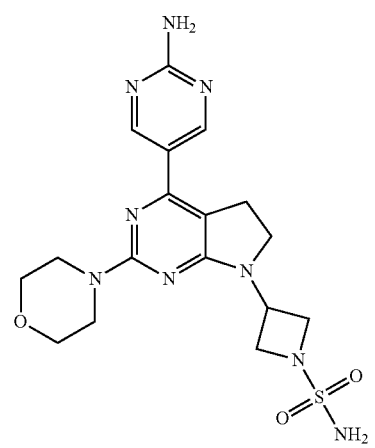<br>3-[4-(2-aminopyrimidin-5-yl)-2-(morpholin-4-yl)-5,6-dihydro-7H-pyrrolo[2,3-d]pyrimidin-7-yl]azetidine-1-sulfonamide | 434.3 | 1H NMR (400 MHz, DMSO-$d_6$) δ ppm 8.75 (s, 2H) 7.04 (s, 2H) 7.03 (br s, 2H) 4.81-4.77 (m, 1H) 3.99-3.98 (m, 2H) 3.88-3.86 (m, 2H) 3.71-3.69 (m, 2H) 3.69-3.64 (m, 8H) 3.17 (t, J = 8.4 Hz, 2H). |

TABLE 1-continued

| Example No./ Scheme | Structure and Compound Name | LRMS m/z [M + H]+ | ¹H NMR or HPLC retention time and method |
|---|---|---|---|
| 73 Scheme A | 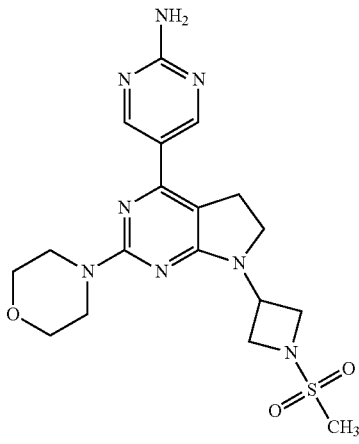<br>5-{7-[1-(methylsulfonyl)azetidin-3-yl]-2-(morpholin-4-yl)-6,7-dihydro-5H-pyrrolo[2,3-d]pyrimidin-4-yl}pyrimidin-2-amine | 433.1 | ¹H NMR (400 MHz, DMSO-d₆) δ ppm 8.76 (s, 2H) 7.05 (s, 2H) 4.93-4.89 (m, 1H) 4.18 (t, J = 7.6 Hz, 2H) 4.06 (t, J = 8.4 Hz, 2H) 3.75 (t, J = 8.2 Hz, 2H) 3.66-3.65 (m, 8H) 3.18 (t, J = 8.0 Hz, 2H) 3.08 (s, 3H). |
| 74* Scheme A | 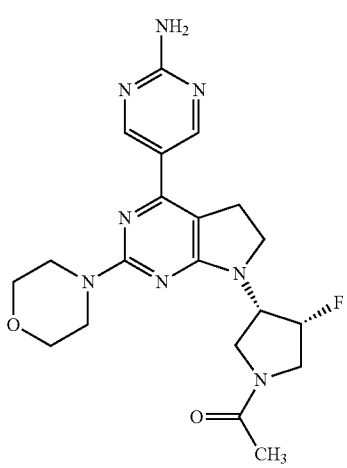<br>1-{(3S,4R)-3-[4-(2-aminopyrimidin-5-yl)-2-(morpholin-4-yl)-5,6-dihydro-7H-pyrrolo[2,3-d]pyrimidin-7-yl]-4-fluoropyrrolidin-1-yl}ethanone | 429.2 | ¹H NMR (400 MHz, CDCl₃) δ ppm 8.85 (s, 2H) 5.45-5.25 (m, 3H) 3.93-3.77 (m, 15H) 3.20-3.10 (m, 2H) 2.12-2.09 (m, 3H). |

TABLE 1-continued

| Example No./ Scheme | Structure and Compound Name | LRMS m/z [M + H]+ | $^1$H NMR or HPLC retention time and method |
|---|---|---|---|
| 75* Scheme A | 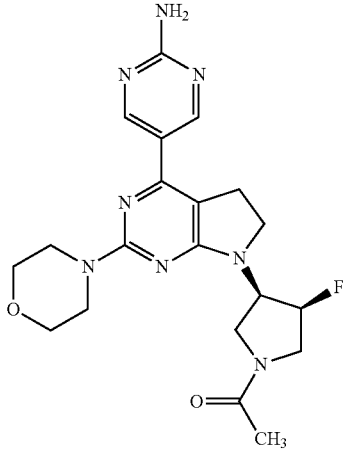 1-{(3R,4S)-3-[4-(2-aminopyrimidin-5-yl)-2-(morpholin-4-yl)-5,6-dihydro-7H-pyrrolo[2,3-d]pyrimidin-7-yl]-4-fluoropyrrolidin-1-yl}ethanone | 429.2 | $^1$H NMR (400 MHz, CDCl$_3$) δ ppm 8.86 (s, 2H) 5.45-5.25 (m, 3H) 3.95-3.60 (m, 15H) 3.20-3.10 (m, 2H) 2.12-2.09 (m, 3H). |
| 76 Scheme A | 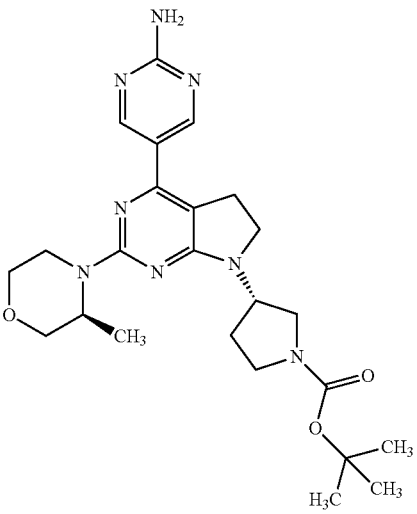 tert-butyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 483.0 | $^1$H NMR (400 MHz, CD$_3$OD) δ ppm 8.81 (s, 2H) 4.78-4.70 (m, 1H) 4.67-4.53 (m, 1H) 4.35 (dd, J = 2.3, 13.6 Hz, 1H) 3.96 (dd, J = 3.4, 11.2 Hz, 1H) 3.80-3.62 (m, 5H) 3.55 (dt, J = 2.9, 11.7 Hz, 2H) 3.49-3.36 (m, 2H) 3.24 (dd, J = 3.8, 13.3 Hz, 1H) 3.17 (t, J = 8.1 Hz, 2H) 2.26-2.13 (m, 2H) 1.49 (s, 9H) 1.27 (d, J = 6.6 Hz, 3H). |

TABLE 1-continued

| Example No./ Scheme | Structure and Compound Name | LRMS m/z [M + H]+ | 1H NMR or HPLC retention time and method |
|---|---|---|---|
| 77 Scheme A | (4R)-4-[4-(2-aminopyrimidin-5-yl)-2-(morpholin-4-yl)-5,6-dihydro-7H-pyrrolo[2,3-d]pyrimidin-7-yl]piperidin-2-one | 397.2 | 1H NMR (400 MHz, DMSO-d6) δ ppm 8.74 (s, 2H) 7.61 (s, 1H) 7.00 (s, 2H) 4.31-4.28 (m, 1H) 3.65-3.43 (m, 11H) 3.22-3.20 (m, 2H) 3.15-3.11 (m, 2H) 2.33-2.28 (m, 1H) 1.93-1.88 (m, 2H). |
| 78 Scheme A | (4S)-4-[4-(2-aminopyrimidin-5-yl)-2-(morpholin-4-yl)-5,6-dihydro-7H-pyrrolo[2,3-d]pyrimidin-7-yl]piperidin-2-one | 397.2 | 1H NMR (400 MHz, DMSO-d6) δ ppm 8.74 (s, 2H) 7.61 (s, 1H) 7.00 (s, 2H) 4.33-4.28 (m, 1H) 3.65-3.55 (m, 11H) 3.22-3.20 (m, 2H) 3.15-3.11 (m, 2H) 2.33-2.28 (m, 1H) 1.93-1.88 (m, 2H). |
| 79 Scheme A | 5-{2-[(3S)-3-methylmorpholin-4-yl]-7-[(3S)-1-(methylsulfonyl)pyrrolidin-3-yl]-6,7-dihydro-5H-pyrrolo[2,3-d]pyrimidin-4-yl}pyrimidin-2-amine | 461.0 | 1H NMR (400 MHz, DMSO-d6) δ ppm 8.74 (s, 2H) 6.98 (s, 2H) 4.68-4.57 (m, 2H) 4.26 (d, J = 11.5 Hz, 1H) 3.89 (dd, J = 3.2, 11.2 Hz, 1H) 3.73-3.60 (m, 3H) 3.60-3.48 (m, 2H) 3.47-3.37 (m, 2H) 3.36-3.28 (m, 2H) 3.18-3.03 (m, 3H) 2.94 (s, 3H) 2.20-2.11 (m, 2H) 1.17 (d, J = 6.6 Hz, 3H). |

TABLE 1-continued

| Example No./ Scheme | Structure and Compound Name | LRMS m/z [M + H]+ | 1H NMR or HPLC retention time and method |
|---|---|---|---|
| 80 Scheme A | 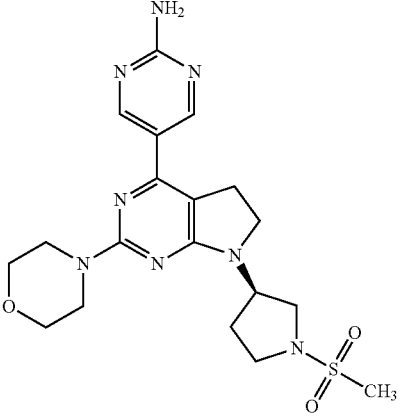 5-{7-[(3R)-1-(methylsulfonyl)pyrrolidin-3-yl]-2-(morpholin-4-yl)-6,7-dihydro-5H-pyrrolo[2,3-d]pyrimidin-4-yl}pyrimidin-2-amine | 447.5 | 1H NMR (400 MHz, DMSO-$d_6$) δ ppm 8.75 (s, 2H) 7.02 (s, 2H) 4.69-4.65 (m, 1H) 3.67-3.64 (m, 10H) 3.49-3.41 (m, 2H) 3.31-3.28 (m, 2H) 3.16-3.14 (m, 2H) 2.96 (s, 3H) 2.16-2.13 (m, 2H). |
| 81 Scheme A | 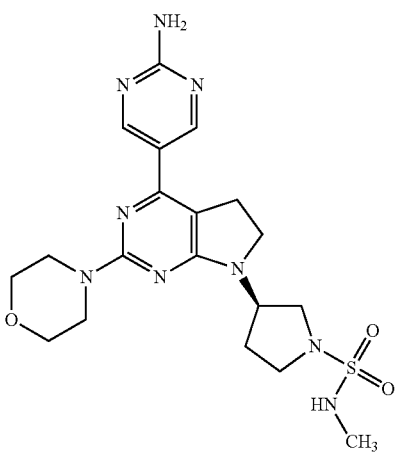 (3R)-3-[4-(2-aminopyrimidin-5-yl)-2-(morpholin-4-yl)-5,6-dihydro-7H-pyrrolo[2,3-d]pyrimidin-7-yl]-N-methylpyrrolidine-1-sulfonamide | 462.1 | 1H NMR (400 MHz, $D_2O$) δ ppm 8.67 (s, 2H) 4.97-4.50 (m, 1H) 3.98-3.94 (m, 2H) 3.83 (s, 8H) 3.60-3.41 (m, 4H) 3.11-3.08 (m, 2H) 2.70 (s, 3H) 2.38-2.28 (m, 2H). |

TABLE 1-continued

| Example No./ Scheme | Structure and Compound Name | LRMS m/z [M + H]+ | $^1$H NMR or HPLC retention time and method |
|---|---|---|---|
| 82 Scheme A | 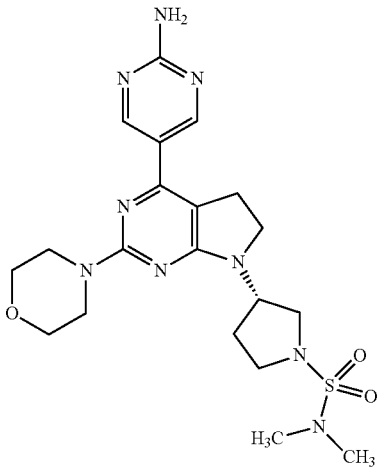<br>(3S)-3-[4-(2-aminopyrimidin-5-yl)-2-(morpholin-4-yl)-5,6-dihydro-7H-pyrrolo[2,3-d]pyrimidin-7-yl]-N,N-dimethylpyrrolidine-1-sulfonamide | 476.1 | $^1$H NMR (400 MHz, DMSO-d$_6$) δ ppm 8.74 (s, 2H) 7.01 (s, 2H) 4.67-4.64 (m, 1H) 3.66-3.61 (m, 10H) 3.48-3.39 (m, 2H) 3.31-3.29 (m, 2H) 3.30 (t, J = 2.0 Hz, 2H) 2.77 (s, 6H) 2.18-2.13 (m, 2H). |
| 83 Scheme A | 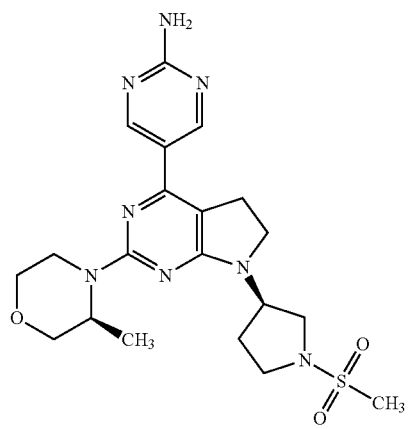<br>5-{2-[(3S)-3-methylmorpholin-4-yl]-7-[(3R)-1-(methylsulfonyl)pyrrolidin-3-yl]-6,7-dihydro-5H-pyrrolo[2,3-d]pyrimidin-4-yl}pyrimidin-2-amine | 461.1 | $^1$H NMR (400 MHz, DMSO-d$_6$) δ ppm 8.74 (s, 2H) 7.01 (s, 2H) 4.65-4.61 (m, 2H) 4.28-4.25 (m, 1H) 3.72-3.68 (m, 1H) 3.62-3.30 (m, 7H) 3.28-3.08 (m, 2H) 3.15-3.11 (m, 3H) 2.95 (s, 3H) 2.18-2.11 (m, 2H) 1.17 (d, J = 6.8 Hz, 3H). |
| 84 Scheme A | 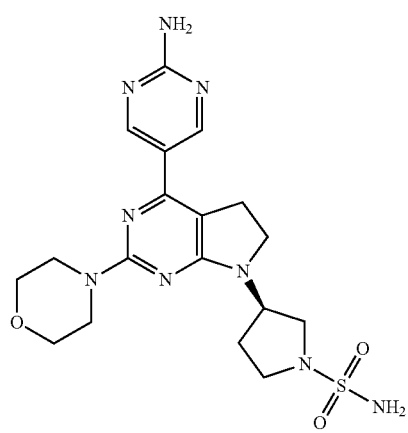<br>(3R)-3-[4-(2-aminopyrimidin-5-yl)-2-(morpholin-4-yl)-5,6-dihydro-7H-pyrrolo[2,3-d]pyrimidin-7-yl]pyrrolidine-1-sulfonamide | 448.0 | $^1$H NMR (400 MHz, DMSO-d$_6$) δ ppm 8.67 (s, 2H) 7.26-7.13 (m, 1H) 6.90 (s, 2H) 4.78-4.75 (m, 1H) 3.74-3.68 (m, 10H) 3.37-3.33 (m, 2H) 3.21-3.14 (m, 5H) 2.17-1.76 (m, 2H). |

TABLE 1-continued

| Example No./ Scheme | Structure and Compound Name | LRMS m/z [M + H]+ | 1H NMR or HPLC retention time and method |
|---|---|---|---|
| 85 Scheme A | 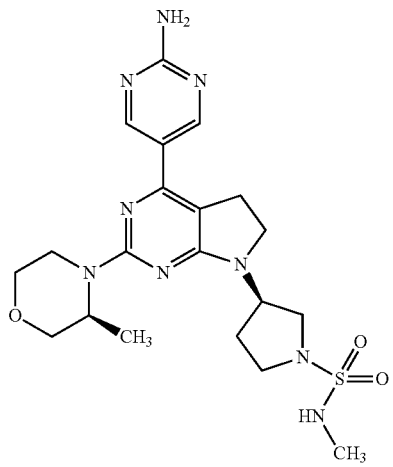<br>(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-N-methylpyrrolidine-1-sulfonamide | 476.0 | 1H NMR (400 MHz, CD3OD) δ ppm 8.69 (s, 2H) 4.68-4.57 (m, 2H) 4.24 (dd, J = 2.4, 13.7 Hz, 1H) 3.84 (dd, J = 3.7, 11.2 Hz, 1H) 3.69-3.55 (m, 4H) 3.50-3.35 (m, 3H) 3.31-3.23 (m, 2H) 3.16-3.03 (m, 3H) 2.58 (s, 3H) 2.19-2.10 (m, 2H) 1.16 (d, J = 6.9 Hz, 3H). |
| 86 Scheme A | 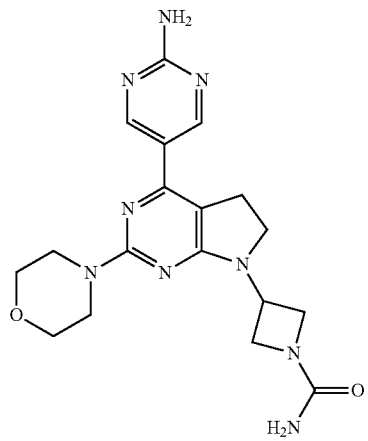<br>3-[4-(2-aminopyrimidin-5-yl)-2-(morpholin-4-yl)-5,6-dihydro-7H-pyrrolo[2,3-d]pyrimidin-7-yl]azetidine-1-carboxamide | 398.1 | 1H NMR (400 MHz, DMSO-d6) δ ppm 8.74 (s, 2H) 7.02 (s, 2H) 5.91 (s, 2H) 4.69-4.67 (m, 1H) 4.07-4.03 (m, 2H) 3.99-3.97 (m, 2H) 3.68-3.66 (m, 2H) 3.66-3.64 (m, 8H) 3.17-3.15 (m, 2H). |

TABLE 1-continued

| Example No./ Scheme | Structure and Compound Name | LRMS m/z [M + H]+ | ¹H NMR or HPLC retention time and method |
|---|---|---|---|
| 87 Scheme A | 5-{7-(3,3-difluorocyclobutyl)-2-[(3S)-3-methylmorpholin-4-yl]-6,7-dihydro-5H-pyrrolo[2,3-d]pyrimidin-4-yl}pyrimidin-2-amine | 404.0 | ¹H NMR (400 MHz, DMSO-d₆) δ ppm 8.73 (s, 2H) 6.98 (s, 2H) 4.64-4.57 (m, 1H) 4.36-4.28 (m, 1H) 4.28-4.22 (m, 1H) 3.88 (dd, J = 11.2, 3.1 Hz, 1H) 3.72-3.65 (m, 1H) 3.62 (t, J = 8.7 Hz, 2H) 3.56 (dd, J = 11.3, 3.1 Hz, 1H) 3.40 (td, J = 11.8, 2.9 Hz, 1H) 3.15-3.09 (m, 3H) 3.09-3.00 (m, 2H) 2.91-2.79 (m, 2H) 1.16 (d, J = 6.6 Hz, 3 H). |
| 88* Scheme A | 5-{7-[(1R)-3,3-difluorocyclopentyl]-2-[(3S)-3-methylmorpholin-4-yl]-6,7-dihydro-5H-pyrrolo[2,3-d]pyrimidin-4-yl}pyrimidin-2-amine | 418.0 | ¹H NMR (400 MHz, DMSO-d₆) δ ppm 8.74 (s, 2H) 7.00 (s, 2H) 4.61-4.57 (m, 2H) 4.26-4.24 (m, 1H) 3.71-3.69 (m, 1H) 3.61-3.59 (m, 1H) 3.58-3.56 (m, 3H) 3.41-3.40 (m, 1H) 3.15-3.08 (m, 3H) 2.39-2.00 (m, 6H) 1.16 (d, J = 6.8 Hz, 3H). |
| 89* Scheme A | 5-{7-[(1S)-3,3-difluorocyclopentyl]-2-[(3S)-3-methylmorpholin-4-yl]-6,7-dihydro-5H-pyrrolo[2,3-d]pyrimidin-4-yl}pyrimidin-2-amine | 418.2 | ¹H NMR (400 MHz, DMSO-d₆) δ ppm 8.74 (s, 2H) 7.00 (s, 2H) 4.61-4.57 (m, 2H) 4.26-4.24 (m, 1H) 3.71-3.69 (m, 1H) 3.61-3.59 (m, 1H) 3.58-3.56 (m, 3H) 3.41-3.40 (m, 1H) 3.15-3.08 (m, 3H) 2.39-2.00 (m, 6H) 1.16 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 90 Scheme A | 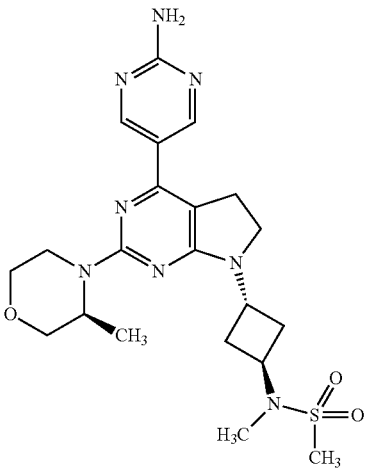<br>N-(trans-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl)-N-methylmethanesulfonamide | 475.1 | 1H NMR (400 MHz, DMSO-$d_6$) δ ppm 8.74 (s, 2H) 7.00 (s, 2H) 4.63-4.47 (m, 3H) 4.30-4.20 (m, 1H) 3.89-3.80 (m, 1H) 3.60-3.52 (m, 3H) 3.70-3.55 (m, 1H) 3.45-3.40 (m, 1H) 3.20-3.05 (m, 3H) 2.83 (d, J = 4.0 Hz, 6H) 2.60-2.50 (m, 4H), 1.15 (d, J = 4.0 Hz, 3H). |
| 91 Scheme A | 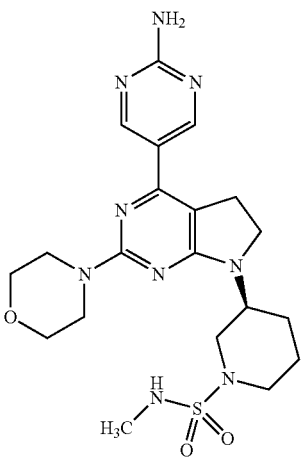<br>(3S)-3-[4-(2-aminopyrimidin-5-yl)-2-(morpholin-4-yl)-5,6-dihydro-7H-pyrrolo[2,3-d]pyrimidin-7-yl]-N-methylpiperidine-1-sulfonamide | 476.1 | 1H NMR (CD$_3$OD 400 MHz) δ ppm 8.80 (s, 2H) 4.13-4.10 (m, 1H) 3.78-3.67 (m, 12H) 3.16 (t, J = 8.0 Hz, 2H) 2.88-2.77 (m, 2H) 2.66 (s, 3H) 1.96-1.90 (m, 2H) 1.82-1.75 (m, 2H). |

TABLE 1-continued

| Example No./ Scheme | Structure and Compound Name | LRMS m/z [M + H]+ | 1H NMR or HPLC retention time and method |
|---|---|---|---|
| 92 Scheme A | 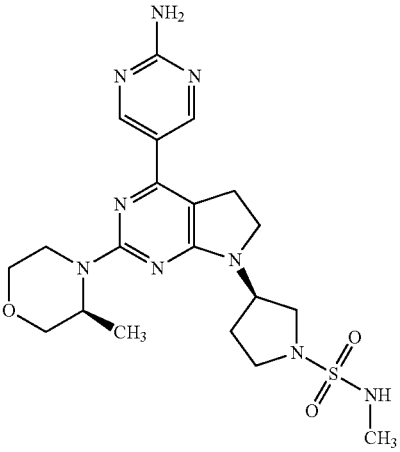 (3R)-3-{4-(2-aminopyrimidin-5-yl)-2-[(3S)-3-methylmorpholin-4-yl]-5,6-dihydro-7H-pyrrolo[2,3-d]pyrimidin-7-yl}-N-methylpyrrolidine-1-sulfonamide | 476.1 | 1H NMR (400 MHz, D$_2$O) δ ppm 8.74 (s, 2H) 4.97-4.94 (m, 1H) 4.61-4.60 (m, 1H) 4.06-3.49 (m, 12H) 3.11-3.08 (m, 2H) 2.70 (s, 3H) 2.37-2.31 (m, 2H) 1.36 (d, J = 6.8 Hz, 3H). |
| 93 Scheme A | 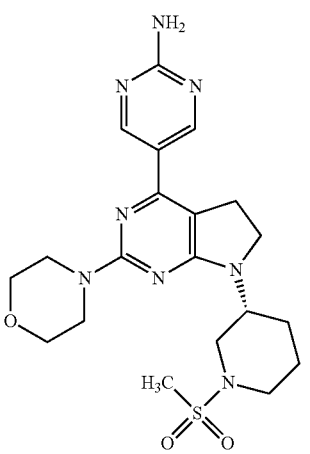 5-{7-[(3R)-1-(methylsulfonyl)piperidin-3-yl]-2-(morpholin-4-yl)-6,7-dihydro-5H-pyrrolo[2,3-d]pyrimidin-4-yl}pyrimidin-2-amine | 461.1 | 1H NMR (400 MHz, DMSO-d$_6$) δ ppm 8.75 (s, 2H) 7.01 (s, 2H) 4.04-3.94 (m, 1H) 3.73-3.58 (m, 11H) 3.55-3.49 (m, 1H) 3.14 (t, J = 8.4 Hz, 2H) 2.89 (s, 3H) 2.80 (t, J = 10.8 Hz, 1H) 2.68 (t, J = 10.8 Hz, 1H) 1.86 (d, J = 9.2 Hz, 2H) 1.71-1.60 (m, 2H). |

| Example No./ Scheme | Structure and Compound Name | LRMS m/z [M + H]+ | 1H NMR or HPLC retention time and method |
|---|---|---|---|
| 94 Scheme A | 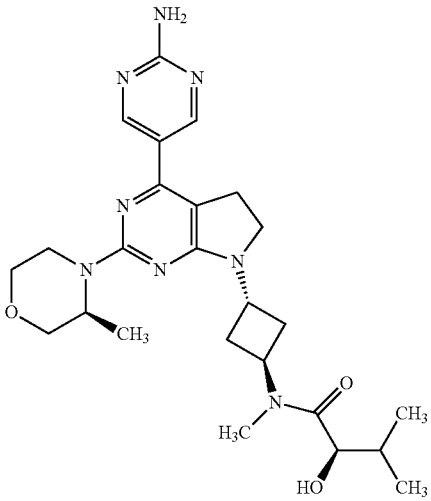 (2R)-N-(trans-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl)-2-hydroxy-N,3-dimethylbutanamide | 519.1 [M + Na]+ | 1H NMR (400 MHz, DMSO) δ ppm 8.58 (s, 2H) 7.40 (br s, 2H) 5.13-4.91 (m 1H) 4.67-4.57 (m, 2H) 4.14-3.97 (m, 5H) 3.76-3.73 (m, 1H) 3.62-3.60 (m, 1H) 3.34-3.31 (m 2H) 3.17-3.13 (m 2H) 3.04-2.94 (m, 3H) 2.64-2.51 (m, 4H) 1.89-1.78 (m, 1H) 1.28 (d, J = 6.8 Hz, 3H) 0.93-0.86 (m, 3H) 0.80 (d, J = 6.8 Hz, 3H). |
| 95 Scheme A | 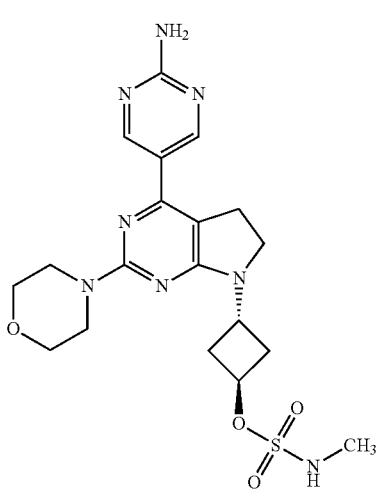 trans-3-[4-(2-aminopyrimidin-5-yl)-2-(morpholin-4-yl)-5,6-dihydro-7H-pyrrolo[2,3-d]pyrimidin-7-yl]cyclobutyl methylsulfamate | 463.0 | 1H NMR (400 MHz, DMSO) δ ppm 8.75 (s, 2H) 7.76 (d, J = 4.0 Hz, 1H) 7.01 (s, 2H) 4.96-4.92 (m, 1H) 4.75-4.71 (m, 1H) 3.65 (s, 12H) 3.31-3.12 (m, 2H) 2.82-2.75 (m, 2H) 2.56-2.45 (m, 3H). |

| Example No./ Scheme | Structure and Compound Name | LRMS m/z [M + H]+ | ¹H NMR or HPLC retention time and method |
|---|---|---|---|
| 96 Scheme A | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidin-1-yl]ethanone | 447.1 [M + Na]+ | ¹H NMR (400 MHz, DMSO-$d_6$) δ ppm 8.74 (s, 2H) 7.01 (s, 2H) 4.70-4.50 (m, 2H) 4.30-4.27 (m, 1H) 3.92-3.85 (m, 1H) 3.75-3.35 (m, 9H) 3.15-3.00 (m, 3H) 2.20-2.00 (m, 2H) 1.95-1.90 (s, 3H) 1.20-1.10 (m, 3H). |
| 97 Scheme A | (3R)-3-[4-(2-aminopyrimidin-5-yl)-2-(morpholin-4-yl)-5,6-dihydro-7H-pyrrolo[2,3-d]pyrimidin-7-yl]-N-methylpiperidine-1-sulfonamide | 476.1 | ¹H NMR (CD$_3$OD 400 MHz) δ ppm 8.80 (s, 2H) 4.17-4.08 (m, 1H) 3.82-3.71 (m, 10H) 3.69-3.63 (m, 2H) 3.17 (t, J = 8.0 Hz, 2H) 2.85 (t, J = 11.0 Hz, 1H) 2.76 (t, J = 11.9 Hz, 1H) 2.66 (s, 3H) 2.01-1.89 (m, 2H) 1.85-1.72 (m, 2H). |
| 98 Scheme A | 1-[(3R,4R)-3-{4-(2-aminopyrimidin-5-yl)-2-[(3S)-3-methylmorpholin-4-yl]-5,6-dihydro-7H-pyrrolo[2,3-d]pyrimidin-7-yl}-4-methoxypyrrolidin-1-yl]ethanone | 455.2 | ¹H NMR (400 MHz, DMSO-$d_6$) δ ppm 8.74 (s, 2H) 7.01 (s, 2H) 4.65-4.45 (m, 2H) 4.27-4.24 (m, 1H) 4.11-3.99 (m, 1H) 3.89-3.80 (m, 2H) 3.73-3.37 (m, 10H) 3.29-3.22 (m, 1H) 3.14-3.04 (m, 3H) 2.03-1.98 (m, 3H) 1.17 (t, J = 6.4 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 99 Scheme A | 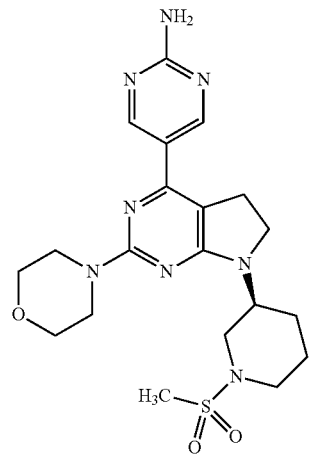<br>5-{7-[(3S)-1-(methylsulfonyl)piperidin-3-yl]-2-(morpholin-4-yl)-6,7-dihydro-5H-pyrrolo[2,3-d]pyrimidin-4-yl}pyrimidin-2-amine | 461.2 | ¹H NMR (400 MHz, DMSO-$d_6$) δ ppm 8.74 (s, 2H) 7.03 (s, 2H) 4.02-3.98 (m, 1H) 3.70-3.60 (m, 11H) 3.54-3.50 (m, 1H) 3.14 (t, J = 8.4 Hz, 2H) 2.89 (s, 3H) 2.80 (t, J = 10.8 Hz, 1H) 2.68 (t, J = 10.8 Hz, 1H) 1.86 (d, J = 11.2 Hz, 2H) 1.68-1.63 (m, 2H). |
| 100 Scheme A | 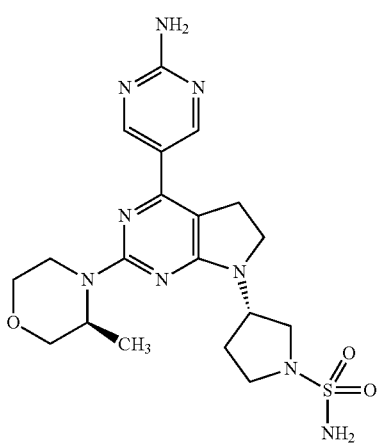<br>(3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-sulfonamide | 462.1 | ¹H NMR (400 MHz, DMSO-$d_6$) δ ppm 8.74 (s, 2H) 7.00 (s, 2H) 6.86 (s, 2H) 4.70-4.55 (m, 2H) 4.30-4.20 (m, 1H) 3.95-3.85 (m, 1H) 3.70-3.55 (m, 3H) 3.30-3.25 (m, 4H) 3.20-3.00 (m, 5H) 2.15-2.05 (m, 2H) 1.20-1.10 (m, 3H). |

TABLE 1-continued

| Example No./ Scheme | Structure and Compound Name | LRMS m/z [M + H]+ | ¹H NMR or HPLC retention time and method |
|---|---|---|---|
| 101 Scheme A | 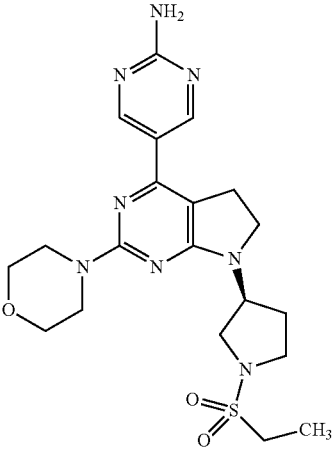 5-{7-[(3S)-1-(ethylsulfonyl)pyrrolidin-3-yl]-2-(morpholin-4-yl)-6,7-dihydro-5H-pyrrolo[2,3-d]pyrimidin-4-yl}pyrimidin-2-amine | 483.1 [M + Na]+ | ¹H NMR (400 MHz, DMSO-d₆) δ ppm 8.73 (s, 2H) 7.06 (s, 2H) 4.68-4.66 (m, 1H) 3.72-3.62 (m, 11H) 3.56-3.42 (m, 3H) 3.18-3.13 (m, 4H) 2.19-2.13 (m, 2H) 1.24 (t, J = 8.0 Hz, 3H). |
| 102 Scheme A | 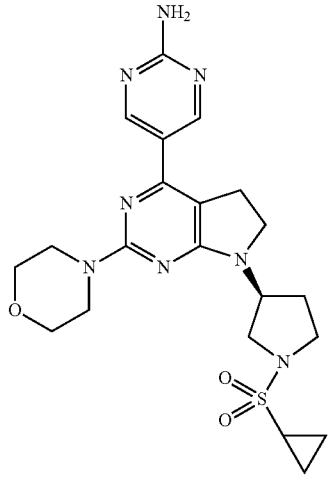 5-{7-[(3S)-1-(cyclopropylsulfonyl)pyrrolidin-3-yl]-2-(morpholin-4-yl)-6,7-dihydro-5H-pyrrolo[2,3-d]pyrimidin-4-yl}pyrimidin-2-amine | 473.1 | ¹H NMR (400 MHz, DMSO-d₆) δ ppm 8.75 (s, 2H) 7.02 (s, 2H) 4.68-4.65 (m, 1H) 3.67-3.55 (m, 12H) 3.51-3.42 (m, 2H) 3.14 (t, J = 8.0 Hz, 2H) 2.77-2.74 (m, 1H) 2.21-2.15 (m, 2H) 1.00-0.96 (m, 4H). |

Note: the NMR above uses $DMSO-d_6$.

TABLE 1-continued

| Example No./ Scheme | Structure and Compound Name | LRMS m/z [M + H]+ | 1H NMR or HPLC retention time and method |
|---|---|---|---|
| 103 Scheme A | 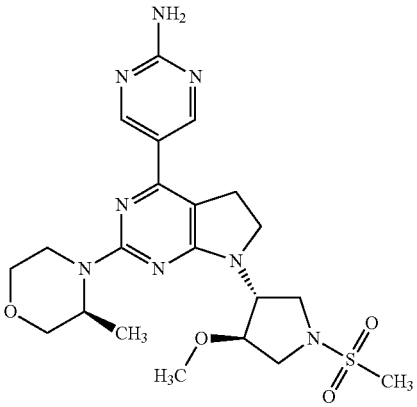 5-{7-[(3R,4R)-4-methoxy-1-(methylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 491.2 | 1H NMR (400 MHz, DMSO-$d_6$) δ ppm 8.76 (s, 2H) 7.04 (s, 2H) 4.62-4.63 (m, 2H) 4.30-4.27 (m, 1H) 4.11-4.12 (m, 1H) 3.90-3.88 (m, 1H) 3.70-3.45 (m, 9H) 3.41-3.16 (m, 6H) 2.98 (s, 3H) 1.18 (s, 3H). |
| 104 Scheme A | 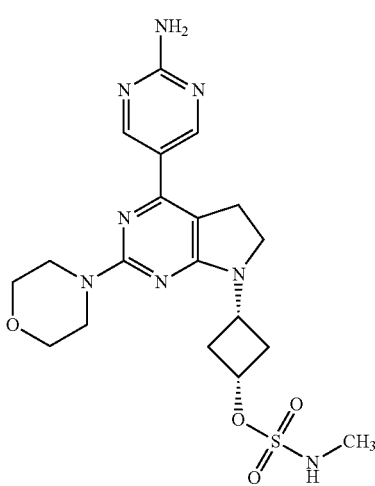 cis-3-[4-(2-aminopyrimidin-5-yl)-2-(morpholin-4-yl)-5,6-dihydro-7H-pyrrolo[2,3-d]pyrimidin-7-yl]cyclobutyl methylsulfamate | 463.1 | 1H NMR (400 MHz, DMSO-$d_6$) δ ppm 8.75 (s, 2H) 7.76-7.73 (m, 1H) 7.02 (s, 2H) 4.60-4.56 (m, 1H) 4.23-4.19 (m, 1H) 3.65 (s, 12H) 3.30-3.11 (m, 2H), 2.68-2.34 (m, 5H). |

TABLE 1-continued

| Example No./ Scheme | Structure and Compound Name | LRMS m/z [M + H]+ | 1H NMR or HPLC retention time and method |
|---|---|---|---|
| 105 Scheme A | 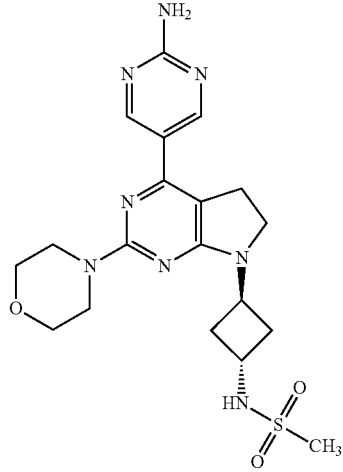 N-{trans-3-[4-(2-aminopyrimidin-5-yl)-2-(morpholin-4-yl)-5,6-dihydro-7H-pyrrolo[2,3-d]pyrimidin-7-yl]cyclobutyl}methanesulfonamide | 447.1 | 1H NMR (400 MHz, DMSO-d6) δ ppm 8.74 (s, 2H) 7.55-7.53 (m, 1H) 7.00 (s, 2H) 4.71-4.67 (m, 1H) 3.93-3.91 (m, 1H) 3.69-3.65 (m, 10H) 3.15-3.11 (m, 2H) 2.88 (s, 3H) 2.55-2.51 (m, 2H) 2.24-2.21 (m, 2H). |
| 106 Scheme A | 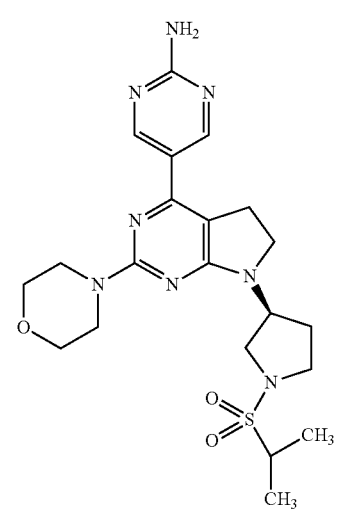 5-{2-(morpholin-4-yl)-7-[(3S)-1-(propan-2-ylsulfonyl)pyrrolidin-3-yl]-6,7-dihydro-5H-pyrrolo[2,3-d]pyrimidin-4-yl}pyrimidin-2-amine | 475.2 | 1H NMR (400 MHz, DMSO-d6) δ ppm 8.75 (s, 2H) 7.02 (s, 2H) 4.68-4.62 (m, 1H) 3.66-3.56 (m, 11H) 3.51-3.43 (m, 4H) 3.14 (t, J = 8.0 Hz, 2H) 2.20-2.15 (m, 2H) 1.26 (d, J = 8.0 Hz, 6H). |

TABLE 1-continued

| Example No./ Scheme | Structure and Compound Name | LRMS m/z [M + H]+ | 1H NMR or HPLC retention time and method |
|---|---|---|---|
| 107 Scheme A | 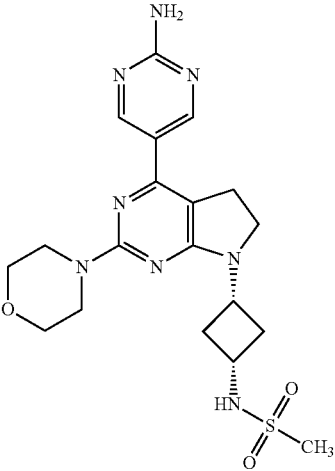 N-{cis-3-[4-(2-aminopyrimidin-5-yl)-2-(morpholin-4-yl)-5,6-dihydro-7H-pyrrolo[2,3-d]pyrimidin-7-yl]cyclobutyl}methanesulfonamide | 447.1 | 1H NMR (400 MHz, DMSO-$d_6$) δ ppm 8.74 (s, 2H) 7.44-7.42 (m 1H) 7.00 (s, 2H) 4.27-4.25 (m, 1H) 3.64-3.54 (m, 12H) 3.15-3.11 (m, 2H) 2.87 (s, 3H) 2.24-2.21 (m, 2H). |
| 108 Scheme A | 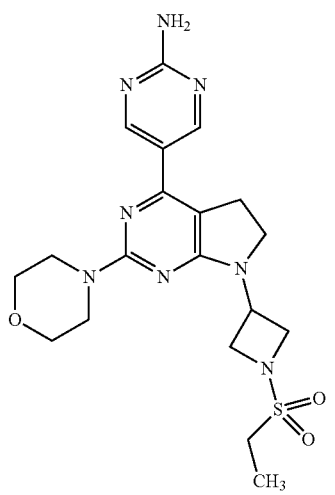 5-{7-[1-(ethylsulfonyl)azetidin-3-yl]-2-(morpholin-4-yl)-6,7-dihydro-5H-pyrrolo[2,3-d]pyrimidin-4-yl}pyrimidin-2-amine | 447.1 | 1H NMR (400 MHz, DMSO-$d_6$) δ ppm 8.75 (s, 2H) 7.03 (s, 2H) 4.85 (t, J = 7.2 Hz, 1H) 4.22-4.18 (m, 2H) 4.04-3.99 (m, 2H) 3.74-3.64 (m, 10H) 3.36-3.15 (m, 4H) 1.24 (t, J = 7.2 Hz, 3H). |

TABLE 1-continued

| Example No./ Scheme | Structure and Compound Name | LRMS m/z [M + H]+ | 1H NMR or HPLC retention time and method |
|---|---|---|---|
| 109 Scheme A | 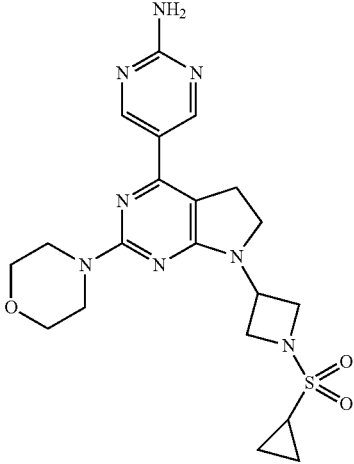<br>5-{7-[1-(cyclopropylsulfonyl)azetidin-3-yl]-2-(morpholin-4-yl)-6,7-dihydro-5H-pyrrolo[2,3-d]pyrimidin-4-yl}pyrimidin-2-amine | 459.1 | 1H NMR (400 MHz, DMSO-d$_6$) δ ppm 8.75 (s, 2H) 7.03 (s, 2H) 4.91 (t, J = 7.2 Hz 1H) 4.27-4.22 (m, 2H) 4.08-4.03 (m, 2H) 3.76-3.72 (m, 2H) 3.70-3.60 (m, 8H) 3.19-3.14 (m, 2H) 2.85-2.82 (m, 1H) 1.08-1.05 (m, 2H) 0.99-0.96 (m, 2H). |
| 110 Scheme A | 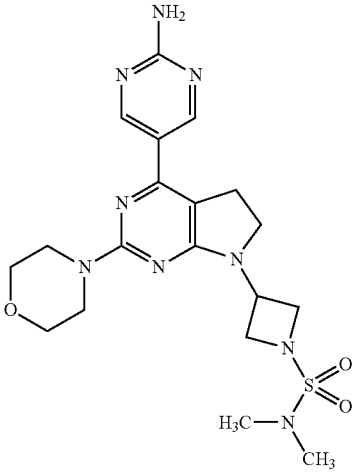<br>3-[4-(2-aminopyrimidin-5-yl)-2-(morpholin-4-yl)-5,6-dihydro-7H-pyrrolo[2,3-d]pyrimidin-7-yl]-N,N-dimethylazetidine-1-sulfonamide | 462.2 | 1H NMR (400 MHz, DMSO-d$_6$) δ ppm 8.75 (s, 2H) 7.03 (s, 2H) 4.85 (t, J = 7.2 Hz, 1H) 4.16-4.12 (m, 2H) 3.99-3.94 (m, 2H) 3.74-3.63 (m, 10H) 3.18-3.16 (m, 2H) 2.75 (s, 6H). |

| Example No./ Scheme | Structure and Compound Name | LRMS m/z [M + H]+ | ¹H NMR or HPLC retention time and method |
|---|---|---|---|
| 111 Scheme A | 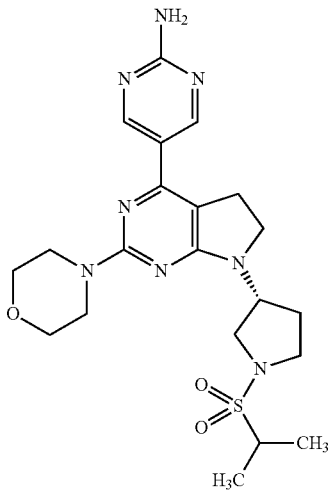 5-{2-(morpholin-4-yl)-7-[(3R)-1-(propan-2-ylsulfonyl)pyrrolidin-3-yl]-6,7-dihydro-5H-pyrrolo[2,3-d]pyrimidin-4-yl}pyrimidin-2-amine | 475.1 | ¹H NMR (400 MHz, DMSO-d₆) δ ppm 8.75 (s, 2H) 7.02 (s, 2H) 4.68-4.60 (m, 1H) 3.66-3.58 (m, 11H) 3.43-3.83 (m, 4H) 3.14 (t, J = 8.0 Hz, 2H) 2.19-2.14 (m, 2H) 1.26 (d, J = 6.8 Hz, 6H). |
| 112 Scheme A | 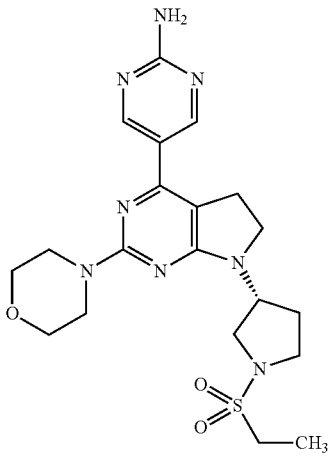 5-{7-[(3R)-1-(ethylsulfonyl)pyrrolidin-3-yl]-2-(morpholin-4-yl)-6,7-dihydro-5H-pyrrolo[2,3-d]pyrimidin-4-yl}pyrimidin-2-amine | 461.2 | ¹H NMR (400 MHz, DMSO-d₆) δ ppm 8.75 (s, 2H) 7.03 (s, 2H) 4.70-4.62 (m, 1H) 3.66-3.61 (m, 10H) 3.54-3.52 (m, 1H) 3.44-3.43 (m, 1H) 3.18-3.13 (m, 4H) 2.18-2.12 (m, 2H) 1.24 (t, J = 7.2 Hz, 5H). |

TABLE 1-continued

| Example No./ Scheme | Structure and Compound Name | LRMS m/z [M + H]+ | $^1$H NMR or HPLC retention time and method |
|---|---|---|---|
| 113 Scheme A | 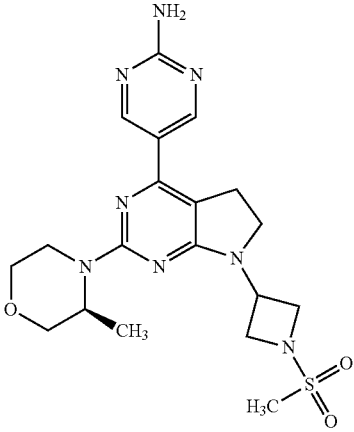<br>5-{2-[(3S)-3-methylmorpholin-4-yl]-7-[1-(methylsulfonyl)azetidin-3-yl]-6,7-dihydro-5H-pyrrolo[2,3-d]pyrimidin-4-yl}pyrimidin-2-amine | 447.1 | $^1$H NMR (600 MHz, DMSO-$d_6$) δ ppm 8.73 (s, 2H) 6.98 (s, 2H) 4.82 (p, J = 7.3 Hz, 1H) 4.63-4.58 (m, 1H) 4.24 (dd, J = 13.6, 1.9 Hz, 1H) 4.19-4.13 (m, 2H) 4.03 (q, J = 7.9 Hz, 2H) 3.87 (dd, J = 11.2, 3.3 Hz, 1H) 3.73-3.65 (m, 3H) 3.54 (dd, J = 11.3, 2.9 Hz, 1H) 3.38-3.22 (m, 1H, overlapped with $H_2O$) 3.17-3.11 (m, 2H) 3.09-3.00 (m, 4H) 1.14 (d, J = 6.7 Hz, 3H). |
| 114 Scheme A | 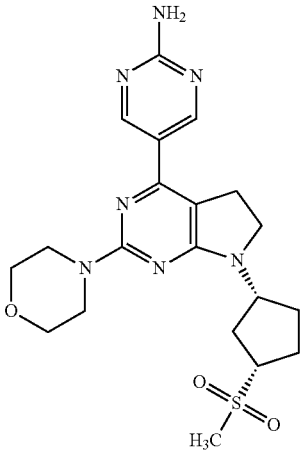<br>5-{7-[(1R,3S)-3-(methylsulfonyl)cyclopentyl]-2-(morpholin-4-yl)-6,7-dihydro-5H-pyrrolo[2,3-d]pyrimidin-4-yl}pyrimidin-2-amine | 446.2 | $^1$H NMR (400 MHz, DMSO-$d_6$) δ ppm 8.74 (s, 2H) 7.00 (s, 2H) 4.51 (t, J = 7.2 Hz, 1H) 3.78 (s, 1H) 3.65-3.56 (m, 10 H) 3.13 (t, J = 8.0 Hz, 2H) 2.97 (s, 3H) 2.14-2.12 (m, 3H) 2.08-1.84 (m, 3H). |

TABLE 1-continued

| Example No./ Scheme | Structure and Compound Name | LRMS m/z [M + H]⁺ | ¹H NMR or HPLC retention time and method |
|---|---|---|---|
| 115 Scheme A | 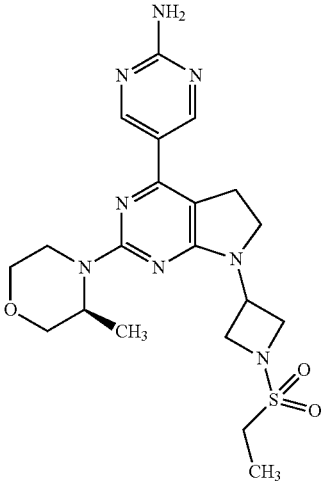 5-{7-[1-(ethylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 461.1 | ¹H NMR (400 MHz, DMSO-$d_6$) δ ppm 8.74 (s, 2H) 7.03 (s, 2H) 4.84-4.82 (m, 1H) 4.64-4.62 (m, 1H) 4.28-4.19 (m, 3H) 4.02-4.00 (m, 2H) 3.83-3.76 (m, 1H) 3.72-3.70 (m, 3H) 3.68-3.57 (m, 1H) 3.21-3.04 (m, 6H) 1.24 (d, J = 7.4 Hz, 3H) 1.16 (d, J = 6.8 Hz, 3H). |
| 116 Scheme A | 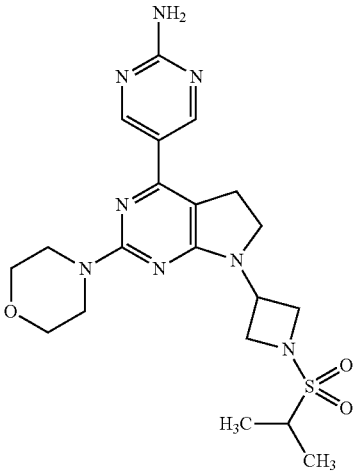 5-{2-(morpholin-4-yl)-7-[1-(propan-2-ylsulfonyl)azetidin-3-yl]-6,7-dihydro-5H-pyrrolo[2,3-d]pyrimidin-4-yl}pyrimidin-2-amine | 461.2 | ¹H NMR (400 MHz, DMSO-$d_6$) δ ppm 8.75 (s, 2H) 7.05 (s, 2H) 4.84 (t, J = 7.2 Hz, 1H) 4.25-4.21 (m, 2H) 4.00-3.97 (m, 2H) 3.73-3.64 (m, 10H) 3.29-3.27 (m, 1H) 3.19-3.16 (m, 2H) 1.26-1.24 (m, 6H). |

TABLE 1-continued

| Example No./ Scheme | Structure and Compound Name | LRMS m/z [M + H]⁺ | ¹H NMR or HPLC retention time and method |
|---|---|---|---|
| 117 Scheme A | 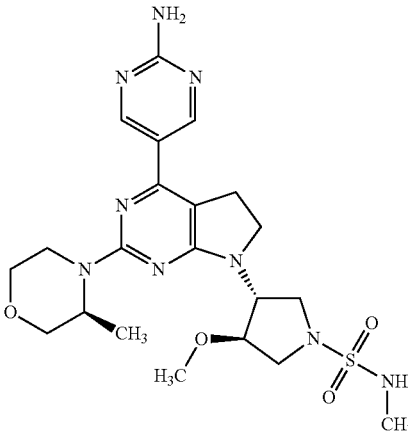<br>(3R,4R)-3-{4-(2-aminopyrimidin-5-yl)-2-[(3S)-3-methylmorpholin-4-yl]-5,6-dihydro-7H-pyrrolo[2,3-d]pyrimidin-7-yl}-4-methoxy-N-methylpyrrolidine-1-sulfonamide | 506.1 | ¹H NMR (400 MHz, DMSO-d₆) δ ppm 8.75 (s, 2H) 7.22-7.17 (m, 1H) 7.02 (s, 2H) 4.63-4.55 (m, 2H) 4.29-4.26 (m, 1H) 4.10-4.09 (m, 1H) 3.92-3.85 (m, 1H) 3.72-3.54 (m, 8H) 3.18-3.14 (m, 5H) 2.58 (d, J = 4.2 Hz, 4H) 1.17 (d, J = 6.0 Hz, 3H). |
| 118 Scheme A | 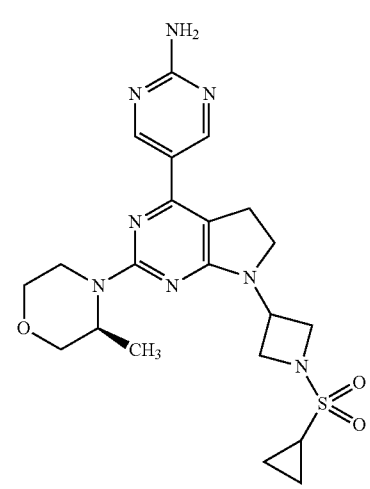<br>5-{7-[1-(cyclopropylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 473.1 | ¹H NMR (400 MHz, DMSO-d₆) δ ppm 8.75 (s, 2H) 7.04 (s, 2H) 4.89-4.86 (m, 1H) 4.63-4.62 (m, 1H) 4.27-4.24 (m, 3H) 4.06-4.04 (m, 2H) 3.83-3.77 (m, 1H) 3.73-3.71 (m, 3H) 3.57-3.58 (m, 1H) 3.19-3.08 (m, 4H) 2.84-2.83 (m, 1H) 1.16 (d, J = 6.4 Hz, 3H) 1.07-1.04 (m, 2H) 0.97-0.96 (m, 2H). |

TABLE 1-continued

| Example No./ Scheme | Structure and Compound Name | LRMS m/z [M + H]+ | ¹H NMR or HPLC retention time and method |
|---|---|---|---|
| 119 Scheme A | 5-{7-[(3S)-1-(ethylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 475.4 | ¹H NMR (400 MHz, DMSO-$d_6$) δ ppm 8.74 (s, 2H) 7.01 (s, 2H) 4.63-4.59 (m, 2H) 4.24-4.20 (m, 1H) 3.87-3.85 (m, 1H) 3.71-3.43 (m, 7H) 3.14-3.11 (m, 5H) 2.18-2.15 (m, 2H) 1.23 (t, J = 7.4 Hz, 3H) 1.16 (d, J = 6.8 Hz, 3H). |
| 120 Scheme A | 3-{4-(2-aminopyrimidin-5-yl)-2-[(3S)-3-methylmorpholin-4-yl]-5,6-dihydro-7H-pyrrolo[2,3-d]pyrimidin-7-yl}-N,N-dimethylazetidine-1-sulfonamide | 476.2 | ¹H NMR (600 MHz, DMSO-$d_6$) δ ppm 8.73 (s, 2H) 6.99 (s, 2H) 4.80 (p, J = 7.4 Hz, 1H) 4.64-4.60 (m, 1H) 4.25 (dd, J = 13.4, 2.2 Hz, 1H) 4.16-4.12 (m, 2H) 3.95 (q, J = 7.9 Hz, 2H) 3.88 (dd, J = 11.2, 3.3 Hz, 1H) 3.73-3.65 (m, 3H) 3.55 (dd, J = 11.3, 3.0 Hz, 1H) 3.45-3.35 (m, 1H, overlapped with H$_2$O) 3.19-3.10 (m, 2H) 3.07 (dt, J = 12.9, 3.7 Hz, 1H) 2.74 (s, 6H) 1.15 (d, J = 6.8 Hz, 3H). |

| Example No./Scheme | Structure and Compound Name | LRMS m/z [M + H]+ | ¹H NMR or HPLC retention time and method |
|---|---|---|---|
| 121 Scheme A | 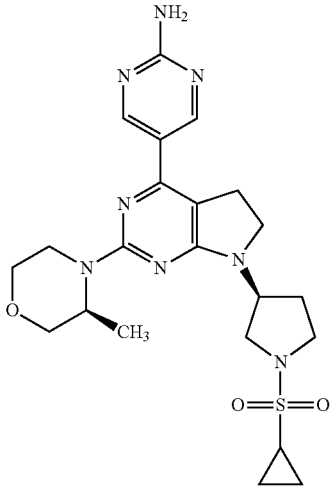<br>5-{7-[(3S)-1-(cyclopropylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 487.1 | ¹H NMR (400 MHz, DMSO-$d_6$) δ ppm 8.74 (s, 2H) 7.01 (s, 2H) 4.65-4.60 (m, 2H) 4.24-4.22 (m, 1H) 3.90-3.88 (m, 1H) 3.71-3.58 (m, 7H) 3.46-3.38 (m, 2H) 3.13-3.11 (m, 3H) 2.75-2.74 (m, 1H) 2.18-2.15 (m, 2H) 1.16 (d, J = 6.8 Hz, 3H) 0.99-0.95 (m, 4H). |
| 122 Scheme A | 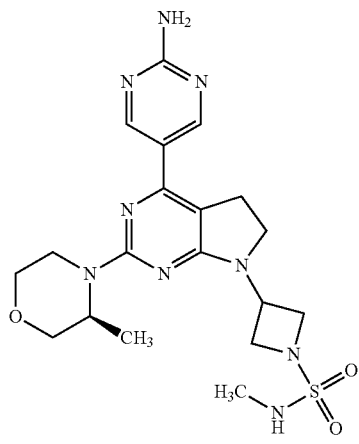<br>3-{4-(2-aminopyrimidin-5-yl)-2-[(3S)-3-methylmorpholin-4-yl]-5,6-dihydro-7H-pyrrolo[2,3-d]pyrimidin-7-yl}-N-methylazetidine-1-sulfonamide | 462.1 | ¹H NMR (600 MHz, DMSO-$d_6$) δ ppm 8.73 (s, 2H) 7.16-7.12 (m, 1H) 6.98 (s, 2H), 4.74 (quin, J = 7.38 Hz, 1H), 4.61 (dq, J = 2.20, 6.72 Hz, 1H), 4.25 (dd, J = 2.29, 13.48 Hz, 1H), 4.03 (t, J = 7.61 Hz, 2H), 3.87 (q, J = 7.46 Hz, 3H), 3.65-3.70 (m, J = 11.19 Hz, 3H), 3.55 (dd, J = 3.12, 11.37 Hz, 1H), 3.35-3.45 (m, 1H, overlapped with H₂O), 3.12-3.17 (m, 2H), 3.06 (dt, J = 3.58, 12.98 Hz, 1H), 2.59 (s, 3H), 1.14 (d, J = 6.79 Hz, 3H). |

TABLE 1-continued

| Example No./ Scheme | Structure and Compound Name | LRMS m/z [M + H]+ | 1H NMR or HPLC retention time and method |
|---|---|---|---|
| 123 Scheme A | 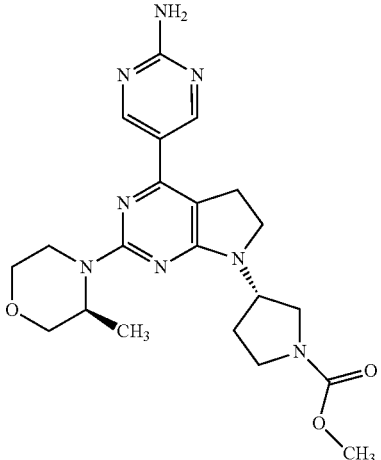<br>methyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 441.1 | 1H NMR (400 MHz, DMSO-$d_6$) δ ppm 8.73 (s, 2H) 7.01 (s, 2H) 4.61-4.56 (m, 1H) 4.27-4.24 (m, 1H) 3.90-3.88 (m, 1H) 3.71-3.68 (m, 1H) 3.59-3.58 (m, 12H) 3.14-3.05 (m, 3H) 2.13-2.09 (m, 2H) 1.16 (d, J = 6.4 Hz, 3H). |
| 124 Scheme A | 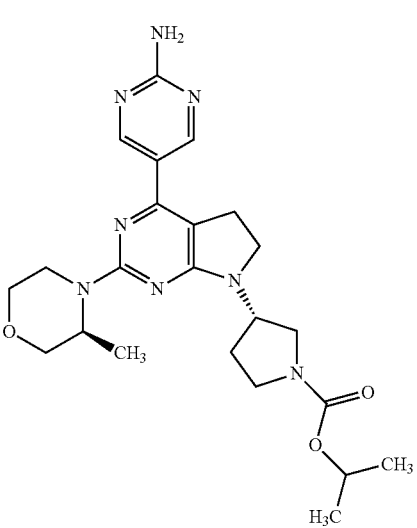<br>propan-2-yl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 469.2 | 1H NMR (400 MHz, DMSO-$d_6$ + $D_2O$) δ ppm 8.47 (s, 2H) 4.73-4.66 (m, 2H) 4.48-4.31 (m, 1H) 3.89-3.34 (m, 12H) 3.02-2.69 (m, 2H) 2.16-2.10 (m, 2H) 1.24 (d, J = 6.4 Hz, 3H) 1.15 (s, 6H). |

TABLE 1-continued

| Example No./ Scheme | Structure and Compound Name | LRMS m/z [M + H]+ | 1H NMR or HPLC retention time and method |
|---|---|---|---|
| 125 Scheme A | 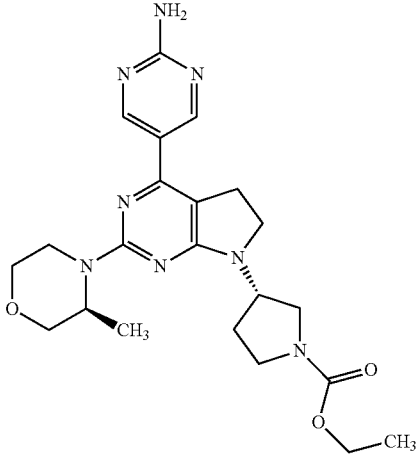<br>ethyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 455.2 | 1H NMR (400 MHz, DMSO-d6) δ ppm 8.70 (s, 2H) 7.01 (s, 2H) 4.56-4.47 (m, 2H) 4.17-4.12 (m, 1H) 4.05-4.02 (m, 2 H) 3.68-3.65 (m, 1H) 3.58-3.34 (m, 6H) 3.08-3.06 (m, 3H) 2.08-2.06 (m, 2H) 1.18-1.11 (m, 6H). |
| 126 Scheme A | 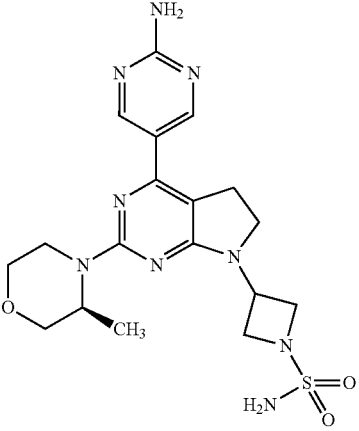<br>3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-sulfonamide | 448.1 | 1H NMR (600 MHz, DMSO-d6) δ ppm 8.74 (s, 2H) 7.07-6.94 (m, 4H) 4.74 (p, J = 7.4 Hz, 1H) 4.63-4.58 (m, 1H) 4.24 (dd, J = 13.3, 1.9 Hz, 1H) 4.00-3.97 (m, 2H) 3.90-3.83 (m, 3H) 3.70-3.65 (m, 3H) 3.55 (dd, J = 11.4, 2.9 Hz, 1H) 3.42-3.38 (m, 1H, overlapped with H2O) 3.17-3.13 (m, 2H) 3.07 (dt, J = 3.7, 12.9 Hz, 1H) 1.15 (d, J = 6.8 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 127 Scheme A | 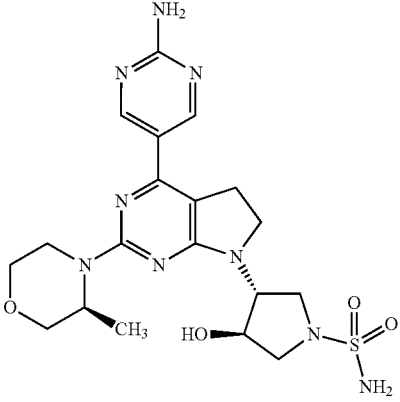<br>(3R,4R)-3-{4-(2-aminopyrimidin-5-yl)-2-[(3S)-3-methylmorpholin-4-yl]-5,6-dihydro-7H-pyrrolo[2,3-d]pyrimidin-7-yl}-4-hydroxypyrrolidine-1-sulfonamide | 478.1 | ¹H NMR (400 MHz, DMSO-d₆) δ ppm 8.75 (s, 2H) 7.00 (s, 2H) 6.87 (s, 2H) 5.50-5.49 (m, 1H) 4.65-4.63 (m, 1H) 4.44-4.25 (m, 3H) 3.90-3.88 (m, 1H) 3.72-3.55 (m, 4H) 3.44-3.38 (m, 3H) 3.18-3.15 (m, 4H) 2.98-2.97 (m, 1H) 1.17 (d, J = 6.4 Hz, 3H). |
| 128 Scheme A | 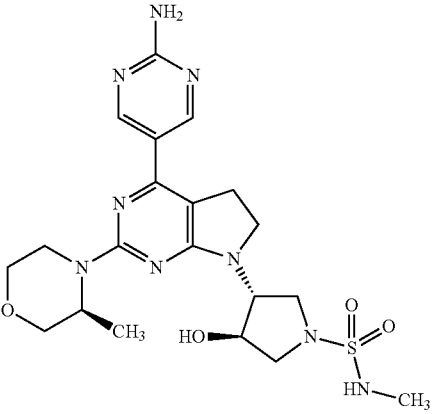<br>(3R,4R)-3-{4-(2-aminopyrimidin-5-yl)-2-[(3S)-3-methylmorpholin-4-yl]-5,6-dihydro-7H-pyrrolo[2,3-d]pyrimidin-7-yl}-4-hydroxy-N-methylpyrrolidine-1-sulfonamide | 492.1 | ¹H NMR (400 MHz, DMSO-d₆) δ ppm 8.74 (s, 2H) 7.12-7.10 (m, 1H) 7.01 (s, 2H) 5.54-5.53 (m, 1H) 4.64-4.63 (m, 1H) 4.46-4.34 (m, 3H) 3.91-3.89 (m, 1H) 3.69-3.41 (m, 6H) 3.17-3.06 (m, 5H) 2.98-2.94 (m, 1H) 2.57 (d, J = 4.8 Hz, 3H) 1.17 (d, J = 6.4 Hz, 3H). |

TABLE 1-continued

| Example No./ Scheme | Structure and Compound Name | LRMS m/z [M + H]+ | 1H NMR or HPLC retention time and method |
|---|---|---|---|
| 129 Scheme A | 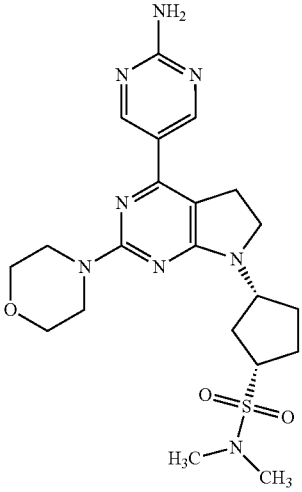<br>(1S,3R)-3-[4-(2-aminopyrimidin-5-yl)-2-(morpholin-4-yl)-5,6-dihydro-7H-pyrrolo[2,3-d]pyrimidin-7-yl]-N,N-dimethylcyclopentanesulfonamide | 475.1 | 1H NMR (400 MHz, CDCl3) δ ppm 8.83 (d, J = 3.2 Hz, 2H) 5.37 (s, 2H) 4.62-4.58 (m, 1H) 3.78-3.77 (m, 8H) 3.66-3.57 (m, 3H) 3.14 (t, J = 8.0 Hz, 2H) 2.92 (d, J = 4.0 Hz, 6H) 2.19-2.14 (m, 2H) 2.13-2.12 (m, 2H) 2.10-1.87 (m, 2H). |
| 130 Scheme A | 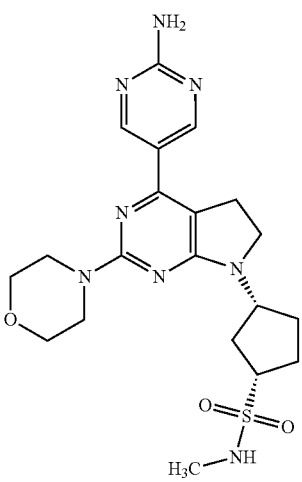<br>(1S,3R)-3-[4-(2-aminopyrimidin-5-yl)-2-(morpholin-4-yl)-5,6-dihydro-7H-pyrrolo[2,3-d]pyrimidin-7-yl]-N-methylcyclopentanesulfonamide | 461.1 | 1H NMR (400 MHz, CDCl3) δ ppm 8.82 (d, J = 2.0 Hz, 2H) 5.81 (s, 2H) 4.64-4.58 (m, 1H) 4.16 (s, 1H) 3.77-3.66 (m, 8H) 3.63-3.57 (m, 3H) 3.13 (t, J = 8.0 Hz, 2H) 2.85 (t, J = 4.8 Hz, 3H) 2.23-2.21 (m, 2H) 2.12-1.94 (m, 4H). |

TABLE 1-continued

| Example No./ Scheme | Structure and Compound Name | LRMS m/z [M + H]+ | 1H NMR or HPLC retention time and method |
|---|---|---|---|
| 131 Scheme A | 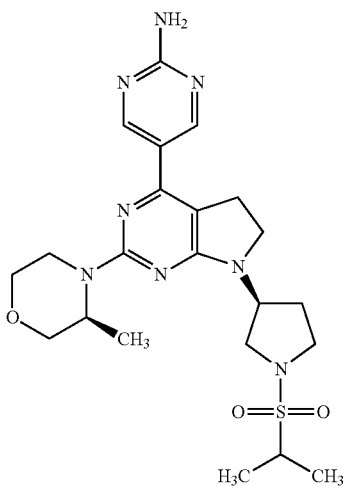<br>5-{2-[(3S)-3-methylmorpholin-4-yl]-7-[(3S)-1-(propan-2-ylsulfonyl)pyrrolidin-3-yl]-6,7-dihydro-5H-pyrrolo[2,3-d]pyrimidin-4-yl}pyrimidin-2-amine | 489.2 | $^1$H NMR (400 MHz, DMSO-$d_6$) δ ppm 8.74 (s, 2H) 7.00 (s, 2H) 4.61-4.57 (m, 2H) 4.24-4.22 (m, 1H) 3.90-3.88 (m, 1H) 3.68-3.47 (m, 10H) 3.13-3.11 (m, 3H) 2.20-2.15 (m, 2H) 1.26 (d, J = 7.6 Hz, 6H) 1.16 (d, J = 6.8 Hz, 3H). |
| 132 Scheme A | 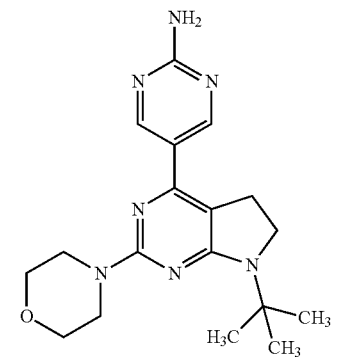<br>5-[7-tert-butyl-2-(morpholin-4-yl)-6,7-dihydro-5H-pyrrolo[2,3-d]pyrimidin-4-yl]pyrimidin-2-amine | 356.1 | $^1$H NMR (400 MHz, DMSO-$d_6$) δ ppm 8.70 (s, 2H) 6.96 (s, 2H) 3.63-3.56 (m, 10H) 3.02-2.98 (m, 2H) 1.41 (s, 9H). |

| Example No./ Scheme | Structure and Compound Name | LRMS m/z [M + H]+ | 1H NMR or HPLC retention time and method |
|---|---|---|---|
| 133 Scheme A | 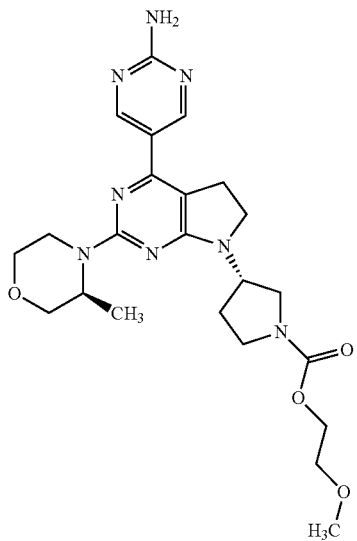<br>2-methoxyethyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 485.2 | 1H NMR (400 MHz, DMSO-$d_6$ + $D_2O$) δ ppm 8.70 (d, J = 5.6 Hz, 2H) 4.56-4.21 (m, 3H) 4.17-4.06 (m, 1H) 3.87-3.85 (m, 1H) 3.67-3.56 (m, 2H) 3.55-3.50 (m, 7H) 3.38-3.35 (m, 3H) 3.25-3.22 (m, 3H) 3.07-3.06 (m, 3H) 2.09 (s, 2H) 1.19-1.11 (m, 3H). |
| 134 Scheme A | 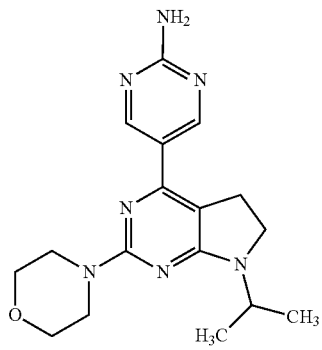<br>5-[2-(morpholin-4-yl)-7-(propan-2-yl)-6,7-dihydro-5H-pyrrolo[2,3-d]pyrimidin-4-yl]pyrimidin-2-amine | 342.1 | 1H NMR (400 MHz, DMSO-$d_6$) δ ppm 8.73 (s, 2H) 6.97(s, 2H) 4.32-4.27(m, 1H) 3.64 (s, 8H) 3.53 (t, J = 8.4 Hz, 2H) 3.10 (t, J = 8.0 Hz, 2H) 1.14 (d, J = 8 Hz, 6H). |

TABLE 1-continued

| Example No./ Scheme | Structure and Compound Name | LRMS m/z [M + H]+ | 1H NMR or HPLC retention time and method |
|---|---|---|---|
| 135 Scheme A | 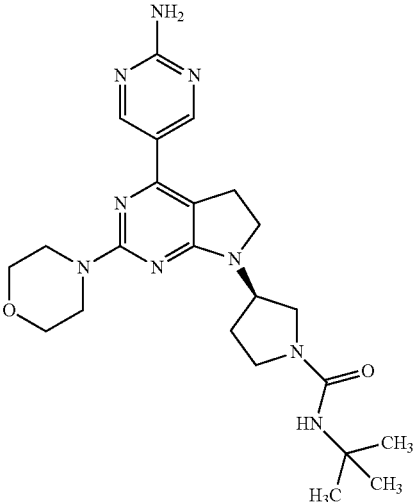<br>(3R)-3-[4-(2-aminopyrimidin-5-yl)-2-(morpholin-4-yl)-5,6-dihydro-7H-pyrrolo[2,3-d]pyrimidin-7-yl]-N-tert-butylpyrrolidine-1-carboxamide | 468.2 | 1H NMR (400 MHz, CDCl3) δ ppm 8.83 (s, 2H) 5.21 (s, 2H) 4.79-4.75 (m, 1H) 4.06 (s, 1H) 3.79 (s, 8H) 3.78-3.60 (m, 4H) 3.39-3.34 (m, 2H) 3.16-3.12 (m, 2H) 2.20-2.15 (m, 2H) 1.36 (s, 9H). |
| 136 Scheme A | 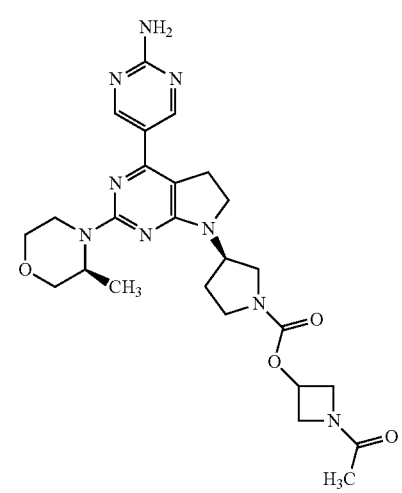<br>1-acetylazetidin-3-yl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 524.2 | 1H NMR (400 MHz, DMSO-d6) δ 8.72 (s, 2H) 7.00 (s, 2H) 5.07-5.04 (m, 1H) 4.59-4.53 (m, 2H) 4.41-4.40 (m, 1H) 4.26-4.22 (m, 1H) 4.11-4.04 (m, 2H) 3.80-3.77 (m, 1H) 3.69-3.67 (m, 3H) 3.59-3.54 (m, 4H) 3.39-3.32 (m, 3H) 3.13-3.09 (m, 3H) 2.13-2.10 (m, 2H) 1.76-1.75 (m, 3H) 1.15 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 137 Scheme A | 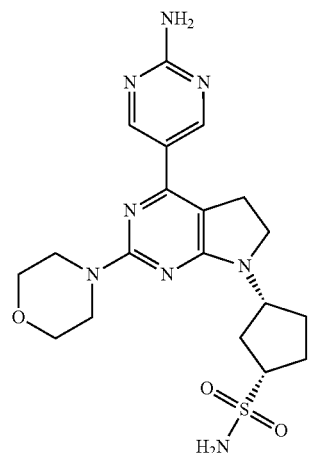(1S,3R)-3-[4-(2-aminopyrimidin-5-yl)-2-(morpholin-4-yl)-5,6-dihydro-7H-pyrrolo[2,3-d]pyrimidin-7-yl]cyclopentanesulfonamide | 447 | 1H NMR (400 MHz, DMSO-$d_6$) δ ppm 8.83 (s, 2H) 5.41 (s, 2H) 4.64 (s, 2H) 3.77 (s, 8H) 3.65-3.57 (br s, 2H) 3.13 (t, J = 7.6 Hz, 2H) 2.40-2.28 (m, 2H) 2.16-1.91 (m, 6H). |
| 138 Scheme A | 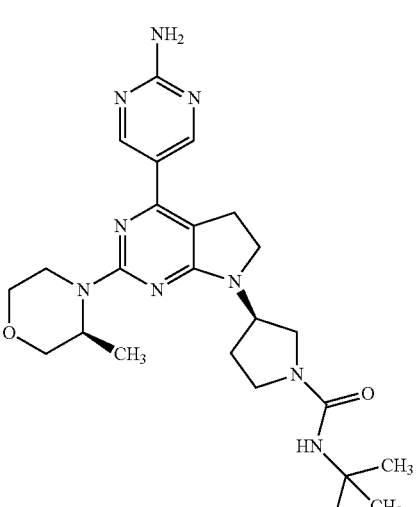(3R)-3-{4-(2-aminopyrimidin-5-yl)-2-[(3S)-3-methylmorpholin-4-yl]-5,6-dihydro-7H-pyrrolo[2,3-d]pyrimidin-7-yl}-N-tert-butylpyrrolidine-1-carboxamide | 482.2 | 1H NMR (400 MHz, CDCl$_3$) δ 8.84 (s, 2H) 5.22 (s, 2H) 4.76-4.73 (m, 2H) 4.35-4.14 (m, 1H) 4.06-4.40 (m, 2H) 3.96-3.76 (m, 7H) 3.55-3.14 (m, 5H) 2.20-2.16 (m, 2H) 1.36 (s, 9H) 1.27 (d, J = 6.4 Hz, 3H). |

TABLE 1-continued

| Example No./ Scheme | Structure and Compound Name | LRMS m/z [M + H]+ | 1H NMR or HPLC retention time and method |
|---|---|---|---|
| 139 Scheme A | (3S)-3-[4-(2-aminopyrimidin-5-yl)-2-(morpholin-4-yl)-5,6-dihydro-7H-pyrrolo[2,3-d]pyrimidin-7-yl]-N-tert-butylpyrrolidine-1-carboxamide | 468.2 | 1H NMR (400 MHz, CDCl3) δ 8.83 (s, 2H) 5.31 (s, 2H) 4.79-4.75 (m, 1H) 4.07 (s, 1H) 3.78 (s, 8H) 3.77-3.60 (m, 4H) 3.39-3.34 (m, 2H) 3.16-3.12 (m, 2H) 2.20-2.13 (m, 2H) 1.36 (s, 9H). |
| 140 Scheme A | (3S)-3-[4-(2-aminopyrimidin-5-yl)-2-[(3S)-3-methylmorpholin-4-yl]-5,6-dihydro-7H-pyrrolo[2,3-d]pyrimidin-7-yl}-N-tert-butylpyrrolidine-1-carboxamide | 482.1 | 1H NMR (400 MHz, CDCl3) δ ppm 8.74 (s, 2H) 7.01 (s, 2H) 5.29 (s, 1H) 4.64-4.57 (m, 2H) 4.52-4.07 (m, 1H) 3.68-3.56 (m, 1H) 3.45-3.44 (m, 1H) 3.43-3.41 (m, 6H) 3.28-3.14 (m, 5H) 2.09-2.04 (m, 2H) 1.26 (s, 9H) 1.17 (d, J = 6.0 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 141 Scheme A | <br>tert-butyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carobxylate | 469.2 | ¹H NMR (400 MHz, DMSO-d₆) δ 8.74 (s, 2H) 6.97 (s, 2H) 4.75-4.67 (m, 1H) 4.63-4.56 (m, 1H) 4.26-4.13 (m, 3H) 4.08-4.00 (m, 2H) 3.90-3.84 (m, 1H) 3.71-3.64 (m, 3H) 3.56 (dd, J = 11.3, 3.0 Hz, 1H) 3.40 (dt, J = 11.7, 2.7 Hz, 1H) 3.17-3.02 (m, 3H) 1.39 (s, 9H) 1.15 (d, J = 6.7 Hz, 3H). |
| 142 Scheme A | 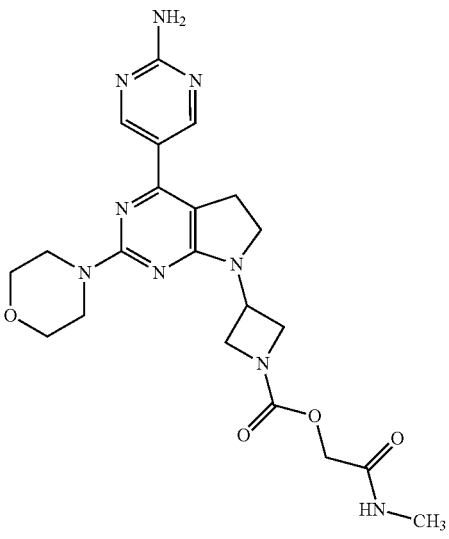<br>2-(methylamino)-2-oxoethyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 470.2 | ¹H NMR (400 MHz DMSO-d₆) δ ppm 8.76 (s, 2H) 7.82 (d, J = 4.8 Hz, 1H) 7.04 (s, 2H) 4.84-4.81 (m, 1H) 4.39 (s, 2H) 4.25-4.14 (m, 4H) 3.74-3.70 (m, 2H) 3.65 (s, 8H) 3.17 (t, J = 8.0 Hz, 2H) 2.62 (d, J = 4.8 Hz, 3H). |

| Example No./Scheme | Structure and Compound Name | LRMS m/z [M + H]+ | ¹H NMR or HPLC retention time and method |
|---|---|---|---|
| 143 Scheme A | 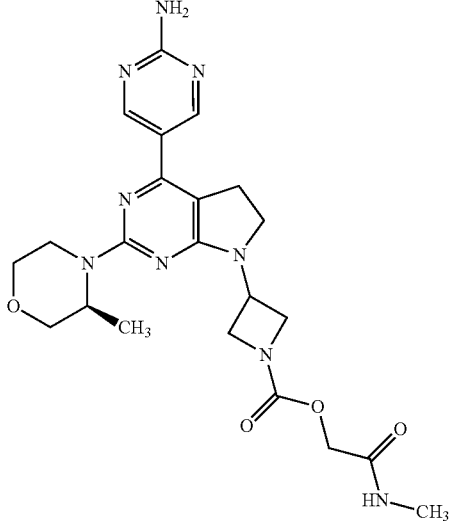<br>2-(methylamino)-2-oxoethyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate | 484.5 | ¹H NMR (400 MHz, DMSO-$d_6$) δ ppm 8.75 (d, J = 8.4 Hz, 2H) 7.83 (s, 1H) 7.03 (d, J = 7.6 Hz, 2H) 4.80-4.78 (m, 1H) 4.60-4.50 (m, 1H) 4.39-4.14 (m, 6H) 3.90-3.80 (m, 1H) 3.60-3.40 (m, 6H) 3.18-3.02 (m, 3H) 2.65-2.61 (m, 3H) 1.16 (t, J = 8.0 Hz, 3H). |
| 144 Scheme A | 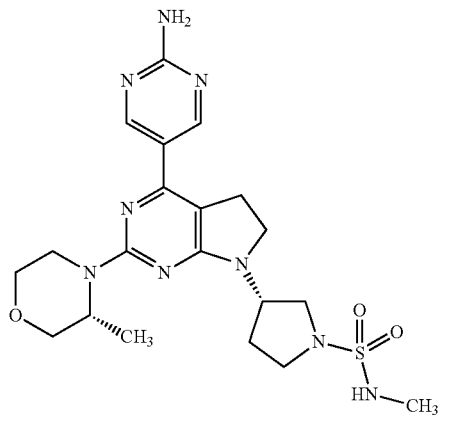<br>(3S)-3-{4-(2-aminopyrimidin-5-yl)-2-[(3R)-3-methylmorpholin-4-yl]-5,6-dihydro-7H-pyrrolo[2,3-d]pyrimidin-7-yl}-N-methylpyrrolidine-1-sulfonamide | 476.1 | ¹H NMR (400 MHz, DMSO-$d_6$) δ ppm 8.73 (s, 2H) 7.09 (q, J = 5.2 Hz, 1H) 7.0 (br s, 2H) 4.65-4.60 (m, 2H) 4.27-4.24 (m, 1H) 3.81-3.85 (m, 1H) 3.68-362 (m, 4H) 3.43-3.41 (m, 2H) 3.33-3.05 (m, 6H) 2.56 (d, J = 4.8 Hz, 3H) 2.15-2.11 (m, 2H) 1.16 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 145 Scheme A | 5-{2-[(3R)-3-methylmorpholin-4-yl]-7-[(3S)-1-(methylsulfonyl)pyrrolidin-3-yl]-6,7-dihydro-5H-pyrrolo[2,3-d]pyrimidin-4-yl}pyrimidin-2-amine | 461.1 | 1H NMR (400 MHz, DMSO-d6) δ 8.74 (s, 2H), 7.02 (brs, 2H) 4.65-4.62 (m, 2H) 4.25-4.21 (m, 1H) 3.88-3.84 (m, 1H) 3.72-3.39 (m, 6H) 3.31-3.29 (m, 3H) 3.16-3.13 (m, 3H) 2.95 (s, 3H) 2.19-2.12 (m, 2H) 1.17 (d, J = 6.8 Hz, 3H). |
| 146** Scheme A | 5-{7-[3-methyl-1-(methylsulfonyl)pyrrolidin-3-yl]-2-(morpholin-4-yl)-6,7-dihydro-5H-pyrrolo[2,3-d]pyrimidin-4-yl}pyrimidin-2-amine | 461.2 | 1H NMR (400 MHz, 80° C., DMSO-d6) δ ppm 8.73 (s, 2H) 6.62 (br s, 2H) 3.94 (d, J = 10.4 Hz, 1H) 3.71-3.65 (m, 9H) 3.62-3.50 (m, 2H) 3.45-3.31 (m, 2H) 3.10 (t, J = 7.95 Hz, 2H) 2.87 (s, 3H) 2.56-2.47 (m, 1H, overlapped with DMSO), 2.16-2.08 (m, 1H) 1.39 (s, 3H). |
| 147 Scheme A | 3-[4-(2-aminopyrimidin-5-yl)-2-(morpholin-4-yl)-5,6-dihydro-7H-pyrrolo[2,3-d]pyrimidin-7-yl]-N-methylazetidine-1-sulfonamide | 448.1 | 1H NMR (400 MHz, DMSO-d6) δ ppm 8.75 (s, 2H) 7.14 (d, J = 4.4 Hz, 1H) 7.00 (s, 2H) 4.85-4.73 (m, 1H) 4.03 (t, J = 7.7 Hz, 2H) 3.88 (t, J = 8.2 Hz, 2H) 3.73-3.60 (m, 10H) 3.21-3.12 (m, 2H) 2.60 (d, J = 4.40 Hz, 3H). |

TABLE 1-continued

| Example No./ Scheme | Structure and Compound Name | LRMS m/z [M + H]+ | 1H NMR or HPLC retention time and method |
|---|---|---|---|
| 148 Scheme A | 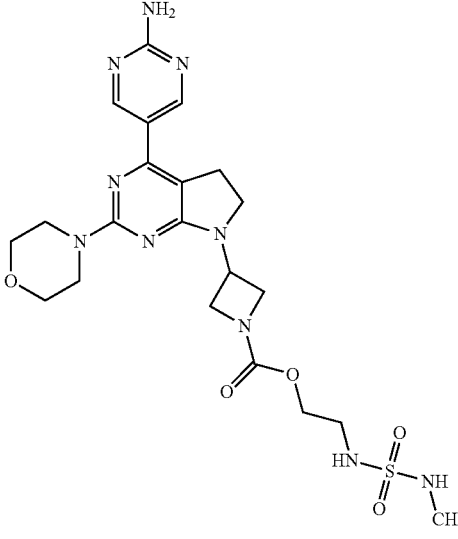 2-[(methylsulfamoyl)amino]ethyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 535.1 | 1H NMR (400 MHz, DMSO-$d_6$) δ ppm 8.74 (s, 2H) 6.95-7.06 (m, 3H) 6.72 (q, J = 5.14 Hz, 1H) 4.75-4.88 (m, 1H) 4.23 (br s, 2H) 4.14 (br s, 2H) 4.01 (t, J = 5.75 Hz, 2H) 3.70 (t, J = 8.07 Hz, 2H) 3.64 (s, 8H) 3.15 (t, J = 8.07 Hz, 2H) 3.02 (q, J = 6.03 Hz, 2H) 2.45 (d, J = 5.14 Hz, 3H). |
| 149 Scheme A | 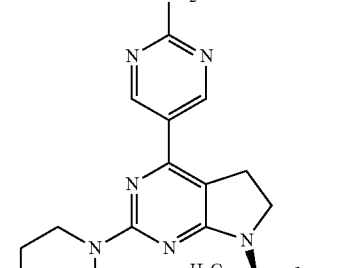 5-{7-[(3S)-3-methyl-1-(methylsulfonyl)pyrrolidin-3-yl]-2-(morpholin-4-yl)-6,7-dihydro-5H-pyrrolo[2,3-d]pyrimidin-4-yl}pyrimidin-2-amine | 461.2 | 1H NMR (400 MHz, DMSO-$d_6$) δ ppm 8.73 (s, 2H) 6.62 (br s, 2H) 3.94 (d, J = 10.4 Hz, 1H) 3.73-3.64 (m, 9H) 3.62-3.50 (m, 2H) 3.45-3.31 (m, 2H) 3.10 (t, J = 8.1 Hz, 2H) 2.87 (s, 3H) 2.56-2.49 (m, 1H, overlapped with DMSO), 2.12 (ddd, J = 12.7, 7.1, 5.8 Hz, 1H) 1.39 (s, 3H). |

TABLE 1-continued

| Example No./ Scheme | Structure and Compound Name | LRMS m/z [M + H]+ | 1H NMR or HPLC retention time and method |
|---|---|---|---|
| 150 Scheme A | 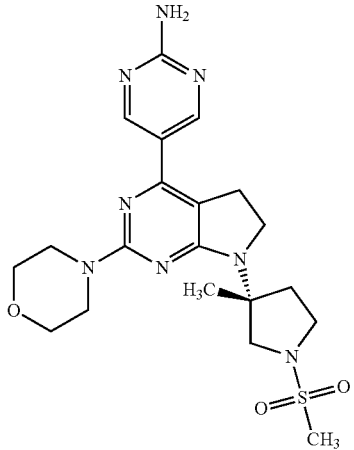 5-{7-[(3R)-3-methyl-1-(methylsulfonyl)pyrrolidin-3-yl]-2-(morpholin-4-yl)-6,7-dihydro-5H-pyrrolo[2,3-d]pyrimidin-4-yl}pyrimidin-2-amine | 461.2 | 1H NMR (400 MHz, 80° C., DMSO-$d_6$) δ ppm 8.73 (s, 2H) 6.62 (br. s., 2H) 3.94 (d, J = 10.15 Hz, 1H) 3.64-3.72 (m, 9H) 3.50-3.62 (m, 2H) 3.31-3.45 (m, 2H) 3.10 (t, J = 8.07 Hz, 2H) 2.86 (s, 3H) 2.48-2.55 (M, 1H, overlapped with DMSO peak) 2.07-2.16 (m, 1H) 1.39 (s, 3H). |
| 151 Scheme A |  2-(dimethylamino)-2-oxoethyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 484.3 | 1H NMR (400 MHz, DMSO-$d_6$) δ ppm 8.72 (s, 2H) 7.24-7.11 (m, 2H) 4.90 (s, 1H) 4.71 (s, 2H) 4.40-4.10 (m, 4H) 3.81 (s, 2H) 3.69-3.67 (m, 8H) 3.17 (t, J = 8.0 Hz, 2H) 2.91 (s, 3H) 2.83 (s, 3H). |

TABLE 1-continued

| Example No./ Scheme | Structure and Compound Name | LRMS m/z [M + H]+ | 1H NMR or HPLC retention time and method |
|---|---|---|---|
| 152 Scheme A | 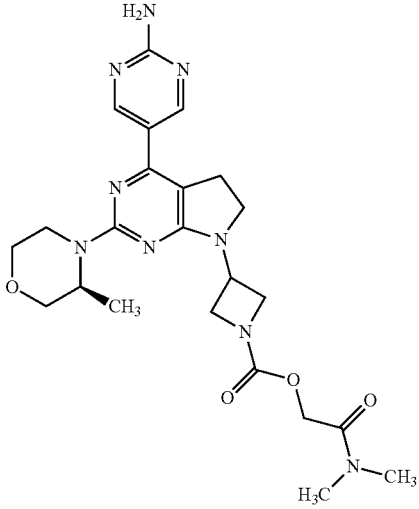<br>2-(dimethylamino)-2-oxoethyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate | 498.3 | 1H NMR (400 MHz, DMSO-$d_6$) δ ppm 8.74 (s, 2H) 7.05 (s, 2H) 4.82-4.80 (m, 1H) 4.70 (s, 2H) 4.61-4.60 (m, 1H) 4.26-4.23 (m, 5H) 3.89-3.88 (m, 1H) 3.72-3.69 (m, 3H) 3.58-3.56 (m, 1H) 3.43-3.40 (m, 1H) 3.18-3.14 (m, 3H) 2.91 (s, 3H) 2.82 (s, 3H) 1.16 (d, J = 6.8 Hz, 3H). |
| 153 Scheme A | 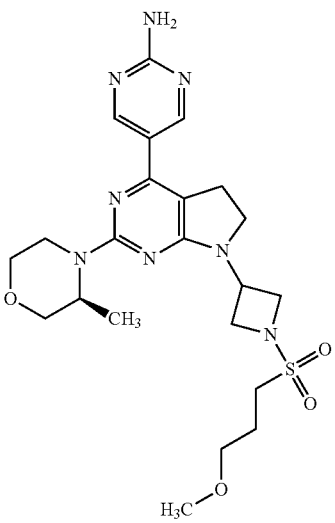<br>5-(7-{1-[(3-methoxypropyl)sulfonyl]azetidin-3-yl}-2-[(3S)-3-methylmorpholin-4-yl]-6,7-dihydro-5H-pyrrolo[2,3-d]pyrimidin-4-yl)pyrimidin-2-amine | 505.1 | 1H NMR (400 MHz, DMSO-$d_6$) δ ppm 8.75 (s, 2H) 7.03 (s, 2H) 4.85-4.81 (m, 1H) 4.65-4.6 (m, 1H) 4.23-4.19 (m, 3H) 4.07-3.99 (m, 2H) 3.92-3.86 (m, 1H) 3.74-3.66 (m, 3H) 3.59-3.53 (m, 1H) 3.43 (t, J = 6.2 Hz, 3H) 3.25 (s, 3H) 3.21-3.14 (m, 4H) 3.11-3.04 (m, 1H) 1.95-1.88 (m, 2H) 1.16 (d, J = 6.4 Hz, 3H). |

TABLE 1-continued

| Example No./ Scheme | Structure and Compound Name | LRMS m/z [M + H]+ | 1H NMR or HPLC retention time and method |
|---|---|---|---|
| 154 Scheme A | 5-(7-{1-[(1-methyl-1H-imidazol-4-yl)sulfonyl]azetidin-3-yl}-2-[(3S)-3-methylmorpholin-4-yl]-6,7-dihydro-5H-pyrrolo[2,3-d]pyrimidin-4-yl)pyrimidin-2-amine | 513.1 | 1H NMR (400 MHz, DMSO-$d_6$) δ ppm 8.70 (s, 2H) 7.94 (s, 2H) 4.75-4.69 (m, 1H) 4.60-4.52 (m, 1H) 4.19 (d, J = 12.8 Hz, 1H) 4.08-3.95 (m, 4H) 3.91-3.84 (m, 1H) 3.76 (s, 3H) 3.55-3.52 (m, 2H) 3.42-3.29 (m, 3H) 3.10-2.99 (m, 3H) 1.13 (d, J = 6.8 Hz, 3H). |
| 155 Scheme A | 5-(7-{1-[(2-methoxyethyl)sulfonyl]azetidin-3-yl}-2-[(3S)-3-methylmorpholin-4-yl]-6,7-dihydro-5H-pyrrolo[2,3-d]pyrimidin-4-yl)pyrimidin-2-amine | 491.1 | 1H NMR (400 MHz, DMSO-$d_6$) δ ppm 8.75 (s, 2H) 7.04 (s, 2H) 4.84-4.80 (m, 1H) 4.68-4.58 (m, 1H) 4.30-4.17 (m, 3H) 4.07-4.02 (m, 2H) 3.91-3.88 (m, 1H) 3.75-3.66 (m, 5H) 3.59-3.43 (m, 4H) 3.31 (s, 3H) 3.17 (t, J = 8.2 Hz, 2H) 3.13-3.04 (m, 1H) 1.16 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 156 Scheme A | oxetan-3-yl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}pyrrolidine-1-carboxylate | 483.2 | 1H NMR (400 MHz DMSO-d$_6$) δ ppm 8.74 (s, 2H) 7.02 (s, 2H) 5.32-5.29 (m, 1H) 4.79-4.75 (m, 2H) 4.63-4.48 (m, 4H) 4.25-4.24 (m, 1H) 3.88-3.87 (m, 1H) 3.71-3.58 (m, 6H) 3.44-3.35 (m, 3H) 3.15-3.11 (m, 3H) 2.13-2.09 (m, 2H) 1.18-1.15 (m, 3H). |
| 157 Scheme A | 5-{7-tert-butyl-2-[(3S)-3-methylmorpholin-4-yl]-6,7-dihydro-5H-pyrrolo[2,3-d]pyrimidin-4-yl}pyrimidin-2-amine | 370.2 | 1H NMR (600 MHz, DMSO-d$_6$) δ ppm 8.69 (s, 2H) 6.91-6.94 (m, 2H) 4.48-4.57 (m, 1H) 4.20 (d, J = 12.3 Hz, 1H) 3.89 (dd, J = 10.9, 2.6 Hz, 1H) 3.70 (d, J = 11.2 Hz, 1H) 3.55-3.61 (m, 3H) 3.38-3.44 (m, 1H, partially overlapped with H$_2$O) 3.07 (dt, J = 12.8, 3.5 Hz, 1H) 3.00 (t, J = 8.1 Hz, 2H) 1.42 (s, 9H), 1.15 (d, J = 6.6 Hz, 3H). |
| 158 Scheme A | 5-[7-(bicyclo[1.1.1]pent-1-yl)-2-(morpholin-4-yl)-6,7-dihydro-5H-pyrrolo[2,3-d]pyrimidin-4-yl]pyrimidin-2-amine | 366.1 | 1H NMR (400 MHz, CDCl$_3$) δ ppm 8.82 (s, 2H) 5.18 (s, 2H) 3.81-3.74 (m, 8H) 3.57 (t, J = 8.0 Hz, 2H) 3.09 (t, J = 8.0 Hz, 2H) 2.50 (s, 1H) 2.18 (s, 6H). |

| Example No./ Scheme | Structure and Compound Name | LRMS m/z [M + H]⁺ | ¹H NMR or HPLC retention time and method |
|---|---|---|---|
| 159 Scheme A | 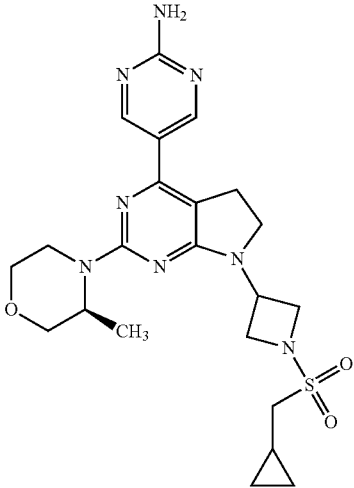<br>5-(7-{1-[(cyclopropylmethyl)sulfonyl]azetidin-3-yl}-2-[(3S)-3-methylmorpholin-4-yl]-6,7-dihydro-5H-pyrrolo[2,3-d]pyrimidin-4-yl)pyrimidin-2-amine | 487.2 | ¹H NMR (400 MHz, DMSO-d₆) δ ppm 8.75 (s, 2H) 7.02 (s, 2H) 4.84-4.80 (m, 1H) 4.64-4.57 (m, 1H) 4.28-4.20 (m, 3H) 4.07-4.04 (m, 2H) 3.88-3.85 (m, 1H) 3.70 (t, J = 9.4 Hz, 3H) 3.58-3.54 (m, 1H) 3.45-3.40 (m, 1H) 3.18-3.05 (m, 6H) 1.16 (d, J = 6.4 Hz, 3H) 0.64-0.61 (m, 2H) 0.40 (d, J = 4.4 Hz, 2H). |
| 160 Scheme A | 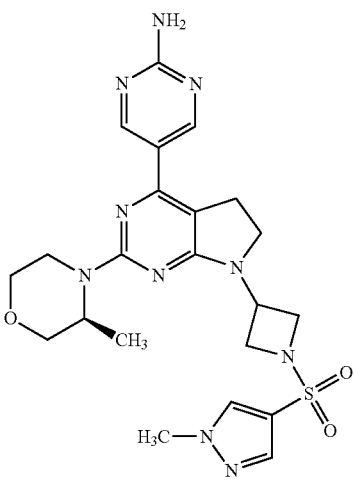<br>5-(2-[(3S)-3-methylmorpholin-4-yl]-7-{1-[(1-methyl-1H-pyrazol-4-yl)sulfonyl]azetidin-3-yl}-6,7-dihydro-5H-pyrrolo[2,3-d]pyrimidin-4-yl)pyrimidin-2-amine | 513.1 | ¹H NMR (400 MHz, DMSO-d₆) δ ppm 8.72 (s, 2H) 8.49 (s, 1H) 7.97 (s, 1H) 7.04 (s, 2H) 4.73 (t, J = 7.2 Hz, 1H) 4.59 (d, J = 5.2 Hz, 1H) 4.22 (d, J = 13.6 Hz, 1H) 3.99 (s, 3H) 3.98-3.80 (m, 8H) 3.68 (d, J = 11.2 Hz, 1H) 3.56-3.53 (m, 1H) 3.11-3.01 (m, 3H) 1.14 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 161 Scheme A | 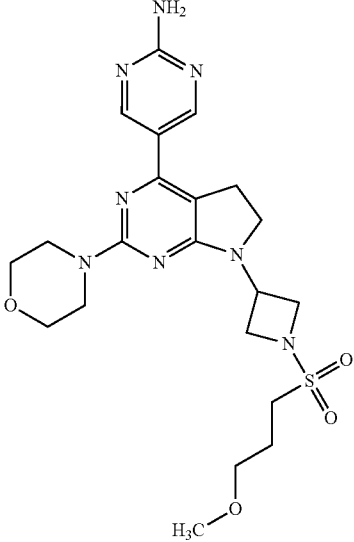<br>5-[7-{1-[(3-methoxypropyl)sulfonyl]azetidin-3-yl}-2-(morpholin-4-yl)-6,7-dihydro-5H-pyrrolo[2,3-d]pyrimidin-4-yl]pyrimidin-2-amine | 491.1 | 1H NMR (400 MHz, DMSO-d6) δ ppm 8.75 (s, 2H) 7.06 (s, 2H) 4.88-4.84 (m, 1H) 4.23-4.20 (m, 2H) 4.06-4.03 (m, 2H) 3.73-3.64 (m, 10H) 3.44-3.42 (m, 2H) 3.25 (s, 3H) 3.20-3.17 (m, 4H) 1.94-1.85 (m, 2H). |
| 162** Scheme A | 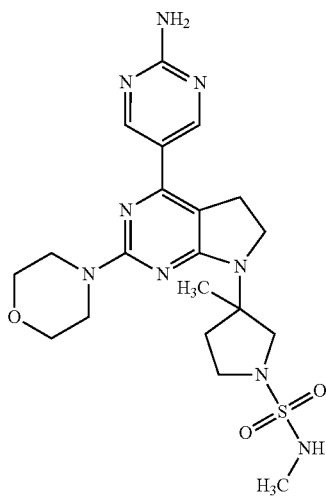<br>3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-sulfonamide | 476.1 | 1H NMR (400 MHz, DMSO-d6) δ ppm 8.72 (s, 2H) 7.01 (q, J = 5.1 Hz, 1H) 6.96 (s, 2H) 3.69-3.50 (m, 12H) 3.37-3.20 (m, 2H, overlapped with H2O) 3.09 (t, J = 8.1 Hz, 2H) 2.53 (d, J = 4.9 Hz, 3H, partially overlapped with DMSO) 2.48-2.40 (m, 1H, overlapped with DMSO) 2.15-2.06 (m, 1H) 1.33 (s, 3H). |

| Example No./ Scheme | Structure and Compound Name | LRMS m/z [M + H]⁺ | ¹H NMR or HPLC retention time and method |
|---|---|---|---|
| 163 Scheme A | 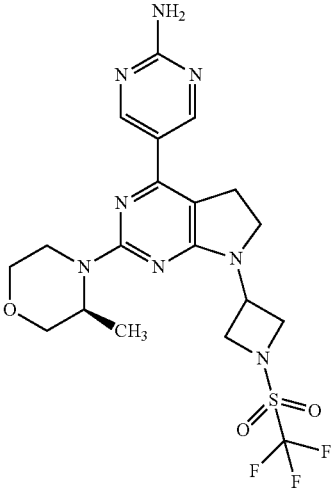<br>5-(2-[(3S)-3-methylmorpholin-4-yl]-7-{1-[(trifluoromethyl)sulfonyl]azetidin-3-yl}-6,7-dihydro-5H-pyrrolo[2,3-d]pyrimidin-4-yl)pyrimidin-2-amine | 501.2 | 1.23 min; SFC Column: ZymorSpher HADP 150 × 21.2 mm I.D, 5 um, Gradient: 16% methanol for 6 min, 16-40% methanol for 0.1 min, hold at 40% methanol for 1.5 min. Total flow 80 g/min. UV 260 nm. |
| 164*** Scheme A | 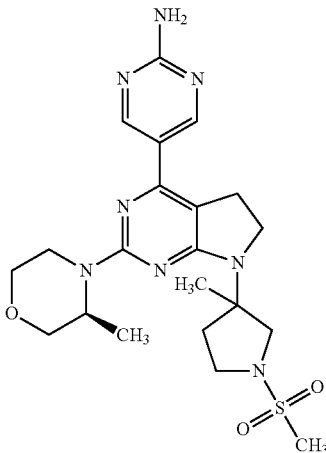<br>5-{7-[3-methyl-1-(methylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 475.2 | ¹H NMR (400 MHz, 80° C., DMSO-$d_6$) δ ppm 8.73 (s, 2H) 6.61 (br s, 2H) 4.60-4.52 (m, 1H) 4.22 (dd, J = 13.7, 2.3 Hz, 1H) 3.99-3.87 (m, J = 10.5 Hz, 2H) 3.73-3.52 (m, 5H) 3.50-3.31 (m, 3H) 3.18-3.07 (m, 3H) 2.86 (d, J = 3.8 Hz, 3H) 2.58-2.52 (m, 1H, overlapped with DMSO) 2.15-2.07 (m, 1H) 1.39 (s, 3H) 1.21 (d, J = 6.9 Hz, 3H). |

| Example No./ Scheme | Structure and Compound Name | LRMS m/z [M + H]+ | ¹H NMR or HPLC retention time and method |
|---|---|---|---|
| 165 Scheme A | 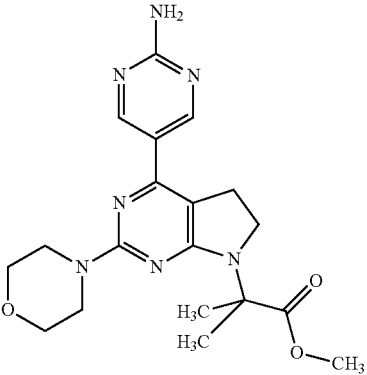methyl 2-[4-(2-aminopyrimidin-5-yl)-2-(morpholin-4-yl)-5,6-dihydro-7H-pyrrolo[2,3-d]pyrimidin-7-yl]-2-methylpropanoate | 400.0 | ¹H NMR (400 MHz, CDCl₃) δ ppm 8.84 (s, 2H) 5.19 (br s, 2H) 3.74-3.70 (m, 10H) 3.67 (s, 3H) 3.16 (t, J = 8.0 Hz, 2H) 1.53 (s, 6H). |
| 166 Scheme A | 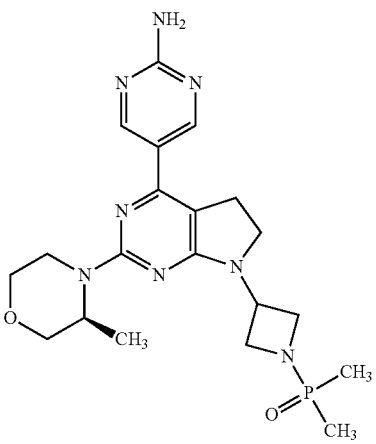5-{7-[1-(dimethylphosphoryl)azetidin-3-yl]-2-[(3S)-3-methylmorpholin-4-yl]-6,7-dihydro-5H-pyrrolo[2,3-d]pyrimidin-4-yl}pyrimidin-2-amine | 445.1 | ¹H NMR (400 MHz, CDCl₃) δ ppm 8.84 (s, 2H) 5.29 (s, 2H) 5.15-5.09 (m, 1H) 4.75-4.67 (m, 1H) 4.34 (d, J = 12.0 Hz, 1H) 4.19-4.08 (m, 2H) 4.00-3.87 (m, 3H) 3.78-3.68 (m, 4H) 3.58-3.51 (m, 1H) 3.26-3.12 (m, 3H) 1.46 (s, 3H) 1.42 (s, 3H) 1.26 (d, J = 6.8 Hz, 3H). |

TABLE 1-continued

| Example No./ Scheme | Structure and Compound Name | LRMS m/z [M + H]+ | 1H NMR or HPLC retention time and method |
|---|---|---|---|
| 167 Scheme A | 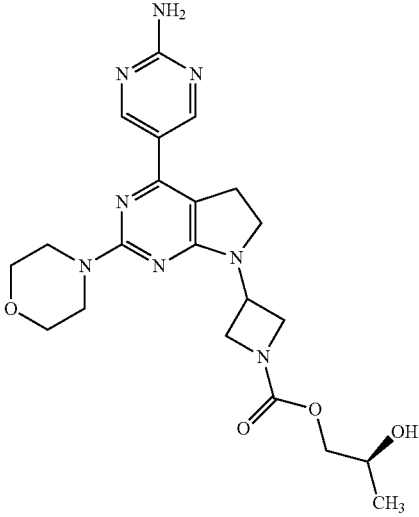<br>(2S)-2-hydroxypropyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 457.3 | 1H NMR (400 MHz, DMSO-$d_6$) δ ppm 8.75 (s, 2H) 7.04 (s, 2H) 4.81-4.77 (m, 2H) 4.23-4.12 (m, 4H) 3.78-3.70 (m, 5H) 3.68-3.64 (m, 8H) 3.17-3.13 (m, 2H) 1.15 (d, J = 6.0 Hz, 3H). |
| 168 Scheme A | 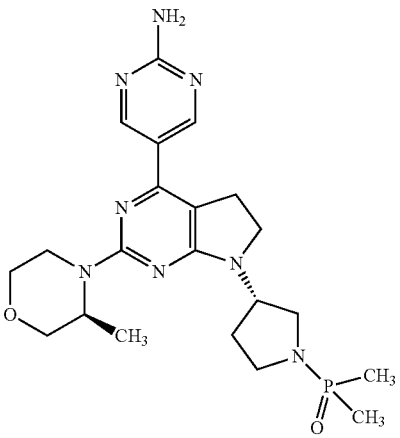<br>5-{7-[(3S)-1-(dimethylphosphoryl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 481.0 [M + Na]+ | 1H NMR (400 MHz DMSO-$d_6$) δ ppm 8.74 (s, 2H) 7.01 (s, 2H) 4.64-4.59 (m, 2H) 4.28-4.25 (m, 1H) 3.88-3.86 (m, 1H) 3.71-3.56 (m, 4H) 3.38-3.12 (m, 3H) 3.12-3.08 (m, 5H) 2.10-2.03 (m, 2H) 1.40 (s, 3H) 1.37 (s, 3H) 1.16 (d, J = 6.8 Hz, 3H). |

TABLE 1-continued

| Example No./ Scheme | Structure and Compound Name | LRMS m/z [M + H]+ | ¹H NMR or HPLC retention time and method |
|---|---|---|---|
| 169 Scheme A | 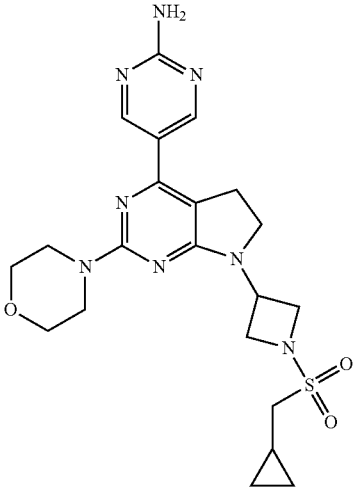<br>5-[7-{1-[(cyclopropylmethyl)sulfonyl]azetidin-3-yl}-2-(morpholin-4-yl)-6,7-dihydro-5H-pyrrolo[2,3-d]pyrimidin-4-yl]pyrimidin-2-amine | 473.1 | ¹H NMR (400 MHz, DMSO-$d_6$) δ ppm 8.75 (s, 2H) 7.04 (s, 2H) 4.88-4.83 (m, 1H) 4.23-4.19 (m, 2H) 4.08-4.03 (m, 2H) 3.75-3.64 (m, 10H) 3.20-3.14 (m, 4H) 1.04 (s, 1H) 0.63-0.59 (m, 2H) 0.41-0.38 (m, 2H). |
| 170 Scheme A | 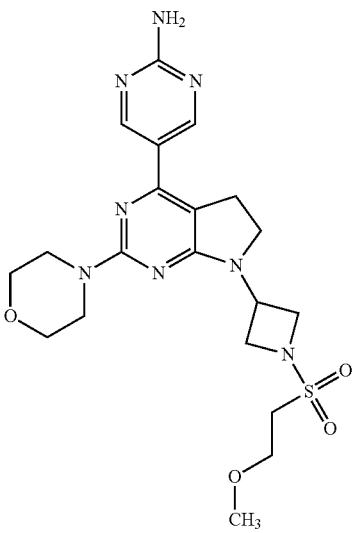<br>5-[7-{1-[(2-methoxyethyl)sulfonyl]azetidin-3-yl}-2-(morpholin-4-yl)-6,7-dihydro-5H-pyrrolo[2,3-d]pyrimidin-4-yl]pyrimidin-2-amine | 477.2 | ¹H NMR (400 MHz, DMSO-$d_6$) δ ppm 8.75 (s, 2H) 7.05 (s, 2H) 4.86-4.84 (m, 1H) 4.22-4.19 (m, 2H) 4.08-4.04 (m, 2H) 3.75-3.64 (m, 12H) 3.51-3.48 (m, 2H) 3.30-3.25 (m, 3H) 3.20-3.15 (m, 2H). |

TABLE 1-continued

| Example No./ Scheme | Structure and Compound Name | LRMS m/z [M + H]⁺ | ¹H NMR or HPLC retention time and method |
|---|---|---|---|
| 171 Scheme B | 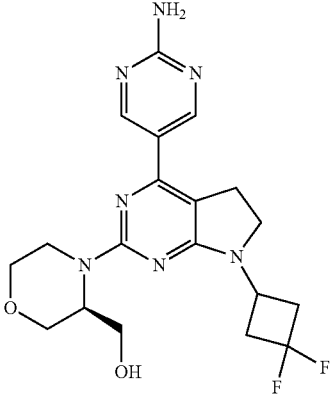 {(3S)-4-[4-(2-aminopyrimidin-5-yl)-7-(3,3-difluorocyclobutyl)-6,7-dihydro-5H-pyrrolo[2,3-d]pyrimidin-2-yl]morpholin-3-yl}methanol | 420.2 | ¹H NMR (600 MHz, DMSO-d₆) δ ppm 8.74 (s, 2H) 6.99 (s, 2H) 4.40-4.47 (m, 1H) 4.27-4.38 (m, 2H) 4.07 (d, J = 11.4 Hz, 1H) 3.86 (dd, J = 11.1, 3.4 Hz, 1H) 3.69 (t, J = 9.9 Hz, 1H) 3.57-3.64 (m, 2H) 3.41-3.46 (m, 1H) 3.36-3.41 (m, 4H) 3.10-3.16 (m, 2H) 2.97-3.06 (m, 2H) 2.80-2.92 (m, 2H). |
| 172 Scheme A | 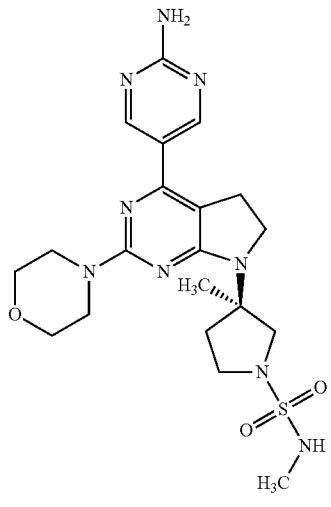 (3R)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-sulfonamide | 476.2 | ¹H NMR (400 MHz, 80° C., DMSO-d₆) δ ppm 8.74 (s, 2H) 6.7 (br s, 1H) 6.62 (br s, 2H) 3.51-3.77 (m, 12H) 3.24-3.41 (m, 2H) 3.10 (t, J = 8.1 Hz, 2H) 2.53-2.59 (m, 4H, partially overlapped with DMSO) 2.07-2.15 (m, 1H) 1.40 (s, 3H). |

TABLE 1-continued

| Example No./ Scheme | Structure and Compound Name | LRMS m/z [M + H]+ | 1H NMR or HPLC retention time and method |
|---|---|---|---|
| 173 Scheme A | (3S)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-sulfonamide | 476.2 | 1H NMR (400 MHz, 80° C., DMSO-d6) δ ppm 8.73 (s, 2H) 6.68 (br s, 1H) 6.62 (br s, 2H) 3.51-3.77 (m, 12H) 3.25-3.39 (m, 2H) 3.10 (t, J = 8.1 Hz, 2H) 2.52-2.59 (m, 4H, partially overlapped with DMSO) 2.07-2.15 (m, 1H) 1.39 (s, 3H). |
| 174 Scheme A | 5-{7-[(3R)-3-methyl-1-(methylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 475.2 | 1H NMR (400 MHz, 80° C., DMSO-d6) δ ppm 8.73 (s, 2H) 6.61 (br s, 2H) 4.52-4.59 (m, 1H) 4.22 (dd, J = 13.6, 2.3 Hz, 1H) 3.86-3.95 (m, 2H) 3.52-3.72 (m, 5H) 3.31-3.49 (m, 3H) 3.07-3.18 (m, 3H) 2.86 (s, 3H), 2.52-2.59 (m, 1H, overlapped with DMSO) 2.07-2.15 (m, 1H) 1.39 (s, 3H) 1.20 (d, J = 6.7 Hz, 3H). |

TABLE 1-continued

| Example No./ Scheme | Structure and Compound Name | LRMS m/z [M + H]+ | ¹H NMR or HPLC retention time and method |
|---|---|---|---|
| 175 Scheme A | 5-{7-[(3S)-3-methyl-1-(methylsulfonyl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 475.1 | ¹H NMR (400 MHz, 80° C., DMSO-d₆) δ ppm 8.73 (s, 2H) 6.61 (br s, 2H) 4.53-4.60 (m, 1H) 4.22 (dd, J = 13.7, 2.0 Hz, 1H) 3.97 (d, J = 10.3 Hz, 1H) 3.90 (dd, J = 11.5, 3.7 Hz, 1H) 3.52-3.74 (m, 5H) 3.31-3.50 (m, 3H) 3.07-3.19 (m, 3H) 2.86 (s, 3H) 2.53-2.61 (m, 1H, overlapped with H₂O) 2.06-2.18 (m, 1H) 1.39 (s, 3H) 1.21 (d, J = 6.7 Hz, 3H). |
| 176 Scheme A | 5-[7-(2,3-dimethylbutan-2-yl)-2-(morpholin-4-yl)-6,7-dihydro-5H-pyrrolo[2,3-d]pyrimidin-4-yl]pyrimidin-2-amine | 384.0 | ¹H NMR (400 MHz, DMSO-d₆) δ ppm 8.81 (s, 2H) 5.15 (br s, 2H) 3.78-3.70 (m, 10H) 3.11-3.02 (m, 3H) 1.36 (s, 6H) 0.88 (d, J = 7.2 Hz, 6H). |
| 177 Scheme A | 5-{7-[(3R)-1-(dimethylphosphoryl)pyrrolidin-3-yl]-2-[(3S)-3-methylmorpholin-4-yl]-6,7-dihydro-5H-pyrrolo[2,3-d]pyrimidin-4-yl}pyrimidin-2-amine | 459.2 | ¹H NMR (400 MHz, CD₃OD) δ ppm 8.81 (d, J = 6.0 Hz, 2H) 4.71-4.67 (m, 2H) 4.32 (d, J = 13.2 Hz, 1H) 3.76-3.73 (m, 1H) 3.72-3.55 (m, 8H) 3.26-3.24 (m, 1H) 3.23-3.21 (m, 4H) 2.37-2.33 (m, 2H) 1.58 (d, J = 14.0 Hz, 1H) 1.40-1.38 (m, 3H) 1.37-1.38 (m, 6H). |

TABLE 1-continued

| Example No./ Scheme | Structure and Compound Name | LRMS m/z [M + H]+ | 1H NMR or HPLC retention time and method |
|---|---|---|---|
| 178 Scheme A | 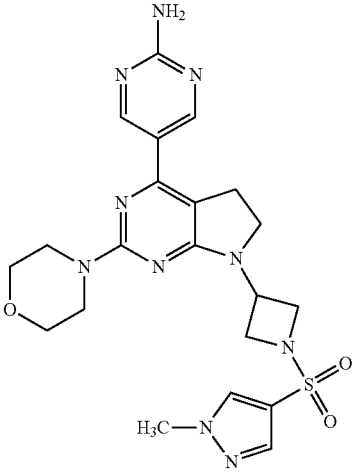<br>5-[7-{1-[(1-methyl-1H-pyrazol-4-yl)sulfonyl]azetidin-3-yl}-2-(morpholin-4-yl)-6,7-dihydro-5H-pyrrolo[2,3-d]pyrimidin-4-yl]pyrimidin-2-amine | 499.2 | 1H NMR (400 MHz, DMSO-$d_6$) δ ppm 8.72 (s, 2H) 8.49 (s, 1H) 7.97 (s, 1H) 7.04 (s, 2H) 4.77-4.75 (m, 1H) 3.96 (s, 3H) 3.95-3.76 (m, 4H) 3.63 (s, 8H) 3.35-3.25 (m, 2H) 3.10-3.05 (m, 2H). |
| 179 Scheme A | 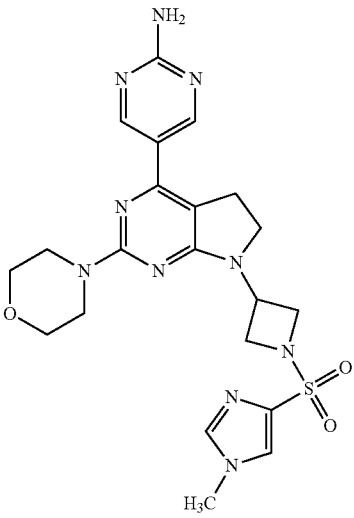<br>5-[7-{1-[(1-methyl-1H-imidazol-4-yl)sulfonyl]azetidin-3-yl}-2-(morpholin-4-yl)-6,7-dihydro-5H-pyrrolo[2,3-d]pyrimidin-4-yl]pyrimidin-2-amine | 521.1 [M + Na]+ | 1H NMR (400 MHz, DMSO-$d_6$) δ ppm 8.72 (s, 2H) 7.97 (s, 2H) 7.04 (s, 2H) 4.79-4.74 (m, 1H) 4.10-4.00 (m, 4H) 3.77 (s, 3H) 3.63 (s, 8H) 3.35-3.25 (m, 2H) 3.10-3.05 (m, 2H). |

TABLE 1-continued

| Example No./ Scheme | Structure and Compound Name | LRMS m/z [M + H]+ | 1H NMR or HPLC retention time and method |
|---|---|---|---|
| 180 Scheme A | 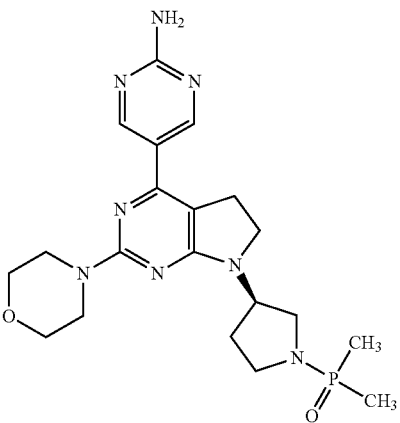<br>5-{7-[(3R)-1-(dimethylphosphoryl)pyrrolidin-3-yl]-2-(morpholin-4-yl)-6,7-dihydro-5H-pyrrolo[2,3-d]pyrimidin-4-yl}pyrimidin-2-amine | N/A | 1H NMR (400 MHz, CD3OD) δ ppm 8.81 (s, 2H) 4.69 (t, J = 7.6 Hz, 1H) 3.80-3.73 (m, 8H) 3.73-3.65 (m, 2H) 3.62-3.50 (m, 3H) 3.45-3.35 (m, 1H) 3.24-3.15 (m, 2H) 2.36-2.31 (m, 2H) 1.39 (d, J = 6.8 Hz, 2H) 1.30 (s, 3H) 1.27 (s, 3H). |
| 181 Scheme A | 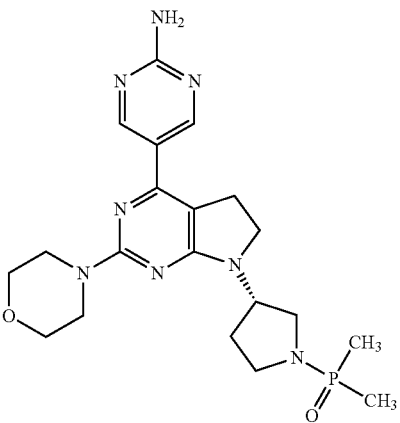<br>5-{7-[(3S)-1-(dimethylphosphoryl)pyrrolidin-3-yl]-2-(morpholin-4-yl)-6,7-dihydro-5H-pyrrolo[2,3-d]pyrimidin-4-yl}pyrimidin-2-amine | N/A | 1H NMR (400 MHz, CD3OD) δ ppm 8.81 (s, 2H) 4.69 (t, J = 7.6 Hz, 1H) 3.90-3.75 (m, 8H) 3.74-3.65 (m, 2H) 3.60-3.50 (m, 3H) 3.45-3.35 (m, 1H) 3.25-3.15 (m, 2H) 2.36-2.31 (m, 2H) 1.39 (d, J = 6.4 Hz, 2H) 1.33 (s, 3H), 1.30 (s, 3H). |

TABLE 1-continued

| Example No./ Scheme | Structure and Compound Name | LRMS m/z [M + H]+ | 1H NMR or HPLC retention time and method |
|---|---|---|---|
| 182 Scheme A | 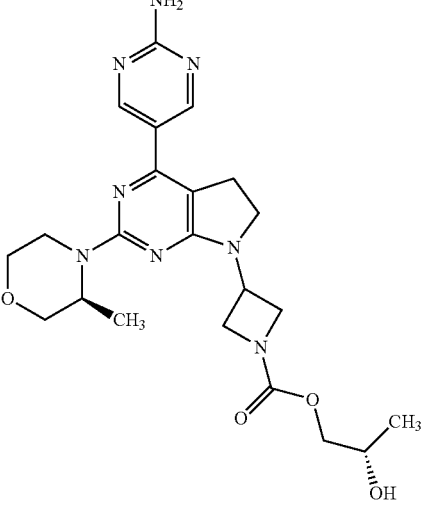 (2S)-2-hydroxypropyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate | 471.2 | 1H NMR (400 MHz, DMSO-d6) δ ppm 8.74 (s, 2H) 7.03 (s, 2H) 4.76-4.75 (m, 2H) 4.73-4.72 (m, 1H) 4.25-4.12 (m, 5H) 3.87-3.75 (m, 7H) 3.70-3.69 (m, 1H) 3.67-3.65 (m, 1H) 3.17-3.13 (m, 3H) 1.15 (d, J = 6.8 Hz, 3H) 1.05 (d, J = 6.0 Hz, 3H). |
| 183 Scheme A | 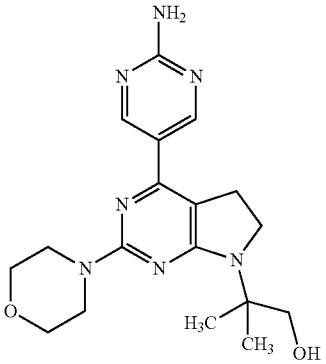 2-[4-(2-aminopyrimidin-5-yl)-2-(morpholin-4-yl)-5,6-dihydro-7H-pyrrolo[2,3-d]pyrimidin-7-yl]-2-methylpropan-1-ol | 372.0 | 1H NMR (400 MHz, DMSO-d6) δ ppm 8.70 (s, 2H) 6.96 (br s, 2H) 4.84 (t, J = 5.4 Hz, 1H) 3.71-3.62 (m, 12H) 3.01 (t, J = 8.2 Hz, 2H) 1.36 (s, 6H). |
| 184 Scheme A | 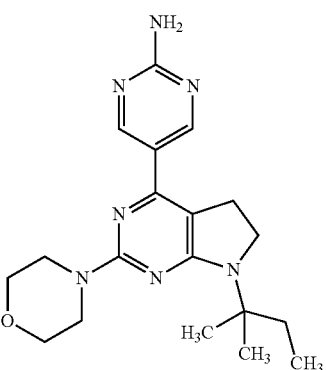 5-[7-(2-methylbutan-2-yl)-2-(morpholin-4-yl)-6,7-dihydro-5H-pyrrolo[2,3-d]pyrimidin-4-yl]pyrimidin-2-amine | 370.1 | 1H NMR (400 MHz, DMSO-d6) δ ppm 8.50 (s, 2H) 3.86-3.68 (m, 10H) 2.97 (t, J = 8.0 Hz, 2H) 1.95-1.92 (m, 2H) 1.39 (s, 6H) 0.79 (t, J = 7.2 Hz, 3H). |

TABLE 1-continued

| Example No./ Scheme | Structure and Compound Name | LRMS m/z [M + H]+ | 1H NMR or HPLC retention time and method |
|---|---|---|---|
| 185 Scheme A | 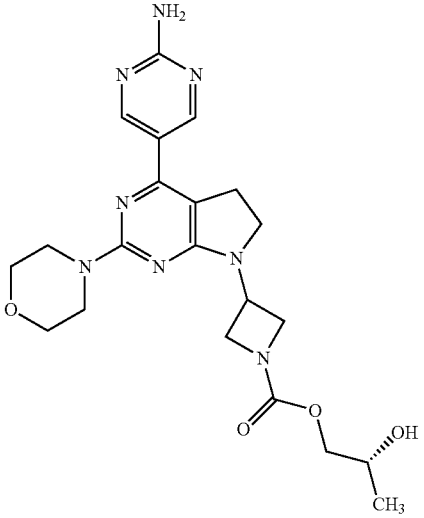<br>(2R)-2-hydroxypropyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 479.3 [M + Na]+ | 1H NMR (400 MHz, DMSO-d6) δ ppm 8.75 (s, 2H) 7.04 (s, 2H) 4.80-4.79 (m, 1H) 4.23-4.12 (m, 4H) 3.82-3.64 (m, 13H) 3.15 (t, J = 6.0 Hz, 2H) 1.05 (d, J = 6.0 Hz, 3H). |
| 186 Scheme A | 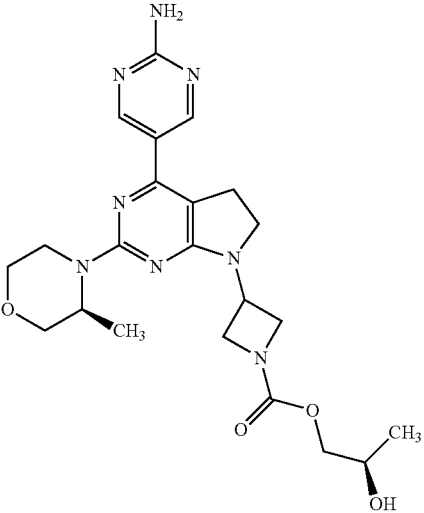<br>(2R)-2-hydroxypropyl 3-{4-(2-aminopyrimidin-5-yl)-2-[(3S)-3-methylmorpholin-4-yl]-5,6-dihydro-7H-pyrrolo[2,3-d]pyrimidin-7-yl}azetidine-1-carboxylate | 493.1 [M + Na]+ | 1H NMR (400 MHz, DMSO-d6) δ ppm 8.74 (s, 2H) 7.03 (s, 2H) 4.77-4.75 (m, 1H) 4.59-4.57 (m, 1H) 4.25-4.05 (m, 5H) 3.87-3.42 (m, 9H) 3.14-3.10 (m, 3H) 1.15 (d, J = 6.8 Hz, 3H) 1.05 (d, J = 6.0 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 187 Scheme A | 5-[7-(2-methylpentan-2-yl)-2-(morpholin-4-yl)-6,7-dihydro-5H-pyrrolo[2,3-d]pyrimidin-4-yl]pyrimidin-2-amine | 384.1 | ¹H NMR (400 MHz, CDCl$_3$) δ ppm 8.82 (s, 2H) 5.19 (s, 2H) 3.86-3.77 (m, 8H) 3.64 (t, J = 8.0 Hz, 2H) 3.03 (t, J = 8.0 Hz, 2H) 1.96-1.94 (m, 2H) 1.40 (s, 6H) 1.33-1.28 (m, 2H) 0.89 (t, J = 8 Hz, 3H). |
| 188 Scheme A | 5-[7-(1-methoxy-2-methylpropan-2-yl)-2-(morpholin-4-yl)-6,7-dihydro-5H-pyrrolo[2,3-d]pyrimidin-4-yl]pyrimidin-2-amine | 386.0 | ¹H NMR (400 MHz, DMSO-d$_6$) δ ppm 8.71 (s, 2H) 6.98 (s, 2H) 3.66-3.63 (m, 12H) 3.25 (s, 3H) 3.03 (t, J = 8.0 Hz, 2H) 1.40 (s, 6H). |
| 189 Scheme A | 5-{7-[1-(dimethylphosphoryl)azetidin-3-yl]-2-(morpholin-4-yl)-6,7-dihydro-5H-pyrrolo[2,3-d]pyrimidin-4-yl}pyrimidin-2-amine | 453.1 [M + Na]⁺ | ¹H NMR (400 MHz, DMSO-d$_6$) δ ppm 8.75 (s, 2H) 7.05 (s, 2H) 4.97 (t, J = 8.0 Hz, 1H) 4.34 (t, J = 9.2 Hz, 2H) 4.06 (t, J = 9.2 Hz, 2H) 3.74 (t, J = 8.0 Hz, 2H) 3.70-3.65 (m, 8H) 3.16 (t, J = 8.4 Hz, 2H) 1.27 (s, 3H) 1.23 (s, 3H). |

TABLE 1-continued

| Example No./ Scheme | Structure and Compound Name | LRMS m/z [M + H]+ | 1H NMR or HPLC retention time and method |
|---|---|---|---|
| 190 Scheme A | 3-[4-(2-aminopyrimidin-5-yl)-2-(morpholin-4-yl)-5,6-dihydro-7H-pyrrolo[2,3-d]pyrimidin-7-yl]-N,3-dimethylazetidine-1-sulfonamide | 462.0 | 1H NMR (400 MHz, CDCl3) δ ppm 8.82 (s, 2H) 5.24 (s, 2H) 4.26 (d, J = 8.0 Hz, 2H) 4.06-4.01 (m, 1H) 3.74 (d, J = 6.8 Hz, 10H) 3.47 (t, J = 7.8 Hz, 2H) 3.15 (t, J = 8.0 Hz, 2H) 2.81 (d, J = 5.2 Hz, 3H) 1.57 (s, 3H). |
| 191 Scheme A | N-{2-[4-(2-aminopyrimidin-5-yl)-2-(morpholin-4-yl)-5,6-dihydro-7H-pyrrolo[2,3-d]pyrimidin-7-yl]-2-methylpropyl}methanesulfonamide | 449.1 | 1H NMR (400 MHz, DMSO-d6 +D2O) δ ppm 8.68 (s, 1H) 8.16 (s, 1H) 3.61-3.52 (m, 12H) 2.99 (m, 2H) 2.80 (s, 3H) 1.33 (s, 6H). |
| 192 Scheme A | 3-[4-(2-aminopyrimidin-5-yl)-2-(morpholin-4-yl)-5,6-dihydro-7H-pyrrolo[2,3-d]pyrimidin-7-yl]-(3R)-3-methylpyrrolidine-1-sulfonamide | 462.1 | 1H NMR (400 MHz, 80° C., DMSO-d6) δ 8.73 (s, 2H) 6.61 (br s, 2H) 6.52 (br s, 2H) 3.71-3.56 (m, 11H) 3.51 (d, J = 9.9 Hz, 1H) 3.37-3.21 (m, 2H) 3.10 (t, J = 8.2 Hz, 2H) 2.59-2.43 (m, 1H, overlapped with DMSO) 2.12-2.04 (m, 1H) 1.40 (s, 3H). |

TABLE 1-continued

| Example No./ Scheme | Structure and Compound Name | LRMS m/z [M + H]+ | ¹H NMR or HPLC retention time and method |
|---|---|---|---|
| 193 Scheme A | 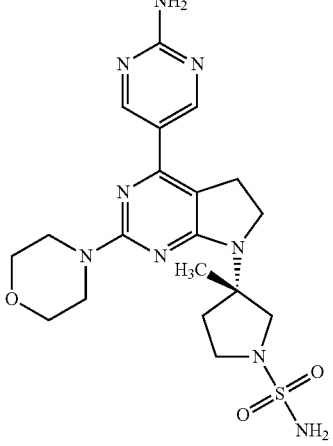<br>3-[4-(2-aminopyrimidin-5-yl)-2-(morpholin-4-yl)-5,6-dihydro-7H-pyrrolo[2,3-d]pyrimidin-7-yl]-(3S)-3-methylpyrrolidine-1-sulfonamide | 426.1 | ¹H NMR (400 MHz, 80° C., DMSO-$d_6$) δ 8.73 (s, 2H) 6.62 (br s, 2H) 6.52 (br s, 2H) 3.71-3.56 (m, 11H) 3.51 (d, J = 9.78 Hz, 1H) 3.37-3.20 (m, 2H) 3.10 (t, J = 8.1 Hz, 2H) 2.59-2.43 (m, 1H, overlapped with DMSO) 2.12-2.04 (m, 1H) 1.39 (s, 3H). |
| 194 Scheme A | 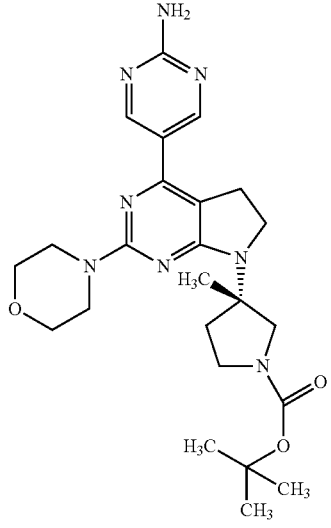<br>tert-butyl 3-[4-(2-aminopyrimidin-5-yl)-2-(morpholin-4-yl)-5,6-dihydro-7H-pyrrolo[2,3-d]pyrimidin-7-yl]-(3S)-3-methylpyrrolidine-1-carboxylate | 483.2 | ¹H NMR (400 MHz, 80° C., DMSO-$d_6$) δ 8.73 (s, 2H) 6.61 (br s, 2H) 3.80-3.63 (m, 11H) 3.54 (q, J = 8.7 Hz, 1H) 3.42-3.35 (m, 1H) 3.33-3.25 (m, 1H) 3.09 (t, J = 8.2 Hz, 2H) 2.44-2.35 (m, 1H) 2.07-2.00 (m, 1H) 1.42 (s, 9H) 1.32 (s, 3H). |

| Example No./ Scheme | Structure and Compound Name | LRMS m/z [M + H]⁺ | ¹H NMR or HPLC retention time and method |
|---|---|---|---|
| 195 Scheme A | 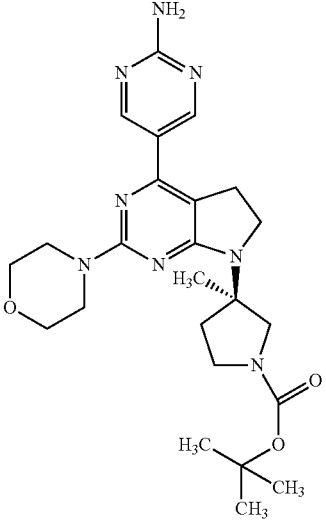<br>tert-butyl 3-[4-(2-aminopyrimidin-5-yl)-2-(morpholin-4-yl)-5,6-dihydro-7H-pyrrolo[2,3-d]pyrimidin-7-yl]-(3R)-3-methylpyrrolidine-1-carboxylate | 483.3 | ¹H NMR (400 MHz, 80° C., DMSO-d$_6$) δ 8.73 (s, 2H) 6.62 (br s, 2H) 3.81-3.62 (m, 11H) 3.54 (q, J = 9.0 Hz, 1H) 3.43-3.35 (m, J = 3.9 Hz, 1H) 3.33-3.25 (m, 1H) 3.09 (t, J = 8.1 Hz, 2H) 2.46-2.34 (m, 1H) 2.08-1.99 (m, 1H) 1.42 (s, 9H), 1.31 (s, 3H). |
| 196 Scheme A | 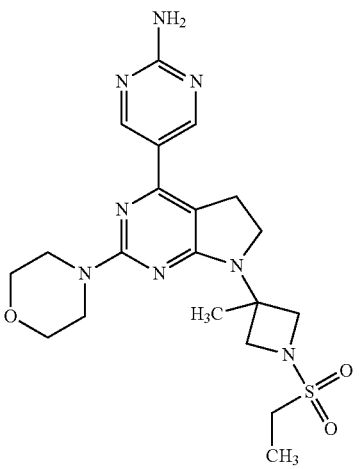<br>5-{7-[1-(ethylsulfonyl)-3-methylazetidin-3-yl]-2-(morpholin-4-yl)-6,7-dihydro-5H-pyrrolo[2,3-d]pyrimidin-4-yl}pyrimidin-2-amine | 461.1 | ¹H NMR (400 MHz, DMSO-d$_6$) δ ppm 8.74 (s, 2H) 7.05 (s, 2H) 4.22 (d, J = 8.0 Hz, 2H) 3.74 (d, J = 8.0 Hz, 2H) 3.64-3.63 (m, 8H) 3.49 (t, J = 7.8 Hz, 2H) 3.19-3.12 (m, 4H) 1.48 (s, 3H) 1.23 (t, J = 7.2 Hz, 3H). |

TABLE 1-continued

| Example No./ Scheme | Structure and Compound Name | LRMS m/z [M + H]+ | 1H NMR or HPLC retention time and method |
|---|---|---|---|
| 197 Scheme A | 5-{7-[1-(cyclopropylsulfonyl)-3-methylazetidin-3-yl]-2-(morpholin-4-yl)-6,7-dihydro-5H-pyrrolo[2,3-d]pyrimidin-4-yl}pyrimidin-2-amine | 473.0 | 1H NMR (400 MHz, DMSO-$d_6$) δ ppm 8.74 (s, 2H) 7.05 (s, 2H) 4.27 (d, J = 8.0 Hz, 2H) 3.78 (d, J = 8.4 Hz, 2H) 3.64-3.63 (m, 8H) 3.50 (t, J = 8.0 Hz, 2H) 3.18-3.12 (m, 2H) 2.83-2.79 (m, 1H) 1.50 (s, 3H) 1.06-1.02 (m, 2H) 0.97-0.94 (m, 2H). |
| 198 Scheme A | 5-{7-[3-methyl-1-(propan-2-ylsulfonyl)azetidin-3-yl]-2-(morpholin-4-yl)-6,7-dihydro-5H-pyrrolo[2,3-d]pyrimidin-4-yl}pyrimidin-2-amine | 475.1 | 1H NMR (400 MHz, DMSO-$d_6$) δ ppm 8.74 (s, 2H) 7.05 (s, 2H) 4.24 (d, J = 8.0 Hz, 2H) 3.72 (d, J = 4.0 Hz, 2H) 3.64-3.63 (m, 8H) 3.49 (t, J = 8.0 Hz, 2H) 3.31-3.28 (m, 1H) 3.16-3.14 (m, 2H) 1.50 (s, 3H) 1.25 (d, J = 6.8 Hz, 6H). |
| 199 Scheme A | 5-[7-[3-methylazetidin-3-yl)-2-(morpholin-4-yl)-6,7-dihydro-5H-pyrrolo[2,3-d]pyrimidin-4-yl]pyrimidin-2-amine | 369.0 | 1H NMR (400 MHz, CDCl$_3$) δ ppm 8.74 (s, 2H) 8.33 (br s, 1H) 7.03 (s, 2H) 4.09 (d, J = 8.4 Hz, 2H) 3.63-3.62 (m, 8H) 3.55 (d, J = 9.2 Hz, 2H) 3.47 (t, J = 7.6 Hz, 2H) 3.13 (t, J = 8.0 Hz, 2H) 1.48 (s, 3H). |

| Example No./ Scheme | Structure and Compound Name | LRMS m/z [M + H]+ | 1H NMR or HPLC retention time and method |
|---|---|---|---|
| 200 Scheme A | 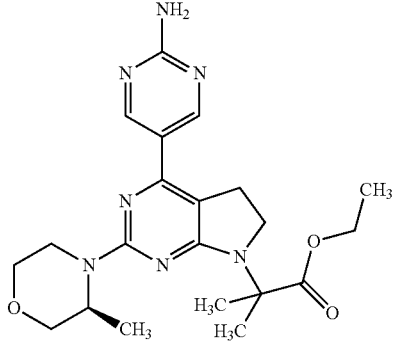<br>ethyl 2-{4-(2-aminopyrimidin-5-yl)-2-[(3S)-3-methylmorpholin-4-yl]-5,6-dihydro-7H-pyrrolo[2,3-d]pyrimidin-7-yl}-2-methylpropanoate | 428.2 | 1H NMR (400 MHz, Acetone-d6) δ ppm 8.80 (s, 2H) 6.22 (br s, 2H) 4.67-4.49 (m, 1H) 4.27 (dd, J = 2.7, 13.6 Hz, 1H) 4.16-4.02 (m, 2H) 3.89 (dd, J = 11.2, 3.5 Hz, 1H) 3.79 (t, J = 8.1 Hz, 2H) 3.74-3.66 (m, 1H) 3.59 (dd, J = 11.2, 3.2 Hz, 1H) 3.43 (dt, J = 11.8, 3.0 Hz, 1H) 3.22-3.15 (m, 2H) 3.15-3.04 (m, 1H) 1.55 (s, 6H) 1.23-1.17 (m, 3H) 1.14 (t, J = 7.1 Hz, 3H). |
| 201 Scheme A | 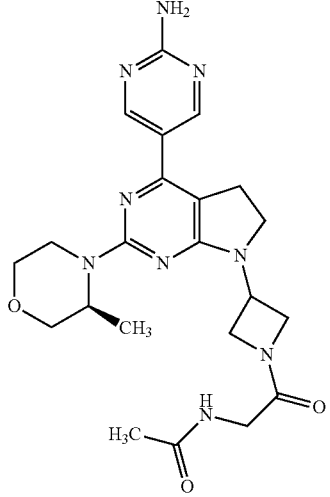<br>N-[2-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-2-oxoethyl]acetamide | 467.1 | 1H NMR (400 MHz, DMSO-d6) δ ppm 8.74 (s, 2H) 8.07 (t, J = 5.2 Hz, 1H) 7.03 (s, 2H) 4.82-4.77 (m, 1H) 4.59-4.58 (m, 1H) 4.49-4.43 (m, 1H) 4.38-4.35 (m, 1H) 4.25-4.17 (m, 1H) 4.11-4.05 (m, 2H) 3.89-3.87 (m, 1H) 3.70-3.67 (m, 1H) 3.57-3.53 (m, 5H) 3.42-3.39 (m, 1H) 3.15 (t, J = 8.0 Hz, 2H) 3.10-3.03 (m, 1H) 1.85 (s, 3H) 1.16-1.13 (m, 3H). |

TABLE 1-continued

| Example No./ Scheme | Structure and Compound Name | LRMS m/z [M + H]+ | 1H NMR or HPLC retention time and method |
|---|---|---|---|
| 202 Scheme A | 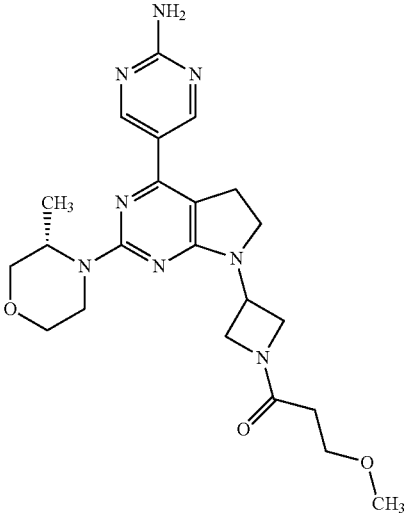<br>1-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-3-methoxypropan-1-one | 455.0 | 1H NMR (400 MHz, DMSO-d6) δ ppm 8.74 (s, 2H) 7.03 (s, 2H) 4.77-4.74 (m, 1H) 4.60-4.58 (m, 1H) 4.44-4.38 (m, 1H) 4.36-4.31 (m, 1H) 4.25-4.22 (m, 1H) 4.17-4.13 (m, 1H) 4.08-4.02 (m, 1H) 3.90-3.86 (m, 1H) 3.69-3.67 (m, 3H) 3.57-3.50 (m, 3H) 3.42-3.36 (m, 1H) 3.22 (s, 3H), 3.15 (t, J = 8 Hz, 2H) 3.10-3.03 (m, 1H) 2.30 (t, J = 6.8 Hz, 2H) 1.15-1.13 (m, 3H). |
| 203 Scheme A | 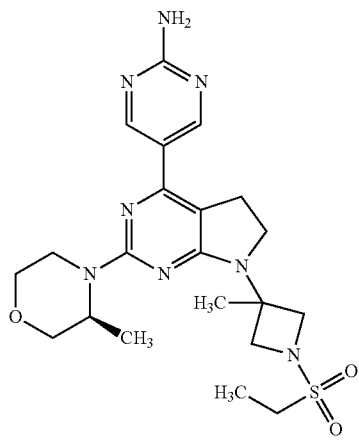<br>5-{7-[1-(ethylsulfonyl)-3-methylazetidin-3-yl]-2-[(3S)-3-methylmorpholin-4-yl]-6,7-dihydro-5H-pyrrolo[2,3-d]pyrimidin-4-yl}pyrimidin-2-amine | 475.1 | 1H NMR (400 MHz, DMSO-d6) δ ppm 8.73 (s, 2H) 7.02 (s, 2H) 4.51-4.50 (m, 1H) 4.24-4.21 (m, 3H) 3.90-3.88 (m, 1H) 3.74-3.72 (m, 3H) 3.56-3.55 (m, 1H) 3.49-3.33 (m, 3H) 3.18-3.13 (m, 5H) 1.49 (s, 3H) 1.23 (t, J = 7.2 Hz, 3H) 1.17 (d, J = 6.8 Hz, 3H). |

| Example No./ Scheme | Structure and Compound Name | LRMS m/z [M + H]+ | ¹H NMR or HPLC retention time and method |
|---|---|---|---|
| 204 Scheme A | 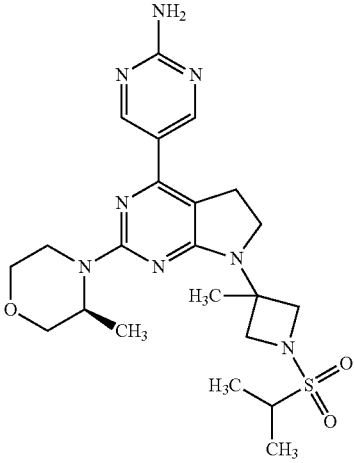<br>5-{2-[(3S)-3-methylmorpholin-4-yl]-7-[3-methyl-1-(propan-2-ylsulfonyl)azetidin-3-yl]-6,7-dihydro-5H-pyrrolo[2,3-d]pyrimidin-4-yl}pyrimidin-2-amine | 489.1 | ¹H NMR (400 MHz, DMSO-$d_6$) δ ppm 8.74 (s, 2H) 7.04 (s, 2H) 4.50 (br s, 1H) 4.35-4.15 (m, 3H) 3.90 (d, J = 8.8 Hz, 1H) 3.71 (d, J = 7.6 Hz, 3H) 3.65-3.55 (m, 1H) 3.50-3.40 (m, 3H) 3.20-3.00 (m, 4H) 1.50 (s, 3H) 1.25 (d, J = 5.6 Hz, 6H) 1.15 (d, J = 5.6 Hz, 3H). |
| 205 Scheme A | 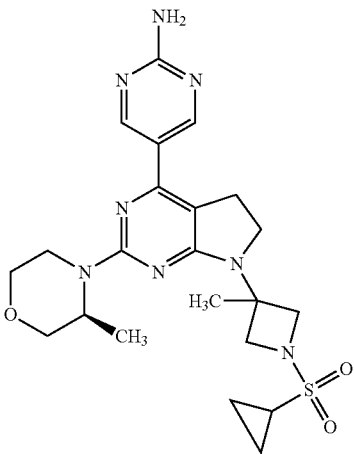<br>5-{7-[1-(cyclopropylsulfonyl)-3-methylazetidin-3-yl]-2-[(3S)-3-methylmorpholin-4-yl]-6,7-dihydro-5H-pyrrolo[2,3-d]pyrimidin-4-yl}pyrimidin-2-amine | 487.1 | ¹H NMR (400 MHz, DMSO-$d_6$) δ ppm 8.74 (s, 2H) 7.04 (s, 2H) 4.50 (d, J = 4.8 Hz, 1H) 4.27 (d, J = 8.4 Hz, 2H) 4.20 (d, J = 12.4 Hz, 1H) 3.90 (dt, J = 2.8 Hz, 10.8 Hz 1H) 3.77 (q, J = 4.0 Hz, 2H) 3.71 (d, J = 11.2 Hz, 1H) 3.55-3.60 (m, 1H) 3.50 (t, J = 8.4 Hz, 2H) 3.38-3.42 (m, 1H) 3.14 (t, J = 7.6 Hz, 2H) 3.05-3.10 (m, 1H) 2.85-2.76 (m, 1H) 1.50 (s, 3H) 1.15 (d, J = 6.4 Hz, 3H) 1.04 (d, J = 15.2 Hz, 2H) 0.94 (d, J = 6.8 Hz, 2H). |

TABLE 1-continued

| Example No./ Scheme | Structure and Compound Name | LRMS m/z [M + H]+ | 1H NMR or HPLC retention time and method |
|---|---|---|---|
| 206 Scheme A | 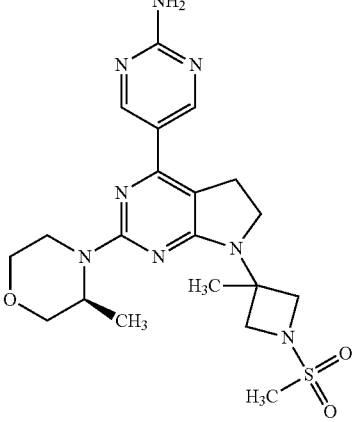 5-{7-[3-methyl-1-(methylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 461.1 | 1H NMR (400 MHz, DMSO-d6) δ ppm 8.73 (s, 2H) 7.02 (s, 2H) 4.51-4.50 (m, 1H) 4.21-4.17 (m, 3H) 3.90-3.88 (m, 1H) 3.76-3.68 (m, 3H) 3.57-3.40 (m, 4H) 3.13 (m, 3H) 3.04 (s, 3H) 1.48 (s, 3H) 1.14 (d, J = 6.8 Hz, 3H). |
| 207 Scheme A | 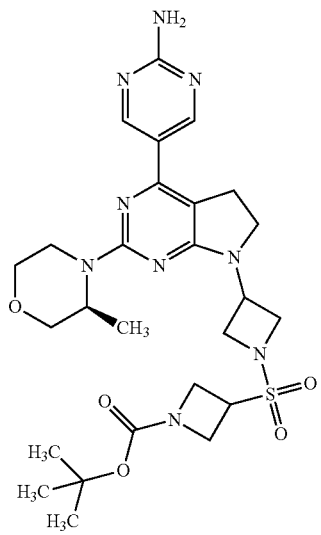 tert-butyl 3-[(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)sulfonyl]azetidine-1-carboxylate | 588.2 | 1H NMR (400 MHz, DMSO-d6) δ ppm 8.74 (s, 2H) 6.99 (s, 2H) 4.85-4.75 (m, 1H) 4.63 (qd, J = 6.4, 2.7 Hz, 1H) 4.43-4.35 (m, 1H) 4.30-4.23 (m, 3H) 4.23-4.14 (m, 2H) 4.05 (td, J = 7.9, 4.5 Hz, 2H) 3.95 (dd, J = 8.6, 5.2 Hz, 2H) 3.88 (dd, J = 11.1, 3.2 Hz, 1H) 3.74-3.64 (m, 3H) 3.55 (dd, J = 11.2, 2.9 Hz, 1H) 3.43-3.36 (m, 1H) 3.15 (t, J = 8.2 Hz, 2H) 3.07 (td, J = 12.8, 3.3 Hz, 1H) 1.40 (s, 9H) 1.15 (d, J = 6.7 Hz, 3H). |

TABLE 1-continued

| Example No./ Scheme | Structure and Compound Name | LRMS m/z [M + H]+ | 1H NMR or HPLC retention time and method |
|---|---|---|---|
| 208 Scheme A | 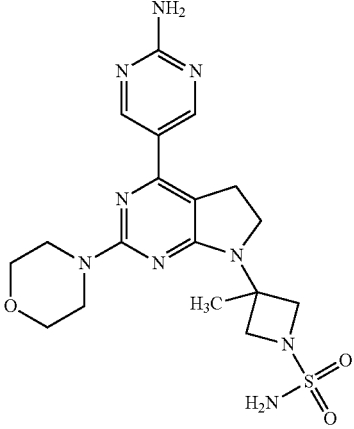 3-[4-(2-aminopyrimidin-5-yl)-2-(morpholin-4-yl)-5,6-dihydro-7H-pyrrolo[2,3-d]pyrimidin-7-yl]-3-methylazetidine-1-sulfonamide | 448.0 | 1H NMR (400 MHz, DMSO-$d_6$) δ ppm 8.69 (s, 2H) 7.19 (br s, 2H) 6.99 (s, 2H) 4.03 (d, J = 8.4 Hz, 2H) 3.67-3.64 (m, 10H) 3.19-3.13 (m, 4H) 1.51 (s, 3H). |
| 209 Scheme A | 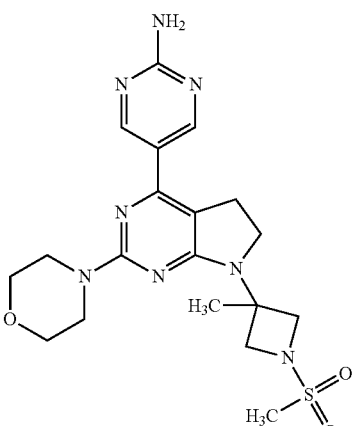 5-{7-[3-methyl-1-(methylsulfonyl)azetidin-3-yl]-2-(morpholin-4-yl)-6,7-dihydro-5H-pyrrolo[2,3-d]pyrimidin-4-yl}pyrimidin-2-amine | 446.9 | 1H NMR (400 MHz, CDCl$_3$) δ ppm 8.74 (s, 2H) 7.04 (s, 2H) 4.20 (d, J = 8.8 Hz, 2H) 3.77 (d, J = 8.8 Hz, 1H) 3.64-3.63 (m, 8H) 3.48-3.34 (m, 2H) 3.16-3.14 (m, 2H) 3.05 (s, 3H) 1.48 (s, 3H). |

TABLE 1-continued

| Example No./ Scheme | Structure and Compound Name | LRMS m/z [M + H]+ | 1H NMR or HPLC retention time and method |
|---|---|---|---|
| 210 Scheme A | N-(2-{3-[4-(2-aminopyrimidin-5-yl)-2-(morpholin-4-yl)-5,6-dihydro-7H-pyrrolo[2,3-d]pyrimidin-7-yl]azetidin-1-yl}-2-oxoethyl)acetamide | 476.0 [M + Na]+ | 1H NMR (400 MHz, DMSO-d$_6$) δ ppm 8.76 (s, 2H) 8.07 (t, J = 5.6 Hz, 1H) 7.03 (s, 2H) 4.84-4.82 (m, 1H) 4.47-4.43 (m, 1H) 4.39-4.35 (m, 1H) 4.20-4.16 (m, 1H) 4.12-4.07 (m, 1H) 3.73-3.65 (m, 12H) 3.17 (t, J = 8.0 Hz, 2H) 1.86 (s, 3H). |
| 211 Scheme A | 1-{3-[4-(2-aminopyrimidin-5-yl)-2-(morpholin-4-yl)-5,6-dihydro-7H-pyrrolo[2,3-d]pyrimidin-7-yl]-(3R)-3-methylpyrrolidin-1-yl}ethanone | 425.0 | 1H NMR (400 MHz, CDCl$_3$) δ ppm 8.83 (s, 2H) 5.28 (s, 2H) 4.09-3.89 (m, 2H) 3.82-3.77 (m, 8H) 3.68-3.52 (m, 4H) 3.10 (t, J = 8.8 Hz, 2H) 2.75-2.15 (m, 1H) 2.07-2.06 (m, 4H) 1.37 (d, J = 2.4 Hz, 3H). |

TABLE 1-continued

| Example No./ Scheme | Structure and Compound Name | LRMS m/z [M + H]+ | $^1$H NMR or HPLC retention time and method |
|---|---|---|---|
| 212 Scheme A | 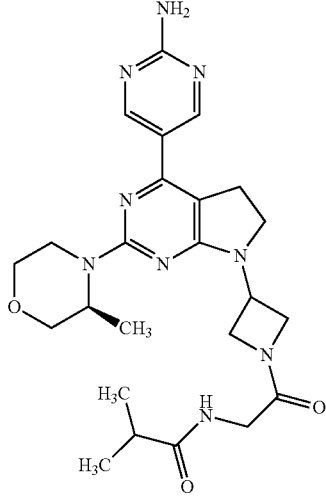 N-[2-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-2-oxoethyl]-2-methylpropanamide | 496.1 | $^1$H NMR (400 MHz, CDCl$_3$) δ ppm 8.85 (s, 2H) 6.35 (s, 1H) 5.23 (s, 2H) 4.87-4.66 (m, 1H) 4.47-4.41 (m, 1H) 4.39-4.32 (m, 5H) 3.96-3.87 (m, 1H) 3.88 (s, 1H) 3.71-3.69 (m, 1H) 3.67-3.66 (m, 3H) 3.55-3.45 (m, 1H) 3.22-3.18 (m, 3H) 2.50-2.43 (m, 1H) 1.27 (d, J = 6.8 Hz, 3H) 1.20 (d, J = 7.2 Hz, 3H). |
| 213 Scheme A | 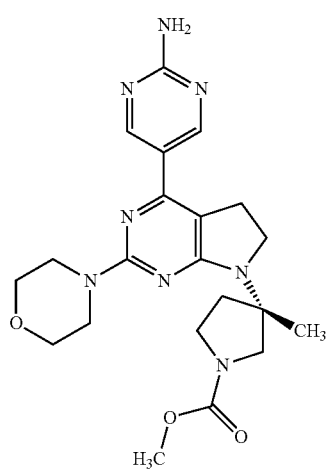 methyl 3-[4-(2-aminopyrimidin-5-yl)-2-(morpholin-4-yl)-5,6-dihydro-7H-pyrrolo[2,3-d]pyrimidin-7-yl]-(3S)-3-methylpyrrolidine-1-carboxylate | 441.1 | $^1$H NMR (400 MHz, CDCl$_3$) δ ppm 8.82 (s, 2H) 5.22 (s, 2H) 3.84-3.77 (m, 1H) 3.61-3.59 (m, 8H) 3.57-3.54 (m, 3H) 3.52-3.40 (m, 5H) 3.10 (t, J = 7.2 Hz, 2H) 2.52-2.43 (m, 1H) 2.41-2.40 (m, 1H) 1.35 (s, 3H). |

TABLE 1-continued

| Example No./ Scheme | Structure and Compound Name | LRMS m/z [M + H]+ | ¹H NMR or HPLC retention time and method |
|---|---|---|---|
| 214 Scheme A | 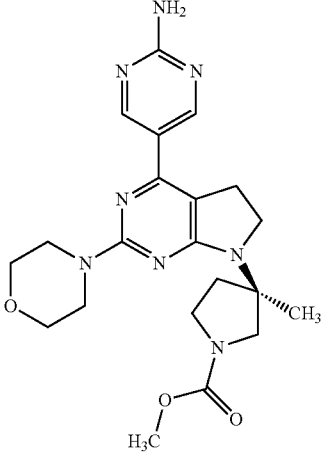<br>methyl 3-[4-(2-aminopyrimidin-5-yl)-2-(morpholin-4-yl)-5,6-dihydro-7H-pyrrolo[2,3-d]pyrimidin-7-yl]-(3R)-3-methylpyrrolidine-1-carboxylate | 441.1 | ¹H NMR (400 MHz, CDCl$_3$) δ ppm 8.82 (s, 2H) 5.22 (s, 2H) 3.84-3.72 (m, 1H) 3.62-3.59 (m, 8H) 3.57-3.52 (m, 3H) 3.49-3.46 (m, 5H) 3.10 (t, J = 7.6 Hz, 2H) 2.52-2.43 (m, 1H) 2.10-2.07 (m, 1H) 1.35 (s, 3H). |
| 215 Scheme A | 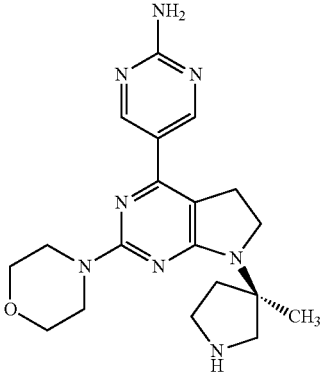<br>5-[7-(3R)-(3-methylpyrrolidin-3-yl)-2-(morpholin-4-yl)-6,7-dihydro-5H-pyrrolo[2,3-d]pyrimidin-4-yl]pyrimidin-2-amine | 382.9 | ¹H NMR (400 MHz, D$_2$O) δ ppm 8.56 (s, 2H) 4.13-4.10 (m, 1H) 3.87-3.79 (m, 2H) 3.78-3.72 (m, 8H) 3.57-3.50 (m, 1H) 3.43 (t, J = 7.2 Hz, 2H) 3.03 (s, 2H) 2.64-2.59 (m, 2H) 2.26-2.21 (m, 1H) 1.49 (s, 3H). |
| 216 Scheme A | 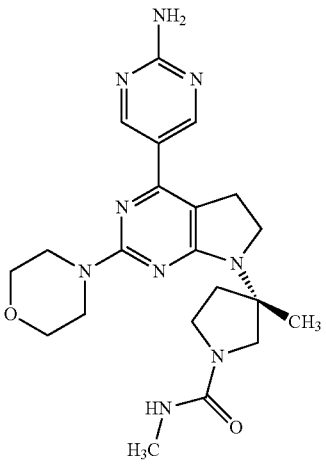<br>(3S)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-carboxamide | 440.1 | ¹H NMR (400 MHz, CDCl$_3$) δ 8.82 (s, 2H) 5.25 (s, 2H) 4.16-4.14 (m, 1H) 3.85-3.77 (m, 10H) 3.64-3.49 (m, 3H) 3.38-3.35 (m, 1H) 3.08 (t, J = 7.6 Hz, 2H) 2.85-2.84 (m, 3H) 2.59-2.56 (m, 1H) 2.17-2.15 (m, 1H) 1.37 (s, 3H). |

| Example No./ Scheme | Structure and Compound Name | LRMS m/z [M + H]+ | 1H NMR or HPLC retention time and method |
|---|---|---|---|
| 217 Scheme A | 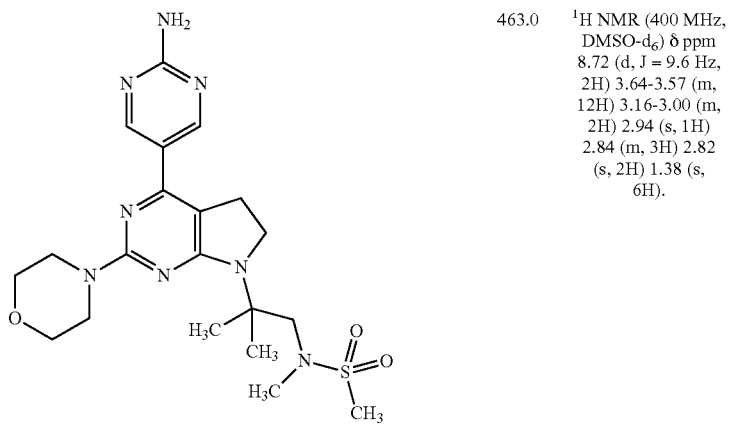 N-{2-[4-(2-aminopyrimidin-5-yl)-2-(morpholin-4-yl)-5,6-dihydro-7H-pyrrolo[2,3-d]pyrimidin-7-yl]-2-methylpropyl}-N-methylmethanesulfonamide | 463.0 | $^1$H NMR (400 MHz, DMSO-d$_6$) δ ppm 8.72 (d, J = 9.6 Hz, 2H) 3.64-3.57 (m, 12H) 3.16-3.00 (m, 2H) 2.94 (s, 1H) 2.84 (m, 3H) 2.82 (s, 2H) 1.38 (s, 6H). |
| 218 Scheme A | 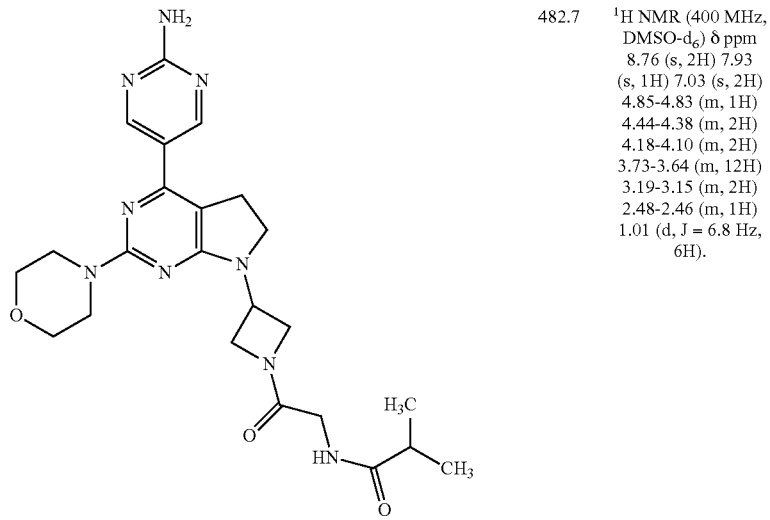 N-(2-{3-[4-(2-aminopyrimidin-5-yl)-2-(morpholin-4-yl)-5,6-dihydro-7H-pyrrolo[2,3-d]pyrimidin-7-yl]azetidin-1-yl}-2-oxoethyl)-2-methylpropanamide | 482.7 | $^1$H NMR (400 MHz, DMSO-d$_6$) δ ppm 8.76 (s, 2H) 7.93 (s, 1H) 7.03 (s, 2H) 4.85-4.83 (m, 1H) 4.44-4.38 (m, 2H) 4.18-4.10 (m, 2H) 3.73-3.64 (m, 12H) 3.19-3.15 (m, 2H) 2.48-2.46 (m, 1H) 1.01 (d, J = 6.8 Hz, 6H). |

TABLE 1-continued

| Example No./ Scheme | Structure and Compound Name | LRMS m/z [M + H]⁺ | ¹H NMR or HPLC retention time and method |
|---|---|---|---|
| 219 Scheme A | 3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidine-1-sulfonamide | 462.3 | ¹H NMR (400 MHz, DMSO-$d_6$) δ ppm 8.73 (s, 2H) 7.02 (s, 2H) 6.96 (s, 2H) 4.51-4.50 (m, 1H) 4.24-4.21 (m, 1H) 4.18-3.99 (m, 2H) 3.90-3.88 (m, 1H) 3.74-3.72 (m, 1H) 3.65-3.55 (m, 3H) 3.49-3.33 (m, 3H) 3.16-3.02 (m, 3H) 1.48 (s, 3H) 1.16 (d, J = 6.8 Hz, 3H). |
| 220 Scheme A | 3-{4-(2-aminopyrimidin-5-yl)-2-[(3S)-3-methylmorpholin-4-yl]-5,6-dihydro-7H-pyrrolo[2,3-d]pyrimidin-7-yl}-N,3-dimethylazetidine-1-sulfonamide | 476.1 | ¹H NMR (400 MHz, DMSO-$d_6$ + $D_2O$) δ ppm 8.60 (s, 2H) 4.46-4.45 (m, 1H) 4.10-4.05 (m, 3H) 3.95-3.93 (m, 1H) 3.74-3.66 (m, 5H) 3.60-3.57 (m, 1H) 3.30-3.24 (m, 2H) 3.14-3.12 (m, 2H) 2.57 (m, 3H) 1.56 (s, 3H) 1.14 (d, J = 6.8 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 221 Scheme A | 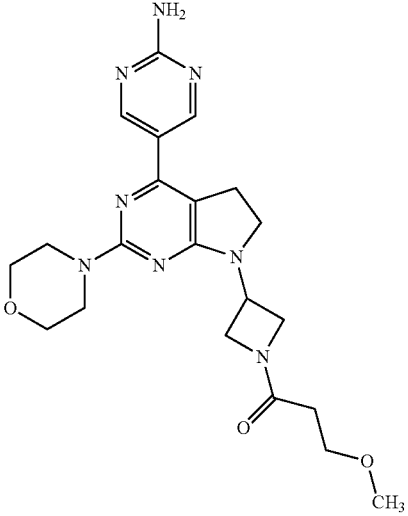<br>1-{3-[4-(2-aminopyrimidin-5-yl)-2-(morpholin-4-yl)-5,6-dihydro-7H-pyrrolo[2,3-d]pyrimidin-7-yl]azetidin-1-yl}-3-methoxypropan-1-one | 441.1 | ¹H NMR (400 MHz, DMSO-$d_6$ + $D_2O$) δ ppm 8.53 (s, 2H) 4.93 (t, J = 6.4 Hz, 1H) 4.45-4.39 (m, 2H) 4.19-4.11 (m, 2H) 3.93-3.89 (m, 2H) 3.70-3.67 (m, 8H) 3.51 (t, J = 6 Hz, 2H) 3.19 (s, 3H) 3.08 (t, J = 7.6 Hz, 2H) 2.30 (t, J = 6.4 Hz, 2H). |
| 222 Scheme A | 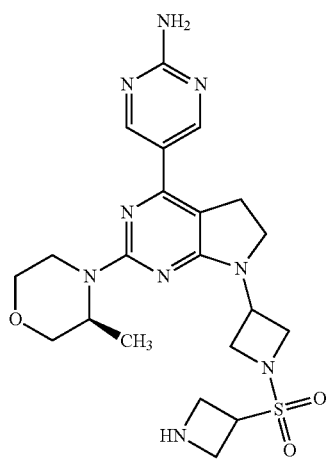<br>5-{7-[1-(azetidin-3-ylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 488.2 | ¹H NMR(400 MHz, DMSO-$d_6$) δ ppm 8.74 (s, 2H) 6.99 (s, 2H) 4.76-4.86 (m, 1H) 4.63 (qd, J = 6.3, 2.9 Hz, 1H) 4.46-4.55 (m, 1H) 4.26 (dd, J = 13.4, 1.5 Hz, 1H) 4.20 (t, J = 7.5 Hz, 2H) 4.00 (td, J = 7.8, 4.9 Hz, 2H) 3.88 (dd, J = 11.5, 3.3 Hz, 1H) 3.76 (t, J = 7.7 Hz, 2H) 3.66-3.72 (m, 3H) 3.64 (t, J = 8.6 Hz, 2 H) 3.55 (dd, J = 11.3, 2.9 Hz, 1 H) 3.34-3.48 (m, 2 H) 3.15 (t, J = 8.2 Hz, 2 H) 3.07 (td, J = 12.9, 3.7 Hz, 1 H) 1.15 (d, J = 6.7 Hz, 3H). |

TABLE 1-continued

| Example No./ Scheme | Structure and Compound Name | LRMS m/z [M + H]+ | ¹H NMR or HPLC retention time and method |
|---|---|---|---|
| 223 Scheme A | 1-{3-[(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)sulfonyl]azetidin-1-yl}ethanone | 530.2 | ¹H NMR (400 MHz, DMSO-d₆) δ ppm 8.74 (s, 2H) 6.99 (s, 2H) 4.77-4.86 (m, 1H) 4.59-4.67 (m, 1H) 4.39-4.48 (m, 2H) 4.23-4.34 (m, 4H) 4.12-4.18 (m, 1H) 4.04-4.12 (m, 2H) 3.93 (dd, J = 10.1, 4.3 Hz, 1H) 3.88 (dd, J = 11.2, 2.9 Hz, 1H) 3.65-3.73 (m, 3H) 3.56 (dd, J = 11.3, 3.0 Hz, 1H) 3.36-3.48 (m, 2H) 3.12-3.16 (m, 1H) 3.07 (td, J = 12.9, 3.6 Hz, 1H) 1.79 (s, 3H) 1.16 (d, J = 6.7 Hz, 3H). |
| 224 Scheme A | 5-{2-[(3R)-3-methylmorpholin-4-yl]-7-[1-(propan-2-ylsulfonyl)azetidin-3-yl]-6,7-dihydro-5H-pyrrolo[2,3-d]pyrimidin-4-yl}pyrimidin-2-amine | 475.1 | ¹H NMR (400 MHz, CDCl₃) δ 8.86 (s, 2H) 5.26 (s, 2H) 4.98-4.94 (m, 1H) 4.76-4.70 (m, 1H) 4.40-4.33 (m, 3H) 4.06-3.95 (m, 3H) 3.76-3.71 (m, 4H) 3.58-3.49 (m, 1H) 3.27-3.12 (m, 4H) 1.38 (d, J = 8 Hz, 6H) 1.28 (d, J = 8 Hz, 3H). |

TABLE 1-continued

| Example No./ Scheme | Structure and Compound Name | LRMS m/z [M + H]+ | 1H NMR or HPLC retention time and method |
|---|---|---|---|
| 225 Scheme A | 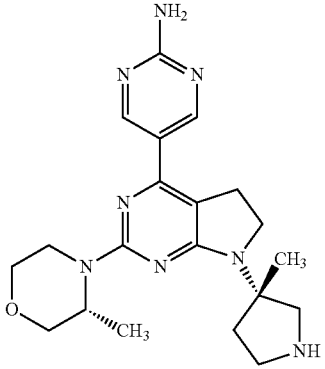<br>5-{2-[(3R)-3-methylmorpholin-4-yl]-7-[(3S)-3-methylpyrrolidin-3-yl]-6,7-dihydro-5H-pyrrolo[2,3-d]pyrimidin-4-yl}pyrimidin-2-amine hydrochloride | 397.0 | 1H NMR (400 MHz, D2O) δ 8.56 (s, 2H) 4.48-4.47 (m, 1H) 4.17-4.14 (m, 1H) 4.06-3.84 (m, 5H) 3.80-3.76 (m, 1H) 3.67-3.47 (m, 5H) 3.09-3.05 (m, 2H) 2.70-2.63 (m, 1H) 2.32-2.25 (m 1H) 1.55 (s, 3H) 1.36 (d, J = 6.8 Hz, 3H). |
| 226 Scheme A | 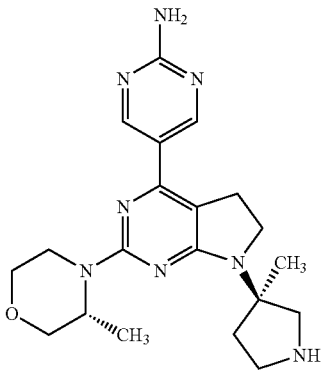<br>5-{2-[(3R)-3-methylmorpholin-4-yl]-7-[(3R)-3-methylpyrrolidin-3-yl]-6,7-dihydro-5H-pyrrolo[2,3-d]pyrimidin-4-yl}pyrimidin-2-amine hydrochloride | 397.1 | 1H NMR (400 MHz, D2O) δ 8.56 (s, 2H) 4.55-4.54 (m, 1H) 4.17-4.14 (m, 1H) 4.06-4.04 (m, 1H) 3.97-3.76 (m, 4H) 3.8-3.77 (m, 1H) 3.67-3.47 (m, 5H) 3.11-3.05 (m, 2H) 2.70-2.63 (m, 1H) 2.32-2.25 (m 1H) 1.55 (s, 3H) 1.36 (d, J = 6.8 Hz, 3H). |
| 227 Scheme A | 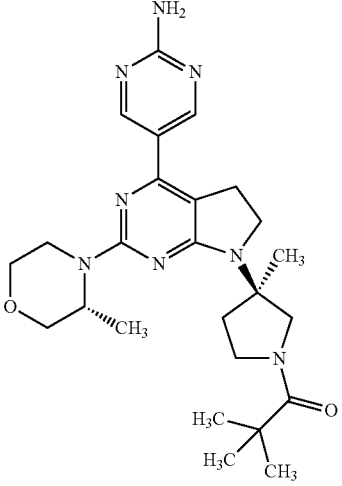<br>2-amino-1-[(3S)-3-{4-(2-aminopyrimidin-5-yl)-2-[(3R)-3-methylmorpholin-4-yl]-5,6-dihydro-7H-pyrrolo[2,3-d]pyrimidin-7-yl}-3-methylpyrrolidin-1-yl]-2-methylpropan-1-one hydrochloride | 482.2 | 1H NMR (400 MHz, D2O) δ 8.61 (s, 2H) 4.37-3.54 (m, 13H) 3.06-3.04 (m, 2H) 2.71-2.48 (m, 1H) 2.30-2.18 (m, 1H) 1.69-1.61 (m, 6H) 1.51-1.50 (d, J = 3.6 Hz, 3H) 1.38-1.35 (m, 3H). |

| Example No./Scheme | Structure and Compound Name | LRMS m/z [M + H]+ | 1H NMR or HPLC retention time and method |
|---|---|---|---|
| 228 Scheme A | 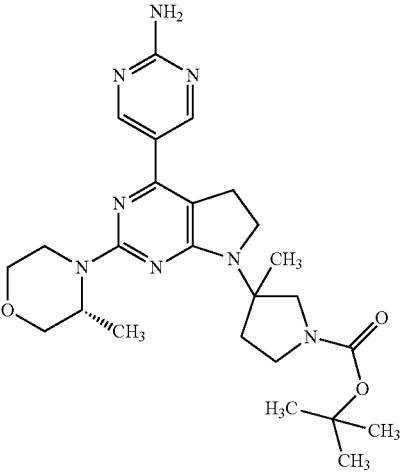<br>tert-butyl 3-{4-(2-aminopyrimidin-5-yl)-2-[(3R)-3-methylmorpholin-4-yl]-5,6-dihydro-7H-pyrrolo[2,3-d]pyrimidin-7-yl}-3-methylpyrrolidine-1-carboxylate | 497.2 | 1H NMR (400 MHz, DMSO) δ 8.71 (s, 2H) 7.00 (s, 2H) 4.51-4.49 (m, 1H) 4.20-4.17 (m, 1H) 3.91-3.69 (m, 2H) 3.67-3.60 (m, 4H) 3.51-3.41 (m, 2H) 3.31-3.20 (m, 2H) 3.18-3.00 (m, 3H) 2.31-2.20 (m, 1H) 2.10-1.95 (m, 1H) 1.39 (s, 9H) 1.27-1.22 (m, 3H) 1.18~1.15 (m, 3H). |
| 229 Scheme A | 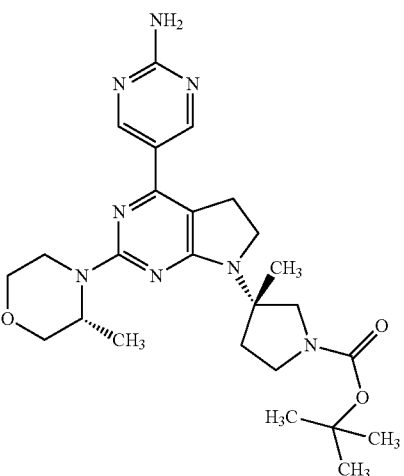<br>tert-butyl (3S)-3-{4-(2-aminopyrimidin-5-yl)-2-[(3R)-3-methylmorpholin-4-yl]-5,6-dihydro-7H-pyrrolo[2,3-d]pyrimidin-7-yl}-3-methylpyrrolidine-1-carboxylate | 497.1 | 1H NMR (400 MHz, D2O) δ 8.82 (s, 2H) 5.21 (s, 2H) 4.64-4.63 (m, 1H) 4.36-4.33 (m, 1H) 3.96-3.91 (m, 2H) 3.79-3.72 (m, 3H) 3.65-3.51 (m, 4H) 3.38-3.32 (m, 1H) 3.28-3.21 (m, 1H) 3.12-3.09 (m, 2H) 2.48-2.27 (m, 1H) 2.11-2.03 (m, 1H) 1.46 (s, 9H) 1.36-1.25 (m, 6H). |

TABLE 1-continued

| Example No./ Scheme | Structure and Compound Name | LRMS m/z [M + H]+ | 1H NMR or HPLC retention time and method |
|---|---|---|---|
| 230 Scheme A | 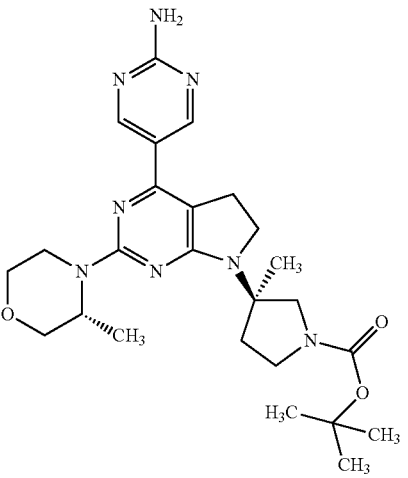<br>tert-butyl (3R)-3-{4-(2-aminopyrimidin-5-yl)-2-[(3R)-3-methylmorpholin-4-yl]-5,6-dihydro-7H-pyrrolo[2,3-d]pyrimidin-7-yl}-3-methylpyrrolidine-1-carboxylate | 497.3 | 1H NMR (CDCl3 400 MHz) δ 8.82 (s, 2H) 5.19 (s, 2H) 4.64-4.63 (m, 1H) 4.33-4.29 (m, 1H) 3.97-3.89 (m, 2H) 3.76-3.71 (m, 3H) 3.65-3.53 (m, 4H) 3.36-3.34 (m, 1H) 3.28-3.21 (m, 1H) 3.12-3.09 (m 2H) 2.54-2.30 (m, 1H) 2.13-2.01 (m, 1H) 1.46 (s, 9H) 1.36-1.25 (m, 6H). |
| 231 Scheme A | 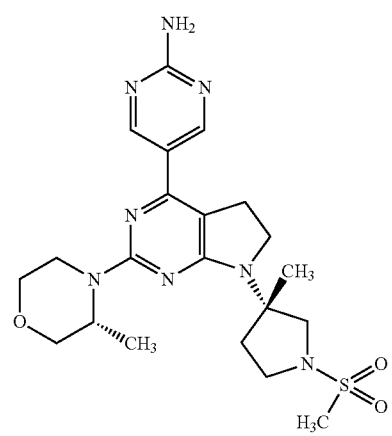<br>5-{7-[(3S)-3-methyl-1-(methylsulfonyl)pyrrolidin-3-yl]-2-[(3R)-3-methylmorpholin-4-yl]-6,7-dihydro-5H-pyrrolo[2,3-d]pyrimidin-4-yl}pyrimidin-2-amine | 475.1 | 1H NMR (400 MHz, CDCl3) δ 8.83 (s, 2H) 5.22 (s, 2H) 4.65-4.55 (m, 1H) 4.30-4.22 (m, 1H) 4.06-3.92 (m, 2H) 3.80-3.70 (m, 3H) 3.69-3.45 (m, 5H) 3.30-3.20 (m, 1H) 3.18-3.09 (m, 2H) 2.82 (s, 3H) 2.60-2.49 (m, 1H) 2.20-2.08 (m, 1H) 1.41 (s, 3H) 1.31 (d, J = 7.2 Hz, 3H). |

TABLE 1-continued

| Example No./ Scheme | Structure and Compound Name | LRMS m/z [M + H]⁺ | ¹H NMR or HPLC retention time and method |
|---|---|---|---|
| 232 Scheme A | 5-{7-[(3R)-3-methyl-1-(methylsulfonyl)pyrrolidin-3-yl]-2-[(3R)-3-methylmorpholin-4-yl]-6,7-dihydro-5H-pyrrolo[2,3-d]pyrimidin-4-yl}pyrimidin-2-amine | 475.1 | ¹H NMR (400 MHz, CDCl₃) δ 8.83 (s, 2H) 5.22 (s, 2H) 4.65-4.55 (m, 1H) 4.30 (d, J = 20 Hz, 1H) 4.06 (d, J = 10.4 Hz, 1H) 3.80 (d, J = 20 Hz, 1H) 3.77-3.45 (m, 8H) 3.30-3.20 (m, 1H) 3.18-3.09 (m, 2H) 2.82 (s, 3H) 2.60-2.49 (m, 1H) 2.20-2.08 (m, 1H) 1.41 (s, 3H) 1.31 (d, J = 7.2 Hz, 3H). |
| 233 Scheme B | (S)-2-amino-1-(3-(4-(2-aminopyrimidin-5-yl)-2-(morpholino-2,2,6,6-d₄)-5,6-dihydro-7H-pyrrolo[2,3-d]pyrimidin-7-yl)-3-methylpyrrolidin-1-yl)-2-methylpropan-1-one | 472.6 | ¹H NMR (400 MHz, 80° C., DMSO-d₆) δ 8.74 (s, 2H) 7.44 (br s, 2H) 6.63 (s, 2H) 4.12-4.26 (m, 1H) 4.00 (br s, 1H) 3.69-3.80 (m, 2H) 3.67 (s, 5H) 3.51-3.62 (m, 2H) 3.07-3.15 (m, 2H) 2.09 (br s, 1H) 1.52 (d, J = 10.7 Hz, 6H) 1.36 (s, 3H). |

| Example No./ Scheme | Structure and Compound Name | LRMS m/z [M + H]+ | ¹H NMR or HPLC retention time and method |
|---|---|---|---|
| 234 Scheme B | 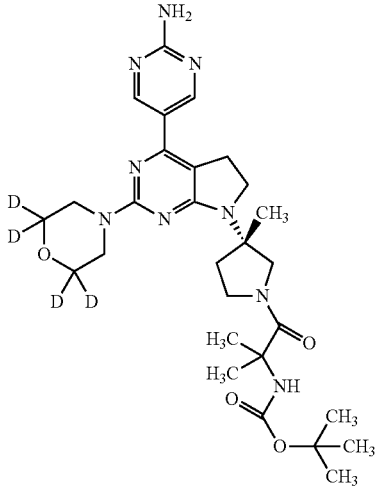<br>tert-butyl (S)-(1-(3-(4-(2-aminopyrimidin-5-yl)-2-(morpholino-2,2,6,6-d₄)-5,6-dihydro-7H-pyrrolo[2,3-d]pyrimidin-7-yl)-3-methylpyrrolidin-1-yl)-2-methyl-1-oxopropan-2-yl)carbamate | 572.7 | ¹H NMR (400 MHz, DMSO-d₆) δ 8.72 (s, 2H) 6.96 (s, 2H) 3.67-3.78 (m, 2H) 3.57-3.67 (m, 5H) 3.37-3.57 (m, 3H) 3.01-3.16 (m, 2H) 1.93-2.23 (m, 2H) 1.36 (s, 9H) 1.20-1.32 (m, 9H). |
| 235 Scheme B | 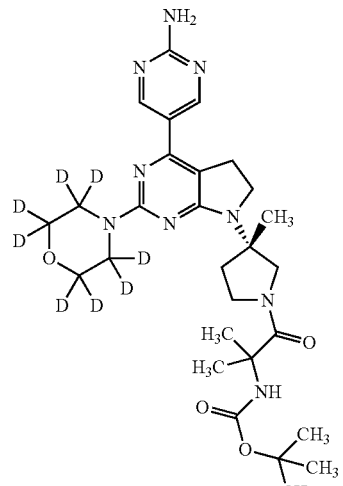<br>tert-butyl (S)-(1-(3-(4-(2-aminopyrimidin-5-yl)-2-(morpholino-d₈)-5,6-dihydro-7H-pyrrolo[2,3-d]pyrimidin-7-yl)-3-methylpyrrolidin-1-yl)-2-methyl-1-oxopropan-2-yl)carbamate | 576.7 | ¹H NMR (400 MHz, DMSO-d₆) δ 8.73 (s, 2H) 6.98 (s, 2H) 3.56-3.80 (m, 3H) 3.38-3.58 (m, 3H) 3.00-3.14 (m, 2H) 1.93-2.26 (m, 2H) 1.36 (s, 9H) 1.24-1.32 (m, 9H). |

TABLE 1-continued

| Example No./ Scheme | Structure and Compound Name | LRMS m/z [M + H]⁺ | ¹H NMR or HPLC retention time and method |
|---|---|---|---|
| 236 Scheme B | 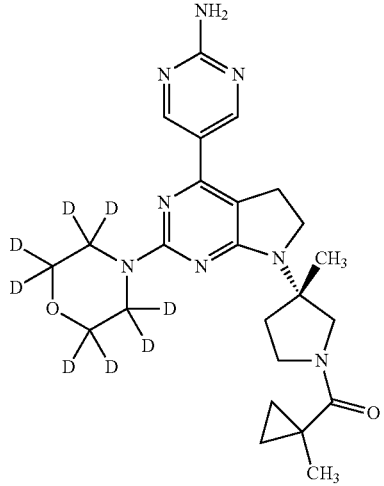<br>(S)-(3-(4-(2-aminopyrimidin-5-yl)-2-(morpholino-d₈)-5,6-dihydro-7H-pyrrolo[2,3-d]pyrimidin-7-yl)-3-methylpyrrolidin-1-yl)(1-methylcyclopropyl)methanone | 473.6 | ¹H NMR (700 MHz, DMSO-d₆) δ 8.73 (s, 2H) 6.99 (s, 2H) 4.31 (d, J = 10.5 Hz, 1 H) 4.02 (d, J = 10.7 Hz, 1H) 3.58-3.78 (m, 2H) 3.45-3.56 (m, 1H) 3.24-3.31 (m, 1H) 3.05-3.15 (m, 2H) 2.17-2.26 (m, 1H) 1.93-2.02 (m, 1H) 1.22 (d, J = 2.6 Hz, 6H) 0.80-0.89 (m, 1H) 0.66-0.76 (m, 1H) 0.38-0.53 (m, 2H). |
| 237 Scheme B | 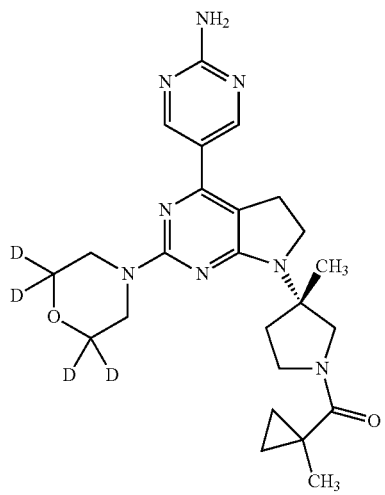<br>(S)-(3-(4-(2-aminopyrimidin-5-yl)-2-(morpholino-2,2,6,6-d₄)-5,6-dihydro-7H-pyrrolo[2,3-d]pyrimidin-7-yl)-3-methylpyrrolidin-1-yl)(1-methylcyclopropyl)methanone | 469.6 | ¹H NMR (700 MHz, DMSO-d₆) δ 8.74 (br s, 2H) 7.00 (br s, 2H) 4.31 (d, J = 10.5 Hz, 1H) 4.02 (d, J = 10.7 Hz, 1H) 3.74 (br s, 1H) 3.58-3.68 (m, 6H) 3.48-3.55 (m, 1H) 3.05-3.14 (m, 2H) 2.17-2.26 (m, 1H) 1.94-2.02 (m, 1H) 1.22 (br s, 6H) 0.81-0.87 (m, 1H) 0.68-0.76 (m, 1H) 0.41-0.53 (m, 2H). |

TABLE 1-continued

| Example No./ Scheme | Structure and Compound Name | LRMS m/z [M + H]+ | 1H NMR or HPLC retention time and method |
|---|---|---|---|
| 238 Scheme B | 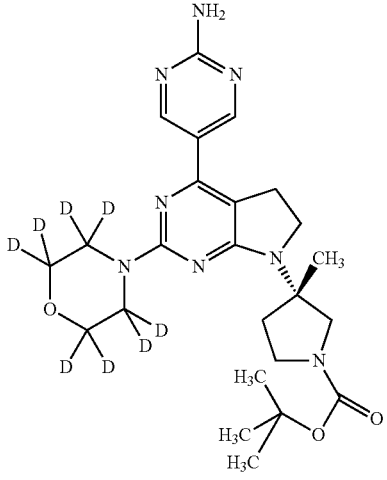<br>tert-butyl (S)-3-(4-(2-aminopyrimidin-5-yl)-2-(morpholino-d$_8$)-5,6-dihydro-7H-pyrrolo[2,3-d]pyrimidin-7-yl)-3-methylpyrrolidine-1-carboxylate | 491.6 | 1H NMR (400 MHz, DMSO-d$_6$) δ 8.72 (s, 2H) 6.96 (s, 2H) 3.83 (d, J = 10.8 Hz, 1H) 3.67 (dd, J = 24.2, 15.0 Hz, 3H) 3.45-3.55 (m, 1H) 3.34-3.41 (m, 1H) 3.04-3.13 (m, 2H) 2.23-2.36 (m, 1H) 1.96-2.08 (m, 1H) 1.40 (s, 9H) 1.21-1.29 (m, 3H). |
| 239 Scheme B | 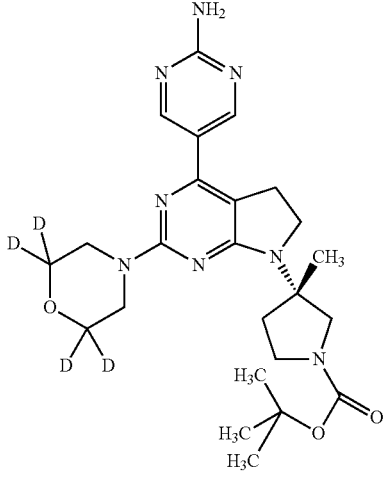<br>tert-butyl (S)-3-(4-(2-aminopyrimidin-5-yl)-2-(morpholino-2,2,6,6-d$_4$)-5,6-dihydro-7H-pyrrolo[2,3-d]pyrimidin-7-yl)-3-methylpyrrolidine-1-carboxylate | 487.6 | 1H NMR (400 MHz, DMSO-d$_6$) δ 8.73 (s, 2H) 6.96 (s, 2H) 3.84 (d, J = 11.0 Hz, 1H) 3.58-3.74 (m, 7H) 3.44-3.56 (m, 2H) 3.04-3.14 (m, 2H) 2.22-2.39 (m, 1H) 1.97-2.10 (m, 1H) 1.40 (s, 8H) 1.22-1.30 (m, 3H). |

*Compounds are single enantiomers; however, absolute stereochemistry is unknown.
**Compounds are racemates
***Compounds are diasteromic mixtures The compounds of Table 2 are prepared according to the general procedures shown in Scheme A, which would be understood by one of ordinary skill in the art.

TABLE 2

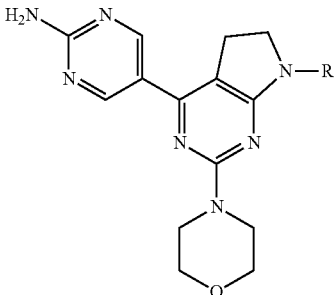

| Example No. | R | IUPAC Name | LRMS m/z [M + H]⁺ | ¹H NMR or LCMS retention time and method |
|---|---|---|---|---|
| 240 | 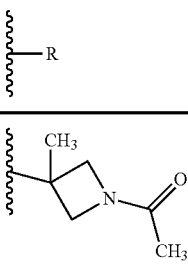 | 1-{3-[4-(2-aminopyrimidin-5-yl)-2-(morpholin-4-yl)-5,6-dihydro-7H-pyrrolo[2,3-d]pyrimidin-7-yl]-3-methylazetidin-1-yl}ethanone | 411.2 | ¹H NMR (400 MHz, DMSO-d₆) δ 8.74 (s, 2H) 7.08 (s, 2H) 4.46 (d, J = 8.4 Hz, 1H) 4.18 (d, J = 10 Hz, 1H) 4.02 (d, J = 8.4 Hz, 1H) 3.74 (d, J = 10 Hz, 1H) 3.67-3.56 (m, 8H) 3.56-3.48 (m, 2H) 3.13 (t, J = 8 Hz, 2H) 1.80 (s, 3H) 1.47 (s, 3H). |
| 241 | 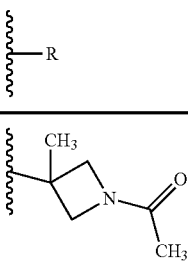 | 1-{3-[4-(2-aminopyrimidin-5-yl)-2-(morpholin-4-yl)-5,6-dihydro-7H-pyrrolo[2,3-d]pyrimidin-7-yl]azetidin-1-yl}-2-hydroxy-2-methylpropan-1-one | 441.1 | ¹H NMR (400 MHz, CDCl₃) δ 8.77 (s, 2H) 5.16 (s, 2H) 4.82-4.79 (m, 1H) 4.56-4.52 (m, 2H) 4.34-4.26 (m, 2H) 3.78-3.61 (m, 10H) 3.47 (s, 1 H) 3.15-3.11 (m, 2H) 1.36 (s, 6H). |
| 242 | 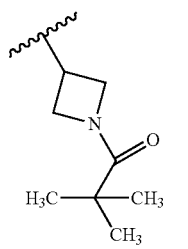 | 1-{3-[4-(2-aminopyrimidin-5-yl)-2-(morpholin-4-yl)-5,6-dihydro-7H-pyrrolo[2,3-d]pyrimidin-7-yl]-3-methylazetidin-1-yl}-2-hydroxy-2-methylpropan-1-one | 455.1 | ¹H NMR (400 MHz, Methanol-d₄) δ 8.81 (s, 2H) 4.65-4.63 (m, 1H) 4.47-4.39 (m, 2H) 3.92-3.90 (m, 1H) 3.77-3.73 (m, 8H) 3.64-3.58 (m, 2H) 3.20-3.16 (m, 2H) 1.56 (s, 3H), 1.42 (s, 3H) 1.39 (s, 3H). |
| 243 | 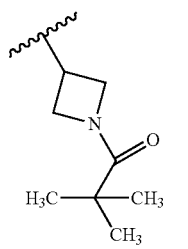 | 2-amino-1-{3-[4-(2-aminopyrimidin-5-yl)-2-(morpholin-4-yl)-5,6-dihydro-7H-pyrrolo[2,3-d]pyrimidin-7-yl]-3-methylazetidin-1-yl}-2-methylpropan-1-one | 454.2 | ¹H NMR (400 MHz, D₂O) δ 8.69 (s, 2H) 4.93 (d, J = 9.0 Hz, 1H) 4.53 (t, J = 0.54 Hz, 2H) 4.07 (d, J = 10.2 Hz, 1H) 3.73-3.96 (m, 10H) 3.10 (t, J = 7.7 Hz, 2H) 1.52-1.70 (m, 9H). |
| 244 | 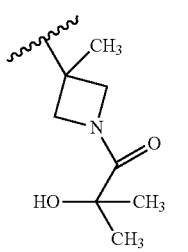 | N-(2-{3-[4-(2-aminopyrimidin-5-yl)-2-(morpholin-4-yl)-5,6-dihydro-7H-pyrrolo[2,3-d]pyrimidin-7-yl]azetidin-1-yl}-2-oxoethyl)propanamide | 489.9 [M + 23] | ¹H NMR (400 MHz, DMSO-d₆) δ 8.96 (s, 2H) 8.00 (s, 1H) 4.78-4.38 (m, 1H) 4.36-4.16 (m, 2H) 4.15-4.18 (m, 2H) 3.67-3.65 (m, 4H) 3.60-3.51 (m, 8H) 3.10 (t, J = 8.4 Hz, 2H) 2.14 (t, J = 8 Hz, 2H) 0.98 (t, J = 7.6 Hz, 3H). |

TABLE 2-continued

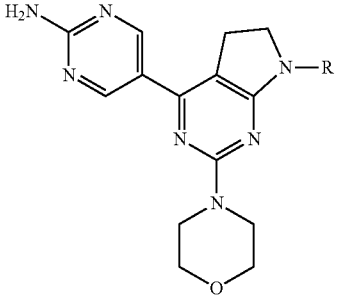

| Example No. | R | IUPAC Name | LRMS m/z [M + H]⁺ | ¹H NMR or LCMS retention time and method |
|---|---|---|---|---|
| 245 | 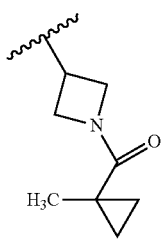 [SMILES: *C1CN(C(=O)C2(C)CC2)C1] | {3-[4-(2-aminopyrimidin-5-yl)-2-(morpholin-4-yl)-5,6-dihydro-7H-pyrrolo[2,3-d]pyrimidin-7-yl]azetidin-1-yl}(1-methylcyclopropyl)methanone | 437.1 | ¹H NMR (400 MHz, CDCl₃) δ 8.77 (s, 2H) 5.19 (s, 2H) 4.81-4.78 (m, 1H) 4.42-4.30 (m, 4H) 3.70-3.63 (m, 10H) 3.14-3.10 (m, 2H) 1.25 (s, 3H) 1.03-1.01 (m, 2H) 0.48-0.45 (m, 2H). |
| 246 |  | {3-[4-(2-aminopyrimidin-5-yl)-2-(morpholin-4-yl)-5,6-dihydro-7H-pyrrolo[2,3-d]pyrimidin-7-yl]-3-methylazetidin-1-yl}(1-methylcyclopropyl)methanone | 451.1 | ¹H NMR (400 MHz, Methanol-d₄) δ 8.82 (s, 2H) 4.65-4.63 (m, 1H) 4.50-4.25 (m, 2H) 4.00-3.80 (m, 1H) 3.77-3.73 (m, 8H) 3.65-3.61 (m, 2H) 3.21-3.17 (m, 2H) 1.58 (s, 3H) 1.35 (s, 3H) 1.05-1.03 (m, 2H) 0.62-0.60 (m, 2H). |
| 247 | 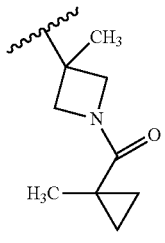 [SMILES: *C1(C)CN(C(=O)C2(C)CC2)C1] | methyl 3-[4-(2-aminopyrimidin-5-yl)-2-(morpholin-4-yl)-5,6-dihydro-7H-pyrrolo[2,3-d]pyrimidin-7-yl]-3-methylazetidine-1-carboxylate | 427.2 | ¹H NMR (400 MHz, DMSO-d₆) δ 8.73 (s, 2H) 7.04 (s, 2H) 4.28 (br s, 2H) 3.79 (br s, 2H) 3.65-3.56 (m, 11H) 3.54-3.49 (m, 2H) 3.13-3.09 (m, 2H) 1.45 (s, 3H). |
| 248 |  | tert-butyl 3-[4-(2-aminopyrimidin-5-yl)-2-(morpholin-4-yl)-5,6-dihydro-7H-pyrrolo[2,3-d]pyrimidin-7-yl]azetidine-1-carboxylate | 455.2 | ¹H NMR (400 MHz, CDCl₃) δ ppm 8.85 (s, 2H) 5.24 (s, 2H) 4.86 (t, J = 6.2 Hz, 1H) 4.22-4.15 (m, 4H) 3.78-3.70 (m, 10H) 3.19 (t, J = 8.2 Hz, 2H) 1.46 (s, 9H). |
| 249 | 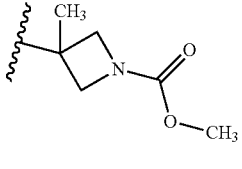 | tert-butyl 3-[4-(2-aminopyrimidin-5-yl)-2-(morpholin-4-yl)-5,6-dihydro-7H-pyrrolo[2,3-d]pyrimidin-7-yl]-3-methylazetidine-1-carboxylate | 469.0 | ¹H NMR (400 MHz, DMSO-d₆) δ 8.73 (s, 2H) 7.00 (s, 2H) 4.19 (d, J = 8.8 Hz, 2H) 3.71 (d, J = 8.4 Hz, 2H) 3.69-3.56 (m, 8H) 3.50-3.48 (m, 2H) 3.10 (t, J = 7.8 Hz, 2H) 1.43 (s, 3H) 1.39 (s, 9H). |

TABLE 2-continued

| Example No. | R | IUPAC Name | LRMS m/z [M + H]⁺ | ¹H NMR or LCMS retention time and method |
|---|---|---|---|---|
| 250 | 3-methyl-3-(N-methylcarbamoyl)azetidin-1-yl (with CH₃, HN-CH₃) | 3-[4-(2-aminopyrimidin-5-yl)-2-(morpholin-4-yl)-5,6-dihydro-7H-pyrrolo[2,3-d]pyrimidin-7-yl]-N,3-dimethylazetidine-1-carboxamide | 426.1 | ¹H NMR (400 MHz, DMSO-d₆) δ 8.73 (s, 2H), 7.03 (s, 2H), 6.33 (s, 1H), 4.10 (d, J = 7.6 Hz, 2H), 3.70-3.59 (m, 11H), 3.11 (t, J = 7.6 Hz, 3H), 2.55-2.53 (m, 3H), 1.44 (s, 3H). ¹H NMR (400 MHz, DMSO-d₆ + D₂O) δ 8.73 (s, 2H) 4.12 (d, J = 8.4 Hz, 2H) 3.69-3.63 (m, 10H) 3.49 (t, J = 7.8 Hz, 2H) 3.10 (t, J = 8.0 Hz, 2H) 2.54 (s, 3H) 1.43 (s, 3H). |
| 251 | 1-(cyclobutylsulfonyl)azetidin-3-yl | 5-{7-[1-(cyclobutylsulfonyl)azetidin-3-yl]-2-(morpholin-4-yl)-6,7-dihydro-5H-pyrrolo[2,3-d]pyrimidin-4-yl}pyrimidin-2-amine | 473.0 | ¹H NMR (400 MHz, DMSO-d₆) δ 8.75 (s, 2H) 7.04 (s, 2H) 4.89-4.82 (m, 1H) 4.21-4.14 (m, 3H) 3.99 (t, J = 8 Hz, 2H) 4.01-3.97 (m, 10H) 3.17 (t, J = 8 Hz, 2H) 2.34-2.26 (m, 4H) 2.01-1.98 (m, 2H). |
| 252 | 1-(azetidin-1-ylsulfonyl)azetidin-3-yl | 5-{7-[1-(azetidin-1-ylsulfonyl)azetidin-3-yl]-2-(morpholin-4-yl)-6,7-dihydro-5H-pyrrolo[2,3-d]pyrimidin-4-yl}pyrimidin-2-amine | 474.2 | ¹H NMR (400 MHz, DMSO-d₆) δ 8.75 (s, 2H) 7.03 (s, 2H) 4.86-4.84 (m, 1H) 4.15-4.13 (m, 2H) 4.01-3.99 (m, 2H) 3.87-3.83 (m, 4H) 3.72-3.64 (m, 10H) 3.18-3.16 (m, 2H) 2.21-2.18 (m, 2H). |
| 253 | (3S)-3-methylpyrrolidin-3-yl | 5-{7-[(3S)-3-methylpyrrolidin-3-yl]-2-(morpholin-4-yl)-6,7-dihydro-5H-pyrrolo[2,3-d]pyrimidin-4-yl}pyrimidin-2-amine hydrochloride | 383.0 | ¹H NMR (400 MHz, D₂O) δ 8.60-8.57 (m, 2H) 4.10 (d, J = 12.4 Hz, 1H) 3.88-3.70 (m, 10H) 3.54 (d, J = 12.5 Hz, 1H) 3.41 (t, J = 7.4 Hz, 2H) 3.03-2.98 (m, 2H) 2.63-2.55 (m, 1H) 2.24-2.17 (m, 1H) 1.47 (s, 3H). |
| 254 | (3R,4S)-4-fluoropyrrolidin-3-yl | 5-{7-[(3R,4S)-4-fluoropyrrolidin-3-yl]-2-(morpholin-4-yl)-6,7-dihydro-5H-pyrrolo[2,3-d]pyrimidin-4-yl}pyrimidin-2-amine hydrochloride | 387.1 | ¹H NMR (400 MHz, D₂O) δ 8.56 (s, 2H) 5.65-5.52 (m, 1H) 5.09-4.96 (m, 1H) 4.02-3.97 (m, 2H) 3.80-3.61 (m, 12H) 3.14-3.09 (m, 2H). |

TABLE 2-continued

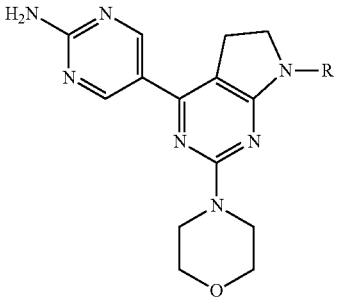

| Example No. | —R | IUPAC Name | LRMS m/z [M + H]+ | 1H NMR or LCMS retention time and method |
|---|---|---|---|---|
| 255 | 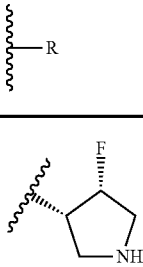 | 5-{7-[(3S,4R)-4-fluoropyrrolidin-3-yl]-2-(morpholin-4-yl)-6,7-dihydro-5H-pyrrolo[2,3-d]pyrimidin-4-yl}pyrimidin-2-amine hydrochloride | 387.0 | 1H NMR (400 MHz, D2O) δ 8.60 (s, 2H), 5.58 (m, 1H), 5.06-4.96 (m, 1H), 4.01-3.96 (m, 2H), 3.83-3.64 (m, 12H), 3.13-3.08 (m, 2H). |
| 256 | 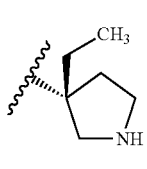 | 5-{7-[(3R)-3-ethylpyrrolidin-3-yl]-2-(morpholin-4-yl)-6,7-dihydro-5H-pyrrolo[2,3-d]pyrimidin-4-yl}pyrimidin-2-amine hydrochloride | 397.1 | 1H NMR (400 MHz, D2O) δ 8.57 (s, 2H), 4.14 (d, J = 12.8 Hz, 1H), 3.93-3.89 (m, 2H), 3.77-3.65 (m, 8H), 3.51 (d, J = 12.8 Hz, 1H), 3.45-3.35 (m, 2H), 3.02 (t, J = 8 Hz, 2H), 2.67-2.61 (m, 1H), 2.26-2.16 (m, 2H), 1.79-1.71 (m, 1H), 0.84 (t, J = 7.4 Hz, 3H). |
| 257 | 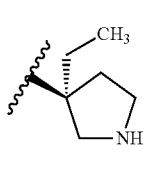 [SMILES: *[C@@]1(CC)CCNC1] | 5-{7-[(3S)-3-ethylpyrrolidin-3-yl)-2-(morpholin-4-yl)-6,7-dihydro-5H-pyrrolo[2,3-d]pyrimidin-4-yl}pyrimidin-2-amine hydrochloride | 397.1 | 1H NMR (400 MHz, D2O) δ 8.59 (s, 2H), 4.14 (d, J = 12.8 Hz, 1H), 3.93-3.89 (m, 2H), 3.77-3.65 (m, 8H), 3.51 (d, J = 13.2 Hz, 1H), 3.45-3.35 (m, 2H), 3.05-3.00 (m, 2H), 2.65-2.60 (m, 1H), 2.26-2.16 (m, 2H), 1.79-1.71 (m, 1H), 0.84 (t, J = 7.4 Hz, 3H). |
| 258 | 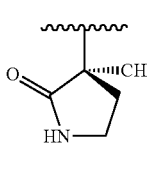 | (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-2-one | 396.9 | retention time = 1.03 min; Column: Waters CSH C18, 4.6 × 50 MM 3.5 μm, 10 mM NH4OAc in water with 2% acetonitrile at 2.5 mL/min. |
| 259 | 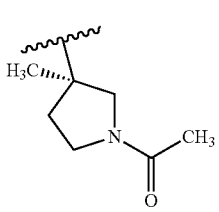 [SMILES: *[C@]1(C)CCN(C(C)=O)C1] | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}ethanone | 425.0 | 1H NMR (400 MHz, CDCl3) δ 8.83 (s, 2H), 5.26 (s, 2H), 4.08-3.88 (m, 2H), 3.83-3.77 (m, 8H), 3.68-3.52 (m, 4H), 3.11 (t, J = 4.4 Hz, 2H), 2.69-2.34 (m, 1H), 2.26-2.04 (m, 4H), 1.37 (d, J = 2.4 Hz, 3H). |

TABLE 2-continued

| Example No. | R | IUPAC Name | LRMS m/z [M + H]+ | 1H NMR or LCMS retention time and method |
|---|---|---|---|---|
| 260 | (3S)-3-methyl-pyrrolidine with N-propanoyl | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}propan-1-one | 439.1 | 1H NMR (400 MHz, DMSO-d6) δ 8.79 (s, 2H), 4.21-4.19 (m, 1H), 4.00-3.95 (m, 2H), 3.90-3.70 (m, 8H), 3.63-3.55 (m, 2H), 3.50-3.40 (m, 1H), 3.17-3.05 (m, 2H), 2.62-2.53 (m, 1H), 2.50-2.28 (m, 2H), 2.25-2.10 (m, 1H), 1.39 (s, 3H), 1.13 (d, J = 7.6 Hz, 3H). |
| 261 | (3R)-3-methyl-pyrrolidine with N-propanoyl | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}propan-1-one | 439.1 | 1H NMR (400 MHz, DMSO-d6) δ 8.79 (s, 2H), 4.21-4.19 (m, 1H), 4.00-3.95 (m, 2H), 3.90-3.70 (m, 8H), 3.63-3.55 (m, 2H), 3.50-3.40 (m, 1H), 3.17-3.05 (m, 2H), 2.62-2.53 (m, 1H), 2.50-2.28 (m, 2H), 2.25-2.10 (m, 1H), 1.39 (s, 3H), 1.13 (d, J = 7.6 Hz, 3H). |
| 262 | (3S)-3-methyl-pyrrolidine with N-(2-methylpropanoyl) | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one | 453.2 | 1H NMR (400 MHz, DMSO-d6) δ 8.74-8.71 (m, 2H), 6.98-6.94 (m, 2H), 4.09 (d, J = 10.5 Hz, 0.5H), 3.88 (d, J = 10.5 Hz, 0.5H), 3.78-3.58 (m, 10.5H), 3.56-3.42 (m, 1.5H), 3.45-3.37 (m, 0.5H), 3.14-3.06 (m, 2H), 2.70-2.57 (m, 1H), 2.36-2.24 (m, 0.5H), 2.20-2.11 (m, 0.5H), 2.08-2.00 (m, 0.5H), 1.89-1.82 (m, 1H), 1.31-1.26 (m, 3H), 1.05-0.95 (m, 6H). |
| 263 | (3R)-3-methyl-pyrrolidine with N-(2-methylpropanoyl) | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one | 453.2 | 1H NMR (400 MHz, DMSO-d6) δ 8.78 (d, J = 2.45 Hz, 2H) 3.97-4.38 (m, 1H) 3.84-3.97 (m, 1H) 3.74 (s, 10H) 3.51-3.68 (m, 2H) 3.03-3.21 (m, 2H) 2.68-2.86 (m, 1H) 2.38-2.68 (m, 1H) 2.03-2.28 (m, 1H) 1.38 (d, J = 4.5 Hz, 3H) 0.90-1.20 (m, 6H). |

TABLE 2-continued

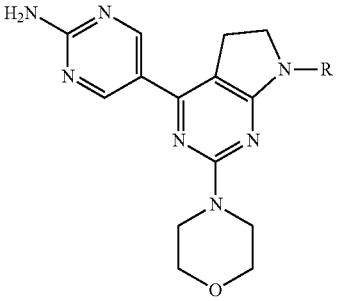

| Example No. | R | IUPAC Name | LRMS m/z [M + H]⁺ | ¹H NMR or LCMS retention time and method |
|---|---|---|---|---|
| 264 | 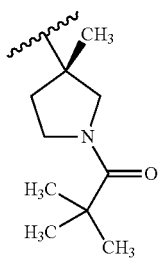 [SMILES: *[C@@]1(C)CCN(C(=O)C(C)(C)C)C1] | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethylpropan-1-one | 467.1 | ¹H NMR (400 MHz, DMSO-d₆) δ 8.72 (s, 2H), 7.02 (s, 2H), 4.28-4.23 (m, 1H), 4.07-4.04 (m, 1H), 3.71-3.64 (m, 10H), 3.54-3.48 (m, 2H), 3.12-3.08 (m, 2H), 2.16-2.14 (m, 1H), 1.96-1.94 (m, 1H), 1.25 (s, 3H), 1.16 (s, 9H). |
| 265 | 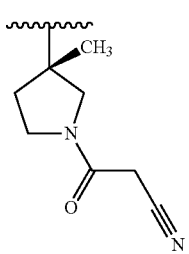 [SMILES: *[C@@]1(C)CCN(C(=O)CC#N)C1] | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-oxopropanenitrile | 450.2 | ¹H NMR (400 MHz, DMSO-d₆) δ 8.72 (s, 2H), 6.96 (s, 2H), 4.02-3.83 (m, 3H), 3.80-3.77 (m, 1H) 3.71-3.59 (m, 10H), 3.57-3.42 (m, 3H), 3.13-3.05 (m, 2H), 1.89-1.78 (m, 1H) 1.32-1.26 (m, 3H). |
| 266 | 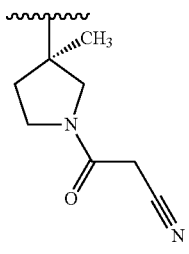 [SMILES: *[C@]1(C)CCN(C(=O)CC#N)C1] | 3-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-oxopropanenitrile | 450.2 | ¹H NMR (400 MHz, DMSO-d₆) δ 8.73 (s, 2H) 6.6 (s, 2H) 4.01 (d, J = 11.0 Hz, 1H) 3.85-3.94 (m, 1H) 3.78-3.85 (m, 2H) 3.74 (d, J = 11.7 Hz, 1H) 3.64-3.70 (m, 9H) 3.48-3.61 (m, 3H) 3.31-3.45 (m, 1H) 3.06-3.13 (m, 2H) 2.53-2.60 (m, 1H) 2.37-2.47 (m, 1H) 2.04-2.21 (m, 1H) 1.36 (s, 3H). |
| 267 | 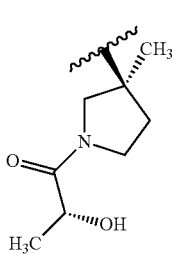 [SMILES: *[C@@]1(C)CCN(C(=O)[C@@H](C)O)C1] | (2R)-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxypropan-1-one | 455.1 | ¹H NMR (400 MHz, D₂O) δ 8.28 (s, 2H), 4.46-4.42 (m, 2H), 3.79 (t, J = 12 Hz, 1H), 3.63-3.54 (m, 8H), 3.50-3.20 (m, 6H), 2.60 (br s, 2H), 2.19-2.15 (m, 1H), 2.00-1.93 (m, 2H), 1.98 (t, J = 5.6 Hz, 3H), 1.08-1.01 (m, 3H). |

TABLE 2-continued

| Example No. | R | IUPAC Name | LRMS m/z [M + H]+ | 1H NMR or LCMS retention time and method |
|---|---|---|---|---|
| 268 | | (2S)-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxypropan-1-one | 455.0 | 1H NMR (400 MHz, D2O) δ 8.32-8.27 (m, 2H), 4.54-4.35 (m, 2H), 3.91 (s, J = 11.2 Hz, 1H), 3.80-3.55 (m, 8H), 3.50-3.30 (m, 6H), 2.62-2.57 (m, 2H), 2.09-2.34 (m, 3H), 1.22-1.14 (m, 3H), 1.04 (d, J = 6 Hz, 3H). |
| 269 | | (2R)-1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxypropan-1-one | 455.1 | 1H NMR (400 MHz, D2O) δ 8.52 (s, 2H), 4.49-4.43 (m, 1H), 4.10-3.40 (m, 14H), 2.95 (t, J = 8 Hz, 2H), 2.60-2.39 (m, 1H), 2.18-2.09 (m, 1H), 1.37 (s, 3H), 1.30-1.17 (m, 3H). |
| 270 | | (2S)-1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxypropan-1-one | 455.1 | 1H NMR (400 MHz, D2O) δ 8.54 (s, 2H), 4.48-4.40 (m, 1H), 4.18-3.36 (m, 14H), 2.94 (t, J = 8 Hz, 2H), 2.59-2.47 (m, 1H), 2.17-2.07 (m, 1H), 1.38 (s, 3H), 1.24-1.20 (m, 3H). |
| 271 | | (2R)-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxy-3-methylbutan-1-one | 483.6 | 1H NMR (400 MHz, 80° C., DMSO-d6) δ 8.74 (s, 2H) 6.62 (br s, 2H) 4.33 (d, J = 6.4 Hz, 1H) 3.94-4.17 (m, 1H) 3.73-3.94 (m, 2H) 3.68 (s, 10H) 3.49-3.61 (m, 2H) 3.38 (br s, 1H) 3.10 (t, J = 8.0 Hz, 2H) 1.99-2.18 (m, 1H) 1.86-1.98 (m, 1H) 1.35 (s, 3H) 0.91 (d, J = 6.7 Hz, 3H) 0.87 (d, J = 6.7 Hz, 3H). |

TABLE 2-continued

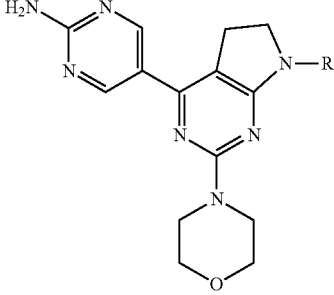

| Example No. | R | IUPAC Name | LRMS m/z [M + H]⁺ | ¹H NMR or LCMS retention time and method |
|---|---|---|---|---|
| 272 | 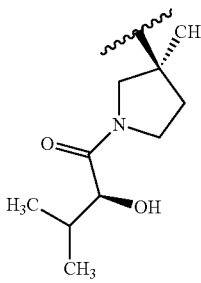 | (2S)-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxy-3-methylbutan-1-one | 483.2 | ¹H NMR (400 MHz, CDCl₃) δ 8.83 (s, 2H), 5.22 (s, 2H), 4.22-4.10 (m, 2H), 3.86-3.53 (m, 13H), 3.18-3.07 (m, 2H), 2.29-2.25 (m, 1H), 2.15-2.08 (m, 1H), 2.07-1.93 (m, 1H), 1.39-1.30 (m, 3H), 1.10-1.07 (m, 3H), 0.90-0.75 (m, 3H). |
| 273* | 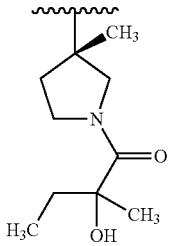 | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxy-2-methylbutan-1-one | 483.2 | ¹H NMR (400 MHz, CDCl₃) δ 8.82 (s, 2H), 5.26 (s, 2H), 4.63-4.51 (m, 1H), 4.31-4.28 (m, 1H), 4.12-4.09 (m, 1H), 3.84-3.48 (m, 11H), 3.20-3.10 (m, 2H), 2.30-2.15 (m, 1H), 2.05-1.95 (m, 1H), 1.78-1.85 (m, 1H), 1.45-1.22 (m, 8H), 0.92-0.75 (m, 3H). |
| 274* | 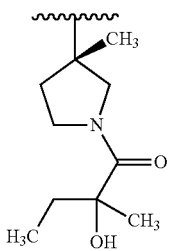 | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxy-2-methylbutan-1-one | 483.2 | ¹H NMR (400 MHz, CDCl₃) δ 8.82 (s, 2H), 5.31 (s, 2H), 4.54-4.46 (m, 1H), 4.28-4.30 (m, 1H), 4.12-4.10 (m, 1H), 3.77-3.52 (m, 11H), 3.15-3.05 (m, 2H), 2.29-2.20 (m, 1H), 2.05-1.84 (m, 1H), 1.78-1.71(m, 1H), 1.45-1.25 (m, 8H), 0.86-0.78 (m, 3H). |
| 275 | 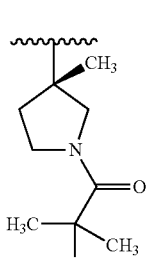 | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-hydroxy-2-methylpropan-1-one | 469.6 | ¹H NMR (400 MHz, 80° C., DMSO-d₆) δ 8.73 (s, 2 H) 6.61 (br s, 2 H) 4.84 (br s, 1 H) 4.06 (br s, 1 H) 3.62-3.75 (m, 10 H) 3.56 (q, J = 8.8 Hz, 2 H) 3.10 (t, J = 8.1 Hz, 2 H) 2.30-2.45 (m, 1 H) 2.02 (br s, 1 H) 1.33 (s, 9 H). |

TABLE 2-continued

| Example No. | R | IUPAC Name | LRMS m/z [M + H]+ | 1H NMR or LCMS retention time and method |
|---|---|---|---|---|
| 276 | (3R)-3-methyl-3-(2-hydroxy-2-methylpropyl) pyrrolidinyl group with H3C and HO-C(CH3)2-CH2- | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-2-ol | 455.2 | 1H NMR (400 MHz, MeOD-d4) δ 8.79 (s, 2 H) 3.55-3.83 (m, 14 H) 3.35 (s, 2 H) 3.12-3.20 (m, 2 H) 2.63-2.73 (m, 1 H) 2.15 (dt, J = 14.0, 7.1 Hz, 1 H) 1.49 (s, 3 H) 1.33 (d, J = 2.6 Hz, 6 H). |
| 277 | (3S)-3-methylpyrrolidinyl with 3-hydroxy-2,2-dimethylpropanoyl | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-hydroxy-2,2-dimethylpropan-1-one | 482.6 | 1H NMR (400 MHz, Methanol-d4) δ 8.79 (s, 2H), 4.42-4.30 (m, 1H), 4.05-3.85 (m, 1H), 3.80-3.65 (m, 8H), 3.60-3.45 (m, 4H), 3.20-3.05 (m, 2H), 2.70-2.50 (m, 1H), 2.35-2.10 (m, 2H), 2.05-1.92 (m, 1H), 1.37 (s, 3H), 1.25-1.15 (m, 6H). |
| 278 | (3S)-3-methylpyrrolidinyl with 2-methoxy-2-methylpropanoyl | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methoxy-2-methylpropan-1-one | 483.6 | 1H NMR (400 MHz, DMSO-d6) δ 8.66 (s, 2 H) 6.90 (s, 2 H) 4.41 (d, J = 11.6 Hz, 0.5 H) 3.94 (d, J = 11.6 Hz, 0.5 H) 3.65-3.83 (m, 1 H) 3.58 (br s, 10 H) 3.27-3.52 (m, 4 H) 2.99-3.07 (m, 3 H) 1.98-2.20 (m, 1 H) 1.91 (br s, 1 H) 1.15-1.30 (m, 9 H). |
| 279 | (3S)-3-methylpyrrolidinyl with methoxyacetyl | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methoxyethanone | 455.5 | 1H NMR (400 MHz, DMSO-d6) δ 8.73 (s, 2 H) 6.62 (br s, 2 H) 3.95-4.05 (m, 3 H) 3.86 (br s, 1 H) 3.68 (s, 9 H) 3.45-3.61 (m, 3 H) 3.29-3.35 (m, 3 H) 3.10 (t, J = 8.0 Hz, 2 H) 2.32-2.43 (m, 1 H) 1.99-2.19 (m, 1 H) 1.34 (s, 3 H). |
| 280 | (3R)-3-methylpyrrolidinyl with methoxyacetyl | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methoxyethanone | 455.2 | 1H NMR (400 MHz, DMSO-d6) δ 8.73 (s, 2 H) 6.61 (br s, 2 H) 3.90-4.09 (m, 3 H) 3.80-3.90 (m, 1 H) 3.64-3.75 (m, 10 H) 3.45-3.60 (m, 3 H) 3.32 (s, 3 H) 3.10 (t, J = 8.13 Hz, 2 H) 1.98-2.22 (m, 1 H) 1.35 (s, 3 H). |

TABLE 2-continued

| Example No. | R | IUPAC Name | LRMS m/z [M + H]+ | 1H NMR or LCMS retention time and method |
|---|---|---|---|---|
| 281 | (3S)-3-methyl-3-amino-1-... pyrrolidine with 3-amino-3-methylbutanoyl group | 3-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-methylbutan-1-one hydrochloride | 482.2 | 1H NMR (400 MHz, D2O) δ 8.58 (s, 2H), 4.15-3.80 (m, 4H), 3.75-3.70 (m, 8H), 3.70-3.40 (m, 2H), 3.10-2.95 (m, 2H), 2.72-2.62 (m, 3H), 2.30-2.20 (m, 1H), 1.45 (d, J = 3.2 Hz, 3H), 1.40-1.30 (m, 6H). |
| 282 | (3R)-pyrrolidine with 2-amino-2-methylpropanoyl | 2-amino-1-{(3R)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-methylpropan-1-one hydrochloride | 454.1 | 1H NMR (400 MHz, Methanol-d4) δ 8.82 (s, 2H), 3.97-3.95 (m, 3H), 3.86-3.82 (m, 11H), 3.22-3.18 (m, 2H), 2.45-2.15 (m, 3H), 1.70 (s, 6H). |
| 283 | (3S)-pyrrolidine with 2-amino-2-methylpropanoyl | 2-amino-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-2-methylpropan-1-one hydrochloride | 454.1 | 1H NMR (400 MHz, Methanol-d4) δ 8.94 (s, 2H), 3.97-3.81 (m, 15H), 3.25-3.19 (m, 2H), 2.45-2.15 (m, 2H), 1.69 (s, 6H). |
| 284 | (3R)-3-ethylpyrrolidine with 2-amino-2-methylpropanoyl | 2-amino-1-{(3R)-3-[4-(2-aminopyrimidin-5-yl)-2-(morpholin-4-yl)-5,6-dihydro-7H-pyrrolo[2,3-d]pyrimidin-7-yl]-3-ethylpyrrolidin-1-yl}-2-methylpropan-1-one hydrochloride | 482.1 | 1H NMR (400 MHz, D2O) δ 8.51 (s, 2H), 4.39-4.11 (m, 1H), 3.94-3.66 (m, 11H), 3.54-3.46 (m, 1H), 3.02-2.97 (m, 2H), 2.70-2.45 (m, 1H), 2.31-1.85 (m, 4H), 1.60-1.51 (m, 6H), 0.85-0.79 (m, 3H). |

TABLE 2-continued

| Example No. | R | IUPAC Name | LRMS m/z [M + H]⁺ | ¹H NMR or LCMS retention time and method |
|---|---|---|---|---|
| 285 | (ethyl-substituted pyrrolidine with 2-amino-2-methylpropanoyl group, 3S) | 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-ethylpyrrolidin-1-yl}-2-methylpropan-1-one hydrochloride | 482.1 | ¹H NMR (400 MHz, D₂O): δ 8.52 (s, 2H), 4.38-4.11 (m, 1H), 3.94-3.66 (m, 11H), 3.54-3.46 (m, 1H), 3.02-2.97 (m, 2H), 2.70-2.46 (m, 1H), 2.29-1.78 (m, 4H), 1.60-1.45 (m, 6H), 0.86-0.79 (m, 3H). |
| 286 | (3R-pyrrolidine with (2R)-valyl group) | (2R)-2-amino-1-{(3R)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-3-methylbutan-1-one hydrochloride | 468.2 | ¹H NMR (400 MHz, Methanol-d4) δ 8.83 (s, 2H), 4.98-4.91 (s, 1H), 4.16-3.71 (m, 15H), 3.25-3.10 (m, 2H), 2.42-2.30 (m, 3H), 1.11 (d, J = 27.6 Hz), 6H. |
| 287 | (3S-pyrrolidine with (2R)-valyl group) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]pyrrolidin-1-yl}-3-methylbutan-1-one hydrochloride | 468.2 | ¹H NMR (400 MHz, Methanol-d₄): δ 8.91-8.88 (m, 2H), 5.10-5.05 (m, 1H), 4.17-3.56 (m, 15H), 3.25-3.10 (m, 2H), 2.41-2.27 (m, 3H), 1.15-1.06 (m, 6H). |
| 288 | (3-methyl-3S-pyrrolidine with (2S)-valyl group) | (2S)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-methylbutan-1-one hydrochloride | 482.2 | ¹H NMR (400 MHz, Methanol-d₄) δ 8.53 (s, 2H), 4.18-3.92 (m, 4H), 3.89-3.58 (m, 11H), 3.11-2.95 (m, 2H), 2.69-2.45 (m, 1H), 2.29-2.18 (m, 2H), 1.45 (s, 3H), 1.04-0.91 (m, 6H). |

TABLE 2-continued

| Example No. | R | IUPAC Name | LRMS m/z [M + H]+ | 1H NMR or LCMS retention time and method |
|---|---|---|---|---|
| 289 | (3R)-3-methyl-3-pyrrolidinyl with N-C(O)-C(CH3)2-NH2 | 2-amino-1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-1-one hydrochloride | 468.2 | 1H NMR (400 MHz, Methanol-d4) δ 8.88 (s, 2H), 4.70-4.04 (m, 2H), 4.02-3.77 (m, 11H), 3.75-3.59 (m, 1H), 3.18 (s, 2H), 2.80-2.53 (m, 1H), 2.40-2.24 (m, 1H), 1.70 (s, 6H), 1.57 (s, 3H). |
| 290* | (3S)-3-methylpyrrolidinyl with N-C(O)-C(CH3)(NH2)-CH2CH3 | 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylbutan-1-one hydrochloride | 482.2 | 1H NMR (400 MHz, D2O) δ 8.58 (s, 2H), 4.37-4.25 (m, 1H), 4.08-3.98 (m, 2H), 3.82-3.75 (m, 9H), 3.57-3.51 (m, 1H), 3.22-2.98 (m, 2H), 2.67-2.35 (m, 1H), 2.26-2.01 (m, 2H), 1.86-1.78 (m, 1H), 1.61 (d, J = 32.4 Hz, 3H), 1.45 (s, 3H), 1.24-1.20 (m, 1H), 0.94-0.85 (m, 3H). |
| 291* | (3S)-3-methylpyrrolidinyl with N-C(O)-C(CH3)(NH2)-CH2CH3 | 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylbutan-1-one hydrochloride | 482.2 | 1H NMR (400 MHz, D2O) δ 8.62 (s, 2H), 4.57-4.05 (m, 1H), 4.03-3.75 (m, 12H), 3.62-3.56 (m, 1H), 3.07-3.01 (m, 2H), 2.69-2.52 (m, 1H), 2.27-2.15 (m, 1H), 2.06-1.84 (m, 2H), 1.68 (s, 3H), 1.51 (d, J = 7.6 Hz, 3H), 0.97-0.94 (m, 1H), 0.82-0.78 (m, 2H). |
| 292 | (3S)-3-methylpyrrolidinyl with N-C(O)-CH(NH2)-CH2-CH2F | (2S)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-fluoropropan-1-one hydrochloride | 472.1 | 1H NMR (400 MHz, Methanol-d4): δ 8.82 (s, 2H), 4.25-3.92 (m, 6H), 3.90-3.73 (m, 12H), 3.33-3.18 (m, 2H), 2.81-2.75 (m, 1H), 2.70-2.51 (m, 1H), 2.49-2.20 (m, 2H), 2.15-1.95 (m, 1H), 1.58 (s, 3H). |

TABLE 2-continued

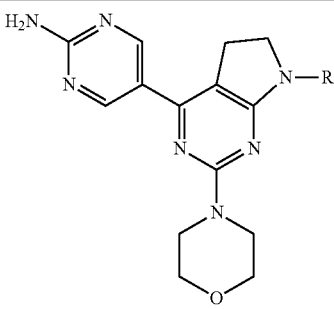

| Example No. | R | IUPAC Name | LRMS m/z [M + H]+ | 1H NMR or LCMS retention time and method |
|---|---|---|---|---|
| 293 | (structure: 3-methyl-3-pyrrolidinyl with N-acyl group bearing CH2F and NH2, (2R)/(3S)) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-fluoropropan-1-one hydrochloride | 494.2 [M + 23] | 1H NMR (400 MHz, Methanol-d4) δ 8.86 (s, 2H), 4.75-4.40 (m, 2H), 4.22-3.75 (m, 15H), 3.30-3.16 (m, 2H), 2.81-2.69 (m, 1H), 2.34-2.03 (m, 3H), 1.59-1.56 (m, 3H). |
| 294* | (structure with additional CH3 on α-carbon) | 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-fluoro-2-methylpropan-1-one hydrochloride | 486.2 | 1H NMR (400 MHz, Methanol-d4) δ 8.78 (s, 2H), 4.86-4.51 (m, 2H), 4.39-4.25 (m, 1H), 3.93-3.80 (m, 2H), 3.80-3.75 (m, 8H), 3.60-3.57 (m, 2H), 3.15-3.11 (m, 2H), 2.65-2.10 (m, 1H), 2.40-2.30 (m, 1H), 2.05-1.95 (m, 1H), 1.37-1.30 (m, 6H). |
| 295* | (structure with additional CH3 on α-carbon, other isomer) | 2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-fluoro-2-methylpropan-1-one hydrochloride | 486.2 | 1H NMR (400 MHz, Methanol-d4) δ 8.78 (s, 2H), 4.60-4.51 (m, 2H), 4.38-4.37 (m, 1H), 4.27-3.10 (m, 2H), 4.05-3.95 (m, 2H), 3.80-3.70 (m, 8H), 3.65-3.50 (m, 3H), 2.65-2.35 (m, 1H), 2.20-2.05 (m, 1H), 1.38-1.29 (m, 6H). |
| 296 | (structure with cyclopropyl and NH2 on α-carbon) | (2S)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropylethanone hydrochloride | 480.2 | 1H NMR (400 MHz, D2O) δ 8.59 (s, 2H), 4.42-4.39 (m, 1H), 4.01-3.92 (m, 4H), 3.90-3.85 (m, 1H), 3.80-3.75 (m, 4H), 3.68-3.59 (m, 4H), 3.58-3.56 (m, 1H), 3.02 (s, 2H), 2.56-2.52 (m, 1H), 2.28-2.16 (m, 1H), 1.45 (d, J = 3.2 Hz, 3H), 1.21-1.19 (m, 1H), 0.77-0.75 (m, 1H), 0.72-0.65 (m, 1H), 0.49-0.32 (m, 2H). |

TABLE 2-continued

| Example No. | R | IUPAC Name | LRMS m/z [M + H]+ | 1H NMR or LCMS retention time and method |
|---|---|---|---|---|
| 297 | (structure with CH3, NH2, cyclopropyl) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropylethanone hydrochloride | 480.3 | 1H NMR (400 MHz, Methanol-d4) δ 8.78 (s, 2H), 4.23-4.21 (m, 1H), 4.20-4.18 (m, 1H), 3.88-3.85 (m, 1H), 3.74-3.71 (m, 9H), 3.69-3.68 (m, 1H), 3.62-3.59 (m, 2H), 3.30-3.14 (m, 2H), 2.52-2.49 (m, 1H), 2.19-2.17 (m, 1H), 1.41 (d, J = 8 Hz, 3H), 1.27-1.24 (m, 1H), 0.83-0.71 (m, 3H), 0.49-0.47 (m, 1H). |
| 298 | (structure with CH3, H3C-NH) | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(methylamino)ethanone | 454.1 | 1H NMR (400 MHz, D2O) δ 8.53 (s, 2H), 4.00-3.90 (m, 6H), 3.85-3.65 (m, 8H), 3.60-3.45 (m, 2H), 3.05-2.95 (m, 2H), 2.70 (s, 3H), 2.65-2.15 (m, 2H), 1.42-1.40 (m, 3H). |
| 299 | (structure with CH3, N(CH3)2) | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(dimethylamino)ethanone | 468.1 | 1H NMR (400 MHz, D2O) δ 8.51-8.48 (m, 2H), 3.83-3.80 (m, 1H), 3.76-3.66 (m, 6H), 3.56-3.36 (m, 9H), 2.87-2.83 (m, 2H), 2.65 (s, 3H), 2.51 (s, 3H), 2.29-2.13 (m, 2H), 1.19 (s, 3H). |
| 300 | (structure with CH3, N(CH3)2) | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(dimethylamino)ethanone | 468.2 | 1H NMR (400 MHz, Methanol-d4) δ 8.79 (s, 2H), 4.18-4.08 (m, 1H), 4.01-3.91 (m, 1H), 3.81-3.67 (m, 10H), 3.65-3.43 (m, 3H), 3.25-3.21 (m, 1H), 3.15-3.10 (m, 2H), 2.62-2.40 (m, 1H), 2.37 (s, 3H), 2.32 (s, 3H), 2.24-2.07 (m, 1H), 1.38 (s, 3H). |

TABLE 2-continued

| Example No. | R | IUPAC Name | LRMS m/z [M + H]⁺ | ¹H NMR or LCMS retention time and method |
|---|---|---|---|---|
| 301 | | (2R)-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(dimethylamino)propan-1-one | 482.2 | ¹H NMR (400 MHz, Methanol-d₄): δ 8.80 (s, 2H), 4.61-4.33 (m, 2H), 4.09-3.95 (m, 2H), 3.90-3.50 (m, 12H), 3.15 (t, J = 7 Hz, 2H), 2.70-2.57 (m, 4H), 2.53 (s, 3H), 2.25-2.10 (m, 1H), 1.43 (s, 6H). |
| 302** | | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(dimethylamino)propan-1-one | 482.3 | ¹H NMR (400 MHz, Methanol-d₄) δ 8.79 (s, 2H), 4.58-4.10 (m, 1H), 4.05-3.50 (m 14H), 3.20-3.09 (m, 2H), 2.75 (s, 3H), 2.71-2.47 (m, 4H), 2.30-2.08 (m, 1H), 1.54-1.27 (m, 6H). |
| 303 | | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-2-(methylamino)propan-1-one hydrochloride | 482.3 | ¹H NMR (400 MHz, 80° C., DMSO-d₆) δ 8.73 (s, 2H), 6.60 (br s, 2H), 4.63-4.26 (m, 1H), 3.98 (d, J = 11.9 Hz, 1H), 3.73-3.47 (m, 12H), 3.10 (t, J = 8.1 Hz, 2H), 2.39-2.28 (m, 1H), 2.14 (s, 3H), 2.06-1.97 (m, 1H), 1.59-1.46 (m, 1H), 1.31 (s, 3H), 1.24 (s, 3H), 1.23 (s, 3H). |
| 304 | | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(dimethylamino)-2-methylpropan-1-one | 496.2 | ¹H NMR (400 MHz, Methanol-d₄) δ 8.78 (s, 2H), 4.61-4.47 (m, 2H), 3.85-3.70 (m, 8H), 3.61-3.51 (m, 3H), 3.15-3.09 (m, 2H), 2.33-2.30 (m, 2H), 2.21-2.14 (m, 4H), 2.01-1.99 (m, 1H), 1.37-1.35 (m, 3H), 1.23-1.21 (m, 6H). |

TABLE 2-continued

| Example No. | R | IUPAC Name | LRMS m/z [M + H]⁺ | ¹H NMR or LCMS retention time and method |
|---|---|---|---|---|
| 305 | (pyrrolidine with 3S-CH₃, N-C(=O)-C(CH₃)₂-CH₂-NH₂) | 3-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethylpropan-1-one hydrochloride | 482.2 | ¹H NMR (400 MHz, Methanol-d₄) δ 8.78 (s, 2H), 4.35-4.25 (m, 1H), 4.15-3.92 (m, 4H), 3.78-3.71 (m, 8H), 3.65-3.59 (m, 1H), 3.29-3.23 (m, 2H), 3.15-3.11 (m, 2H), 2.72-2.46 (m, 1H), 3.32-2.18 (m, 1H), 1.43 (s, 3H), 1.39-1.32 (m, 6H). |
| 306 | (pyrrolidine with 3S-CH₃, N-C(=O)-C(CH₃)₂-CH₂-NH-CH₃) | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethyl-3-(methylamino)propan-1-one hydrochloride | 496.3 | ¹H NMR (400 MHz, Methanol-d₄) δ 8.88 (s, 2H), 4.25-4.22 (m, 1H), 4.07-3.95 (m, 4H), 3.95-3.80 (m, 9H), 3.65-3.55 (m, 1H), 3.16-3.09 (m, 4H), 2.49-2.48 (m, 3H), 2.45-2.20 (m, 1H), 1.55-1.54 (m, 3H), 1.32-1.29 (m, 6H). |
| 307 | (pyrrolidine with 3S-CH₃, N-C(=O)-C(CH₃)(F)(F) with CH₃) | 3-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-difluoropropan-1-one hydrochloride | 490.2 | ¹H NMR (400 MHz, Methanol-d₄) δ 8.90 (s, 2H), 4.23-3.92 (m, 4H), 3.90-3.61 (m, 12H), 3.25-3.12 (m, 2H), 2.81-2.52 (m, 1H), 2.40-2.19 (m, 1H), 1.56 (d, J = 11.6 Hz, 3H). |
| 308 | (pyrrolidine with 3R-CH₃, N-C(=O)-CH₂-CF₃) | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoropropan-1-one | 493.2 | ¹H NMR (400 MHz, Methanol-d₄) δ 8.78 (s, 2H), 4.22-4.14 (m, 1H), 4.10-3.92 (m, 1H), 3.81-3.72 (m, 9H), 3.67-3.35 (m, 5H), 3.18-3.09 (m, 2H), 2.66-2.39 (m, 1H), 2.23-2.12 (m, 1H), 1.39 (s, 3H). |
| 309 | (pyrrolidine with 3S-CH₃, N-C(=O)-CH₂-CF₃) | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoropropan-1-one | 493.2 | ¹H NMR (400 MHz, Methanol-d₄) δ 8.78 (s, 2H), 4.22-4.14 (m, 1H), 4.10-3.92 (m, 1H), 3.81-3.72 (m, 9H), 3.70-3.52 (m, 2H), 3.50-3.35 (m, 3H), 3.18-3.09 (m, 2H), 2.70-2.41 (m, 1H), 2.25-2.15 (m, 1H), 1.39 (s, 3H). |

TABLE 2-continued

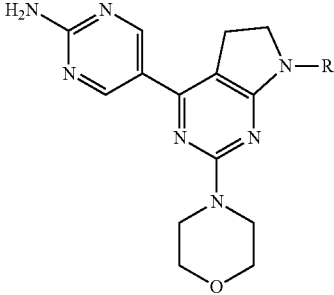

| Example No. | R | IUPAC Name | LRMS m/z [M + H]⁺ | ¹H NMR or LCMS retention time and method |
|---|---|---|---|---|
| 310 | (CH₃, H₂N, CH₃, CH₃ substituent) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3-methylbutan-1-one hydrochloride | 482.3 | ¹H NMR (400 MHz, DMSO-d₆) δ 8.77-8.69 (m, 2H), 7.00-6.92 (m, 2H), 4.03-3.94 (m, 1H), 3.65 (s, 13H), 3.19-3.04 (m, 3H), 2.60-2.23 (m, 1H, overlapped with DMSO), 2.16-1.97 (m, 1H), 1.82-1.60 (m, 3H), 1.32-1.25 (m, 3H), 0.92-0.79 (m, 6H). |
| 311 | (CH₃, F, F, F, CH₃, NH₂ substituent) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoro-2-methylpropan-1-one hydrochloride | 522.3 | ¹H NMR (400 MHz, CDCl₃) δ 8.82 (s, 2H), 5.24 (s, 2H), 4.77-4.24 (m, 1H), 4.09-4.06 (m, 1H), 3.77-3.67 (m, 8H), 3.64-3.50 (m, 4H), 3.11-3.09 (m, 2H), 2.27-2.06 (m, 2H), 1.77-1.66 (m, 2H), 1.59 (s, 3H), 1.37-1.25 (m, 3H). |
| 312 | (CH₃, F, F, F, CH₃, NH₂ substituent) | (2S)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoro-2-methylpropan-1-one hydrochloride | 522.3 | ¹H NMR (400 MHz, CDCl₃) δ 8.83 (s, 2H), 5.25 (s, 2H), 4.60-4.57-4.10 (m, 1H), 3.88-3.77 (m, 1H), 3.75-3.72 (m, 8H), 3.59-3.58 (m, 4H), 3.12-3.10 (m, 2H), 2.31-2.03 (m, 2H), 1.82-1.76 (m, 2H), 1.59 (s, 3H), 1.38-1.26 (m, 3H). |
| 313 | (CH₃, F, F, F, NH₂ substituent) | (2R)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoropropan-1-one hydrochloride | 508.2 | ¹H NMR (400 MHz, D₂O) δ 8.56 (s, 2H), 5.25-5.22 (m, 1H), 4.42-3.63 (m, 14 H), 3.00-2.97 (m, 2H), 2.58-2.54 (m, 1H), 2.28-2.21 (m, 1H), 1.43 (d, J = 11.6 Hz, 3H). |

TABLE 2-continued

| Example No. | R | IUPAC Name | LRMS m/z [M + H]+ | 1H NMR or LCMS retention time and method |
|---|---|---|---|---|
| 314 | (pyrrolidine with CH3 at 3-position, N-acyl with C(=O)-CH(NH2)-CH2-CF3... actually C(=O) connected to CH(NH2) with CF3) | (2S)-2-amino-1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-3,3,3-trifluoropropan-1-one hydrochloride | 508.2 | 1H NMR (400 MHz, D2O) δ 8.56 (s, 2H), 5.25-5.18 (m, 1H), 4.4-3.92 (m, 1H), 3.86-3.56 (m, 13H), 3.01-2.99 (m, 2H), 2.76-2.55 (m, 1H), 2.23-2.20 (m, 1H), 1.45 (d, J = 5.6 Hz, 3H). |
| 315* | (pyrrolidine with CH3, N-C(=O)-CH(CH3)-C(=O)-NH2) | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-3-oxopropanamide | 482.3 | 1H NMR (400 MHz, Methanol-d4) δ 8.78-8.77 (m, 2H), 4.14-4.09 (m, 2H), 3.99-3.51 (m, 13H), 3.12-3.11 (m, 2H), 2.71-2.69-2.37 (m, 1H), 2.17-1.89 (m, 1H), 1.40-1.28 (m, 6H). |
| 316* | (pyrrolidine with CH3, N-C(=O)-CH(CH3)-C(=O)-NH2) | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-3-oxopropanamide | 482.3 | 1H NMR (400 MHz, Methanol-d4) δ 8.77 (s, 2H), 3.98-3.70 (m, 2H), 3.62-3.55 (m, 13H), 3.13-3.11 (m, 2H), 2.60-2.48 (m, 1H), 2.20-2.12 (m, 1H), 1.41-1.28 (m, 6H). |
| 317** | (pyrrolidine with CH3, N-C(=O)-CH(CH3)-C(=O)-NH2) | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-3-oxopropanamide | 482.3 | 1H NMR (400 MHz, D2O) δ 8.51 (s, 2H), 4.09-3.95 (m, 1H), 3.76-3.45 (m, 14H), 2.87-2.86 (m, 2H), 2.44-2.31 (m, 1H), 2.20-1.99 (m, 1H), 1.38-1.31 (m, 3H), 1.29-1.21 (m, 3H). |

TABLE 2-continued

| Example No. | R | IUPAC Name | LRMS m/z [M + H]+ | 1H NMR or LCMS retention time and method |
|---|---|---|---|---|
| 318 | (3S)-3-methyl-pyrrolidin with N-C(O)-C(CH3)2-C(O)NH2 | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethyl-3-oxopropanamide | 496.3 | 1H NMR (400 MHz, D2O) δ 8.46-8.44 (m, 2H), 3.82-3.45 (m, 14H), 2.81 (br s, 2H), 2.12-2.09 (m, 1H), 1.99-1.98 (m, 1H), 1.35-1.16 (m, 9H). |
| 319 | (3S)-3-methyl-pyrrolidin with N-C(O)-C(CH3)2-COOH | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethyl-3-oxopropanoic acid | 497.3 | 1H NMR (400 MHz, D2O) δ 8.49 (s, 2H), 4.13-4.11 (m, 1H), 4.08-3.84 (m, 11H), 3.55-3.53 (m, 2H), 3.04-3.01 (m, 2H), 2.68-2.39 (m, 1H), 2.13-2.12 (m, 1H), 1.46-1.31 (m, 9H). |
| 320** | (3S)-3-methyl-pyrrolidin with N-C(O)-CH(CH3)-COOH | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-3-oxopropanoic acid | 483.2 | 1H NMR (400 MHz, D2O) δ 8.45 (s, 2H), 4.03-3.73 (m, 15H), 3.02-2.99 (m, 2H), 2.70-2.44 (m, 1H), 2.19-2.16 (m, 1H), 1.43-1.39 (m, 3H), 1.26 (s, 3H). |
| 321** | (3S)-3-methyl-pyrrolidin with N-C(O)-CH(CH3)-C(O)OCH2CH3 | ethyl 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methyl-3-oxopropanoate | 511.3 | 1H NMR (400 MHz, CDCl3) δ 8.82-8.81 (m, 2H), 5.28-5.27 (m, 2H), 4.19-4.11 (m, 3H), 3.77-3.50 (m, 14H), 3.12-3.09 (m, 2H), 2.75-2.04 (m, 1H), 2.32-2.29 (m, 1H), 1.44-1.40 (m, 6H), 1.35-1.27 (m, 3H). |

TABLE 2-continued

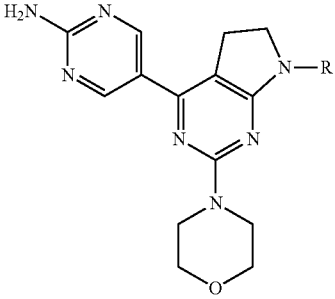

| Example No. | R | IUPAC Name | LRMS m/z [M + H]⁺ | ¹H NMR or LCMS retention time and method |
|---|---|---|---|---|
| 322 | 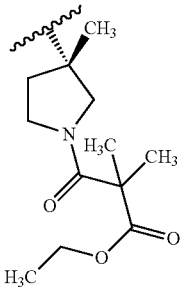 | ethyl 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2,2-dimethyl-3-oxopropanoate | 525.4 | ¹H NMR (400 MHz, CDCl₃) δ 8.82 (s, 2H), 5.19 (s, 2H), 4.19-4.15 (m, 2H), 4.13-4.03 (m, 1H), 3.83-3.82 (m, 9H), 3.77-3.74 (m, 2H), 3.66-3.50 (m, 2H), 3.11-3.09 (m, 2H), 2.22-2.19 (m, 1H), 2.05-2.03 (m, 1H), 1.46-1.45 (m, 6H), 1.27-1.21 (m, 6H). |
| 323 | 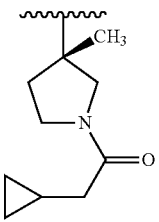 [SMILES: *[C@@]1(C)CCN(C(=O)CC2CC2)C1] | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropylethanone | 465.6 | ¹H NMR (400 MHz, DMSO-d₆) δ 8.72 (s, 2 H) 6.97 (s, 2 H) 3.69-3.86 (m, 2 H) 3.64 (s, 9 H) 3.38-3.56 (m, 3 H) 3.04-3.14 (m, 2 H) 2.26-2.37 (m, 1 H) 1.98-2.24 (m, 3 H) 1.28 (d, J = 2.6 Hz, 3 H) 0.90-1.01 (m, 1 H) 0.40-0.48 (m, 2 H) 0.07-0.14 (m, 2 H). |
| 324 | 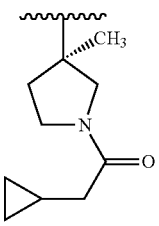 [SMILES: *[C@]1(C)CCN(C(=O)CC2CC2)C1] | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropylethanone | 465.3 | ¹H NMR (400 MHz, MeOD-d₄) δ 8.78 (d, J = 1.7 Hz, 2H) 3.89-4.27 (m, 2H) 3.74 (d, J = 0.7 Hz, 9H) 3.54-3.72 (m, 3H) 3.40-3.51 (m, 1H) 3.09-3.18 (m, 2H) 2.40-2.66 (m, 1H) 2.25-2.34 (m, 2H) 2.07-2.25 (m, 1H) 1.39 (d, J = 2.9 Hz, 3H) 0.99-1.12 (m, 1H) 0.50-0.57 (m, 2H) 0.15-0.22 (m, 2H). |
| 325 | 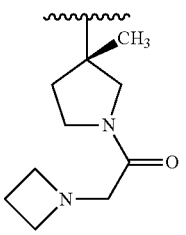 [SMILES: *[C@@]1(C)CCN(C(=O)CN2CCC2)C1] | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-(azetidin-1-yl)ethanone | 480.2 | ¹H NMR (400 MHz, Methanol-d₄) δ 8.77 (s, 2H), 4.65-4.62 (m, 2H), 4.15-3.92 (m, 6H), 3.78-3.61 (m, 8H), 3.65-3.49 (m, 4H), 3.19-3.06 (m, 2H), 2.61-2.56 (m, 1H), 2.43-2.32 (m, 2H), 2.21-2.16 (m, 1H), 1.43-1.40 (m, 3H). |

TABLE 2-continued

| Example No. | R | IUPAC Name | LRMS m/z [M + H]+ | 1H NMR or LCMS retention time and method |
|---|---|---|---|---|
| 326* | (3R)-3-methyl pyrrolidinyl with 2-cyclopropyl-2-hydroxyacetyl | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropyl-2-hydroxyethanone | 481.1 | 1H NMR (400 MHz, CDCl3) δ 8.82 (s, 2H), 5.24 (s, 2H), 4.15-4.05 (m, 3H), 3.78-3.70 (m, 8H), 3.69-3.53 (m, 5H), 3.14-3.10 (m, 2H), 2.68-2.07 (m, 1H), 2.39-2.15 (m, 1H), 1.37 (d, J = 25.2 Hz, 3H), 1.07-0.95 (m, 1H), 0.59-0.35 (m, 4H). |
| 327* | (3R)-3-methyl pyrrolidinyl with 2-cyclopropyl-2-hydroxyacetyl | 1-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-cyclopropyl-2-hydroxyethanone | 481.1 | 1H NMR (400 MHz, CDCl3) δ 8.82 (s, 2H), 5.26 (s, 2H), 4.28-3.93 (m, 3H), 3.78-3.45 (m, 13H), 3.18-3.05 (m, 2H), 2.82-2.35 (m, 1H), 2.25-1.95 (m, 1H), 1.39 (d, J = 4 Hz, 3H), 1.13-1.03 (m, 1H), 0.60-0.42 (m, 4H). |
| 328 | (3S)-3-methyl pyrrolidinyl with cyclopropylcarbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(cyclopropyl)methanone | 451.1 | 1H NMR (400 MHz, DMSO-d6) δ 8.72 (s, 2H), 7.01 (s, 2H), 4.21-3.96 (m, 1H), 3.77-3.73 (m, 1H), 3.67-3.63 (m, 10H), 3.54-3.42 (m, 2H), 3.10-3.09 (m, 2H), 2.38-2.34 (m, 1H), 2.20-2.05 (m, 1H), 1.77-1.68 (m, 1H), 1.32-1.28 (m, 3H), 0.73-0.72 (m, 4H). |
| 329 | (3S)-3-methyl pyrrolidinyl with (1-methylcyclopropyl)carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methylcyclopropyl)methanone | 465.6 | 1H NMR (400 MHz, 80° C., DMSO-d6) δ 8.74 (s, 2H) 6.61 (br s, 2H) 4.09 (br s, 1H) 3.96-4.03 (m, 1H) 3.64-3.75 (m, 9H) 3.39-3.62 (m, 3H) 3.11 (t, J = 8.1 Hz, 2H) 2.30-2.44 (m, 1H) 2.01-2.11 (m, 1H) 1.29 (d, J = 19.7 Hz, 6H) 0.85-0.92 (m, 1H) 0.76-0.83 (m, 1H) 0.42-0.55 (m, 2H). |

TABLE 2-continued

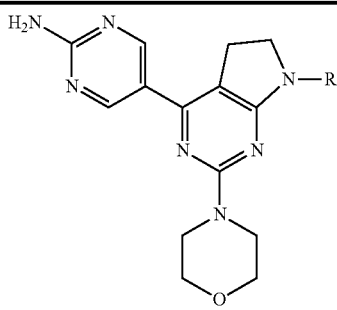

| Example No. | R | IUPAC Name | LRMS m/z [M + H]+ | 1H NMR or LCMS retention time and method |
|---|---|---|---|---|
| 330 | (3R)-3-methyl-pyrrolidin-3-yl with N-C(=O)-(1-methylcyclopropyl) | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methylcyclopropyl)methanone | 465.3 | 1H NMR (400 MHz, DMSO-d6) δ 8.73 (br s, 2H) 6.66 (br s, 1H) 4.07 (br s, 1H) 3.95-4.04 (m, 1 H) 3.65-3.79 (m, 9 H) 3.58 (q, J = 9.0 Hz, 1H) 3.38-3.54 (m, 2H) 3.11 (t, J = 8.0 Hz, 3H) 2.32-2.44 (m, 1H) 2.01-2.13 (m, 1H) 1.32 (s, 3H) 1.24-1.29 (m, 3H) 0.85-0.93 (m, 1H) 0.74-0.83 (m, 1H) 0.45-0.54 (m, 2H). |
| 331 | (3S)-3-methyl-pyrrolidin-3-yl with N-C(=O)-(1-fluorocyclopropyl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-fluorocyclopropyl)methanone | 468.5 | 1H NMR (400 MHz, Methanol-d4) δ 8.78 (s, 2H), 4.45-4.30 (m, 1H), 4.10-3.80 (m, 2H), 3.75-3.65 (m, 8H), 3.60-3.45 (m, 3H), 3.20-3.05 (m, 2H), 2.65-2.40 (m, 1H), 2.25-2.00 (m, 1H), 1.40-1.37(m, 3H), 1.30-1.15 (m, 4H). |
| 332 | (3S)-3-methyl-pyrrolidin-3-yl with N-C(=O)-[(1R,2S)-2-fluorocyclopropyl] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1R,2S)-2-fluorocyclopropyl]methanone | 469.1 | 1H NMR (400 MHz, Methanol-d4) δ 8.80 (s, 2H), 4.60-4.52 (s, 1H), 4.29 (s, 1H), 4.01-3.69 (m, 10H), 3.66-3.42 (m, 2H), 3.20-3.10 (m, 2H), 2.71-2.42 (m, 1H), 2.87-2.10 (m, 2H), 1.55-1.27 (m, 6H). |
| 333 | (3S)-3-methyl-pyrrolidin-3-yl with N-C(=O)-[(1S,2R)-2-fluorocyclopropyl] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1S,2R)-2-fluorocyclopropyl]methanone | 469.2 | 1H NMR (400 MHz, Methanol-d4) δ 8.80 (s, 2H), 4.12-3.70 (m, 12H), 3.67-3.43 (m, 2H), 3.21-3.09 (m, 2H), 2.71-2.47 (m, 1H), 2.38-2.10 (m, 2H), 1.55-1.40 (m, 4H), 1.38-1.24 (m, 2H). |
| 334 | (3S)-3-methyl-pyrrolidin-3-yl with N-C(=O)-[(1S,2S)-2-fluorocyclopropyl] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1S,2S)-2-fluorocyclopropyl]methanone | 469.2 | 1H NMR (400 MHz, Methanol-d4) δ 8.80 (s, 2H), 4.58-4.49 (m, 1H), 4.05-3.71 (m, 11H), 3.68-3.47 (m, 2H), 3.20-3.10 (m, 2H), 2.73-2.61 (m, 1H), 2.28-2.00 (m, 2H), 1.76-1.64 (m, 1H), 1.50-1.36 (m, 4H), 1.15-1.05 (m, 1H). |

TABLE 2-continued

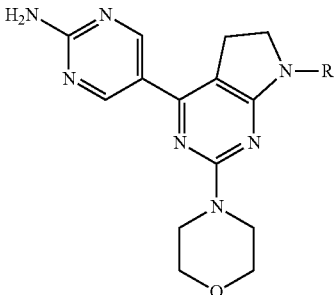

| Example No. | R | IUPAC Name | LRMS m/z [M + H]⁺ | ¹H NMR or LCMS retention time and method |
|---|---|---|---|---|
| 335 | (3S)-methyl pyrrolidine with (1R,2R)-2-fluorocyclopropyl carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1R,2R)-2-fluorocyclopropyl]methanone | 469.2 | ¹H NMR (400 MHz, Methanol-d₄) δ 8.80 (s, 2H), 4.33-4.10 (m, 1H), 4.00-3.91 (m, 1H), 3.89-3.69 (m, 10H), 3.67-3.45 (m, 2H), 3.20-3.08 (m, 2H), 2.75-2.40 (m, 1H), 2.29-2.15 (m, 1H), 2.10-1.97 (m, 1H), 1.79-1.65 (m, 1H), 1.43-1.37 (m, 3H), 1.18-1.05 (m, 2H). |
| 336 | (3S)-methyl pyrrolidine with (1R)-2,2-difluorocyclopropyl carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1R)-2,2-difluorocyclopropyl]methanone | | ¹H NMR (400 MHz, CDCl₃) δ 8.82 (s, 2H), 5.23 (s, 2H), 4.31-3.90 (m, 2H), 3.80-3.51 (m, 12H), 3.18-3.07 (m, 2H), 2.81-2.46 (m, 2H), 2.30-2.12 (m, 2H), 2.05-1.95 (m, 1H), 1.40-1.37 (m, 3H). |
| 337 | (3S)-methyl pyrrolidine with (1S)-2,2-difluorocyclopropyl carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(1S)-2,2-difluorocyclopropyl]methanone | 487.2 | ¹H NMR (400 MHz, CDCl₃) δ 8.83 (s, 2H), 5.26 (s, 2H), 4.38-4.36 (m, 1H), 3.98-3.95 (m, 1H), 3.76-3.51 (m, 12H), 3.14-3.09 (m, 2H), 2.84-2.04 (m, 4H), 2.47-2.44 (m, 1H), 1.38-1.34 (m, 3H). |
| 338 | (3S)-methyl pyrrolidine with (1-hydroxycyclopropyl) carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-hydroxycyclopropyl)methanone | 466.6 | ¹H NMR (400 MHz, Methanol-d₄) δ 8.78 (s, 2H), 4.55-4.35 (m, 1H), 4.15-3.88 (m, 2H), 3.80-3.70 (m, 9H), 3.66-3.40 (m, 2H), 3.20-2.90 (m, 2H), 2.70-2.42 (m, 1H), 2.20-2.00 (m, 1H), 1.39 (d, J = 18.4 Hz, 3H), 1.25-1.05 (m, 2H), 0.92-0.88 (m, 2H). |
| 339 | (3S)-methyl pyrrolidine with [1-(hydroxymethyl)cyclopropyl] carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[1-(hydroxymethyl)cyclopropyl]methanone | 480.6 | ¹H NMR (400 MHz, Methanol-d₄) δ 8.80 (s, 2H), 4.57-4.46 (m, 1H), 4.25-4.15 (m, 1H), 4.05-3.90 (m, 1H), 3.83-3.70 (m, 9H), 3.69-3.40 (m, 3H), 3.23-3.05 (m, 2H), 2.60-2.30 (m, 1H), 2.20-2.00 (m, 1H), 1.42-1.23 (m, 5H), 1.02-0.70 (m, 3H). |

TABLE 2-continued

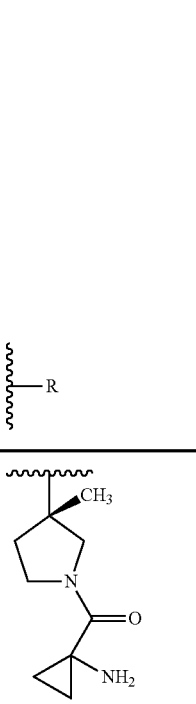

| Example No. | R | IUPAC Name | LRMS m/z [M + H]+ | 1H NMR or LCMS retention time and method |
|---|---|---|---|---|
| 340 | 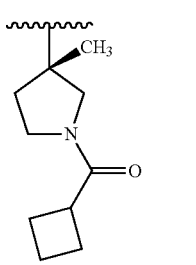 [SMILES: *[C@@]1(C)CCN(C(=O)C2CCC2)C1] | (1-aminocyclopropyl){(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}methanone hydrochloride | 466.2 | 1H NMR (400 MHz, D2O) δ 8.58 (s, 2H), 4.19-3.45 (m, 14H), 3.04-2.95 (m, 2H), 2.62-2.41 (m, 1H), 2.25-2.10 (m, 1H), 1.65-1.32 (m, 7H). |
| 341 | 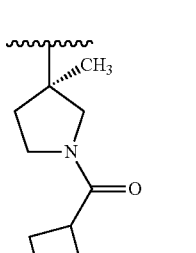 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(cyclobutyl)methanone | 465.6 | 1H NMR (400 MHz, DMSO-d6) δ 8.72 (s, 2H) 6.96 (s, 2H) 3.89 (d, J = 10.5 Hz, 1H) 3.71-3.77 (m, 1H) 3.59-3.70 (m, 9H) 3.40-3.55 (m, 2H) 3.15-3.24 (m, 1H) 3.05-3.13 (m, 2H) 2.24-2.46 (m, 1H) 1.97-2.20 (m, 5H) 1.84-1.95 (m, 2H) 1.69-1.81 (m, 1H) 1.22-1.30 (m, 3H). |
| 342 | | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(cyclobutyl)methanone | 465.2 | 1H NMR (400 MHz, DMSO-d6) δ 8.72 (s, 2H) 6.64 (br s, 2H) 3.78-3.98 (m, 1H) 3.74 (br s, 1H) 3.69 (br s, 9H) 3.51-3.61 (m, 1H) 3.46 (t, J = 8.9 Hz, 1H) 3.31-3.41 (m, 1H) 3.14-3.29 (m, 2H) 3.08-3.14 (m, 2H) 2.15-2.22 (m, 2H) 2.09-2.15 (m, 2H) 1.99-2.09 (m, 1H) 1.86-1.99 (m, 1H) 1.75-1.85 (m, 1H) 1.33 (br s, 3H). |
| 343 | 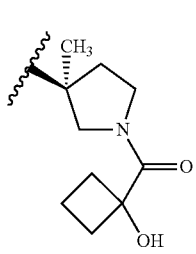 [SMILES: *[C@@]1(C)CCN(C(=O)C2(O)CCC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-hydroxycyclobutyl)methanone | 481.1 | 1H NMR (400 MHz, DMSO-d6) δ 8.98 (s, 2H), 7.01 (s, 1H), 5.80 (s, 1H), 4.19 (d, J = 11.6 Hz, 1H), 3.86-3.83 (m, 1H), 3.75-3.60 (m, 9H), 3.57-3.45 (m, 2H), 3.20-3.05 (m, 2H), 2.30-2.20 (m, 1H), 2.10-1.95 (m, 3H), 1.80-1.65 (m, 1H), 1.55-1.48 (m, 2H), 1.30-1.25 (m, 1H), 1.22 (s, 3H). |

TABLE 2-continued

| Example No. | R | IUPAC Name | LRMS m/z [M + H]+ | 1H NMR or LCMS retention time and method |
|---|---|---|---|---|
| 344 | (3R)-3-methyl-3-... pyrrolidine with 1-hydroxycyclobutyl carbonyl | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-hydroxycyclobutyl)methanone | 481.1 | 1H NMR (400 MHz, MeOD) δ 8.77 (s, 2H), 4.31 (d, J = 12 Hz, 1H), 4.18-4.06 (m, 1H), 4.05-3.90 (m, 1H), 3.83-3.72 (m, 8H), 3.62-3.45 (m, 3H), 3.15-3.05 (m, 2H), 2.70-2.50 (m, 2H), 2.45-2.30 (m, 1H), 2.10-2.00 (m, 3H), 1.80-1.65 (m, 1H), 1.65-1.55 (m, 1H), 1.40-1.32 (m, 3H). |
| 345 | (3S)-3-methyl pyrrolidine with 3-hydroxycyclobutyl carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-hydroxycyclobutyl)methanone | 481.2 | 1H NMR (400 MHz, Methanol-d4) δ 8.80-8.79 (m, 2H), 4.18-3.89 (m, 3H), 3.81-3.70 (m, 9H), 3.66-3.43 (m, 3H), 3.17-3.09 (m, 2H), 2.85-2.72 (m, 1H), 2.63-2.42 (m, 3H), 2.22-2.05 (m, 3H), 1.38 (s, 3H). |
| 346 | (3S)-3-methyl pyrrolidine with 1-aminocyclobutyl carbonyl | (1-aminocyclobutyl){(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}methanone | 480.1 | 1H NMR (400 MHz, D2O) δ 8.62 (s, 2H), 4.65-4.60 (m, 1H), 4.15-4.12 (m, 1H), 4.11-4.09 (m, 1H), 4.05-3.92 (m, 1H), 3.86-3.84 (m, 1H), 3.76-3.75 (m, 1H), 3.72-3.69 (m, 2H), 3.65-3.62 (m, 4H), 3.61-3.60 (m, 1H), 3.09-3.07 (m, 2H), 2.98-2.89 (m, 2H), 2.67-2.65 (m, 1H), 2.56-2.32 (m, 4H), 2.28-2.15 (m, 1H), 1.55 (d, J = 16 Hz, 3H), 1.34-1.33 (m, 1H). |
| 347 | (3S)-3-methyl pyrrolidine with (2S)-azetidin-2-yl carbonyl | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-azetidin-2-yl]methanone hydrochloride | 466.1 | 1H NMR (400 MHz, D2O) δ 8.54 (s, 2H), 5.34 (br s, 1H), 4.22-4.13 (m, 1H), 4.11-4.03 (m, 1H), 4.01-3.91 (m, 3H), 3.86-3.74 (m, 8H), 3.65-3.56 (m, 2H), 3.44-3.34 (m, 1H), 3.09-2.99 (m, 2H), 2.95-2.75 (m, 1H), 2.69-2.48 (m, 2H), 2.30-2.19 (m, 1H), 1.48-1.44 (m, 3H). |

TABLE 2-continued

| Example No. | R | IUPAC Name | LRMS m/z [M + H]+ | 1H NMR or LCMS retention time and method |
|---|---|---|---|---|
| 348** | (pyrrolidine with 3-CH3, N-C(=O)-azetidin-2-yl NH) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(azetidin-2-yl)methanone hydrochloride | 466.1 | 1H NMR (400 MHz, D2O) δ 8.54 (s, 2H), 5.26 (br s, 1H), 4.15-4.05 (br s, 1H), 4.04-3.94 (m, 1H), 3.93-3.83 (m, 3H), 3.80-3.66 (m, 8H), 3.60-3.45 (m, 2H), 3.40-3.26 (m, 1H), 3.00-2.91 (m, 2H), 2.86-2.68 (m, 1H), 2.61-2.41 (m, 2H), 2.23-2.12 (m, 1H), 1.41-1.35 (m, 3H). |
| 349 | (pyrrolidine with 3-CH3, N-C(=O)-azetidin-3-yl NH) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(azetidin-3-yl)methanone hydrochloride | 466.1 | 1H NMR (400 MHz, D2O) δ 8.56 (s, 2H), 4.27-4.23 (m, 4H), 4.00-3.82 (m, 4H), 3.80-3.77 (m, 5H), 3.75-3.67 (m, 4H), 3.57-3.51 (m, 2H), 3.02-3.01 (m, 2H), 2.67-2.55 (m, 1H), 2.23-2.22 (m, 1H), 2.43 (d, J = 3.6 Hz, 3H). |
| 350 | (pyrrolidine with 3-CH3, N-C(=O)-(2S)-2-methylazetidin-2-yl NH) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-2-methylazetidin-2-yl]methanone hydrochloride | 480.2 | 1H NMR (400 MHz, D2O) δ 8.56 (s, 2H), 4.14-4.08 (m, 2H), 3.94-3.55 (m, 14H), 3.04-3.01 (m, 2H), 2.85-2.60 (m, 1H), 2.52-2.48 (m, 2H), 2.22-2.17 (m, 1H), 1.85 (d, J = 6.8 Hz, 3H), 1.47 (d, J = 14.8 Hz, 3H). |
| 351 | (pyrrolidine with 3-CH3, N-C(=O)-(2R)-2-methylazetidin-2-yl NH) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2R)-2-methylazetidin-2-yl]methanone | 480.1 | 1H NMR (400 MHz, D2O, 80° C.) δ 8.89 (s, 2H), 4.45-4.43 (m, 4H), 4.40-3.89 (m, 12H), 3.38-3.31 (m, 2H), 2.97 (s, 1H), 2.85 (s, 1H), 2.63-2.56 (m, 1H), 2.40-2.38 (m, 1H), 2.30-2.14 (m, 3H), 1.82 (s, 3H). |

TABLE 2-continued

| Example No. | R | IUPAC Name | LRMS m/z [M + H]+ | 1H NMR or LCMS retention time and method |
|---|---|---|---|---|
| 352 | (pyrrolidine with CH3, N-acyl with 3-fluoroazetidin-3-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-fluoroazetidin-3-yl)methanone hydrochloride | 484.2 | 1H NMR (400 MHz, 80° C., DMSO-d6) δ 8.73 (s, 2H), 6.60 (s, 2H), 4.07-3.95 (m, 3H), 3.92-3.40 (m, 16H), 3.10 (t, J = 8.1 Hz, 1H), 2.42-2.32 (m, 1H), 2.19-2.02 (m, 2H), 1.34-1.24 (m, 3H). |
| 353 | (pyrrolidine with CH3, N-acyl with (2R)-1-methylazetidin-2-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2R)-1-methylazetidin-2-yl]methanone | 480.2 | 1H NMR (400 MHz, Methanol-d4) δ 8.78 (s, 2H), 5.02-4.98 (m, 1H), 4.24-3.82 (m, 3H), 3.80-3.70 (m, 10H), 3.67-3.52 (m, 3H), 3.39-3.30 (m, 1H), 3.14-3.06 (m, 2H), 2.85-2.72 (m, 3H), 2.65-2.32 (m, 2H), 2.25-2.05 (m, 1H), 1.40 (d, J = 8.8 Hz, 3H). |
| 354 | (pyrrolidine with CH3, N-acyl with (2S)-1-methylazetidin-2-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-1-methylazetidin-2-yl]methanone | 480.2 | 1H NMR (400 MHz, Methanol d4) δ 8.78 (s, 2H), 4.93-4.87 (m, 1H), 4.17-3.95 (m, 2H), 3.90-3.70 (m, 11H), 3.63-3.45 (m, 3H), 3.17-3.05 (m, 2H), 2.80-2.60 (m, 4H), 2.50-2.35 (m, 2H), 2.25-2.10 (m, 1H), 1.39 (s, 3H). |
| 355 | (pyrrolidine with CH3, N-acyl with 1,2-dimethylazetidin-2-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1,2-dimethylazetidin-2-yl)methanone | 494.2 | 1H NMR (400 MHz, DMSO-d6) δ 8.73 (s, 2H), 7.02 (s, 2H), 4.28-4.25 (m, 1H), 3.74-7.50 (m, 15H), 3.11-3.10 (m, 2H), 2.60-2.58 (m, 1H), 2.13-1.95 (m, 3H), 1.65 (s, 1H), 1.51 (s, 2H), 1.30 (s, 3H), 1.23 (s, 3H). |

TABLE 2-continued

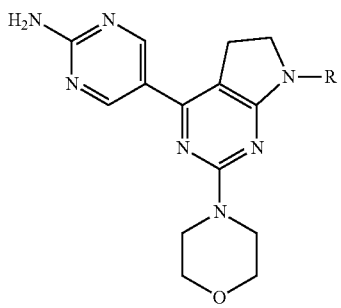

| Example No. | R | IUPAC Name | LRMS m/z [M + H]+ | ¹H NMR or LCMS retention time and method |
|---|---|---|---|---|
| 356 | (pyrrolidine with CH₃, linked to 1-methylazetidin-3-yl)methanone | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methylazetidin-3-yl)methanone | 480.2 | ¹H NMR (400 MHz, D₂O) δ 8.41-8.40 (m, 2H), 4.33-4.18 (m, 4H), 3.91-3.88 (m, 1H), 3.77-3.75 (m, 1H), 3.70-3.68 (m, 5H), 3.66-3.61 (m, 6H), 3.42-3.33 (m, 2H), 2.86 (d, J = 28 Hz, 3H), 2.62-2.49 (m, 2H), 2.25-2.10 (m, 2H), 1.15 (d, J = 28 Hz, 3H). |
| 357 | (pyrrolidine with CH₃, linked via carbonyl to azetidine-N-Boc) | tert-butyl (2S)-2-({(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)azetidine-1-carboxylate | 566.2 | ¹H NMR (400 MHz, DMSO-d₆) δ 8.73 (s, 2H), 7.02 (s, 2H), 4.81-4.73 (m, 1H), 4.02-3.95 (m, 1H), 3.85-3.72 (m, 4H), 3.70-3.62 (m, 11H), 3.55-3.45 (m, 2H), 3.14-3.08 (m, 2H), 2.16-1.97 (m, 2H), 1.36-1.07 (m, 12H). |
| 358** | (pyrrolidine with CH₃, linked via carbonyl to azetidine-N-Boc) | tert-butyl 2-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)azetidine-1-carboxylate | 566.1 | ¹H NMR (400 MHz, DMSO-d₆) δ 8.72 (s, 2H), 7.02 (s, 2H), 4.80 (br s, 1H), 4.04 (br s, 1H), 3.80-3.75 (m, 4H), 3.66-3.50 (m, 13H), 3.09-3.08 (m, 2H), 2.34-2.01 (m, 2H), 1.35-1.07 (m, 12H). |

TABLE 2-continued

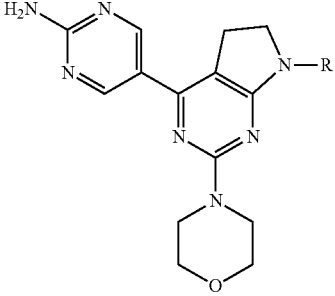

| Example No. | R | IUPAC Name | LRMS m/z [M + H]+ | 1H NMR or LCMS retention time and method |
|---|---|---|---|---|
| 359 | 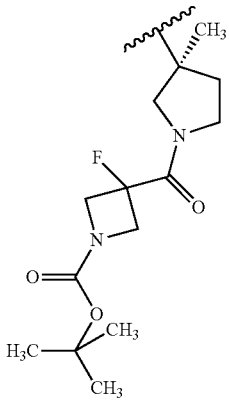 [SMILES: *[C@@]1(C)CCN(C(=O)C2(F)CN(C(=O)OC(C)(C)C)C2)C1] | tert-butyl 3-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)-3-fluoroazetidine-1-carboxylate | 584.4 | 1H NMR (400 MHz, DMSO-d6) δ 8.72 (s, 2H), 6.97 (s, 2H), 4.51-4.27 (m, 2H), 4.14-.3.75 (m, 4H), 3.70-3.40 (12H), 3.14-3.07 (m, 2H), 2.37-2.29 (m, 1H), 2.16-1.98 (m, 1H), 1.41-1.35 (m, 9H), 1.33-1.27 (m, 3H). |
| 360 | 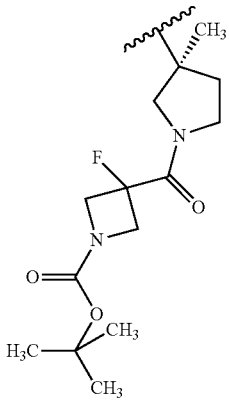 [SMILES: *[C@@]1(C)CCN(C(=O)C2(F)CN(C(=O)OC(C)(C)C)C2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(azetidin-1-yl)methanone | 466.1 | 1H NMR (400 MHz, DMSO-d6 + D2O) δ 8.70 (s, 2H), 3.89-3.83 (m, 4H), 3.75-3.72 (m, 1H), 3.63-3.60 (m, 10H), 3.49-3.47 (m, 1H), 3.27-3.25 (m, 2H), 3.07-3.03 (m, 2H), 2.31-2.28 (m, 1H), 2.13-2.10 (m, 2H), 2.01-1.98 (m, 1H), 1.23 (s, 3H). |
| 361 | 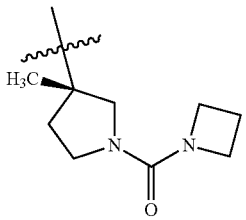 [SMILES: *[C@@]1(C)CCN(C(=O)N2CCC2)C1] | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(azetidin-1-yl)methanone | 466.1 | 1H NMR (400 MHz, DMSO-d6) δ 8.72 (s, 2H), 7.01 (s, 2H), 3.90-3.83 (m, 4H), 3.75-3.73 (m, 1H), 3.65-3.62 (m, 10H), 3.51-3.49 (m, 2H), 3.28-3.22 (m, 1H), 3.11-3.08 (m, 2H), 2.34-2.31 (m, 1H), 2.15-2.12 (m, 2H), 2.09-2.02 (m, 1H), 1.25 (s, 3H). |
| 362 | 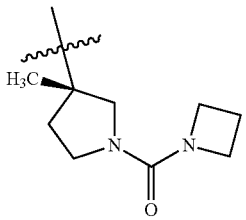 [SMILES: *[C@@]1(C)CCN(C(=O)N2CCC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-3,3-dimethylazetidin-2-yl]methanone hydrochloride | 494.2 | retention time = 0.633 min. Column: WatersAcquityBEH C18, 2.1 × 30 mm, 1.7 μm particle size; Column Temperature 80° C. Solvent A: Water (0.1% formic acid + 0.05% ammonium formate) Solvent B: Acetonitrile (5% H2O + 0.1% formic acid + 0.05% ammonium formate) Gradient for 3 min Method: 5-95% B in 2.5 min, 95% B 2.5-3.0 min; Flow rate 1.2 mL/min |

TABLE 2-continued

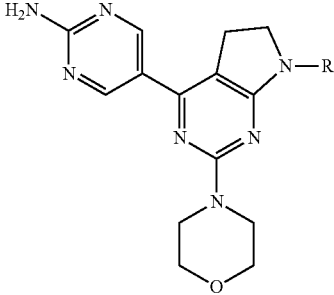

| Example No. | R | IUPAC Name | LRMS m/z [M + H]⁺ | ¹H NMR or LCMS retention time and method |
|---|---|---|---|---|
| 363 | 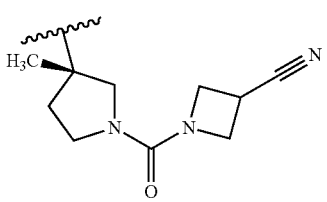 [SMILES: *[C@@]1(C)CCN(C(=O)N2CC(C#N)C2)C1] | 1-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)azetidine-3-carbonitrile | 491.2 | ¹H NMR (400 MHz, DMSO-$d_6$ + $D_2O$) δ 8.70 (s, 2H), 4.16-4.12 (m, 2H), 3.98-3.95 (m, 2H), 3.73-3.70 (m, 1H), 3.67-3.64 (m, 11H), 3.49-3.40 (m, 1H), 3.28-3.25 (m, 2H), 3.08-3.04 (m, 2H), 2.33-2.28 (m, 1H), 2.06-1.99 (m, 1H), 1.23 (s, 3H). |
| 364 | 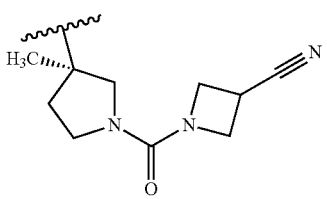 [SMILES: *[C@]1(C)CCN(C(=O)N2CC(C#N)C2)C1] | 1-({(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)azetidine-3-carbonitrile | 491.2 | ¹H NMR (400 MHz, DMSO-$d_6$) δ 8.73 (s, 2H), 7.02 (s, 2H), 4.19-4.13 (m, 2H), 4.02-3.97 (m, 2H), 3.76-3.59 (m, 11H), 3.52-3.48 (m, 2H), 3.11-3.07 (m, 2H), 2.34-2.28 (m, 1H), 2.05-1.95 (m, 1H), 1.25 (s, 3H). |
| 365 | 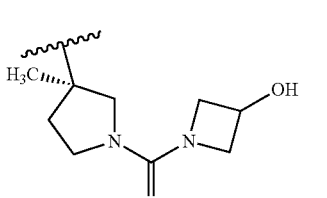 | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-hydroxyazetidin-1-yl)methanone | 482.1 | ¹H NMR (400 MHz, DMSO-$d_6$) δ 8.72 (s, 2H), 7.01 (s, 2H), 4.39-4.36 (m, 1H), 4.02-3.98 (m, 2H), 3.73-3.66 (m, 1H), 3.62-3.58 (m, 12H), 3.33-3.29 (m, 4H), 3.11-3.09 (m, 2H), 2.35-2.28 (m, 1H), 2.04-2.01 (m, 1H), 1.25 (s, 3H). ¹H NMR (400 MHz, DMSO-$d_6$) δ 8.70 (s, 2H), 4.37-4.34 (m, 1H), 4.06-4.01 (m, 2H), 3.65-3.58 (m, 10H), 3.49-3.46 (m, 1H), 3.31-3.27 (m, 2H), 3.07-3.02 (t, J = 8 Hz, 2H), 2.29-2.24 (m, 1H), 2.01-1.98 (m, 1H), 1.22 (s, 3H). |
| 366 | 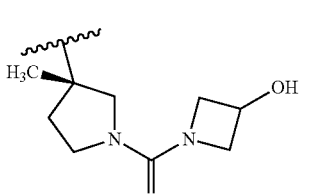 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-hydroxyazetidin-1-yl)methanone | 482.1 | ¹H NMR (400 MHz, DMSO-$d_6$ + $D_2O$) δ 8.70 (s, 2H), 4.35-4.34 (m, 1H), 4.03-4.00 (m, 2H), 3.75-3.70 (m, 1H), 3.63-3.55 (m, 12H), 3.55-3.46 (m, 1H), 3.35-3.25 (m, 2H), 3.07-3.03 (m, 2H), 2.30-2.27 (m, 1H), 2.00-1.98 (m, 1H), 1.22 (s, 3H). |

TABLE 2-continued

| Example No. | R | IUPAC Name | LRMS m/z [M + H]+ | 1H NMR or LCMS retention time and method |
|---|---|---|---|---|
| 367 | (3S)-3-methyl, 3-[pyrrolidinyl]-N-C(O)-azetidine-OCH3 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-methoxyazetidin-1-yl)methanone | 496.1 | 1H NMR (400 MHz, DMSO-d6 + D2O) δ 8.68 (s, 2H), 4.10-4.00 (m, 3H), 3.74-3.69 (m, 1H), 3.68-3.61 (m, 12H), 3.47-3.45 (m, 1H), 3.30-3.25 (m, 2H), 3.16 (s, 3H), 3.05-3.00 (m, 2H), 2.28-2.25 (m, 1H), 1.99-1.97 (m, 1H), 1.21 (s, 3H). |
| 368 | (3R)-3-methyl, 3-[pyrrolidinyl]-N-C(O)-azetidine-OCH3 | {(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-methoxyazetidin-1-yl)methanone | 496.2 | 1H NMR (400 MHz, DMSO-d6) δ 8.72 (s, 2H), 7.01 (s, 2H), 4.14-4.10 (m, 1H), 4.04-4.01 (m, 2H), 3.74-3.65 (m, 12H), 3.51-3.49 (m, 2H), 3.30-3.28 (m, 2H), 3.19 (s, 3H), 3.11-3.06 (t, J = 8 Hz, 2H), 2.36-2.28 (m, 1H), 2.04-2.01 (m, 1H), 1.25 (s, 3H). |
| 369 | (3S)-3-methyl, 3-[pyrrolidinyl]-N-C(O)-azetidine-OH, CH3 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-hydroxy-3-methylazetidin-1-yl)methanone | 496.3 | 1H NMR (400 MHz, Methanol-d4) δ 8.76 (s, 2H), 3.93-3.82 (m, 6H), 3.80-3.72 (m, 9H), 3.65-3.55 (m, 1H), 3.52-3.33 (m, 2H), 3.15-3.06 (m, 2H), 2.46-2.43 (m, 1H), 2.09-1.95 (m, 1H), 1.47 (s, 3H), 1.35 (s, 3H). |
| 370 | (3S)-3-methyl-pyrrolidinyl-C(O)-(2S)-azetidine-N-C(O)-OC(CH3)3 | tert-butyl (2S)-2-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)azetidine-1-carboxylate | 566.6 | 1H NMR (400 MHz, DMSO-d6) δ 8.72 (s, 2H), 7.02 (s, 2H), 4.80 (br s, 1H), 4.06 (br s, 1H), 3.87-3.71 (m, 4H), 3.70-3.60 (m, 11H), 3.57-3.46 (m, 2H), 3.10 (br s, 2H), 2.16-1.92 (m, 2H), 1.36-1.29 (m, 12H). |

TABLE 2-continued

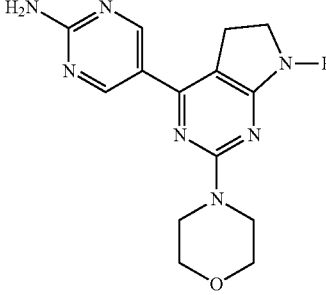

| Example No. | R | IUPAC Name | LRMS m/z [M + H]+ | 1H NMR or LCMS retention time and method |
|---|---|---|---|---|
| 371 | 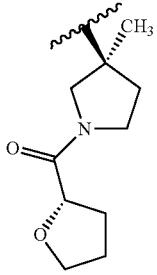 [SMILES: *[C@@]1(C)CCN(C(=O)[C@@H]2CCCO2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-tetrahydrofuran-2-yl]methanone | 481.2 | 1H NMR (400 MHz, DMSO-$d_6$) δ 8.70 (s, 2H), 7.10 (s, 2H), 4.54-4.44 (m, 1H), 4.06 (s, 1H), 3.85-3.70 (m, 5H), 3.65-3.45 (m, 10H), 3.11 (t, J = 6.8 Hz, 2H), 2.40-1.75 (m, 6H), 1.312 (d, J = 3.6 Hz, 3H). |
| 372 | 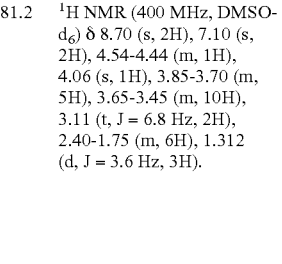 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2R)-tetrahydrofuran-2-yl]methanone | 481.2 | 1H NMR (400 MHz, DMSO-$d_6$ + $D_2O$) δ 8.70 (s, 2H), 4.50-4.43 (m, 1H), 4.09-4.06 (m, 1H), 3.80-3.75 (m, 5H), 3.70-3.35 (m, 10H), 3.05 (br s, 2H), 2.03-1.83 (m, 6H), 1.26 (d, J = 4.0 Hz, 3H). |
| 373 | 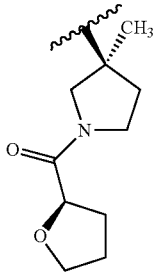 [SMILES: *[C@@]1(C)CCN(C(=O)[C@H]2CCCO2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(3S)-tetrahydrofuran-3-yl]methanone | 481.1 | 1H NMR (400 MHz, $CDCl_3$) δ 8.82 (d, J = 4.0 Hz, 2H) 5.21 (s, 2H) 4.23-4.20 (m, 1H) 4.10-4.00 (m, 1H) 3.95-3.85 (m, 4H) 3.80-3.70 (m, 8H) 3.70-3.50 (m, 4H) 3.20-3.05 (m, 2H) 2.40-2.35 (m, 1H) 2.30-2.20 (m, 2H) 2.15-2.00 (m, 2H) 1.36 (d, J = 3.6 Hz, 3H). |
| 374 | 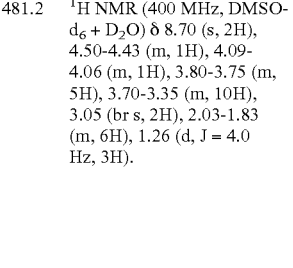 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(3R)-tetrahydrofuran-3-yl]methanone | 481.1 | 1H NMR (400 MHz, DMSO-$d_6$) δ 8.73 (s, 2H), 7.02 (s, 2H), 4.09-4.06 (m, 1H), 3.91 (t, J = 8.0 Hz, 3H), 3.80-3.75 (m, 4H), 3.70-3.60 (m, 8H), 3.25-3.00 (m, 4H), 4.45-4.43 (m, 1H), 2.05-1.95 (m, 4H), 1.29 (d, J = 4.8 Hz, 3H). |

TABLE 2-continued

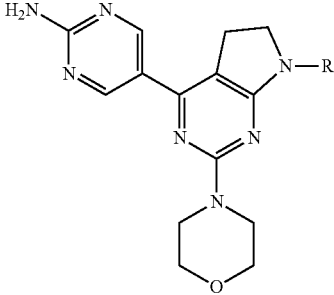

| Example No. | R | IUPAC Name | LRMS m/z [M + H]⁺ | ¹H NMR or LCMS retention time and method |
|---|---|---|---|---|
| 375* | 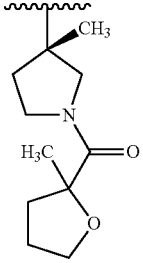 [SMILES: *[C@@]1(C)CCN(C(=O)C2(C)CCCO2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(2-methyltetrahydro-furan-2-yl)methanone hydrochloride | 495.6 | ¹H NMR (700 MHz, DMSO-$d_6$) δ 8.72 (br s, 2 H) 6.98 (br s, 2 H) 4.46 (d, J = 11.6 Hz, 1 H) 3.73-3.92 (m, 3 H) 3.59-3.70 (m, 11 H) 3.45-3.56 (m, 1 H) 3.38-3.43 (m, 1 H) 3.05-3.14 (m, 2 H) 2.10-2.21 (m, 1 H) 1.94-2.00 (m, 1 H) 1.79-1.87 (m, 1 H) 1.65-1.76 (m, 1 H) 1.53-1.60 (m, 1 H) 1.34 (s, 3 H) 1.21 (s, 3 H). |
| 376* | 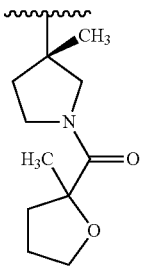 [SMILES: *[C@@]1(C)CCN(C(=O)C2(C)CCCO2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(2-methyltetrahydrofuran-2-yl)methanone | 495.6 | ¹H NMR (400 MHz, DMSO-$d_6$) δ 8.73 (s, 2 H) 6.61 (br s, 2 H) 3.82-3.90 (m, 2 H) 3.63-3.78 (m, 12 H) 3.49-3.60 (m, 2 H) 3.21 (d, J = 5.0 Hz, 3 H) 3.06-3.14 (m, 2 H) 1.82-1.96 (m, 1 H) 1.71-1.83 (m, 1 H) 1.54-1.65 (m, 1 H) 1.33 (s, 6 H). |
| 377 | 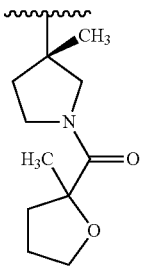 [SMILES: *[C@@]1(C)CCN(C(=O)C2(C)CCCO2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2S)-pyrrolidin-2-yl]methanone hydrochloride | 480.1 | ¹H NMR (400 MHz, D₂O) δ 8.56-8.51 (m, 2H), 4.53-4.51 (m, 1H), 4.10-3.51 (m, 2H), 3.95-3.70 (m, 12H), 3.35-3.31 (m, 2H), 2.99-2.95 (m, 2H), 2.47-2.00 (m, 3H), 1.99-1.88 (m, 3H), 1.39 (d, J = 2.4 Hz, 3H). |
| 378 | 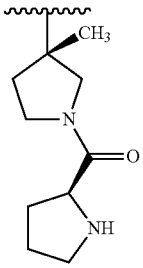 [SMILES: *[C@@]1(C)CCN(C(=O)[C@@H]2CCCN2)C1] | (5S)-5-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)pyrrolidin-2-one | 494.2 | ¹H NMR (400 MHz, DMSO-$d_6$) δ 8.72 (s, 2 H), 7.73 (d, J = 6.5 Hz, 1H), 6.96 (s, 2H), 4.37-4.30 (m, 1 H), 4.14 (d, J = 10.5 Hz, 0.5H), 3.88-3.82 (m, 1 H) 3.76-3.60 (m, 10.5 H), 3.57-3.43 (m, 2.5 H) 3.42-3.35 (m, 1 H) 3.13-3.06 (m, 2 H), 1.92-1.85 (m, 4.5H), 1.30-1.28 (m, 3H). |

TABLE 2-continued

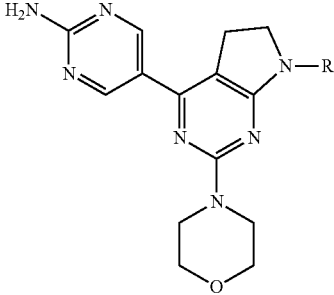

| Example No. | R | IUPAC Name | LRMS m/z [M + H]⁺ | ¹H NMR or LCMS retention time and method |
|---|---|---|---|---|
| 379 | 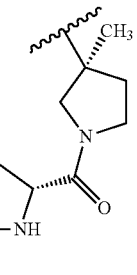 | (5R)-5-({(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}carbonyl)pyrrolidin-2-one | 494.2 | ¹H NMR (700 MHz, DMSO-$d_6$) δ 8.72 (s, 2H), 7.74 (d, J = 30.1 Hz, 1H), 7.01-6.97 (m, 2H), 4.37-4.32 (m, 0.5H), 4.30-4.26 (m, 0.5H), 4.06 (d, J = 10.6 Hz, 0.5H), 3.85-3.81 (m, 1H), 3.76-3.43 (m, 13H), 3.13-3.05 (m, 2H), 2.35-2.24 (m, 1.5H), 2.19-2.03 (m, 3H), 1.94-1.86 (m, 1H), 1.30-1.27 (m, 3H). |
| 380* | 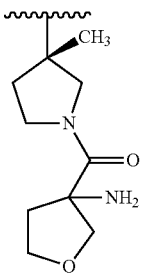 [SMILES: *[C@@]1(C)CCN(C(=O)C2(N)CCOC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-aminotetrahydrofuran-3-yl)methanone hydrochloride | 496.2 | ¹H NMR (400 MHz, $D_2O$) δ 8.59 (s, 2H), 4.42-4.40 (m, 1H), 4.22-4.19 (m, 2H), 3.94-3.61 (m, 15H), 3.00-2.97 (m, 2H), 2.63-2.44 (m, 2H), 2.30-2.11 (m, 2H), 1.46 (s, 3H). |
| 381* | 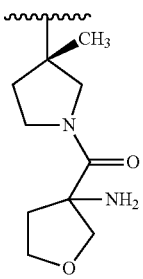 [SMILES: *[C@@]1(C)CCN(C(=O)C2(N)CCOC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-aminotetrahydrofuran-3-yl)methanone hydrochloride | 496.3 | ¹H NMR (400 MHz, $D_2O$) δ 8.59 (s, 2H), 4.41-4.34 (m, 2H), 4.25-4.10 (m, 2H), 3.93-3.60 (m, 14H), 2.98-2.96 (m, 2H), 2.70-2.60 (m, 1H), 2.45-2.15 (m, 3H), 1.44 (s, 3H). |
| 382 | 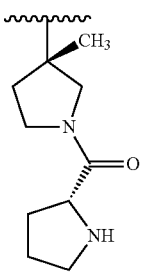 [SMILES: *[C@@]1(C)CCN(C(=O)[C@H]2CCCN2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(2R)-pyrrolidin-2-yl]methanone hydrochloride | 480.1 | ¹H NMR (400 MHz, $D_2O$) δ 8.52 (s, 2H), 4.55-4.40 (m, 1H), 4.10-3.80 (m, 6H), 3.75-3.60 (m, 8H), 3.45-3.25 (m, 2H), 3.00-2.90 (m, 2H), 2.70-2.60 (m, 1H), 2.50-2.40 (m, 1H), 2.25-2.15 (m, 1H), 2.05-1.95 (m, 2H), 1.80-1.70 (m, 1H), 1.41 (d, J = 9.6 Hz, 3H). |

TABLE 2-continued

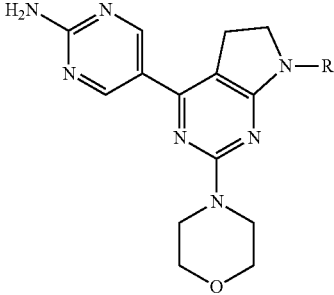

| Example No. | R | IUPAC Name | LRMS m/z [M + H]⁺ | ¹H NMR or LCMS retention time and method |
|---|---|---|---|---|
| 383 | 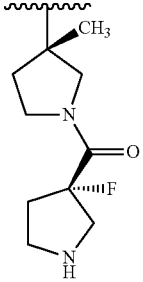 [SMILES: *[C@@]1(C)CCN(C(=O)[C@]2(F)CCNC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}[(3S)-3-fluoropyrrolidin-3-yl]methanone hydrochloride | 498.3 | ¹H NMR (400 MHz, Methanol-d₄) δ 8.90 (s, 2H), 4.37-4.28 (m, 1H), 4.19-3.94 (m, 5H), 3.90-3.77 (m, 10H), 3.65-3.55 (m, 2H), 3.23-3.14 (m, 2H), 2.79-2.53 (m, 3H), 2.35-2.19 (m, 1H), 1.58 (d, J = 6 Hz, 3H). |
| 384 | 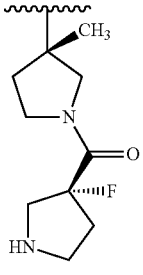 [SMILES: *[C@@]1(C)CCN(C(=O)[C@@]2(F)CCNC2)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3R)-3-fluoropyrrolidin-3-yl]methanone hydrochloride | 498.3 | ¹H NMR (400 MHz, Methanol-d₄) δ 8.86 (s, 2H), 4.36-4.24 (m, 1H), 4.13-3.93 (m, 5H), 3.90-3.76 (m, 9H), 3.73-3.55 (m, 3H), 3.22-3.13 (m, 2H), 2.74-2.49 (m, 3H), 2.36-2.23 (m, 1H), 1.56 (d, J = 6.8 Hz, 3H). |
| 385 | 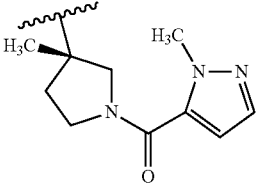 [SMILES: *[C@@]1(C)CCN(C(=O)c2ccnn2C)C1] | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methyl-1H-pyrazol-5-yl)methanone | 491.3 | ¹H NMR (400 MHz, DMSO-d₆) δ 8.69-8.65 (m, 2H), 7.52-7.48 (m, 1H), 6.98-7.01 (m, 2H), 6.74-6.56 (m, 1H), 4.21-4.01 (m, 2H), 3.82-3.77 (m, 3H), 3.69-3.65 (m, 4H), 3.63-3.56 (m, 3H), 3.53-3.42 (m, 4H), 3.12-3.02 (m, 2H), 2.76-2.74 (m, 1H), 2.13-2.11 (m, 1H), 1.39-1.38 (m, 1H), 1.24 (s, 3H). |
| 386 | 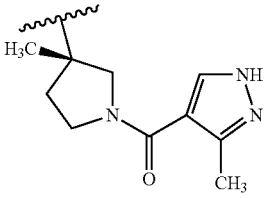 | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(3-methyl-1H-pyrazol-4-yl)methanone | 491.3 | ¹H NMR (400 MHz, Methanol-d₄) δ 8.77-8.76 (m, 2H), 7.90-7.80 (m, 1H), 7.38-7.35 & 4.02-4.01 (m, 1H), 4.24-4.15 (m, 1H), 3.75-3.59 (m, 12H), 3.15-3.12 (m, 2H), 2.56-2.39 (m, 4H), 2.13-2.12 (m, 1H), 1.44-1.30 (m, 3H). |

TABLE 2-continued

| Example No. | R | IUPAC Name | LRMS m/z [M + H]⁺ | ¹H NMR or LCMS retention time and method |
|---|---|---|---|---|
| 387 | (3S)-3-methyl-pyrrolidine with N-C(O)-(1H-pyrazol-4-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1H-pyrazol-4-yl)methanone | 477.2 | ¹H NMR (400 MHz, Methanol-d₄) δ 8.78-8.77 (m, 2H), 8.08-8.03 (m, 2H), 4.58-4.49 (m, 1H), 4.47-4.32 (m, 1H), 4.29-3.91 (m, 1H), 3.75-3.58 (m, 11H), 3.12-3.11 (m, 2H), 2.66-2.45 (m, 1H), 2.27-2.13 (m, 1H), 1.45-1.34 (m, 3H). |
| 388 | (3S)-3-methyl-pyrrolidine with N-C(O)-(1H-imidazol-2-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1H-imidazol-2-yl)methanone | 477.2 | ¹H NMR (400 MHz, CDCl₃) δ 11.06 (br s, 1H), 8.82 (s, 2H), 7.23-7.15 (m, 2H), 5.38 (s, 2H), 4.86-4.71 (m, 1H), 4.24-4.12 (m, 2H), 3.85-3.75 (m, 8H), 3.75-3.50 (m, 3H), 3.11 (t, J = 7.2 Hz, 2H), 2.65-2.50 (m, 1H), 2.25-1.95 (m, 1H), 1.43-1.39 (m, 3H). |
| 389 | (3S)-3-methyl-pyrrolidine with N-C(O)-(1H-pyrazol-3-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1H-pyrazol-3-yl)methanone | 477.2 | ¹H NMR (400 MHz, CDCl₃) δ 8.83 (s, 2H), 7.63-7.62 (m, 1H), 6.73-6.70 (m, 1H), 5.33 (s, 2H), 4.48-4.33 (m, 1H), 4.20-4.00 (m, 1H), 3.95-3.80 (m, 1H), 3.79-3.70 (m, 7H), 3.65-3.50 (m, 3H), 3.15-3.05 (m, 2H), 2.80-2.40 (m, 2H), 2.30-2.05 (m, 2H), 1.43-1.37 (m, 3H). |
| 390 | (3S)-3-methyl-pyrrolidine with N-C(O)-(1-methyl-1H-imidazol-2-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methyl-1H-imidazol-2-yl)methanone | 491.3 | ¹H NMR (400 MHz, CDCl₃) δ 8.82 (s, 2H), 7.07-6.94 (m, 2H), 5.26 (s, 2H), 4.61 (s, 1H), 4.25-4.05 (m, 1H), 3.99 (s, 3H), 3.85-3.70 (m, 7H), 3.70-3.50 (m, 3H), 3.11 (t, J = 8 Hz, 2H), 2.60-2.00 (m, 4H), 1.44-1.36 (m, 3H). |
| 391 | (3S)-3-methyl-pyrrolidine with N-C(O)-(1-methyl-1H-pyrazol-3-yl) | {(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}(1-methyl-1H-pyrazol-3-yl)methanone | 491.3 | ¹H NMR (400 MHz, Methanol-d₄) δ 8.79-8.78 (m, 2H), 7.67-7.63 (m, 1H), 6.74-6.71 (m, 1H), 4.60-4.36 (m, 1H), 4.33-3.98 (m, 2H), 3.97-3.87 (m, 3H), 3.77-3.71 (m, 10H), 3.69-3.61 (m, 1H), 3.29-3.13 (m, 2H), 2.60-2.57 (m, 1H), 2.21-2.12 (m, 1H), 1.45-1.39 (m, 3H). |

TABLE 2-continued

| Example No. | R | IUPAC Name | LRMS m/z [M + H]+ | ¹H NMR or LCMS retention time and method |
|---|---|---|---|---|
| 392 | (3S)-3-methyl-pyrrolidine with N-methylcarboximidamide | (3S)-3-[4-(2-aminopyrimidin-5-yl)-2-(morpholin-4-yl)-5,6-dihydro-7H-pyrrolo[2,3-d]pyrimidin-7-yl]-N,3-dimethylpyrrolidine-1-carboximidamide | 439.2 | ¹H NMR (400 MHz, D₂O) δ 8.60 (t, J = 4.6 Hz, 2H), 4.02-3.97 (m, 2H), 3.88-3.72 (m, 10 H), 3.54-3.53 (m, 2H), 3.06-3.03 (m, 2H), 2.84 (s, 3H), 2.73-2.70 (m, 1H), 2.30-2.27 (m, 1H), 1.52 (s, 3H). |
| 393 | (3R)-3-methylpyrrolidine with N-ethylcarboxamide | (3R)-3-[4-(2-aminopyrimidin-5-yl)-2-(morpholin-4-yl)-5,6-dihydro-7H-pyrrolo[2,3-d]pyrimidin-7-yl]-N-ethyl-3-methylpyrrolidine-1-carboxamide | 476.3 [M + 23] | ¹H NMR (400 MHz, DMSO + D₂O) δ 8.66 (s, 2H), 3.72-3.69 (m, 1H), 3.69-3.53 (m, 10H), 3.46-3.44 (m, 1H), 3.23-3.21 (m, 2H), 3.02-2.99 (m, 4H), 2.35-2.32 (m, 1H), 2.05-2.02 (m, 1H), 1.22 (s, 3H), 0.96 (t, J = 7.0 Hz, 3H). |
| 394 | (3R)-3-methylpyrrolidine with N-isopropylcarboxamide | (3R)-3-[4-(2-aminopyrimidin-5-yl)-2-(morpholin-4-yl)-5,6-dihydro-7H-pyrrolo[2,3-d]pyrimidin-7-yl]-3-methyl-N-(propan-2-yl)pyrrolidine-1-carboxamide | 490.4 [M + 23] | ¹H NMR (400 MHz, CDCl₃) δ 8.82 (s, 2H), 5.21 (s, 2H), 3.98-3.94 (m, 2H), 3.84-3.77 (m, 9H), 3.64-3.54 (m, 4H), 3.34-3.32 (m, 1H), 3.12-3.08 (m, 2H), 2.53-2.52 (m, 1H), 2.14-2.13 (m, 1H), 1.36 (s, 3H), 1.17 (d, J = 6.0, 6H). |
| 395 | (3S)-3-methylpyrrolidine with N-isopropylcarboxamide | (3S)-3-[4-(2-aminopyrimidin-5-yl)-2-(morpholin-4-yl)-5,6-dihydro-7H-pyrrolo[2,3-d]pyrimidin-7-yl]-3-methyl-N-(propan-2-yl)pyrrolidine-1-carboxamide | 468.1 | ¹H NMR (400 MHz, CDCl₃) δ 8.82 (s, 2H), 5.21 (s, 2H), 4.05-3.75 (m, 2H), 3.85-3.70 (m, 9H), 3.65-3.45 (m, 5H), 3.15-3.05 (m, 2H), 2.60-2.49 (m, 1H), 2.25-2.10 (m, 1H), 1.36 (s, 3H), 1.17 (d, J = 6.0 Hz, 6H). |
| 396 | (3R)-3-methylpyrrolidine with N-tert-butylcarboxamide | (3R)-3-[4-(2-aminopyrimidin-5-yl)-2-(morpholin-4-yl)-5,6-dihydro-7H-pyrrolo[2,3-d]pyrimidin-7-yl]-N-tert-butyl-3-methylpyrrolidine-1-carboxamide | 482.3 | ¹H NMR (400 MHz, DMSO-d₆) δ 8.72 (s, 2H), 7.00 (s, 2H), 5.24 (s, 1H), 3.68-3.61 (m, 11H), 3.47-3.45 (m, 1H), 3.28-3.20 (m, 2H), 3.03-2.99 (m, 2H), 2.37-2.34 (m, 1H), 2.08-2.06 (m, 1H), 1.20 (s, 12H). |

TABLE 2-continued

| Example No. | R | IUPAC Name | LRMS m/z [M + H]+ | 1H NMR or LCMS retention time and method |
|---|---|---|---|---|
| 397 | (3S)-3-methyl-N-tert-butyl pyrrolidine with carboxamide | (3S)-3-[4-(2-aminopyrimidin-5-yl)-2-(morpholin-4-yl)-5,6-dihydro-7H-pyrrolo[2,3-d]pyrimidin-7-yl]-N-tert-butyl-3-methylpyrrolidine-1-carboxamide | 482.2 | 1H NMR (400 MHz, DMSO-d6) δ 8.72 (s, 2H), 7.01 (brs, 2H), 5.33 (brs, 1H), 3.65-3.63 (m, 11H), 3.63-3.60 (m, 1H), 3.40-3.32 (m, 2H), 3.11-3.07 (m, 2H), 2.33-2.31 (m, 1H), 2.09-2.07 (m, 1H), 1.25 (s, 12H). |
| 398 | (3R)-3-methylpyrrolidinyl acetamide | 2-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}acetamide | 440.5 | 1H NMR (400 MHz, DMSO-d6) δ 8.65 (s, 2 H) 7.17 (d, J = 40.9 Hz, 2 H) 6.89 (s, 2 H) 3.45-3.68 (m, 11 H) 2.61-3.13 (m, 6 H) 2.31-2.41 (m, 2 H) 1.83-1.99 (m, 1 H) 1.30 (s, 3 H). |
| 399 | (3S)-3-methylpyrrolidinyl acetamide | 2-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}acetamide | 440.2 | 1H NMR (600 MHz, DMSO-d6) δ 8.70 (s, 2H), 7.12 (s, 1H), 7.06 (s, 1H), 6.95 (s, 2H), 3.66-3.53 (m, 9H), 3.10-3.02 (m, 2H), 3.02-2.95 (m, 2H), 2.88 (d, J = 9.3 Hz, 1H), 2.80-2.74 (m, 1H), 2.61-2.54 (m, 1H), 2.42-2.35 (m, 1H), 1.95-1.85 (m, 3H), 1.35 (s, 3H). |
| 400 | (3R)-3-methylpyrrolidinyl N-methylacetamide | 2-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-N-methylacetamide | 454.5 | 1H NMR (400 MHz, DMSO-d6) δ 8.72 (s, 2 H) 7.74 (br s, 1 H) 6.95 (s, 2 H) 3.49-3.74 (m, 11 H) 2.71-3.21 (m, 6 H) 2.62 (d, J = 4.5 Hz, 3 H) 2.33-2.49 (m, 2 H) 1.90-2.05 (m, 1 H) 1.37 (s, 3 H). |
| 401 | (3S)-3-methylpyrrolidinyl N-methylacetamide | 2-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-N-methylacetamide | 454.3 | 1H NMR (700 MHz, DMSO-d6) δ 8.72 (s, 2H), 7.86 (br s, 1H), 6.99 (s, 2H), 3.67-3.58 (m, 9.5H), 3.58-3.49 (m, 1.5H), 3.12-3.02 (m, 3.5H), 2.65-2.60 (m, 3H), 2.45 (br s, 1H), 2.03-1.95 (m, 1H), 1.36 (s, 3H), 1.22 (s, 0.5H). |

TABLE 2-continued

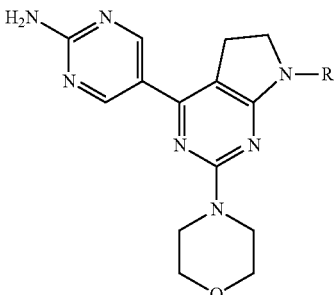

| Example No. | R | IUPAC Name | LRMS m/z [M + H]+ | 1H NMR or LCMS retention time and method |
|---|---|---|---|---|
| 402 | 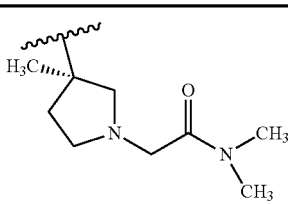 | 2-{(3R)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-N,N-dimethylacetamide | 468.2 | 1H NMR (400 MHz, DMSO-$d_6$) δ 8.72 (s, 2 H) 6.58 (s, 2 H) 3.60-3.69 (m, 10 H) 3.25-3.37 (m, 3 H) 3.21 (s, 1 H) 3.04-3.13 (m, 3 H) 2.86 (d, J = 9.3 Hz, 2 H) 2.78 (td, J = 8.4, 6.1 Hz, 2 H) 2.66 (td, J = 8.8, 5.7 Hz, 1 H) 2.45 (dd, J = 9.6, 3.5 Hz, 1 H) 1.94 (ddd, J = 13.1, 7.8, 5.7 Hz, 1 H) 1.89 (s, 2 H) 1.40 (s, 3 H). |
| 403 | 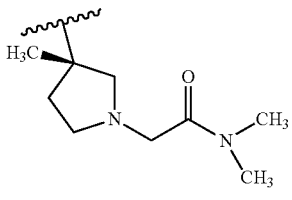 | 2-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-N,N-dimethylacetamide | 468.3 | 1H NMR (600 MHz, DMSO-$d_6$) δ 8.73 (s, 2H), 7.00 (s, 2H), 4.14-3.93 (m, 2H), 3.67-3.51 (m, 11H) 3.24-3.16 (m, 1H), 3.09 (t, J = 8.1 Hz, 2H), 2.94 (s, 3H), 2.86 (s, 3H), 2.57-2.51 (m, 1H), 2.09-2.03 (m 1H), 1.37 (s, 3H). |
| 404 | 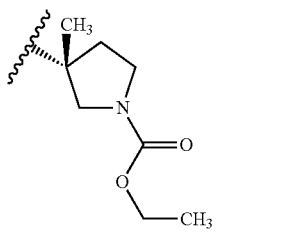 [SMILES: *[C@]1(C)CCN(C(=O)OCC)C1] | ethyl (3R)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 455.4 | 1H NMR (400 MHz, CDCl$_3$) δ 8.82 (s, 2H), 5.21 (br s, 2H), 4.15 (m, 2H), 3.83-3.82 (m, 2H), 3.77-3.76 (m 8H), 3.63-3.52 (m, 4H), 3.10-3.08 (m, 2H), 2.48-2.39 (m, 1H), 2.12-2.07 (m, 1H), 1.34 (s, 3H), 1.24 (m, 3H). |
| 405 | 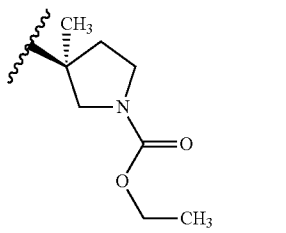 [SMILES: *[C@@]1(C)CCN(C(=O)OCC)C1] | ethyl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 477.1 [M + 23] | 1H NMR (400 MHz, CDCl$_3$) δ 8.83 (s, 2H), 5.19 (br s, 2H), 4.17-4.14 (m, 2H), 3.84-3.78 (m, 1H), 3.64-3.62 (m, 8H), 3.57-3.42 (m, 5H), 3.13-3.11 (m, 2H), 2.49-2.40 (m, 1H), 2.18-2.10 (m, 1H), 1.36 (s, 3H), 1.27 (q, J = 7.2 Hz, 3H). |
| 406 | 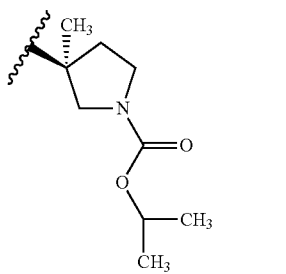 [SMILES: *[C@@]1(C)CCN(C(=O)OC(C)C)C1] | propan-2-yl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 469.2 | 1H NMR (400 MHz, CDCl$_3$) δ 8.82 (s, 2H), 5.19 (br s, 2H), 4.92-4.90 (m, 1H), 3.86-3.82 (m, 1H), 3.78-3.76 (m, 8H), 3.63-3.39 (m, 5H), 3.11-3.09 (m, 2H), 2.51-2.49 (m, 1H), 2.09-1.95 (m, 1H), 1.42-1.32 (m, 3H), 1.31-1.20 (m, 6H). |

TABLE 2-continued

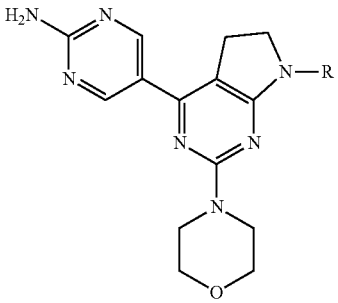

| Example No. | —R | IUPAC Name | LRMS m/z [M + H]⁺ | ¹H NMR or LCMS retention time and method |
|---|---|---|---|---|
| 407 | 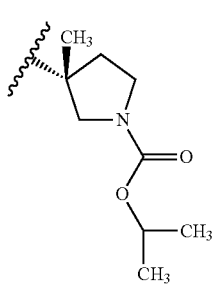 [SMILES: *[C@]1(C)CCN(C(=O)OC(C)C)C1] | propan-2-yl (3R)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 469.3 | ¹H NMR (400 MHz, CDCl₃) δ 8.82 (s, 2H), 5.20 (br s, 2H), 4.95-4.89 (m, 1H), 3.85-3.77 (m, 10H), 3.63-3.40 (m, 4H), 3.10-3.09 (m, 2H), 2.46-2.37 (m, 1H), 2.11-2.05 (m, 1H), 1.35-1.27 (m, 3H), 1.26-1.23 (m, 6H). |
| 408 | 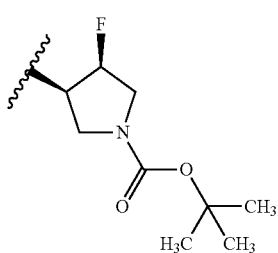 [SMILES: *[C@@H]1CN(C(=O)OC(C)(C)C)C[C@@H]1F] | tert-butyl (3R,4S)-3-[4-(2-aminopyrimidin-5-yl)-2-(morpholin-4-yl)-5,6-dihydro-7H-pyrrolo[2,3-d]pyrimidin-7-yl]-4-fluoropyrrolidine-1-carboxylate | 487.2 | ¹H NMR (400 MHz, CDCl₃) δ 8.86 (s, 2H), 5.37-5.25 (m, 3H), 4.73-4.65 (m, 1H), 3.91-3.87 (m, 1H), 3.78-3.59 (m, 13H), 3.18-3.17 (m, 2H), 1.49 (s, 9H). |
| 409 | 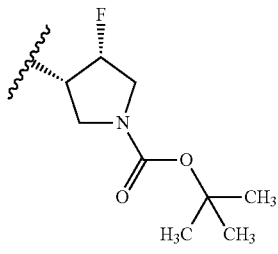 [SMILES: *[C@H]1CN(C(=O)OC(C)(C)C)C[C@H]1F] | tert-butyl (3S,4R)-3-[4-(2-aminopyrimidin-5-yl)-2-(morpholin-4-yl)-5,6-dihydro-7H-pyrrolo[2,3-d]pyrimidin-7-yl]-4-fluoropyrrolidine-1-carboxylate | 487.1 | ¹H NMR (400 MHz, CDCl₃) δ 8.86 (s, 2H), 5.35-5.24 (m, 3H), 4.72-4.64 (m, 1H), 3.90-3.88 (m, 1H), 3.77-3.14 (m, 13H), 3.19-3.14 (m, 2H), 1.48 (s, 9H). |
| 410 | 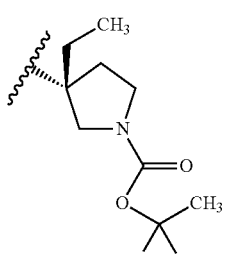 | tert-butyl (3R)-3-[4-(2-aminopyrimidin-5-yl)-2-(morpholin-4-yl)-5,6-dihydro-7H-pyrrolo[2,3-d]pyrimidin-7-yl]-3-ethylpyrrolidine-1-carboxylate | 497.2 | ¹H NMR (400 MHz, CDCl₃) δ ppm 8.83 (s, 2H), 5.18 (s, 2H), 3.97-3.89 (m, 1H), 3.76-3.72 (m, 9H), 3.67-3.64 (m, 1H), 3.41-3.38 (m, 3H), 3.14-3.10 (m, 2H), 2.78-2.46 (m, 1H), 2.08-1.96 (m, 3H), 1.47 (s, 9H), 0.91-0.86 (m, 3H). |

TABLE 2-continued

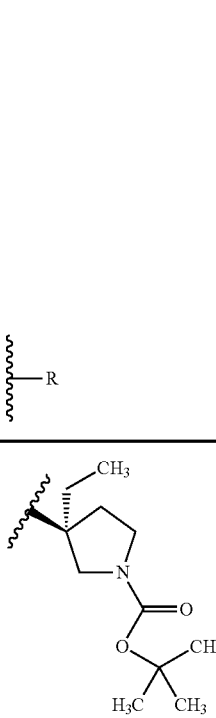

| Example No. | R | IUPAC Name | LRMS m/z [M + H]+ | 1H NMR or LCMS retention time and method |
|---|---|---|---|---|
| 411 | 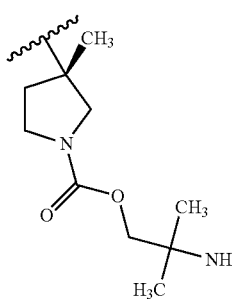 | tert-butyl (3S)-3-[4-(2-aminopyrimidin-5-yl)-2-(morpholin-4-yl)-5,6-dihydro-7H-pyrrolo[2,3-d]pyrimidin-7-yl]-3-ethylpyrrolidine-1-carboxylate | 497.3 | 1H NMR (400 MHz, CDCl3) δ 8.83 (s, 2H), 5.17 (s, 2H), 3.98-3.92 (m, 1H), 3.76-3.67 (m, 9H), 3.67-3.65 (m, 1H), 3.55-3.37 (m, 3H), 3.14-3.10 (m, 2H), 2.78-2.46 (m, 1H), 2.08-1.95 (m, 3H), 1.47 (s, 9H), 0.91-0.86 (m, 3H). |
| 412 | 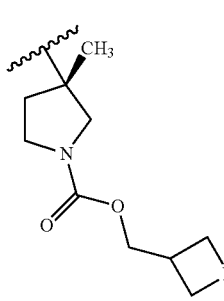 | 2-amino-2-methylpropyl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate hydrochloride | 498.3 | 1H NMR (400 MHz, D2O) δ 8.60-8.58 (m, 2H), 4.09-4.07 (m, 2H), 3.94-3.73 (m, 12H), 3.60-3.40 (m, 2H), 3.00-2.96 (m, 2H), 2.54-2.51 (m, 1H), 2.20-2.10 (m, 1H), 1.42 (s, 3H), 1.33 (s, 6H). |
| 413 | 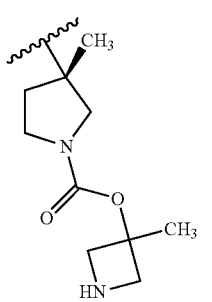 [SMILES: *[C@@]1(C)CCN(C(=O)OC2(C)CNC2)C1] | azetidin-3-ylmethyl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate hydrochloride | 496.2 | 1H NMR (400 MHz, D2O) δ 8.38 (s, 2H), 4.19-3.98 (m, 6H), 3.64-3.24 (m, 15H), 2.70-2.69 (m, 2H), 2.02-2.00 (m, 2H), 1.10 (s, 3H). |
| 414 | | 3-methylazetidin-3-yl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate hydrochloride | 496.1 | 1H NMR (400 MHz, Methanol-d4) δ 8.78 (s, 2H), 4.36-4.33 (m, 2H), 4.31-4.06 (m, 2H), 4.03-4.02 (m, 1H), 3.92-3.85 (m, 1H), 3.73-3.59 (m, 8H), 3.57-3.55 (m, 4H), 3.14-3.11 (m, 2H), 2.51-2.49 (m, 1H), 2.14-2.13 (m, 1H), 1.73-1.71 (d, J = 6.8 Hz, 3H), 1.73 (s, 3H). |

TABLE 2-continued

| Example No. | R | IUPAC Name | LRMS m/z [M + H]+ | 1H NMR or LCMS retention time and method |
|---|---|---|---|---|
| 415 | azetidin-3-yl, 3-methyl pyrrolidine with N-Boc-azetidine carbamate | azetidin-3-yl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate hydrochloride | 482.2 | 1H NMR (400 MHz, DMSO-d6 + D2O) δ 8.64 (s, 2H), 5.09-5.06 (m, 1H), 4.24-4.23 (m, 1H), 4.02-3.95 (m, 2H), 3.76-3.74 (m, 2H), 3.67-3.35 (m, 10H), 3.61-3.35 (m, 3H), 2.97-2.96 (m, 2H), 2.27-2.24 (m, 1H), 2.02-2.00 (m, 1H), 1.21 (s, 3H). |
| 416 | (3R)-1-methylpyrrolidin-3-yl carbamate, 3-methylpyrrolidine | (3R)-1-methylpyrrolidin-3-yl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 510.2 | 1H NMR (400 MHz, D2O) δ 8.54-8.53 (m, 2H), 5.31 (s, 1H), 3.81-3.39 (m, 18H), 2.96-2.94 (m, 5H), 2.49-2.12 (m, 4H), 1.31-1.28 (m, 3H). |
| 417 | (3S)-1-methylpyrrolidin-3-yl carbamate, 3-methylpyrrolidine | (3S)-1-methylpyrrolidin-3-yl (3S)-3-[4-(2-aminopyrimidin-5-yl)-2-(morpholin-4-yl)-5,6-dihydro-7H-pyrrolo[2,3-d]pyrimidin-7-yl]-3-methylpyrrolidine-1-carboxylate | 510.2 | 1H NMR (400 MHz, D2O) δ 8.57-8.56 (m, 2H), 5.38-5.34 (m, 1H), 3.88-3.66 (m, 14H), 3.47-3.46 (m, 4H), 3.02-3.01 (m, 5H), 2.73-2.19 (m, 4H), 1.36 (s, 3H). |
| 418 | 1,3-dimethylpyrrolidin-3-yl (S) | 5-{7-[(3S)-1,3-dimethylpyrrolidin-3-yl]-2-(morpholin-4-yl)-6,7-dihydro-5H-pyrrolo[2,3-d]pyrimidin-4-yl}pyrimidin-2-amine | 397.1 | 1H NMR (400 MHz, DMSO-d6) δ 8.73 (s, 2H), 7.02 (s, 2H), 3.65-3.46 (m, 14H), 3.11-3.10 (m, 2H), 2.80 (s, 3H), 2.61-2.57 (m, 1H), 2.13-2.09 (m, 1H), 1.39 (s, 3H). |
| 419 | 1,3-dimethylpyrrolidin-3-yl (R) | 5-{7-[(3R)-1,3-dimethylpyrrolidin-3-yl]-2-(morpholin-4-yl)-6,7-dihydro-5H-pyrrolo[2,3-d]pyrimidin-4-yl}pyrimidin-2-amine | 397.1 | 1H NMR (400 MHz, DMSO-d6) δ 8.72 (s, 2H), 7.01 (s, 2H), 3.64-3.49 (m, 14H), 3.11-3.06 (m, 2H), 2.78 (s, 3H), 2.61-2.58 (m, 1H), 2.12-1.97 (m, 1H), 1.39 (s, 3H). |

TABLE 2-continued

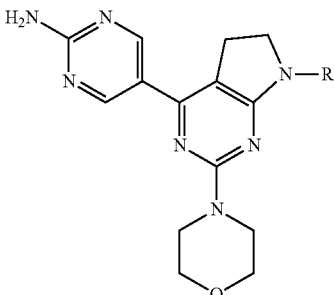

| Example No. | R | IUPAC Name | LRMS m/z [M + H]+ | 1H NMR or LCMS retention time and method |
|---|---|---|---|---|
| 420 | | 5-{7-[(3S)-3-methyl-1-(propan-2-yl)pyrrolidin-3-yl]-2-(morpholin-4-yl)-6,7-dihydro-5H-pyrrolo[2,3-d]pyrimidin-4-yl}pyrimidin-2-amine | 425.1 | 1H NMR (400 MHz, CDCl3) δ 8.74 (s, 2H), 5.20 (s, 2H), 4.31-4.32 (m, 1H), 3.89-3.49 (m, 11H), 3.45-3.32 (m, 1H), 3.26-3.21 (m, 1H), 3.15-2.94 (m, 3H), 2.44-2.37 (m, 1H), 2.26-2.17 (m, 1H), 1.50-1.24 (m, 9H). |
| 421 | | 5-{7-[(3S)-1-(2,2-difluoroethyl)-3-methylpyrrolidin-3-yl]-2-(morpholin-4-yl)-6,7-dihydro-5H-pyrrolo[2,3-d]pyrimidin-4-yl}pyrimidin-2-amine | 447.1 | 1H NMR (400 MHz, CDCl3) δ 8.81 (s, 2H), 6.02-5.74 (m, 1H), 5.21 (s, 2H), 3.76-3.92 (m, 8H), 3.72-3.60 (m, 2H), 3.25-3.35 (m, 1H), 3.10-2.82 (m, 7H), 2.52-2.48 (m, 1H), 2.00-1.95 (m, 1H), 1.40 (s, 3H). |
| 422 | | 1-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropan-2-ol | 455.2 | 1H NMR (400 MHz, CD2Cl2) δ 8.83 (s, 2H), 5.24 (s, 2H), 3.86-3.44 (m, 12H), 3.18-.2.89 (m, 5H), 2.65-2.50 (m, 1H), 2.19-2.02 (m, 1H), 1.47 (s, 3H), 1.36-1.16 (m 6H). |
| 423 | | methyl 2-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropanoate | 483.2 | 1H NMR (600 MHz, DMSO-d6) δ 8.71 (s, 2H), 6.95 (br s, 2H), 3.74-3.52 (m, 13H, partially overlapped with water), 3.19 (d, J = 9.2 Hz, 1H), 3.11-3.01 (m, 3H), 2.84-2.79 (m, 2H), 2.32-2.26 (m, 1H), 1.92-1.86 (m, 1H), 1.28-1.22 (m, 9H). |
| 424 | | 2-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}-2-methylpropanamide | 468.2 | 1H NMR (400 MHz, DMSO-d6) δ 8.72 (s, 2H), 6.94 (s, 4H), 3.66-3.56 (m, 10H), 3.10-3.01 (m, 3H), 2.90-2.86 (m, 1H), 2.77-2.63 (m, 2H), 2.37-2.29 (m, 1H), 1.96-1.87 (m, 1H), 1.35 (s, 3H), 1.14 (s, 3H), 1.12 (s, 3H). |

TABLE 2-continued

| Example No. | R | IUPAC Name | LRMS m/z [M + H]+ | 1H NMR or LCMS retention time and method |
|---|---|---|---|---|
| 425 | H3C, cyclopentyl-pyrrolidine-methyl | 5-{7-[(3S)-1-cyclopentyl-3-methylpyrrolidin-3-yl]-2-(morpholin-4-yl)-6,7-dihydro-5H-pyrrolo[2,3-d]pyrimidin-4-yl}pyrimidin-2-amine | 451.2 | 1H NMR (400 MHz, CDCl3) δ 8.82 (s, 2H), 5.32 (s, 2H), 4.49-4.36 (m, 1H), 3.87-3.64 (m, 11H), 3.41-3.37 (m, 2H), 3.15-3.01 (m, 3H), 2.54-2.45 (m, 1H), 2.36-2.18 (m, 1H), 2.06-1.94 (m, 6H), 1.65-1.55 (m, 2H), 1.51 (s, 3H). |
| 426* | H3C, methylpyrrolidinone pyrrolidine | (3S)-3-[4-(2-aminopyrimidin-5-yl)-2-(morpholin-4-yl)-5,6-dihydro-7H-pyrrolo[2,3-d]pyrimidin-7-yl]-1',3-dimethyl-1,3'-bipyrrolidin-2'-one | 480.2 | 1H NMR (400 MHz, Methanol-d4) δ 8.79 (s, 2 H), 3.77-3.75 (m, 8 H), 3.71-3.68 (m, 2 H), 3.46-3.37 (m, 5 H), 3.14-3.10 (m, 2 H), 3.05-3.00 (m, 1 H), 2.86 (s, 4H), 2.60-2.50 (m, 1 H), 2.30-2.20 (m, 1 H), 2.05-1.92 (m, 2 H), 1.44 (s, 3 H). |
| 427* | H3C, methylpyrrolidinone pyrrolidine | (3S)-3-[4-(2-aminopyrimidin-5-yl)-2-(morpholin-4-yl)-5,6-dihydro-7H-pyrrolo[2,3-d]pyrimidin-7-yl]-1',3-dimethyl-1,3'-bipyrrolidin-2'-one | 480.2 | 1H NMR (400 MHz, Methanol-d4) δ 8.79 (s, 2 H), 4.08-4.04 (m, 1 H), 3.76-3.65 (m, 11 H), 3.43-3.41 (m, 2 H), 3.25-3.12 (m, 5 H), 2.88 (s, 3 H), 2.58-2.55 (m, 1 H), 2.40-2.30 (m, 1 H), 2.10-2.03 (m, 2 H), 1.45 (s, 3 H). |
| 428* | H3C, piperidinone pyrrolidine | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}piperidin-2-one | 480.2 | 1H NMR (400 MHz, Methanol-d4) δ 8.81 (s, 2H), 3.76-3.63 (m, 9H), 3.50-3.35 (m, 4H), 3.30-3.15 (m, 6H), 2.70-2.65 (m, 1H), 2.23-2.19 (m, 1H), 2.12-2.00 (m, 2H), 1.96-1.90 (m, 2H), 1.49 (s, 3H). |
| 429* | H3C, piperidinone pyrrolidine | 3-{(3S)-3-[4-(2-aminopyrimidin-5-yl)-2-(morpholin-4-yl)-5,6-dihydro-7H-pyrrolo[2,3-d]pyrimidin-7-yl]-3-methylpyrrolidin-1-yl}piperidin-2-one | 480.2 | 1H NMR (400 MHz, Methanol-d4) δ 8.80 (s, 2H), 4.20-4.16 (m, 1H), 3.75-3.63 (m, 10H), 3.33-3.13 (m, 8H), 2.59-2.55 (m, 1H), 2.23-2.19 (m, 1H), 2.12-2.00 (m, 2H), 1.90-1.82 (m, 2H), 1.47 (s, 3H). |

TABLE 2-continued

| Example No. | R | IUPAC Name | LRMS m/z [M + H]⁺ | ¹H NMR or LCMS retention time and method |
|---|---|---|---|---|
| 430 | 4-methylpiperidin-4-yl (NH) | 5-[7-(4-methylpiperidin-4-yl)-2-(morpholin-4-yl)-6,7-dihydro-5H-pyrrolo[2,3-d]pyrimidin-4-yl]pyrimidin-2-amine hydrochloride | 397.1 | ¹H NMR (400 MHz, Methanol-d₄) δ 8.84 (s, 2H), 3.96-3.92 (m, 2H), 3.81-3.72 (m, 10H), 3.31-3.23 (m, 2H), 3.18-3.09 (m, 2H), 2.92-2.82 (m, 2H), 2.09-2.04 (m, 2H), 1.51 (s, 3H). |
| 431* | 3-methylpiperidin-3-yl | 5-[7-(3-methylpiperidin-3-yl)-2-(morpholin-4-yl)-6,7-dihydro-5H-pyrrolo[2,3-d]pyrimidin-4-yl]pyrimidin-2-amine hydrochloride | 397.1 | ¹H NMR (400 MHz, Methanol-d₄) δ 8.89 (s, 2H), 4.00-3.83 (m, 11H), 3.42-3.38 (m, 1H), 3.24-3.14 (m, 4H), 2.49-2.45 (m, 1H), 2.04-1.99 (m, 2H), 1.82-1.80 (m, 1H), 1.48 (s, 3H). |
| 432* | 3-methylpiperidin-3-yl | 5-[7-(3-methylpiperidin-3-yl)-2-(morpholin-4-yl)-6,7-dihydro-5H-pyrrolo[2,3-d]pyrimidin-4-yl]pyrimidin-2-amine hydrochloride | 397.1 | ¹H NMR (400 MHz, Methanol-d₄) δ 8.89 (s, 2H), 4.00-3.76 (m, 11H), 3.39-3.34 (m, 1H), 3.23-3.14 (m, 4H), 2.49-2.45 (m, 1H), 2.04-1.99 (m, 2H), 1.82-1.79 (m, 1H), 1.48 (s, 3H). |
| 433 | N-Boc-4-methylpiperidin-4-yl | tert-butyl 4-[4-(2-aminopyrimidin-5-yl)-2-(morpholin-4-yl)-5,6-dihydro-7H-pyrrolo[2,3-d]pyrimidin-7-yl]-4-methylpiperidine-1-carboxylate | 497.2 | ¹H NMR (400 MHz, Methanol-d₄) δ 8.77 (s, 2H), 3.74-3.71 (m, 10H), 3.70-3.63 (m, 2H), 3.31-3.19 (m, 2H), 3.10-3.06 (m, 2H), 2.73-2.70 (m, 2H), 1.65-1.55 (m, 2H), 1.46 (s, 9H), 1.29 (s, 3H). |
| 434** | N-Boc-3-methylpiperidin-3-yl | tert-butyl 3-[4-(2-aminopyrimidin-5-yl)-2-(morpholin-4-yl)-5,6-dihydro-7H-pyrrolo[2,3-d]pyrimidin-7-yl]-3-methylpiperidine-1-carboxylate | 497.2 | ¹H NMR (400 MHz, Methanol-d₄) δ 8.78 (s, 2H), 3.76-3.70 (m, 12H), 3.09-3.05 (m, 3H), 1.67-1.65 (m, 4H), 1.50-1.35 (m, 13H). |

TABLE 2-continued

| Example No. | R | IUPAC Name | LRMS m/z [M + H]+ | 1H NMR or LCMS retention time and method |
|---|---|---|---|---|
| 435** | | 5-{7-[3-(methylsulfonyl)-3-azabicyclo[3.1.0]hex-1-yl]-2-(morpholin-4-yl)-6,7-dihydro-5H-pyrrolo[2,3-d]pyrimidin-4-yl}pyrimidin-2-amine | 481.1 [M + 23] | 1H NMR (400 MHz, CDCl3) δ 8.83 (s, 2H), 5.27 (s, 2H), 3.78-3.68 (m, 8H), 3.66-3.65 (m, 2H), 3.60-3.57 (m, 3H), 3.42-3.40 (m, 1H), 3.16-3.12 (m, 2H), 2.85 (s, 3H), 2.0 (s, 1H), 1.24 (m, 1H), 1.15-1.06 (m, 1H). |
| 436 | | 5-{7-[(1S,5R)-3-(methylsulfonyl)-3-azabicyclo[3.1.0]hex-1-yl]-2-(morpholin-4-yl)-6,7-dihydro-5H-pyrrolo[2,3-d]pyrimidin-4-yl}pyrimidin-2-amine | 459.1 | 1H NMR (400 MHz, CDCl3) δ 8.83 (s, 2H), 5.21 (s, 2H), 3.78-3.68 (m, 8H), 3.66-3.57 (m, 5H), 3.42-3.40 (m, 1H), 3.16-3.12 (m, 2H), 2.85 (s, 3H), 2.0 (s, 1H), 1.24 (m, 1H), 1.14-1.12 (m, 1H). |
| 437 | | 5-{7-[(1R,5S)-3-(methylsulfonyl)-3-azabicyclo[3.1.0]hex-1-yl]-2-(morpholin-4-yl)-6,7-dihydro-5H-pyrrolo[2,3-d]pyrimidin-4-yl}pyrimidin-2-amine | 459.1 | 1H NMR (400 MHz, CDCl3) δ 8.84 (s, 2H), 5.24 (s, 2H), 3.78-3.70 (m, 8H), 3.69-3.64 (m, 2H), 3.61-3.57 (m, 3H), 3.42-3.40 (m, 1H), 3.16-3.12 (m, 2H), 2.85 (s, 3H), 2.0 (s, 1H), 1.28-1.20 (m, 1H), 1.14-1.12 (m, 1H). |
| 438 | | tert-butyl (1S,4S,5S)-5-[4-(2-aminopyrimidin-5-yl)-2-(morpholin-4-yl)-5,6-dihydro-7H-pyrrolo[2,3-d]pyrimidin-7-yl]-2-azabicyclo[2.1.1]hexane-2-carboxylate | 481.2 | 1H NMR (400 MHz, DMSO-d6) δ 8.73 (s, 2H), 7.02 (s, 2H), 4.43-4.39 (m, 1H), 3.63-3.61 (m, 8H), 3.39-3.34 (m, 1H), 3.27-3.07 (m, 8H), 1.74-1.72 (m, 1H), 1.42 (s, 9H). |

TABLE 2-continued

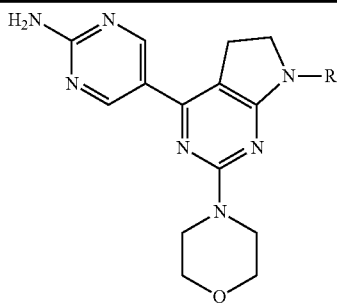

| Example No. | R | IUPAC Name | LRMS m/z [M + H]+ | 1H NMR or LCMS retention time and method |
|---|---|---|---|---|
| 439* | 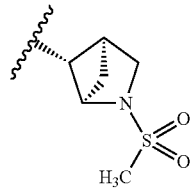 [SMILES: *[C@@H]1[C@@H]2C[C@H]1N(S(C)(=O)=O)C2] | 5-{7-[(1R,4R,5R)-2-(methylsulfonyl)-2-azabicyclo[2.1.1]hex-5-yl]-2-(morpholin-4-yl)-6,7-dihydro-5H-pyrrolo[2,3-d]pyrimidin-4-yl}pyrimidin-2-amine | 459.1 | 1H NMR (400 MHz, DMSO-d6) δ 8.73 (s, 2H), 7.02 (s, 2H), 4.41-4.39 (m, 1H), 3.62-3.60 (m, 8H), 3.50-3.43 (m, 1H), 3.43-3.40 (m, 2H), 3.17-3.16 (m, 1H), 3.15-3.12 (m, 4H), 2.98 (s, 3H), 1.73-1.70 (m, 1H), 1.50-1.48 (m, 1H). |
| 440* | 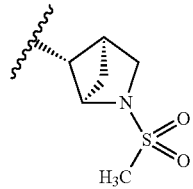 | 5-{7-[(1R,4R,5R)-2-(methylsulfonyl)-2-azabicyclo[2.1.1]hex-5-yl]-2-(morpholin-4-yl)-6,7-dihydro-5H-pyrrolo[2,3-d]pyrimidin-4-yl}pyrimidin-2-amine | 459.2 | 1H NMR (400 MHz, DMSO-d6) δ 8.73 (s, 2H), 7.02 (s, 2H), 4.41-4.39 (m, 1H), 3.63-3.60 (m, 8H), 3.49-3.41 (m, 1H), 3.40-3.37 (m 2H), 3.24-3.22 (m, 1H), 3.17-3.12 (m, 4H), 2.98 (s, 3H), 1.73-1.71 (m, 1H), 1.50-1.48 (m, 1H). |
| 441 | 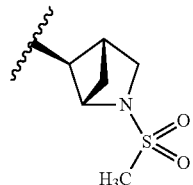 | 5-{7-[(1S,4S,5S)-2-(methylsulfonyl)-2-azabicyclo[2.1.1]hex-5-yl]-2-(morpholin-4-yl)-6,7-dihydro-5H-pyrrolo[2,3-d]pyrimidin-4-yl}pyrimidin-2-amine | 459.2 | 1H NMR (400 MHz, DMSO-d6) δ 8.72 (s, 2H), 6.99 (s, 2H), 4.39-4.37 (m, 1H), 3.62-3.60 (m, 8H), 3.60-3.45 (m, 1H), 3.47-3.33 (m, 3H), 3.24-3.22 (m, 1H), 3.15-3.10 (m, 3H), 2.96 (s, 3H), 1.71-1.70 (m, 1H), 1.49-1.47 (m, 1H). |

*Compounds are single enantiomers; however, absolute stereochemistry is unknown.
**Compounds are racemates The compounds of Table 3 are prepared according to the general procedures shown in Scheme A, which would be understood by one of ordinary skill in the art.

TABLE 3

| Example No. | R | IUPAC Name | LRMS m/z [M + H]+ | 1H NMR or LCMS retention time and method |
|---|---|---|---|---|
| 442 | cis-cyclobutyl-NH2 | 5-{7-(cis-3-aminocyclobutyl)-2-[(3S)-3-methylmorpholin-4-yl]-6,7-dihydro-5H-pyrrolo[2,3-d]pyrimidin-4-yl}pyrimidin-2-amine hydrochloride | 383.1 | 1H NMR (400 MHz, Methanol-d4) δ 8.74 (s, 2H), 4.71-4.67 (m, 2H), 4.15-4.10 (m, 1H), 4.04-4.00 (m, 3H), 3.85-3.50 (m, 5H), 3.21-3.17 (m, 2H), 2.77-2.74 (m, 2H), 2.61-2.58 (m, 2H), 1.42 (d, J = 6.8 Hz, 3H). |
| 443 | trans-cyclobutyl-NH2 | 5-{7-(trans-3-aminocyclobutyl)-2-[(3S)-3-methylmorpholin-4-yl]-6,7-dihydro-5H-pyrrolo[2,3-d]pyrimidin-4-yl}pyrimidin-2-amine hydrochloride | 383.1 | 1H NMR (400 MHz, D2O) δ 8.65 (s, 2H), 5.08-5.00 (m, 1H), 4.61 (s, 1H), 4.06-3.97 (m, 5H), 3.90-3.70 (m, 2H), 3.70-3.50 (m, 2H), 3.15-2.90 (m, 4H), 2.61-2.57 (m, 2H), 1.36 (d, J = 6.8 Hz, 3H). |
| 444 | cis-cyclobutyl-NHCH3 | 5-{7-[cis-3-(methylamino)cyclobutyl]-2-[(3S)-3-methylmorpholin-4-yl]-6,7-dihydro-5H-pyrrolo[2,3-d]pyrimidin-4-yl}pyrimidin-2-amine hydrochloride | 397.1 | 1H NMR (400 MHz, Methanol-d4) δ 8.74 (s, 2H), 4.72-4.67 (m, 2H), 4.13-4.10 (m, 1H), 4.05-4.01 (m, 3H), 3.82-3.77 (m, 2H), 3.61-3.50 (m, 3H), 3.21-3.17 (m, 2H), 2.78-2.75 (m, 2H), 2.69 (s, 3H), 2.69-2.65 (m, 2H), 1.42 (d, J = 6.8 Hz, 3H). |
| 445 | trans-cyclobutyl-NHCH3 | 5-{7-[trans-3-(methylamino)cyclobutyl]-2-[(3S)-3-methylmorpholin-4-yl]-6,7-dihydro-5H-pyrrolo[2,3-d]pyrimidin-4-yl}pyrimidin-2-amine hydrochloride | 397.1 | 1H NMR (400 MHz, D2O) δ 8.66 (s, 2H), 4.99-4.97 (m, 1H), 4.65-4.55 (m, 1H), 4.06-3.84 (m, 8H), 3.80-3.64 (m, 2H), 3.11-3.09 (m, 2H), 2.94-2.93 (m, 2H), 2.69 (s, 3H), 2.67-2.64 (m, 2H), 1.36 (d, J =7.2 Hz, 3H). |
| 446 | trans-cyclobutyl-NHBoc | tert-butyl (trans-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl)carbamate | 483.2 | 1H NMR (400 MHz, Methanol-d4) δ 8.80 (s, 2H), 4.75-4.70 (m, 2H), 4.34 (d, J = 12.6 Hz, 1H), 4.10 (s, 1H), 3.94 (d, J = 4 Hz, 1H), 3.79-3.71 (m, 4H), 3.60-3.50 (m, 1H), 3.22-3.14 (m, 3H), 2.74-2.71 (m, 2H), 2.27-2.23 (m, 2H), 1.47 (s, 9H), 1.26 (d, J = 6.8 Hz, 3H). |

TABLE 3-continued

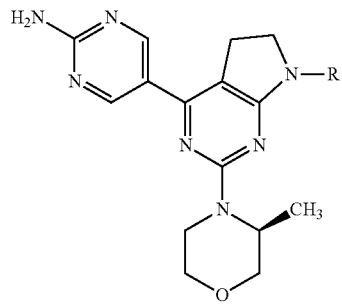

| Example No. | R 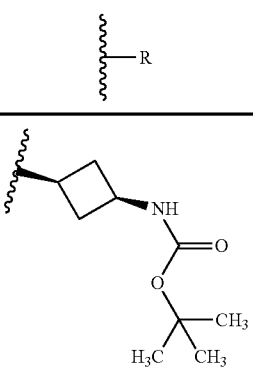 | IUPAC Name | LRMS m/z [M + H]+ | 1H NMR or LCMS retention time and method |
|---|---|---|---|---|
| 447 | 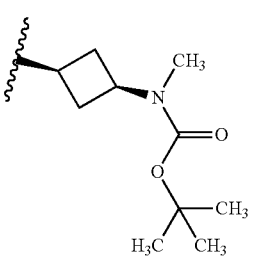 [SMILES: *[C@H]1C[C@@H](N(C)C(=O)OC(C)(C)C)C1] | tert-butyl (cis-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl) carbamate | 483.2 | 1H NMR (400 MHz, Methanol-d4) δ 8.80 (s, 2H), 4.36-4.26 (m, 2H), 3.94-3.90 (m, 1H), 3.79-3.66 (m, 5H), 3.55-3.50 (m, 1H), 3.25-3.15 (m, 4H), 2.58-2.54 (m, 2H), 2.26-2.23 (m, 2H), 1.46 (s, 9H), 1.27 (d, J = 6.4 Hz, 3H). |
| 448 | 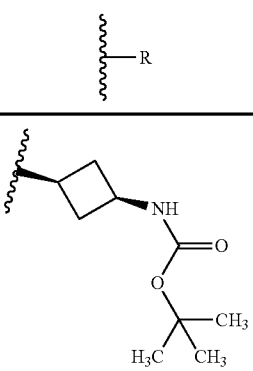 | tert-butyl (cis-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl)methyl carbamate | 497.2 | 1H NMR (400 MHz, Methanol-d4) δ 8.81 (s, 2H), 4.36-4.33 (m, 1H), 4.22-4.18 (m, 2H), 3.97-3.95 (m, 1H), 3.79-3.69 (m, 4H), 3.55-3.50 (m, 1H), 3.25-3.16 (m, 4H), 2.88 (s, 3H), 2.52-2.48 (m, 4H), 1.49 (s, 9H), 1.27 (d, J = 6.4 Hz, 3H). |
| 449 | 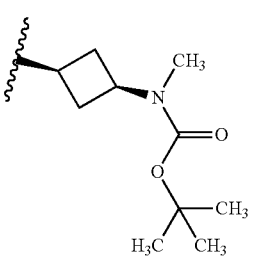 [SMILES: *[C@H]1C[C@@H](N(C)C(=O)OC(C)(C)C)C1] | tert-butyl (trans-3-{4-(2-aminopyrimidin-5-yl)-2-[(3S)-3-methylmorpholin-4-yl]-5,6-dihydro-7H-pyrrolo[2,3-d]pyrimidin-7-yl}cyclobutyl)methyl carbamate | 497.3 | 1H NMR (400 MHz, CDCl3) δ 8.85 (s, 2H), 5.22 (br s, 2H), 4.89-4.69 (m, 2H), 4.60-4.51 (m, 1H), 4.37-4.34 (m, 1H), 3.96-3.95 (m, 1H), 3.75-3.71 (m, 4H), 3.60-3.52 (m, 1H), 3.17-3.15 (m, 3H), 2.92 (s, 3H), 2.60-2.55 (m, 4H), 1.47 (s, 9H), 1.27 (d, J = 6.4 Hz, 3H). |
| 450 | 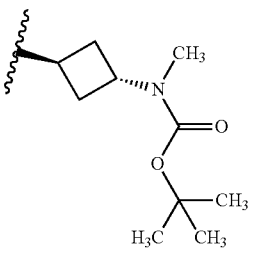 [SMILES: *[C@H]1C[C@H](N(C)C(=O)OC(C)(C)C)C1] | 5-{7-(3-methylazetidin-3-yl)-2-[(3S)-3-methylmorpholin-4-yl]-6,7-dihydro-5H-pyrrolo[2,3-d]pyrimidin-4-yl}pyrimidin-2-amine hydrochloride | 383.2 | 1H NMR (400 MHz, DMSO-d6) δ 8.72 (s, 2H), 4.55-4.45 (m, 1H), 4.28-4.22 (m, 2H), 4.20-4.15 (m, 1H), 3.90-3.85 (m, 1H), 3.72-3.70 (m, 2H), 3.55-3.35 (m, 5H), 3.15-3.00 (m, 3H), 1.48 (m, 3H), 1.13 (d, J = 6.4 Hz, 3H). |
| 451 | 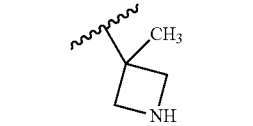 | 1-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)ethanone | 410.9 | 1H NMR (400 MHz, D2O) δ 8.55 (s, 2H), 4.45-4.35 (m, 1H), 4.05 (d, J = 12.8 Hz, 1H), 4.92-3.83 (m, 4H), 3.80-3.65 (m, 2H), 3.60-3.50 (m, 2H), 3.40-3.35 (m, 3H), 2.96 (t, J = 7.2 Hz, 2H), 2.65-2.50 (m, 1H), 2.25-2.10 (m, 1H), 1.44 (s, 3H), 1.25 (d, J = 6.8 Hz, 3H). |

TABLE 3-continued

| Example No. | R | IUPAC Name | LRMS m/z [M + H]+ | 1H NMR or LCMS retention time and method |
|---|---|---|---|---|
| 452 | 3-methyl-3-(acetylazetidine) | 1-(3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidin-1-yl)ethanone | 425.2 | 1H NMR (400 MHz, DMSO-d6): δ 8.74 (s, 2H), 7.04 (s, 2H), 4.58-4.42 (m, 2H), 4.24-4.15 (m, 2H), 4.01 (d, J = 8.4 Hz, 1H), 3.94-3.87 (m, 1H), 3.72 (t, J = 9.2 Hz, 2H), 3.62-3.48 (m, 3H), 3.46-3.42 (m, 1H), 3.15-3.02 (m, 3H), 1.80 (s, 3H), 1.46 (s, 3H), 1.16 (d, J = 6.4 Hz, 3H). |
| 453 | azetidin-3-yl isobutyryl | 1-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-2-methylpropan-1-one | 439.1 | 1H NMR (400 MHz, DMSO-d6) δ 8.74 (s, 2H), 7.04 (s, 2H), 4.82-4.72 (m, 1H), 4.60 (br s, 1H), 4.47-4.32 (m, 2H), 4.25-4.13 (m, 2H), 4.09-4.00 (m, 1H), 3.88 (d, J = 9 Hz, 1H), 3.73-3.64 (m, 3H), 3.56 (d, J = 10.5 Hz, 1H), 3.33-3.25 (m, 1H), 3.15 (t, J = 7.8 Hz, 2H), 3.07 (t, J = 11.3 Hz, 1H), 2.48-2.43 (m, 1H), 1.18-1.12 (m, 3H), 1.02-0.94 (m, 6H). |
| 454 | azetidin-3-yl 2-hydroxy-2-methylpropanoyl | 1-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-2-hydroxy-2-methylpropan-1-one | 455.1 | 1H NMR (400 MHz, Methanol-d4) δ 8.82 (s, 2H), 4.89-4.72 (m, 4H), 4.45-4.20 (m, 3H), 4.00-3.90 (m, 1H), 3.78-3.71 (m, 4H), 3.55-3.45 (m, 1H), 3.24-3.19 (m, 3H), 1.41 (s, 3H), 1.40 (s, 3H), 1.26 (d, J = 6.8 Hz, 3H). |
| 455 | 3-methyl-3-(2-hydroxy-2-methylpropanoyl)azetidine | 1-(3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidin-1-yl)-2-hydroxy-2-methylpropan-1-one | 469.2 | 1H NMR (400 MHz, Methanol-d4) δ 8.81 (s, 2H), 4.70-4.60 (m, 2H), 4.47-4.29 (m, 3H), 3.95-3.85 (m, 2H), 3.80-3.65 (m, 2H), 3.61-3.50 (m, 3H), 3.21-3.17 (m, 3H), 1.56 (s, 3H), 1.42 (s, 3H), 1.39 (s, 3H), 1.27 (d, J = 6.4 Hz, 3H). |

TABLE 3-continued

| Example No. | R | IUPAC Name | LRMS m/z [M + H]+ | 1H NMR or LCMS retention time and method |
|---|---|---|---|---|
| 456 | azetidine with 3-CH3 and N-C(O)-C(CH3)2-NH2 | 2-amino-1-(3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidin-1-yl)-2-methylpropan-1-one hydrochloride | 468.3 | 1H NMR (400 MHz, D2O) δ 8.57 (s, 2H), 4.92 (d, J = 9.6 Hz, 2H), 4.50 (m, 2H), 3.95-4.05 (m, 7H), 3.31-3.69 (m, 2H), 3.06 (m, 2H), 1.52-1.61 (m, 9H), 1.30 (d, J = 5.6 Hz, 3H). |
| 457 | azetidine with N-C(O)-CH2-NH-C(O)-CH2CH3 | N-[2-(3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)-2-oxoethyl]propanamide | 504.1 [M + 23] | 1H NMR (400 MHz, DMSO-d6/D2O) δ 8.96 (s, 2H), 8.00 (s, 1H), 4.78-4.38 (m, 1H), 4.36-4.16 (m, 2H), 4.15-4.18 (m, 2H), 3.67-3.65 (m, 4H), 3.60-3.51 (m, 8H), 3.10 (t, J = 8.4 Hz, 2H), 2.14 (t, J = 8 Hz, 2H), 0.98 (t, J = 7.6 Hz, 3H). |
| 458 | azetidine with N-C(O)-(1-methylcyclopropyl) | (3-{4-(2-aminopyrimidin-5-yl)-2-[(3S)-3-methylmorpholin-4-yl]-5,6-dihydro-7H-pyrrolo[2,3-d]pyrimidin-7-yl}azetidin-1-yl)(1-methylcyclopropyl)methanone | 451.1 | 1H NMR (400 MHz, CDCl3): δ 8.78 (s, 2H), 5.17 (s, 2H), 4.78-4.76 (m, 1H), 4.64-4.62 (m, 1H), 4.45-4.25 (m, 5H), 3.91-3.85 (m, 1H), 3.68-3.62 (m, 4H), 3.48-3.42 (m, 1H), 3.14-3.10 (m, 3H), 1.25 (s, 3H), 1.20 (d, J = 6.8 Hz, 3H), 1.03-1.01 (m, 2H), 0.47-0.45 (m, 2H). |
| 459 | azetidine with 3-CH3 and N-C(O)-(1-methylcyclopropyl) | (3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidin-1-yl)(1-methylcyclopropyl)methanone | 465.1 | 1H NMR (400 MHz, Methanol-d4) δ 8.70 (s, 2H), 4.54-4.50 (m, 2H), 4.30-4.17 (m, 3H), 3.86-3.70 (m, 2H), 3.68-3.55 (m, 2H), 3.50-3.40 (m, 3H), 3.09-3.05 (m, 3H), 1.46 (s, 3H), 1.23 (s, 3H), 1.15 (d, 3H, J = 6.8 Hz), 0.93-0.92 (m, 2H), 0.49-0.47 (m, 2H). |

TABLE 3-continued

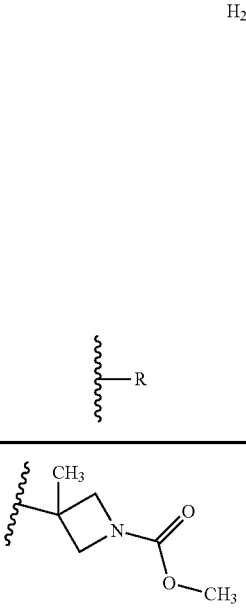

| Example No. | R | IUPAC Name | LRMS m/z [M + H]⁺ | ¹H NMR or LCMS retention time and method |
|---|---|---|---|---|
| 460 | 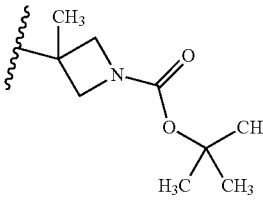 | methyl 3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidine-1-carboxylate | 441.1 | ¹H NMR (400 MHz, DMSO-d₆) δ 8.73 (s, 2H), 7.03 (s, 2H), 4.53-4.45 (br s, 1H), 4.53-4.45 (br s, 2H), 4.18 (d, J = 12.8 Hz, 1H), 3.90 (d, J = 9.2 Hz, 1H), 3.83-3.74 (br s, 2H), 3.70 (d, J = 11.2 Hz, 1H), 3.61-3.49 (m, 7H), 3.15-3.0 (m, 3H), 1.46 (s, 3H), 1.15 (d, J = 6.4 Hz, 3H). |
| 461 | 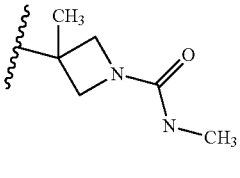 | tert-butyl 3-{4-(2-aminopyrimidin-5-yl)-2-[(3S)-3-methylmorpholin-4-yl]-5,6-dihydro-7H-pyrrolo[2,3-d]pyrimidin-7-yl}-3-methylazetidine-1-carboxylate | 483.1 | ¹H NMR: (400 MHz, DMSO-d₆) δ 8.73 (s, 2H), 7.03 (s, 2H), 4.51-4.49 (m, 1H), 4.20 (d, J = 8.8 Hz, 3H), 3.91-3.86 (m, 1H), 3.74-3.69 (m, 3H), 3.59-3.57 (m, 1H), 3.52-3.45 (m, 3H), 3.14-3.10 (m, 3H), 1.45 (s, 3H), 1.40 (s, 9H), 1.15 (d, J = 6.8 Hz, 3H). |
| 462 | 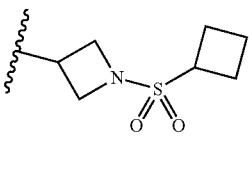 [SMILES: *C1CN(S(=O)(=O)C2CCC2)C1] | 3-{4-(2-aminopyrimidin-5-yl)-2-[(3S)-3-methylmorpholin-4-yl]-5,6-dihydro-7H-pyrrolo[2,3-d]pyrimidin-7-yl}-N,3-dimethylazetidine-1-carboxamide | 440.0 | ¹H NMR (400 MHz, DMSO-d₆) δ 8.73 (s, 2H), 7.02 (s, 2H), 6.33 (br s, 1H), 4.51 (br s, 1H), 4.20 (d, J = 14 Hz, 1H), 4.11 (t, J = 7.6 Hz, 2H), 3.93-3.86 (m, 1H), 3.73-3.62 (m, 5H), 3.61-3.56 (m, 1H), 3.13-3.03 (m, 4H), 2.56-2.53 (m, 3H), 1.44 (s, 3H), 1.16 (d, J = 6.4 Hz, 3H). |
| 463 | 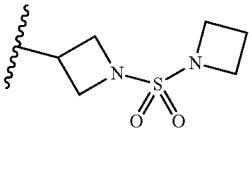 [SMILES: *C1CN(S(=O)(=O)N2CCC2)C1] | 5-{7-[1-(cyclobutylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 487.1 | ¹H NMR (400 MHz, DMSO-d₆) δ 8.75 (s, 2H), 7.04 (s, 2H), 4.83-4.80 (m, 1H), 4.80-4.21 (m, 1H), 4.21-4.13 (m, 4H), 3.99-3.97 (m, 2H), 3.71-3.68 (m, 1H), 3.58-3.57 (m, 3H), 3.57-3.55 (m, 1H), 3.18-3.14 (m, 4H), 2.34-2.27 (m, 4H), 2.26-1.99 (m, 2H), 1.16 (d, J = 6.4 Hz, 3H). |
| 464 |  | 5-{7-[1-(azetidin-1-ylsulfonyl)azetidin-3-yl]-2-[(3S)-3-methylmorpholin-4-yl]-6,7-dihydro-5H-pyrrolo[2,3-d]pyrimidin-4-yl}pyrimidin-2-amine | 488.1 | ¹H NMR (400 MHz, CDCl₃) δ 8.84 (s, 2H), 5.22 (s, 2H), 4.93-4.66 (m, 3H), 4.33-4.21 (m 3H), 4.04-3.93 (m, 5H), 3.75-3.69 (m, 4H), 3.71-3.70 (m, 1H), 3.54-3.49 (m, 1H), 3.23-3.18 (m, 3H), 2.30-2.22 (m, 2H), 1.26 (d, J = 6.8 Hz, 3H). |

TABLE 3-continued

| Example No. | R | IUPAC Name | LRMS m/z [M + H]⁺ | ¹H NMR or LCMS retention time and method |
|---|---|---|---|---|
| 465 | (3S)-3-methylpyrrolidin-3-yl (CH₃ wedge, NH) | 5-{2-[(3S)-3-methylmorpholin-4-yl]-7-[(3S)-3-methylpyrrolidin-3-yl]-6,7-dihydro-5H-pyrrolo[2,3-d]pyrimidin-4-yl}pyrimidin-2-amine hydrochloride | 397.2 | ¹H NMR (400 MHz, 80° C., DMSO-d₆) δ 8.72 (s, 2H), 6.58 (br s, 2H), 4.62-4.54 (m, 1H), 4.27-4.20 (m, 1H), 3.92-3.87 (m, 1H), 3.72-3.57 (m, 4H), 3.45 (dt, J = 3.0, 11.6 Hz, 1H), 3.30 (d, J = 11.4 Hz, 1H), 3.22-3.03 (m, 4H, partially overlapped with water peak), 2.96-2.90 (m, 2H, partially overlapped with water peak), 2.36-2.27 (m, 1H), 1.92-185 (m, 1H), 1.33 (s, 3H), 1.20 (d, J = 6.7 Hz, 3H). |
| 466 | (3R)-3-methylpyrrolidin-3-yl (CH₃ dashed, NH) | 5-{2-[(3S)-3-methylmorpholin-4-yl]-7-[(3R)-3-methylpyrrolidin-3-yl]-6,7-dihydro-5H-pyrrolo[2,3-d]pyrimidin-4-yl}pyrimidin-2-amine hydrochloride | 397.1 | ¹H NMR (400 MHz, D₂O) δ 8.55 (s, 2H), 4.45-4.35 (m, 1H), 4.05 (d, J = 12.8 Hz, 1H), 4.92-3.83 (m, 4H), 3.80-3.65 (m, 2H), 3.60-3.50 (m, 2H), 3.40-3.35 (m, 3H), 2.96 (t, J = 7.2 Hz, 2H), 2.65-2.50 (m, 2H), 2.25-2.10 (m, 1H), 1.44 (s, 3H), 1.25 (d, J = 6.8 Hz, 3H). |
| 467 | (3S,4R)-3,4-dimethylpyrrolidin-3-yl | 5-{7-[(3S,4R)-3,4-dimethylpyrrolidin-3-yl]-2-[(3S)-3-methylmorpholin-4-yl]-6,7-dihydro-5H-pyrrolo[2,3-d]pyrimidin-4-yl}pyrimidin-2-amine hydrochloride | 411.2 | ¹H NMR (400 MHz, D₂O) δ 8.53 (s, 2H), 4.55-4.45 (m, 1H), 4.10-4.06 (m, 1H), 3.96-3.45 (m, 10H), 3.02-2.98 (m, 4H), 1.40 (s, 3H), 1.45 (s, 3H), 1.27 (d, J = 6.8 Hz, 3H), 1.09 (d, J = 6.4 Hz, 3H). |
| 468 | (3R,4S)-3,4-dimethylpyrrolidin-3-yl | 5-{7-[(3R,4S)-3,4-dimethylpyrrolidin-3-yl]-2-[(3S)-3-methylmorpholin-4-yl]-6,7-dihydro-5H-pyrrolo[2,3-d]pyrimidin-4-yl}pyrimidin-2-amine hydrochloride | 411.2 | ¹H NMR (400 MHz, D₂O) δ 8.51-8.49 (m, 2H), 4.45-4.35 (m, 1H), 4.15-3.90 (m, 5H), 3.83-3.47 (m, 6H), 3.10-2.90 (m, 4H), 1.42 (s, 3H), 1.30-1.25 (m, 3H), 1.13-1.05 (m, 3H). |

TABLE 3-continued

| Example No. | R | IUPAC Name | LRMS m/z [M + H]+ | 1H NMR or LCMS retention time and method |
|---|---|---|---|---|
| 469 | (3S)-3-methylpyrrolidine with N-acetyl (CH3 up, wedge) | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]ethanone | 439.2 | 1H NMR (400 MHz, 80° C., DMSO-d6) δ 8.72 (s, 2H), 6.67 (br s, 2H), 4.61-4.53 (m, 1H), 4.27-4.20 (m, 1H), 4.05-3.26 (m, 11H), 3.17-3.09 (m, 2H, overlapped with water), 2.58-2.32 (m, 1H, overlapped with DMSO), 2.20-2.00 (m, 1H), 1.94 (s, 3H), 1.36-1.32 (m, 3H), 1.20 (d, J = 6.7 Hz, 3H). |
| 470 | (3R)-3-methylpyrrolidine with N-acetyl | 1-[(3R)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]ethanone | 439.1 | 1H NMR (400 MHz, CDCl3): δ 8.83 (d, J = 5.6 Hz, 2H), 5.24 (s, 2H), 4.70-4.60 (m, 1H), 4.31 (d, J = 12.4 Hz, 1H), 4.10-3.90 (m, 3H), 3.85-3.75 (m, 3H), 3.70-3.50 (m, 4H), 3.25 (t, J = 12 Hz, 1H), 3.15-3.05 (m, 2H), 2.75-2.65 (m, 1H), 2.35-2.20 (m, 1H), 2.07 (d, J = 4.0 Hz, 3H), 1.37 (s, 3H), 1.28 (t, J = 7.2 Hz, 3H). |
| 471 | (3S)-3-methylpyrrolidine with N-C(O)-CH(OH)CH3 | (2R)-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-hydroxypropan-1-one | 469.2 | 1H NMR (400 MHz, Methanol-d4) δ 8.80 (s, 2H), 4.83 (s, 1H), 4.40-4.30 (m, 3H), 4.08-3.97 (m, 2H), 3.79-3.40 (m, 7H), 3.30-3.15 (m, 1H), 3.15-3.10 (m, 2H), 2.70-2.40 (m, 1H), 2.24-2.07 (m, 1H), 1.41 (s, 3H), 1.36 (t, J = 6.0 Hz, 3H), 1.30 (t, J = 6.4 Hz, 3H). |
| 472 | (3S)-3-methylpyrrolidine with N-C(O)-CH(OH)CH(CH3)2 | (2R)-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-hydroxy-3-methylbutan-1-one | 497.2 | 1H NMR (400 MHz, Methanol-d4) δ 8.79 (s, 2H), 4.69-4.67 (m, 1H), 4.34-4.27 (m, 1H), 4.24-4.18 (m, 1H), 4.09-3.91 (m, 3H), 3.81-3.43 (m, 7H), 3.28-3.10 (m, 3H), 2.74-2.41 (m, 1H), 2.23-1.94 (m, 2H), 1.40 (d, J = 10.4 Hz, 3H), 1.30 (t, J = 6.8 Hz, 3H), 1.12-0.92 (m, 6H). |

TABLE 3-continued

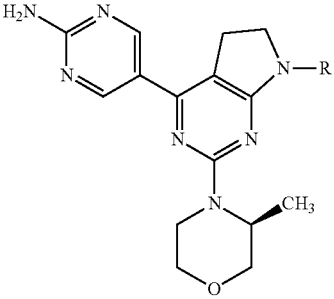

| Example No. | R | IUPAC Name | LRMS m/z [M + H]+ | 1H NMR or LCMS retention time and method |
|---|---|---|---|---|
| 473 | 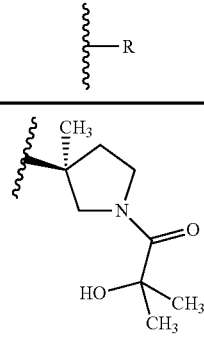 | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-hydroxy-2-methylpropan-1-one | 483.1 | 1H NMR (400 MHz, Methanol-d4) δ 8.77 (s, 2H), 4.63-4.60 (m, 2H), 4.30-3.95 (m, 4H), 3.79-3.72 (m, 3H), 3.58-3.55 (m, 3H), 3.30-3.11 (m, 3H), 2.37-2.01 (m, 2H), 1.43-1.24 (m, 12H). |
| 474 | 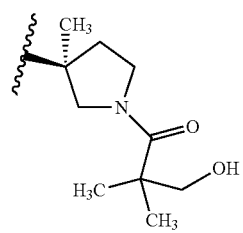 [SMILES: *[C@@]1(C)CCN(C(=O)C(C)(C)CO)C1] | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-hydroxy-2,2-dimethylpropan-1-one hydrochloride | 497.2 | 1H NMR (400 MHz, DMSO-d6) δ 8.72 (s, 2H), 7.00 (s, 2H), 4.64-4.59 (m, 2H), 4.34-4.30 (m, 2H), 3.92-3.89 (m, 2H), 3.69-3.42 (m, 10H), 3.32-3.10 (m, 3H), 2.17-1.91 (m, 1H), 1.26 (s, 3H), 1.19 (d, J = 6.4 Hz, 3H), 1.13 (t, J = 8.4 Hz, 6H). |
| 475 | 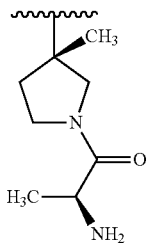 | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]propan-1-one hydrochloride | 468.2 | 1H NMR (400 MHz, D2O) δ 8.62-8.61 (m, 2H), 4.53-4.51 (m, 1H), 3.81-3.78 (m, 1H), 4.21-3.6 (m, 9H), 3.61-3.48 (m, 3H), 3.06-3.01 (m, 2H), 2.63-2.49 (m, 1H), 2.25-2.21 (m, 1H), 1.51-1.43 (m, 6H), 1.34 (d, J = 6.8 Hz, 3H). |
| 476 | 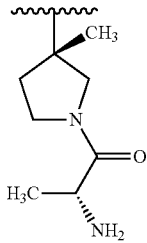 | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]propan-1-one hydrochloride | 468.2 | 1H NMR (400 MHz, D2O) δ 8.62 (s, 2H), 4.53-4.49 (m, 1H), 4.33-4.09 (m, 1H), 4.03-3.85 (m, 4H), 3.78-3.72 (m, 3H), 3.61-3.58 (m, 1H), 3.53-3.48 (m, 2H), 3.47-3.46 (m, 2H), 3.05-2.96 (m, 2H), 2.65-2.45 (m, 1H), 2.25-2.15 (m, 1H), 1.51-1.44 (m, 6H), 1.34 (d, J = 2.4 Hz, 3H). |
| 477 | 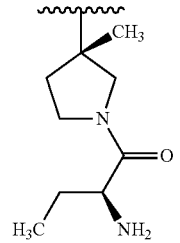 | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]butan-1-one hydrochloride | 482.4 | 1H NMR (400 MHz, D2O) δ 8.61 (s, 2H), 4.55-4.51 (m, 1H), 4.33-4.26 (m, 1H), 4.23-3.21 (m, 1H), 4.15-4.12 (m, 1H), 3.96-3.87 (m, 4H), 3.76-3.72 (m, 2H), 3.67-3.56 (m, 4H), 3.09-2.96 (m, 2H), 2.67-2.45 (m, 1H), 2.25-2.15 (m, 1H), 1.98-1.76 (m, 2H), 1.49 (d, J = 2.4 Hz, 3H), 1.39-1.37 3H), 1.03-0.94 (m, 3H). |

TABLE 3-continued

| Example No. | R | IUPAC Name | LRMS m/z [M + H]⁺ | ¹H NMR or LCMS retention time and method |
|---|---|---|---|---|
| 478 | 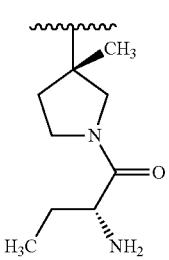 | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]butan-1-one hydrochloride | 482.3 | ¹H NMR (400 MHz, D₂O) δ 8.51 (s, 2H), 4.55-4.51 (m, 1H), 4.30-4.26 (m, 1H), 4.13-3.11 (m, 1H), 4.05-4.02 (m, 1H), 3.86-3.77 (m, 2H), 3.76-3.72 (m, 2H), 3.67-3.56 (m, 4H), 3.53-3.46 (m, 2H), 3.04-3.01 (m, 2H), 2.65-2.15 (m, 1H), 2.26-2.23 (m, 1H), 1.47-1.35 (m, 2H), 1.46 (d, J = 8.8 Hz, 3H), 1.33-1.32 (m, 3H), 0.99-0.92 (m, 3H). |
| 479 | 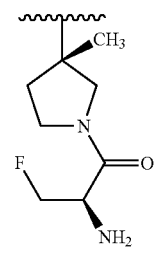 [SMILES: *[C@@]1(C)CCN(C(=O)[C@@H](N)CF)C1] | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-fluoropropan-1-one hydrochloride | 486.3 | ¹H NMR (400 MHz, Methanol-d₄) δ 8.79 (s, 2H), 4.85-4.75 (m, 2H), 4.72-3.65 (m, 1H), 4.53-4.49 (m, 1H), 4.38-4.20 (m, 2H), 4.08-3.92 (m, 2H), 3.82-3.45 (m, 7H), 3.30-3.25 (m, 1H), 3.20-3.10 (m, 2H), 2.75-2.35 (m, 1H), 2.25-2.02 (m, 1H), 1.39 (d, J = 13.6 Hz, 3H), 1.30 (s, 3H). |
| 480 | 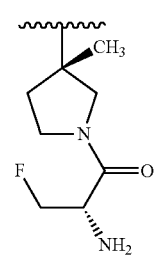 [SMILES: *[C@@]1(C)CCN(C(=O)[C@H](N)CF)C1] | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-fluoropropan-1-one hydrochloride | 486.3 | ¹H NMR (400 MHz, Methanol-d₄) δ 8.79 (s, 2H), 4.85-4.75 (m, 2H), 4.72-3.65 (m, 1H), 4.53-4.49 (m, 1H), 4.38-4.20 (m, 2H), 4.08-3.92 (m, 2H), 3.82-3.45 (m, 7H), 3.30-3.25 (m, 1H), 3.20-3.10 (m, 2H), 2.75-2.35 (m, 1H), 2.25-2.02 (m, 1H), 1.39 (d, J = 13.6 Hz, 3H), 1.30 (s, 3H). |
| 481 | 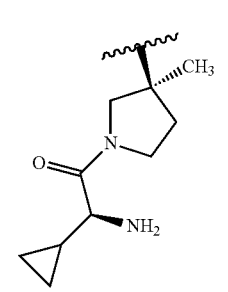 [SMILES: *[C@@]1(C)CCN(C(=O)[C@@H](N)C2CC2)C1] | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-cyclopropylethanone hydrochloride | 494.2 | ¹H NMR (400 MHz, D₂O) δ 8.62 (s, 2H), 4.72-4.69 (m, 3H, partially overlapping with D2O), 4.32-4.08 (m, 2H), 4.07-3.97 (m, 4H), 3.89-3.81 (m, 1H), 3.78-3.75 (m, 2H), 3.65-3.63 (m, 2H), 3.10-3.06 (m, 2H), 2.63-2.62 (m, 1H), 2.33-2.22 (m, 1H), 1.51 (d, J = 4 Hz, 3H), 1.39 (t, J = 6 Hz, 3H), 1.27-1.25 (m, 1H), 0.84-0.82 (m, 1H), 0.73-0.71 (m, 1H), 0.69-0.35 (m, 2H). |

TABLE 3-continued

| Example No. | R | IUPAC Name | LRMS m/z [M + H]+ | 1H NMR or LCMS retention time and method |
|---|---|---|---|---|
| 482 | (structure with 3-methylpyrrolidine, cyclopropyl, NH2) | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-cyclopropylethanone hydrochloride | 494.3 | 1H NMR (400 MHz, Methanol-d4) δ 8.80 (s, 2H), 4.65-4.63 (m, 1H), 4.29-4.21 (m, 2H), 4.06-3.96 (m, 2H), 3.77-3.76 (m, 1H), 3.74-3.71 (m, 4H), 3.62-3.27 (m, 3H), 3.15-3.13 (m, 1H), 3.11-3.09 (m, 2H), 2.70-2.53 (m, 2H), 1.42 (d, J = 11.2 Hz, 3H), 1.29-1.26 (m, 4H), 0.83-0.71 (m, 3H), 0.51-0.48 (m, 1H). |
| 483 | (structure with 3-methylpyrrolidine and dimethylamino) | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-(dimethylamino)ethanone | 482.2 | 1H NMR (400 MHz, Methanol-d4) δ 8.80 (s, 2H), 4.69-4.67 (m, 1H), 4.39-4.30 (m, 1H), 4.20-3.90 (m, 3H), 3.80-3.40 (m, 7H), 3.30-3.10 (m, 5H), 2.70-2.40 (m, 1H), 2.45 (d, J = 12.0 Hz, 6H), 2.25-2.10 (m, 1H), 1.40 (s, 3H), 1.30 (t, J = 7.6 hz, 3H). |
| 484 | (structure with 3-methylpyrrolidine and 2,2-dimethylpropan with NH2) | 3-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2,2-dimethylpropan-1-one hydrochloride | 496.3 | 1H NMR (400 MHz, D2O) δ 8.58 (s, 2H), 4.67-4.63 (m, 1H), 4.32-4.28 (m, 1H), 4.12-4.06 (m, 1H), 3.96-3.94 (m, 2H), 3.92-3.87 (m, 2H), 3.86-3.85 (m, 2H), 3.67-3.55 (m, 4H), 3.13-2.96 (m, 4H), 2.69-2.43 (m, 1H), 2.35-2.13 (m, 1H), 1.49 (s, 3H), 1.39-1.34 (m, 9H). |
| 485 | (structure with 3-methylpyrrolidine, hydroxy, methyl, NH2) | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-hydroxy-2-methylpropan-1-one hydrochloride | 498.3 | 1H NMR (400 MHz, D2O) δ 8.58 (s, 2H), 4.60-4.50 (m, 1H), 4.29-4.02 (m, 1H), 3.99-3.76 (m, 10H), 3.60-3.57 (m, 3H), 3.04-2.98 (m, 2H), 2.60-2.47 (m, 1H), 2.15-2.03 (m, 1H), 1.58 (d, J = 6.0 Hz, 3H), 1.47 (d, J = 3.6 Hz, 3H), 1.34 (t, J = 6.4 Hz, 3H). |

TABLE 3-continued

| Example No. | R | IUPAC Name | LRMS m/z [M + H]+ | 1H NMR or LCMS retention time and method |
|---|---|---|---|---|
| 486 | (pyrrolidine with CH3, N-acyl, CH(NH2)(CH3)CH2OH) | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-hydroxy-2-methylpropan-1-one hydrochloride | 498.2 | 1H NMR (400 MHz, D2O) δ 8.56 (s, 2H), 4.54-4.50 (m, 4.26-3.75 (m, 11H), 3.56-3.48 (m, 3H), 3.00-1H), 2.15-2.05 (m, 1H), 1.58-1.52 (m, 3H), 1.45 (s, 3H), 1.32 (t, J = 5.6 Hz, 3H). |
| 487** | (pyrrolidine with CH3, N-acyl, C(NH2)(CH3)CH2OH) | 2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3-hydroxy-2-methylpropan-1-one hydrochloride | 498.3 | 1H NMR (400 MHz, D2O) δ 8.56 (s, 2H), 4.56-4.50 (m, 1H), 4.26-3.76 (m, 11H), 3.56-3.48 (m, 3H), 3.04-3.00 (m, 2H), 2.67-2.50 (m, 1H), 2.26-2.14 (m, 1H), 1.59-1.54 (m, 3H), 1.47 (s, 3H), 1.34 (t, J = 5.4 Hz, 3H). |
| 488 | (pyrrolidine with CH3, N-acyl-C(CH3)2-NHCH3) | 1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2-methyl-2-(methylamino)propan-1-one hydrochloride | 496.3 | 1H NMR (400 MHz, D2O) δ 8.67 (s, 2H), 4.80-4.58 (m, 1H), 4.34-3.83 (m, 9H), 3.67-3.50 (m, 3H), 3.08-3.04 (m, 2H), 2.71-2.50 (m, 4H), 2.30-2.20 (m, 1H), 1.71-1.63 (m, 6H), 1.52 (s, 3H), 1.40 (t, J = 7.0 Hz, 3H). |
| 489 | (pyrrolidine with CH3, N-acyl-CF2-CH2NH2) | 3-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-2,2-difluoropropan-1-one hydrochloride | 504.3 | 1H NMR (400 MHz, Methanol-d4) δ 8.76 (s, 2H), 4.46-4.22 (m, 1H), 4.20-3.96 (m, 5H), 3.90-3.52 (m, 8H), 3.23-3.12 (m, 2H), 2.81-2.52 (m, 1H), 2.38-1.97 (m, 2H), 1.65-1.51 (m, 3H), 1.43 (s, 3H). |

TABLE 3-continued

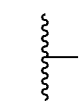

| Example No. | R | IUPAC Name | LRMS m/z [M + H]+ | 1H NMR or LCMS retention time and method |
|---|---|---|---|---|
| 490 | 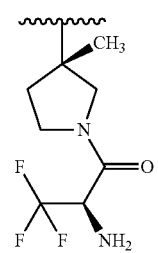 [SMILES: *[C@@]1(C)CCN(C(=O)[C@@H](N)C(F)(F)F)C1] | (2R)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3,3,3-trifluoropropan-1-one hydrochloride | 522.3 | 1H NMR (400 MHz, D$_2$O) δ 8.58 (s, 2H), 5.26-5.10 (m, 1H), 4.48-4.42 (m, 1H), 4.21-4.11 (m, 1H), 4.01-3.75 (m, 8H), 3.59-3.50 (m, 3H), 3.01-2.96 (m, 2H), 2.73-2.56 (m, 1H), 2.45-2.44 (m, 1H), 1.45 (s, 3H), 1.31 (m, 3H). |
| 491 | 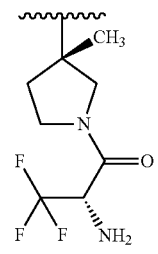 [SMILES: *[C@@]1(C)CCN(C(=O)[C@H](N)C(F)(F)F)C1] | (2S)-2-amino-1-[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]-3,3,3-trifluoropropan-1-one hydrochloride | 522.3 | 1H NMR (400 MHz, D$_2$O) δ 8.62 (s, 2H), 5.31-5.21 (m, 1H), 4.54-4.49 (m, 1H), 4.34-3.52 (m, 12H), 3.04-3.01 (m, 2H), 2.65-2.58 (m, 1H), 2.38-2.12 (m, 1H), 1.48 (d, J = 9.2 Hz, 3H), 1.36-1.20 (m, 3H). |
| 492 | 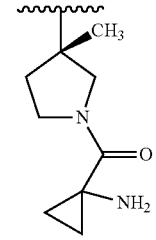 [SMILES: *[C@@]1(C)CCN(C(=O)C2(N)CC2)C1] | (1-aminocyclopropyl)[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]methanone hydrochloride | 480.2 | 1H NMR (400 MHz, D$_2$O) δ ppm 8.59 (s, 2H), 4.03-3.58 (m, 13H), 3.04-2.98 (m, 2H), 2.60-2.43 (m, 1H), 2.43-2.24 (m, 1H), 1.53-1.33 (m, 10H). |
| 493 | 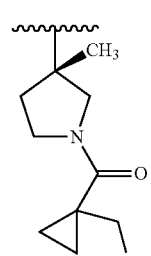 | [1-(aminomethyl)cyclopropyl][(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]methanone hydrochloride | 494.2 | 1H NMR (400 MHz, D$_2$O) δ 8.61 (s, 2H), 4.58-4.53 (m, 1H), 4.33-4.26 (m, 1H), 4.15-3.87 (m, 8H), 3.65-3.49 (m, 3H), 3.36-3.07 (m, 4H), 2.66-2.48 (m, 1H), 2.15-2.12 (m, 1H), 1.49 (s, 3H), 1.39-1.33 (m, 3H), 1.20-0.98 (m, 4H). |

TABLE 3-continued

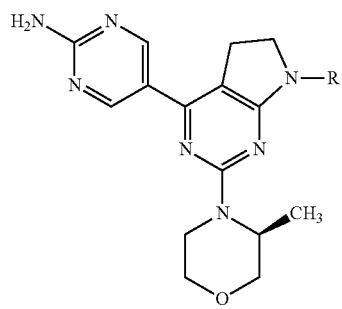

| Example No. | R | IUPAC Name | LRMS m/z [M + H]⁺ | ¹H NMR or LCMS retention time and method |
|---|---|---|---|---|
| 494 |  | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl][(2R)-2-methylazetidin-2-yl]methanone hydrochloride | 494.3 | ¹H NMR (400 MHz, D₂O) δ 8.61 (s, 2H), 4.54-4.49 (m, 1H), 4.08-3.74 (m, 10H), 3.62-3.54 (m, 4H), 3.03-2.96 (m, 3H), 2.61-2.49 (m, 2H), 2.22-2.21 (m, 1H), 1.87-1.79 (m, 3H), 1.45 (d, J = 6.0 Hz, 3H), 1.35 (t, J = 7.6 Hz, 3H). |
| 495 | 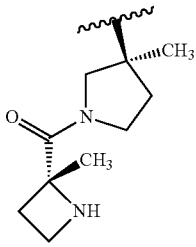 [SMILES: *[C@@]1(C)CCN(C(=O)[C@@]2(C)CCN2)C1] | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl][(2S)-2-methylazetidin-2-yl]methanone hydrochloride | 494.3 | ¹H NMR (400 MHz, D₂O) δ 8.59 (s, 2H), 4.54-4.49 (m, 1H), 4.09-3.73 (m, 10H), 3.59-3.51 (m, 4H), 3.03-2.86 (m, 3H), 2.53-2.47 (m, 2H), 2.24-2.21 (m, 1H), 1.85 (d, J = 9.2 Hz, 3H), 1.45 (d, J = 10.0 Hz, 3H) 1.33 (t, J = 8.0 Hz, 3H). |
| 496 | 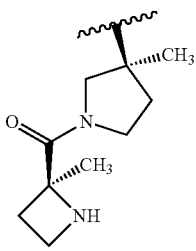 [SMILES: *[C@@]1(C)CCN(C(=O)[C@]2(C)CCN2)C1] | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl](3-fluoroazetidin-3-yl)methanone hydrochloride | 498.2 | ¹H NMR (400 MHz, 80° C., DMSO-d₆) δ 8.73 (s, 2H), 6.61 (br s, 2H), 4.62-4.56 (m, 1H), 4.26-4.21 (m, 1H), 4.09-3.42 (m, 14H), 3.20-3.06 (m, 3H), 2.60-2.33 (m, 1H, overlapped with DMSO), 2.18-2.00 (m, J = 4.6 Hz, 1H), 1.38-1.29 (m, 3H), 1.23 (d, J = 6.7 Hz, 3H). |
| 497 | 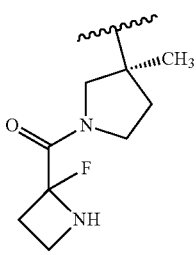 [SMILES: *[C@@]1(C)CCN(C(=O)C2(F)CCN2)C1] | tert-butyl 3-{[(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl]carbonyl}-3-fluoroazetidine-1-carboxylate | 598.3 | ¹H NMR (400 MHz, 80° C., DMSO-d₆) δ 8.73 (s, 2H), 6.61 (br s, 2H), 4.59 (br s, 1H), 4.50-4.32 (m, 2H), 4.24 (dd, J = 1.8, 13.4 Hz, 1H), 4.14-3.77 (m, 5H), 3.73-3.42 (m, 7H), 3.21-3.05 (m, 3H), 2.62 2.34 (m, 1H, overlapped with DMSO), 2.20-2.00 (m, 1H), 1.41 (s, 9H), 1.34 (br s, 3H), 1.23 (d, J = 6.6 Hz, 3H). |

TABLE 3-continued

| Example No. | R | IUPAC Name | LRMS m/z [M + H]+ | 1H NMR or LCMS retention time and method |
|---|---|---|---|---|
| 498 | | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl](3-methoxyazetidin-1-yl)methanone | 510.6 | 1H NMR (400 MHz, DMSO-d6) δ 8.71 (s, 2H) 6.96 (s, 2H) 4.50-4.61 (m, 1H) 4.22 (d, J = 13.3 Hz, 1H) 4.08-4.16 (m, 1H) 3.98-4.07 (m, 2H) 3.87-3.94 (m, 1H) 3.37-3.81 (m, 11H) 3.19 (s, 3H) 3.04-3.15 (m, 3H) 2.29-2.39 (m, 1H) 1.99-2.08 (m, 1H) 1.26 (s, 3H) 1.19 (d, J = 6.6 Hz, 3H). |
| 499 | | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl][(3R)-tetrahydrofuran-3-yl]methanone | 495.2 | 1H NMR (400 MHz, DMSO-d6): δ 8.73 (s, 2H), 7.00 (s, 2H), 4.53-4.51 (m, 1H), 4.22-4.20 (m, 1H), 3.99-3.98 (m, 1H), 3.91-3.89 (m, 2H), 3.76-3.51 (m, 11H), 3.11-3.09 (m, 4H), 2.28-2.25 (m, 1H), 2.06-1.99 (m, 3H), 1.29 (d, J = 4.4 Hz, 3H), 1.19 (d, J = 6.4 Hz, 3H). |
| 500 | | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl][(3S)-tetrahydrofuran-3-yl]methanone | 495.2 | 1H NMR (400 MHz, DMSO-d6): δ 8.72 (s, 2H), 7.01 (s, 2H), 4.53-4.51 (m, 1H), 4.24-4.22 (m, 1H), 3.93-3.90 (m, 1H), 3.89-3.75 (m, 3H), 3.73-3.44 (m, 10H), 3.11-3.09 (m, 4H), 2.28-2.25 (m, 1H), 1.99-1.95 (m, 3H), 1.30 (s, 3H), 1.18 (d, J = 6.4 Hz, 3H). |
| 501 | | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl][(2R)-tetrahydrofuran-2-yl]methanone | 495.2 | 1H NMR (400 MHz, Methanol-d4) δ 8.77 (d, J = 2 Hz, 2H), 4.64-4.62 (m, 1H), 4.27-4.22 (m, 2H), 4.04-3.59 (m, 12H), 3.30-3.13 (m, 3H), 2.60-2.40 (m, 1H), 2.22-2.19 (m, 1H), 2.08-1.93 (m, 4H), 1.39 (s, 3H), 1.28 (d, J = 6.8 Hz, 3H). |

TABLE 3-continued

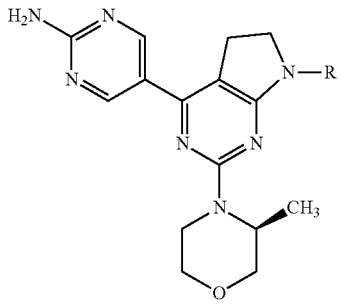

| Example No. | R | IUPAC Name | LRMS m/z [M + H]+ | 1H NMR or LCMS retention time and method |
|---|---|---|---|---|
| 502* | (3S)-3-methyl-pyrrolidine with N-C(=O)-C(NH2) linked to tetrahydrofuran-3-yl | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl](3-aminotetrahydrofuran-3-yl)methanone hydrochloride | 510.3 | 1H NMR (400 MHz, D2O): δ 8.54-8.53 (m, 2H), 4.44-3.45 (m, 17H), 3.00-2.96 (m, 2H), 2.64-2.44 (m, 2H), 2.31-2.15 (m, 2H), 1.30 (d, J = 6.8 Hz, 3H), 1.21 (d, J = 6.8 Hz, 3H). |
| 503* | (3S)-3-methyl-pyrrolidine with N-C(=O)-C(NH2) linked to tetrahydrofuran-3-yl | [(3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidin-1-yl](3-aminotetrahydrofuran-3-yl)methanone hydrochloride | 510.3 | 1H NMR (400 MHz, D2O) δ 8.53 (s, 2H), 4.42-3.45 (m, 17H), 3.00-2.99 (m, 2H), 2.74-2.64 (m, 1H), 2.43-2.14 (m, 3H), 1.44 (d, J = 4.8 Hz, 3H), 1.31 (d, J = 7.2 Hz, 3H). |
| 504 | (3S)-3-methylpyrrolidine with N-C(=NH)-NHCH3 | (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-N,3-dimethylpyrrolidine-1-carboximidamide | 453.2 | 1H NMR (400 MHz, D2O) δ ppm 8.61 (s, 2H), 4.52-4.51 (m, 1H), 4.14-3.54 (m, 13H), 3.08-3.04 (m, 2H), 2.86 (s, 3H), 2.74-2.72 (m, 1H), 2.31-2.28 (m, 1H), 1.54 (s, 3H), 1.37 (d, J = 6.8 Hz, 3H). |
| 505 | (3R)-3-methylpyrrolidine with N-C(=O)-NHCH3 | (3R)-3-{4-(2-aminopyrimidin-5-yl)-2-[(3S)-3-methylmorpholin-4-yl]-5,6-dihydro-7H-pyrrolo[2,3-d]pyrimidin-7-yl}-N,3-dimethylpyrrolidine-1-carboxamide | 454.2 | 1H NMR (400 MHz, CDCl3) δ 8.83 (s, 2H), 5.27 (s, 2H), 4.70-4.60 (m, 1H), 4.32-4.29 (m, 1H), 4.20-4.12 (m, 1H), 4.05-3.98 (m, 1H), 3.85-3.70 (m, 4H), 3.65-3.45 (m, 3H), 3.40-3.30 (m, 1H), 3.30-3.20 (m, 2H), 3.10 (t, J = 8.0 Hz, 2H), 2.85 (d, J = 4.8 Hz, 3H), 2.60-2.50 (m, 1H), 2.20-2.10 (m, 1H), 1.37 (s, 3H), 1.28 (d, J = 6.4 Hz, 3H). |

TABLE 3-continued

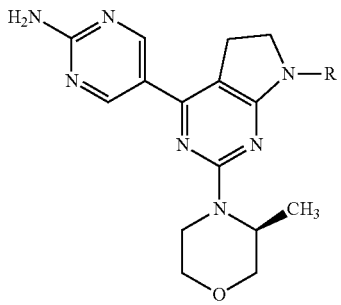

| Example No. | R | IUPAC Name | LRMS m/z [M + H]+ | 1H NMR or LCMS retention time and method |
|---|---|---|---|---|
| 506 | (3S)-3-methyl-pyrrolidine with N-methylcarboxamide | (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-N,3-dimethylpyrrolidine-1-carboxamide | 454.1 | 1H NMR (400 MHz, Methanol-d4) 8.78 (s, 2H), 4.67-4.65 (m, 1H), 4.30 (d, J = 11.6 Hz, 1H), 4.00-3.95 (m, 1H), 3.95 (d, J = 12 Hz, 1H), 3.80-3.78 (m, 2H), 3.77-3.75 (m, 2H), 3.65-3.50 (m, 2H), 3.45-3.41 (m, 1H), 3.35-3.33 (m, 1H), 3.24-3.20 (m 1H), 3.15-3.3.07 (m, 2H), 2.74 (s, 3H), 2.65-2.54 (m, 1H), 2.20-2.10 (m, 1H), 1.37 (s, 3H), 1.27 (d, J = 6.4 Hz, 3H). |
| 507 | (3S)-3-methyl-pyrrolidine with N-ethylcarboxamide | (3S)-3-[4-(2-aminopyrimidin-5-yl)-2-(morpholin-4-yl)-5,6-dihydro-7H-pyrrolo[2,3-d]pyrimidin-7-yl]-N-ethyl-3-methylpyrrolidine-1-carboxamide | 476.1 [M + 23] | 1H NMR (400 MHz, DMSO-d6) δ 8.73 (s, 2H), 7.02 (s, 2H), 6.11 (t, J = 5.6 Hz, 1H), 3.72-3.58 (m, 10H), 3.55-3.47 (m, 2H), 3.30-3.20 (m, 2H), 3.18-3.05 (m, 4H) 2.43-2.38 (m, 1H), 2.15-2.05 (m, 1H), 1.28 (s, 3H), 1.02 (t, J = 6.8 Hz, 3H). |
| 508 | (3S)-3-methyl-pyrrolidine with methyl carboxylate | methyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidine-1-carboxylate | 455.0 | 1H NMR (400 MHz, CDCl3) δ 8.81 (s, 2H), 5.40 (s, 2H), 4.70-4.60 (m, 1H), 4.45-4.32 (m, 1H), 4.20-4.10 (m, 1H), 3.91-3.82 (m, 3H), 3.79-3.3.70 (m, 5H), 3.65-3.50 (m, 3H), 3.45-3.38 (m, 1H), 3.35-3.28 (m, 1H), 3.20-3.05 (m, 2H) 2.55-2.40 (m, 1H) 2.15-2.03 (m, 1H) 1.38 (s, 3H) 1.31 (d, J = 7.2 Hz, 3H). |
| 509 | (3R)-3-methyl-pyrrolidine with methyl carboxylate | methyl (3R)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidine-1-carboxylate | 455.1 | 1H NMR (400 MHz, CDCl3) δ 8.83 (s, 2H) 5.28 (s, 2H) 4.70-4.60 (m, 1H) 4.33 (d, J = 13.6 Hz, 1H) 3.99 (d, J = 11.2 Hz, 1H) 3.90-3.80 (m, 4H) 3.80-3.70 (m, 3H) 3.65-3.40 (m, 5H) 3.26 (t, J = 8.0 Hz, 1H) 3.10 (t, J = 8.0 Hz, 2H) 2.55-2.40 (m, 1H) 2.35-2.05 (m, 1H) 1.36 (s, 3H) 1.30-1.20 (m, 3H). |

TABLE 3-continued

| Example No. | R | IUPAC Name | LRMS m/z [M + H]+ | 1H NMR or LCMS retention time and method |
|---|---|---|---|---|
| 510 | | tert-butyl (3S,4R)-3-{4-(2-aminopyrimidin-5-yl)-2-[(3S)-3-methylmorpholin-4-yl]-5,6-dihydro-7H-pyrrolo[2,3-d]pyrimidin-7-yl}-3,4-dimethylpyrrolidine-1-carboxylate | 511.3 | 1H NMR (400 MHz, CDCl3) δ 8.81 (s, 2H), 5.21 (s, 2H) 4.66-4.63 (m, 1H) 4.32-4.28 (m, 1H) 4.04-3.89 (m, 2H) 3.78-3.56 (m, 7H) 3.30-3.08 (m, 3H) 3.06-2.84 (m, 2H) 1.45 (s, 9H) 1.37-1.27 (m, 6H) 1.10-1.05 (m, 3H). |
| 511 | | tert-butyl (3R,4S)-3-{4-(2-aminopyrimidin-5-yl)-2-[(3S)-3-methylmorpholin-4-yl]-5,6-dihydro-7H-pyrrolo[2,3-d]pyrimidin-7-yl}-3,4-dimethylpyrrolidine-1-carboxylate | 511.4 | 1H NMR (400 MHz, CDCl3) δ 8.81 (s, 2H) 5.23 (s, 2H) 4.66-4.58 (m, 1H) 4.42-4.32 (m, 1H) 3.96-3.58 (m, 9H) 3.32-3.22 (m, 1H) 3.15-3.05 (m, 2H) 3.07-2.99 (m, 2H) 1.46 (s, 9H) 1.37-1.27 (m, 6H) 1.10-1.07 (m, 3H). |
| 512 | | tert-butyl (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpyrrolidine-1-carboxylate | 497.3 | 1H NMR (400 MHz, 80° C., DMSO-d6) δ 8.72 (s, 2H) 6.61 (br s, 2H) 4.62-4.54 (m, 1H) 4.26-4.19 (m, 1H) 3.90 (dd, J = 3.3, 11.1 Hz, 1H) 3.79-3.36 (m, 8H) 3.33-3.24 (m, 1H) 3.19-3.07 (m, 3H, partially overlapped with water) 2.44-2.34 (m, 1H) 2.07-1.99 (m, 1H) 1.42 (s, 9H), 1.32 (s, 3H) 1.22 (d, J = 6.6 Hz, 3H). |
| 513 | | 5-{7-[(3S)-1,3-dimethylpyrrolidin-3-yl]-2-[(3S)-3-methylmorpholin-4-yl]-6,7-dihydro-5H-pyrrolo[2,3-d]pyrimidin-4-yl}pyrimidin-2-amine | 411.1 | 1H NMR (400 MHz, Methanol-d4) δ 8.80 (s, 2H) 4.70-4.55 (m, 1H) 4.26 (d, J = 14 Hz, 1H), 3.97 (d, J = 10.6 Hz, 1H) 3.85-3.68 (m, 4H) 3.65-3.52 (m, 3H) 3.25-3.12 (m, 5H, partially overlapping with methanol peak) 2.99 (s, 3H) 2.82-2.69 (m, 1H) 2.27-2.15 (m, 1H) 1.49 (s, 3H) 1.28 (d, J = 6.8 Hz, 3H). |

TABLE 3-continued

| Example No. | R | IUPAC Name | LRMS m/z [M + H]+ | 1H NMR or LCMS retention time and method |
|---|---|---|---|---|
| 514* | H3C-[pyrrolidine with pyrrolidinone] | (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methyl-1,3'-bipyrrolidin-2'-one | 480.2 | 1H NMR (400 MHz, Methanol-d4) δ 8.79 (s, 2H) 4.70-4.67 (m, 1H) 4.33-4.30 (m, 1H) 4.00-3.95 (m, 1H) 3.78-3.65 (m, 4H) 3.60-3.50 (m, 1H) 3.41-3.35 (m, 3H) 3.25-3.15 (m, 3H) 3.14-3.06 (m, 3H) 2.88-2.85 (m, 1H) 2.54-2.52 (m, 1H) 2.35-2.30 (m, 1H) 2.13-2.11 (m, 1H) 1.98-1.96 (m, 1H) 1.44 (s, 3H) 1.27 (d, J = 6.8 Hz, 3H). |
| 515* | H3C-[pyrrolidine with pyrrolidinone] | (3S)-3-{4-(2-aminopyrimidin-5-yl)-2-[(3S)-3-methylmorpholin-4-yl]-5,6-dihydro-7H-pyrrolo[2,3-d]pyrimidin-7-yl}-3-methyl-1,3'-bipyrrolidin-2'-one | 480.2 | 1H NMR (400 MHz, Methanol-d4) δ 8.79 (s, 2H) 4.67-4.63 (m, 1H) 4.31-4.27 (m, 1H) 4.10-3.98 (m, 2H) 3.82-3.70 (m, 3H) 3.58-3.50 (m, 3H) 3.50-3.37 (m, 5H) 3.25-3.15 (m, 3H), 2.65-2.63 (m, 1H) 2.55-2.50 (m, 1H) 2.22-2.14 (m, 2H) 1.50 (s, 3H) 1.30 (d, J = 6.8 Hz, 3H). |
| 516 | 4-methylpiperidine (CH3 at 4) | 5-{2-[(3S)-3-methylmorpholin-4-yl]-7-(4-methylpiperidin-4-yl)-6,7-dihydro-5H-pyrrolo[2,3-d]pyrimidin-4-yl}pyrimidin-2-amine hydrochloride | 411.1 | 1H NMR (400 MHz, D2O) δ 8.62 (s, 2H) 4.47 (s, 2H) 4.15-3.95 (m, 2H) 3.83-3.80 (m, 1H) 3.73-3.60 (m, 1H) 3.59-3.56 (m, 3H) 3.35-3.20 (m, 4H) 3.02-2.85 (m, 4H) 1.87 (t, J = 11.6 Hz, 2H) 1.31 (s, 3H) 1.19 (d, J = 6.8 Hz, 3H). |
| 517* | 3-methylpiperidine (CH3 at 3) | 5-{2-[(3S)-3-methylmorpholin-4-yl]-7-(3-methylpiperidin-3-yl)-6,7-dihydro-5H-pyrrolo[2,3-d]pyrimidin-4-yl}pyrimidin-2-amine hydrochloride | 411.1 | 1H NMR (400 MHz, Methanol-d4) δ 8.66 (s, 2H) 4.45-4.36 (m, 1H) 4.06 (d, J = 11.2 Hz, 1H) 4.01-3.80 (m, 4H) 3.75-3.60 (m, 1H) 3.59-3.29 (m, 4H) 3.20-3.01 (m, 4H) 2.45 (d, J = 13.6 Hz, 1H) 2.02-1.79 (m, 2H) 1.75-1.60 (m, 1H) 1.38 (s, 3H) 1.37 (d, J = 7.2 Hz, 3H). |
| 518* | 3-methylpiperidine (CH3 at 3) | 5-{2-[(3S)-3-methylmorpholin-4-yl]-7-(3-methylpiperidin-3-yl)-6,7-dihydro-5H-pyrrolo[2,3-d]pyrimidin-4-yl}pyrimidin-2-amine hydrochloride | 411.1 | 1H NMR (400 MHz, Methanol-d4) δ 8.56 (s, 2H) 4.88-4.81 (m, 2H) 4.52-4.46 (m, 1H) 3.88 (d, J = 9.2 Hz, 1H) 3.80-3.72 (m, 5H) 3.66-3.45 (m, 2H) 3.40-3.29 (m, 1H) 3.26-3.20 (m, 1H) 3.18-2.95 (m, 2H) 2.37 (d, J = 14.8 Hz, 1H) 1.97-1.62 (m, 3H) 1.37 (s, 3H) 1.31 (d, J = 7.2 Hz, 3H). |

TABLE 3-continued

| Example No. | R | IUPAC Name | LRMS m/z [M + H]+ | ¹H NMR or LCMS retention time and method |
|---|---|---|---|---|
| 519 | | tert-butyl 4-{4-(2-aminopyrimidin-5-yl)-2-[(3S)-3-methylmorpholin-4-yl]-5,6-dihydro-7H-pyrrolo[2,3-d]pyrimidin-7-yl}-4-methylpiperidine-1-carboxylate | 511.2 | ¹H NMR (400 MHz, CDCl₃) δ 8.82 (s, 2H), 5.20 (s, 2H) 4.60-4.50 (m, 1H) 4.27-4.24 (m, 1H) 4.00-3.96 (m, 1H) 3.76-3.51 (m, 8H) 3.30-3.20 (m, 3H) 3.07-3.03 (m, 2H) 2.70-2.30 (m, 3H) 1.46 (s, 9H) 1.29 (s, 3H) 1.25 (d, J = 6.4 Hz, 3H). |
| 520** | | tert-butyl 3-{4-(2-aminopyrimidin-5-yl)-2-[(3S)-3-methylmorpholin-4-yl]-5,6-dihydro-7H-pyrrolo[2,3-d]pyrimidin-7-yl}-3-methylpiperidine-1-carboxylate | 511.2 | ¹H NMR (400 MHz, Methanol-d₄) δ 8.74 (s, 2H) 4.72-4.55 (m, 2H) 4.27 (d, J = 14.8 Hz, 1H) 3.97 (d, J = 9.2 Hz, 1H) 3.80-3.55 (m, 7H) 3.28-3.17 (m, 2H) 3.08-2.90 (m, 2H) 1.70-1.58 (m, 4H) 1.55-1.35 (m, 7H) 1.34-1.30 (m, 5H) 1.29-1.22 (m, 3H). |
| 521 | | tert-butyl (1R,5S,6s)-6-{4-(2-aminopyrimidin-5-yl)-2-[(3S)-3-methylmorpholin-4-yl]-5,6-dihydro-7H-pyrrolo[2,3-d]pyrimidin-7-yl}-3-azabicyclo[3.1.0]hexane-3-carboxylate | 495.2 | ¹H NMR (400 MHz, CDCl₃) δ 8.83 (s, 2H) 5.24 (s, 2H) 4.75-4.70 (m, 1H) 4.42-4.40 (m, 1H) 3.98 (d, J = 3.2 Hz, 1H) 3.80-3.43 (m, 9H) 3.30-3.19 (m, 1H) 3.13-3.02 (m, 2H) 2.22 (s, 1H) 2.00-1.89 (m, 2H) 1.49 (s, 9H) 1.30-1.26 (m, 3H). |
| 522 | | 5-{7-[(1R,5S,6s)-3-azabicyclo[3.1.0]hex-6-yl]-2-[(3S)-3-methylmorpholin-4-yl]-6,7-dihydro-5H-pyrrolo[2,3-d]pyrimidin-4-yl}pyrimidin-2-amine hydrochloride | 395.1 | ¹H NMR (400 MHz, D₂O) δ 8.62 (s, 2H) 4.22-4.05 (m, 2H) 3.95-3.79 (m, 4H) 3.74-3.52 (m, 7H) 3.16-3.01 (m, 1H) 2.90-2.77 (m, 1H) 2.55-2.42 (m, 2H) 1.39 (d, J = 6.4 Hz, 3H). |

TABLE 3-continued

| Example No. | R | IUPAC Name | LRMS m/z [M + H]+ | ¹H NMR or LCMS retention time and method |
|---|---|---|---|---|
| 523 | (bicyclic azabicyclo[2.1.1]hexyl with Boc) | tert-butyl (1S,4S,5S)-5-{4-(2-aminopyrimidin-5-yl)-2-[(3S)-3-methylmorpholin-4-yl]-5,6-dihydro-7H-pyrrolo[2,3-d]pyrimidin-7-yl}-2-azabicyclo[2.1.1]hexane-2-carboxylate | 495.3 | ¹H NMR (400 MHz, CDCl₃) δ 8.82-8.81 (m, 2H) 5.21 (s, 2H) 4.64-4.63 (m, 1H) 4.51-4.45 (m, 1H) 4.32-4.29 (m, 1H) 3.97-3.94 (m, 1H) 3.74-3.38 (m, 4H) 3.32-3.20 (m, 6H) 3.04-2.98 (m, 2H) 1.74-1.72 (m, 1H) 1.49-1.45 (m, 10H) 1.28-1.25 (m, 3H). |
| 524 | (bicyclic azabicyclo[2.1.1]hexyl with Boc) | tert-butyl (1R,4R,5R)-5-{4-(2-aminopyrimidin-5-yl)-2-[(3S)-3-methylmorpholin-4-yl]-5,6-dihydro-7H-pyrrolo[2,3-d]pyrimidin-7-yl}-2-azabicyclo[2.1.1]hexane-2-carboxylate | 495.3 | ¹H NMR (400 MHz, CDCl₃) δ 8.82-8.80 (m, 2H) 5.21 (s, 2H) 4.66-4.64 (m, 1H) 4.50-4.45 (m, 1H) 4.29-4.26 (m, 1H) 3.95-3.94 (m, 1H) 3.75-3.38 (m, 4H) 3.37-3.20 (m, 6H) 3.04-3.03 (m, 2H) 1.72-1.70 (m, 1H) 1.47-1.44 (m, 10H) 1.25-1.24 (m, 3H). |
| 525 | (azabicyclo[2.1.1]hex-5-yl NH) | 5-{7-[(1S,4S,5S)-2-azabicyclo[2.1.1]hex-5-yl]-2-[(3S)-3-methylmorpholin-4-yl]-6,7-dihydro-5H-pyrrolo[2,3-d]pyrimidin-4-yl}pyrimidin-2-amine hydrochloride | 395.1 | ¹H NMR (400 MHz, D₂O) δ 8.56 (s, 2H) 4.76-4.70 (m, 1H) 4.45-4.44 (m, 1H) 4.00-3.99 (m, 1H) 3.87-3.79 (m, 1H) 3.77-3.73 (m, 2H) 3.73-3.39 (m, 7H) 3.39-3.32 (m, 1H) 3.05-3.03 (m, 2H) 2.01-1.99 (m, 1H) 1.56-1.54 (m, 1H) 1.29 (d, J = 7.2 Hz, 3H). |
| 526 | (azabicyclo[2.1.1]hex-5-yl NH) | 5-{7-[(1R,4R,5R)-2-azabicyclo[2.1.1]hex-5-yl]-2-[(3S)-3-methylmorpholin-4-yl]-6,7-dihydro-5H-pyrrolo[2,3-d]pyrimidin-4-yl}pyrimidin-2-amine hydrochloride | 395.1 | ¹H NMR (400 MHz, D₂O) δ 8.56 (s, 2H) 4.66-4.64 (m, 1H) 4.44-4.42 (m, 1H) 3.97-3.96 (m, 1H) 3.81-3.78 (m, 1H) 3.73-3.42 (m, 9H) 3.33-3.32 (m, 1H) 3.03-3.02 (m, 2H) 2.01-1.98 (m, 1H) 1.56-1.54 (m, 1H) 1.29 (d, J = 6.8 Hz, 3H). |
| 527 | (azabicyclo[3.1.0]hexyl with Boc) | tert-butyl (1S,5R)-1-{4-(2-aminopyrimidin-5-yl)-2-[(3S)-3-methylmorpholin-4-yl]-5,6-dihydro-7H-pyrrolo[2,3-d]pyrimidin-7-yl}-3-azabicyclo[3.1.0]hexane-3-carboxylate | 495.3 | ¹H NMR (400 MHz, Methanol-d₄) δ 8.81 (s, 2H) 4.72-4.70 (m, 1H) 4.37 (d, J = 11.6 Hz, 1H) 3.99-3.95 (m, 1H) 3.80-3.55 (m, 8H) 3.45-3.35 (m, 1H) 3.25-3.10 (m, 3H) 1.96-1.94 (m, 1H) 1.46 (d, J = 6 Hz, 9H) 1.30-1.25 (m, 4H) 0.74-0.71 (m, 1H). |

TABLE 3-continued

| Example No. | R | IUPAC Name | LRMS m/z [M + H]+ | 1H NMR or LCMS retention time and method |
|---|---|---|---|---|
| 528 | (tert-butyl carbamate-substituted 3-azabicyclo[3.1.0]hexane) | tert-butyl (1R,5S)-1-{4-(2-aminopyrimidin-5-yl)-2-[(3S)-3-methylmorpholin-4-yl]-5,6-dihydro-7H-pyrrolo[2,3-d]pyrimidin-7-yl}-3-azabicyclo[3.1.0]hexane-3-carboxylate | 495.3 | 1H NMR (400 MHz, Methanol-d4) δ 8.81 (s, 2H) 4.74-4.73 (m, 1H) 4.36 (d, J = 11.6 Hz, 1H) 3.98-3.95 (m, 1H) 3.80-3.56 (m, 8H) 3.45-3.35 (m, 1H) 3.25-3.16 (m, 3H) 1.97-1.95 (m, 1H) 1.47 (d, J = 2.8 Hz, 9H) 1.30-1.24 (m, 4H) 0.74-0.72 (m, 1H). |
| 529 | ((1R,5S)-3-azabicyclo[3.1.0]hex-1-yl, NH) | 5-{7-[(1R,5S)-3-azabicyclo[3.1.0]hex-1-yl]-2-[(3S)-3-methylmorpholin-4-yl]-6,7-dihydro-5H-pyrrolo[2,3-d]pyrimidin-4-yl}pyrimidin-2-amine hydrochloride | 395.1 | 1H NMR (400 MHz, D2O) δ 8.57-8.54 (m, 2H), 4.54-4.53 (m, 1H) 4.05-3.90 (m, 2H) 3.86-3.43 (m, 10H) 3.01 (t, J = 8 Hz, 2H) 2.32-2.27 (m, 1H) 1.48 (t, J = 8.4 Hz, 1H) 1.30 (d, J = 7.2 Hz, 3H) 1.15 (t, J = 6.4 Hz, 1H). |
| 530 | ((1S,5R)-3-azabicyclo[3.1.0]hex-1-yl, NH) | 5-{7-[(1S,5R)-3-azabicyclo[3.1.0]hex-1-yl]-2-[(3S)-3-methylmorpholin-4-yl]-6,7-dihydro-5H-pyrrolo[2,3-d]pyrimidin-4-yl}pyrimidin-2-amine hydrochloride | 395.1 | 1H NMR (400 MHz, D2O) δ 8.61-8.59 (m, 2H) 4.51-4.49 (m, 1H) 4.00-3.90 (m, 2H) 3.85-3.42 (m, 10H) 3.02-3.01 (m, 2H) 2.30-2.29 (m, 1H) 1.50-1.47 (m, 1H) 1.31-1.29 (m, 3H) 1.14-1.13 (m, 1H). |

*Compounds are single enantiomers; however, absolute stereochemistry is unknown.
**Compounds are racemates Enzyme Production for Biochemical Assays:
1) PI3Kα Complex (Full Length p110α and p85α) ("PI3KA_FL")

Genes encoding for full length p110α and p85α subunits of PI3Kα complex were subcloned from existing constructs into pFASTBAC Dual vector (Life Technologies, Carlsbad, Calif.) using standard cloning procedures. Gene encoding p110α subunit was subcloned into polyhedrine promoter while gene encoding p85α subunit was subcloned into p10 promoter. Additionally, sequence encoding for histidine tag and Tobacco Etch Virus ("TEV") cleavage site preceded p110α ORF (Open Reading Frame). Recombinant baculovirus was generated using Bac-to-Bac protocol (Life Technologies, Carlsbad, Calif.) and large scale expression was conducted in Sf21 (Life Technologies, Carlsbad, Calif.) cells at a multiplicity of infection ("MOI")=1 for 72 hours. Cells were lyzed in 50 mM Tris pH 8.0, 250 mM NaCl, 5% glycerol, 0.25 mM TCEP, and 20 mM imidazole. The PI3Kα complex was purified from clarified supernatant using Immobilized Metalo Affinity Chromatography ("IMAC"). The protein was eluted from the column using 50 mM Tris pH 8.0, 200 mM NaCl, 5% glycerol, 0.25 mM TCEP, and 200 mM imidazole, and further desalted into 50 mM Tris pH 8.0, 20 mM NaCl, and 0.25 mM TCEP prior to loading on MonoQ sepharose (GE Healthcare, Piscataway, N.J.). PI3Kα complex was eluted from MonoQ sepharose over 20 column volumes using 0-30% gradient of buffer B (50 mM Tris pH 8.0, 1 M NaCl, and 0.25 mM TCEP). The peak fractions were pulled together and loaded on Superdex 200 26/60 SEC column equilibrated in 50 mM Tris pH 8.0, 200 mM NaCl, and 0.5 mM TCEP. Following SEC, chromatography peak fractions were pulled and concentrated to 1.87 mg/mL. Purity and integrity of the complex was confirmed using LCMS, analytical SEC and SDS-PAGE (sodium dodecyl sulfate polyacrylamide gel electrophoresis) analysis.

2) p110α-iSH2 p85α Complex (Full Length p110α and p85α iSH2)("PI3KA_Act")

Genes encoding for full length p110α and p85α nSH-iSH2=niSH2 (p85a aminoacids 322-600) subunits of PI3Kα complex were subcloned from existing constructs into pFASTBAC Dual vector (Life Technologies, Carlsbad, Calif.) using standard cloning procedures. Gene encoding p110α subunit was subcloned into polyhedrine promoter while gene encoding p85α niSH2 domains was subcloned into p10 promoter. Additionally, Human Rhinovirus 3C Protease ("HRV 3C") site was introduced between nSH2 and iSH2, replacing aminoacids 431-438 of p85α with LEV-LFQGP HRV 3C recognition sequence, using standard QuickChange mutagenesis protocol (Agilent Technologies, CA). Recombinant baculovirus was generated using Bac-to-Bac protocol (Life Technologies, Carlsbad, Calif.). Large scale expression was conducted in Sf21 (Life Technologies, Carlsbad, Calif.) cells at a multiplicity of infection ("MOI") =1 for 48 hours. Cells were lyzed in 50 mM Tris pH 8.0, 250 mM NaCl, 5% glycerol, 0.25 mM TCEP, and 20 mM imidazole. The p110α-niSH2 p85α complex was purified from clarified supernatant using Immobilized Metalo Affinity Chromatography ("IMAC"). The protein was eluted from the column using 50 mM Tris pH 8.0, 200 mM NaCl, 0.25 mM TCEP, and 200 mM imidazole. Following elution p110α-niSH2 p85α complex was dialyzed against 4 liters of 50 mM Tris pH 8.0, 200 mM NaCl, 0.25 mM TCEP, and 40 mM imidazole in the presence of PreScission Protease (1:70 molar ratio of Protease to Protein) and TEV protease (1:40 molar ratio protease to protein) for 16 hours at 4° C. The protein was further purified using reverse IMAC to remove cleaved histidine tag and contaminants captured during initial IMAC purification. The mixture of p110α-iSH2 p85α complex and cleaved nSH2 was recovered in reverse IMAC 40 mM imidazole flow through and 60 mM imidazole wash fractions. Those fractions were pulled together and loaded on Superdex 200 26/60 SEC column equilibrated in 25 mM Tris, pH 8.0, 100 mM NaCl, 2% glycerol, and 2 mM TCEP. Following SEC, chromatography peak fractions containing p110α-iSH2 p85α complex were pulled and concentrated to 4.3 mg/mL. Purity and integrity of the complex was confirmed using LCMS, analytical SEC and SDS-PAGE (sodium dodecyl sulfate polyacrylamide gel electrophoresis) analysis.

Biochemical Assays

The biochemical assays of kinase activity of full-length PI3Kα (full-length p110α/p85a) or truncated PI3Kα (p110α/iSH2 p85a) were conducted using a fluorescence polarization format similar to the procedure of Yuan J., et al., (2011) "PF-04691502, a Potent and Selective Oral Inhibitor of PI3K and mTOR Kinases with Antitumor Activity", Mol Cancer Ther. 10, 2189-2199. The enzymatic reactions were conducted in 50 μL volumes in 96-well plates. The reactions contained human recombinant PI3Kα (2 nM full-length p110α/p85α or 0.5 nM p110α/iSH2 p85) and 30 μM phosphatidylinositol 4,5-bisphosphate ("PIP2") (Cayman Chemical Company, Ann Arbor, Mich.) and were sonicated for 1 minute prior to adding PI3Kα enzyme (PI3KA_Act or PI3KA_FL), DMSO or test compound (12-point 3-fold serial dilution, 3 μM top dose, 2° A) DMSO final concentration), 5 mM $MgCl_2$, 50 mM HEPES pH 7.4, 150 mM NaCl, 1 mM DTT ((2S,3S)-1,4-bis(sulfanyl)butane-2,3-diol), and 0.05% 3-[(3-cholamidopropyl)dimethylammonio]-1-propanesulfonate ("CHAPS"). The reactions were initiated by the addition of ATP (41 μM, ~Km-level, for full-length p110α/p85 or 1 mM ATP for p110α/iSH2 p85), following a 15-min preincubation. The reactions were incubated for 30 min at room temperature, stopped with EDTA pH 8 (10 mM final concentration). In a detection plate, 15 μL of detector/probe mixture, containing 480 nM GST-Grp1 PH domain protein (University of Dundee, Dundee, UK) and 12 nM carboxytetramethylrhodamine ("TAMRA")-tagged fluorescent phosphatidylinositol (3,4,5)-triphosphate ("PIP3") (Echelon Biosciences, Inc., Salt Lake City, Utah) in assay buffer, was mixed with 15 μL of kinase reaction mixture. The plate was shaken for 30 minutes and fluorescence polarization values were measured on an LJL Analyst HT plate reader (Molecular Devices, Sunnyvale, Calif.). The inhibitors were shown to be ATP-competitive from kinetic and crystallographic studies. The inhibition constants (Ki) were calculated by fitting fluorescence polarization values, corresponding to initial reaction rates, to the Morrison equation (Morrison, J. F. (1969) Kinetics of the reversible inhibition of enzyme catalysed reactions by tight-binding inhibitors. Biochim. Biophys. Acta 185, 269-286) for tight-binding competitive inhibitors using non-linear regression method (GraphPad Prism, GraphPad Software, San Diego, Calif.).

The results of the biological assays for the compounds tested are listed in Table 4.

TABLE 4

| Example No. | PI3KA_Act Ki (nM) | PI3KA_FL Ki (nM) | Example No. | PI3KA_Act Ki (nM) | PI3KA_FL Ki (nM) |
|---|---|---|---|---|---|
| 1 | 0.102 | ≤0.229 | 2 | 0.160 | N/D |
| 3 | 118.146 | N/D | 4 | 0.023 | N/D |
| 5 | 0.024 | N/D | 6 | 0.096 | N/D |
| 7 | 0.091 | N/D | 8 | 0.019 | N/D |
| 9 | <0.018 | N/D | 10 | <0.018 | N/D |
| 11 | N/D | 4.095 | 12 | N/D | 1.130 |
| 13 | 0.211 | 0.307 | 14 | N/D | 6.843 |
| 15 | N/D | 0.856 | 16 | N/D | 1.423 |
| 17 | N/D | 4.273 | 18 | N/D | 2.706 |
| 19 | N/D | 0.528 | 20 | 0.153 | ≤0.229 |
| 21 | N/D | 5.393 | 22 | N/D | ≤0.229 |
| 23 | N/D | 9.696 | 24 | N/D | 0.961 |
| 25 | N/D | ≤0.229 | 26 | N/D | 0.423 |
| 27 | N/D | 1.025 | 28 | N/D | 0.521 |
| 29 | N/D | 5.828 | 30 | N/D | 1.188 |
| 31 | N/D | ≤0.229 | 32 | N/D | 0.841 |
| 33 | N/D | 5.195 | 34 | 0.730 | 0.469 |
| 35 | 0.311 | 0.393 | 36 | N/D | 19.031 |
| 37 | N/D | 7.189 | 38 | 0.124 | 0.228 |
| 39 | N/D | 0.738 | 40 | N/D | 0.416 |
| 41 | N/D | 1.376 | 42 | N/D | 7.677 |
| 43 | N/D | 1.310 | 44 | N/D | 1.965 |
| 45 | N/D | 9.034 | 46 | 0.187 | 0.412 |
| 47 | N/D | 3.320 | 48 | N/D | 3.543 |

TABLE 4-continued

| Example No. | PI3KA_Act Ki (nM) | PI3KA_FL Ki (nM) | Example No. | PI3KA_Act Ki (nM) | PI3KA_FL Ki (nM) |
|---|---|---|---|---|---|
| 49 | N/D | 0.722 | 50 | N/D | 18.596 |
| 51 | N/D | 18.619 | 52 | N/D | 2.799 |
| 53 | N/D | 0.774 | 54 | N/D | 8.634 |
| 55 | N/D | 3.904 | 56 | N/D | 35.745 |
| 57 | 0.465 | 0.318 | 58 | N/D | 0.794 |
| 59 | 0.122 | ≤0.229 | 60 | N/D | 27.752 |
| 61 | 0.235 | 0.234 | 62 | N/D | 0.888 |
| 63 | N/D | 6.612 | 64 | N/D | 0.508 |
| 65 | N/D | ≤0.229 | 66 | N/D | 0.926 |
| 67 | N/D | 1.899 | 68 | N/D | 9.393 |
| 69 | N/D | 1.144 | 70 | N/D | 4.601 |
| 71 | N/D | 8.899 | 72 | 0.129 | ≤0.229 |
| 73 | 0.303 | 0.350 | 74 | 2.441 | 5.079 |
| 75 | N/D | 1.106 | 76 | 0.182 | 0.359 |
| 77 | N/D | 8.025 | 78 | N/D | 14.681 |
| 79 | 0.257 | ≤0.229 | 80 | N/D | 1.247 |
| 81 | N/D | 0.788 | 82 | 0.100 | 0.240 |
| 83 | N/D | 0.761 | 84 | N/D | 3.507 |
| 85 | 0.239 | 0.283 | 86 | N/D | 3.673 |
| 87 | N/D | 0.462 | 88 | N/D | 0.674 |
| 89 | N/D | 1.247 | 90 | N/D | 0.403 |
| 91 | N/D | 1.472 | 92 | 0.376 | 0.475 |
| 93 | 0.603 | 0.506 | 94 | N/D | 2.371 |
| 95 | 0.078 | ≤0.229 | 96 | N/D | 2.093 |
| 97 | N/D | 3.632 | 98 | N/D | 1.244 |
| 99 | N/D | 2.122 | 100 | 0.132 | ≤0.229 |
| 101 | 0.093 | ≤0.229 | 102 | 0.067 | ≤0.229 |
| 103 | N/D | 0.557 | 104 | 0.079 | ≤0.229 |
| 105 | 0.157 | 0.285 | 106 | 0.064 | ≤0.229 |
| 107 | N/D | 1.388 | 108 | 0.122 | ≤0.229 |
| 109 | 0.118 | ≤0.229 | 110 | N/D | 0.735 |
| 111 | 0.151 | ≤0.229 | 112 | N/D | 0.491 |
| 113 | 0.289 | ≤0.229 | 114 | N/D | 1.268 |
| 115 | 0.105 | ≤0.229 | 116 | N/D | 0.961 |
| 117 | 0.179 | 0.256 | 118 | 0.030 | ≤0.229 |
| 119 | 0.059 | ≤0.229 | 120 | 0.030 | ≤0.229 |
| 121 | 0.056 | ≤0.229 | 122 | 0.064 | ≤0.229 |
| 123 | 0.069 | ≤0.229 | 124 | N/D | 0.333 |
| 125 | 0.087 | ≤0.229 | 126 | 0.219 | ≤0.229 |
| 127 | N/D | 0.789 | 128 | 0.126 | ≤0.229 |
| 129 | N/D | 0.380 | 130 | N/D | 0.352 |
| 131 | 0.044 | ≤0.229 | 132 | 0.150 | ≤0.229 |
| 133 | N/D | 0.468 | 134 | N/D | 3.883 |
| 135 | N/D | 5.159 | 136 | 0.099 | ≤0.229 |
| 137 | N/D | 0.664 | 138 | N/D | 5.547 |
| 139 | N/D | 0.596 | 140 | 0.318 | N/D |
| 141 | 0.471 | N/D | 142 | 0.159 | N/D |
| 143 | 0.262 | N/D | 144 | 3.251 | N/D |
| 145 | 4.011 | N/D | 146 | 0.015 | ≤0.229 |
| 147 | 0.064 | N/D | 148 | 0.094 | N/D |
| 149 | 0.027 | N/D | 150 | 0.044 | N/D |
| 151 | 0.107 | N/D | 152 | 0.103 | N/D |
| 153 | 0.105 | N/D | 154 | 0.286 | N/D |
| 155 | 0.116 | N/D | 156 | 0.088 | N/D |
| 157 | 0.173 | N/D | 158 | 0.200 | N/D |
| 159 | 0.097 | N/D | 160 | 0.221 | N/D |
| 161 | 0.202 | N/D | 162 | <0.018 | N/D |
| 163 | 0.188 | N/D | 164 | 0.030 | N/D |
| 165 | 0.449 | N/D | 166 | 0.280 | N/D |
| 167 | 0.230 | N/D | 168 | 0.297 | N/D |
| 169 | 0.129 | N/D | 170 | 0.124 | N/D |
| 171 | 2.745 | N/D | 172 | 0.029 | N/D |
| 173 | <0.018 | N/D | 174 | 0.030 | N/D |
| 175 | 0.023 | N/D | 176 | 0.462 | N/D |
| 177 | 0.615 | N/D | 178 | 0.125 | N/D |
| 179 | 0.344 | N/D | 180 | 1.759 | N/D |
| 181 | 0.296 | N/D | 182 | 0.357 | N/D |
| 183 | 0.393 | N/D | 184 | 0.647 | N/D |
| 185 | 0.182 | N/D | 186 | 0.274 | N/D |
| 187 | 0.839 | N/D | 188 | 0.642 | N/D |
| 189 | 1.162 | N/D | 190 | 0.040 | N/D |
| 191 | 0.881 | N/D | 192 | 0.053 | N/D |
| 193 | 0.027 | N/D | 194 | <0.018 | N/D |
| 195 | 0.166 | N/D | 196 | 0.024 | N/D |
| 197 | 0.040 | N/D | 198 | 0.024 | N/D |
| 199 | 0.151 | N/D | 200 | 0.909 | N/D |
| 201 | 1.400 | N/D | 202 | 1.037 | N/D |

TABLE 4-continued

| Example No. | PI3KA_Act Ki (nM) | PI3KA_FL Ki (nM) | Example No. | PI3KA_Act Ki (nM) | PI3KA_FL Ki (nM) |
|---|---|---|---|---|---|
| 203 | 0.032 | N/D | 204 | <0.018 | N/D |
| 205 | 0.021 | N/D | 206 | 0.031 | N/D |
| 207 | 0.100 | N/D | 208 | 0.062 | N/D |
| 209 | 0.045 | N/D | 210 | 0.898 | N/D |
| 211 | 0.078 | N/D | 212 | 0.534 | N/D |
| 213 | 0.030 | N/D | 214 | 0.128 | N/D |
| 215 | 0.476 | N/D | 216 | 0.124 | N/D |
| 217 | 0.191 | N/D | 218 | 0.751 | N/D |
| 219 | 0.037 | N/D | 220 | 0.053 | N/D |
| 221 | 1.291 | N/D | 222 | 0.101 | N/D |
| 223 | 0.393 | N/D | 224 | 2.296 | N/D |
| 225 | 4.151 | N/D | 226 | 7.437 | N/D |
| 227 | 1.040 | N/D | 228 | 0.164 | N/D |
| 229 | 0.055 | N/D | 230 | 6.996 | N/D |
| 231 | 1.493 | N/D | 232 | 4.263 | N/D |
| 233 | <0.018 | N/D | 234 | 0.509 | N/D |
| 235 | 0.693 | N/D | 236 | <0.018 | N/D |
| 237 | 0.025 | N/D | 238 | <0.018 | N/D |
| 239 | <0.018 | N/D | 240 | 0.093 | N/D |
| 241 | 1.174 | N/D | 242 | 0.158 | N/D |
| 243 | 0.165 | N/D | 244 | 0.598 | N/D |
| 245 | 4.212 | N/D | 246 | 0.060 | N/D |
| 247 | 0.055 | N/D | 248 | 0.212 | N/D |
| 249 | 0.019 | N/D | 250 | 0.120 | N/D |
| 251 | 1.652 | N/D | 252 | 0.158 | N/D |
| 253 | 0.160 | N/D | 254 | 1.893 | N/D |
| 255 | 1.168 | N/D | 256 | 1.131 | N/D |
| 257 | 0.955 | N/D | 258 | 31.787 | N/D |
| 259 | 0.139 | N/D | 260 | 0.030 | N/D |
| 261 | 0.143 | N/D | 262 | <0.018 | N/D |
| 263 | 0.122 | N/D | 264 | <0.018 | N/D |
| 265 | 0.048 | N/D | 266 | 0.139 | N/D |
| 267 | 0.041 | N/D | 268 | 0.100 | N/D |
| 269 | 0.222 | N/D | 270 | 0.074 | N/D |
| 271 | 0.016 | N/D | 272 | 0.022 | N/D |
| 273 | 0.087 | N/D | 274 | 0.145 | N/D |
| 275 | 0.030 | N/D | 276 | 0.182 | N/D |
| 277 | 0.034 | N/D | 278 | <0.018 | N/D |
| 279 | 0.027 | N/D | 280 | 0.154 | N/D |
| 281 | 0.024 | N/D | 282 | 4.040 | N/D |
| 283 | 0.208 | N/D | 284 | 0.368 | N/D |
| 285 | 0.089 | N/D | 286 | 5.810 | N/D |
| 287 | 0.462 | N/D | 288 | 0.141 | N/D |
| 289 | 0.075 | N/D | 290 | <0.018 | N/D |
| 291 | <0.018 | N/D | 292 | <0.018 | N/D |
| 293 | 0.086 | N/D | 294 | <0.018 | N/D |
| 295 | <0.018 | N/D | 296 | <0.018 | N/D |
| 297 | 0.019 | N/D | 298 | <0.018 | N/D |
| 299 | <0.018 | N/D | 300 | 0.669 | N/D |
| 301 | 0.073 | N/D | 302 | 0.038 | N/D |
| 303 | 0.025 | N/D | 304 | <0.018 | N/D |
| 305 | 0.036 | N/D | 306 | <0.018 | N/D |
| 307 | <0.018 | N/D | 308 | 0.126 | N/D |
| 309 | 0.056 | N/D | 310 | 0.022 | N/D |
| 311 | 0.054 | N/D | 312 | 0.037 | N/D |
| 313 | 0.128 | N/D | 314 | <0.018 | N/D |
| 315 | <0.018 | N/D | 316 | 0.019 | N/D |
| 317 | <0.018 | N/D | 318 | 0.076 | N/D |
| 319 | 2.266 | N/D | 320 | 0.318 | N/D |
| 321 | 0.042 | N/D | 322 | <0.018 | N/D |
| 323 | <0.018 | N/D | 324 | 0.198 | N/D |
| 325 | 0.058 | N/D | 326 | 0.048 | N/D |
| 327 | 0.028 | N/D | 328 | 0.024 | N/D |
| 329 | <0.018 | N/D | 330 | 0.152 | N/D |
| 331 | <0.018 | N/D | 332 | <0.018 | N/D |
| 333 | <0.018 | N/D | 334 | 0.021 | N/D |
| 335 | <0.018 | N/D | 336 | 0.054 | N/D |
| 337 | <0.018 | N/D | 338 | 0.071 | N/D |
| 339 | 0.080 | N/D | 340 | 0.234 | N/D |
| 341 | <0.018 | N/D | 342 | 0.141 | N/D |
| 343 | 0.089 | N/D | 344 | 0.098 | N/D |
| 345 | 0.028 | N/D | 346 | 0.125 | N/D |
| 347 | 0.075 | N/D | 348 | 0.066 | N/D |
| 349 | 0.026 | N/D | 350 | 0.045 | N/D |
| 351 | 0.059 | N/D | 352 | <0.018 | N/D |
| 353 | 0.078 | N/D | 354 | 0.049 | N/D |
| 355 | 0.102 | N/D | 356 | 0.037 | N/D |

TABLE 4-continued

| Example No. | PI3KA_Act Ki (nM) | PI3KA_FL Ki (nM) | Example No. | PI3KA_Act Ki (nM) | PI3KA_FL Ki (nM) |
|---|---|---|---|---|---|
| 357 | 0.144 | N/D | 358 | 0.171 | N/D |
| 359 | 0.128 | N/D | 360 | <0.018 | N/D |
| 361 | 0.078 | N/D | 362 | 0.041 | N/D |
| 363 | 0.039 | N/D | 364 | 0.262 | N/D |
| 365 | 0.063 | N/D | 366 | 0.021 | N/D |
| 367 | <0.018 | N/D | 368 | 0.127 | N/D |
| 369 | <0.018 | N/D | 370 | 0.184 | N/D |
| 371 | 0.091 | N/D | 372 | 0.040 | N/D |
| 373 | 0.028 | N/D | 374 | 0.027 | N/D |
| 375 | 0.043 | N/D | 376 | 0.090 | N/D |
| 377 | 0.026 | N/D | 378 | 0.082 | N/D |
| 379 | 0.061 | N/D | 380 | 0.030 | N/D |
| 381 | 0.030 | N/D | 382 | <0.018 | N/D |
| 383 | <0.018 | N/D | 384 | <0.018 | N/D |
| 385 | <0.018 | N/D | 386 | <0.018 | N/D |
| 387 | <0.018 | N/D | 388 | <0.018 | N/D |
| 389 | <0.018 | N/D | 390 | 0.084 | N/D |
| 391 | 0.022 | N/D | 392 | 0.101 | N/D |
| 393 | 0.085 | N/D | 394 | 0.112 | N/D |
| 395 | 0.352 | N/D | 396 | 0.121 | N/D |
| 397 | 0.101 | N/D | 398 | 0.411 | N/D |
| 399 | 0.074 | N/D | 400 | 0.781 | N/D |
| 401 | 0.109 | N/D | 402 | 0.872 | N/D |
| 403 | 0.053 | N/D | 404 | 0.128 | N/D |
| 405 | <0.018 | N/D | 406 | <0.018 | N/D |
| 407 | 0.235 | N/D | 408 | 1.085 | N/D |
| 409 | 0.168 | N/D | 410 | 0.262 | N/D |
| 411 | <0.018 | N/D | 412 | <0.018 | N/D |
| 413 | <0.018 | N/D | 414 | 0.039 | N/D |
| 415 | <0.018 | N/D | 416 | <0.018 | N/D |
| 417 | <0.018 | N/D | 418 | 0.320 | N/D |
| 419 | 1.990 | N/D | 420 | 0.601 | N/D |
| 421 | 0.071 | N/D | 422 | 0.415 | N/D |
| 423 | 0.445 | N/D | 424 | 0.321 | N/D |
| 425 | 0.311 | N/D | 426 | 0.051 | N/D |
| 427 | 0.073 | N/D | 428 | 0.067 | N/D |
| 429 | 0.160 | N/D | 430 | 0.785 | N/D |
| 431 | 14.544 | N/D | 432 | 11.739 | N/D |
| 433 | 0.024 | N/D | 434 | 0.220 | N/D |
| 435 | 0.132 | N/D | 436 | 0.189 | N/D |
| 437 | 0.603 | N/D | 438 | 7.455 | N/D |
| 439 | 1.514 | N/D | 440 | 0.178 | N/D |
| 441 | 0.432 | N/D | 442 | 1.349 | N/D |
| 443 | 0.944 | N/D | 444 | 2.125 | N/D |
| 445 | 0.993 | N/D | 446 | 0.433 | N/D |
| 447 | 0.644 | N/D | 448 | 0.690 | N/D |
| 449 | 0.294 | N/D | 450 | 0.167 | N/D |
| 451 | 0.595 | N/D | 452 | 0.090 | N/D |
| 453 | 0.973 | N/D | 454 | 0.387 | N/D |
| 455 | 0.187 | N/D | 456 | 0.063 | N/D |
| 457 | 0.691 | N/D | 458 | 0.159 | N/D |
| 459 | 0.057 | N/D | 460 | 0.047 | N/D |
| 461 | 0.040 | N/D | 462 | 0.057 | N/D |
| 463 | 0.169 | N/D | 464 | 0.193 | N/D |
| 465 | 0.160 | N/D | 466 | 0.303 | N/D |
| 467 | 0.106 | N/D | 468 | 0.634 | N/D |
| 469 | 0.052 | N/D | 470 | 0.070 | N/D |
| 471 | 0.037 | N/D | 472 | 0.044 | N/D |
| 473 | 0.076 | N/D | 474 | 0.045 | N/D |
| 475 | 0.068 | N/D | 476 | <0.018 | N/D |
| 477 | 0.038 | N/D | 478 | 0.026 | N/D |
| 479 | 0.026 | N/D | 480 | <0.018 | N/D |
| 481 | 0.149 | N/D | 482 | 0.022 | N/D |
| 483 | 0.049 | N/D | 484 | <0.018 | N/D |
| 485 | <0.018 | N/D | 486 | <0.018 | N/D |
| 487 | 0.011 | N/D | 488 | <0.018 | N/D |
| 489 | <0.018 | N/D | 490 | <0.018 | N/D |
| 491 | 0.050 | N/D | 492 | 0.101 | N/D |
| 493 | 0.061 | N/D | 494 | 0.046 | N/D |
| 495 | 0.031 | N/D | 496 | <0.018 | N/D |
| 497 | 0.056 | N/D | 498 | 0.048 | N/D |
| 499 | 0.048 | N/D | 500 | 0.064 | N/D |
| 501 | 0.035 | N/D | 502 | 0.064 | N/D |
| 503 | 0.091 | N/D | 504 | 0.109 | N/D |
| 505 | 0.139 | N/D | 506 | 0.061 | N/D |
| 507 | 0.082 | N/D | 508 | <0.018 | N/D |
| 509 | 0.135 | N/D | 510 | <0.018 | N/D |

TABLE 4-continued

| Example No. | PI3KA_Act Ki (nM) | PI3KA_FL Ki (nM) | Example No. | PI3KA_Act Ki (nM) | PI3KA_FL Ki (nM) |
|---|---|---|---|---|---|
| 511 | 0.915 | N/D | 512 | <0.018 | N/D |
| 513 | 0.418 | N/D | 514 | 0.068 | N/D |
| 515 | <0.081 | N/D | 516 | 0.346 | N/D |
| 517 | 9.319 | N/D | 518 | 11.285 | N/D |
| 519 | 0.036 | N/D | 520 | 0.663 | N/D |
| 521 | 0.170 | N/D | 522 | 6.845 | N/D |
| 523 | 5.209 | N/D | 524 | 1.872 | N/D |
| 525 | 4.504 | N/D | 526 | 9.425 | N/D |
| 527 | <0.018 | N/D | 528 | 0.092 | N/D |
| 529 | 0.595 | N/D | 530 | 2.624 | N/D |

What is claimed is:
1. A compound of formula (II)

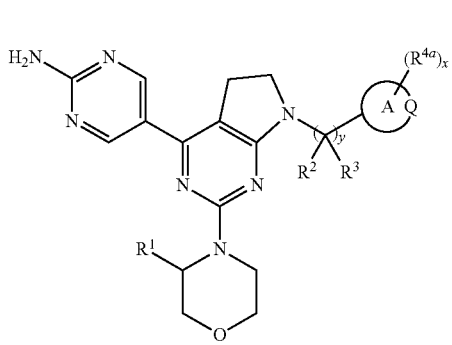

or a pharmaceutically acceptable salt thereof,
wherein
$R^1$ is hydrogen, methyl, —$CH_2OH$, or —$CH_2F$;
y is 0 or 1;
$R^2$ is hydrogen, cyano, $C_1$-$C_3$ alkyl, or —$CF_3$;
$R^3$ is hydrogen or $C_1$-$C_3$ alkyl;
ring A is $C_3$-$C_8$ cycloalkyl or 4-8 membered heterocycloalkyl;
Q is —$C(R^9)(R^{10})$—, —$N(R^{11})$— or —O—;
x is 0, 1, 2, 3, or 4;
each $R^{4a}$ is independently selected from the group consisting of fluorine, cyano, oxo, methyl, —$CH_2F$, —$CHF_2$, —$CF_3$, —$CH_2OH$, hydroxy, and methoxy;
$R^9$ is hydrogen,
fluorine,
cyano,
hydroxy,
$C_1$-$C_3$ alkoxy,
—$S(O)R^{32}$,
—O—$S(O)_2R^{33}$,
—[$N(R^{26})$]$_h$—$C(O)R^{34}$,
—[$N(R^{27})$]$_i$—$C(O)[N(R^{35})(R^{36})]$,
—[$N(R^{28})$]$_j$—$C(O)OR^{37}$,
—[$N(R^{29})$]$_k$—$S(O)_2R^{38}$,
—[$N(R^{30})$]$_l$—$S(O)_2[N(R^{39})(R^{40})]$, or
—[$N(R^{31})$]$_o$—$P(O)(CH_3)_2$;
$R^{10}$ is hydrogen, fluorine, or $C_1$-$C_3$ alkyl;
$R^{11}$ is hydrogen,
—$(CH_2)_p$—$C(O)R^{41}$,
—$(CH_2)_q$—$C(O)[N(R^{42})(R^{43})]$,
—$(CH_2)_r$—$C(O)OR^{44}$,
—$(CH_2)_s$—$S(O)_2R^{45}$,
—$(CH_2)_t$—$S(O)_2[N(R^{46})(R^{47})]$,
—$(CH_2)_u$—$R^{48}$, or
—$P(O)(CH_3)_2$,
$R^{26}$, $R^{27}$, $R^{28}$, $R^{29}$, $R^{30}$ and $R^{31}$ are each independently hydrogen or methyl;
h, i, j, k, l, o, p, q, r, s, t, and u are each independently 0 or 1;
$R^{32}$ is $C_1$-$C_4$ alkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;
$R^{33}$ is $C_1$-$C_4$ alkyl, —$NH_2$, —$NHCH_3$, —$N(CH_3)_2$, or $C_3$-$C_5$ cycloalkyl, wherein the $C_1$-$C_4$ alkyl is optionally substituted by one substituent selected from the group consisting of fluorine, cyano, hydroxy, $C_1$-$C_4$ alkoxy, —$NH_2$, —$NHCH_3$, and —$N(CH_3)_2$;
$R^{34}$ and $R^{41}$ are each independently hydrogen, $C_1$-$C_4$ alkyl, $C_3$-$C_6$ cycloalkyl, 4-6 membered heterocycloalkyl, or 5 membered heteroaryl, wherein the $C_1$-$C_4$ alkyl, the $C_3$-$C_6$ cycloalkyl, and the 4-6 membered heterocycloalkyl are each independently optionally substituted by one, two, or three substituents selected from the group consisting of fluorine, cyano, oxo, $C_1$-$C_4$ alkyl, —$CH_2F$, —$CHF_2$, —$CF_3$, hydroxy, $C_1$-$C_4$ alkoxy, —$C(O)NH_2$, —$C(O)OH$, —$C(O)OCH_3$, —$NH_2$, —$NHCH_3$, —$N(CH_3)_2$, —[$N(R^{49})$]-$C(O)R^{50}$, $C_3$-$C_4$ cycloalkyl, and 4-5 membered heterocycloalkyl, further wherein the 5 membered heteroaryl is optionally substituted by one substituent selected from the group consisting of fluorine, cyano, hydroxy, methoxy, —$NH_2$, and —$NHCH_3$;
$R^{35}$ and $R^{42}$ are each independently hydrogen, $C_1$-$C_4$ alkyl, $C_3$-$C_4$ cycloalkyl, or 4-5 membered heterocycloalkyl;
$R^{36}$ and $R^{43}$ are each independently hydrogen or $C_1$-$C_4$ alkyl; or
$R^{35}$ and $R^{36}$ together with the nitrogen to which they are attached and $R^{42}$ and $R^{43}$ together with the nitrogen to which they are attached, each independently form a 4-5 membered heterocycloalkyl ring, wherein the 4-5 membered heterocycloalkyl ring formed is optionally substituted by one, two, or three substituents selected from the group consisting of fluorine, cyano, oxo, $C_1$-$C_4$ alkyl, hydroxy, and methoxy;
$R^{37}$ and $R^{44}$ are each independently $C_1$-$C_4$ alkyl, $C_3$-$C_4$ cycloalkyl, or 4-5 membered heterocycloalkyl, wherein the $C_1$-$C_4$ alkyl is optionally substituted by one, two, or three substituents selected from the group consisting of fluorine, cyano, hydroxy, methoxy, —$C(O)NH_2$, —$C(O)NHCH_3$, —$C(O)N(CH_3)_2$, —NH—$S(O)_2NH_2$, —NH—$S(O)_2NHCH_3$, and —NH—$S(O)_2N(CH_3)_2$, further wherein the $C_3$-$C_4$ cycloalkyl and the 4-5 membered heterocycloalkyl are each optionally substituted by one or two substituents selected from the group consisting of fluorine, cyano, methyl, hydroxy, methoxy, and —C(O)CH$_3$;

R$^{38}$ and R$^{45}$ are each independently C$_1$-C$_4$ alkyl, —CF$_3$, C$_1$-C$_4$ alkoxy, —(CH$_2$)$_v$—(C$_3$-C$_4$ cycloalkyl), 4-5 membered heterocycloalkyl, or 5-6 membered heteroaryl, wherein the C$_1$-C$_4$ alkyl is optionally substituted by one substituent selected from the group consisting of fluorine, cyano, hydroxy, and methoxy, further wherein the 4-5 membered heterocycloalkyl and the 5-6 membered heteroaryl are each independently optionally substituted by one or two substituents selected from the group consisting of fluorine, cyano, C$_1$-C$_4$ alkyl, hydroxy, methoxy, —C(O)(C$_1$-C$_4$ alkyl), and —C(O)[O—(C$_1$-C$_4$ alkyl)];

v is 0 or 1;

R$^{39}$ and R$^{46}$ are each independently hydrogen, C$_1$-C$_4$ alkyl, C$_3$-C$_4$ cycloalkyl, or 4-5 membered heterocycloalkyl;

R$^{40}$ and R$^{47}$ are each independently hydrogen or C$_1$-C$_4$ alkyl; or

R$^{39}$ and R$^{40}$ together with the nitrogen to which they are attached and R$^{46}$ and R$^{47}$ together with the nitrogen to which they are attached, each independently form a 4-5 membered heterocycloalkyl ring, wherein the 4-5 membered heterocycloalkyl ring formed is optionally substituted by one or two substituents selected from the group consisting of fluorine, cyano, C$_1$-C$_4$ alkyl, hydroxy, and methoxy;

R$^{48}$ is C$_1$-C$_4$ alkyl, C$_3$-C$_4$ cycloalkyl, or 4-6 membered heterocycloalkyl, wherein the C$_1$-C$_4$ alkyl is optionally substituted by one, two, or three substituents selected from the group consisting of fluorine, cyano, hydroxy, methoxy, —C(O)NH$_2$, —C(O)NHCH$_3$, —C(O)N(CH$_3$)$_2$, —NH$_2$, —NHCH$_3$, and —N(CH$_3$)$_2$, further wherein the C$_3$-C$_4$ cycloalkyl and the 4-6 membered heterocycloalkyl are each optionally substituted by one, two, three, or four substituents selected from the group consisting of fluorine, cyano, methyl, hydroxy, methoxy, oxo, —CF$_3$, and —C(O)CH$_3$;

R$^{49}$ is hydrogen or methyl; and

R$^{50}$ is C$_1$-C$_4$ alkyl, —CF$_3$, C$_1$-C$_4$ alkoxy, —NH$_2$, —NHCH$_3$, —N(CH$_3$)$_2$, C$_3$-C$_5$ cycloalkyl, or 4-6 membered heterocycloalkyl.

2. The compound or salt of claim 1, wherein R$^1$ is hydrogen or methyl.

3. The compound or salt of claim 1, wherein y is 0.

4. The compound or salt of claim 1, wherein x is 0, 1, or 2.

5. The compound or salt of claim 1, wherein R$^{4a}$ is methyl and x is 1 or 2.

6. The compound or salt of claim 1, wherein R$^{4a}$ is oxo and x is 1.

7. The compound or salt of claim 1, wherein Q is —C(R$^9$)(R$^{10}$)—.

8. The compound or salt of claim 1, wherein Q is —N(R$^{11}$)—.

9. The compound or salt of claim 8, wherein R$^{11}$ is hydrogen.

10. The compound or salt of claim 8, wherein R$^{11}$ is —(CH$_2$)$_p$—C(O)R$^{41}$.

11. The compound or salt of claim 10, wherein p is 0.

12. The compound or salt of claim 10, wherein R$^{41}$ is C$_1$-C$_4$ alkyl, wherein the C$_1$-C$_4$ alkyl is optionally substituted by —NH$_2$.

13. The compound or salt of claim 1, having formula (VI)

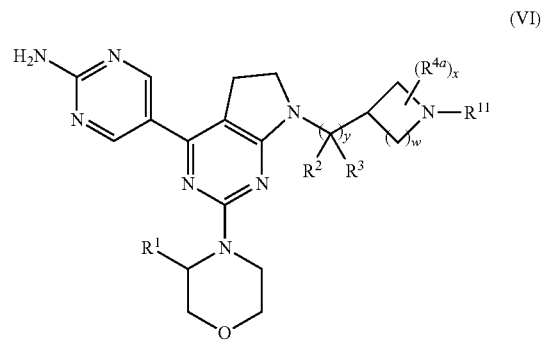

(VI)

wherein w is 1, 2, or 3.

14. The compound or salt of claim 1, having formula (VIII):

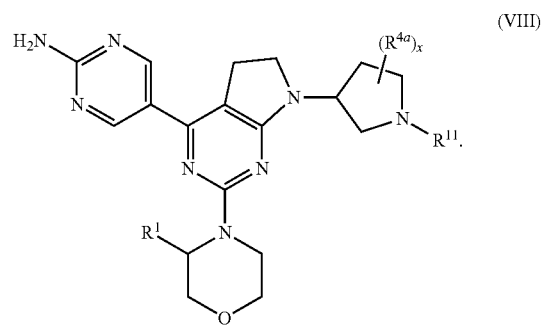

(VIII)

15. The compound or salt of claim 1, having formula (VIIIa):

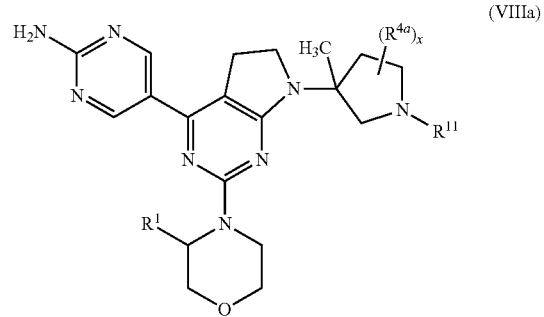

(VIIIa)

wherein x is 0, 1, or 2.

16. A compound, which is selected from the group consisting of

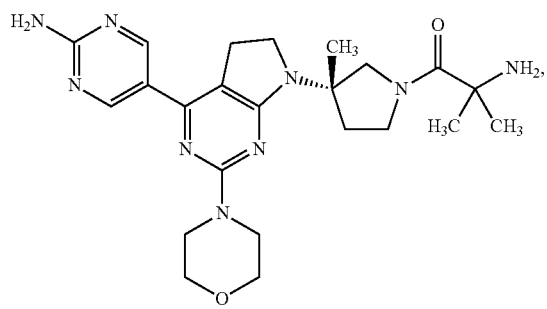

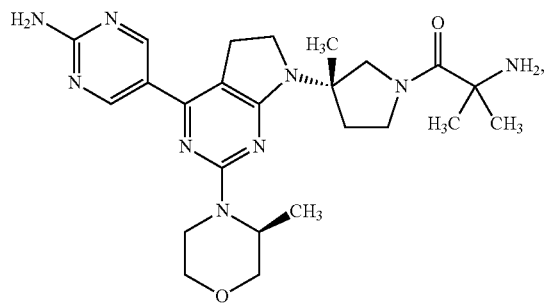

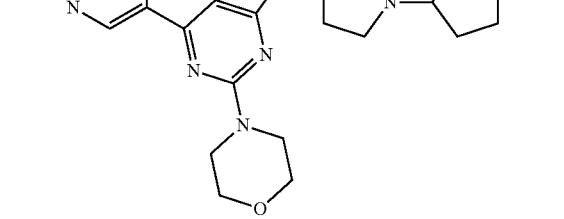

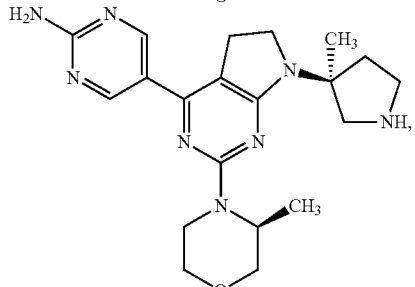

or a pharmaceutically acceptable salt thereof.

17. A pharmaceutical composition comprising a compound of claim 1, or a pharmaceutically acceptable salt thereof, and a pharmaceutically acceptable carrier or diluent.

18. A combination of a compound of claim 1, or a pharmaceutically acceptable salt thereof, with an anti-tumor agent or with radiation therapy.

* * * * *